(12) United States Patent
Osterhout et al.

(10) Patent No.: US 12,398,396 B2
(45) Date of Patent: Aug. 26, 2025

(54) METHODS FOR ENHANCING MICROBIAL PRODUCTION OF SPECIFIC LENGTH FATTY ALCOHOLS IN THE PRESENCE OF METHANOL

(71) Applicant: Genomatica, Inc., San Diego, CA (US)

(72) Inventors: Robin E. Osterhout, San Diego, CA (US); Anthony P. Burgard, Elizabeth, PA (US); Priti Pharkya, San Diego, CA (US); Stefan Andrae, San Diego, CA (US)

(73) Assignee: Genomatica, Inc., San Diego, CA (US)

( * ) Notice: Subject to any disclaimer, the term of this patent is extended or adjusted under 35 U.S.C. 154(b) by 503 days.

(21) Appl. No.: 17/516,424

(22) Filed: Nov. 1, 2021

(65) Prior Publication Data

US 2022/0348932 A1    Nov. 3, 2022

Related U.S. Application Data

(63) Continuation of application No. 15/038,922, filed as application No. PCT/US2014/067282 on Nov. 25, 2014, now abandoned.

(60) Provisional application No. 61/945,003, filed on Feb. 26, 2014, provisional application No. 61/911,374, filed on Dec. 3, 2013, provisional application No. 61/908,652, filed on Nov. 25, 2013.

(51) Int. Cl.
| | |
|---|---|
| *C12N 9/90* | (2006.01) |
| *C12N 9/04* | (2006.01) |
| *C12N 9/10* | (2006.01) |
| *C12N 9/88* | (2006.01) |
| *C12N 15/52* | (2006.01) |
| *C12P 7/04* | (2006.01) |

(52) U.S. Cl.
CPC ........... *C12N 15/52* (2013.01); *C12N 9/0006* (2013.01); *C12N 9/1022* (2013.01); *C12N 9/88* (2013.01); *C12N 9/90* (2013.01); *C12P 7/04* (2013.01); *C12Y 101/01244* (2013.01); *C12Y 202/01003* (2013.01); *C12Y 401/02043* (2013.01); *C12Y 503/01027* (2013.01)

(58) Field of Classification Search
CPC ...... C12N 15/81; C12N 15/70; C12N 9/1007; C12N 9/1022; C12N 9/0067; C12N 9/0006; C12P 5/026; C12P 7/04; C12P 7/42; C12P 7/02; C12Y 101/01244; C12Y 101/03013; C12Y 101/02007; C12Y 202/01003
USPC ...................................................... 435/252.3
See application file for complete search history.

(56) References Cited

U.S. PATENT DOCUMENTS

| | | |
|---|---|---|
| 5,352,590 A | 10/1994 | Kato et al. |
| 5,958,745 A | 9/1999 | Gruys et al. |
| 6,280,972 B1 | 8/2001 | Yasueda |
| 6,331,428 B1 | 12/2001 | Kato |
| 6,630,341 B2 | 10/2003 | Kato et al. |
| 6,686,194 B1 | 2/2004 | Mutzel et al. |
| 6,911,332 B2 | 6/2005 | Usuda et al. |
| 7,127,379 B2 | 10/2006 | Palsson et al. |
| 7,160,704 B2 | 1/2007 | Takeshita et al. |
| 7,163,810 B2 | 1/2007 | Yasueda et al. |
| 7,192,748 B2 | 3/2007 | Usuda et al. |
| 7,211,416 B2 | 5/2007 | Asahara et al. |
| 8,048,624 B1 | 11/2011 | Lynch |
| 2002/0012939 A1 | 1/2002 | Palsson |
| 2002/0168654 A1 | 11/2002 | Maranas et al. |
| 2003/0059792 A1 | 3/2003 | Palsson et al. |
| 2003/0224363 A1 | 12/2003 | Park et al. |
| 2004/0009466 A1 | 1/2004 | Maranas et al. |
| 2004/0029149 A1 | 2/2004 | Palsson et al. |
| 2004/0072723 A1 | 4/2004 | Palsson et al. |
| 2006/0040365 A1 | 2/2006 | Kozlov et al. |
| 2009/0047719 A1 | 2/2009 | Burgard et al. |
| 2009/0191593 A1 | 7/2009 | Burk et al. |
| 2010/0203614 A1 | 8/2010 | Wahlen et al. |
| 2010/0298612 A1 | 11/2010 | Behrouzian et al. |

(Continued)

FOREIGN PATENT DOCUMENTS

| | | |
|---|---|---|
| EP | 1605048 A1 | 12/2005 |
| EP | 2062967 A1 | 11/2007 |

(Continued)

OTHER PUBLICATIONS

Kisselev L., (Structure, 2002, vol. 10: 8-9.*

(Continued)

*Primary Examiner* — Robert B Mondesi
*Assistant Examiner* — Mohammad Y Meah
(74) *Attorney, Agent, or Firm* — Greenberg Traurig, LLP

(57) ABSTRACT

The invention provides non-naturally occurring microbial organisms having a formaldehyde fixation pathway, a formate assimilation pathway, and/or a methanol metabolic pathway in combination with a fatty alcohol, fatty aldehyde, fatty acid or isopropanol pathway, wherein the microbial organisms selectively produce a fatty alcohol, fatty aldehyde or fatty acid of a specified length or isopropanol. The microbial organisms provided advantageously enhance the production of substrates and/or pathway intermediates for the production of chain length specific fatty alcohols, fatty aldehydes, fatty acids or isopropanol. In some aspects, the microbial organisms of the invention have select gene disruptions or enzyme attenuations that increase production of fatty alcohols, fatty aldehydes or fatty acids. The invention additionally provides methods of using the above microbial organisms to produce a fatty alcohol, a fatty aldehyde, a fatty acid or isopropanol.

28 Claims, 21 Drawing Sheets

Specification includes a Sequence Listing.

(56) References Cited

U.S. PATENT DOCUMENTS

| | | |
|---|---|---|
| 2011/0000125 A1 | 1/2011 | McDaniel et al. |
| 2011/0195461 A1 | 8/2011 | Burk et al. |
| 2011/0207203 A1 | 8/2011 | Reppas et al. |
| 2011/0250663 A1 | 10/2011 | Schirmer et al. |
| 2012/0003652 A1 | 1/2012 | Reeves et al. |
| 2012/0009640 A1 | 1/2012 | Behrouzian et al. |
| 2012/0064622 A1 | 3/2012 | Fischer et al. |
| 2012/0070868 A1 | 3/2012 | Lee et al. |
| 2012/0142979 A1 | 6/2012 | Keasling et al. |
| 2012/0276587 A1 | 11/2012 | Beck et al. |
| 2013/0066035 A1 | 3/2013 | Burgard et al. |
| 2013/0089906 A1 | 4/2013 | Beck et al. |
| 2013/0295616 A1 | 11/2013 | Muramatsu et al. |
| 2014/0051136 A1 | 2/2014 | Liao et al. |
| 2014/0127765 A1 | 5/2014 | Osterhout et al. |
| 2014/0248669 A1 | 9/2014 | Marliere |
| 2014/0273144 A1 | 9/2014 | Hawkins et al. |
| 2014/0273164 A1 | 9/2014 | Liao et al. |
| 2014/0273165 A1 | 9/2014 | Liao et al. |
| 2017/0159075 A1 | 6/2017 | OSterhout et al. |

FOREIGN PATENT DOCUMENTS

| | | |
|---|---|---|
| EP | 2947143 A1 | 1/2014 |
| WO | WO 2003/078643 A1 | 9/2003 |
| WO | WO 2004/024876 A2 | 3/2004 |
| WO | WO 2006/016705 A1 | 2/2006 |
| WO | WO 2007/136762 A2 | 11/2007 |
| WO | WO 2007/141208 A2 | 12/2007 |
| WO | WO 2008/113041 A2 | 9/2008 |
| WO | WO 2008/144791 A2 | 12/2008 |
| WO | WO 2010/104938 A1 | 3/2010 |
| WO | WO 2010/068953 A2 | 6/2010 |
| WO | WO 2010/135624 A2 | 11/2010 |
| WO | WO 2011/159853 A1 | 12/2011 |
| WO | WO 2012/098662 A1 | 7/2012 |
| WO | WO 2012/129555 A2 | 9/2012 |
| WO | WO 2013/007786 A1 | 1/2013 |
| WO | WO 2013/048557 A1 | 4/2013 |
| WO | WO 2013/066568 A1 | 5/2013 |
| WO | WO 2013/069634 A1 | 5/2013 |
| WO | WO 2013/071172 A1 | 5/2013 |
| WO | WO 2013/110797 A1 | 8/2013 |
| WO | WO 2013/112939 A2 | 8/2013 |
| WO | WO 2013/181647 A2 | 12/2013 |
| WO | WO 2014/062564 A1 | 4/2014 |
| WO | WO 2014/066235 A1 | 5/2014 |
| WO | WO 2014/081803 A1 | 5/2014 |
| WO | WO 2014/144135 A2 | 9/2014 |
| WO | WO 2014/152434 A2 | 9/2014 |
| WO | WO 2014/153036 A1 | 9/2014 |
| WO | WO 2014/153207 A2 | 9/2014 |
| WO | WO 2015/077752 A1 | 5/2015 |
| WO | WO 2015/084633 A1 | 6/2015 |

OTHER PUBLICATIONS

Witkowski et al., (Biochemistry 38:11643-11650, 1999.*
Whisstock et al., (Quarterly Reviews of Biophysics 2003, vol. 36 (3): 307-340.*
Devos et al., (Proteins: Structure, Function and Genetics, 2000, vol. 41: 98-107.*
Abdel-Hamid et al., "Pyruvate Oxidase Contributes to the Aerobic Growth Efficiency of Escherichia coli," Microbiol., 147:1483-1498 (2001).
Afolabi et al., "Site-directed Mutagenesis and X-ray Crystallography of the PQQ-containing Quinoprotein Methanol Dehydrogenase and Its Electron Acceptor, Cytochrome c(L)," Biochem., 40:9799-9809 (2001).
Agnihotri et al., "Enoyl-CoA Hydratase. Reaction, Mechanism, and Inhibition," Bioorg. Med. Chem., 11:9-20 (2003).
Alber et al., "Malonyl-coenzyme A Reductase in the Modified 3-hydroxypropionate Cycle for Autotrophic Carbon Fixation in Archaeal Metallosphaera and Sulfolobus SPP," J. Bacteriol., 188:8551-8559 (2006).
Alber et al., "Study of an Alternate Glyoxylate Cycle for Acetate Assimilation by Rhodobacter Sphaeroides," Mol. Microbiol., 61(2):297-309 (2006).
Alper et al., "Tuning Genetic Control Through Promoter Engineering," Proc. Natl. Acad. Sci. USA, 102(36):12678-12683 (2005).
An et al., "A Gene Cluster Encoding malonyl-CoA Decarboxylase (MatA), malonyl-CoA Synthetase (MatB) and a Putative Dicarboxylate Carrier Protein (MatC) in Rhizobium Trifolii—Cloning, Sequencing, and Expression of the Enzymes in Escherichia coli," Eur. J. Biochem., 257(2):395-402 (1998).
Andreesen et al., "Formate Dehydrogenase of Clostridium Thermoaceticum: Incorporation of selenium-75, and the Effects of Selenite, Molybdate, and Tungstate on the Enzyme," J. Bacteriol., 116(2):867-873 (1973).
Angov, "Codon Usage: Nature's Roadmap to Expression and Folding of Proteins," Biotechnol. J., 6(6):650-659 (2011).
Anthony, "How Half a Century of Research Was Required to Understand Bacterial Growth on C1 and C2 Compounds; The Story of the Serine Cycle and the ethylmalonyl-CoA Pathway," Science Prog., 94:109-137 (2011).
Aoshima et al., "A Novel Enzyme, citryl-CoA Lyase, Catalysing the Second Step of the Citrate Cleavage Reaction in Hydrogenobacter Thermophilus TK-6," Mol. Microbiol., 52(3):763-770 (2004).
Aoshima, "Novel Enzyme Reactions Related to the Tricarboxylic Acid Cycle: phylogenetic/functional Implications and Biotechnological Applications," Appl. Microbiol. Biotechnol., 75(2):249-255 (2007).
Aragon et al., "A Survey of Enzymes Which Generate or Use Acetoacetyl Thioesters in Rat Liver," J. Biol. Chem., 258(8):4725-4733 (1983).
Araujo et al., "Before It Gtes Started: Regulating Translation at the 5' UTR," Comp. Funct. Genomics, Article ID 475731, 8 pages (2012).
Arent et al., "The Multifunctional Protein in Peroxisomal Beta-Oxidation: Structure and Substrate Specificity of the Arabidopsis thaliana Protein MFP2," J. Biol. Chem., 285(31):24066-24077 (2010).
Arfman et al., "Purification and Characterization of an Activator Protein for Methanol Dehydrogenase From Thermotolerant Bacillus SPP," J. Biol. Chem., 266(6):3955-3960 (1991).
Arikawa et al., "Soluble Fumarate Reductase Isoenzymes From Saccharomyces cerevisiae are Required for Anaerobic Growth," Microbiol. Lett., 165(1):111-116 (1998).
Arps et al., "Genetics of Serine Pathway Enzymes in Methylobacterium Extorquens AMI: Phosphoenolpyruvate Carboxylase and Malyl Coenzyme A Lyase," J. Bacteriol., 175(12):3776-3783 (1993).
Arraiano et al., "The Critical Role of RNA Processing and Degradation in the Control of Gene Expression," FEMS Microbiol. Rev., 34(5):883-932 (2010).
Atsumi et al., "Metabolic Engineering of Escherichia coli for 1-butanol Production," Metab. Eng., 10(6):305-311 (2008).
Atteia et al., "Pyruvate Formate-Lyase and a Novel Route of Eukaryotic ATP Synthesis in Chlamydomonas Mitochondria," J. Biol. Chem., 281(15):9909-9918 (2006).
Autio et al., "The 3-hydroxyacyl-ACP Dehydratase of Mitochondrial Fatty Acid Synthesis in Trypanosoma Brucei," FEBS Lett., 582(5):729-733 (2008).
Azcarate-Peril et al., "Transcriptional and Functional Analysis of Oxalyl-Coenzyme A (CoA) Decarboxylase and formyl-CoA Transferase Genes From Lactobacillus Acidophilus," Appl. Environ. Microbiol., 72(3):1891-1899 (2006).
Baetz et al., "Purification and Characterization of Formyl-Coenzyme A Transferase From Oxalobacter Formigenes," J. Bacteriol., 172(7):3537-3540 (1990).
Bakker et al., "Stoichiometry and Compartmentation of NADH Metabolism in Saccharomyces cerevisiae," FEMS Microbiol. Rev., 24:15-37 (2001).
Barker et al., "Butyryl-CoA:acetoacetate CoA-transferase From a Lysine-Fermenting Clostridium," J. Biol. Chem., 253(4):1219-1225 (1978).

(56) References Cited

OTHER PUBLICATIONS

Barker et al., "Pathway of Lysine Degradation in Fusobacterium Nucleatum," *J. Bacteriol.*, 152(1):201-207 (1982).
Barrowman et al., "Immunological comparison of microbial TPP-dependent non-oxidative α-keto acid decarboxylases." *FEMS Microbiol. Lett.*, 34:57-60 (1986).
Baudin et al., "A Simple and Efficient Method for Direct Gene Deletion in *Saccharomyces cerevisiae*," *Nucleic Acids Res.*, 21(14):3329-3330 (1993).
Bekal et al., "Purification of Leuconostoc Mesenteroides Citrate Lyase and Cloning and Characterization of the citCDEFG Gene Cluster," *J. Bacteriol.*, 180(3):647-654 (1998).
Benning et al., "New Reactions in the Crotonase Superfamily: Structure of Methylmalonyl CoA Decarboxylase From *Escherichia coli*," *Biochemistry*, 39(16):4630-4639 (2000).
Beopoulos et al., "Control of Lipid Accumulation in the Yeast Yarrowia Lipolytica," *Appl. Environ. Microbiol.*, 74:7779-7789 (2008).
Berg et al., "A 3-hydroxypropionate/4-hydroxybutyrate Autotrophic Carbon Dioxide Assimilation Pathway in Archaea," *Science*, 318:1782-1786 (2007).
Bergler et al., "The Enoyl-[Acyl-Carrier-Protein] Reductase (FabI) of *Escherichia coli*, Which Catalyzes a Key Regulatory Step in Fatty Acid Biosynthesis, Accepts NADH and NADPH as Cofactors and is Inhibited by palmitoyl-CoA," *Eur. J. Biochem.*, 242(3):689-694 (1996).
Bergquist et al., "Degenerate Oligonucleotide Gene Shuffling (DOGS) and Random Drift Mutagenesis (RNDM): Two Complementary Techniques for Enzyme Evolution," *Biomol. Eng.*, 22:63-72 (2005).
Bergquist et al., "Degenerate Oligonucleotide Gene Shuffling," *Methods Mol. Biol.*, 352:191-204 (2007).
Bernhard et al., "Functional and Structural Role of the Cytochrome B Subunit of the Membrane-Bound Hydrogenase Complex of Alcaligenes Eutrophus H16," *Eur. J. Biochem.*, 248(1):179-186 (1997).
Bessoule et al., "Fatty Acid Synthesis in Mitochondria From *Saccharomyces cerevisiae*," *FEBS Lett.*, 214(1):158-162 (1987).
Bianchi et al., "*Escherichia coli* Ferredoxin NADP+ Reductase: Activation of *E. coli* Anaerobic Ribonucleotide Reduction, Cloning of the Gene (Fpr), and Overexpression of the Protein," *J. Bacteriol.*, 175(6):1590-1595 (1993).
Binstock et al., "Fatty Acid Oxidation Complex From *Escherichia coli*," *Methods Enzymol.*, 71 Pt C:403-411 (1981).
Blaschkowski et al., "Routes of Flavodoxin and Ferredoxin Reduction in *Escherichia coli*. CoA-acylating Pyruvate: Flavodoxin and NADPH: Flavodoxin Oxidoreductases Participating in the Activation of Pyruvate Formate-Lyase," *Eur. J. Biochem.*, 12(3)3:563-569 (1982).
Bleykasten-Brosshans et al., "Transposable Elements in Yeasts," *C. R. Biol.*, 33(8-9):679-686 (2011).
Blodgett et al., "Molecular Cloning, Sequence Analysis, and Heterologous Expression of the Phosphinothricin Tripeptide Biosynthetic Gene Cluster from *Streptomyces viridochromogenes* DSM 40736," *Antimicrob. Agents Chemotherapy*, 49(1):230-240 (2005).
Bobik et al., "HPLC Assay for methylmalonyl-CoA Epimerase," *Anal. Bioanal. Chem.*, 375(3):344-349 (2003).
Bobik et al., "Identification of the Human methylmalonyl-CoA Racemase Gene Based on the Analysis of Prokaryotic Gene Arrangements. Implications for Decoding the Human Genome," *J. Biol. Chem.*, 276(40):37194-37198 (2001).
Bocanegra et al., "Creation of an NADP-dependent Pyruvate Dehydrogenase Multienzyme Complex by Protein Engineering," *Biochemistry*, 32(11):2737-2740 (1993).
Bock et al., "Purification and Characterization of Two Extremely Thermostable Enzymes, Phosphate Acetyltransferase and Acetate Kinase, From the Hyperthermophilic Eubacterium Thermotoga Maritima," *J. Bacteriol.*, 181(6):1861-1867 (1999).
Bogorad et al., "Synthetic Non-Oxidative Glycolysis Enables Complete Carbon Conservation," *Nature*, 502(7473):693-697 (2013).
Boles et al., "Characterization of a Glucose-Repressed Pyruvate Kinase (Pyk2p) in *Saccharomyces cerevisiae* That is Catalytically Insensitive to fructose-1,6-bisphosphate," *J. Bacteriol.*, 179(9):2987-2993 (1997).
Bonner et al., "Purification and Properties of Fatty Acyl Thioesterase I From *Escherichia coli*," *J. Biol. Chem.*, 247(10):3123-3133 (1972).
Bose et al., "Genetic Analysis of the Methanol- and Methylamine-Specific Methyltransferase 2 Genes of Methanosarcina Acetivorans C2A," *J. Bacteriol.*, 190(11):4017-4026 (2008).
Bott et al., "Klebsiella Pneumoniae Genes for Citrate Lyase and Citrate Lyase Ligase: Localization, Sequencing, and Expression," *Mol. Microbiol.*, 14(2):347-356 (1994).
Bott et al., "Methylmalonyl-CoA Decarboxylase From Propionigenium Modestum—Cloning and Sequencing of the Structural Genes and Purification of the Enzyme Complex," *Eur. J. Biochem.*, 250(2):590-599 (1997).
Bott, "Anaerobic Citrate Metabolism and Its Regulation in Enterobacteria," *Arch. Microbiol.*, 167(2-3):78-88 (1997).
Boubekeur et al., "Participation of Acetaldehyde Dehydrogenases in Ethanol and Pyruvate Metabolism of the Yeast *Saccharomyces cerevisiae*," *Eur. J. Biochem.*, 268(19):5057-5065 (2001).
Bower et al., "Cloning, Sequencing, and Characterization of the Bacillus Subtilis Biotin Biosynthetic Operon," *J. Bacteriol.*, 178(14):4122-4130 (1996).
Boynton et al., "Cloning, Sequencing, and Expression of Clustered Genes Encoding Beta-Hydroxybutyryl-Coenzyme A (CoA) Dehydrogenase, Crotonase, and butyryl-CoA Dehydrogenase From Clostridium Acetobutylicum ATCC 824," *J. Bacteriol.*, 178(11):3015-3024 (1996).
Bozzi et al., "Structural and Biochemical Studies of Alcohol Dehydrogenase Isozymes From Kluyveromyces Lactis," *Biochim. Biophys. Acta*, 1339(1):133-142 (1997).
Brachmann et al., "Designer Deletion Strains Derived From *Saccharomyces cerevisiae* S288C: A Useful Set of Strains and Plasmids for PCR-mediated Gene Disruption and Other Applications," *Yeast*, 14(2):115-132 (1998).
Bradford et al., "A Rapid and Sensitive Method for the Quantitation of Microgram Quantities of Protein Utilizing the Principle of Protein-Dye Binding," *Anal. Biochem.*, 72:248-254 (1976).
Brasen et al., "Unusual ADP-forming Acetyl-Coenzyme A Synthetases From the Mesophilic Halophilic Euryarchaeon Haloarcula Marismortui and From the Hyperthermophilic Crenarchaeon Pyrobaculum Aerophilum," *Arch. Microbiol.*, 182:277-287 (2004).
Bricker et al., "A Mitochondrial Pyruvate Carrier Required for Pyruvate Uptake in Yeast, Drosophila, and Humans," *Science*, 337(6090):96-100 (2012).
Brizio et al., "Over-expression in *Escherichia coli*, Functional Characterization and Refolding of Rat Dimethylglycine Dehydrogenase," *Protein Expr. Purif.*, (37)2:434-442 (2004).
Brown et al., "The Enzymic Interconversion of Acetate and Acetyl-Coenzyme A in *Escherichia coli*," *J. Gen. Microbiol.*, 102(2):327-336 (1977).
Brugger et al., "Characteristics of Fungal Phytases From Aspergillus Fumigatus and Sartorya Fumigata," *Appl. Microbiol. Biotech.*, 63:383-389 (2004).
Buck et al., "Cloning and Expression of the succinyl-CoA Synthetase Genes of *Escherichia coli* K12," *J. Gen. Microbiol.*, 132(6):1753-1762 (1986).
Buck et al., "Primary Structure of the succinyl-CoA Synthetase of *Escherichia coli*," *Biochemistry*, 24:6245-6252 (1985).
Burgdorf et al., "The Soluble NAD+-Reducing [NiFe]-hydrogenase From Ralstonia Eutropha H16 Consists of Six Subunits and can be Specifically Activated by NADPH," *J. Bact.*, 187(9):3122-3132 (2005).
Burke et al., "The Isolation, Characterization, and Sequence of the Pyruvate Kinase Gene of *Saccharomyces cerevisiae*," *J. Biol. Chem.*, 258(4):2193-2201 (1983).
Buu et al., "Functional Characterization and Localization of acetyl-CoA Hydrolase, Ach1p, in *Saccharomyces cerevisiae*," *J. Biol. Chem.*, 278(19):17203-17209 (2003).
Cabre et al., "Purification and properties of bovine liver aldehyde oxidase," *Biochem. Soc. Trans.*, 15:882-883 (1987).

(56) References Cited

OTHER PUBLICATIONS

Campbell et al., "The Enigmatic *Escherichia coli* fadE Gene is yafH," *J. Bacteriol.*, 184(13):3759-3764 (2002).
Campbell et al., "A New *Escherichia coli* Metabolic Competency: Growth on Fatty Acids by a Novel Anaerobic Beta-Oxidation Pathway," *Mol. Microbiol.*, 47(3):793-805 (2003).
Carter et al., "Ferrous Ion-Dependent L-serine Dehydratase From *Clostridium Acidiurici*," *J. Bacteriol.*, 109(2):757-763 (1972).
Cary et al., "Cloning and Expression of Clostridium Acetobutylicum ATCC 824 Acetoacetyl-Coenzyme A:acetate/butyrate:coenzyme A-transferase in *Escherichia coli,*" *Appl. Environ. Microbiol.*, 56(6):1576-1583 (1990).
Castel et al., "RNA Interference in the Nucleus: Roles for Small RNAs in Transcription, Epigenetics and Beyond" *Nat. Rev. Genet.*, 14(2):100-112 (2013).
Castillo et al., "A Mutant D-Fructose-6-Phosphate Aldolase (Ala129Ser) with Improved Affinity towards Dihydroxyacetone for the Synthesis of Polyhydroxylated Compounds," *Adv. Synth. Catal.*, 352(6):1039-1046 (2010).
Chandra et al., "Pyruvate Decarboxylase: A Key Enzyme for the Oxidative Metabolism of Lactic Acid by Acetobacter Pasteurianus," *Arch. Microbiol.*, 176(6):443-451 (2001).
Chao et al., "The Effects of Wall Populations on Coexistence of Bacteria in the Liquid Phase of Chemostat Cultures," *J. Gen. Microbiol.*, 131:1229-1236 (1985).
Chen et al., "Cloning and Characterization of the WAX2 Gene of *Arabidopsis* Involved in Cuticle Membrane and Wax Production," *Plant Cell*, 15(5):1170-1185 (2003).
Chen et al., "Phosphoenolpyruvate Carboxykinase Assayed at Physiological Concentrations of Metal Ions Has a High Affinity for CO2," *Plant Physiol.*, 128(1):160-164 (2002).
Cheng et al., "Mammalian Wax Biosynthesis. I. Identification of Two Fatty acyl-Coenzyme A Reductases With Different Substrate Specificities and Tissue Distributions," *J. Biol. Chem.*, 279(36):37789-37797 (2004).
Chinen et al., "Innovative metabolic pathway design for efficient 1-glutamate production by suppressing CO2 emission," *J. Biosci. Bioeng.*, 103(3):262-269 (2007).
Chistoserdova et al., "Genetics of the Serine Cycle in Methylobacterium Extorquens AM1: Cloning, Sequence, Mutation, and Physiological Effect of glyA, the Gene for Serine Hydroxymethyltransferase," *J. Bacteriol.*, 176:6759-6762 (1994).
Choi et al., "Beta-Ketoacyl-Acyl Carrier Protein Synthase III (FabH) is a Determining Factor in Branched-Chain Fatty Acid Biosynthesis," *J. Bacteriol.*, 182:365-370 (2000).
Cicchillo et al., "*Escherichia coli* L-serine Deaminase Requires a [4Fe—4S] Cluster in Catalysis," *J. Biol. Chem.*, 279(31):32418-32425 (2004).
Circello et al., "Molecular Cloning and Heterologous Expression of the Dehydrophos Biosynthetic Gene Cluster," *Chem. Biol.*, 179(4):402-411 (2010).
Clark et al., "Purification and Properties of 5,10-methylenetetrahydrofolate Reductase, an Iron-Sulfur Flavoprotein From Clostridium Formicoaceticum," *J. Biol. Chem.*, 259(17):10845-10849 (1984).
Clark, "Molybdenum Cofactor Negative Mutants of *Escherichia coli* Use Citrate Anaerobically," *FEMS Microbiol. Lett.*, 55(3):245-249 (1990).
Coco et al., "DNA Shuffling Method for Generating Highly Recombined Genes and Evolved Enzymes," *Nat. Biotechnol.*, 19(4):354-359 (2001).
Colasante et al., "Mitochondrial Carrier Family Inventory of Trypanosoma Brucei Brucei: Identification, Expression and Subcellular Localisation," *Mol. Biochem. Parasit.*, 167:104-117 (2009).
Colonna et al., "Synthesis and radiocarbon evidence of terephthalate polyesters completely prepared from renewable resources," *Green Chemistry*, 13:2543-2548 (2011).
Conrad et al., "D- and L-isoleucine Metabolism and Regulation of Their Pathways in Pseudomonas Putida," *J. Bacteriol.*, 118(1):103-111 (1974).

Coppi, "The Hydrogenases of Geobacter Sulfurreducens: A Comparative Genomic Perspective," *Microbiology*, 151:1239-1254 (2005).
Cordente et al., "Mutagenesis of Specific Amino Acids Converts Carnitine Acetyltransferase into Carnitine Palmitoyltransferase," *Biochem.*, 45:6133-6141 (2006).
Corthesy-Theulaz et al., "Cloning and Characterization of Helicobacter Pylori Succinyl CoA:acetoacetate CoA-transferase, a Novel Prokaryotic Member of the CoA-transferase Family," *J. Biol. Chem.*, 272:25659-25667 (1997).
Cotelesage et al., "How Does an Enzyme Recognize CO2?," *Int. J. Biochem. Cell Biol.*, 39(6):1204-1210 (2007).
Cracknell et al., "A Kinetic and Thermodynamic Understanding of O2 Tolerance in [NiFe]-hydrogenases," *Proc. Nat. Acad. Sci. USA*, 106(49):20681-20686 (2009).
Cronan, "Avant Garde Fatty Acid Synthesis by Trypanosomes," *Cell*, 126(4):641-643 (2006).
Cruz et al., "Gene-specific Involvement of Beta-Oxidation in Wound-Activated Responses in *Arabidopsis,*" *Plant Physiol.*, 135(1):85-94 (2004).
Currie et al., "Authentication and dating of biomass compnents of industrial materials; links to sustainable technology," *Nucl. Instr. Meth. Phys. Res. B*, 172:281-287 (2000).
Daigaku et al., "Loss of Heterozygosity in Yeast Can Occur by Ultraviolet Irradiation During the S Phase of the Cell Cycle," *Mut. Res.*, 600(1-2):177-183 (2006).
D'Ari et al., "Purification, Characterization, Cloning, and Amino Acid Sequence of the Bifunctional Enzyme 5,10-methylenetetrahydrofolate dehydrogenase/5,10-methenyltetrahydrofolate Cyclohydrolase From *Escherichia coli,*" *J. Biol. Chem.*, 266:23953-23958 (1991).
Das et al., "Characterization of a Corrinoid Protein Involved in the C1 Metabolism of Strict Anaerobic Bacterium Moorella Thermoacetica," *Proteins*, 67(1):167-176 (2007).
Datsenko et al., "One-step Inactivation of Chromosomal Genes in *Escherichia coli* K-12 Using PCR Products," *Proc. Natl. Acad. Sci. USA*, 97(12):6640-6645 (2000).
Davie et al., "Expression and Assembly of a Functional E1 Component (Alpha 2 Beta 2) of Mammalian Branched-Chain Alpha-Ketoacid Dehydrogenase Complex in *Escherichia coli,*" *J. Biol. Chem.*, 267(23):16601-16606 (1992).
Davis et al., "Overproduction of acetyl-CoA Carboxylase Activity Increases the Rate of Fatty Acid Biosynthesis in *Escherichia coli,*" *J. Biol. Chem.*, 275(37):28593-28598 (2000).
De Bok et al., "Two W-containing Formate Dehydrogenases (CO2-reductases) Involved in Syntrophic Propionate Oxidation by Syntrophobacter Fumaroxidans," *Eur. J. Biochem.*, 270(11):2476-2485 (2003).
De Crecy et al., "Development of a Novel Continuous Culture Device for Experimental Evolution of Bacterial Populations," *Appl. Microbiol. Biotechnol.*, 77(2):489-496 (2007).
De Graef et al., "The Steady-State Internal Redox State (NADH/NAD) Reflects the External Redox State and is Correlated With Catabolic Adaptation in *Escherichia coli,*" *J. Bacteriol.*, 181(8):2351-2357 (1999).
De Smidt et al., "The Alcohol Dehydrogenases of *Saccharomyces cerevisiae*: A Comprehensive Review," *FEMS Yeast Res.*, 8:967-978 (2008).
De Vries et al., "Functional Characterization of Mitochondrial Carnitine Palmitoyltransferases I and II Expressed in the Yeast Pichia Pastoris," *Biochem.* 36(17):5285-5292 (1997).
Deana et al., "Substrate Specificity of a dicarboxyl-CoA: Dicarboxylic Acid Coenzyme A Transferase From Rat Liver Mitochondria," *Biochem. Int.*, 26(4):767-773 (1992).
Dehesh et al., "Two Novel Thioesterases Are Key Determinants of the Bimodal Distribution of Acyl Chain Length of *Cuphea palustris* Seed Oil," *Plant Physiol.*, 110(1):203-210 (1996).
Dekishima et al., "Extending Carbon Chain Length of 1-butanol Pathway for 1-hexanol Synthesis From Glucose by Engineered *Escherichia coli,*" *J. Am. Chem. Soc.*, 133(30):11399-11401 (2011).
Dellomonaco et al., "Engineered Reversal of the β-oxidation Cycle for the Synthesis of Fuels and Chemicals," *Nature*, 476:355-359 (2011).

(56) References Cited

OTHER PUBLICATIONS

Denic et al., "A Molecular Caliper Mechanism for Determining Very Long-Chain Fatty Acid Length," *Cell*, 130:663-677 (2008).
Devos et al., "Practical Limits of Function Prediction," *Proteins: Structure, Function, and Genetics*, 41:98-107 (2000).
Di Gennaro et al., "Styrene Lower Catabolic Pathway in Pseudomonas Fluorescens ST: Identification and Characterization of Genes for Phenylacetic Acid Degradation," *Arch. Microbiol.*, 188(2):117-125 (2007).
Diaz et al., "Characterization of the Hca Cluster Encoding the Dioxygenolytic Pathway for Initial Catabolism of 3-phenylpropionic Acid in *Escherichia coli* K-12," *J. Bacteriol.*, 180(11):2915-2923 (1998).
Dickenson et al., "An Investigation of the Metabolism of Isoleucine to Active Amyl Alcohol in *Saccharomyces cerevisiae*," *J. Biol. Chem.*, 275(15):10937-10942 (2000).
Dietrich et al., "High-throughput Metabolic Engineering: Advances in Small-Molecule Screening and Selection," *Annu. Rev. Biochem.*, 79:563-590 (2010).
Doan et al., "Functional expression of five *Arabidopsis* fatty acyl-CoA reductase genes in *Escherichia coli*," *J. Plant Physiol.*, 166(8): 787-796 (2006).
Dobbek et al., "Crystal Structure of a Carbon Monoxide Dehydrogenase Reveals a [Ni—4Fe—5S] Cluster," *Science*, 293(5533):1281-1285 (2001).
Donovan et al., "Review: Optimizing Inducer and Culture Conditions for Expression of Foreign Proteins Under the Control of the Lac Promoter," *J. Ind. Microbiol.*, 16(3):145-154 (1996).
Doten et al., "Cloning and Genetic Organization of the Pca Gene Cluster From Acinetobacter Calcoaceticus," *J. Bacteriol.*, 169(7):3168-3174 (1987).
Drake et al., "Physiology of the Thermophilic Acetogen Moorella Thermoacetica," *Res. Microbiol.*, 155(10):869-883 (2004).
Drake, "Demonstration of Hydrogenase in Extracts of the Homoacetate-Fermenting Bacterium Clostridium Thermoaceticum," *J. Bacteriol.*, 150(2):702-709 (1982).
Drewke et al., "Ethanol Formation in adh0 Mutants Reveals the Existence of a Novel Acetaldehyde-Reducing Activity in *Saccharomyces cerevisiae*," *J. Bacteriol.*, 172:3909-3917 (1990).
Du et al., Lactococcus Lactis fabH, Encoding Beta-Ketoacyl-Acyl Carrier Protein Synthase, can be Functionally Replaced by the Plasmodium Falciparum Congener, *Appl. Environ. Microbiol.*, 76:3959-3966 (2010).
Duncan et al., "Acetate Utilization and Butyryl Coenzyme A (CoA):acetate-CoA Transferase in Butyrate-Producing Bacteria From the Human Large Intestine," *Appl. Environ. Microbiol.*, 68(10):5186-5190 (2002).
Duran et al., "Characterization of cDNA Clones for the 2-methyl Branched-Chain enoyl-CoA Reductase. An Enzyme Involved in Branched-Chain Fatty Acid Synthesis in Anaerobic Mitochondria of the Parasitic Nematode Ascaris Suum," *J. Biol. Chem.*, 268(30):22391-22396 (1993).
Durre et al., "Solventogenic Enzymes of Clostridium Acetobutylicum: Catalytic Properties, Genetic Organization, and Transcriptional Regulation," *FEMS Microbiol. Rev.*, 17(3):251-262 (1995).
Dykhuizen, "Chemostats Used for Studying Natural Selection and Adaptive Evolution," *Methods Enzymol.*, 613-631 (1993).
Ehsani et al., "Reversal of Coenzyme Specificity of 2,3-butanediol Dehydrogenase From *Saccharomyces cerevisae* and in Vivo Functional Analysis," *Biotechnol. Bioeng.*, 104(2):381-389 (2009).
Eikmanns et al., "The Phosphoenolpyruvate Carboxylase Gene of Corynebacterium Glutamicum: Molecular Cloning, Nucleotide Sequence, and Expression," *Mol. Gen. Genet.*, 218(2):330-339 (1989).
Eisen et al., "The Complete Genome Sequence of Chlorobium Tepidum TLS, a Photosynthetic, Anaerobic, Green-Sulfur Bacterium," *Proc. Natl. Acad. Sci. USA*, 99(14):9509-9514 (2002).
Elgersma et al., "Peroxisomal and Mitochondrial Carnitine Acetyltransferases of *Saccharomyces cerevisiae* are Encoded by a Single Gene," *EMBO J.*, 14:3472-3479 (1995).

Enomoto et al., "Cloning and Sequencing of the Gene Encoding the Soluble Fumarate Reductase From *Saccharomyces cerevisiae*," *DNA Res.*, 3(4):263-267 (1996).
Fan et al., "Disruption of a Gene Encoding Glycerol 3-phosphatase From Candida Albicans Impairs Intracellular Glycerol Accumulation-Mediated Salt-Tolerance," *FEMS Microbiol. Lett.*, 245(1):107-116 (2005).
Farhi et al., "Harnessing Yeast Subcellular Compartments for the Production of Plant Terpenoids," *Met. Eng.*, 13(5):474-481 (2011).
Fernandes et al., "Cloning, Sequencing and Characterization of a Fatty Acid Synthase-Encoding Gene From Mycobacterium Tuberculosis Var. Bovis BCG," *Gene* 170(1):95-99 (1996).
Fernandez-Valverde et al., "Purification of Pseudomonas Putida Acyl Coenzyme A Ligase Active With a Range of Aliphatic and Aromatic Substrates," *Appl. Environ. Microbiol.*, 59:1149-1154 (1993).
Ferrandez et al., "Genetic Characterization and Expression in Heterologous Hosts of the 3-(3-hydroxyphenyl)propionate Catabolic Pathway of *Escherichia coli* K-12," *J. Bacteriol.*, 179(8):2573-2581 (1997).
Fong et al., "Description and Interpretation of Adaptive Evolution of *Escherichia coli* K-12 MG1655 by Using a Genome-Scale in Silico Metabolic Model," *J. Bacteriol.*, 185(21):6400-6408 (2003).
Fong et al., "In Silico Design and Adaptive Evolution of *Escherichia coli* for Production of Lactic Acid," *Biotechnol. Bioeng.*, 91:643-648 (2005).
Fong et al., "Metabolic Gene-Deletion Strains of *Escherichia coli* Evolve to Computationally Predicted Growth Phenotypes," *Nat. Genet.*, 36(10):1056-1058 (2004).
Fontaine et al., "Molecular Characterization and Transcriptional Analysis of adhE2, the Gene Encoding the NADH-dependent aldehyde/alcohol Dehydrogenase Responsible for Butanol Production in Alcohologenic Cultures of Clostridium Acetobutylicum ATCC 824," *J. Bacteriol.*, 184(3):821-830 (2002).
Ford et al., "Molecular Properties of the lys1+ Gene and the Regulation of Alpha-Aminoadipate Reductase in Schizosaccharomyces pombe," *Curr. Genet.*, 28(2):131-137 (1995).
Fox et al., "Characterization of the Region Encoding the CO-induced Hydrogenase of Rhodospirillum Rubrum," *J. Bacteriol.*, 178(21):6200-6208 (1996).
Fox et al., "Isolation and Characterization of Homogeneous Acetate Kinase From *Salmonella typhimurium* and *Escherichia coli*," *J. Biol. Chem.*, 261(29):13487-13497 (1986).
Fuchs, "Alternative Pathways of Carbon Dioxide Fixation: Insights Into the Early Evolution of Life?," *Annu. Rev. Microbiol.*, 65:631-658 (2011).
Fujii et al., "Activation of Methionine Synthase: Further Characterization of Flavoprotein System," *Arch. Biochem. Biophys.*, 178(2):662-670 (1977).
Fujii et al., "Error-prone Rolling Circle Amplification: The Simplest Random Mutagenesis Protocol," *Nat. Protoc.*, 1(5): 2493-2497 (2006).
Fujii et al., "One-step Random Mutagenesis by Error-Prone Rolling Circle Amplification," *Nucleic Acids Res.*, 32:e145 (2004).
Fujinaga et al., "Cloning and Expression in *Escherichia coli* of the Gene Encoding the [2Fe—2S] Ferredoxin From Clostridium Pasteurianum," *Biochem. Biophys. Res. Comm.*, 192(3):1115-1122 (1993).
Fukao et al., "Succinyl-CoA:3-ketoacid CoA Transferase (SCOT): Cloning of the Human SCOT Gene, Tertiary Structural Modeling of the Human SCOT Monomer, and Characterization of Three Pathogenic Mutations," *Genomics*, 68:144-151 (2000).
Fukui et al., "Engineering of Ralstonia Eutropha for Production of poly(3-hydroxybutyrate-co-3-hydroxyhexanoate) From Fructose and Solid-State Properties of the Copolymer," *Biomacromolecules* 3(3):618-624 (2002).
Fuller et al., "Proton Transfer in methylmalonyl-CoA Epimerase From Propionibacterium Shermanii. The Reaction of (2R)-methylmalonyl-CoA in Tritiated Water," *Biochem. J.*, 213(3):643-650 (1983).
Furdui et al., "The Role of Pyruvate Ferredoxin Oxidoreductase in Pyruvate Synthesis During Autotrophic Growth by the Wood-Ljungdahl Pathway," *J. Biol. Chem.*, 275(37):28494-28499 (2000).

(56) References Cited

OTHER PUBLICATIONS

Furumoto et al., "Isolation and Characterization of cDNAs for Differentially Accumulated Transcripts Between Mesophyll Cells and Bundle Sheath Strands of Maize Leaves," *Plant Cell Physiol.*, 41(11):1200-1209 (2000).
Galagan et al., "The Genome of *M. acetivorans* Reveals Extensive Metabolic and Physiological Diversity," *Genome Res.*, 12(4):532-542 (2002).
Garattini et al., "Mammalian Aldehyde Oxidases: Genetics, Evolution and Biochemistry," *Cell Mol. Life Sci.*, 65:1019-1048 (2008).
Germer et al., "Overexpression, Isolation, and Spectroscopic Characterization of the Bidirectional [NiFe] Hydrogenase From *Synechocystis* Sp. PCC 6803," *J. Biol. Chem.*, 284(52):36462-36472 (2009).
Giaever et al., "Functional profiling of the *Saccharomyces cerevisiae* genome," *Nature* 418:387-391 (2002).
Gibbs et al., "Degenerate Oligonucleotide Gene Shuffling (DOGS): A Method for Enhancing the Frequency of Recombination With Family Shuffling," *Gene*, 271(1):13-20 (2001).
Gibson et al., "Physical and Genetic Interactions of Cytosolic Malate Dehydrogenase With Other Gluconeogenic Enzymes," *J. Biol. Chem.*, 278(28):25628-25636 (2003).
Gobel et al., "Degradation of Aromatics and Chloroaromatics by *Pseudomonas* Sp. Strain B13: Cloning, Characterization, and Analysis of Sequences Encoding 3-oxoadipate:succinyl-coenzyme A (CoA) Transferase and 3-oxoadipyl-CoA Thiolase," *J. Bacteriol.*, 184(1):216-223 (2002).
Goenrich et al., "A Glutathione-Dependent Formaldehyde-Activating Enzyme (Gfa) From Paracoccus Denitrificans Detected and Purified via Two-Dimensional Proton Exchange NMR Spectroscopy," *J. Biol. Chem.*, 277(5):3069-3072 (2002).
Goenrich et al., "Formaldehyde activating enzyme (Fae) and hexulose-6-phosphate synthase (Hps) in Methanosarcina barkeri: a possible function in ribose-5-phosphate biosynthesis," *Arch. Microbiol.*, 184(1):41-48 (2005).
Gonzalez et al., "Genetic Analysis of Carboxydothermus Hydrogenoformans Carbon Monoxide Dehydrogenase Genes cooF and cooS," *FEMS Microbiol. Lett.*, 191(2):243-247 (2000).
Green et al., "Catabolism of Alpha-Ketoglutarate by a sucA Mutant of Bradyrhizobium Japonicum: Evidence for an Alternative Tricarboxylic Acid Cycle," *J. Bacteriol.*, 182(10):2838-2844 (2000).
Grill et al., "Characterization of Fructose 6 Phosphate Phosphoketolases Purified From Bifidobacterium Species," *Curr. Microbiol.*, 31(1):49-54 (1995).
Gueldener et al., "A Second Set of loxP Marker Cassettes for Cre-mediated Multiple Gene Knockouts in Budding Yeast," *Nucleic Acids Res.*, 30(6):e23 (2002).
Gulick et al., "The 1.75 Å Crystal Structure of Acetyl-CoA Synthetase Bound to Adenosine-5'-propylphosphate and Coenzyme A†," *Biochemistry*, 42:2866-2873 (2003).
Guo et al., "Posttranslational Activation, Site-Directed Mutation and Phylogenetic Analyses of the Lysine Biosynthesis Enzymes Alpha-Aminoadipate Reductase Lys1p (AAR) and the Phosphopantetheinyl Transferase Lys7p (PPTase) From *Schizosaccharomyces pombe*," *Yeast*, 21(15):1279-1288 (2004).
Guo et al., "Preferential Hydrolysis of Aberrant Intermediates by the Type II Thioesterase in *Escherichia coli* Nonribosomal Enterobactin Synthesis: Substrate Specificities and Mutagenic Studies on the Active-Site Residues," *Biochemistry* 48(8):1712-1722 (2009).
Guo et al., "Site-directed Mutational Analysis of the Novel Catalytic Domains of Alpha-Aminoadipate Reductase (Lys2p) From Candida Albicans," *Mol. Genet. Genomics*, 269(2):271-279 (2003).
Gurvitz, "The Essential Mycobacterial Genes, fabG1 and fabG4, Encode 3-oxoacyl-thioester Reductases That are Functional in Yeast Mitochondrial Fatty Acid Synthase Type 2," *Mol. Genet. Genomics*, 282(4):407-416 (2009).
Gutierrez et al., "Structure-guided Redesign of D-fructose-6-phosphate Aldolase From *E. coli*: Remarkable Activity and Selectivity Towards Acceptor Substrates by Two-Point Mutation," *Chem. Commun. (Camb)*, 47(20):5762-5764 (2011).

Hagemeier et al., "Insight Into the Mechanism of Biological Methanol Activation Based on the Crystal Structure of the Methanol-Cobalamin Methyltransferase Complex," *Proc. Natl. Acad. Sci. U.S.A.*, 103(50):18917-18922 (2006).
Hager et al., "Flavoprotein-catalyzed Pyruvate Oxidation in Lactobacillus Delbrueckii," *Fed. Proc.*, 13(3):734-738 (1954).
Haller et al., "Discovering New Enzymes and Metabolic Pathways: Conversion of Succinate to Propionate by *Escherichia coli*," *Biochemistry*, 39(16):4622-4629 (2000).
Hanai et al., "Engineered Synthetic Pathway for Isopropanol Production in *Escherichia coli*," *Appl. Environ. Microbiol.*, 73:7814-7818 (2007).
Hansen et al., "De Novo Biosynthesis of Vanillin in Fission Yeast (*Schizosaccharomyces pombe*) and Baker's Yeast (*Saccharomyces cerevisiae*)," *Appl. Environ. Microbiol.*, 75(9):2765-2774 (2009).
Hansen et al., "The Effect of the lacY Gene on the Induction of IPTG Inducible Promoters, Studied in *Escherichia coli* and Pseudomonas Fluorescens," *Curr. Microbiol.*, 36(6):341-347 (1998).
Hanson et al., "Methanotrophic Bacteria," *Microbiol. Rev.*, 60:439-471 (1996).
Harms et al., "Methylcobalamin: Coenzyme M Methyltransferase Isoenzymes MtaA and MtbA From Methanosarcina Barkeri. Cloning, Sequencing and Differential Transcription of the Encoding Genes, and Functional Overexpression of the mtaA Gene in *Escherichia coli*," *Eur. J. Biochem.*, 235(3):653-659 (1996).
Harrison et al., "The pimFABCDE Operon From Rhodopseudomonas Palustris Mediates Dicarboxylic Acid Degradation and Participates in Anaerobic Benzoate Degradation," *Microbiology* 151:727-736 (2005).
Hartmanis, "Butyrate Kinase From Clostridium Acetobutylicum," *J. Biol. Chem.*, 262(2):617-621 (1987).
Harwood et al., "Identification of the pcaRKF Gene Cluster From Pseudomonas Putida: Involvement in Chemotaxis, Biodegradation, and Transport of 4-hydroxybenzoate," *J. Bacteriol.*, 176(21):6479-6488 (1994).
Hasegawa et al., "Transcriptional regulation of ketone body-utilizing enzyme, acetoacetyl-CoA synthetase, by C/EBPα during adipocyte differentiation," *Biochim. Biophys. Acta*, 1779:414-419 (2008).
Hasson et al., "The Crystal Structure of Benzoylformate Decarboxylase at 1.6 Å Resolution: Diversity of Catalytic Residues in Thiamin Diphosphate-Dependent Enzymes," *Biochemistry*, 37(28):9918-9930 (1998).
Hatrongjit et al., "A novel NADP+-dependent formate dehydrogenase from Burkholderia stabilis 15516: Screening, purification and characterization," *Enzyme Microbial Tech.*, 46:557-561 (2010).
Hayaishi et al., "Enzymatic Decarboxylation of Malonic Acid," *J. Biol. Chem.*, 215(1):125-136 (1955).
Hayaishi et al., "Enzymatic Studies on the Metabolism of Beta-Alanine," *J. Biol. Chem.*, 236:781-890 (1961).
Hayes et al., "Combining Computational and Experimental Screening for Rapid Optimization of Protein Properties," *Proc. Natl. Acad. Sci. USA*, 99(25):15926-15931 (2002).
Hayes, "Transposon-based Strategies for Microbial Functional Genomics and Proteomics," *Annu. Rev. Genet.*, 37:3-29 (2003).
Hayman et al., "Purification and Characterization of a Tartrate-Resistant Acid Phosphatase From Human Osteoclastomas," *Biochem. J.*, 261(2):601-609 (1989).
Haywood et al., "Characterization of two 3-ketothiolases possessing differing substrate specificities in the polyhydroxyalkanoate synthesizing organism Alcaligenes eutrophus," *FEMS Microbiol. Lett.*, 52:91-96 (1988).
He et al., "Molecular Cloning, Expression in *Escherichia coli*, and Characterization of a Novel L-3-hydroxyacyl Coenzyme A Dehydrogenase From Pig Liver," *Biochim. Biophys. Acta*, 1392(1):119-126 (1998).
Heath et al., "A Conserved Histidine is Essential for Glycerolipid Acyltransferase Catalysis," *J. Bacteriol.*, 180:1425-1430 (1998).
Heath et al., "A Triclosan-Resistant Bacterial Enzyme," *Nature* 406(6792):145-146 (2000).
Heath et al., "The Enoyl-[Acyl-Carrier-Protein] Reductases FabI and FabL From Bacillus Subtilis," *J. Biol. Chem.*, 275(51):40128-40133 (2000).

(56) References Cited

OTHER PUBLICATIONS

Heath, "Regulation of Fatty Acid Elongation and Initiation by Acyl-Acyl Carrier Protein in *Escherichia coli*," *J. Biol. Chem.*, 271(4):1833-1836 (1996).

Heggeset et al., "Genome Sequence of Thermotolerant Bacillus Methanolicus: Features and Regulation Related to Methylotrophy and Production of L-lysine and L-glutamate From Methanol," *Appl. Environ. Microbiol.*, 78(15):5170-5181 (2012).

Heil et al., "Glycine Binds the Transcriptional Accessory Protein GcvR to Disrupt a GcvA/GcvR Interaction and Allow GcvA-mediated Activation of the *Escherichia coli* gcvTHP Operon," *Microbiol.*, 148:2203-2214 (2002).

Hektor et al., "Identification of a Magnesium-Dependent NAD(P)(H)-binding Domain in the Nicotinoprotein Methanol Dehydrogenase From Bacillus Methanolicus," *J. Biol. Chem.*, 277(49):46966-46973 (2002).

Hemschemeier et al., "Biochemical and Physiological Characterization of the Pyruvate Formate-Lyase Pfl1 of Chlamydomonas Reinhardtii, a Typically Bacterial Enzyme in a Eukaryotic Alga," *Eukaryot. Cell*, 7:518-526 (2008).

Henning et al., "Identification of Novel Benzoylformate Decarboxylases by Growth Selection," *Appl .Environ. Microbiol.*, 72(12):7510-7517 (2006).

Herrmann et al., "Biogenesis of Cytochrome Oxidase-Sophisticated Assembly Lines in the Mitochondrial Inner Membrane," *Gene*, 354:43-52 (2005).

Herrmann et al., "Energy Conservation via Electron-Transferring Flavoprotein in Anaerobic Bacteria," *J. Bacteriol.*, 190(3):784-791 (2008).

Herzig et al., "Identification and Functional Expression of the Mitochondrial Pyruvate Carrier," *Science*, 337:93-96 (2012).

Hesslinger et al., "Novel Keto Acid Formate-Lyase and Propionate Kinase Enzymes are Components of an Anaerobic Pathway in *Escherichia coli* That Degrades L-threonine to Propionate," *Mol. Microbiol.*, 27:477-492 (1998).

Hibbert et al., "Directed Evolution of Biocatalytic Processes," *Biomol. Eng.*, 22:11-19 (2005).

Hidaka et al., "Cloning and Nucleotide Sequence of Fosfomycin Biosynthetic Genes of *Streptomyces wedmorensis*," *Mol. Gen. Genet.*, 249:274-280 (1995).

Hijarrubia et al., "Domain Structure Characterization of the Multifunctional Alpha-Aminoadipate Reductase From Penicillium Chrysogenum by Limited Proteolysis. Activation of Alpha-Aminoadipate Does Not Require the Peptidyl Carrier Protein Box or the Reduction Domain," *J. Biol. Chem.*, 278(10):8250-8256 (2003).

Hijikata et al., "Rat Peroxisomal 3-ketoacyl-CoA Thiolase Gene. Occurrence of Two Closely Related but Differentially Regulated Genes," *J. Biol. Chem.*, 265(8):4600-4606 (1990).

Hillmer et al., "Particulate Nature of Enzymes Involved in the Fermentation of Ethanol and Acetate by Clostridium Kluyveri," *FEBS Lett.*, 21(3):351-354 (1972).

Hillmer et al., "Solubilization and Partial Characterization of Particulate Dehydrogenases from Clostridium Kluyveri," *Biochim. Biophys. Acta*, 3334:12-23 (1974).

Hilpert et al., "Conversion of the Chemical Energy of methylmalonyl-CoA Decarboxylation Into a Na+ Gradient," *Nature*, 296(5857):584-585 (1982).

Hiltunen et al., "Peroxisomal Multifunctional Beta-Oxidation Protein of *Saccharomyces cerevisiae*. Molecular Analysis of the fox2 Gene and Gene Product," *J. Biol. Chem.*, 267(10):6646-6653 (1992).

Hiser et al., "ERG10 From *Saccharomyces cerevisiae* Encodes acetoacetyl-CoA Thiolase," *J. Biol. Chem.*, 269(50):31383-31389 (1994).

Hochstrasser, "Ubiquitin-dependent Protein Degradation," *Annual Rev. Genet.*, 30:405-439 (1996).

Hoffmann et al., "Stereochemistry of the methylmalonyl-CoA Decarboxylation Reaction," *FEBS. Lett.*, 220(1):121-125 (1987).

Hoffmeister et al., "Mitochondrial trans-2-enoyl-CoA Reductase of Wax Ester Fermentation From Euglena Gracilis Defines a New Family of Enzymes Involved in Lipid Synthesis," *J. Biol. Chem.*, 280:4329-4338 (2005).

Hofvander et al., "A Prokaryotic acyl-CoA Reductase Performing Reduction of Fatty acyl-CoA to Fatty Alcohol," *FEBS Lett.*, 585(22):3538-3543 (2011).

Hohmann et al., "Characterisation of PDC2, a Gene Necessary for High Level Expression of Pyruvate Decarboxylase Structural Genes in *Saccharomyces cerevisiae*," *Mol. Gen. Genet.*, 241:657-666 (1993).

Horie et al., "Existence of acetyl-CoA-dependent Chain Elongation System in Hepatic Peroxisomes of Rat: Effects of Clofibrate and di-(2-ethylhexyl)phthalate on the Activity," *Arch. Biochem. Biophys.*, 274(1):64-73 (1989).

Horiguchi et al., "Peroxisomal Catalase in the Methylotrophic Yeast Candida Boidinii: Transport Efficiency and Metabolic Significance ," *J. Bacteriol.*, 183:6372-6383 (2001).

Houseley et al., "The Many Pathways of RNA Degradation," *Cell*, 136(4):763-776 (2009).

Huang et al., "Identification and Characterization of a Second Butyrate Kinase From Clostridium Acetobutylicum ATCC 824," *J. Mol. Microbiol. Biotechnol.*, 2(1):33-38 (2000).

Huder et al., "Sequence of the Sodium Ion Pump methylmalonyl-CoA Decarboxylase From Veillonella Parvula," *J. Biol. Chem.*, 268(33):24564-24571 (1993).

Hugler et al., "Autotrophic CO2 Fixation via the Reductive Tricarboxylic Acid Cycle in Different Lineages Within the Phylum Aquificae: Evidence for Two Ways of Citrate Cleavage," *Environ. Microbiol.*, 9(1):81-92 (2007).

Hugler et al., "Malonyl-coenzyme A Reductase From Chloroflexus Aurantiacus, a Key Enzyme of the 3-hydroxypropionate Cycle for Autotrophic CO(2) Fixation," *J. Bacteriol.*, 184:2404-2410 (2002).

Huisman et al., "Enzyme Evolution for Chemical Process Applications," *Biocatalysis in the Pharmaceutical and Biotechnology Industries*, Patel ed., CRC Press, Boca Raton, FL, pp. 717-742 (2007).

Hunaiti et al., "Malonyl-CoA Decarboxylase From *Streptomyces erythreus*: Purification, Properties, and Possible Role in the Production of Erythromycin," *Arch. Biochem. Biophys.*, 229(2):426-439 (1984).

Hynes et al., "ATP-citrate Lyase is Required for Production of Cytosolic Acetyl Coenzyme A and Development in Aspergillus Nidulans," *Eukaryotic Cell*, 9(7):1039-1048 (2010).

Hynes et al., "Role of Carnitine Acetyltransferases in Acetyl Coenzyme A Metabolism in Aspergillus Nidulans," *Euk. Cell*, 10:547-555 (2011).

Ibarra et al., "*Escherichia coli* K-12 Undergoes Adaptive Evolution to Achieve in Silico Predicted Optimal Growth," *Nature*, 420(6912):186-189 (2002).

Ingram-Smith et al., "AMP-forming acetyl-CoA Synthetases in Archaea Show Unexpected Diversity in Substrate Utilization," *Archaea* 2:95-107 (2007).

Ingram-Smith et al., "Characterization of the Acetate Binding Pocket in the Methanosarcina Thermophila Acetate Kinase," *J. Bacteriol.*, 187(7):2386-2394 (2005).

Inoue et al., "Purification and Characterization of a Novel Alcohol Dehydrogenase From *Leifsonia* Sp. Strain S749: A Promising Biocatalyst for an Asymmetric Hydrogen Transfer Bioreduction," *Appl. Environ. Microbiol.*, 71(7):3633-3641 (2005).

Inui et al., "Fatty Acid Synthesis in Mitochondria of Euglena Gracilis," *Eur. J. Biochem.*, 142(1):121-126 (1984).

Iram et al., "The Beta-Oxidation Systems of *Escherichia coli* and *Salmonella enterica* are Not Functionally Equivalent," *J. Bacteriol.*, 188(2):599-608 (2006).

Ishige et al., "Wax Ester Production From N-Alkanes by *Acinetobacter* Sp. Strain M-1: Ultrastructure of Cellular Inclusions and Role of Acyl Coenzyme A Reductase," *Appl. Environ. Microbiol.*, 68:1192-1195 (2002).

Ismail et al., "Functional Genomics by NMR Spectroscopy. Phenylacetate Catabolism in *Escherichia coli*," *Eur. J. Biochem.*, 270(14):3047-3054 (2003).

(56) References Cited

OTHER PUBLICATIONS

Ito et al., "Cloning and High-Level Expression of the Glutathione-Independent Formaldehyde Dehydrogenase Gene From Pseudomonas Putida," *J. Bacteriol.*, 176(9):2483-2491 (1994).
Iwakura et al., "Studies on Regulatory Functions of Malic Enzymes. VI. Purification and Molecular Properties of NADP-linked Malic Enzyme From *Escherichia coli* W," *J. Biochem.*, 85(5):1355-1365 (1979).
Jacobi et al., "The Hyp Operon Gene Products are Required for the Maturation of Catalytically Active Hydrogenase Isoenzymes in *Escherichia coli,*" *Arch. Microbiol.*, 158(6):444-451 (1992).
Jakobsen et al., "Upregulated Transcription of Plasmid and Chromosomal Ribulose Monophosphate Pathway Genes is Critical for Methanol Assimilation Rate and Methanol Tolerance in the Methylotrophic Bacterium Bacillus methanolicus," *J. Bacteriol.*, 188(8):3063-3072 (2006).
Javidpour et al., "Biochemical and Structural Studies of NADH-dependent FabG Used to Increase the Bacterial Production of Fatty Acids Under Anaerobic Conditions," *Appl. Environ. Microbiol.*, 80(2):497-505 (2014).
Jenkins et al., "Genetic and Molecular Characterization of the Genes Involved in Short-Chain Fatty Acid Degradation in *Escherichia coli*: The Ato System," *J. Bacteriol.*, 169(1):42-52 (1987).
Jenni et al., "Structure of Fungal Fatty Acid Synthase and Implications for Iterative Substrate Shuttling," *Science*, 316(5822):254-261 (2007).
Jeong et al., "Cloning and Characterization of a Gene Encoding Phosphoketolase in a Lactobacillus Paraplantarum Isolated From Kimchi," *J. Microbiol. Biotechnol.*, 17(5):822-829 (2007).
Jerome et al., "Development of a Fed-Batch Process for the Production of a Dye-Linked Formaldehyde Dehydrogenase in Hyphomicrobium Zavarzinii ZV 580," *Appl. Microbiol. Biotechnol.*, 77(4):779-788 (2007).
Jo et al., "Cloning, Expression, and Characterization of an Aldehyde Dehydrogenase From *Escherichia coli* K-12 That Utilizes 3-Hydroxypropionaldehyde as a Substrate," *Appl. Microbiol. Biotechnol.*, 81(1):51-60 (2008).
Jogl et al., "Crystal Structure of Yeast Acetyl-Coenzyme A Synthetase in Complex With AMP," *Biochemistry*, 43:1425-1431 (2004).
Jojima et al., "Production of Isopropanol by Metabolically Engineered *Escherichia coli*," *Appl. Microbiol. Biotechnol.*, 77:1219-1224 (2008).
Jones et al., "Acetone-butanol Fermentation Revisited," *Microbiol. Rev.*, 50(4):484-524 (1986).
Kai et al., "Phosphoenolpyruvate Carboxylase: Three-Dimensional Structure and Molecular Mechanisms," *Arch. Biochem. Biophys.*, 414(2):170-179 (2003).
Kallen et al., "Methylene Reductase: Responsible for the in Vitro Formation of Formaldehyde From 5-methyltetrahydrofolic Acid," *J. Biol. Chem.*, 241(24):5851-5863 (1966).
Kanao et al., "Kinetic and Biochemical Analyses on the Reaction Mechanism of a Bacterial ATP-citrate Lyase," *Eur. J. Biochem.*, 269(14):3409-3416 (2002).
Kapatral et al., "Genome Sequence and Analysis of the Oral Bacterium Fusobacterium Nucleatum Strain ATCC 25586," *J. Bact.*, 184(7):2005-2018 (2002).
Karlen et al., "Absolute determination of the activity of two $C^{14}$ dating standards," *Arkiv Geofysik*, 4:465-471 (1968).
Kaschabek et al., "Degradation of Aromatics and Chloroaromatics by *Pseudomonas* Sp. Strain B13: Purification and Characterization of 3-oxoadipate:succinyl-coenzyme A (CoA) Transferase and 3-oxoadipyl-CoA Thiolase," *J. Bacteriol.*, 184(1):207-215 (2002).
Kastanoitis et al., "Htd2p/Yhr067p is a Yeast 3-hydroxyacyl-ACP Dehydratase Essential for Mitochondrial Function and Morphology," *Mol. Micro.*, 53(5):1407-1421 (2004).
Kather et al., "Another Unusual Type of Citric Acid Cycle Enzyme in Helicobacter Pylori: The Malate:quinone Oxidoreductase," *J. Bacteriol.*, 182(11):3204-3209 (2000).

Kato et al., "The Physiological Role of the Ribulose Monophosphate Pathway in Bacteria and Archaea," *BioSci. Biotechnol. Biochem.*, 70(1):10-21 (2006).
Kawasaki et al., "Transcriptional Gene Silencing by Short Interfering RNAs *Curr. Opin. Mol. Ther.*, 7(2):125-131 (2005).
Kazahaya et al., "Aerobic Dissimilation of Glucose by Heterolactic Bacteria," *J. Gen. Appl. Microbiol.*, 18:43-55 (1972).
Kedishvili et al., "Mammalian Methylmalonate-Semialdehyde Dehydrogenase," *Methods Enzymol.*, 324:207-218 (2000).
Kegg Enzyme EC 4.1.2.43, 2020. Retrieved from the internet: https://www.genome.jp/dbget-bin/www_bget?ec:4.1 .2.43.
Kellum et al., "Effects of Cultivation Gas Phase on Hydrogenase of the Acetogen Clostridium Thermoaceticum," *J. Bacteriol.*, 160(1):466-469 (1984).
Kern et al., "Engineering primary metabolic pathways of industrial micro-organisms," *J. Bacteriol.*, 129:6-29 (2007).
Kerscher et al., "A Single External Enzyme Confers Alternative NADH:ubiquinone Oxidoreductase Activity in Yarrowia Lipolytica," *J. Cell Sci.*, 112:2347-2354 (1999).
Kessler et al., "Pyruvate-formate-lyase-deactivase and acetyl-CoA Reductase Activities of *Escherichia coli* Reside on a Polymeric Protein Particle Encoded by adhE," *FEBS Lett.*, 281(1-2):59-63 (1991).
Khoury et al., "Computational Design of Candida Boidinii Xylose Reductase for Altered Cofactor Specificity," *Protein Sci.*, 18(10):2125-2138 (2009).
Kiema et al., "Mutagenic and Enzymological Studies of the Hydratase and Isomerase Activities of 2-enoyl-CoA hydratase-1," *Biochem.*, 38:2991-2999 (1999).
Kikuchi et al., "Glycine Cleavage System: Reaction Mechanism, Physiological Significance, and Hyperglycinemia," *Proc. Jpn. Acad. Ser.*, 84:246-263 (2008).
Killenberg-Jabs et al., "Active Oligomeric States of Pyruvate Decarboxylase and Their Functional Characterization," *Eur. J. Biochem.*, 268(6):1698-1704 (2001).
Kim et al., "Both Subunits of ATP-citrate Lyase From Chlorobium Tepidum Contribute to Catalytic Activity," *J. Bacteriol.*, 188(18):6544-6552 (2006).
Kim et al., "Construction of an *Escherichia coli* K-12 Mutant for Homoethanologenic Fermentation of Glucose or Xylose Without Foreign Genes," *Appl. Environ. Microbiol.*, 73(6):1766-1771 (2007).
Kim et al., "Dihydrolipoamide Dehydrogenase Mutation Alters the NADH Sensitivity of Pyruvate Dehydrogenase Complex of *Escherichia coli* K-12," *J. Bacteriol.*, 190(11):3851-3858 (2008).
Kim et al., Effect of Overexpression of Actinobacillus Succinogenes Phosphoenolpyruvate Carboxykinase on Succinate Production in *Escherichia coli,Appl. Environ. Microbiol.*, 70(2):1238-1241 (2004).
Kinoshita et al., "Purification of two alcohol dehydrogenases from Zymomonas mobilis and their properties," *Appl. Microbiol. Biotechnol.*, 22:249-254 (1985).
Kisselev et al., "Polypeptide Release Factors in Prokaryotes and Eukaryotes: Same Function, Different Structure," *Structure*, 10:8-9 (2002).
Kloosterman et al., "Molecular, Biochemical, and Functional Characterization of a Nudix Hydrolase Protein That Stimulates the Activity of a Nicotinoprotein Alcohol Dehydrogenase," *J. Biol. Chem.*, 277(38):34785-34792 (2002).
Klyosov, "Kinetics and Specificity of Human Liver Aldehyde Dehydrogenases Toward Aliphatic, Aromatic, and Fused Polycyclic Aldehydes," *Biochemistry*, 35(14):4457-4467 (1996).
Knappe et al., "Post-translational Activation Introduces a Free Radical Into Pyruvate Formate-Lyase," *Proc. Natl. Acad. Sci. U.S. A.*, 81:1332-1335 (1984).
Knutzon et al., "Isolation and Characterization of Two Safflower Oleoyl-Acyl Carrier Protein Thioesterase cDNA Clones," *Plant Physiol.*, 100:1751-1758 (1992).
Kocharin et al., "Improved Polyhydroxybutyrate Production by *Saccharomyces cerevisiae* Through the Use of the Phosphoketolase Pathway," *Biotechnol Bioeng.*, 110(8):2216-2224 (2013).
Kohlwein et al., "Tsc13p is Required for Fatty Acid Elongation and Localizes to a Novel Structure at the Nuclear-Vacuolar Interface in *Saccharomyces cerevisiae,*" *Mol. Cell. Biol.*, 21:109-125 (2001).

(56) References Cited

OTHER PUBLICATIONS

Koland et al., "Proximity of Reactive Cysteine Residue and Flavin in *Escherichia coli* Pyruvate Oxidase as Estimated by Fluorescence Energy Transfer," *Biochemistry* 21(18):4438-4442 (1982).
Koo et al., "Cloning and Characterization of the Bifunctional alcohol/acetaldehyde Dehydrogenase Gene (adhE) in Leuconostoc Mesenteroides Isolated From Kimchi ," *Biotechnol. Lett.*, 27:505-510 (2005).
Koo et al., "Functional Evaluation of the Genes Involved in Malonate Decarboxylation by Acinetobacter Calcoaceticus," *Eur. J. Biochem.*, 266(2):683-690 (1999).
Korolev et al., "Autotracing of *Escherichia coli* Acetate CoA-transferase Alpha-Subunit Structure Using 3.4 A MAD and 1.9 A Native Data," *Acta Crystallogr. D. Biol. Crystallogr.*, 58:2116-2121 (2002).
Korotkova et al., "MeaB is a Component of the methylmalonyl-CoA Mutase Complex Required for Protection of the Enzyme From Inactivation," *J. Biol. Chem.*, 279(14):13652-13658 (2004).
Kosaka et al., "Characterization of the Sol Operon in Butanol-Hyperproducing Clostridium Saccharoperbutylacetonicum Strain N1-4 and Its Degeneration Mechanism," *Biosci. Biotechnol. Biochem.*, 71:58-68 (2007).
Kostrew et al., "The Crystal Structure of PfFabZ, the Unique beta-hydroxyacyl-ACP Dehydratase Involved in Fatty Acid Biosynthesis of Plasmodium Falciparum," *Protein Sci.*, 14(6):1570-1580 (2005).
Koutz et al., "Structural Comparison of the Pichia Pastoris Alcohol Oxidase Genes," *Yeast* 5(3):167-177 (1989).
Kowalchuk et al., "Contrasting Patterns of Evolutionary Divergence Within the Acinetobacter Calcoaceticus Pca Operon," *Gene*, 146(1):23-30 (1994).
Kreimeyer et al., "Identification of the Last Unknown Genes in the Fermentation Pathway of Lysine ," *J. Biol. Chem.*, 282(10):7191-7197 (2007).
Krieger et al., "Pyruvate Decarboxylase From Kluyveromyces Lactis. An Enzyme With an Extraordinary Substrate Activation Behaviour," *Eur. J. Biochem.*, 269(13):3256-3263 (2002).
Kuhnl et al., "Functional Analysis of the methylmalonyl-CoA Epimerase From Caenorhabditis Elegans," *FEBSJ.*, 272(6):1465-1477 (2005).
Kurdistani et al., "Histone Acetylation and Deacetylation in Yeast," *Nat. Rev. Mol. Cell Biol.*, 4(4):276-284 (2003).
Kuznetsova et al., "Enzyme Genomics: Application of General Enzymatic Screens to Discover New Enzymes," *FEMS Microbiol. Rev.*, 29(2):263-279 (2005).
Kwon et al., "Influence of Gluconeogenic Phosphoenolpyruvate Carboxykinase (PCK) Expression on Succinic Acid Fermentation in *Escherichia coli* Under High Bicarbonate Condition," *J. Microbiol. Biotechnol.*, 16(9):1448-1452 (2006).
Laivenieks et al., "Cloning, Sequencing, and Overexpression of the Anaerobiospirillum Succiniciproducens Phosphoenolpyruvate Carboxykinase (pckA) Gene," *Appl. Environ. Microbiol.*, 63(6):2273-2280 (1997).
Lamas-Maceiras et al., "Amplification and Disruption of the phenylacetyl-CoA Ligase Gene of Penicillium Chrysogenum Encoding an Aryl-Capping Enzyme That Supplies Phenylacetic Acid to the Isopenicillin N-acyltransferase," *Biochem. J.*, 395:147-155 (2005).
Lametschwandtner et al., "The Difference in Recognition of Terminal Tripeptides as Peroxisomal Targeting Signal 1 Between Yeast and Human is Due to Different Affinities of Their Receptor Pex5p to the Cognate Signal and to Residues Adjacent to It," *J. Biol. Chem.*, 273(50):33635-33643 (1998).
Lea et al., "Does Phosphoenolpyruvate Carboxykinase Have a Role in Both Amino Acid and Carbohydrate Metabolism?," *Amino Acids*, 20(3):225-241 (2001).
Leal et al., "PduP is a Coenzyme-A-Acylating Propionaldehyde Dehydrogenase Associated With the Polyhedral Bodies Involved in B12-dependent 1,2-propanediol Degradation by *Salmonella enterica* Serovar Typhimurium LT2," *Arch. Microbiol.*, 180(5):353-361 (2003).

Ledeboer et al., "Molecular Cloning and Characterization of a Gene Coding for Methanol Oxidase in Hansenula Polymorpha," *Nucl. Acids Res.*, 13(9):3063-3082 (1985).
Leduc et al., "The Hotdog Thioesterase EntH (YbdB) Plays a Role in Vivo in Optimal Enterobactin Biosynthesis by Interacting With the ArCP Domain of EntB," *J. Bacteriol.*, 189(19):7112-7126 (2007).
Lee et al., "A Fatty-Acid Synthesis Mechanism Specialized for Parasitism," *Nat. Rev. Microbiol.*, 5(4):287-297 (2007).
Lee et al., "A new approach to directed gene evolution by recombined extension on truncated templates (RETT)," *J. Molec. Catalysis*, 26:119-129 (2003).
Lee et al., "Antisense Technology in Molecular and Cellular Bioengineering," *Curr. Opin. Biotechnol.*, 14(5):505-511 (2003).
Lee et al., "Biosynthesis of Enantiopure (S)-3-hydroxybutyric Acid in Metabolically Engineered *Escherichia coli,*" *Appl. Microbiol. Biotechnol.*, 79(4):633-641 (2008).
Lee et al., "Chaperonin GroESL Mediates the Protein Folding of Human Liver Mitochondrial Aldehyde Dehydrogenase in *Escherichia coli,*" *Biochem. Biophys. Res. Commun.*, 298(2):216-224 (2002).
Lee et al., "Cloning and Characterization of Mannheimia succiniciproducens MBEL55E Phosphoenolpyruvate Carboxykinase (pckA) Gene," *Biotechnol. Bioprocess Eng.*, 7:95-99 (2002).
Lee et al., "Cloning and Characterization of the Gene Encoding Phosphoketolase in Leuconostoc Mesenteroides Isolated From Kimchi," *Biotechnol Lett.*, 27(12):853-858 (2005).
Lee et al., "Crystallization and Preliminary X-ray Crystallographic Studies of Enoyl-Acyl Carrier Protein Reductase (FabI) From Psuedomonas Aeruginosa," *Acta Cryst. Sect. F.*, 67:214-216 (2011).
Lee et al., "Cysteine-286 as the Site of Acylation of the Lux-specific Fatty acyl-CoA Reductase," *Biochim. Biophys. Acta.*, 1338: 215-222 (1997).
Lee et al., "Fatty Acid Synthesis by Elongases in Trypanosomes," *Cell* 126(4):691-699 (2006).
Lehtio et al., "Crystal Structure of a Glycyl Radical Enzyme From Archaeoglobus Fulgidus," *J. Mol. Biol.*, 357(1):221-235 (2006).
Lehtio et al., "The Pyruvate Formate Lyase Family: Sequences, Structures and Activation," *Protein Eng. Des. Sel.*, 17(6):545-552 (2004).
Lenski et al., "Dynamics of Adaptation and Diversification: A 10,000-generation Experiment With Bacterial Populations," *Proc. Natl. Acad. Sci. USA*, 91(15):6808-6814 (1994).
Leppanen et al., "Pyruvate Formate Lyase is Structurally Homologous to Type I Ribonucleotide Reductase," *Structure*, 7(7):733-744 (1999).
Leskovac et al., "The Three Zinc-Containing Alcohol Dehydrogenases From Baker's Yeast, *Saccharomyces cerevisiae,*" *FEMS Yeast Res.*, 2(4):481-494 (2002).
Lessner et al., "An Unconventional Pathway for Reduction of $CO_2$ to Methane in CO-grown Methanosarcina Acetivorans Revealed by Proteomics ," *Proc. Natl. Acad. Sci. U.S.A.*, 103(47):17921-17926 (2006).
Leys et al., "Channelling and Formation of 'Active' Formaldehyde in Dimethylglycine Oxidase," *EMBO J.*, 22(16):4038-4048 (2003).
Li et al., "Effects of Substitution of Tryptophan 412 in the Substrate Activation Pathway of Yeast Pyruvate Decarboxylase," *Biochemistry*, 38(31):10004-10012 (1999).
Li et al., "Integrated Electromicrobial Conversion of $CO_2$ to Higher Alcohols," *Science*, 335:1596 (2012).
Li et al., "Properties of Nicotinamide Adenine Dinucleotide Phosphate-Dependent Formate Dehydrogenase From Clostridium Thermoaceticum," *J. Bacteriol.*, 92(2):405-412 (1966).
Lingen et al., "Alteration of the Substrate Specificity of Benzoylformate Decarboxylase From Pseudomonas Putida by Directed Evolution," *Chembiochem.* 4(8):721-726 (2003).
Lingen et al., "Improving the Carboligase Activity of Benzoylformate Decarboxylase From Pseudomonas Putida by a Combination of Directed Evolution and Site-Directed Mutagenesis," *Protein Eng.*, 15(7):585-593 (2002).
Liu et al., "Two novel metal-independent long-chain alkyl alcohol dehydrogenases from Geobacillus thermodenitrificans NG80-2," *Microbiol . . . ,* 155:2078-2085 (2009).

(56) References Cited

OTHER PUBLICATIONS

Liu et al., "Expression and Purification of His-tagged Rat Mitochondrial Short-Chain 3-hydroxyacyl-CoA Dehydrogenase Wild-Type and Ser137 Mutant Proteins," *Prot. Expr. Purif.*, 37:344-351 (2004).

Liu et al., "Gene Cloning, Biochemical Characterization and Physiological Role of a Thermostable Low-Specificity L-threonine Aldolase From *Escherichia coli*," *Eur. J. Biochem.*, 255(1):220-226 (1998).

Liu et al., "The GLY1 Gene of *Saccharomyces cerevisiae* Encodes a Low-Specific L-threonine Aldolase That Catalyzes Cleavage of L-allo-threonine and L-threonine to Glycine—Expression of the Gene in *Escherichia coli* and Purification and Characterization of the Enzyme," *Eur. J. Biochem.*, 245(2):289-293 (1997).

Lobo et al., "A *Streptomyces collinus* Thiolase With Novel acetyl-CoA:acyl Carrier Protein Transacylase Activity," *Biochem.*, 40:11955-11964 (2001).

Lomakin et al., "The Crystal Structure of Yeast Fatty Acid Synthase, a Cellular Machine With Eight Active Sites Working Together," *Cell*, 129(2):319-332 (2007).

Longtine et al., "Additional Modules for Versatile and Economical PCR-based Gene Deletion and Modification in *Saccharomyces cerevisiae*," *Yeast* 14(10):953-961 (1998).

Lorquet et al., "Characterization and Functional Analysis of the poxB Gene, Which Encodes Pyruvate Oxidase in Lactobacillus Plantarum," *J. Bacteriol.*, 186(12):3749-3759 (2004).

Louis et al., "Restricted Distribution of the Butyrate Kinase Pathway Among Butyrate-Producing Bacteria From the Human Colon," *J. Bacteriol.*, 186(7):2099-2106 (2004).

Lovell et al., "Cloning and Expression in *Escherichia coli* of the Clostridium Thermoaceticum Gene Encoding Thermostable Formyltetrahydrofolate Synthetase," *Arch. Microbiol.*, 149:280-285 (1988).

Lovell et al., "Primary Structure of the Thermostable Formyltetrahydrofolate Synthetase from Clostridium Thermoaceticum," *Biochemistry*, 29:5687-5694 (1990).

Low et al., "Mimicking Somatic Hypermutation: Affinity Maturation of Antibodies Displayed on Bacteriophage Using a Bacterial Mutator Strain," *J. Mol. Biol.*, 260(3):359-368 (1996).

Lu et al., "Sequence and Expression of the Gene Encoding the corrinoid/iron-sulfur Protein From Clostridium Thermoaceticum and Reconstitution of the Recombinant Protein to Full Activity," *J. Biol. Chem.*, 268:5605-5614 (1993).

Lucas et al., "The Aspergillus Nidulans Carnitine Carrier Encoded by the acuH Gene is Exclusively Located in the Mitochondria," *FEMS Microbiol Lett.*, 201:193-198 (2006).

Luers et al., "The Pichia Pastoris Dihydroxyacetone Kinase is a PTS1-containing, but Cytosolic, Protein That is Essential for Growth on Methanol," *Yeast* 14(8):759-771 (1998).

Luo et al., "Purification, Identification, and Properties of a *Saccharomyces cerevisiae* Oleate-Activated Upstream Activating Sequence-Binding Protein That is Involved in the Activation of POX1," *J. Biol. Chem.*, 271(20):12068-12075 (1996).

Luo et al., "Identification and Characterization of the Propanediol Utilization Protein PduP of Lactobacillus Reuteri for 3-hydroxypropionic Acid Production From Glycerol," *Appl. Microbiol. Biotech.*, 89(3):697-703 (2011).

Lutz et al., "Creating Multiple-Crossover DNA Libraries Independent of Sequence Identity," *Proc. Natl. Acad. Sci. USA*, 98(20):11248-11253 (2001).

Lutz et al., "Independent and Tight Regulation of Transcriptional Units in *Escherichia coli* via the LacR/O, the TetR/O and AraC/I1-I2 Regulatory Elements," *Nucleic Acids Res.*, 25(6):1203-1210 (1997).

Lutz et al., "Rapid Generation of Incremental Truncation Libraries for Protein Engineering Using Alpha-Phosphothioate Nucleotides," *Nucleic Acids Res.*, 29(4):e16 (2001).

Maaheimo et al., "Central Carbon Metabolism of *Saccharomyces cerevisiae* Explored by Biosynthetic Fractional (13)C Labeling of Common Amino Acids," *Eur. J. Biochem.*, 268:2464-2479 (2001).

Machado et al., "A Selection Platform for Carbon Chain Elongation Using the CoA-dependent Pathway to Produce Linear Higher Alcohols," *Met. Eng.*, 14(5):504-511 (2012).

Machielsen et al., "Cofactor engineering of Lactobacillus brevis alcohol dehydrogenase by computational design," *Eng. Life Sci.*, 9(1):38-44 (2009).

Mack et al., "Conversion of Glutaconate CoA-transferase From Acidaminococcus Fermentans Into an acyl-CoA Hydrolase by Site-Directed Mutagenesis," *FEBS. Lett.*, 405(2):209-212 (1997).

Maeda et al., "Enhanced Hydrogen Production From Glucose by Metabolically Engineered *Escherichia coli*," *Appl. Microbiol. Biotechnol.*, 77(4):879-890 (2007).

Maeder et al., "The Methanosarcina Barkeri Genome: Comparative Analysis With Methanosarcina Acetivorans and Methanosarcina Mazei Reveals Extensive Rearrangement Within Methanosarcinal Genomes," *J. Bacteriol.*, 188(22):7922-7931 (2006).

Makuc et al., "The Putative Monocarboxylate Permeases of the Yeast *Saccharomyces cerevisiae* Do Not Transport Monocarboxylic Acids Across the Plasma Membrane," *Yeast*, 18(12):1131-1143 (2001).

Mann et al., "Proteomic Analysis of Post-Translational Modifications," *Nature Biotech.*, 21(3):255-261 (2003).

Mann, "An International Reference Materical for Radiocarbon Dating," *Radiocarbon*, 25(2):519-527 (1983).

Mannaerts et al., "Peroxisomal Lipid Degradation via Beta- and Alpha-Oxidation in Mammals," *Cell Biochem. Biphys.*, 32:73-87 (2000).

Marolewski et al., "Cloning and Characterization of a New Purine Biosynthetic Enzyme: A Non-Folate Glycinamide Ribonucleotide Transformylase From *E. coli*," *Biochemistry* 33(9):2531-2537 (1994).

Martin et al., "Engineering a Mevalonate Pathway in *Escherichia coli* for Production of Terpenoids," *Nat. Biotechnol.*, 21(7):796-802 (2003).

Martinez-Blanco et al., "Purification and Biochemical Characterization of phenylacetyl-CoA Ligase From Pseudomonas Putida. A Specific Enzyme for the Catabolism of Phenylacetic Acid," *J. Biol. Chem.*, 265:7084-7090 (1990).

Mattevi et al., "Atomic Structure of the Cubic Core of the Pyruvate Dehydrogenase Multienzyme Complex," *Science*. 255(5051):1544-1550 (1992).

Matthies et al., "Reciprocal Isomerization of Butyrate and Isobutyrate by the Strictly Anaerobic Bacterium Strain WoG13 and Methanogenic Isobutyrate Degradation by a Defined Triculture," *Appl. Environ. Microbiol.*, 58(5):1435-1439 (1992).

McAlister-Henn et al., "Isolation and Expression of the Gene Encoding Yeast Mitochondrial Malate Dehydrogenase," *J. Bacteriol.*, 169(11):5157-5166 (1987).

McCarthy, "Crystal Structure of Methylmalonyl-Coenzyme A Epimerase From P. Shermanii: A Novel Enzymatic Function on an Ancient Metal Binding Scaffold," *Structure* 9(7):637-646 (2001).

McCue et al., "Gene Expression and Stress Response Mediated by the Epigenetic Regulation of a Transposable Element Small RNA," *PLoS Genet.*, 8(2):e1002474 (2012).

McNeil et al., "Cloning and Molecular Characterization of Three Genes, Including Two Genes Encoding Serine Hydroxymethyltransferases, Whose Inactivation is Required to Render Yeast Auxotrophic for Glycine," *J. Biol. Chem.*, 269:9155-9165 (1994).

McNeil et al., "Glycine Metabolism in Candida Albicans: Characterization of the Serine Hydroxymethyltransferase (SHM1, SHM2) and Threonine Aldolase (GLY1) Genes," *Yeast*, 16(2):167-175 (2000).

Meijer et al., "Gene Deletion of Cytosolic ATP: Citrate Lyase Leads to Altered Organic Acid Production in Aspergillus Niger," *J. Ind. Microbiol. Biotechnol.*, 36(10):1275-1280 (2009).

Meile et al., "Characterization of the D-xylulose 5-phosphate/D-fructose 6-phosphate Phosphoketolase Gene (Xfp) From Bifidobacterium Lactis," *J. Bacteriol.*, 183(9):2929-2936 (2001).

Melchiorsen et al., "The Level of Pyruvate-Formate Lyase Controls the Shift From Homolactic to Mixed-Acid Product Formation in Lactococcus Lactis," *Appl. Microbiol. Biotechnol.*, 58(3):338-344 (2002).

(56) References Cited

OTHER PUBLICATIONS

Mellgren et al., "Mqo, a Tricarboxylic Acid Cycle Enzyme, is Required for Virulence of Pseudomonas Syringae Pv. Tomato Strain DC3000 on *Arabidopsis thaliana,*" *J. Bacteriol.,* 191:3132-3142 (2009).
Membrillo et al., "Evolution of the adhE Gene Product of *Escherichia coli* From a Functional Reductase to a Dehydrogenase. Genetic and Biochemical Studies of the Mutant Proteins ," *J. Biol. Chem.,* 275(43):33869-33875 (2000).
Menon et al., "Mechanism of the Clostridium Thermoaceticum Pyruvate:ferredoxin Oxidoreductase: Evidence for the Common Catalytic Intermediacy of the Hydroxyethylthiamine Pyrophosphate Radical," *Biochemistry* 36(28):8484-8494 (1997).
Menzel et al., "Enzymatic Evidence for an Involvement of Pyruvate Dehydrogenase in the Anaerobic Glycerol Metabolism of Klebsiella Pneumoniae," *J. Biotechnol.,* 56(2):135-142 (1997).
Merilainen et al., "The Thiolase Reaction Mechanism: The Importance of Asn316 and His348 for Stabilizing the Enolate Intermediate of the Claisen Condensation," *Biochemistry,* 48(46):11011-11025 (2009).
Metz et al., "Purification of a Jojoba Embryo Fatty Acyl-Coenzyme A Reductase and Expression of Its cDNA in High Erucic Acid Rapeseed," *Plant Physiol.,* 122(3):635-644 (2000).
Mikkelsen et al., "Microbial Production of Indolylglucosinolate Through Engineering of a Multi-Gene Pathway in a Versatile Yeast Expression Platform," *Met. Eng.,* 14(2):104-111 (2012).
Miko, "Phenotype Variability: Penetrance and Expressivity," *Nature Education* 1(1):137 (2008).
Minard et al., "Isolation, Nucleotide Sequence Analysis, and Disruption of the MDH2 Gene From *Saccharomyces cerevisiae*: Evidence for Three Isozymes of Yeast Malate Dehydrogenase," *Mol. Cell. Biol.,* 11(1):370-380 (1991).
Mitsuhashi et al., "Disruption of Malate:quinone Oxidoreductase Increases L-lysine Production by Corynebacterium Glutamicum," *Biosci. Biotechnol. Biochem.,* 70(11):2803-2806 (2006).
Mitsui et al., "Formaldehyde Fixation Contributes to Detoxification for Growth of a Nonmethylotroph, Burkholderia Cepacia TM1, on Vanillic Acid," *Appl. Environ. Microbiol.,* 69(10):6128-6132 (2003).
Molin et al., "Dihydroxyacetone Kinases in *Saccharomyces cerevisiae* are Involved in Detoxification of Dihydroxyacetone," *J. Biol. Chem.,* 278(3):1415-1423 (2003).
Morita et al., "Bacteril Distribution of Glycolaldehyde Dehydrogenase in Relation to Vitamin B6 Biosynthesis," *Agric. Biol. Chem.,* 43:185-186 (1979).
Morris et al., "Nucleotide Sequence of the LYS2 Gene of *Saccharomyces cerevisiae*: Homology to Bacillus Brevis Tyrocidine Synthetase 1," *Gene* 98(1):141-145 (1991).
Morton et al., "The Primary Structure of the Subunits of Carbon Monoxide dehydrogenase/acetyl-CoA Synthase From Clostridium Thermoaceticum," *J. Biol. Chem.,* 266:23824-23828 (1991).
Mukhopadhyay et al., "Pyruvate Carboxylase From Mycobacterium Smegmatis: Stabilization, Rapid Purification, Molecular and Biochemical Characterization and Regulation of the Cellular Level," *Biochim. Biophys. Acta,* 1475(3):191-206 (2000).
Mukhopadhyay et al., "The fdxA Ferredoxin Gene Can Down-Regulate frxA Nitroreductase Gene Expression and is Essential in Many Strains of Helicobacter Pylori," *J. Bacteriol.,* 185(9):2927-2935 (2003).
Muller et al., "Nucleotide Exchange and Excision Technology (Next) DNA Shuffling: A Robust Method for DNA Fragmentation and Directed Evolution," *Nucleic Acids Res.,* 33(13):e117 (2005).
Muller et al., "The Refined Structures of a Stabilized Mutant and of Wild-Type Pyruvate Oxidase From Lactobacillus Plantarum," *J. Mol. Biol.,* 237:315-335 (1994).
Muratsubaki et al., "One of the Fumarate Reductase Isoenzymes From *Saccharomyces cerevisiae* is Encoded by the OSMI Gene," *Arch. Biochem. Biophys.,* 352(2):175-181 (1998).
Musfeldt et al., "Crystal Structure of Yeast Acetyl-Coenzyme A Synthetase in Complex With AMP ," *J. Bacteriol.,* 184:636-644 (2002).

Myronova et al., "Three-dimensional Structure Determination of a Protein Supercomplex That Oxidizes Methane to Formaldehyde in Methylococcus Capsulatus (Bath)," *Biochem* 45(39):11905-11914 (2006).
Naesby et al., "Yeast artificial chromosomes employed for random assembly of biosynthetic pathways and production of diverse compounds in *Saccharomyces cerevisiae,*" *Microb. Cell Fact.,* 8:49-56 (2009).
Nagashima et al., "Long-chain n-alkanol dehydrogenase from Pseudomonas putida," *J. Ferment. Bioeng.,* 82:328-333 (1996).
Naggert et al., "Cloning, Sequencing, and Characterization of *Escherichia coli* Thioesterase II," *J. Biol. Chem.,* 266(17):11044-11050 (1991).
Nagi et al., "Biochemical Properties of Short- and Long-Chain Rat Liver Microsomal trans- 2-enoyl Coenzyme A Reductase," *Arch. Biochem. Biophys.,* 226(1):50-64 (1983).
Nagy et al., "Formyltetrahydrofolate Hydrolase, a Regulatory Enzyme That Functions to Balance Pools of Tetrahydrofolate and One-Carbon Tetrahydrofolate Adducts in *Escherichia coli,*" *J. Bacteriol.,* 177(5):1292-1298 (1995).
Naidu et al., "Characterization of a Three-Component Vanillate O-demethylase From Moorella Thermoacetica," *J. Bacteriol.,* 183(11):3276-3281 (2001).
Nakagawa et al., "Alcohol Oxidase Hybrid Oligomers Formed in Vivo and in Vitro," *Yeast* 15(12):1223-1230 (1999).
Nakahigashi et al., "Nucleotide Sequence of the fadA and fadB Genes From *Escherichia coli,*" *Nucleic Acids Res.,* 18(16):4937 (1990).
Nakai et al., "A Knowledge Base for Predicting Protein Localization Sites in Eukaryotic Cells," *Genomics,* 14(4):897-911 (1992).
Nakamura et al., "Studies on Malonic Semialdehyde Dehydrogenase From Pseudomonas Aeruginosa," *Biochim. Biophys. Acta,* 50:147-152 (1961).
Nakano et al., "Characterization of Anaerobic Fermentative Growth of Bacillus Subtilis: Identification of Fermentation End Products and Genes Required for Growth," *J. Bacteriol.,* 179(21):6749-6755 (1997).
Nakashita et al., "Identification and Expression of the Gene Encoding Phosphonopyruvate Decarboxylase of *Streptomyces hygroscopicus,*" *Biochim. Biophys. Acta,* 1490(1-2):159-162 (2000).
Nakazawa et al., "Pyruvate:NADP+ Oxidoreductase is Stabilized by Its Cofactor, Thiamin Pyrophosphate, in Mitochondria of Euglena Gracilis," *Arch. Biochem. Biophys.,* 411(2):183-188 (2003).
Nashizawa et al., "Regulation of Inducible Gene Expression by Natural Antisense Transcripts," *Front. Biosci.,* 17:938-958 (2012).
Navarro-Avino et al., "A Proposal for Nomenclature of Aldehyde Dehydrogenases in *Saccharomyces cerevisiae* and Characterization of the Stress-Inducible ALD2 and ALD3 Genes," *Yeast,* 15(10A):829-842 (1999).
Ness et al., "Synthetic Shuffling Expands Functional Protein Diversity by Allowing Amino Acids to Recombine Independently," *Nat. Biotechnol.,* 20(12):1251-1255 (2002).
Netzer et al., "Cometabolism of a Nongrowth Substrate: L-serine Utilization by Corynebacterium Glutamicum," *Appl. Environ. Microbiol.,* 70(12):7148-7155 (2004).
Neuberger et al., "Prediction of Peroxisomal Targeting Signal 1 Containing Proteins From Amino Acid Sequence," *J. Mol. Biol.,* 328(3):581-592 (2003).
Nguyen et al., "Fatty Acid Synthase Impacts the Pathobiology of Candida Parapsilosis in Vitro and During Mammalian Infection," *PLoS One,* 22:e8421 (2009).
Nie et al., "Identification and Characterization of *Escherichia coli* Thioesterase III That Functions in Fatty Acid Beta-Oxidation," *Biochem.,* 47(29):7744-7751 (2008).
Nilekani et al., "Purification and Properties of Citrate Lyase From *Escherichia coli,*" *Biochemistry,* 22(20):4657-4663 (1983).
Nogales et al., "Characterization of the Last Step of the Aerobic Phenylacetic Acid Degradation Pathway," *Microbiology* 153:357-365 (2007).
Nowrousian et al., "The Fungal acl1 and acl2 Genes Encode Two Polypeptides With Homology to the N- and C-terminal Parts of the Animal ATP Citrate Lyase Polypeptide," *Curr. Genet.,* 37(3):189-193 (2000).

(56) References Cited

OTHER PUBLICATIONS

Nunn et al., "The Nucleotide Sequence and Deduced Amino Acid Sequence of the Genes for Cytochrome cL and a Hypothetical Second Subunit of the Methanol Dehydrogenase of Methylobacterium AM1," *Nucl. Acid. Res.*, 16:7722 (1988).
O'Brien et al., "Chemical, Physical and Enzymatic Comparisons of Formyltetrahydrofolate Synthetases From Thermo- and Mesophilic Clostridia," *Experientia Suppl.*, 26:249-262 (1976).
O'Brien et al., "Evidence for a Complex of Three Beta-Oxidation Enzymes in *Escherichia coli*: Induction and Localization," *J. Bacteriol.*, 132(2):532-540 (1977).
O'Brien et al., "Regulation by Lipids of Cofactor Binding to a Peripheral Membrane Enzyme: Binding of Thiamin Pyrophosphate to Pyruvate Oxidase," *Biochemistry* 16(14):3105-3109 (1977).
O'Brien et al., "Studies of the Thiamin Pyrophosphate Binding Site of *Escherichia coli* Pyruvate Oxidase. Evidence for an Essential Tryptophan Residue," *J. Biol. Chem.*, 255(8):3302-3307 (1980).
O'Sullivan, "Aptasensors—the Future of Biosensing?," *Anal. Bioanal. Chem.*, 372(1):44-48 (2002).
Oey et al., "dif-1 and Colt, Both Implicated in Early Embryonic Development, Encode Carnitine Acylcarnitine Translocase," *Mol. Genet. Metab.*, 85:121-124 (2005).
Oh et al., "Structural Analysis of the FDS Operon Encoding the NAD+-linked Formate Dehydrogenase of Ralstonia Eutropha," *J. Biol. Chem.*, 273(41):26349-26360 (1998).
Ohgami et al., "Expression of acetoacetyl-CoA Synthetase, a Novel Cytosolic Ketone Body-Utilizing Enzyme, in Human Brain," *Biochem. Pharmacol.*, 65:989-994 (2003).
Okamura et al., "Cloning and Nucleotide Sequence of the GCV Operon Encoding the *Escherichia coli* Glycine-Cleavage System," *Eur. J. Biochem.*, 216:539-548 (1993).
Okamura et al., "Unprecedented Acetoacetyl-Coenzyme A Synthesizing Enzyme of the Thiolase Superfamily Involved in the Mevalonate Pathway," *Proc. Natl. Acad. Sci. USA*, 107(25):11265-11270 (2010).
Oku et al., "Biosynthesis of Branched-Chain Fatty Acids in Bacillus Subtilis. A Decarboxylase is Essential for Branched-Chain Fatty Acid Synthetase," *J. Biol. Chem.*, 263(34):18386-18396 (1988).
Olivera et al., "Molecular Characterization of the Phenylacetic Acid Catabolic Pathway in Pseudomonas Putida U: The phenylacetyl-CoA Catabolon," *Proc. Natl. Acad. Sci. U.S.A.*, 95(11):6419-6424 (1998).
Ordonez et al., "Methylene Reductase: Responsible for the in Vitro Formation of Formaldehyde From 5-methyltetrahydrofolic Acid," *Psychopharmacol Commun.*, 1(3):253-260 (1975).
Orita et al., "Bifunctional Enzyme Fusion of 3-hexulose-6-phosphate Synthase and 6-phospho-3-hexuloisomerase," *Appl. Microbiol. Biotechnol.*, 76:439-445 (2007).
Oshima et al., "Regulation of Phosphatase Synthesis in *Saccharomyces cerevisiae*—A Review," *Gene*, 179:171-177 (1996).
Ostermeier et al., "A Combinatorial Approach to Hybrid Enzymes Independent of DNA Homology," *Nat. Biotechnol.*, 17(12):1205-1209 (1999).
Ostermeier et al., "Combinatorial Protein Engineering by Incremental Truncation," *Proc. Natl. Acad. Sci. USA*, 96(7):3562-3567 (1999).
Otten et al., "Directed Evolution: Selecting Today's Biocatalysts," *Biomol. Eng.*, 22:1-9 (2005).
Overkamp et al., "In Vivo Analysis of the Mechanisms for Oxidation of Cytosolic NADH by *Saccharomyces cerevisiae* Mitochondria," *J. Bacteriol.*, 182(10):2823-2830 (2000).
Padovani, "Assembly and Protection of the Radical Enzyme, methylmalonyl-CoA Mutase, by Its Chaperone," *Biochemistry*, 45(30):9300-9306 (2006).
Palmieri et al., "Identification of Mitochondrial Carriers in *Saccharomyces cerevisiae* by Transport Assay of Reconstituted Recombinant Proteins," *Biochimica et Biophys. Acta*, 1757:1249-1262 (2006).
Palosaari et al., "Purification and Properties of the Inducible Coenzyme A-linked Butyraldehyde Dehydrogenase From Clostridium Acetobutylicum," *J. Bacteriol.*, 170(7):2971-2976 (1988).

Papini et al., "Physiological Characterization of Recombinant *Saccharomyces cerevisiae* Expressing the Aspergillus Nidulans Phosphoketolase Pathway: Validation of Activity Through 13C-based Metabolic Flux Analysis," *Appl. Microbiol. Biotechnol.*, 95(4):1001-1010 (2012).
Park et al., "Biosynthesis of poly(3-hydroxybutyrate-co-3-hydroxyalkanoates) by Metabolically Engineered *Escherichia coli* Strains," *Appl. Biochem. Biotechnol.*, 113-116:335-346 (2004).
Park et al., "Growth of Mycobacteria on Carbon Monoxide and Methanol," *J. Bacteriol.*, 185(1):142-147 (2003).
Park et al., "Identification and Characterization of a New Enoyl Coenzyme A Hydratase Involved in Biosynthesis of Medium-Chain-Length Polyhydroxyalkanoates in Recombinant *Escherichia coli*," *J. Bacteriol.*, 185(18):5391-5397 (2003).
Park et al., "New FadB Homologous Enzymes and Their Use in Enhanced Biosynthesis of Medium-Chain-Length Polyhydroxyalkanoates in FadB Mutant *Escherichia coli*," *Biotechnol. Bioeng.*, 86(6):681-686 (2004).
Park et al., "Purifications and Characterizations of a Ferredoxin and Its Related 2-oxoacid: ferredoxin Oxidoreductase From the Hyperthermophilic Archaeon, Sulfolobus Solfataricus P1," *J. Biochem. Mol. Biol.*, 39(1):46-54 (2006).
Parkin et al., "Rapid and Efficient Electrocatalytic CO2/CO Interconversions by Carboxydothermus Hydrogenoformans CO Dehydrogenase I on an Electrode," *J. Am. Chem. Soc.*, 129(34):10328-10329 (2007).
Pasquinelli, "MicroRNAs and Their Targets: Recognition, Regulation and an Emerging Reciprocal Relationship," *Nat. Rev. Genet.*, 13(4):271-282 (2012).
Passoth et al., "Molecular Cloning of Alcohol Dehydrogenase Genes of the Yeast Pichia Stipitis and Identification of the Fermentative ADH," *Yeast*, 14:1311-1323 (1998).
Pauli et al., "Ato Operon: A Highly Inducible System for Acetoacetate and Butyrate Degradation in *Escherichia coli*," *Eur. J. Biochem.*, 29(3):553-562 (1972).
Paxton et al., "Role of Branched-Chain 2-oxo Acid Dehydrogenase and Pyruvate Dehydrogenase in 2-oxobutyrate Metabolism," *Biochem. J.*, 234(2):295-303 (1986).
Peretz et al., "Molecular Cloning, Nucleotide Sequencing, and Expression of Genes Encoding Alcohol Dehydrogenases From the Thermophile Thermoanaerobacter Brockii and the Mesophile Clostridium Beijerinckii," *Anaerobe* 3(4):259-270 (1997).
Perez et al., "*Escherichia coli* YqhD Exhibits Aldehyde Reductase Activity and Protects From the Harmful Effect of Lipid Peroxidation-Derived Aldehydes," *J. Biol. Chem.*, 283(12):7346-7353 (2008).
Petersen et al., "Purification of Acetoacetate Decarboxylase From Clostridium Acetobutylicum ATCC 824 and Cloning of the Acetoacetate Decarboxylase Gene in *Escherichia coli*," *Appl. Environ. Microbiol.*, 56(11):3491-3498 (1990).
Pierce et al., "The Complete Genome Sequence of Moorella Thermoacetica (F. Clostridium Thermoaceticum)," *Environ. Microbiol.*, 10:2550-2573 (2008).
Pieulle et al., "Isolation and Analysis of the Gene Encoding the Pyruvate-Ferredoxin Oxidoreductase of Desulfovibrio Africanus, Production of the Recombinant Enzyme in *Escherichia coli*, and Effect of Carboxy-Terminal Deletions on Its Stability," *J. Bacteriol.*, 179(18):5684-5692 (1997).
Plamann et al., "Characterization of the *Escherichia coli* Gene for Serine Hydroxymethyltransferase," *Gene*, 22:9-18 (1983).
Ploux et al., "The NADPH-linked acetoacetyl-CoA Reductase From Zoogloea Ramigera. Characterization and Mechanistic Studies of the Cloned Enzyme Over-Produced in *Escherichia coli*," *Eur. J. Biochem.*, 174(1):177-182 (1988).
Poehlein et al., "An Ancient Pathway Combining Carbon Dioxide Fixation with the Generation and Utilization of a Sodium Ion Gradient for ATP Synthesis," *PLoS One*, 7:e33439 (2012).
Pohl et al., "Remarkably Broad Substrate Tolerance of malonyl-CoA Synthetase, an Enzyme Capable of Intracellular Synthesis of Polyketide Precursors," *J. Am. Chem. Soc.*, 123(24):5822-5823 (2001).
Poletto et al., "Selection of an *Escherichia coli* Host That Expresses Mutant Forms of Mycobacterium Tuberculosis 2-trans enoyl-

(56) References Cited

OTHER PUBLICATIONS

ACP(CoA) Reductase and 3-ketoacyl-ACP(CoA) Reductase Enzymes ," *Prot. Expr. Purif.*, 34:118-125 (2004).
Polovnikova et al., "Structural and Kinetic Analysis of Catalysis by a Thiamin Diphosphate-Dependent Enzyme, Benzoylformate Decarboxylase," *Biochemistry*, 42(7):1820-1830 (2003).
Popp et al., "Fermentative Production of L-glycerol 3-phosphate Utilizing a *Saccharomyces cerevisiae* Strain With an Engineered Glycerol Biosynthetic Pathway," *Biotechnol. Bioeng.*, 100(3):497-505 (2008).
Porter et al., "Enzymatic Properties of Dimethylglycine Dehydrogenase and Sarcosine Dehydrogenase From Rat Liver," *Arch. Biochem. Biophys.*, 243(2):396-407 (1985).
Portnoy et al., "Aerobic Fermentation of D-glucose by an Evolved Cytochrome Oxidase-Deficient *Escherichia coli* Strain," *Appl. Environ. Microbiol.*, 74(24):7561-7569 (2008).
Powlowski et al., "Purification and Properties of the Physically Associated Meta-Cleavage Pathway Enzymes 4-hydroxy-2-ketovalerate Aldolase and Aldehyde Dehydrogenase (Acylating) From *Pseudomonas* Sp. Strain CF600 ," *J. Bacteriol.*, 175:377-385 (1993).
Prescott et al., "Acyl Carrier Protein," *Adv. Enzymol. Relat. Areas Mol.*, 36:269-311 (1972).
Priefert et al., "Identification and Molecular Characterization of the Acetyl Coenzyme A Synthetase Gene (acoE) of Alcaligenes Eutrophus ," *J. Bacteriol.*, 174:6590-6599 (1992).
Pritchard et al., "A General Model of Error-Prone PCR," *J. Theor. Biol.*, 234(4):497-509 (2005).
Pritchett et al., "Genetic, Physiological and Biochemical Characterization of Multiple Methanol Methyltransferase Isozymes in Methanosarcina Acetivorans C2A," *Mol. Microbiol.*, 56(5):1183-1194 (2005).
Pronk et al., "Pyruvate Metabolism in *Saccharomyces cerevisiae*," *Yeast*, 12(16):1607-1633 (1996).
Przybyla-Zawilask et al., "Genes of succinyl-CoA Ligase From *Saccharomyces cerevisiae*," *Eur. J. Biochem.*, 258(2):736-743 (1998).
Quash et al., "Novel Competitive Irreversible Inhibitors of Aldehyde Dehydrogenase (ALDH1): Restoration of Chemosensitivity of L1210 Cells Overexpressing ALDH1 and Induction of Apoptosis in BAF(3) Cells Overexpressing bcl(2)," *Biochem. Pharmacol.*, 64(8):1279-1292 (2002).
Rado et al., "Phosphotransacetylase From Bacillus Subtilis: Purification and Physiological Studies," *Biochim. Biophys. Acta*, 321(1):114-125 (1973).
Rafi et al., "Structure of Acyl Carrier Protein Bound to FabI, the FASII Enoyl Reductase From *Escherichia coli*," *J. Biol. Chem.*, 281(51):39285-39293 (2006).
Ragsdale, "Enzymology of the wood-Ljungdahl Pathway of Acetogenesis," *Ann. NY Acad. Sci.*, 1125:129-136 (2008).
Ragsdale, "Life With Carbon Monoxide," *Crit. Rev. Biochem. Mol. Biol.*, 39:165-195 (2004).
Ragsdale, "Pyruvate Ferredoxin Oxidoreductase and Its Radical Intermediate," *Chem. Rev.*, 103(6):2333-2346 (2003).
Rajpal et al., "A General Method for Greatly Improving the Affinity of Antibodies by Using Combinatorial Libraries," *Proc. Natl. Acad. Sci. USA*, 102(24):8466-8471 (2005).
Rakhely et al., "Cyanobacterial-type, Heteropentameric, NAD+-reducing NiFe Hydrogenase in the Purple Sulfur Photosynthetic Bacterium Thiocapsa Roseopersicina," *Appl. Environ. Microbiol.*, 70(2):722-728 (2004).
Ramos-Montanez et al., "Polymorphism and Regulation of the spxB (Pyruvate Oxidase) Virulence Factor Gene by a CBS-HotDog Domain Protein (SpxR) in Serotype 2 *Streptococcus pneumoniae*," *Mol. Micro.*, 67(4):729-746 (2008).
Ramos-Vera et al., "Autotrophic Carbon Dioxide Assimilation in Thermoproteales Revisited," *J. Bacteriol.*, 191(13):4286-4297 (2009).
Ramsay et al., "Molecular Enzymology of Carnitine Transfer and Transport," *Biochim. Biophys Acta*, 1546:21-42 (2001).

Rangarajan et al., "Structure of [NiFe] Hydrogenase Maturation Protein HypE From *Escherichia coli* and Its Interaction With HypF," *J. Bacteriol.*, 190(4):1447-1458 (2008).
Reda et al., "Reversible Interconversion of Carbon Dioxide and Formate by an Electroactive Enzyme," *Proc. Natl. Acad. Sci. USA*, 105(31):10654-10658 (2008).
Reetz et al., "Directed Evolution of an Enantioselective Enzyme Through Combinatorial Multiple-Cassette Mutagenesis," *Angew. Chem. Int. Ed Engl.*, 40(19):3589-3591 (2001).
Reetz et al., "Iterative Saturation Mutagenesis (ISM) for Rapid Directed Evolution of Functional Enzymes," *Nat. Protoc.*, 2(4):891-903 (2007).
Reetz et al., "Iterative Saturation Mutagenesis on the Basis of B Factors as a Strategy for Increasing Protein Thermostability," *Angew. Chem. Int. Ed. Engl.*, 45(46):7745-7751 (2006).
Reid et al., "*E. coli* Alkaline Phosphatase," *The Enzymes, vol. IV, 3$^{rd}$ Edition*, Boyer ed., Academic Press, New York, NY, pp. 373-415 (1971).
Reidhaar-Olson et al., "Combinatorial Cassette Mutagenesis as a Probe of the Informational Content of Protein Sequences," *Science*, 241(4861):53-57 (1988).
Reidhaar-Olson et al., "Random Mutagenesis of Protein Sequences Using Oligonucleotide Cassettes," *Methods Enzymol.*, 208:564-586 (1991).
Reiser et al., "Isolation of Mutants of Acinetobacter Calcoaceticus Deficient in Wax Ester Synthesis and Complementation of One Mutation With a Gene Encoding a Fatty Acyl Coenzyme A Reductase," *J. Bacteriol.*, 179:2969-2975 (1997).
Ricagno et al., "Formyl-CoA Transferase Encloses the CoA Binding Site at the Interface of an Interlocked Dimer," *EMBO J.*, 22(13):3210-3219 (2003).
Ringnér et al., "Folding Free Energies of 5'-UTRs Impact Post-Transcriptional Regulation on a Genomic Scale in Yeast," *PLoS Comput. Biol.*, 1(7):e72 (2005).
Riviere et al., "Acetyl:succinate CoA-transferase in Procyclic Trypanosoma Brucei. Gene Identification and Role in Carbohydrate Metabolism," *J. Biol. Chem.*, 279(44):45337-45346 (2004).
Ro et al., "Dihydroxyacetone Synthase From a Methanol-Utilizing Carboxydobacterium, Acinetobacter Sp. Strain JC1 DSM 3803," *J. Bacteriol.*, 179(19):6041-6047 (1997).
Roberts et al., "Cloning and Expression of the Gene Cluster Encoding Key Proteins Involved in acetyl-CoA Synthesis in Clostridium Thermoaceticum: CO Dehydrogenase, the corrinoid/Fe—S Protein, and Methyltransferase," *Proc. Natl. Acad. Sci. U.S.A.*, 86:32-36 (1989).
Roberts et al., "The Role of Enoyl-Coa Hydratase in the Metabolism of Isoleucine by Pseudomonas Putida," *Arch. Microbiol.*, 117(1):99-108 (1978).
Robinson et al., "Studies on Rat Brain Acyl-Coenzyme A Hydrolase (Short Chain)," *Biochem. Biophys. Res. Commun.*, 71(4):959-965 (1976).
Rock et al., "Role of Feedback Regulation of Pantothenate Kinase (CoaA) in Control of Coenzyme A Levels in *Escherichia coli*," *J. Bacteriol.*, 185: 3410-3415 (2003).
Rose et al., "Molecular Cloning of the Gene for the Yeast Homolog (ACB) of Diazepam Binding inhibitor/endozepine/acyl-CoA-binding Protein," *Proc. Nat. Acad. Sci. USA*, 89(23):11287-11291 (1992).
Rother et al., "Anaerobic Growth of Methanosarcina Acetivorans C2A on Carbon Monoxide: An Unusual Way of Life for a Methanogenic Archaeon," *Proc. Natl. Acad. Sci. U.S.A.*, 101(48):16929-16934 (2004).
Rother et al., "Genetic and Proteomic Analyses of CO Utilization by Methanosarcina Acetivorans," *Arch. Microbiol.*, 188(5):463-472 (2007).
Rowland et al., "CER4 Encodes an Alcohol-Forming Fatty Acyl-Coenzyme A Reductase Involved in Cuticular Wax Production in *Arabidopsis*," *Plant Physiol.*, 142(3):866-877 (2006).
Russell et al., Peptide Signals Encode Protein Localization *J. Bact.*, 189(21)7581-7585 (2007).
Sadowski, "The Flp Recombinase of the 2-microns Plasmid of *Saccharomyces cerevisiae*," *Prog. Nucleic Acid Res. Mol. Biol.*, 51:53-91 (1995).

(56) References Cited

OTHER PUBLICATIONS

Sakai et al., "Cloning and Sequencing of the Alcohol Oxidase-Encoding Gene (AOD1) From the Formaldehyde-Producing Asporogeneous Methylotrophic Yeast, Candida Boidinii S2," *Gene*, 114(1):67-73 (1992).

Salas et al., "Characterization of Substrate Specificity of Plant FatA and FatB acyl-ACP Thioesterases," *Arch. Biochem. Biophys.*, 403(1):25-34 (2002).

Sass et al., "Folding of Fumarase During Mitochondrial Import Determines Its Dual Targeting in Yeast," *J. Biol. Chem.*, 278(46):45109-45116 (2003).

Sato et al., "Poly [(R)-3-hydroxybutyrate] formation in *Escherichia coli* from glucose through an enoyl-CoA hydratase-mediated pathway," *J. Biosci. Bioeng.*, 103:38-44 (2007).

Sauer et al., "Methanol:coenzyme M Methyltransferase From Methanosarcina Barkeri. Purification, Properties and Encoding Genes of the Corrinoid Protein MT1," *Eur. J. Biochem.*, 243(3):670-677 (1997).

Sawers et al., "Characterization and Physiological Roles of Membrane-Bound Hydrogenase Isoenzymes From *Salmonella typhimurium*," *J. Bacteriol.*, 168(1):398-404 (1986).

Sawers et al., "Differential Expression of Hydrogenase Isoenzymes in *Escherichia coli* K-12: Evidence for a Third Isoenzyme," *J. Bacteriol.*, 164(3):1324-1331 (1985).

Sawers et al., "Purification and Properties of Membrane-Bound Hydrogenase Isoenzyme 1 From Anaerobically Grown *Escherichia coli* K12," *Eur. J. Biochem.*, 156(2):265-275 (1986).

Sawers, "The Hydrogenases and Formate Dehydrogenases of *Escherichia coli*," *Antonie Van Leeuwenhoek*, 66(1-3):57-88 (1994).

Schiedel et al., "Cloning, Expression, and Purification of Glyoxysomal 3-oxoacyl-CoA Thiolase From Sunflower Cotyledons," *Prot. Expr. Purif.*, 33(1):25-33 (2004).

Schink et al., "The Membrane-Bound Hydrogenase of Alcaligenes Eutrophus. I. Solubilization, Purification, and Biochemical Properties," *Biochim. Biophys. Acta*, 56(2):315-324 (1979).

Schirmer et al., "Microbial Biosynthesis of Alkanes," *Science*, 329(5991):559-562 (2010).

Schjerling et al., "Disruption of the Gene Encoding the acyl-CoA-binding Protein (ACB1) Perturbs acyl-CoA Metabolism in *Saccharomyces cerevisiae*," *J. Biol. Chem.*, 271(37):22514-22521 (1996).

Schneider et al., "Biosynthesis of the Prosthetic Group of Citrate Lyase," *Biochemistry*, 39(31):9438-9450 (2000).

Schneider et al., "Purification and Properties of Soluble Hydrogenase From Alcaligenes Eutrophus H 16," *Biochim. Biophys. Acta*, 452(1):66-80 (1976).

Schreiner et al., "Pyruvate:quinone Oxidoreductase in Corynebacterium Glutamicum: Molecular Analysis of the Pqo Gene, Significance of the Enzyme, and Phylogenetic Aspects," *J. Bacteriol.*, 188(4):1341-1350 (2006).

Schurmann et al., "Fructose-6-phosphate Aldolase is a Novel Class I Aldolase From *Escherichia coli* and is Related to a Novel Group of Bacterial Transaldolases," *J. Biol. Chem.*, 276(14):11055-11061 (2001).

Schweitzer et al., *J. Biotechnol.*, "The Serine Hydroxymethyltransferase Gene glyA in Corynebacterium Glutamicum is Controlled by GlyR," 139:214-221 (2009).

Seedorf et al., "The Genome of Clostridium Kluyveri, a Strict Anaerobe With Unique Metabolic Features," *Proc. Natl. Acad. Sci. USA*, 105(6):2128-2133 (2008).

Sekimoto et al., "Cloning and Molecular Characterization of Plant Aldehyde Oxidase," *J. Biol. Chem.*, 272(24):15280-15285 (1997).

Sekoguchi et al., "A Novel Mitochondrial Carnitine-Acylcarnitine Translocase Induced by Partial Hepatectomy and Fasting," *J. Biol. Chem.*, 278:38796-38802 (2003).

Selifonova et al., "Rapid Evolution of Novel Traits in Microorganisms," *Appl. Environ. Microbiol.*, 67(8):3645-3649 (2001).

Sen et al., "Developments in Directed Evolution for Improving Enzyme Functions," *Appl. Biochem. Biotechnol.*, 143(3):212-223 (2007).

Serov et al., "Engineering of Coenzyme Specificity of Formate Dehydrogenase From *Saccharomyces cerevisiae*," *Biochem. J.*, 367(Pt. 3):841-847 (2002).

Servinsky et al., "Arabinose is Metabolized via a Phosphoketolase Pathway in Clostridium Acetobutylicum ATCC 824," *J. Ind. Microbiol. Biotechnol.*, 39(12)1859-1867 (2012).

Sgorbati et al., "Purification and Properties of Two fructose-6-phosphate Phosphoketolases in Bifidobacterium," *Antonie Van Leeuwenhoek*, 42(1-2):49-57 (1976).

Shah et al., "Repressible Alkaline Phosphatase of *Staphylococcus aureus*," *J. Bacteriol.*, 94:780-781 (1967).

Shao et al., "Random-priming in Vitro Recombination: An Effective Tool for Directed Evolution," *Nucleic Acids Res.*, 26(2):681-683 (1998).

Sheppard et al., "Purification and Properties of NADH-dependent 5,10-methylenetetrahydrofolate Reductase (MetF) From *Escherichia coli*," *J. Bacteriol.*, 181(3):718-725 (1999).

Shigeoka et al., "Characterization and Molecular Properties of 2-oxoglutarate Decarboxylase From Euglena Gracilis," *Arch. Biochem. Biophys.*, 288(1):22-28 (1991).

Shimakata et al., "Purification and Characterization of 2-enoyl-CoA Reductase of Mycobacterium Smegmatis," *J. Biochem.*, 89(4):1075-1080 (1981).

Shimakata et al., "Purification of Plant acetyl-CoA:acyl Carrier Protein Transacylase," *Methods Enzym.*, 122:53-59 (1986).

Shimomura et al., "3-hydroxyisobutyryl-CoA Hydrolase," *Methods Enzymol.*, 324:229-240 (2000).

Shimomura et al., "Purification and Partial Characterization of 3-hydroxyisobutyryl-coenzyme A Hydrolase of Rat Liver," *J. Biol. Chem.*, 269(19):14248-14253 (1994).

Shingler et al., "Nucleotide Sequence and Functional Analysis of the Complete phenol/3,4-dimethylphenol Catabolic Pathway of *Pseudomonas* Sp. Strain CF600," *J. Bacteriol.*, 174(3):711-724 (1992).

Sieber et al., "Libraries of Hybrid Proteins From Distantly Related Sequences," *Nat. Biotechnol.* 19(5):456-460 (2001).

Siegert et al., "Exchanging the Substrate Specificities of Pyruvate Decarboxylase From Zymomonas Mobilis and Benzoylformate Decarboxylase From Pseudomonas Putida," *Protein Eng. Des. Sel.*, 18(7):345-357 (2005).

Siew et al., "Localization and Characteristics of Rat Liver Mitochondrial Aldehyde Dehydrogenases," *Arch. Biochem. Biophys.*, 176(2):638-649 (1976).

Sikorski et al., "A System of Shuttle Vectors and Yeast Host Strains Designed for Efficient Manipulation of DNA in *Saccharomyces cerevisiae*," *Genetics*, 122(1):19-27 (1989).

Simanshu et al., "Structure and Function of Enzymes Involved in the Anaerobic Degradation of L-threonine to Propionate," *J. Biosci.*, 32(6):1195-1206 (2007).

Simicevic et al., "DNA-centered Approaches to Characterize Regulatory protein-DNA Interaction Complexes," *Mol. Biosyst.*, 6(3):462-468 (2010).

Simon et al., "cDNA Cloning of *Brassica napus* malonyl-CoA:ACP Transacylase (MCAT) (Fab D) and Complementation of an *E. coli* MCAT Mutant ," *FEBS Lett.*, 435:204-206 (1998).

Singh, "Identification of Genes Encoding Acyl-Coa Reductases and Aldehyde Reductases in Mycobacterial Genome by Characterization of the Reductases Expressed in *E coli*," University of Central Florida, pp. 1-40 (2007).

Skarstedt et al., "*Escherichia coli* Acetate Kinase Mechanism Studied by Net Initial Rate, Equilibrium, and Independent Isotopic Exchange Kinetics," *J. Biol. Chem.*, 251:6775-6783 (1976).

Slater et al., "Multiple Beta-Ketothiolases Mediate Poly(beta-Hydroxyalkanoate) Copolymer Synthesis in Ralstonia Eutropha," *J. Bacteriol.*, 180(8):1979-1987 (1998).

Smit et al., "Identification, Cloning, and Characterization of a Lactococcus Lactis Branched-Chain Alpha-Keto Acid Decarboxylase Involved in Flavor Formation," *Appl. Environ. Microbiol.*, 71(1):303-311 (2005).

Smith et al., "Structural and Functional Organization of the Animal Fatty Acid Synthase," *Prog. Lipid Res.*, 42(4):289-317 (2003).

(56) References Cited

OTHER PUBLICATIONS

Smith et al., "Purification and Characteristics of a Gamma-Glutamyl Kinase Involved in *Escherichia coli* Proline Biosynthesis," *J. Bacteriol.*, 157(2):545-551 (1984).
Smith, "The Animal Fatty Acid Synthase: One Gene, One Polypeptide, Seven Enzymes," *FASEB J.*, 8(15):1248-1259 (1994).
Sohling et al., "Molecular Analysis of the Anaerobic Succinate Degradation Pathway in Clostridium Kluyveri," *J. Bacteriol.*, 178(3):871-880 (1996).
Sohling et al., "Purification and Characterization of a coenzyme-A-dependent Succinate-Semialdehyde Dehydrogenase From Clostridium Kluyveri," *Eur. J. Biochem.*, 212(1):121-127 (1993).
Soini et al., "High Cell Density Media for *Escherichia coli* are Generally Designed for Aerobic Cultivations—Consequences for Large-Scale Bioprocesses and Shake Flask Cultures," *Microb. Cell Fact.*, 7:26 (2008).
Sonderegger et al., "Metabolic Engineering of a Phosphoketolase Pathway for Pentose Catabolismin *Saccharomyces cerevisiae*," *Appl. Environ. Microbiol.*, 70(5):2892-2897 (2004).
Song et al., "Structure, Function, and Mechanism of the Phenylacetate Pathway Hot Dog-Fold Thioesterase PaaI," *J. Biol. Chem.*, 281(16):11028-11038 (2006).
Speer et al., "Sequence of the Gene for a NAD(P)-dependent Formaldehyde Dehydrogenase (Class III Alcohol Dehydrogenase) From a Marine Methanotroph Methylobacter Marinus A45," *FEMS Microbiol. Lett.*, 121(3):349-355 (1994).
Spellerberg et al., "Pyruvate Oxidase, as a Determinant of Virulence in *Streptococcus pneumoniae*," *Mol. Micro.*, 19(4):803-813 (1996).
Sramek et al., "Purification and Properties of *Escherichia coli* Coenzyme A-transferase," *Arch. Biochem. Biophys.*, 171(1):14-26 (1975).
St. Maurice et al., "Flavodoxin:quinone Reductase (FqrB): A Redox Partner of Pyruvate:ferredoxin Oxidoreductase That Reversibly Couples Pyruvate Oxidation to NADPH Production in Helicobacter Pylori and Campylobacter Jejuni," *J. Bacteriol.*, 189(13):4764-4773 (2007).
Stadtman, "Phosphotransacetylase from Clostridium kluyveri: Ae~P+ CoA⇌ Ac~ SCOA+ Pi," *Methods Enzymol.*, 1:596-599 (1955).
Starai et al., "Residue Leu-641 of Acetyl-CoA Synthetase is Critical for the Acetylation of Residue Lys-609 by the Protein Acetyltransferase Enzyme of *Salmonella enterica*," *J. Biol. Chem.*, 280(28):26200-26205 (2005).
Steffan et al., "Isolation and Characterization of the Yeast Gene Encoding the MDH3 Isozyme of Malate Dehydrogenase," *J. Biol. Chem.*, 267(34):24708-24715 (1992).
Steinbuchel et al., "A Multifunctional Fermentative Alcohol Dehydrogenase From the Strict Aerobe Alcaligenes Eutrophus: Purification and Properties," *Eur. J. Biochem.*, 141(3):555-564 (1984).
Steinbuchel et al., "NAD-linked L(+)-lactate Dehydrogenase From the Strict Aerobe Alcaligenes Eutrophus. 2. Kinetic Properties and Inhibition by Oxaloacetate," *Eur. J. Biochem.*, 130:329-334 (1983).
Stemmer, "DNA Shuffling by Random Fragmentation and Reassembly: In Vitro Recombination for Molecular Evolution," *Proc. Natl. Acad. Sci. USA*, 91:10747-10751 (1994).
Stemmer, "Rapid Evolution of a Protein in Vitro by DNA Shuffling," *Nature*, 370(6488):389-391 (1994).
Stephanopoulos, "Synthetic Biology and Metabolic Engineering," *ACS Synth. Biol.*, 1(11):514-525 (2012).
Stines-Chaumeil et al., "Mechanistic Characterization of the MSDH (Methylmalonate Semialdehyde Dehydrogenase) From Bacillus Subtilis," *Biochem. J.*, 395(1):107-115 (2006).
Stols et al., "New Vectors for Co-Expression of Proteins: Structure of Bacillus Subtilis ScoAB Obtained by High-Throughput Protocols," *Protein. Expr. Purif.*, 53(2):396-403 (2007).
Stols et al., "Expression of Ascaris Suum Malic Enzyme in a Mutant *Escherichia coli* Allows Production of Succinic Acid From Glucose," *Appl. Biochem. Biotechnol.*, 63-65(1):153-158 (1997).
Stols et al., "Production of Succinic Acid Through Overexpression of NAD(+)-dependent Malic Enzyme in an *Escherichia coli* Mutant," *Appl. Environ. Microbiol.*, 63(7):2695-2701 (1997).
Strejbis et al., "Enzymology of the Carnitine Biosynthesis Pathway," *IUBMB Life*, 62(5):357-362 (2010).
Strijbis et al., "Contributions of Carnitine Acetyltransferases to Intracellular Acetyl Unit Transport in Candida Albicans," *J. Biol. Chem.*, 285:24335-24346 (2010).
Strijbis et al., "Identification and Characterization of a Complete Carnitine Biosynthesis Pathway in Candida Albicans," *FASEB J.*, 23(8):2349-2359 (2009).
Stuible et al., "A Novel Phosphopantetheine:protein Transferase Activating Yeast Mitochondrial Acyl Carrier Protein," *J. Biol. Chem.*, 273(35):22334-22339 (1998).
Suematsu et al., "Molecular Cloning and Functional Expression of Rat Liver Cytosolic acetyl-CoA Hydrolase," *Eur. J. Biochem.*, 268(9):2700-2709 (2001).
Sulzenbacher et al., "Crystal Structure of *E.coli* Alcohol Dehydrogenase YqhD: Evidence of a Covalently Modified NADP Coenzyme," *J. Mol. Biol.*, 342(2):489-502 (2004).
Sumper et al., "Acetyl-CoA Carboxylase From Yeast," *Methods Enzym.*, 71:34-37 (1981).
Sunga et al., "The Pichia Pastoris Formaldehyde Dehydrogenase Gene (FLD1) as a Marker for Selection of Multicopy Expression Strains of P. Pastoris," *Gene* 330:39-47 (2004).
Sunohara et al., "Nascent-peptide-mediated Ribosome Stalling at a Stop Codon Induces mRNA Cleavage Resulting in Nonstop mRNA That is Recognized by tmRNA," *RNA* 10(3):378-386 (2004).
Sunohara et al., "Ribosome Stalling During Translation Elongation Induces Cleavage of mRNA Being Translated in *Escherichia coli*," *J. Biol. Chem.*, 279(15):15368-15375 (2004).
Suzuki et al., "*Corynebacterium* Sp. U-96 Contains a Cluster of Genes of Enzymes for the Catabolismof Sarcosine to Pyruvate," *Biosci. Biotechnol. Biochem.*, 69(5):952-956 (2005).
Suzuki et al., "GriC and GriD Constitute a Carboxylic Acid Reductase Involved in Grixazone Biosynthesis in *Streptomyces griseus*," *J. Antibiot.*, 60(6):380-387 (2007).
Suzuki et al., "Overexpression, Crystallization and Preliminary X-ray Analysis of xylulose-5-phosphate/fructose-6-phosphate Phosphoketolase From Bifidobacterium Breve," *Acta Crystallogr Sect F Struct Biol Cryst Commun.*, 66(Pt 8):941-943 (2010).
Suzuki, "Phosphotransacetylase of *Escherichia coli* B, Activation by Pyruvate and Inhibition by NADH and Certain Nucleotides," *Biochim. Biophys. Acta*, 191:559-569 (1969).
Svetlitchnyi et al., "A Functional Ni—Ni-[4Fe—4S] Cluster in the Monomeric acetyl-CoA Synthase From Carboxydothermus Hydrogenoformans," *Proc. Natl. Acad. Sci. U.S.A.*, 101(2):446-451 (2004).
Svetlitchnyi et al., "Two Membrane-Associated NiFeS-carbon Monoxide Dehydrogenases From the Anaerobic Carbon-Monoxide-Utilizing Eubacterium Carboxydothermus Hydrogenoformans," *J. Bacteriol.*, 183:5134-5144 (2001).
Takacs et al., "Formate Hydrogenlyase in the Hyperthermophilic Archaeon, Thermococcus Litoralis," *BMC.Microbiol.*, 8:88 (2008).
Takahashi et al., "Functional Assignment of the ORF2-iscS-iscU-iscA-hscB-hscA-fdx-ORF3 Gene Cluster Involved in the Assembly of Fe—S Clusters in *Escherichia coli*," *J. Biochem.*, 126(5):917-926 (1999).
Takahashi et al., "Metabolic Pathways for Cytotoxic End Product Formation From Glutamate- and Aspartate-Containing Peptides by Porphyromonas Gingivalis," *J. Bacteriol.*, 182:4704-4710 (2000).
Takahashi-Abbe et al., "Biochemical and Functional Properties of a Pyruvate Formate-Lyase (PFL)-activating System in Streptococcus Mutans," *Oral. Microbiol. Immunol.*, 18(5):293-297 (2003).
Takamura et al., "Purification and Some Properties of Malonate Decarboxylase from Pseudomonas Ovalis: An Oligomeric Enzyme with Bifunctional Properties," *Biochem. Int.*, 3:483-491 (1981).
Takeo, "Existence and Properties of Two Malic Enzymes in *Escherichia coli* Especially of NAD-linked Enzyme," *J. Biochem.*, 66(3):379-387 (1969).

(56) References Cited

OTHER PUBLICATIONS

Tallant et al., "Methylthiol:coenzyme M Methyltransferase From Methanosarcina Barkeri, an Enzyme of Methanogenesis From Dimethylsulfide and Methylmercaptopropionate," *J. Bacteriol.*, 179(22):6902-6911 (1997).
Tallant et al., "Coenzyme M Methylase Activity of the 480-kilodalton Corrinoid Protein From Methanosarcina Barkeri," *J. Bacteriol.*, 178(5):1295-1301 (1996).
Tallant et al., "The MtsA Subunit of the Methylthiol:coenzyme M Methyltransferase of Methanosarcina Barkeri Catalyses Both Half-Reactions of Corrinoid-Dependent Dimethylsulfide: Coenzyme M Methyl Transfer," *J. Biol. Chem.*, 276(6):4485-4493 (2001).
Tanaka et al., "Cloning and Characterization of a Human Orthologue of Testis-Specific Succinyl CoA: 3-oxo Acid CoA Transferase (Scot-t) cDNA," *Mol. Hum. Reprod.*, 8:16-23 (2002).
Tani et al., "Glycolaldehyde Dehydrognase, Its Involvement in Vitamin $B_6$ Biosynthetic Pathway of *Escherichia coli* B," *Agr. Biol. Chem.*, 38(10):2057-2058 (1974).
Tani et al., "Separation and Characterization of Glycolaldehyde Dehydrogenase Isozymes in *Escherichia coli* B," *Agric. Biol. Chem.*, 42:63-68 (1978).
Tani et al., "Thermostable NADP(+)-dependent Medium-Chain Alcohol Dehydrogenase From *Acinetobacter* Sp. Strain M-1: Purification and Characterization and Gene Expression in *Escherichia coli*," *Appl. Environ. Microbiol.*, 66(12):5231-5235 (2000).
Ter Schure et al., "Pyruvate Decarboxylase Catalyzes Decarboxylation of Branched-Chain 2-oxo Acids but is Not Essential for Fusel Alcohol Production by *Saccharomyces cerevisiae*," *Appl. Environ. Microbiol.*, 64(4):1303-1307 (1998).
Thauer, "Microbiology. A Fifth Pathway of Carbon Fixation," *Science*, 318:1732-1733 (2007).
Thorndike et al., "Production of Formaldehyde From N5-methyltetrahydrofolate by Normal and Leukemic Leukocytes," *Cancer Res.*, 37(4):1125-1132 (1977).
Thornton et al., "Primary Structure of the Monomer of the 12S Subunit of Transcarboxylase as Deduced From DNA and Characterization of the Product Expressed in *Escherichia coli*," *J. Bacteriol.*, 175(17):5301-5308 (1993).
Tian et al., "Variant Tricarboxylic Acid Cycle in Mycobacterium Tuberculosis: Identification of Alpha-Ketoglutarate Decarboxylase," *Proc. Natl. Acad. Sci. USA*, 102(30):10670-10675 (2005).
Todd et al., "Molecular dissection of bacterial acrylate catabolism—unexpected links with dimethylsulfoniopropionate catabolismand dimethyl sulfide production," *Environ. Microbiol.*, 12(2):237-243 (2010).
Todisco et al., "Identification of the Mitochondrial NAD+ Transporter in *Saccharomyces cerevisiae*," *J. Biol. Chem.*, 281(3):1524-1531 (2006).
Tokunaga et al., "Separation and Properties of the NAD-linked and NADP-linked Isozymes of Succinic Semialdehyde Dehydrogenase in Euglena Gracilis Z," *Biochem. Biophys. Act.* 429(1):55-62 (1976).
Toth et al., "The Ald Gene, Encoding a Coenzyme A-acylating Aldehyde Dehydrogenase, Distinguishes Clostridium Beijerinckii and Two Other Solvent-Producing Clostridia From Clostridium Acetobutylicum," *Appl. Environ. Microbiol.*, 65:4973-4980 (1999).
Toyota et al., "Differential Substrate Specificity and Kinetic Behavior of *Escherichia coli* YfdW and Oxalobacter Formigenes Formyl Coenzyme A Transferase," *J. Bacteriol.*, 190(7):2556-2564 (2008).
Tseng et al., "Metabolic Engineering of *Escherichia coli* for Enhanced Production of (R)- and (S)-3-hydroxybutyrate," *Appl. Environ. Microbiol.*, 75(10):3137-3145 (2009).
Tucci et al., "A Novel Prokaryotic trans-2-enoyl-CoA Reductase From the Spirochete Treponema Denticola," *FEBS Lett.*, 581(8):1561-1566 (2007).
Uttaro et al., "Purification and Characterisation of a Novel Iso-Propanol Dehydrogenase From *Phytomonas* Sp," *Mol. Biochem. Parasitol.*, 85(2):213-219 (1997).
Valdes-Hevia et al., "Isolation and Characterization of the Gene Encoding Phosphoenolpyruvate Carboxykinase From *Saccharomyces cerevisiae*" *FEBS Lett.*, 258(2):313-316 (1989).

Vamecq et al., "The Microsomal dicarboxylyl-CoA Synthetase," *Biochemical J.*, 230:683-693 (1985).
Van Der Klei et al., "The Hansenula Polymorpha per6 Mutant is Affected in Two Adjacent Genes Which Encode Dihydroxyacetone Kinase and a Novel Protein, Pak1p, Involved in Peroxisome Integrity," *Curr. Genet.*, 34(1):1-11 (1998).
Van Grinsven et al.,"Acetate:succinate CoA-transferase in the Hydrogenosomes of Trichomonas Vaginalis: Identification and Characterization," *J. Biol. Chem.*, 283(3):1411-1418 (2008).
Van Maris et al., "Overproduction of Threonine Aldolase Circumvents the Biosynthetic Role of Pyruvate Decarboxylase in Glucose-Limited Chemostat Cultures of *Saccharomyces cerevisiae*," *Appl. Environ. Microbiol.*, 69(4):2094-2099 (2003).
Van Mourik et al., "Functional analysis of a Campylobacter jejuni alkaline phosphatase secreted via the Tat export machinery," *Microbiol.*, 154:584-592 (2008).
Van Mullem et al., "Construction of a Set of *Saccharomyces cerevisiae* Vectors Designed for Recombinational Cloning," *Yeast*, 20(8):739-746 (2003).
Van Roermund et al., "The Human Peroxisomal ABC Half Transporter ALDP Functions as a Homodimer and Accepts acyl-CoA Esters," *FASEB J.*, 22:4201-4208 (2008).
Van Roermund et al., "The Membrane of Peroxisomes in *Saccharomyces cerevisiae* is Impermeable to NAD(H) and acetyl-CoA Under in Vivo Conditions," *EMBO J.*, 14:3480-3486 (1995).
Van Vliet et al., "The Iron-Induced Ferredoxin FdxA of Campylobacter Jejuni is Involved in Aerotolerance," *FEMS Microbiol. Lett.*, 196(2):189-193 (2001).
Vanderwinkel et al., "Growth of *Escherichia coli* on Fatty Acids: Requirement for Coenzyme A Transferase Activity," *Biochem. Biophys. Res. Commun.*, 33(6):902-908 (1968).
Vardar-Schara et al., "Metabolically Engineered Bacteria for Producing Hydrogen via Fermentation," *Microbial Biotechnol.*, 1(2):107-125 (2008).
Vazquez et al., "Phosphotransbutyrylase Expression in Bacillus Megaterium," *Curr. Microbiol.*, 42(5):345-349 (2001).
Vellanki et al., "Expression of Hepatitis B Surface Antigen in *Saccharomyces cerevisiae* Utilizing glyceraldeyhyde-3-phosphate Dehydrogenase Promoter of Pichia Pastoris," *Biotechnol. Lett.*, 29(2):313-318 (2007).
Venkitasubramanian et al., "Biocatalytic Reduction of Carboxylic Acids: Mechanism and Applications," *Biocatalysis in the Pharmaceutical and Biotechnology Industires*, Patel ed., CRC Press LLC, Boca Raton, FL, pp. 425-440 (2006).
Venkitasubramanian et al., "Reduction of Carboxylic Acids by Nocardia Aldehyde Oxidoreductase Requires a Phosphopantetheinylated Enzyme," *J. Biol. Chem.*, 282(1):478-485 (2007).
Verleur et al., "Transport of Activated Fatty Acids by the Peroxisomal ATP-binding-cassette Transporter Pxa2 in a Semi-Intact Yeast Cell System," *Eur. J. Biochem.*, 249(3):657-661 (1997).
Verwoert et al., "Cloning, Nucleotide Sequence, and Expression of the *Escherichia coli* fabD Gene, Encoding Malonyl Coenzyme A-acyl Carrier Protein Transacylase," *J. Bacteriol.*, 174:2851-2857 (1992).
Volkov et al., "Random Chimeragenesis by Heteroduplex Recombination," *Methods Enzymol.*, 328:456-463 (2000).
Volkov et al., "Recombination and Chimeragenesis by in Vitro Heteroduplex Formation and in Vivo Repair," *Nucleic Acids Res.*, 27(18):e18 (1999).
Vonck et al., "Electron Microscopic Analysis and Biochemical Characterization of a Novel Methanol Dehydrogenase From the Thermotolerant *Bacillus* Sp. C1," *J. Biol. Chem.*, 266(6):3949-3954 (1991).
Vorholt et al., "Novel Formaldehyde-Activating Enzyme in Methylobacterium Extorquens AMI Required for Growth on Methanol," *J. Bacteriol.*, 182(23):6645-6650 (2000).
Wahlen et al., "Purification, Characterization, and Potential Bacterial Wax Production Role of an NADPH-dependent Fatty Aldehyde Reductase From Marinobacter Aquaeolei VT8," *Appl. Environ. Microbiol.*, 75(9):2758-2764 (2009).
Wakil et al., "Studies on the Fatty Acid Oxidizing System of Animal Tissues. VI. beta-Hydroxyacyl Coenzyme A Dehydrogenase," *J. Biol. Chem.*, 207(2):631-638 (1954).

(56) References Cited

OTHER PUBLICATIONS

Walker et al., "Yeast Pyruvate Carboxylase: Identification of Two Genes Encoding Isoenzymes," *Biochem. Biophys. Res. Commun.*, 176(3):1210-1217 (1991).
Walter et al., "Molecular Characterization of Two Clostridium Acetobutylicum ATCC 824 Butanol Dehydrogenase Isozyme Genes," *J. Bacteriol.*, 174(22):7149-7158 (1992).
Walter et al., "Sequence and Arrangement of Two Genes of the Butyrate-Synthesis Pathway of Clostridium Acetobutylicum ATCC 824," *Gene*, 134(1):107-111 (1993).
Wang et al., "NADP+ Reduction With Reduced Ferredoxin and NADP+ Reduction With NADH are Coupled via an Electron-Bifurcating Enzyme Complex in Clostridium Kluyveri," *J. Bacteriol.*, 192(19):5115-5123 (2010).
Wang et al., "Activation of Silent Genes by Transposons Tn5 and Tn10," *Genetics*, 120(4):875-885 (1988).
Wang et al., "Identification of a Type III Thioesterase Reveals the Function of an Operon Crucial for Mtb Virulence," *Chem. Biol.*, 14(5):543-551 (2007).
Wang et al., "Molecular Cloning and Functional Identification of a Novel phenylacetyl-CoA Ligase Gene From Penicillium Chrysogenum," *Biochem. Biophy. Res. Commun.*, 360(2):453-458 (2007).
Wang et al., "Molecular Cloning, Characterization, and Potential Roles of Cytosolic and Mitochondrial Aldehyde Dehydrogenases in Ethanol Metabolism in *Saccharomyces cerevisiae*," *J. Bacteriol.*, 180(4):822-830 (1998).
Wang et al., "Overview of Regulatory Strategies and Molecular Elements in Metabolic Engineering of Bacteria," *Mol. Biotechnol.* 52(2):300-308 (2012).
Weidner et al., "Molecular Characterization of the Genes Encoding Pyruvate Formate-Lyase and Its Activating Enzyme of Clostridium Pasteurianum," *J. Bacteriol.*, 178(8):2440-2444 (1996).
Welch et al., "Purification and Characterization of the NADH-dependent Butanol Dehydrogenase From Clostridium Acetobutylicum (ATCC 824)," *Arch. Biochem. Biophys.*, 273(2):309-318 (1989).
Werther et al., "Amino Acids Allosterically Regulate the Thiamine Diphosphate-Dependent Alpha-Keto Acid Decarboxylase From Mycobacterium Tuberculosis," *J. Biol. Chem.*, 283(9):5344-5354 (2008).
Westin et al., "The Identification of a succinyl-CoA Thioesterase Suggests a Novel Pathway for Succinate Production in Peroxisomes," *J. Biol. Chem.*, 280(46):38125-38132 (2005).
Whisstock et al., "Prediction of Protein Function from Protein Sequence and Struxture," *Quarterly Reviews of Biophysics*, 3:307-340 (2003).
White et al., "The structural biology of type II fatty acid biosynthesis," *Annu. Rev. Biochem.*, 74:791-831 (2005).
Whitehead et al., "Cloning and Expression in *Escherichia coli* of the Gene for 10-formyltetrahydrofolate Synthetase From Clostridium Acidiurici ("Clostridium Acidi-Urici")," *J. Bacteriol.*, 167:205-209 (1986).
Whitehead et al., "Nucleotide Sequence of the Clostridium Acidiurici ("Clostridium Acidi-Urici") Gene for 10-formyltetrahydrofolate Synthetase Shows Extensive Amino Acid Homology With the Trifunctional Enzyme C1-tetrahydrofolate Synthase From *Saccharomyces cerevisiae*," *J. Bacteriol.*, 170:3255-3261 (1988).
Wieland et al., "Engineering of Ribozyme-Based Riboswitches for Mammalian Cells," *Methods*, 56(3):351-357 (2012).
Wiesenborn et al., "Coenzyme A Transferase From Clostridium Acetobutylicum ATCC 824 and Its Role in the Uptake of Acids," *Appl. Environ. Microbiol.*, 55(2):323-329 (1989).
Wiesenborn et al., "Phosphotransbutyrylase From Clostridium Acetobutylicum ATCC 824 and Its Role in Acidogenesis," *Appl. Environ. Microbiol.*, 55(2):317-322 (1989).
Winkler et al., "A New Type of a Multifunctional Beta-Oxidation Enzyme in Euglena," *Plant Physiol.*, 131(2):753-762 (2003).
Winzeler et al., "Functional Characterization of the *S. cerevisiae* Genome by Gene Deletion and Parallel Analysis," *Science*, 285(5429):901-906 (1999).
Winzer et al., "Acetate Kinase From Clostridium Acetobutylicum: A Highly Specific Enzyme That is Actively Transcribed During Acidogenesis and Solventogenesis," *Microbioloy*, 143 (Pt 10):3279-3286 (1997).
Winzer et al., "Differential Regulation of Two Thiolase Genes From Clostridium Acetobutylicum DSM 792," *J. Mol. Microbiol. Biotechnol.*, 2(4):531-541 (2000).
Witkowski et al., "Conversion of a beta-ketoacyl synthase to a malonyl decarboxylase by replacement of the active-site cysteine with glutamine," *Biochemistry*, 38:11643-11650 (1999).
Wong et al., "Molecular Properties of Pyruvate Formate-Lyase Activating Enzyme," *Biochemistry*, 32:14102-14110 (1993).
Wong et al., "Sequence Saturation Mutagenesis (SeSaM): A Novel Method for Directed Evolution," *Nucleic Acids Res.*, 32(3):e26 (2004).
Wong et al., "Sequence Saturation Mutagenesis With Tunable Mutation Frequencies," *Anal. Biochem.*, 341(1):187-189 (2005).
Wong et al., "Transversion-enriched Sequence Saturation Mutagenesis (SeSaM-Tv+): A Random Mutagenesis Method With Consecutive Nucleotide Exchanges That Complements the Bias of Error-Prone PCR," *Biotechnol. J.*, 3(1):74-82 (2008).
Wrensford et al., "An Acyl-Coenzyme A Chain Length Dependent Assay for 3-oxoacyl-coenzyme A Thiolases Employing Acetyldithio-Coenzyme A," *Anal. Biochem.*, 192:49-54 (1991).
Wu et al., "Life in Hot Carbon Monoxide: The Complete Genome Sequence of Carboxydothermus Hydrogenoformans Z-2901," *PLoS Genet.*, 1:e65 (2005).
Wu et al., "Site-saturation mutagenesis of formate dehydrogenase from Candida bodinii creating effective NADP+-dependent FDH enzymes," *J. Mol. Cat. B: Enzym.*, 61(3-4):157-161 (2009).
Wynn et al., "Chaperonins groEL and groES Promote Assembly of Heterotetramers (Alpha 2 Beta 2) of Mammalian Mitochondrial Branched-Chain Alpha-Keto Acid Decarboxylase in *Escherichia coli*," *J. Biol. Chem.*, 267(18):12400-12403 (1992).
Wynn et al., "Cloning and Expression in *Escherichia coli* of Mature E1 Beta Subunit of Bovine Mitochondrial Branched-Chain Alpha-Keto Acid Dehydrogenase Complex. Mapping of the E1 Beta-Binding Region on E2," *J. Biol. Chem.*, 267(3):1881-1887 (1992).
Yabutani et al., "Analysis of Beta-Ketothiolase and acetoacetyl-CoA Reductase Genes of a Methylotrophic Bacterium, Paracoccus Denitrificans, and Their Expression in *Escherichia coli*," *FEMS Microbiol. Lett.*, 133:85-90 (1995).
Yamamoto et al., "Carboxylation Reaction Catalyzed by 2-oxoglutarate:ferredoxin Oxidoreductases From Hydrogenobacter Thermophilus," *Extremophiles*, 14(1):79-85 (2010).
Yamamoto et al., "Purification and Properties of NADP-dependent Formate Dehydrogenase From Clostridium Thermoaceticum, a Tungsten-Selenium-Iron Protein," *J. Biol. Chem.*, 258(3):1826-1832 (1983).
Yang et al., "Nucleotide Sequence of the fadA Gene. Primary Structure of 3-ketoacyl-coenzyme A Thiolase From *Escherichia coli* and the Structural Organization of the fadAB Operon," *J. Biol. Chem.*, 265(18):10424-10429 (1990).
Yang et al., "Collaborative Spirit of Histone Deacetylases in Regulating Chromatin Structure and Gene Expression," *Curr. Opin. Genet. Dev.*, 13(2):143-153 (2003).
Yang et al., "Location of the fadBA Operon on the Physical Map of *Escherichia coli*," *J. Bacteriol.*, 173(23):7405-7406 (1991).
Yang et al., "Nucleotide Sequence of the Promoter and fadB Gene of the fadBA Operon and Primary Structure of the Multifunctional Fatty Acid Oxidation Protein From *Escherichia coli*," *Biochemistry*, 30(27):6788-6795 (1990).
Yasueda et al., "Bacillus Subtilis yckG and yckF Encode Two Key Enzymes of the Ribulose Monophosphate Pathway Used by Methylotrophs, and yckH is Required for Their Expression," *J. Bacteriol.*, 181(23):7154-7160 (1999).
Yebra et al., "Identification of a Gene Cluster Enabling Lactobacillus Casei BL23 to Utilize Myo-Inositol," *Appl. Envirn. Microbiol.*, 73(12):3850-3858 (2007).
Yin et al., "The Gene Encoding xylulose-5-phosphate/fructose-6-phosphate Phosphoketolase (Xfp) is Conserved Among *Bifidobacterium*

(56) References Cited

OTHER PUBLICATIONS

Species Within a More Variable Region of the Genome and Both are Useful for Strain Identification," *FEMS Microbiol Lett.*, 246(2):251-257 (2005).

Ylianttila et al., "Crystal structure of yeast peroxisomal multifunctional enzyme: structural basis for substrate specificity of (3R)-hydroxyacyl-CoA dehydrogenase units," *J. Mol. Biol.*, 358:1286-1295 (2006).

Ylianttila et al., "Site-directed Mutagenesis to Enable and Improve Crystallizability of Candida Tropicalis (3R)-hydroxyacyl-CoA Dehydrogenase," *Biochem. Biophys. Res. Commun.*, 324(1):25-30 (2004).

Yoon et al., "NADH:ferredoxin reductase and NAD-reducing hydrogenase activities in Hydrogenobacter thermophilus strain TK-6," *FEMS Microbiol. Lett.*, 139:139-142 (1996).

Youngleson et al., "Homology Between Hydroxybutyryl and Hydroxyacyl Coenzyme A Dehydrogenase Enzymes From Clostridium Acetobutylicum Fermentation and Vertebrate Fatty Acid Beta-Oxidation Pathways," *J. Bacteriol.*, 171(12):6800-6807 (1989).

Yu et al., "Enzymatic Functions of Wild Tomato Methylketone Synthases 1 and 2," *Plant Physiol.*, 154(1):67-77 (2010).

Yuan et al., "Prokaryotic Ubiquitin-Like This Fusion Enhances the Heterologous Protein Overexpression and Aggregation in *Escherichia coli*," *PLoS One*, 8(4):e62529 (2013).

Yurimoto et al., "Yeast Methylotrophy: Metabolism, Gene Regulation and Peroxisome Homeostasis," *Int. J. Microbiol.*, 101298 (2011).

Zaccai et al., "Crystal Structure of a 3-oxoacyl-(acylcarrier Protein) Reductase (BA3989) From Bacillus Anthracis at 2.4-A Resolution," *Prot. Struct. Funct. Gen.*, 70(2):562-567 (2008).

Zeiher et al., "Identification and Characterization of Mitochondrial Acetyl-Coenzyme A Hydrolase From *Pisum sativum* L. Seedlings," *Plant. Physiol.*, 94(1):20-27 (1990).

Zeng et al., "Expression and Purification of His-tagged Rat Mitochondrial 3-ketoacyl-CoA Thiolase Wild-Type and His352 Mutant Proteins," *Prot. Expr. Purif.*, 35: 320-326 (2004).

Zhang et al., "Key Residues Responsible for Acyl Carrier Protein and Beta-Ketoacyl-Acyl Carrier Protein Reductase (FabG) Interaction," *J. Biol. Chem.*, 278(52):52935-52943 (2003).

Zhang et al., "Metabolic evolution of energy-conserving pathways for succinate production in *Escherichia coli*," *Proc. Natl. Acad. Sci. USA*, 106(48):20180-20185 (2009).

Zhang et al., "The Phosphonopyruvate Decarboxylase From Bacteroides Fragilis," *J. Biol. Chem.*, 278(42):41302-41308 (2003).

Zhang et al., "The Tricarboxylic Acid Cycle in Cyanobacteria," *Science*, 334(6062):1551-1553 (2011).

Zhao et al., "Molecular Evolution by Staggered Extension Process (StEP) in Vitro Recombination," *Nat. Biotechnol.*, 16(3):258-261 (1998).

Zhou et al., "Engineering a Native Homoethanol Pathway in *Escherichia coli* B for Ethanol Production," *Biotechnol. Lett.*, 30(2):335-342 (2008).

Zhou et al., "Expression, Purification, and Characterization of Human malonyl-CoA Decarboxylase," *Prot. Expr. Pur.*, 34(2):261-269 (2004).

Zhou et al., "Isolation, Crystallization and Preliminary X-ray Analysis of a Methanol-Induced Corrinoid Protein From Moorella Thermoacetica," *Acta Crystallogr. Sect. F. Struct. Biol. Cyrst. Commun.*, 61:537-540 (2005).

Zhou et al., "The Remarkable Structural and Functional Organization of the Eukaryotic Pyruvate Dehydrogenase Complexes," *Proc. Natl. Acad. Sci. USA*, 98(26):14802-14807 (2001).

Zhu et al., "Cleavage-dependent Ligation by the FLP Recombinase. Characterization of a Mutant FLP Protein With an Alteration in a Catalytic Amino Acid," *J. Biol. Chem.*, 270(39):23044-23054 (1995).

Zhuang et al., "The YbgC Protein Encoded by the ybgC Gene of the Tol-Pal Gene Cluster of Haemophilus Influenzae Catalyzes Acyl-Coenzyme A Thioester Hydrolysis," *FEBS Lett.*, 516(1-3):161-163 (2002).

\* cited by examiner

EV2: two empty plasmid control
EV3: three empty plasmid control
Thl: 1491/560
Hbd: 1495
Ald: 707
Adh: 28
PDH: ALD6+Acs$_m$

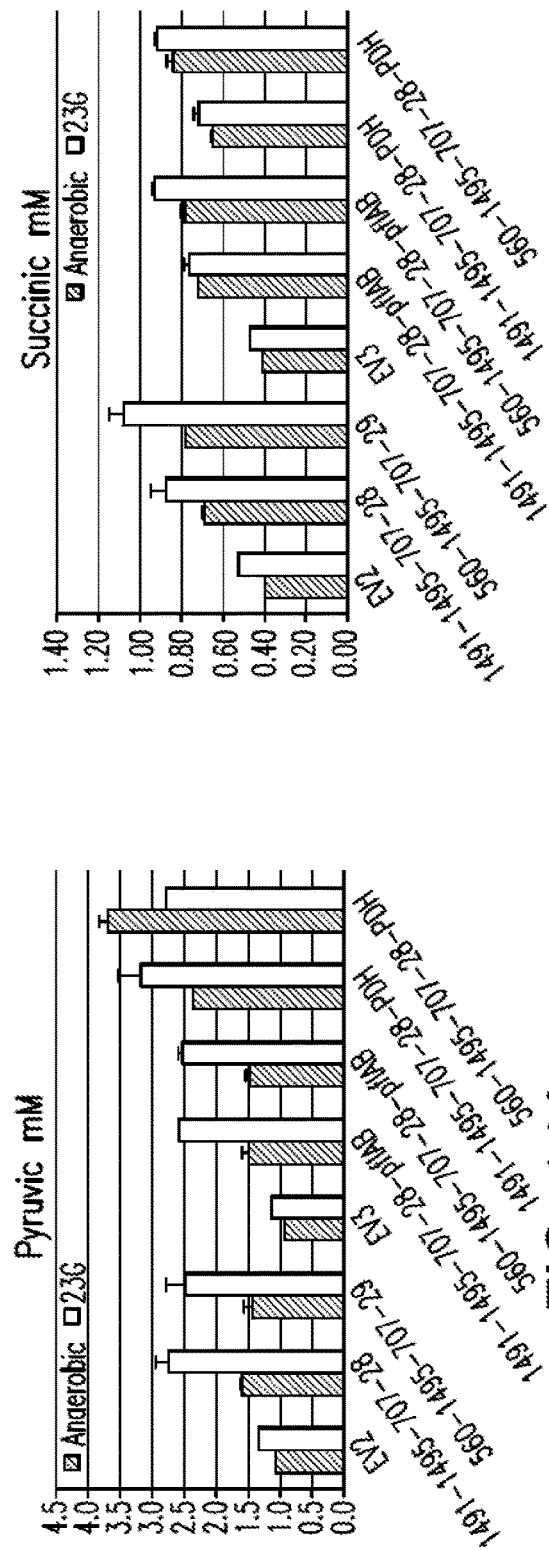
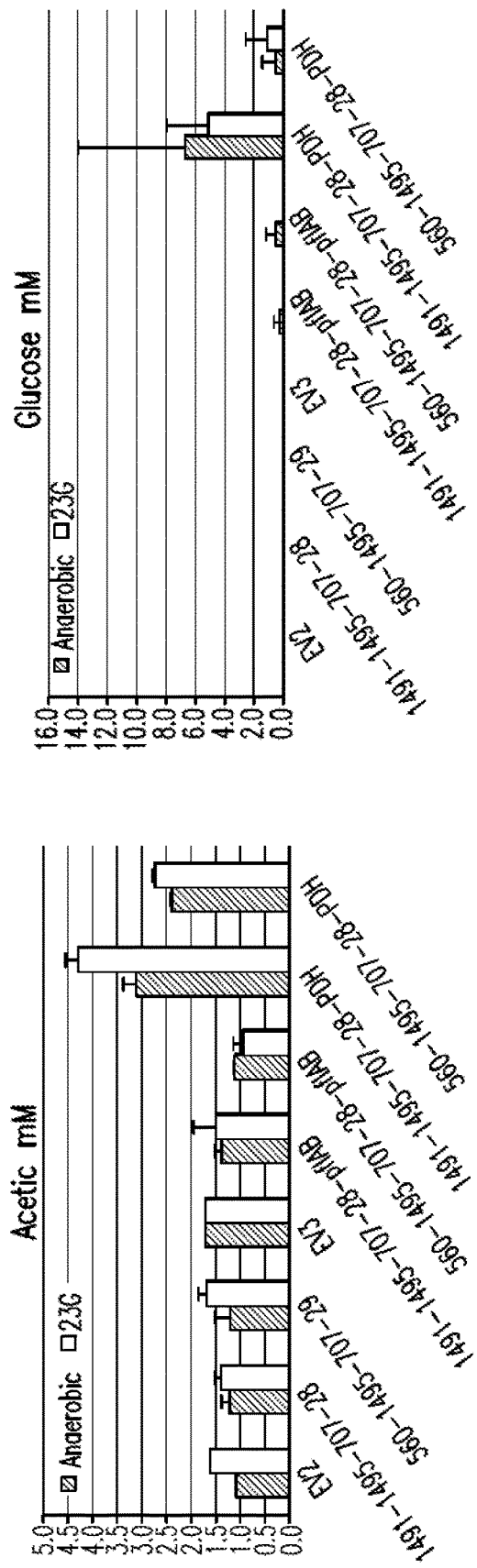
FIG. 14A
FIG. 14B
FIG. 14C
FIG. 14D

METHODS FOR ENHANCING MICROBIAL PRODUCTION OF SPECIFIC LENGTH FATTY ALCOHOLS IN THE PRESENCE OF METHANOL

CROSS-REFERENCE TO RELATED APPLICATIONS

This application is a continuation of United States application Ser. No. 15/038,922, ABN, which is a United States National Stage Application under 35 U.S.C. § 371 of International Patent Application No. PCT/US2014/067282, filed Nov. 25, 2014, which claims the benefit of priority of U.S. Provisional Application Nos. 61/945,003, filed Feb. 26, 2014, 61/911,374, filed Dec. 3, 2013, and 61/908,652, filed Nov. 25, 2013, the entire contents of which are each incorporated herein by reference.

SEQUENCE LISTING

The instant application contains a Sequence Listing which has been submitted electronically in ASCII format and is hereby incorporated by reference in its entirety. Said ASCII copy, created on Jan. 5, 2022, is named 199683-999336_US_SL.txt and is 23,022 bytes in size.

BACKGROUND OF THE INVENTION

The present invention relates generally to biosynthetic processes, and more specifically to organisms having specific length fatty alcohol, fatty aldehyde or fatty acid biosynthetic capacity or having isopropanol biosynthetic capacity.

Primary alcohols are a product class of compounds having a variety of industrial applications which include a variety of biofuels and specialty chemicals. Primary alcohols also can be used to make a large number of additional industrial products including polymers and surfactants. For example, higher primary alcohols, also known as fatty alcohols ($C_4$-$C_{24}$) and their ethoxylates are used as surfactants in many consumer detergents, cleaning products and personal care products worldwide such as laundry powders and liquids, dishwashing liquid and hard surface cleaners. They are also used in the manufacture of a variety of industrial chemicals and in lubricating oil additives. Specific length fatty alcohols, such as octanol and hexanol, have useful organoleptic properties and have long been employed as fragrance and flavor materials. Smaller chain length $C_4$-$C_8$ alcohols (e.g., butanol) are used as chemical intermediates for production of derivatives such as acrylates used in paints, coatings, and adhesives applications.

Fatty alcohols are currently produced from, for example, hydrogenation of fatty acids, hydroformylation of terminal olefins, partial oxidation of n-paraffins and the A1-catalyzed polymerization of ethylene. Unfortunately, it is not commercially viable to produce fatty alcohols directly from the oxidation of petroleum-based linear hydrocarbons (n-paraffins). This impracticality is because the oxidation of n-paraffins produces primarily secondary alcohols, tertiary alcohols or ketones, or a mixture of these compounds, but does not produce high yields of fatty alcohols. Additionally, currently known methods for producing fatty alcohols suffer from the disadvantage that they are restricted to feedstock which is relatively expensive, notably ethylene, which is produced via the thermal cracking of petroleum. In addition, current methods require several steps, and several catalyst types.

Fatty alcohol production by microorganisms involves fatty acid synthesis followed by acyl-reduction steps. The universal fatty acid biosynthesis pathway found in most cells has been investigated for production of fatty alcohols and other fatty acid derivatives. There is currently a great deal of improvement that can be achieved to provide more efficient biosynthesis pathways for fatty alcohol production with significantly higher theoretical product and energy yields.

Isopropanol (IPA) is a colorless, flammable liquid that mixes completely with most solvents, including water. The largest use for IPA is as a solvent, including its well known yet small use as "rubbing alcohol," which is a mixture of IPA and water. As a solvent, IPA is found in many everyday products such as paints, lacquers, thinners, inks, adhesives, general-purpose cleaners, disinfectants, cosmetics, toiletries, de-icers, and pharmaceuticals. Low-grade IPA is also used in motor oils. The second largest use is as a chemical intermediate for the production of isopropylamines, isopropylethers, and isopropyl esters. Isopropanol can potentially be dehydrated to form propylene, a polymer precursor with an annual market of more than 2 million metric tons.

Current global production capacity of IPA is approximately 6 B lb/yr, with approximately 74% of global IPA capacity concentrated in the US, Europe, and Japan. Isopropanol is manufactured by two petrochemical routes. The predominant process entails the hydration of propylene either with or without sulfuric acid catalysis. Secondarily, IPA is produced via hydrogenation of acetone, which is a by-product formed in the production of phenol and propylene oxide. High-priced propylene is currently driving costs up and margins down throughout the chemical industry motivating the need for an expanded range of low cost feedstocks.

Thus, there exists a need for alternative means for effectively producing commercial quantities of fatty alcohols, isopropanol and related compounds. The present invention satisfies this need and provides related advantages as well.

SUMMARY OF INVENTION

The invention provides non-naturally occurring microbial organisms containing a fatty alcohol, fatty aldehyde, fatty acid or isopropanol pathway. For production of a fatty alcohol, fatty aldehyde, or fatty acid, in some embodiments, the non-naturally occurring microbial organism of the invention has: a formaldehyde fixation pathway, a formate assimilation pathway, and/or a methanol metabolic pathway; and a malonyl-CoA independent fatty acyl-CoA elongation (MI-FAE) cycle and/or a malonyl-CoA dependent fatty acyl-CoA elongation (MD-FAE) cycle in combination with a termination pathway, as depicted in FIGS. 1, 2, 7, 8 and 10. Alternatively, in some embodiments, the non-naturally occurring microbial organism of the invention has: a formaldehyde fixation pathway, a formate assimilation pathway, and/or a methanol metabolic pathway; and a fatty acyl-ACP elongation (FAACPE) cycle in combination with a termination pathway, as depicted in FIGS. 1, 10 and 12.

For production of isopropanol, in some embodiments, the non-naturally occurring microbial organism of the invention has: a formaldehyde fixation pathway, a formate assimilation pathway, and/or a methanol metabolic pathway; and an isopropanol pathway, as depicted in FIGS. 1, 10 and 11.

In one aspect, the formaldehyde fixation pathway, formate assimilation pathway, and/or a methanol metabolic pathway present in the microbial organisms of the invention enhances the availability of substrates and/or pathway intermediates, such as acetyl-CoA and malonyl-CoA, and/or reducing equivalents, which can be utilized for fatty alcohol, fatty aldehyde, fatty acid, or isopropanol production through one or more fatty alcohol, fatty aldehyde, fatty acid, or isopropanol pathways of the invention. For example, in some embodiments, a non-naturally occurring microbial organism of the invention that includes a methanol metabolic pathway can enhance the availability of reducing equivalents in the presence of methanol and/or convert methanol to formaldehyde, a substrate for the formaldehyde fixation pathway. Likewise, a non-naturally occurring microbial organism of the invention having a formate assimilation pathway can reutilize formate to generate substrates and pathway intermediates such as formaldehyde, pyruvate and/or acetyl-CoA. Such substrates, intermediates and reducing equivalents can be used to increase the yield of a fatty alcohol, a fatty aldehyde, a fatty acid, or isopropanol produced by the microbial organism.

In some embodiments, the microbial organisms of the invention advantageously enhance the production of substrates and/or pathway intermediates for the production of a chain length specific fatty alcohol, fatty aldehyde, fatty acid. Accordingly, some embodiments, one or more enzymes of the formaldehyde fixation pathway, formate assimilation pathway, methanol metabolic pathway, MI-FAE cycle, MD-FAE cycle, FAACPE cycle or termination pathway is encoded by at least one exogenous nucleic acid and is expressed in a sufficient amount to produce a fatty alcohol, fatty aldehyde or fatty acid of Formula (I):

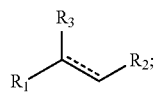
(I)

wherein $R_1$ is $C_{1-24}$ linear alkyl; $R_2$ is $CH_2OH$, CHO, or COOH; $R_3$ is H, OH, or oxo (=O); and ------ represents a single or double bond with the proviso that the valency of the carbon atom to which $R_3$ is attached is four. In order to be able to produce a chain length specific compound, the enzymes of the MI-FAE cycle, the MD-FAE cycle, the FAACPE cycle and/or the termination pathway are selective for a particular substrate. Accordingly, in some embodiments, the substrate of each of the enzymes of the MI-FAE cycle, the MD-FAE cycle and/or the termination pathway are independently selected from a compound of Formula (II), malonyl-CoA, propionyl-CoA or acetyl-CoA:

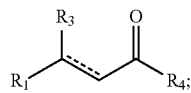
(II)

wherein $R_1$ is $C_{1-24}$ linear alkyl; $R_3$ is H, OH, or oxo (=O); $R_4$ is S-CoA, ACP, OH or H; and ------ represents a single or double bond with the proviso that the valency of the carbon atom to which $R_3$ is attached is four, wherein said one or more enzymes of the MI-FAE cycle are each selective for a compound of Formula (II) having a number of carbon atoms at $R_1$ that is no greater than the number of carbon atoms at $R_1$ of said fatty alcohol, fatty aldehyde or fatty acid of Formula (I), wherein said one or more enzymes of the MD-FAE cycle are each selective for a compound of Formula (II) having a number of carbon atoms at $R_1$ that is no greater than the number of carbon atoms at $R_1$ of said fatty alcohol, fatty aldehyde or fatty acid of Formula (I), and wherein said one or more enzymes of the termination pathway are each selective for a compound of Formula (II) having a number of carbon atoms at $R_1$ that is no less than the number of carbon atoms at $R_1$ of said fatty alcohol, fatty aldehyde or fatty acid of Formula (I). Alternatively, in some embodiments, the substrate of each of the enzymes of the FAACPE cycle and/or the termination pathway are independently selected from a compound of Formula (II) or malonyl-ACP:

(II)

wherein $R_1$ is $C_{1-24}$ linear alkyl; $R_3$ is H, OH, or oxo (=O); $R_4$ is S-CoA, ACP, OH or H; and ------ represents a single or double bond with the proviso that the valency of the carbon atom to which $R_3$ is attached is four, wherein the one or more enzymes of the FAACPE cycle are each selective for a compound of Formula (II) having a number of carbon atoms at $R_1$ that is no greater than the number of carbon atoms at $R_1$ of said compound of Formula (I), and wherein the one or more enzymes of the termination pathway are each selective for a compound of Formula (II) having a number of carbon atoms at $R_1$ that is no less than the number of carbon atoms at $R_1$ of said compound of Formula (I).

In some embodiments, the invention provides a non-naturally occurring microbial organism containing a fatty alcohol, fatty aldehyde, fatty acid or isopropanol pathway further having an acetyl-CoA pathway, a methanol oxidation pathway, a hydrogenase and/or a carbon monoxide dehydrogenase. Accordingly, in some embodiments, the invention provides a non-naturally occurring microbial organism having a fatty alcohol, fatty aldehyde, fatty acid or isopropanol pathway, wherein the microbial organism further includes an acetyl-CoA pathway and at least one exogenous nucleic acid encoding an acetyl-CoA pathway enzyme expressed in a sufficient amount to produce or enhance carbon flux through acetyl-CoA, wherein the acetyl-CoA pathway includes a pathway shown in FIG. 1, 3, 4, 5 or 6. In some embodiments, the invention provides a non-naturally occurring microbial organism having a fatty alcohol, fatty aldehyde, fatty acid or isopropanol pathway, wherein the microbial organism further includes a methanol oxidation pathway enzyme expressed in a sufficient amount to produce formaldehyde in the presense of methanol. An exemplary methanol oxidation pathway enzyme is a methanol dehydrognease as depicted in FIG. 1, Step A. In some embodiments, the invention provides a non-naturally occurring microbial organism having a fatty alcohol, fatty aldehyde, fatty acid or isopropanol pathway, wherein the microbial organism further includes a hydrogenase and/or a carbon monoxide dehydrogenase for generating reducing equivalents as depicted in FIG. 10.

In some embodiments, the invention provides a non-naturally occurring microbial organism having a fatty alcohol, fatty aldehyde or fatty acid pathway, wherein the microbial organism has one or more gene disruptions, wherein the one or more gene disruptions occur in endogenous genes encoding proteins or enzymes involved in: native production of ethanol, glycerol, pyruvate, acetate, formate, lactate, $CO_2$, fatty acids, or malonyl-CoA by said microbial organism; transfer of pathway intermediates to cellular compartments other than the cytosol; or native degradation of a MI-FAE cycle intermediate, MD-FAE cycle intermediate, FAACPE cycle intermediate or a termination pathway intermediate by the microbial organism, the one or more gene disruptions confer increased production of a fatty alcohol, fatty aldehyde or fatty acid in the microbial organism.

In some embodiments, the invention provides a non-naturally occurring microbial organism having a fatty alcohol, fatty aldehyde or fatty acid pathway, wherein one or more enzymes of the MI-FAE cycle, MD-FAE cycle, FAACPE cycle or the termination pathway preferentially react with an NADH cofactor or have reduced preference for reacting with an NAD(P)H cofactor.

In some embodiments, the invention provides a non-naturally occurring microbial organism having a fatty alcohol, fatty aldehyde or fatty acid pathway, wherein the microbial organism has one or more gene disruptions in genes encoding proteins or enzymes that result in an increased ratio of NAD(P)H to NAD(P) present in the cytosol of the microbial organism following the disruptions.

In some embodiments, the non-naturally occurring microbial organism of the invention is Crabtree positive and is in culture medium comprising excess glucose. In such conditions, as described herein, the microbial organism can result in increasing the ratio of NAD(P)H to NAD(P) present in the cytosol of the microbial organism.

In some embodiments, the invention provides a non-naturally occurring microbial organism having a fatty alcohol, fatty aldehyde or fatty acid pathway, wherein the microbial organism has at least one exogenous nucleic acid encoding an extracellular transporter or an extracellular transport system for a fatty alcohol, fatty aldehyde or fatty acid of the invention.

In some embodiments, the invention provides a non-naturally occurring microbial organism having a fatty alcohol, fatty aldehyde or fatty acid pathway, wherein the microbial organism one or more endogenous enzymes involved in: native production of ethanol, glycerol, pyruvate, acetate, formate, lactate, $CO_2$, fatty acids, or malonyl-CoA by said microbial organism; transfer of pathway intermediates to cellular compartments other than the cytosol; or native degradation of a MI-FAE cycle intermediate, a MD-FAE cycle intermediate, FAACPE cycle intermediate or a termination pathway intermediate by said microbial organism, has attenuated enzyme activity or expression levels.

In some embodiments, the invention provides a non-naturally occurring microbial organism having a fatty alcohol, fatty aldehyde or fatty acid pathway, wherein the microbial organism has attenuated enzyme activity or expression levels for one or more endogenous enzymes involved in the oxidation of NAD(P)H or NADH.

In some embodiments, the invention provides a non-naturally occurring microbial organism having a fatty alcohol, fatty aldehyde or fatty acid pathway, wherein the microbial organism further includes attenuation of one or more endogenous enzymes, which enhances carbon flux through acetyl-CoA, or a gene disruption of one or more endogenous nucleic acids encoding such enzymes. For example, in some aspects, the endogenous enzyme can be selected from DHA kinase, methanol oxidase, PQQ-dependent methanol dehydrogenase, DHA synthase or any combination thereof.

The invention further provides non-naturally occurring microbial organisms that have elevated or enhanced synthesis or yields of acetyl-CoA (e.g. intracellular) or biosynthetic products such as a fatty alcohol, fatty aldehyde, fatty acid or isopropanol and methods of using those non-naturally occurring organisms to produce such biosynthetic products. The enhanced synthesis of intracellular acetyl-CoA enables enhanced production of a fatty alcohol, fatty aldehyde, fatty acid or isopropanol from which acetyl-CoA is an intermediate and further, may have been rate limiting.

In some embodiments, the invention provides a non-naturally occurring microbial organism having a fatty alcohol, fatty aldehyde or fatty acid pathway, wherein the microbial organism further includes attenuation of one or more endogenous enzymes of a competing formaldehyde assimilation or dissimilation pathway or a gene disruption of one or more endogenous nucleic acids encoding enzymes of a competing formaldehyde assimilation or dissimilation pathway. Examples of these endogenous enzymes are described herein.

The invention additionally provides methods of using the above microbial organisms to produce a fatty alcohol, a fatty aldehyde, a fatty acid or isopropanol by culturing a non-naturally occurring microbial organism containing a fatty alcohol, fatty aldehyde, fatty acid or isopropnaol pathway as described herein under conditions and for a sufficient period of time to produce a fatty alcohol, fatty aldehyde, fatty acid or isopropanol.

The invention still further provides a bioderived fatty alcohol, fatty aldehyde, fatty acid or isopropanol produced by a microbial organism of the invention, culture medium having the bioderived fatty alcohol, fatty aldehyde, fatty acid or isopropanol of the invention, compositions having the bioderived fatty alcohol, fatty aldehyde, fatty acid or isopropanol of the invention, a biobased product comprising the bioderived fatty alcohol, fatty aldehyde, fatty acid or isopropanol of the invention, and a process for producing a bioderived fatty alcohol, fatty aldehyde, fatty acid or isopropanol of the invention.

BRIEF DESCRIPTION OF THE DRAWINGS

FIGS. 14A-14D depict the production of pyruvic acid (FIG. 14A), succinic acid (FIG. 14B), acetic acid (FIG. 14C) or glucose (FIG. 14D) in S. cerevisiae transformed with plasmids comprising genes encoding various MI-FAE cycle and termination pathway enzymes, either with or without pflAV or PDH bypass, as provided in Example XIII.

DETAILED DESCRIPTION OF THE INVENTION

Figure 1:
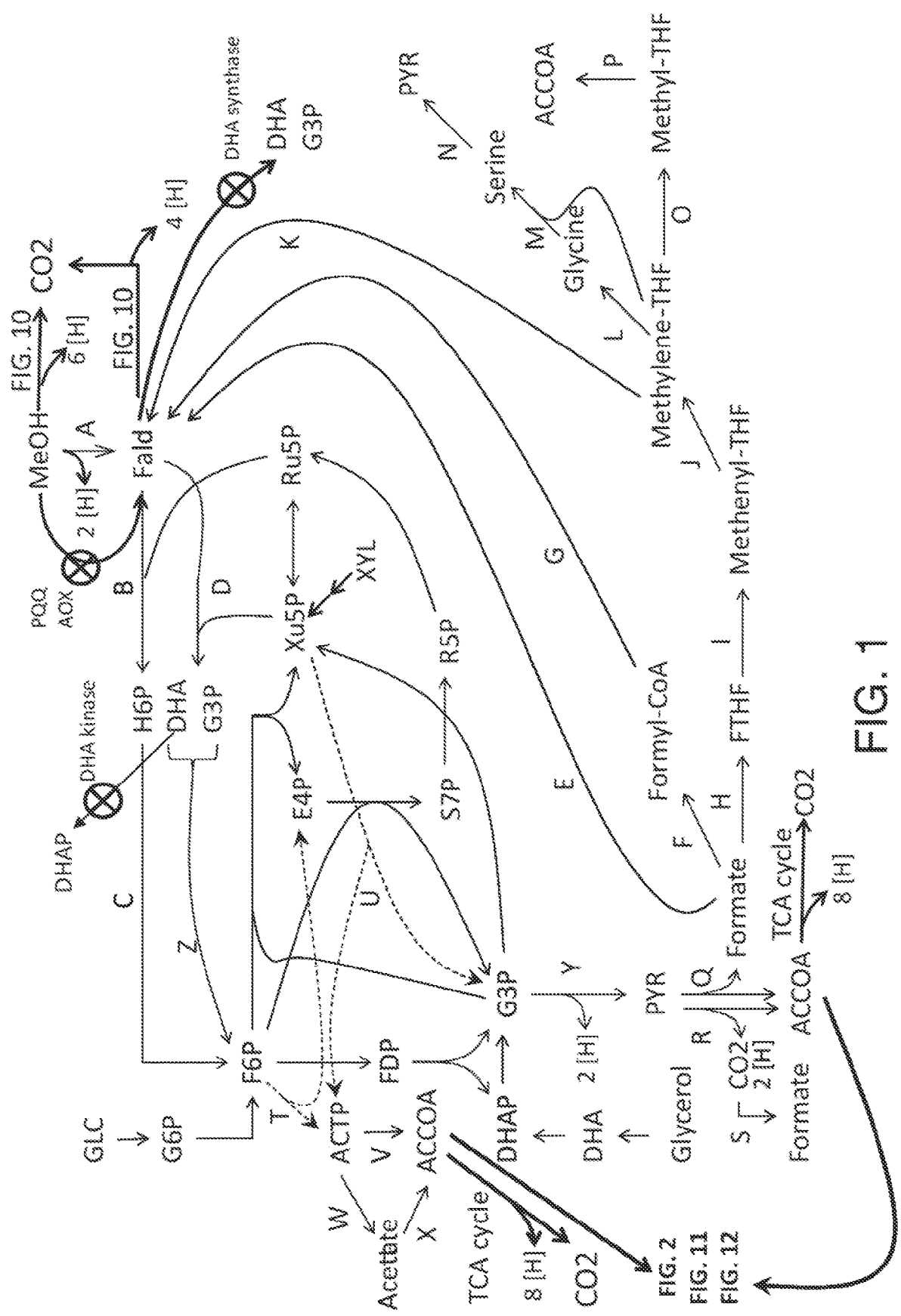
FIG. 1 shows exemplary metabolic pathways enabling the conversion of $CO_2$, formate, formaldehyde (Fald), methanol (MeOH), glycerol, xylose (XYL) and glucose (GLC) to acetyl-CoA (ACCOA) and exemplary endogenous enzyme targets for optional attenuation or disruption. The exemplary pathways and endogenous enzyme targets can be combined with the cycles and pathways depicted herein that utilize ACCOA, such as those depicted in FIGS. 1, 11 and 12. The enzyme targets are indicated by arrows having "X" markings. The endogenous enzyme targets include DHA kinase, methanol oxidase (AOX), PQQ-dependent methanol dehydrogenase (PQQ) and/or DHA synthase. The enzymatic transformations shown are carried out by the following enzymes: A) methanol dehydrogenase, B) 3-hexulose-6-phosphate synthase, C) 6-phospho-3-hexuloisomerase, D) dihydroxyacetone synthase, E) formate reductase, F) formate ligase, formate transferase, or formate synthetase, G) formyl-CoA reductase, H) formyltetrahydrofolate synthetase, I) methenyltetrahydrofolate cyclohydrolase, J) methylenetetrahydrofolate dehydrogenase, K) spontaneous or formaldehyde-forming enzyme, L) glycine cleavage system, M) serine hydroxymethyltransferase, N) serine deaminase, O) methylenetetrahydrofolate reductase, P) acetyl-CoA synthase, Q) pyruvate formate lyase, R) pyruvate dehydrogenase, pyruvate ferredoxin oxidoreductase, or pyruvate:NADP+ oxidoreductase, S) formate dehydrogenase, T) fructose-6-phosphate phosphoketolase, U) xylulose-5-phosphate phosphoketolase, V) phosphotransacetylase, W) acetate kinase, X) acetyl-coa transferase, synthetase, or ligase, Y) lower glycolysis including glyceraldehyde-3-phosphate dehydrogenase, Z) fructose-6-phosphate aldolase. See abbreviation list below for compound names.

The present invention is directed to metabolic and biosynthetic processes and microbial organisms capable of producing fatty alcohols, fatty aldehydes, fatty acids or isopropanol. The invention disclosed herein is based, at least in part, on non-naturally occurring microbial organisms capable of synthesizing fatty alcohols, fatty aldehydes, or fatty acids using a formaldehyde fixation pathway, a formate assimilation pathway and/or a methoanol metabolic pathway with a malonyl-CoA-independent fatty acid elongation (MI-FAE) cycle and/or malonyl-CoA dependent fatty acid elongation cycle (MD-FAE) cycle in combination with a termination pathway, or in some embodiments a fatty acyl-ACP elongation (FAACPE) cycle in combination with a termination pathway. The invention disclosed herein is also based, at least in part, on non-naturally occurring microbial organisms capable of synthesizing isopropanol using a formaldehyde fixation pathway, a formate assimilation pathway and/or a methoanol metabolic pathway in combination with an isopropanol pathway. Additionally, in some embodiments, the non-naturally occurring microbial organisms can further include a methanol oxidation pathway, an acetyl-CoA pathway, a hydrogenase and/or a carbon monoxide dehydrogenase.

The following is a list of abbreviations and their corresponding compound or composition names. These abbreviations, which are used throughout the disclosure and the figures. It is understood that one of ordinary skill in the art can readily identify these compounds/compositions by such nomenclature. MeOH or MEOH=methanol; Fald=formaldehyde; GLC=glucose; G6P=glucose-6-phosphate; H6P=hexulose-6-phosphate; F6P=fructose-6-phosphate; FDP=fructose diphosphate or fructose-1,6-diphosphate; DHA=dihydroxyacetone; DHAP=dihydroxyacetone phosphate; G3P=and glyceraldehyde-3-phosphate; PYR=pyruvate; ACTP=acetyl-phosphate; ACCOA=acetyl-CoA; AACOA=acetoacetyl-CoA; MALCOA=malonyl-CoA; FTHF=formyltetrahydrofolate; THF=tetrahydrofolate; E4P=erythrose-4-phosphate: Xu5P=xyulose-5-phosphate; Ru5P=ribulose-5-phosphate; 57P=sedoheptulose-7-phosphate: $R_5P$=ribose-5-phosphate; TCA=tricarboxylic acid; PEP=Phosphoenolpyruvate; OAA=Oxaloacetate; MAL=malate; FUM=Fumarate; SUCC=Succinate; SUCCOA=Succinyl-CoA; (R)-MMCOA=R-Methylmalonyl-CoA; (S)-MMCOA=S-Methylmalonyl-CoA; PPCOA=Propionyl-CoA.

It is also understood that association of multiple steps in a pathway can be indicated by linking their step identifiers with or without spaces or punctuation; for example, the following are equivalent to describe the 4-step pathway comprising Step W, Step X, Step Y and Step Z: steps WXYZ or W,X,Y,Z or W;X;Y;Z or W-X-Y-Z. One of ordinary skill can readily distinguish a single step designator of "AA" or "AB" or "AD" from a multiple step pathway description based on context and use in the description and figures herein.

As used herein, the term "non-naturally occurring" when used in reference to a microbial organism or microorganism of the invention is intended to mean that the microbial organism has at least one genetic alteration not normally found in a naturally occurring strain of the referenced species, including wild-type strains of the referenced species. Genetic alterations include, for example, modifications introducing expressible nucleic acids encoding metabolic polypeptides, other nucleic acid additions, nucleic acid deletions and/or other functional disruption of the microbial organism's genetic material. Such modifications include, for example, coding regions and functional fragments thereof, for heterologous, homologous or both heterologous and homologous polypeptides for the referenced species. Additional modifications include, for example, non-coding regulatory regions in which the modifications alter expression of a gene or operon. Exemplary metabolic polypeptides include enzymes or proteins within a fatty alcohol, fatty aldehyde or fatty alcohol biosynthetic pathway.

A metabolic modification refers to a biochemical reaction that is altered from its naturally occurring state. Therefore, non-naturally occurring microorganisms can have genetic modifications to nucleic acids encoding metabolic polypeptides, or functional fragments thereof. Exemplary metabolic modifications are disclosed herein.

As used herein, the term "isolated" when used in reference to a microbial organism is intended to mean an organism that is substantially free of at least one component as the referenced microbial organism is found in nature. The term includes a microbial organism that is removed from some or all components as it is found in its natural environment. The term also includes a microbial organism that is removed from some or all components as the microbial organism is found in non-naturally occurring environments. Therefore, an isolated microbial organism is partly or completely separated from other substances as it is found in nature or as it is grown, stored or subsisted in non-naturally occurring environments. Specific examples of isolated microbial organisms include partially pure microbes, substantially pure microbes and microbes cultured in a medium that is non-naturally occurring.

As used herein, the terms "microbial," "microbial organism" or "microorganism" are intended to mean any organism that exists as a microscopic cell that is included within the domains of archaea, bacteria or eukarya. Therefore, the term is intended to encompass prokaryotic or eukaryotic cells or organisms having a microscopic size and includes bacteria, archaea and eubacteria of all species as well as eukaryotic microorganisms such as yeast and fungi. The term also includes cell cultures of any species that can be cultured for the production of a biochemical.

As used herein, the term "CoA" or "coenzyme A" is intended to mean an organic cofactor or prosthetic group (nonprotein portion of an enzyme) whose presence is required for the activity of many enzymes (the apoenzyme) to form an active enzyme system. Coenzyme A functions in certain condensing enzymes, acts in acetyl or other acyl group transfer and in fatty acid synthesis and oxidation, pyruvate oxidation and in other acetylation.

As used herein, the term "ACP" or "acyl carrier protein" refers to any of the relatively small acidic proteins that are associated with the fatty acid synthase system of many organisms, from bacteria to plants. ACPs can contain one 4'-phosphopantetheine prosthetic group bound covalently by a phosphate ester bond to the hydroxyl group of a serine residue. The sulfhydryl group of the 4'-phosphopantetheine moiety serves as an anchor to which acyl intermediates are (thio)esterified during fatty-acid synthesis. An example of an ACP is *Escherichia coli* ACP, a separate single protein, containing 77 amino-acid residues (8.85 kDa), wherein the phosphopantetheine group is linked to serine 36.

As used herein, the term "substantially anaerobic" when used in reference to a culture or growth condition is intended to mean that the amount of oxygen is less than about 10% of saturation for dissolved oxygen in liquid media. The term also is intended to include sealed chambers of liquid or solid medium maintained with an atmosphere of less than about 1% oxygen.

"Exogenous" as it is used herein is intended to mean that the referenced molecule or the referenced activity is introduced into the host microbial organism. The molecule can be introduced, for example, by introduction of an encoding nucleic acid into the host genetic material such as by integration into a host chromosome or as non-chromosomal genetic material such as a plasmid. Therefore, the term as it is used in reference to expression of an encoding nucleic acid refers to introduction of the encoding nucleic acid in an expressible form into the microbial organism. When used in reference to a biosynthetic activity, the term refers to an activity that is introduced into the host reference organism. The source can be, for example, a homologous or heterologous encoding nucleic acid that expresses the referenced activity following introduction into the host microbial organism. Therefore, the term "endogenous" refers to a referenced molecule or activity that is present in the host. Similarly, the term when used in reference to expression of an encoding nucleic acid refers to expression of an encoding nucleic acid contained within the microbial organism. The term "heterologous" refers to a molecule or activity derived from a source other than the referenced species whereas "homologous" refers to a molecule or activity derived from the host microbial organism. Accordingly, exogenous expression of an encoding nucleic acid of the invention can utilize either or both a heterologous or homologous encoding nucleic acid.

It is understood that when more than one exogenous nucleic acid is included in a microbial organism that the more than one exogenous nucleic acids refers to the referenced encoding nucleic acid or biosynthetic activity, as discussed above. It is further understood, as disclosed herein, that such more than one exogenous nucleic acids can be introduced into the host microbial organism on separate nucleic acid molecules, on polycistronic nucleic acid molecules, or a combination thereof, and still be considered as more than one exogenous nucleic acid. For example, as disclosed herein a microbial organism can be engineered to express two or more exogenous nucleic acids encoding a desired pathway enzyme or protein. In the case where two exogenous nucleic acids encoding a desired activity are introduced into a host microbial organism, it is understood that the two exogenous nucleic acids can be introduced as a single nucleic acid, for example, on a single plasmid, on separate plasmids, can be integrated into the host chromosome at a single site or multiple sites, and still be considered as two exogenous nucleic acids. Similarly, it is understood that more than two exogenous nucleic acids can be introduced into a host organism in any desired combination, for example, on a single plasmid, on separate plasmids, can be integrated into the host chromosome at a single site or multiple sites, and still be considered as two or more exogenous nucleic acids, for example three exogenous nucleic acids. Thus, the number of referenced exogenous nucleic acids or biosynthetic activities refers to the number of encoding nucleic acids or the number of biosynthetic activities, not the number of separate nucleic acids introduced into the host organism.

As used herein, the term "gene disruption," or grammatical equivalents thereof, is intended to mean a genetic alteration that renders the encoded gene product inactive or attenuated. The genetic alteration can be, for example, deletion of the entire gene, deletion of a regulatory sequence required for transcription or translation, deletion of a portion of the gene which results in a truncated gene product, or by any of various mutation strategies that inactivate or attenuate the encoded gene product, for example, replacement of a gene's promoter with a weaker promoter, replacement or insertion of one or more amino acid of the encoded protein to reduce its activity, stability or concentration, or inactivation of a gene's transactivating factor such as a regulatory protein. One particularly useful method of gene disruption is complete gene deletion because it reduces or eliminates the occurrence of genetic reversions in the non-naturally occurring microorganisms of the invention. A gene disruption also includes a null mutation, which refers to a mutation within a gene or a region containing a gene that results in the gene not being transcribed into RNA and/or translated into a functional gene product. Such a null mutation can arise from many types of mutations including, for example, inactivating point mutations, deletion of a portion of a gene, entire gene deletions, or deletion of chromosomal segments.

As used herein, the term "growth-coupled" when used in reference to the production of a biochemical product is intended to mean that the biosynthesis of the referenced biochemical product is produced during the growth phase of a microorganism. In a particular embodiment, the growth-coupled production can be obligatory, meaning that the biosynthesis of the referenced biochemical is an obligatory product produced during the growth phase of a microorganism.

As used herein, the term "attenuate," or grammatical equivalents thereof, is intended to mean to weaken, reduce or diminish the activity or amount of an enzyme or protein. Attenuation of the activity or amount of an enzyme or protein can mimic complete disruption if the attenuation causes the activity or amount to fall below a critical level required for a given pathway to function. However, the attenuation of the activity or amount of an enzyme or protein that mimics complete disruption for one pathway, can still be sufficient for a separate pathway to continue to function. For example, attenuation of an endogenous enzyme or protein can be sufficient to mimic the complete disruption of the same enzyme or protein for production of a fatty alcohol, fatty aldehyde or fatty acid product of the invention, but the remaining activity or amount of enzyme or protein can still be sufficient to maintain other pathways, such as a pathway that is critical for the host microbial organism to survive, reproduce or grow. Attenuation of an enzyme or protein can also be weakening, reducing or diminishing the activity or amount of the enzyme or protein in an amount that is sufficient to increase yield of a fatty alcohol, fatty aldehyde or fatty acid product of the invention, but does not necessarily mimic complete disruption of the enzyme or protein.

The term "fatty alcohol," as used herein, is intended to mean an aliphatic compound that contains one or more hydroxyl groups and contains a chain of 4 or more carbon atoms. The fatty alcohol possesses the group —CH$_2$OH that can be oxidized so as to form a corresponding aldehyde or acid having the same number of carbon atoms. A fatty alcohol can also be a saturated fatty alcohol, an unsaturated fatty alcohol, a 1,3-diol, or a 3-oxo-alkan-1-ol. Exemplary fatty alcohols include a compound of Formula (III)—(VI):

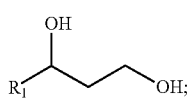
(III)

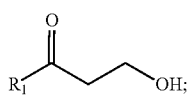
(IV)

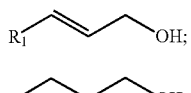
(V)

(VI)

wherein R$_1$ is a C$_{1-24}$ linear alkyl.

The term "fatty aldehyde," as used herein, is intended to mean an aliphatic compound that contains an aldehyde (CHO) group and contains a chain of 4 or more carbon atoms. The fatty aldehyde can be reduced to form the corresponding alcohol or oxidized to form the carboxylic acid having the same number of carbon atoms. A fatty aldehyde can also be a saturated fatty aldehyde, an unsaturated fatty aldehyde, a 3-hydroxyaldehyde or 3-oxoaldehyde. Exemplary fatty aldehydes include a compound of Formula (VII)—(X):

(VII)

(VIII)

(IX)

(X)

wherein R$_1$ is a C$_{1-24}$ linear alkyl.

The term "fatty acid," as used herein, is intended to mean an aliphatic compound that contains a carboxylic acid group and contains a chain of 4 or more carbon atoms. The fatty acid can be reduced to form the corresponding alcohol or aldehyde having the same number of carbon atoms. A fatty acid can also be a saturated fatty acid, an unsaturated fatty acid, a 3-hydroxyacid or a 3-oxoacids. Exemplary fatty acids include a compound of Formula (XI)—(XIV):

(XI)

(XII)

(XIII)

(XIV)

wherein R$_1$ is a C$_{1-24}$ linear alkyl.

The term "alkyl" refers to a linear saturated monovalent hydrocarbon. The alkyl can be a linear saturated monovalent hydrocarbon that has 1 to 24 (C$_{1-24}$), 1 to 17 (C$_{1-17}$), or 9 to 13 (C$_{9-13}$) carbon atoms. Examples of alkyl groups include, but are not limited to, methyl, ethyl, prowl, butyl, pentyl, hexyl, heptyl, octyl, nonyl, decyl, undecyl and dodecyl. For example, C$_{9-13}$ alkyl refers to a linear saturated monovalent hydrocarbon of 9 to 13 carbon atoms.

As used herein, "isopropanol" is intended to mean a secondary alcohol, with the molecular formula of C$_3$H$_8$O and a molecular mass of 60.1 g/mol, wherein the alcohol carbon is attached to two other carbons. This attachment is sometimes shown as $(CH_3)_2CHOH$. Isopropanol is also known in the art as propan-2-ol, 2-propanol or the abbreviation IPA. Isopropanol is an isomer of n-propanol.

As used herein, the phrase "enhance carbon flux" is intended to mean to intensify, increase, or further improve the extent or flow of metabolic carbon through or to a desired pathway, pathway product, intermediate, or compound. The intensity, increase or improvement can be relative to a predetermined baseline of a pathway product, intermediate or compound. For example, an increased yield of acetyl-CoA can be achieved per mole of methanol with a phosphoketolase enzyme described herein (see, e.g., FIG. 1) than in the absence of a phosphoketolase enzyme. Similarly, an increased yield of acetyl-CoA can be achieved per mole of methanol with the formale assimilation enzymes (see, e.g., FIG. 1) than in the absence of the enzymes. Since an increased yield of acetyl-CoA can be achieved, a higher yield of acetyl-CoA derived products, such as fatty alcohols, fatty acids, fatty aldehydes or isopropanol of the invention, can also be achieved.

Figure 10:
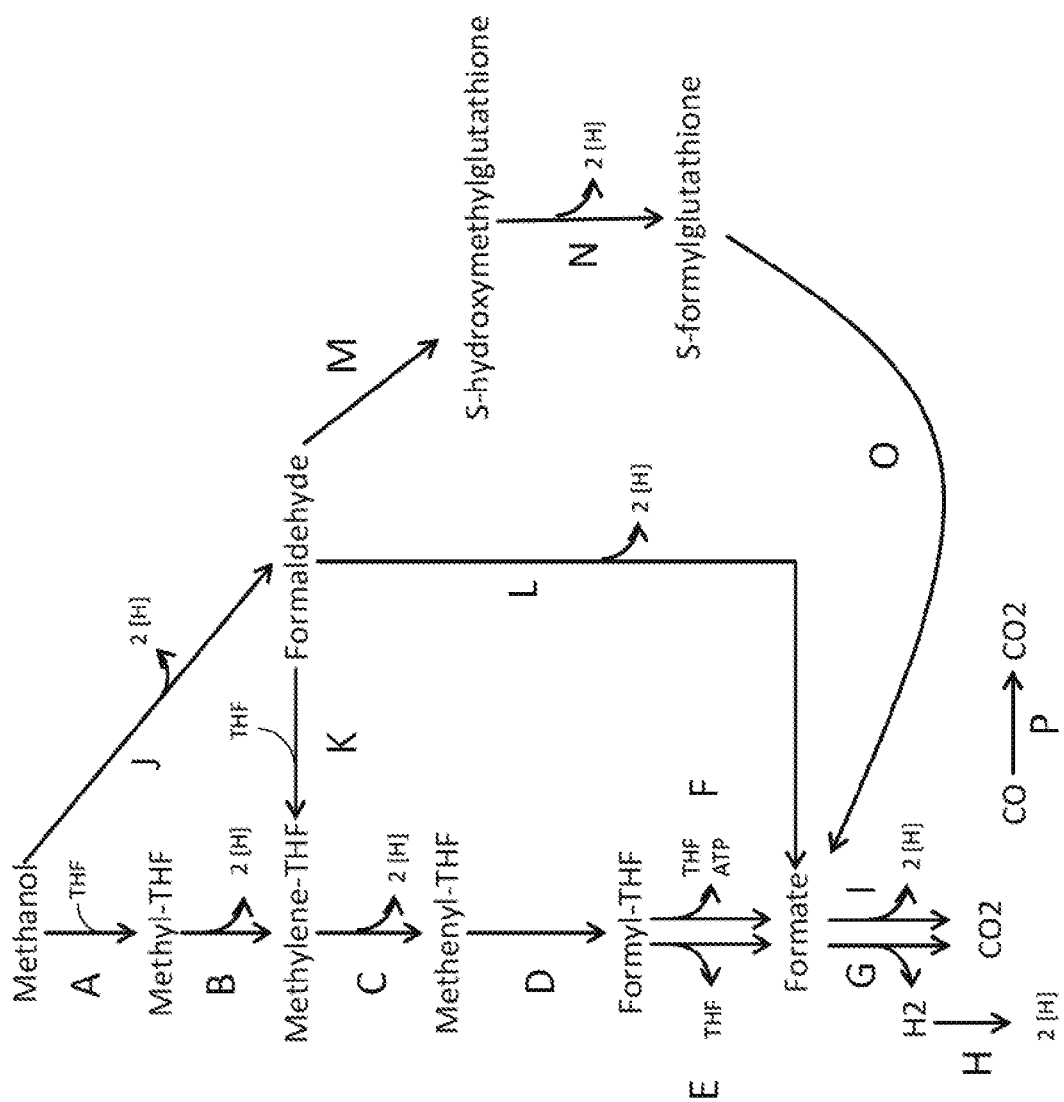
FIG. 10 shows exemplary metabolic pathways that provide the extraction of reducing equivalents from methanol, hydrogen, or carbon monoxide. Enzymes are: A) methanol methyltransferase, B) methylenetetrahydrofolate reductase, C) methylenetetrahydrofolate dehydrogenase, D) methenyltetrahydrofolate cyclohydrolase, E) formyltetrahydrofolate deformylase, F) formyltetrahydrofolate synthetase, G) formate hydrogen lyase, H) hydrogenase, I) formate dehydrogenase, J) methanol dehydrogenase, K) spontaneous or formaldehyde activating enzyme, L) formaldehyde dehydrogenase, M) spontaneous or S-(hydroxymethyl)glutathione synthase, N) Glutathione-Dependent Formaldehyde Dehydrogenase, O) S-formylglutathione hydrolase, P) carbon monoxide dehydrogenase. See abbreviation list below for compound names.

Provided herein are methanol metabolic pathways and a methanol oxidation pathway to improve that availability of reducing equivaments and/or substrants for production of a compound of the invention. Because methanol is a relatively inexpensive organic feedstock that can be used as a redox, energy, and carbon source for the production of chemicals such as fatty alcohols, fatty acids, fatty aldehydes or isopropanol, and their intermediates, it is a desireable substrate for the non-naturally occurring microbial organisms of the invention. Employing one or more methanol metabolic enzymes as described herein, for example as shown in FIGS. 1 and 10, methanol can enter central metabolism in most production hosts by employing methanol dehydrogenase (FIG. 1, step A) along with a pathway for formaldehyde assimilation. One exemplary formaldehyde assimilation pathway that can utilize formaldehyde produced from the oxidation of methanol is shown in FIG. 1, which involves condensation of formaldehyde and D-ribulose-5-phosphate to form hexulose-6-phosphate (H6P) by hexulose-6-phosphate synthase (FIG. 1, step B). The enzyme can use $Mg^{2+}$ or $Mn^{2+}$ for maximal activity, although other metal ions are useful, and even non-metal-ion-dependent mechanisms are contemplated. H6P is converted into fructose-6-phosphate by 6-phospho-3-hexuloisomerase (FIG. 1, step C). Another exemplary pathway that involves the detoxification and assimilation of formaldehyde produced from the oxidation of methanol proceeds through dihydroxyacetone. Dihydroxyacetone synthase (FIG. 1, step D) is a transketolase that first transfers a glycoaldehyde group from xylulose-5-phosphate to formaldehyde, resulting in the formation of dihydroxyacetone (DHA) and glyceraldehyde-3-phosphate (G3P), which is an intermediate in glycolysis. The DHA obtained from DHA synthase can be then further phosphorylated to form DHA phosphate by a DHA kinase DHAP can be assimilated into glycolysis, e.g. via isomerization to G3P, and several other pathways. Alternatively, DHA and G3P can be converted by fructose-6-phosphate aldolase to form fructose-6-phosphate (F6P).

By combining the pathways for methanol oxidation (FIG. 1, step A) and formaldehyde fixation (FIG. 1, Steps B and C or Step D), molar yields of 0.333 mol acetyl-CoA/mol methanol can be achieved for production of a fatty alcohol, a fatty acid, a fatty aldehyde, isopropanol, and their intermediates. The following maximum theoretical yield stoichiometries for a fatty alcohol (e.g., a C12), a fatty acid (e.g., a C12), a fatty aldehyde (e.g., a C12), isopropanol are thus made possible by combining the steps for methanol oxidation, formaldehyde fixation, and product synthesis.

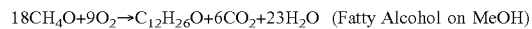

18CH$_4$O+9O$_2$→C$_{12}$H$_{26}$O+6CO$_2$+23H$_2$O  (Fatty Alcohol on MeOH)

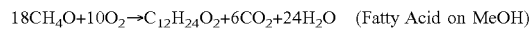

18CH$_4$O+10O$_2$→C$_{12}$H$_{24}$O$_2$+6CO$_2$+24H$_2$O  (Fatty Acid on MeOH)

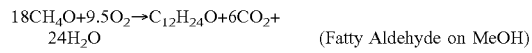

18CH$_4$O+9.5O$_2$→C$_{12}$H$_{24}$O+6CO$_2$+24H$_2$O  (Fatty Aldehyde on MeOH)

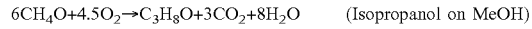

6CH$_4$O+4.5O$_2$→C$_3$H$_8$O+3CO$_2$+8H$_2$O  (Isopropanol on MeOH)

The yield on several substrates, including methanol, can be further increased by capturing some of the carbon lost from the conversion of pathway intermediates, e.g. pyruvate to acetyl-CoA, using one of the formate reutilization pathways shown in FIG. 1. For example, the $CO_2$ generated by conversion of pyruvate to acetyl-CoA (FIG. 1, step R) can be converted to formate via formate dehydrogenase (FIG. 1, step S). Alternatively, pyruvate formate lyase, which forms formate directly instead of $CO_2$, can be used to convert pyruvate to acetyl-CoA (FIG. 1, step Q). Formate can be converted to formaldehyde by using: 1) formate reductase (FIG. 1, step E), 2) a formyl-CoA synthetase, transferase, or ligase along with formyl-CoA reductase (FIG. 1, steps F-G), or 3) formyltetrahydrofolate synthetase, methenyltetrahydrofolate cyclohydrolase, methylenetetrahydrofolate dehydrogenase, and formaldehyde-forming enzyme (FIG. 1, steps H—I-J-K). Conversion of methylene-THF to formaldehyde alternatively will occur spontaneously. Alternatively, formate can be reutilized by converting it to pyruvate or acetyl-CoA using FIG. 1, steps H—I-J-L-M-N or FIG. 1, steps H—I-J-O—P, respectively. Formate reutilization is also useful when formate is an external carbon source. For example, formate can be obtained from organocatalytic, electrochemical, or photoelectrochemical conversion of $CO_2$ to formate. An alternative source of methanol for use in the present methods is organocatalytic, electrochemical, or photoelectrochemical conversion of $CO_2$ to methanol, By combining the pathways for methanol oxidation (FIG. 1, step A), formaldehyde fixation (FIG. 1, Steps B and C or Step D), and formate reutilization, molar yields as high as 0.500 mol acetyl-CoA/mol methanol can be achieved for production of a fatty alcohol, a fatty acid, a fatty aldehyde, isopropanol, and their intermediates. Thus, for example, the following maximum theoretical yield stoichiometries for a fatty alcohol (e.g., a C12), a fatty acid (e.g., a C12), a fatty aldehyde (e.g., a C12), and isopropanol are thus made possible by combining the steps for methanol oxidation, formaldehyde fixation, formate reutilization, and product synthesis.

12CH$_4$O→C$_{12}$H$_{26}$O+11H$_2$O  (Fatty Alcohol on MeOH)

12CH$_4$O+O$_2$—C$_{12}$H$_{24}$O$_2$+12H$_2$O  (Fatty Acid on MeOH)

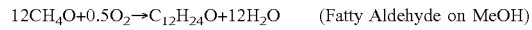

12CH$_4$O+0.5O$_2$→C$_{12}$H$_{24}$O+12H$_2$O  (Fatty Aldehyde on MeOH)

4CH$_4$O+1.5O$_2$→C$_3$H$_8$O+4H$_2$O+CO$_2$  (Isopropanol on MeOH)

By combining pathways for formaldehyde fixation and formate reutilization, yield increases on additional substrates are also available including but not limited to glucose, glycerol, sucrose, fructose, xylose, arabinose and galactose. For example, the following maximum theoretical yield stoichiometries for a fatty alcohol (e.g., a C12), a fatty acid (e.g., a C12), a fatty aldehyde (e.g., a C12), and isopropanol on glucose are made possible by combining the steps for formaldehyde fixation, formate reutilization, and product synthesis.

$3C_6H_{12}O_6 \rightarrow C_{12}H_{26}O + 5H_2O + 6CO_2$ (Fatty Alcohol on glucose)

$3C_6H_{12}O_6 \rightarrow 1.0588 C_{12}H_{24}O_2 + 5.2941 H_2O + 5.2941 CO_2$ (Fatty Acid on glucose)

$3C_6H_{12}O_6 \rightarrow 1.0286 C_{12}H_{24}O + 5.6571 H_2O + 5.6571 CO_2$ (Fatty Aldehyde on glucose)

$C_6H_{12}O_6 \rightarrow 1.3333 C_3H_8O + 0.6667 H_2O + 2CO_2$ (Isopropanol on glucose)

Similarly, the maximum theoretical yield of a fatty alcohol, a fatty acid, a fatty aldehyde, or isopropanol from glycerol can be increased by enabling fixation of formaldehyde from generation and utilization of formate. The following maximum theoretical yield stoichiometries for a fatty alcohol (e.g., a C12), a fatty acid (e.g., a C12), a fatty aldehyde (e.g., a C12), and isopropanol on glycerol are thus made possible by combining the steps for formaldehyde fixation, formate reutilization, and product synthesis.

$6C_3H_8O_3 \rightarrow 1.1667 C_{12}H_{26}O + 8.3333 H_2O + 4CO_2$ (Fatty Alcohol on glycerol)

$6C_3H_8O_3 \rightarrow 1.2353 C_{12}H_{24}O_2 + 9.1765 H_2O + 3.1765 CO_2$ (Fatty Acid on glycerol)

$6C_3H_8O_3 \rightarrow 1.2000 C_{12}H_{24}O + 9.6000 H_2O + 3.6000 CO_2$ (Fatty Aldehyde on glycerol)

$C_3H_8O_3 \rightarrow 0.7778 C_3H_8O + 0.8889 H_2O + 0.6667 CO_2$ (Isopropanol on glycerol)

In numerous engineered pathways, product yields based on carbohydrate feedstock are hampered by insufficient reducing equivalents or by loss of reducing equivalents to byproducts. Methanol is a relatively inexpensive organic feedstock that can be used to generate reducing equivalents by employing one or more methanol metabolic enzymes as shown in FIG. 10. Reducing equivalents can also be extracted from hydrogen and carbon monoxide by employing hydrogenase and carbon monoxide dehydrogenase enzymes, respectively, as shown in FIG. 10. The reducing equivalents are then passed to acceptors such as oxidized ferredoxins, oxidized quinones, oxidized cytochromes, NAD(P)+, water, or hydrogen peroxide to form reduced ferredoxin, reduced quinones, reduced cytochromes, NAD(P)H, $H_2$, or water, respectively. Reduced ferredoxin, reduced quinones and NAD(P)H are particularly useful as they can serve as redox carriers for various Wood-Ljungdahl pathway, reductive TCA cycle, or product pathway enzymes.

The reducing equivalents produced by the metabolism of methanol, hydrogen, and carbon monoxide can be used to power several fatty alcohol, fatty acid, fatty aldehyde, and isopropanol production pathways. For example, the maximum theoretical yield of a fatty alcohol, a fatty acid, a fatty aldehyde, or isopropanol from glucose and glycerol can be increased by enabling fixation of formaldehyde, formate reutilization, and extraction of reducing equivalents from an external source such as hydrogen. In fact, by combining pathways for formaldehyde fixation, formate reutilization, reducing equivalent extraction, and product synthesis, the following maximum theoretical yield stoichiometries for fatty alcohol, a fatty acid, a fatty aldehyde, and isopropanol on glucose and glycerol are made possible.

$2C_6H_{12}O_6 + 12H_2 \rightarrow C_{12}H_{26}O + 11H_2O$ (Fatty Alcohol on glucose+external redox)

$2C_6H_{12}O_6 + 10H_2 \rightarrow C_{12}H_{24}O_2 + 10H_2O$ (Fatty Acid on glucose+external redox)

$2C_6H_{12}O_6 + 11H_2 \rightarrow C_{12}H_{24}O + 11H_2O$ (Fatty Aldehyde on glucose+external redox)

$C_6H_{12}O_6 + 6H_2 \rightarrow 2C_3H_8O + 4H_2O$ (Isopropanol on glucose+external redox)

$4C_3H_8O_3 + 8H_2 \rightarrow C_{12}H_{26}O + 11H_2O$ (Fatty Alcohol on glycerol+external redox)

$4C_3H_8O_3 + 6H_2 \rightarrow C_{12}H_{24}O_2 + 10H_2O$ (Fatty Acid on glycerol+external redox)

$4C_3H_8O_3 + 7H_2 \rightarrow C_{12}H_{24}O + 11H_2O$ (Fatty Aldehyde on glycerol+external redox)

$C_3H_8O_3 + 2H_2 \rightarrow C_3H_8O + 2H_2O$ (Isopropanol on glycerol+external redox)

In most instances, achieving such maximum yield stoichiometries may require some oxidation of reducing equivalents (e.g., $H_2 + \frac{1}{2}O_2 \rightarrow H_2O$, $CO + \frac{1}{2}O_2 \rightarrow CO_2$, $CH_4O + 1.5 O_2 \rightarrow CO_2 + 2H_2O$, $C_6H_{12}O_6 + 6O_2 \rightarrow 6CO_2 + 6H_2O$) to provide sufficient energy for the substrate to product pathways to operate. Nevertheless, if sufficient reducing equivalents are available, enabling pathways for fixation of formaldehyde, formate reutilization, extraction of reducing equivalents, and product synthesis can even lead to production of a fatty alcohol, a fatty acid, a fatty aldehyde, isopropanol, and their intermediates, directly from $CO_2$.

Pathways identified herein, and particularly pathways exemplified in specific combinations presented herein, are superior over other pathways based in part on the applicant's ranking of pathways based on attributes including maximum theoretical compound yield, maximal carbon flux, maximal production of reducing equivalents, minimal production of $CO_2$, pathway length, number of non-native steps, thermodynamic feasibility, number of enzymes active on pathway substrates or structurally similar substrates, and having steps with currently characterized enzymes, and furthermore, the latter pathways are even more favored by having in addition at least the fewest number of non-native steps required, the most enzymes known active on pathway substrates or structurally similar substrates, and the fewest total number of steps from central metabolism.

In some embodiments, the microorganisms of the invention can utilize a heterologous MI-FAE cycle and/or a MD-FAE cycle coupled with an acyl-CoA termination pathway to form fatty alcohols, fatty aldehydes, or fatty acids. The MI-FAE cycle can include a thiolase, a 3-oxoacyl-CoA reductase, a 3-hydroxyacyl-CoA dehydratase and an enoyl-CoA reductase. The MD-FAE cycle can include an elongase, a 3-oxoacyl-CoA reductase, a 3-hydroxyacyl-CoA dehydratase and an enoyl-CoA reductase. Each passage through the MI-FAE cycle and/or the MD-FAE cycle results in the formation of an acyl-CoA elongated by a single two carbon unit compared to the acyl-CoA substrate entering the elongation cycle. Products can be even or odd chain length, depending on the initial substrate entering the acyl-CoA elongation pathway, i.e. two acety-CoA substrates, malonyl-CoA or one acetyl-CoA substrate combined with a propionyl-CoA substrate. Elongation of the two acetyl-CoA substrates or malonyl-CoA produces an even chain length product, whereas elongation with the propionyl-CoA substrate produces an odd chain length product. A termination pathway catalyzes the conversion of a MI-FAE intermediate and/or a MD-FAE intermediate, such as the acyl-CoA, to its corresponding fatty alcohol, fatty aldehyde, or fatty acid product. MI-FAE cycle, MD-FAE cycle and termination pathway enzymes can be expressed in one or more compartments of the microorganism. For example, in one embodiment, all MI-FAE cycle and termination pathway enzymes are expressed in the cytosol. In another embodiment, all MD-FAE cycle and termination pathway enzymes are expressed in the cytosol. Additionally, the microorganisms of the invention can be engineered to optionally secret the desired product into the culture media or fermentation broth for further manipulation or isolation.

In some embodiments, the microorganisms of the invention can utilize a heterologous FAACPE cycle coupled with an acyl-ACP termination pathway to form fatty alcohols, fatty aldehydes, or fatty acids. The FAACPE cycle can include a β-ketoacyl-ACP synthase, a β-ketoacyl-ACP reductase, a β-hydroxyacyl-ACP reductase, and a enoyl ACP-reductase. Each passage through the FAACPE cycle results in the formation of an acyl-ACP elongated by a single two carbon unit compared to the acyl-ACP substrate entering the elongation cycle. Products can be even or odd chain length, depending on the initial substrate entering the FAACPE pathway, i.e. acetoacetyl-ACP or 3-oxovaleryl-ACP. Elongation of the acetoacetyl-ACP substrates produces an even chain length product, whereas elongation with the 3-oxovaleryl-ACP substrate produces an odd chain length product. A termination pathway catalyzes the conversion of a FAACPE intermediate, such as the acyl-ACP, to its corresponding fatty alcohol, fatty aldehyde, or fatty acid product FAACPE cycle and termination pathway enzymes can be expressed in one or more compartments of the microorganism. For example, in one embodiment, all FAACPE cycle and termination pathway enzymes are expressed in the cytosol. Additionally, the microorganisms of the invention can be engineered to optionally secret the desired product into the culture media or fermentation broth for further manipulation or isolation.

Products of the invention include fatty alcohols, fatty aldehydes, or fatty acids derived from intermediates of the MI-FAE cycle, MD-FAE cycle, and/or FAACPE cycle. For example, alcohol products can include saturated fatty alcohols, unsaturated fatty alcohols, 1,3-diols, and 3-oxo-alkan-1-ols. Aldehyde products can include saturated fatty aldehydes, unsaturated fatty aldehydes, 3-hydroxyaldehydes and 3-oxoaldehydes. Acid products can include saturated fatty acids, unsaturated fatty acids, 3-hydroxyacids and 3-oxoacids. These products can further be converted to derivatives such as fatty esters, either by chemical or enzymatic means. Methods for converting fatty alcohols to esters are well known in the art. Another product of the invention is isopropanol.

The invention also encompasses fatty alcohol, fatty aldehyde, and fatty acid chain-length control strategies in conjunction with host strain engineering strategies, such that the non-naturally occurring microorganism of the invention efficiently directs carbon and reducing equivalents toward fermentation products of a specific chain length.

Recombinant microorganisms of the invention can produce commercial quantities of a fatty alcohol, fatty aldehyde, or fatty acid ranging in chain length from four carbon atoms ($C_4$) to twenty-four carbon atoms ($C_{24}$) or more carbon atoms. The microorganism of the invention can produce a desired product that is at least 50%, 60%, 70%, 75%, 85%, 90%, 95% or more selective for a particular chain length. The carbon chain-length of the product can be controlled by one or more enzymes of the MI-FAE cycle (steps A/B/C/D of FIG. 7) and/or one or more enzymes of the MD-FAE cycle (steps E/B/C/D of FIG. 7) in combination with one or more termination pathway enzymes (steps E-N of FIG. 8). Chain length can be capped during the elongation cycle by one or more MI-FAE cycle enzymes (thiolase, 3-oxoacyl-CoA reductase, 3-hydroxyacyl-CoA dehydratase and/or enoyl-CoA reductase) exhibiting selectivity for MI-FAE cycle substrates having a number of carbon atoms that are no greater than the desired product size. Alternatively, or in addition, chain length can be capped during the elongation cycle by one or more MD-FAE cycle enzymes (elongase, 3-oxoacyl-CoA reductase, 3-hydroxyacyl-CoA dehydratase and/or enoyl-CoA reductase). Chain length can be further constrained by one or more enzymes catalyzing the conversion of the MI-FAE cycle intermediate to the fatty alcohol, fatty aldehyde or fatty acid product such that the one or more termination enzymes only reacts with substrates having a number of carbon atoms that are no less than the desired fatty alcohol, fatty aldehyde or fatty acid product.

The termination pathway enzymes catalyzing conversion of a MI-FAE-CoA intermediate or MD-FAE-CoA intermediate to a fatty alcohol can include enzyme combinations of a fatty acyl-CoA reductase (alcohol or aldehyde forming), a fatty aldehyde reductase, an acyl-ACP reductase, an acyl-CoA:ACP acyltransferase, a thioesterase, an acyl-CoA hydrolase and/or a carboxylic acid reductase (see, e.g., pathways G; E/F; K/J/F; H/N/F; or K/LN/F of FIG. 8). Termination pathway enzymes for converting a MI-FAE-CoA intermediate or MD-FAE-CoA intermediate to a fatty acid can include enzyme combinations of a thioesterase, a CoA hydrolase, an acyl-CoA:ACP acyltransferase, an aldehyde dehydrogenase and/or an acyl-ACP reductase (see, e.g., pathways H; K/L; E/N; K/J/N of FIG. 8). For production of a fatty aldehyde, the termination pathway enzymes can include enzyme combinations of a fatty acyl-CoA reductase (aldehyde forming), an acyl-ACP reductase, an acyl-CoA:ACP acyltransferase, a thioesterase, an acyl-CoA hydrolase and/or a carboxylic acid reductase (see, e.g., pathways E; K/J; H/N; or K/LN of FIG. 8).

Figure 12:
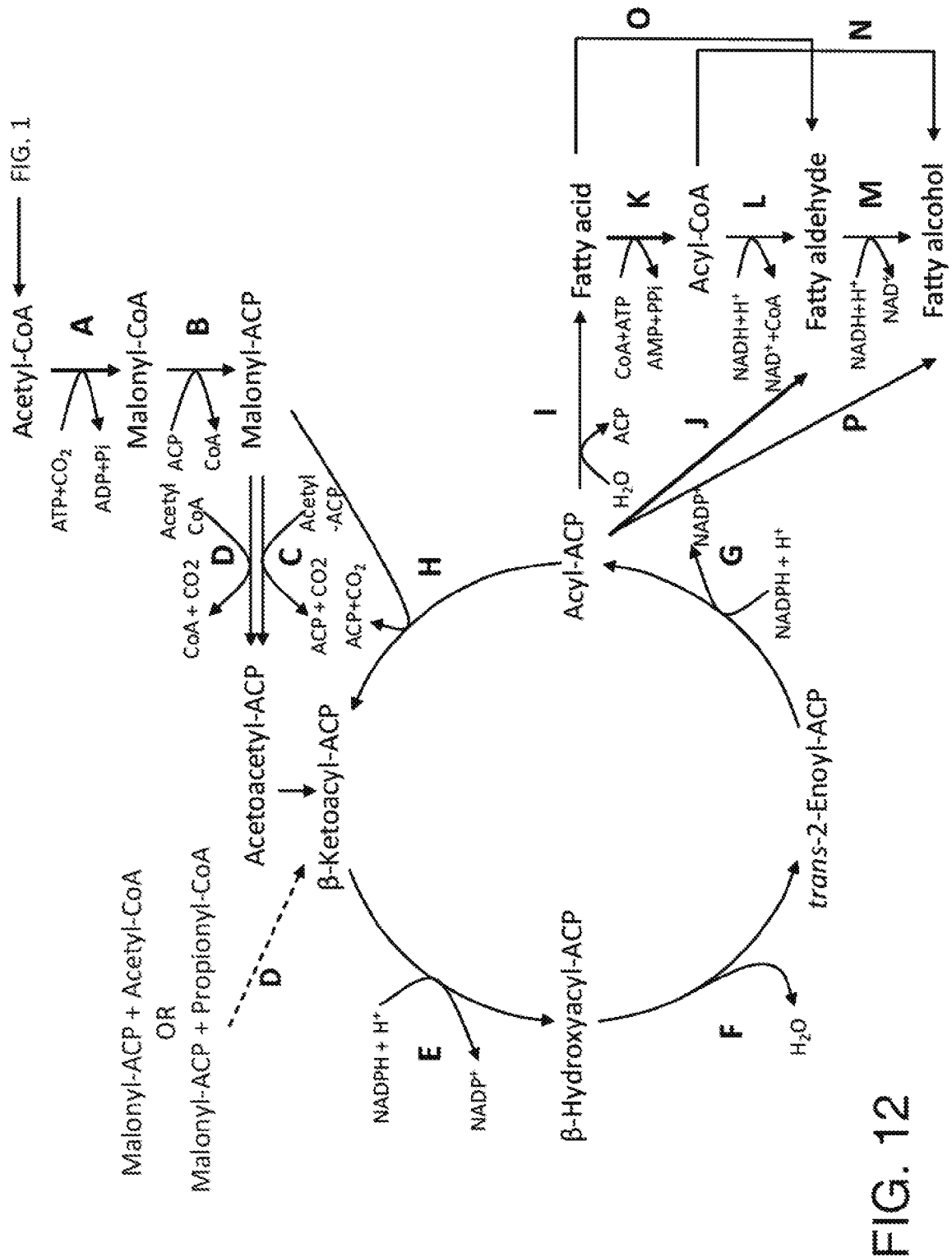
FIG. 12 shows an exemplary β-ketoacyl-ACP pathway, a FAACPE cycle in combination with termination pathways for production of fatty alcohols, aldehydes, or acids from the acyl-ACP intermediate of the FAACPE cycle. Enzymes are: A) Acetyl-CoA carboxylase, B) Malonyl-CoA ACP transacylase, C) Acetoacetyl-ACP synthase, D) β-Ketoacyl-ACP synthase, E) β-Ketoacyl-ACP reductase, F) β-Hydroxyacyl-ACP reductase, G) Enoyl ACP-reductase, H) β-Ketoacyl-ACP synthase, I) Thioesterase, J) Fatty acyl-ACP reductase, K) Acyl-CoA synthase, L) Acyl-CoA reductase, M) Fatty aldehyde reductase, N) Fatty alcohol forming acyl-CoA reductase (FAR), O) Carboxylic acid reductase (CAR), and P) acyl-ACP reductase (alcohol forming).

The carbon chain-length of the product can also be controlled by one or more enzymes of the FAACPE cycle (steps H/E/F/G of FIG. 12) in combination with one or more termination pathway enzymes (steps I-O of FIG. 12). Chain length can be capped during the elongation cycle by one or more FAACPE cycle enzymes (β-ketoacyl-ACP synthase, β-ketoacyl-ACP reductase, β-hydroxyacyl-ACP reductase, and/or enoyl ACP-reductase) exhibiting selectivity for FAACPE cycle substrates having a number of carbon atoms that are no greater than the desired product size. Chain length can be further constrained by one or more enzymes catalyzing the conversion of the FAACPE cycle intermediate to the fatty alcohol, fatty aldehyde or fatty acid product such that the one or more termination enzymes only reacts with substrates having a number of carbon atoms that are no less than the desired fatty alcohol, fatty aldehyde or fatty acid product.

The termination pathway enzymes catalyzing conversion of a FAACPE cycle intermediate to a fatty alcohol can include enzyme combinations of a thioesterase, a fatty acyl-ACP reductase, an acyl-CoA synthase, an acyl-CoA reductase, a fatty aldehyde reductase, a fatty alcohol forming acyl-CoA reductase (FAR), and/or a carboxylic acid reductase (CAR) (see, e.g., pathways J/M; I/K/L/M; I/O/M; and I/K/N of FIG. 12). Termination pathway enzyme for converting a FAACPE intermediate to a fatty acid can include a thioesterase (see, e.g., pathways I of FIG. 12). For production of a fatty aldehyde, the termination pathway enzymes can include combinations of a thioesterase, a fatty acyl-ACP reductase, an acyl-CoA synthase, an acyl-CoA reductase, a fatty aldehyde reductase, and/or a carboxylic acid reductase (CAR), (see, e.g., pathways J; I/K/L; and I/O of FIG. 12).

The non-naturally occurring microbial organisms of the invention can also efficiently direct cellular resources, including carbon, energy and reducing equivalents, to the production of fatty alcohols, fatty aldehydes and fatty acids, thereby resulting in improved yield, productivity and/or titer relative to a naturally occurring organism. In one embodiment, the microorganism is modified to increase cytosolic acetyl-CoA levels. In another embodiment, the microorganism is modified to efficiently direct cytosolic acyl-CoA into fatty alcohols, fatty aldehydes or fatty acids rather than other byproducts or cellular processes. Enzymes or pathways that lead to the formation of byproducts can be attenuated or deleted. Exemplary byproducts include, but are not limited to, ethanol, glycerol, lactate, acetate, esters and carbon dioxide. Additional byproducts can include fatty-acyl-CoA derivatives such as alcohols, alkenes, alkanes, esters, acids and aldehydes. Accordingly, a byproduct can include any fermentation product diverting carbon and/or reducing equivalents from the product of interest.

In another embodiment, the availability of reducing equivalents or redox ratio is increased. In yet another embodiment, the cofactor requirements of the microorganism are balanced such that the same reduced cofactors generated during carbon assimilation and central metabolism are utilized by MI-FAE cycle, MD-FAE cycle and/or termination pathway enzymes. In yet another embodiment, the fatty alcohol, fatty aldehyde or fatty acid producing organism expresses a transporter which exports the fatty alcohol, fatty aldehyde or fatty acid from the cell.

Microbial organisms capable of fatty alcohol production are exemplified herein with reference to the *Saccharomyces cerevisaie* genetic background. However, with the complete genome sequence available now for thousands of species (with more than half of these available on public databases such as the NCBI), the identification of an alternate species homolog for one or more genes, including for example, orthologs, paralogs and nonorthologous gene displacements, and the interchange of genetic alterations between eukaryotic organisms is routine and well known in the art. Accordingly, the metabolic alterations enabling production of fatty alcohols described herein with reference to a particular organism such as Saccharomyces cerevisiae can be readily applied to other microorganisms. Given the teachings and guidance provided herein, those skilled in the art understand that a metabolic alteration exemplified in one organism can be applied equally to other organisms.

The methods of the invention are applicable to various prokaryotic and eukaryotic organisms such as bacteria, yeast and fungus. For example, the yeast can include *Saccharomyces cerevisiae* and *Rhizopus arrhizus*. Exemplary eukaryotic organisms can also include Crabtree positive and negative yeasts, and yeasts in the genera *Saccharomyces, Kluyveromyces, Candida* or *Pichia*. Further exempahy eukaryotic species include those selected from *Schizosaccharomyces pombe, Kluyveromyces lactis, Kluyveromyces marxianus, Aspergillus terreus, Aspergillus niger, Rhizopus arrhizus, Rhizopus oryzae, Candida albicans, Candida boidtnii, Candida sonorensis, Candida tropicalis, Yarrowia lipolytica* and *Pichia pastoris*. Additionally, select cells from larger eukaryotic organisms are also applicable to methods of the present invention. Exemplary bacteria include species selected from *Escherichia coli, Klebsiella oxytoca, Anaerobiospinllum succiniciproducens, Actinobacillus succinogenes, Mannheimia succiniciproducens, Rhizobium etli, Bacillus subtilis, Corynebacterium glutamicum, Gluconobacter oxydans, Zymomonas mobilis, Lactococcus lactis, Lactobacillus plantarum, Streptomyces coelicolor, Clostridum acetobutylicum, Pseudomonas fluorescens,* and *Pseudomonas putida*.

In some aspects of the invention, production of fatty alcohols, fatty aldehydes and fatty acids through the MI-FAE cycle and termination pathways disclosed herein are particularly useful because the cycle and pathways result in higher product and ATP yields than through naturally occurring biosynthetic pathways such as the well-known malonyl-CoA dependent fatty acid synthesis pathway, or in some aspects the malonyl-ACP dependent fatty acid sysnthesis pathway. For example, using acetyl-CoA as a C2 extension unit (e.g. step A, FIG. 2) instead of malonyl-acyl carrier protein (malonyl-ACP) saves one ATP molecule per unit flux of acetyl-CoA entering the MI-FAE cycle. The MI-FAE cycle results in acyl-CoA instead of acyl-ACP, and can preclude the need of the ATP-consuming acyl-CoA synthase reactions for the production of octanol and other fatty alcohols, fatty aldehydes or fatty acids if acetyl-CoA is used as the extender unit. The fatty alcohol, fatty aldehyde and fatty acid producing organisms of the invention can additionally allow the use of biosynthetic processes to convert low cost renewable feedstock for the manufacture of chemical products.

The eukaryotic organism of the invention can be further engineered to metabolize and/or co-utilize a variety of feedstocks including glucose, xylose, fructose, syngas, methanol, and the like.

Chain length control can be achieved using a combination of highly active enzymes with suitable substrate ranges appropriate for biosynthesis of the desired fatty alcohol, fatty aldehyde, or fatty acid. Chain length of the product can be controlled using one or more enzymes of MI-FAE cycle, MD-FAE cycle, FAACPE cycle or termination pathway. As described herein, chain length can be capped during the MI-FAE cycle by one or more MI-FAE cycle enzymes (thiolase, 3-oxoacyl-CoA reductase, 3-hydroxyacyl-CoA dehydratase and/or enoyl-CoA reductase), in the case of the MD-FAE cycle, one or more MD-FAE cycle enzymes (elongase, 3-oxoacyl-CoA reductase, 3-hydroxyacyl-CoA dehydratase and/or enoyl-CoA reductase), and in the case of the FAACPE cycle, one or more enzymes (β-ketoacyl-ACP synthase, β-ketoacylcl-ACP reductase, β-hydroxyacyl-ACP reductase and/or enoyl ACP-reductase), exhibiting selectivity for MI-FAE cycle, MD-FAE cycle and/or FAACPE cycle substrates having a number of carbon atoms that are no greater than the desired product size. Since enzymes are reversible, any of the elongation pathway enzymes can serve in this capacity. Selecting enzymes with broad substrate ranges but defined chain-length boundaries enables the use of a single enzyme to catalyze multiple cycles of elongation, while conferring product specificity. To further hone specificity and prevent the accumulation of shorter byproducts, selectivity is further constrained by product-forming termination enzymes, such that one or more enzymes are selective for acyl-CoA, acyl-ACP or other termination pathway substrates having a number of carbon atoms that are no less than the desired chain length. The deletion or attenuation of endogenous pathway enzymes that produce different chain length products can further hone product specificity.

Using the approaches outlined herein, one skilled in the art can select enzymes from the literature with characterized substrate ranges that selectively produce a fatty alcohol, fatty aldehyde or fatty acid product of a specific chain length. To selectively produce fatty alcohols, fatty aldehydes or fatty acids of a desired length, one can utilize combinations of known enzymes in the literature with different selectivity ranges as described above. For example, a non-naturally occurring microbial organism that produces $C_{16}$ fatty alcohol can express enzymes such as the Rattus norvegicus Acaala thiolase and the enoyl-CoA reducatse of Mycobacterium smegmatis, which only accept substrates up to length $C_{16}$. Coupling one or both chain elongation enzymes with a $C_{16}$-$C_{18}$ fatty acyl-CoA reductase (alcohol or aldehyde forming) such as FAR of Simmondsia chinensis further increases product specificity by reducing the synthesis of shorter alcohol products. As another example, a non-naturally occurring microbial organism of the invention can selectively produce alcohols of length $C_{14}$ by combining the 3-hydroxyacyl-CoA dehydratase of Arabidopsis thaliana with the acyl-CoA reductase Ac1 of Acinetobacter sp. Strain M-1. To produce 3-oxoacids of length $C_{14}$, one can, for example, combine the rat thiolase with the 3-oxoacyl-CoA hydrolase of Solanum lycopersicum. As still a further example, to produce $C_{18}$ fatty acids, one can combine the Salmonella enterica fadE enoyl-CoA reductase with the tesB thioesterase of E. coli. In yet another example, selective production of $C_6$ alcohols are formed by combining the paaH1 thiolase from Ralstonia eutropha with the Leifsonia sp. S749 alcohol dehydrogenase lsadh.

Exemplary MI-FAE cycle, MD-FAE cycle and termination pathway enzymes are described in detail in Example IV. The biosynthetic enzymes described herein exhibit varying degrees of substrate specificity. Exemplary substrate ranges of enzymes characterized in the literature are shown in the table below and described in further detail in Example IV.

| Pathway step | Chain length | Gene | Organism |
|---|---|---|---|
| 2A | C4 | AtoB | Escherichia coli |
| 2A | C6 | PhaD | Pseudomonas putida |
| 2A | C6-C8 | BktB | Ralstonia eutropha |
| 2A | C10-C16 | Acaa1a | Rattus norvegicus |
| 2B | C4 | Hbd | Clostridium acetobutylicum |
| 2B | C4-C6 | paaH1 | Ralstonia eutropha |
| 2B | C4-C10 | HADH | Sus scrofa |
| 2B/C | C4-C18 | FadB | Escherichia coli |
| 2B/C | C4-C18 | Fox2 | Candida tropicalis |
| 2B/C | C4-C18 | Fox2 | Saccharomyces cerevisiae |
| 2C | C4-C6 | crt | Clostridium acetobutylicum |
| 2C | C4-C7 | pimF | Rhodopseudomonas palustris |
| 2C | C4-C14 | MFP2 | Arabidopsis thaliana |
| 2D | C4-C6 | ECR1 | Euglena gracilis |
| 2D | C6-C8 | ECR3 | Euglena gracilis |
| 2D | C8-10 | ECR2 | Euglena gracilis |
| 2D | C8-C16 | ECR | Rattus norvegicus |
| 2D | C10-C16 | ECR | Mycobacterium smegmatis |
| 2D | C2-C18 | fadE | Salmonella enterica |
| 2E | C2-C4 | bphG | Pseudomonas sp |
| 2E | C4 | Bld | Clostridium saccharoperbutylacetonicum |
| 2E | C12-C20 | ACR | Acinetobacter calcoaceticus |
| 2E | C14-C18 | Acr1 | Acinetobacter sp. Strain M-1 |
| 2E | C16-C18 | Rv1543, Rv3391 | Mycobacterium tuberculosis |
| 2E | C18 | FAR1, FAR2 | Mus musculus |
| 2E | C12-C20 | orf1594 | Synechococcus elongatus PCC7942 |
| 2E | C6-C18 | Maqu_2220 | Marinobacter aquaeolei |
| 2F | C6-C7 | lsadh | Leifsonia sp. S749 |
| 2F | C2-C8 | yqhD | Escherichia coli |
| 2F | C3-C10 | Adh | Pseudomonas putida |
| 2F | C2-C14 | alrA | Acinetobacter sp. strain M-1 |
| 2F | C2-C30 | ADH1 | Geobacillus thermodenitrificans |
| 2F | C3-C8 | ADH6 | Saccharomyces cerevisiae s288c |
| 2G | C2 | adhE | Escherichia coli |
| 2G | C2-C8 | adhe2 | Clostridium acetobutylicum |
| 2G | C14-C16 | At3g11980 | Arabidopsis thaliana |
| 2G | C16 | At3g44560 | Arabidopsis thaliana |
| 2G | C16-C18 | FAR | Simmondsia chinensis |
| 2H | C4 | Cat2 | Clostridium kluyveri |
| 2H | C4-C6 | Acot12 | Rattus norvegicus |
| 2H | C14 | MKS2 | Solanum lycopersicum |
| 2L | C8-C10 | fatB2 | Cuphea hookeriana |
| 2L | C12 | fatB | Umbellularia california |
| 2L | C14-C16 | fatB3 | Cuphea hookeriana |
| 2L | C18 | tesA | Escherichia coli |
| 2N | C12-C18 | Car | Nocardia iowensis |
| 2N | C12-C16 | Car | Mycobacterium sp. (strain JLS) |
| 2O | C4-C8 | ELO1 | Trypanosoma brucei |
| 2O | C10-C12 | ELO2 | Trypanosoma brucei |
| 2O | C14-C16 | ELO3 | Trypanosoma brucei |
| 2O | C14-C16 | ELO1 | Saccharomyces cerevisiae |
| 2O | C18-C20 | ELO2 | Saccharomyces cerevisiae |
| 2O | C22-C24 | ELO3 | Saccharomyces cerevisiae |

Figure 6:
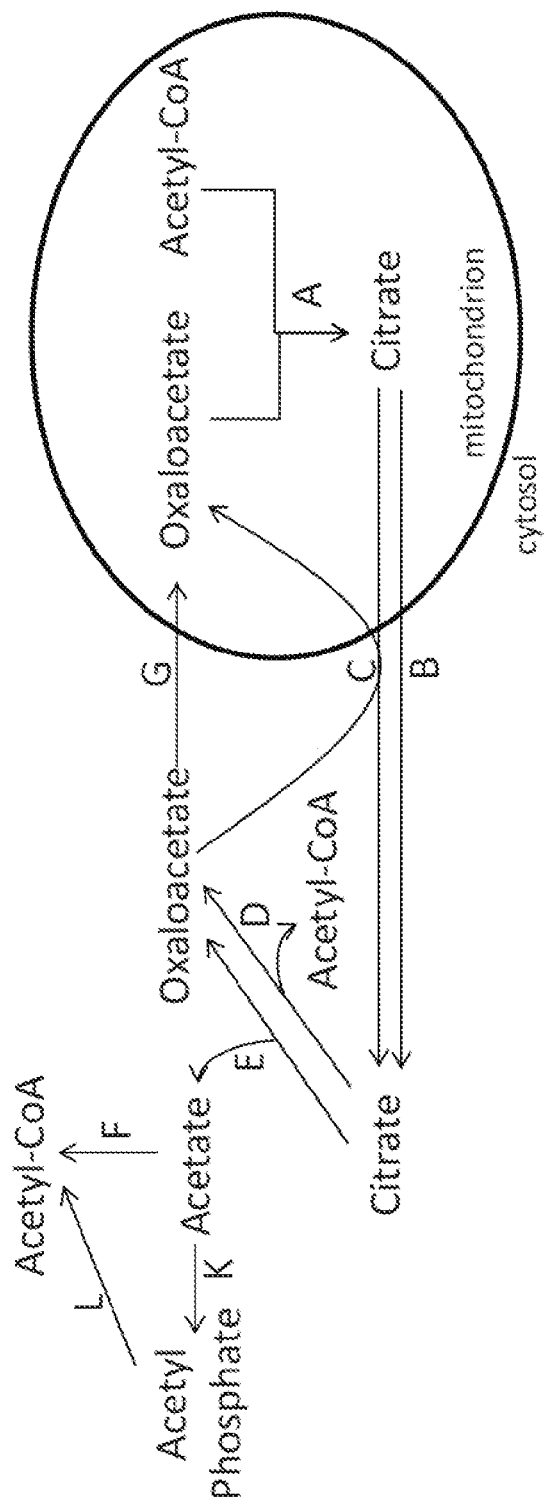
FIG. 6 shows exemplary pathways for production of cytosolic acetyl-CoA from mitochondrial acetyl-CoA using citrate and oxaloacetate transporters. Enzymes are: A. citrate synthase; B. citrate transporter; C. citrate/oxaloacetate transporter; D. ATP citrate lyase; E. citrate lyase; F. acetyl-CoA synthetase or transferase; G) oxaloacetate transporter; K) acetate kinase; and L) phosphotransacetylase.

Taking into account the differences in chain-length specificities of each enzyme in the MI-FAE cycle, MD-FAE cycle or FAACPE cycle, one skilled in the art can select one or more enzymes for catalyzing each elongation cycle reaction step (e.g., steps A-D or steps E/B/C/D of FIG. 6, or H/E/F/G of FIG. 12). For example, for the thiolase step of the MI-FAE cycle, some thiolase enzymes such as bktB of Ralstonia eutropha catalyze the elongation of short- and medium-chain acyl-CoA intermediates ($C_6$-$C_8$), whereas others such as Acaala of R. norvegicus are active on longer-chain substrates ($C_{10}$-$C_{16}$). Thus, a microbial organism producing a fatty alcohol, fatty aldehyde or fatty acid can comprise one, two, three, four or more variants of a thiolase, elongase, 3-oxoacyl-CoA reductase, 3-hydroxyacyl-CoA dehydratase and/or enoyl-CoA reductase.

Chain length specificity of enzymes can be assayed by methods well known in the art (eg. Wrensford et al, *Anal Biochem* 192:49-54 (1991)). The substrate ranges of fatty alcohol, fatty aldehyde, or fatty acid producing enzymes can be further extended or narrowed by methods well known in the art. Variants of biologically-occurring enzymes can be generated, for example, by rational and directed evolution, mutagenesis and enzyme shuffling as described herein. As one example, a rational engineering approach for altering chain length specificity was taken by Denic and Weissman (Denic and Weissman, *Cell* 130:663-77 (2008)). Denic and Weissman mapped the region of the yeast elongase protein ELOp responsible for chain length, and introduced mutations to vary the length of fatty acid products. In this instance, the geometry of the hydrophobic substrate pocket set an upper boundary on chain length. A similar approach can be useful for altering the chain length specificities of enzymes of the MI-FAE cycle, MD-FAE cycle and/or termination pathways.

Enzyme mutagenesis, expression in a host, and screening for fatty alcohol production is another useful approach for generating enzyme variants with improved properties for the desired application. For example, US patent application 2012/0009640 lists hundreds of variants of *Mannobacter algicola* and *Marinobacter aquaeolei* FAR enzymes with improved activity over the wild type enzyme, and varying product profiles.

Enzyme mutagenesis (random or directed) in conjunction with a selection platform is another useful approach. For example, Machado and coworkers developed a selection platform aimed at increasing the activity of acyl-CoA elongation cycle enzymes on longer chain length substrates (Machado et al., *Met Eng* 14(5):504-511(2012)). Machado et al. identified the chain-length limiting step of their pathway (a 3-hydroxyacyl-CoA dehydrogenase) and evolved it for improved activity on $C_6$-$C_8$ substrates using an anaerobic growth rescue platform. Additional variants of enzymes useful for producing fatty alcohols are listed in the table below

| Enzyme | Protein/GenBankID/GI number | Organism | Variant(s) | Reference |
|---|---|---|---|---|
| 3-Ketoacyl-CoA thiolase | Acaa2 NP_569117.1 GI: 18426866 | *Rattus norvegicus* | H352A, H352E, H352K, H352Y | Zeng et al., Prot. Expr. Purif. 35: 320-326 (2004) |
| 3-Hydroxyacyl-CoA dehydrogenase | Hadh NP_476534.1 GI: 17105336 | *Rattus norvegicus* | S137A, S137C, S137T | Liu et al., Prot. Expr. Purif. 37: 344-351 (2004). |
| Enoyl-CoA hydratase | Ech1 NP_072116.1 GI: 12018256 | *Rattus norvegicus* | E144A, E144A/Q162L, E164A, Q162A, Q162L, Q162M | Kiema et al., Biochem. 38: 2991-2999 (1999) |
| Enoyl-CoA reductase | InhA AAY54545.1 GI: 66737267 | *Mycobacterium tuberculosis* | K165A, K165Q, Y158F | Poletto,S. et al., Prot. Expr. Purif. 34: 118-125 (2004). |
| Acyl-CoA reductase | LuxC AAT00788.1 GI:46561111 | *Photobacterium phosphoreum* | C171S, C279S, C286S | Lee, C. et al., Biochim. Biophys. Acta. 1338: 215-222 (1997). |
| Alcohol dehydrogenase | YADH-1 P00330.4 GI: 1168350 | *Saccharomyces cerevisiae* | D223G, D49N, E68Q, G204A, G224I, H47R, H51E, L203A | Leskovac et al., FEMS Yeast Res. 2(4): 481-94 (2002). |
| Fatty alcohol forming acyl-CoA reductase (FAR) | AdhE NP_415757.1 GI: 16129202 | *Escherichia coli* | A267T/E568K, A267T | Membrillo et al., J. Biol. Chem. 275(43): 333869-75 (2000). |

Those skilled in the art will understand that the genetic alterations, including metabolic modifications exemplified herein, are described with reference to a suitable host organism such as *E. coli* or *S. cerevisiae* and their corresponding metabolic reactions or a suitable source organism for desired genetic material such as genes for a desired metabolic pathway. However, given the complete genome sequencing of a wide variety of organisms and the high level of skill in the area of genomics, those skilled in the art will readily be able to apply the teachings and guidance provided herein to essentially all other organisms. For example, the metabolic alterations exemplified herein can readily be applied to other species by incorporating the same or analogous encoding nucleic acid from species other than the referenced species. Such genetic alterations include, for example, genetic alterations of species homologs, in general, and in particular, orthologs, paralogs or nonorthologous gene displacements.

An ortholog is a gene or genes that are related by vertical descent and are responsible for substantially the same or identical functions in different organisms. For example, mouse epoxide hydrolase and human epoxide hydrolase can be considered orthologs for the biological function of hydrolysis of epoxides. Genes are related by vertical descent when, for example, they share sequence similarity of sufficient amount to indicate they are homologous, or related by evolution from a common ancestor. Genes can also be considered orthologs if they share three-dimensional structure but not necessarily sequence similarity, of a sufficient amount to indicate that they have evolved from a common ancestor to the extent that the primary sequence similarity is not identifiable. Genes that are orthologous can encode proteins with sequence similarity of about 25% to 100% amino acid sequence identity. Genes encoding proteins sharing an amino acid similarity less that 25% can also be considered to have arisen by vertical descent if their three-dimensional structure also shows similarities. Members of the serine protease family of enzymes, including tissue plasminogen activator and elastase, are considered to have arisen by vertical descent from a common ancestor.

Orthologs include genes or their encoded gene products that through, for example, evolution, have diverged in structure or overall activity. For example, where one species encodes a gene product exhibiting two functions and where such functions have been separated into distinct genes in a second species, the three genes and their corresponding products are considered to be orthologs. For the production of a biochemical product, those skilled in the art will understand that the orthologous gene harboring the metabolic activity to be introduced or disrupted is to be chosen for construction of the non-naturally occurring microorganism. An example of orthologs exhibiting separable activities is where distinct activities have been separated into distinct gene products between two or more species or within a single species. A specific example is the separation of elastase proteolysis and plasminogen proteolysis, two types of serine protease activity, into distinct molecules as plasminogen activator and elastase. A second example is the separation of mycoplasma 5'-3' exonuclease and Drosophila DNA polymerase III activity. The DNA polymerase from the first species can be considered an ortholog to either or both of the exonuclease or the polymerase from the second species and vice versa.

In contrast, paralogs are homologs related by, for example, duplication followed by evolutionary divergence and have similar or common, but not identical functions. Paralogs can originate or derive from, for example, the same species or from a different species. For example, microsomal epoxide hydrolase (epoxide hydrolase I) and soluble epoxide hydrolase (epoxide hydrolase II) can be considered paralogs because they represent two distinct enzymes, co-evolved from a common ancestor, that catalyze distinct reactions and have distinct functions in the same species. Paralogs are proteins from the same species with significant sequence similarity to each other suggesting that they are homologous, or related through co-evolution from a common ancestor. Groups of paralogous protein families include HipA homologs, luciferase genes, peptidases, and others.

A nonorthologous gene displacement is a nonorthologous gene from one species that can substitute for a referenced gene function in a different species. Substitution includes, for example, being able to perform substantially the same or a similar function in the species of origin compared to the referenced function in the different species. Although generally, a nonorthologous gene displacement will be identifiable as structurally related to a known gene encoding the referenced function, less structurally related but functionally similar genes and their corresponding gene products nevertheless will still fall within the meaning of the term as it is used herein. Functional similarity requires, for example, at least some structural similarity in the active site or binding region of a nonorthologous gene product compared to a gene encoding the function sought to be substituted. Therefore, a nonorthologous gene includes, for example, a paralog or an unrelated gene.

Therefore, in identifying and constructing the non-naturally occurring microbial organisms of the invention having fatty alcohol, fatty aldehyde or fatty acid biosynthetic capability, those skilled in the art will understand with applying the teaching and guidance provided herein to a particular species that the identification of metabolic modifications can include identification and inclusion or inactivation of orthologs. To the extent that paralogs and/or nonorthologous gene displacements are present in the referenced microorganism that encode an enzyme catalyzing a similar or substantially similar metabolic reaction, those skilled in the art also can utilize these evolutionarily related genes. Similarly for a gene disruption, evolutionally related genes can also be disrupted or deleted in a host microbial organism to reduce or eliminate functional redundancy of enzymatic activities targeted for disruption.

Orthologs, paralogs and nonorthologous gene displacements can be determined by methods well known to those skilled in the art. For example, inspection of nucleic acid or amino acid sequences for two polypeptides will reveal sequence identity and similarities between the compared sequences. Based on such similarities, one skilled in the art can determine if the similarity is sufficiently high to indicate the proteins are related through evolution from a common ancestor. Algorithms well known to those skilled in the art, such as Align, BLAST, Clustal W and others compare and determine a raw sequence similarity or identity, and also determine the presence or significance of gaps in the sequence which can be assigned a weight or score. Such algorithms also are known in the art and are similarly applicable for determining nucleotide sequence similarity or identity. Parameters for sufficient similarity to determine relatedness are computed based on well known methods for calculating statistical similarity, or the chance of finding a similar match in a random polypeptide, and the significance of the match determined A computer comparison of two or more sequences can, if desired, also be optimized visually by those skilled in the art. Related gene products or proteins can be expected to have a high similarity, for example, 25% to 100% sequence identity. Proteins that are unrelated can have an identity which is essentially the same as would be expected to occur by chance, if a database of sufficient size is scanned (about 5%). Sequences between 5% and 24% may or may not represent sufficient homology to conclude that the compared sequences are related. Additional statistical analysis to determine the significance of such matches given the size of the data set can be carried out to determine the relevance of these sequences.

Exemplary parameters for determining relatedness of two or more sequences using the BLAST algorithm, for example, can be as set forth below. Briefly, amino acid sequence alignments can be performed using BLASTP version 2.0.8 (Jan. 5, 1999) and the following parameters: Matrix: 0 BLOSUM62; gap open: 11; gap extension: 1; x_dropoff: 50; expect: 10.0; wordsize: 3; filter: on. Nucleic acid sequence alignments can be performed using BLASTN version 2.0.6 (Sep. 16, 1998) and the following parameters: Match: 1; mismatch: −2; gap open: 5; gap extension: 2; x_dropoff: 50; expect: 10.0; wordsize: 11; filter: off. Those skilled in the art will know what modifications can be made to the above parameters to either increase or decrease the stringency of the comparison, for example, and determine the relatedness of two or more sequences.

Figure 2:
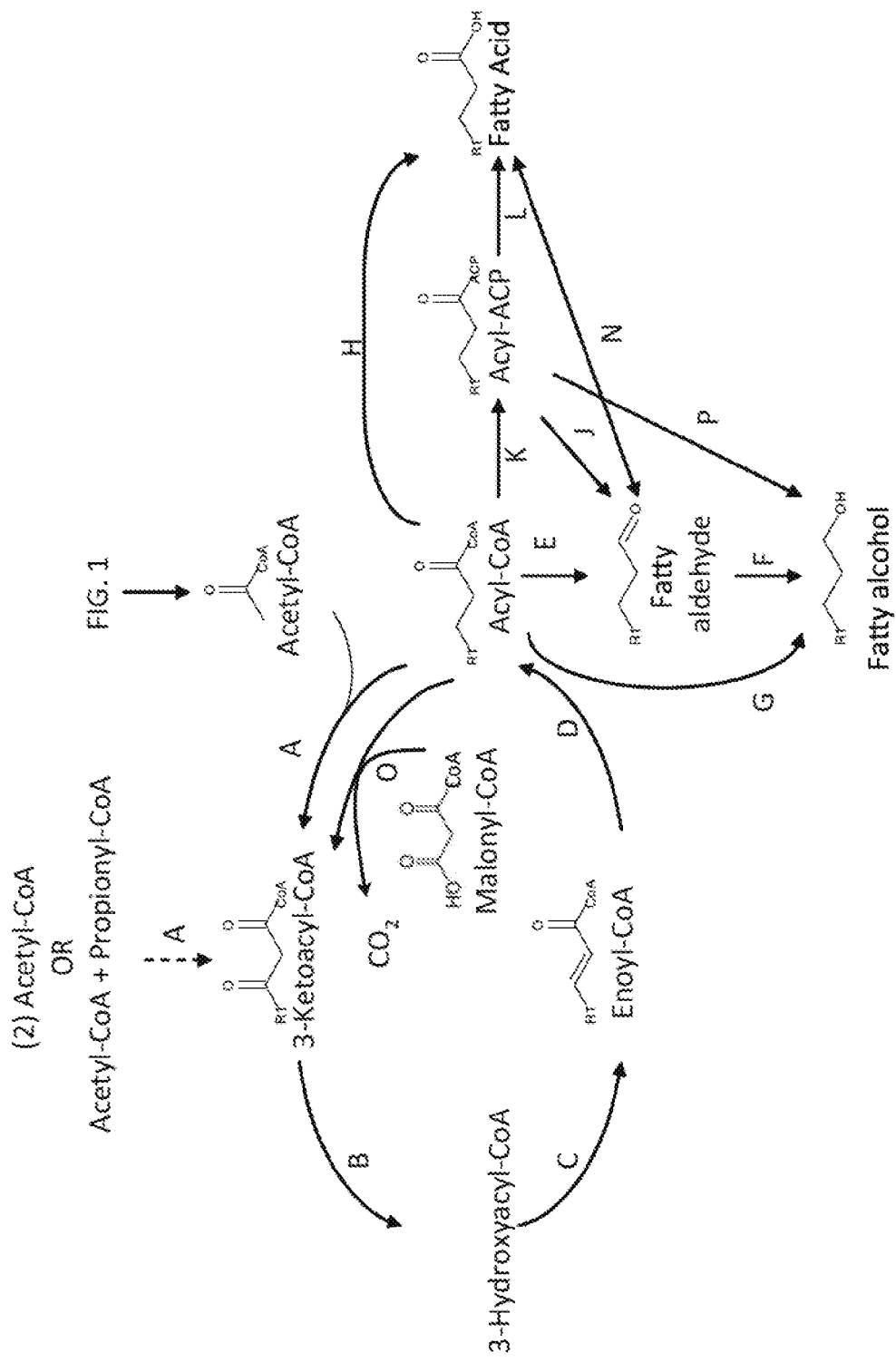
FIG. 2 shows an exemplary MI-FAE cycle and/or MD-FAE cycle in combination with termination pathways for production of fatty alcohols, aldehydes, or acids from the acyl-CoA intermediate of the MI-FAE cycle or MD-FAE cycle. Enzymes are: A. Thiolase; B. 3-Oxoacyl-CoA reductase; C. 3-Hydroxyacyl-CoA dehydratase; D. Enoyl-CoA reductase; E. Acyl-CoA reductase (aldehyde forming); F. Alcohol dehydrogenase; G. Acyl-CoA reductase (alcohol forming); H. acyl-CoA hydrolase, transferase or synthase; J. Acyl-ACP reductase; K. Acyl-CoA:ACP acyltransferase; L. Thioesterase; N. Aldehyde dehydrogenase (acid forming) or carboxylic acid reductase; O. Elongase; and P. acyl-ACP reductase (alcohol forming).
Figure 7:
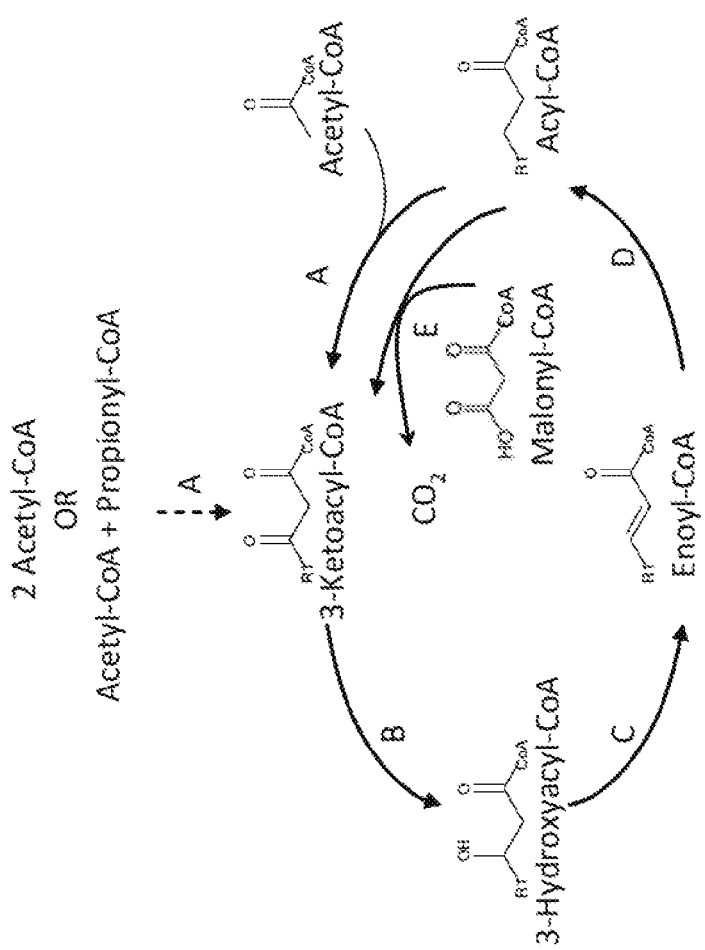
FIG. 7 shows an exemplary MI-FAE cycle and/or MD-FAE cycle for elongating the linear alkyl of $R_1$. Enzymes are: A. Thiolase; B. 3-Ketoacyl-CoA reductase; C. 3-Hydroxyacyl-CoA dehydratase; D. Enoyl-CoA reductase; and E. Elongase.
Figure 8:
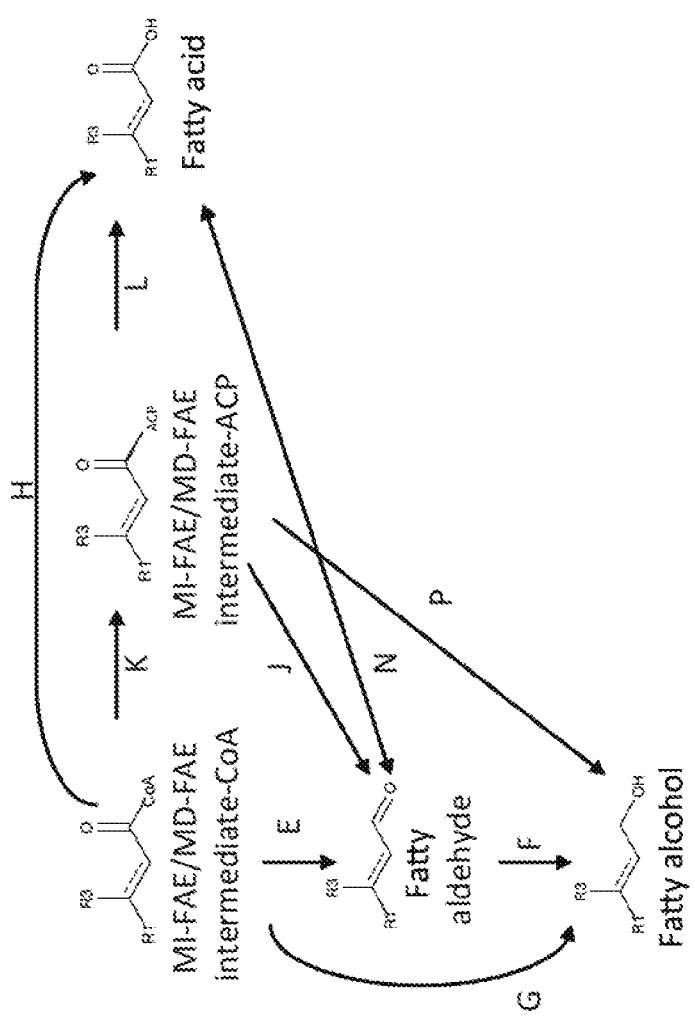
FIG. 8 shows an exemplary termination cycle for generating a fatty alcohol, fatty aldehyde or fatty acid from any of the MI-FAE cycle intermediates or MD-FAE cycle intermediates of FIG. 7. Enzymes are: E. MI-FAE/MD-FAE intermediate-CoA reductase (aldehyde forming); F. Alcohol dehydrogenase; G. MI-FAE/MD-FAE intermediate-CoA reductase (alcohol forming); H. MI-FAE/MD-FAE intermediate-CoA hydrolase, transferase or synthase; J. MI-FAE/MD-FAE intermediate-ACP reductase; K. MI-FAE/MD-FAE intermediate-CoA:ACP acyltransferase; L. Thioesterase; N. Aldehyde dehydrogenase (acid forming) or carboxylic acid reductase; and P. acyl-ACP reductase (alcohol forming). $R_1$ is C1-24 linear alkyl; $R_3$ is H, OH, or oxo (=O) and $\overline{\phantom{----}}$ represents a single or double bond with the proviso that the valency of the carbon atom to which $R_3$ is attached is four.

In some embodiments, the invention provides a non-naturally occurring microbial organism having: (i) a formaldehyde fixation pathway; (ii) a formate assimilation pathway; and/or (iii) a methanol metabolic pathway as depicted in FIGS. 1 and 10, and a MI-FAE cycle or a MD-FAE cycle in combination with a termination pathway as depicted in FIGS. 2, 7 and 8, wherein said formaldehyde fixation pathway comprises: (1) 1B and 1C; (2) 1D; or (3) 1D and 1Z, wherein 1B is a 3-hexulose-6-phosphate synthase, wherein 1C is a 6-phospho-3-hexuloisomerase, wherein 1D is a dihydroxyacetone synthase, wherein 1Z is a fructose-6-phosphate aldolase, wherein said formate assimilation pathway comprises a pathway selected from: (4) 1E; (5) 1F, and 1G; (6) 1H, 1I, 1J, and 1K; (7) 1H, 1I, 1J, 1L, 1M, and 1N; (8) 1E, 1H, 1I, 1J, 1L, 1M, and 1N; (9) 1F, 1G, 1H, 1I, 1J, 1L, 1M, and 1N; (10) 1K, 1H, 1I, 1J, 1L, 1M, and 1N; and (11) 1H, 1I, 1J, 1O, and 1P, wherein 1E is a formate reductase, 1F is a formate ligase, a formate transferase, or a formate synthetase, wherein 1G is a formyl-CoA reductase, wherein 1H is a formyltetrahydrofolate synthetase, wherein 1I is a methenyltetrahydrofolate cyclohydrolase, wherein 1J is a methylenetetrahydrofolate dehydrogenase, wherein 1K is a formaldehyde-forming enzyme or spontaneous, wherein 1L is a glycine cleavage system, wherein 1M is a serine hydroxymethyltransferase, wherein 1N is a serine deaminase, wherein 1O is a methylenetetrahydrofolate reductase, wherein 1P is an acetyl-CoA synthase, wherein said methanol metabolic pathway comprises a pathway selected from: (12) 10J; (13) 10A, (14) 10A and 10B; (15) 10A, 10B and 10C; (16) 10J, 10K and 10C; (17) 10J, 10M, and 10N; (18) 10J and 10L; (19) 10J, 10L and 10G; (20) 10J, 10L, and 10I; (21) 10A, 10B, 10C, 10D, and 10E; (22) 10A, 10B, 10C, 10D, and 10F; (23) 10J, 10K, 10C, 10D, and 10E; (24) 10J, 10K, 10C, 10D, and 10F; (25) 10J, 10M, 10N, and 10O; (26) 10A, 10B, 10C, 10D, 10E, and 10G; (27) 10A, 10B, 10C, 10D, 10F, and 10G; (28) 10J, 10K, 10C, 10D, 10E, and 10G; (29) 10J, 10K, 10C, 10D, 10F, and 10G; (30) 10J, 10M, 10N, 10O, and 10G; (31) 10A, 10B, 10C, 10D, 10E, and 10I; (32) 10A, 10B, 10C, 10D, 10F, and 10I; (33) 10J, 10K, 10C, 10D, 10E, and 10I; (34) 10J, 10K, 10C, 10D, 10F, and 10I; and (35) 10J, 10M, 10N, 10O, and 10I, wherein 10A is a methanol methyltransferase, wherein 10B is a methylenetetrahydrofolate reductase, wherein 10C is a methylenetetrahydrofolate dehydrogenase, wherein 10D is a methenyltetrahydrofolate cyclohydrolase, wherein 10E is a formyltetrahydrofolate deformylase, wherein 10F is a formyltetrahydrofolate synthetase, wherein 10G is a formate hydrogen lyase, wherein 10I is a formate dehydrogenase, wherein 10J is a methanol dehydrogenase, wherein 10K is a formaldehyde activating enzyme or spontaneous, wherein 10L is a formaldehyde dehydrogenase, wherein 10M is a S-(hydroxymethyl)glutathione synthase or spontaneous, wherein 10N is a glutathione-dependent formaldehyde dehydrogenase, wherein 10O is a S-formylglutathione hydrolase, wherein the MI-FAE cycle includes one or more thiolase, one or more 3-oxoacyl-CoA reductase, one or more 3-hydroxyacyl-CoA dehydratase, and one or more enoyl-CoA reductase, wherein the MD-FAE cycle includes one or more elongase, one or more 3-oxoacyl-CoA reductase, one or more 3-hydroxyacyl-CoA dehydratase, and one or more enoyl-CoA reductase, wherein the termination pathway includes a pathway selected from: (36) 2H; (37) 2K and 2L; (38) 2E and 2N; (39) 2K, 2J, and 2N; (40) 2E; (41) 2K and 2J; (42) 2H and 2N; (43) 2K, 2L, and 2N; (44) 2E and 2F; (45) 2K, 2J, and 2F; (46) 2H, 2N, and 2F; (47) 2K, 2L, 2N, and 2F; (48) 2G; (49) 2P, wherein 2E is an acyl- CoA reductase (aldehyde forming), wherein 2F is an alcohol dehydrogenase, wherein 2G is an acyl-CoA reductase (alcohol forming), wherein 2H is an acyl-CoA hydrolase, acyl-CoA transferase or acyl-CoA synthase, wherein 2J is an acyl-ACP reductase, wherein 2K is an acyl-CoA:ACP acyltransferase, wherein 2L is a thioesterase, wherein 2N is an aldehyde dehydrogenase (acid forming) or a carboxylic acid reductase, wherein 2P is an acyl-ACP reductase (alcohol forming) wherein an enzyme of the formaldehyde fixation pathway, the formate assimilation pathway, the methanol metabolic pathway, the MI-FAE cycle, MD-FAE cycle or termination pathway is encoded by at least one exogenous nucleic acid and is expressed in a sufficient amount to produce a compound of Formula (I):

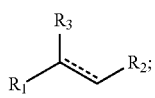
(I)

wherein $R_1$ is $C_{1-24}$ linear alkyl; $R_2$ is $CH_2OH$, CHO, or COOH; $R_3$ is H, OH, or oxo (=O); and ------ represents a single or double bond with the proviso that the valency of the carbon atom to which $R_3$ is attached is four, wherein the substrate of each of said enzymes of the MI-FAE cycle, the MD-FAE cycle and the termination pathway are independently selected from a compound of Formula (II), malonyl-CoA, propionyl-CoA or acetyl-CoA:

(II)

wherein $R_1$ is $C_{1-24}$ linear alkyl; $R_3$ is H, OH, or oxo (=O); $R_4$ is S-CoA, ACP, OH or H; and ------ represents a single or double bond with the proviso that the valency of the carbon atom to which $R_3$ is attached is four; wherein said one or more enzymes of the MI-FAE cycle are each selective for a compound of Formula (II) having a number of carbon atoms at $R_1$ that is no greater than the number of carbon atoms at $R_1$ of said compound of Formula (I), wherein said one or more enzymes of the MD-FAE cycle are each selective for a compound of Formula (II) having a number of carbon atoms at $R_1$ that is no greater than the number of carbon atoms at $R_1$ of said compound of Formula (I), and wherein said one or more enzymes of the termination pathway are each selective for a compound of Formula (II) having a number of carbon atoms at $R_1$ that is no less than the number of carbon atoms at $R_1$ of said compound of Formula (I).

In some embodiments, the invention provides a non-naturally occurring microbial organism having: (i) a formaldehyde fixation pathway; (ii) a formate assimilation pathway; and/or (iii) a methanol metabolic pathway as depicted in FIGS. 1 and 10, and a FAACPE cycle in combination with a termination pathway as depicted in FIG. 12, wherein said formaldehyde fixation pathway comprises: (1) 1B and 1C; (2) 1D; (3) 1D and 1Z, wherein 1B is a 3-hexulose-6-phosphate synthase, wherein 1C is a 6-phospho-3-hexuloisomerase, wherein 1D is a dihydroxyacetone synthase, wherein 1Z is a fructose-6-phosphate aldolase, wherein said formate assimilation pathway comprises a pathway selected from: (4) 1E; (5) 1F, and 1G; (6) 1H, 1I, 1J, and 1K; (7) 1H, 1I, 1J, 1L, 1M, and 1N; (8) 1E, 1H, 1I, 1J, 1L, 1M, and 1N; (9) 1F, 1G, 1H, 1I, 1J, 1L, 1M, and 1N; (10) 1K, 1H, 1I, 1J, 1L, 1M, and 1N; and (11) 1H, 1I, 1J, 1O, and 1P, wherein 1E is a formate reductase, 1F is a formate ligase, a formate transferase, or a formate synthetase, wherein 1G is a formyl-CoA reductase, wherein 1H is a formyltetrahydrofolate synthetase, wherein 1I is a methenyltetrahydrofolate cyclohydrolase, wherein 1J is a methylenetetrahydrofolate dehydrogenase, wherein 1K is a formaldehyde-forming enzyme or spontaneous, wherein 1L is a glycine cleavage system, wherein 1M is a serine hydroxymethyltransferase, wherein 1N is a serine deaminase, wherein 1O is a methylenetetrahydrofolate reductase, wherein 1P is an acetyl-CoA synthase, wherein said methanol metabolic pathway comprises a pathway selected from: (12) 10J; (13) 10A, (14) 10A and 10B; (15) 10A, 10B and 10C; (16) 10J, 10K and 10C; (17) 10J, 10M, and 10N; (18) 10J and 10L; (19) 10J, 10L and 10G; (20) 10J, 10L, and 10I; (21) 10A, 10B, 10C, 10D, and 10E; (22) 10A, 10B, 10C, 10D, and 10F; (23) 10J, 10K, 10C, 10D, and 10E; (24) 10J, 10K, 10C, 10D, and 10F; (25) 10J, 10M, 10N, and 10O; (26) 10A, 10B, 10C, 10D, 10E, and 10G; (27) 10A, 10B, 10C, 10D, 10F, and 10G; (28) 10J, 10K, 10C, 10D, 10E, and 10G; (29) 10J, 10K, 10C, 10D, 10F, and 10G; (30) 10J, 10M, 10N, 10O, and 10G; (31) 10A, 10B, 10C, 10D, 10E, and 10I; (32) 10A, 10B, 10C, 10D, 10F, and 10I; (33) 10J, 10K, 10C, 10D, 10E, and 10I; (34) 10J, 10K, 10C, 10D, 10F, and 10I; and (35) 10J, 10M, 10N, 10O, and 10I, wherein 10A is a methanol methyltransferase, wherein 10B is a methylenetetrahydrofolate reductase, wherein 10C is a methylenetetrahydrofolate dehydrogenase, wherein 10D is a methenyltetrahydrofolate cyclohydrolase, wherein 10E is a formyltetrahydrofolate deformylase, wherein 10F is a formyltetrahydrofolate synthetase, wherein 10G is a formate hydrogen lyase, wherein 10I is a formate dehydrogenase, wherein 10J is a methanol dehydrogenase, wherein 10K is a formaldehyde activating enzyme or spontaneous, wherein 10L is a formaldehyde dehydrogenase, wherein 10M is a S-(hydroxymethyl)glutathione synthase or spontaneous, wherein 10N is a glutathione-dependent formaldehyde dehydrogenase, wherein 10O is a S-formylglutathione hydrolase, wherein said FAACPE cycle comprises one or more β-ketoacyl-ACP synthase, one or more β-ketoacyl-ACP reductase, one or more β-hydroxyacyl-ACP reductase, and one or more enoyl ACP-reductase, wherein said termination pathway comprises a pathway selected from: (36) 12I; (37) 12J; (38) 12I, 12K, and 12L; (39) 12I and 12O; (40) 12J and 12M; (41) 12I, 12K, 12L, and 12M; (42) 12I, 12O, and 12M; (43) 12I, 12K and 12N; (44) 12P, wherein 12I is a thioesterase, wherein 12J is a fatty acyl-ACP reductase, wherein 12K is an acyl-CoA synthase, wherein 12L is an acyl-CoA reductase, wherein 12M is a fatty aldehyde reductase, wherein 12N is a fatty alcohol forming acyl-CoA reductase (FAR), wherein 12O is a carboxylic acid reductase (CAR), wherein 12P is an acyl-ACP reductase (alcohol forming), wherein an enzyme of the formaldehyde fixation pathway, the formate assimilation pathway, the methanol metabolic pathway, the FAACPE cycle or the termination pathway is encoded by at least one exogenous nucleic acid and is expressed in a sufficient amount to produce a compound of Formula (I):

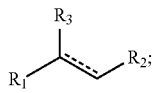

(I)

wherein $R_1$ is $C_{1-24}$ linear alkyl; $R_2$ is $CH_2OH$, CHO, or COOH; $R_3$ is H, OH, or oxo (=O); and ------ represents a single or double bond with the proviso that the valency of the carbon atom to which $R_3$ is attached is four, wherein the substrate of each of said enzymes of the FAACPE cycle and the termination pathway are independently selected from a compound of Formula (II) or malonyl-ACP:

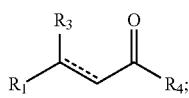

(II)

wherein $R_1$ is $C_{1-24}$ linear alkyl; $R_3$ is H, OH, or oxo (=O); $R_4$ is S-CoA, ACP, OH or H; and ------ represents a single or double bond with the proviso that the valency of the carbon atom to which $R_3$ is attached is four; wherein said one or more enzymes of the FAACPE cycle are each selective for a compound of Formula (II) having a number of carbon atoms at $R_1$ that is no greater than the number of carbon atoms at $R_1$ of said compound of Formula (I), and wherein said one or more enzymes of the termination pathway are each selective for a compound of Formula (II) having a number of carbon atoms at $R_1$ that is no less than the number of carbon atoms at $R_1$ of said compound of Formula (I).

In some embodiments, the non-naturally occurring microbial organism of the invention has a combination of one or more pathways for generating substrates, intermediates and/or reducing equivalents that can be used with elongation cycles and termination pathways described herein for producing a fatty alcohol, fatty acid or fatty aldehyde of the invention. Accordingly, in some embodiments, the microbial organism has a formaldehyde fixation pathway and a MI-FAE cycle in combination with a termination pathway. In some embodiments, the microbial organism has a formate assimilation pathway and a MI-FAE cycle in combination with a termination pathway. In some embodiments, the microbial organism has a formaldehyde fixation pathway, a formate assimilation pathway, and a MI-FAE cycle in combination with a termination pathway. In some embodiments, the microbial organism has a formaldehyde fixation pathway and a MD-FAE cycle in combination with a termination pathway. In some embodiments, the microbial organism has a formate assimilation pathway and a MD-FAE cycle in combination with a termination pathway. In some embodiments, the microbial organism has a formaldehyde fixation pathway, a formate assimilation pathway, and a MD-FAE cycle in combination with a termination pathway. In some embodiments, the microbial organism has a methanol metabolic pathway and a MI-FAE cycle in combination with a termination pathway. In some embodiments, the microbial organism has a methanol metabolic pathway and a MD-FAE cycle in combination with a termination pathway. In some embodiments, the microbial organism has a formaldehyde fixation pathway, a methanol metabolic pathway and a MI-FAE cycle in combination with a termination pathway. In some embodiments, the microbial organism has a formate assimilation pathway, a methanol metabolic pathway and a MI-FAE cycle in combination with a termination pathway. In some embodiments, the microbial organism has a formaldehyde fixation pathway, a formate assimilation pathway, a methanol metabolic pathway and a MI-FAE cycle in combination with a termination pathway. In some embodiments, the microbial organism has a formaldehyde fixation pathway, a methanol metabolic pathway and a MD-FAE cycle in combination with a termination pathway. In some embodiments, the microbial organism has a formate assimilation pathway, a methanol metabolic pathway and a MD-FAE cycle in combination with a termination pathway. In some embodiments, the microbial organism has a formaldehyde fixation pathway, a formate assimilation pathway, a methanol metabolic pathway and MD-FAE cycle in combination with a termination pathway. In some embodiments, the microbial organism has a formaldehyde fixation pathway and an FAACPE cycle in combination with a termination pathway. In some embodiments, the microbial organism has a formate assimilation pathway and an FAACPE cycle in combination with a termination pathway. In some embodiments, the microbial organism has a formaldehyde fixation pathway, a formate assimilation pathway, and an FAACPE cycle in combination with a termination pathway. In some embodiments, the microbial organism has a methanol metabolic pathway and an FAACPE cycle in combination with a termination pathway. In some embodiments, the microbial organism has a formaldehyde fixation pathway, a methanol metabolic pathway and an FAACPE cycle in combination with a termination pathway. In some embodiments, the microbial organism has a formate assimilation pathway, a methanol metabolic pathway and an FAACPE cycle in combination with a termination pathway. In some embodiments, the microbial organism has a formaldehyde fixation pathway, a formate assimilation pathway, a methanol metabolic pathway and an FAACPE cycle in combination with a termination pathway.

In some embodiment, the non-naturally occurring microbial organism of the invention having FAACPE cycle in combination with a termiatnion pathway as described herein, can further include a pathway for production of substrants for the FAACPE cycle, such as acetoacetyl-ACP or 3-oxovalery-ACP. Accordingly, in some embodiments, the microbial organism further comprises an acetoacetyl-ACP pathway of: (1) 12A, 12B, and 12C; or (2) 12A, 12B, and 12D, wherein 12A is an acetyl-CoA carboxylase, wherein 12B is malonyl-CoA ACP transacylase, wherein 12C is an acetoacetyl-ACP synthase, and wherein 12D is a β-ketoacyl-ACP synthase. In some embodiments, the microbial organism further comprises a 3-oxovalery-ACP pathway comprising an acetyl-CoA carboxylase, a malonyl-CoA ACP transacylase, and a β-ketoacyl-ACP synthase In some aspects of the invention, an enzyme of the acetoacetyl-ACP pathway is encoded by at least one exogenous nucleic acid and is expressed in a sufficient amount to produce acetoacetyl-ACP wherein the acetoacetyl-ACP is a β-ketoacyl-ACP of the FAACPE cycle. In some aspects of the invention, an enzyme of the 3-oxovalery-ACP pathway is encoded by at least one exogenous nucleic acid and is expressed in a sufficient amount to produce 3-oxovalery-ACP, wherein the 3-oxovalery-ACP is a β-ketoacyl-ACP of the FAACPE cycle.

In some aspects of the invention, non-naturally occurring microbial organism of the invention can produce a compound of Formula (I) wherein $R_1$ is $C_{1\text{-}17}$ linear alkyl. In another aspect of the invention, the $R_1$ of the compound of Formula (I) is $C_1$ linear alkyl, $C_2$ linear alkyl, $C_3$ linear alkyl, $C_4$ linear alkyl, $C_5$ linear alkyl, $C_6$ linear alkyl, $C_7$ linear alkyl, $C_8$ linear alkyl, $C_9$ linear alkyl, $C_{10}$ linear alkyl, $C_{11}$, linear alkyl, $C_{12}$ linear alkyl or $C_{13}$ linear alkyl, $C_{14}$ linear alkyl, $C_{15}$ linear alkyl, $C_{16}$ linear alkyl, $C_{17}$ linear alkyl, $C_{18}$ linear alkyl, $C_{19}$ linear alkyl, $C_{20}$ linear alkyl, $C_{21}$ linear alkyl, $C_{22}$ linear alkyl, $C_{23}$ linear alkyl, or $C_{24}$ linear alkyl.

In some aspects of the invention, the microbial organism includes two, three, or four exogenous nucleic acids each encoding an enzyme of the MI-FAE cycle, the MD-FAE cycle, or the FAACPE cycle. In some aspects of the invention, the microbial organism includes two, three, or four exogenous nucleic acids each encoding an enzyme of the termination pathway. In some aspects of the invention, the microbial organism includes one, two, three, four, five, six, seven, or eight exogenous nucleic acids each encoding a formaldehyde fixation pathway enzyme, a formate assimilation pathway enzyme, or a methanol metabolic pathway enzyme. In some aspects of the invention, the microbial organism includes exogenous nucleic acids encoding each of the enzymes of at least one of the pathways selected from (1)-(49) for a microbial organism having a MI-FAE cycle or a MD-FAE cycle in combination with a termination pathway as depicted in FIGS. 1, 2, 7, 8 and 10. In some aspects of the invention, the microbial organism includes exogenous nucleic acids encoding each of the enzymes of at least one of the pathways selected from (1)-(44) for a microbial organism having a fatty acyl-ACP elongation (FAACPE) cycle in combination with a termination pathway as depicted in FIGS. 1, 10 and 12.

In some embodiments, the invention provides a non naturally occurring microbial organism, wherein the one or more enzymes of the MI-FAE cycle, MD-FAE cycle, FAACPE cycle or termination pathway is expressed in a sufficient amount to produce a fatty alcohol selected from the Formulas (III)—(VI):

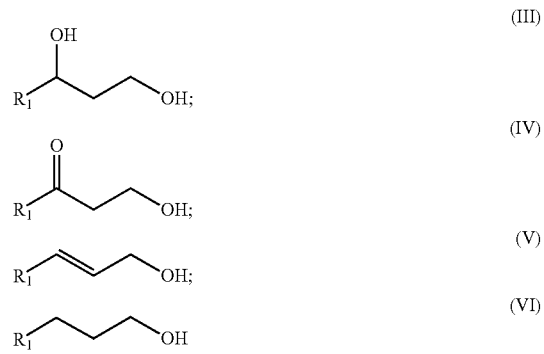

wherein $R_1$ is $C_{1\text{-}24}$ linear alkyl, or alternatively $R_1$ is $C_{1\text{-}17}$ linear alkyl, or alternatively $R_1$ is $C_{9\text{-}13}$ linear alkyl. In some aspects of the invention, $R_1$ is $C_1$ linear alkyl, $C_2$ linear alkyl, $C_3$ linear alkyl, $C_4$ linear alkyl, $C_5$ linear alkyl, $C_6$ linear alkyl, $C_7$ linear alkyl, $C_8$ linear alkyl, $C_9$ linear alkyl, $C_{10}$ linear alkyl, $C_{11}$, linear alkyl, $C_{12}$ linear alkyl, $C_{13}$ linear alkyl, $C_{14}$ linear alkyl, $C_{15}$ linear alkyl, $C_{16}$ linear alkyl, $C_{17}$ linear alkyl, $C_{18}$ linear alkyl, $C_{19}$ linear alkyl, $C_{20}$ linear alkyl, $C_{21}$ linear alkyl, $C_{22}$ linear alkyl, $C_{23}$ linear alkyl, or $C_{24}$ linear alkyl.

In some embodiments, the invention provides a non naturally occurring microbial organism, wherein the one or more enzymes of the MI-FAE cycle, MD-FAE cycle, FAACPE cycle or termination pathway is expressed in a sufficient amount to produce a fatty aldehyde selected from the Formula (VII)—(X):

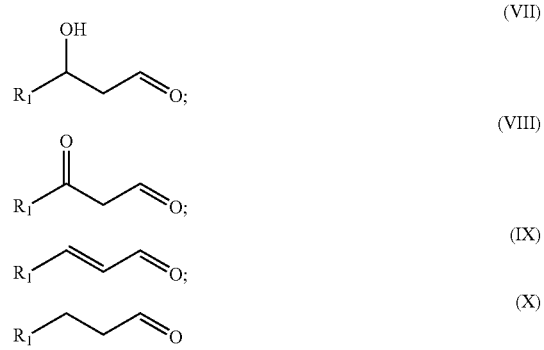

wherein $R_1$ is $C_{1\text{-}24}$ linear alkyl, or alternatively $R_1$ is $C_{1\text{-}17}$ linear alkyl, or alternatively $R_1$ is $C_{9\text{-}13}$ linear alkyl. In some aspects of the invention, $R_1$ is $C_1$ linear alkyl, $C_2$ linear alkyl, $C_3$ linear alkyl, $C_4$ linear alkyl, $C_5$ linear alkyl, $C_6$ linear alkyl, $C_7$ linear alkyl, $C_8$ linear alkyl, $C_9$ linear alkyl, $C_{10}$ linear alkyl, $C_{11}$, linear alkyl, $C_{12}$ linear alkyl, $C_{13}$ linear alkyl, $C_{14}$ linear alkyl, $C_{15}$ linear alkyl, $C_{16}$ linear alkyl, $C_{17}$ linear alkyl, $C_{18}$ linear alkyl, $C_{19}$ linear alkyl, $C_{20}$ linear alkyl, $C_{21}$ linear alkyl, $C_{22}$ linear alkyl, $C_{23}$ linear alkyl, or $C_{24}$ linear alkyl.

In some embodiments, the invention provides a non naturally occurring microbial organism, wherein the one or more enzymes of the MI-FAE cycle, MD-FAE cycle, FAACPE cycle or termination pathway is expressed in a sufficient amount to produce a fatty acid selected from the Formula (XI)—(XIV):

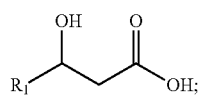
(XI)

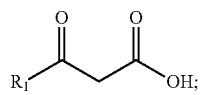
(XII)

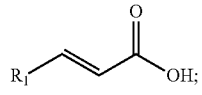
(XIII)

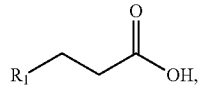
(XIV)

wherein $R_1$ is $C_{1-24}$ linear alkyl, or alternatively $R_1$ is $C_{1-17}$ linear alkyl, or alternatively $R_1$ is $C_{9-13}$ linear alkyl. In some aspects of the invention, $R_1$ is $C_1$ linear alkyl, $C_2$ linear alkyl, $C_3$ linear alkyl, $C_4$ linear alkyl, $C_5$ linear alkyl, $C_6$ linear alkyl, $C_7$ linear alkyl, $C_8$ linear alkyl, $C_9$ linear alkyl, $C_{10}$ linear alkyl, $C_{11}$, linear alkyl, $C_{12}$ linear alkyl, $C_{13}$ linear alkyl, $C_{14}$ linear alkyl, $C_{15}$ linear alkyl, $C_{16}$ linear alkyl, $C_{17}$ linear alkyl, $C_{18}$ linear alkyl, $C_{19}$ linear alkyl, $C_{20}$ linear alkyl, $C_{21}$ linear alkyl, $C_{22}$ linear alkyl, $C_{23}$ linear alkyl, or $C_{24}$ linear alkyl.

In some embodiments, the invention provides a non naturally occurring microbial organism, wherein one or more enzymes of the MI-FAE cycle and/or MD-FAE cycle are each selective for a compound of Formula (II) wherein $R_1$ is $C_{1-24}$ linear alkyl, or alternatively $R_1$ is $C_{1-17}$ linear alkyl, or alternatively $R_1$ is $C_{9-13}$ linear alkyl. In some aspects of the invention, $R_1$ is $C_1$ linear alkyl, $C_2$ linear alkyl, $C_3$ linear alkyl, $C_4$ linear alkyl, $C_5$ linear alkyl, $C_6$ linear alkyl, $C_7$ linear alkyl, $C_8$ linear alkyl, $C_9$ linear alkyl, $C_{10}$ linear alkyl, $C_{11}$, linear alkyl, $C_{12}$ linear alkyl, $C_{13}$ linear alkyl, $C_{14}$ linear alkyl, $C_{15}$ linear alkyl, $C_{16}$ linear alkyl, $C_{17}$ linear alkyl, $C_{18}$ linear alkyl, $C_{19}$ linear alkyl, $C_{20}$ linear alkyl, $C_{21}$ linear alkyl, $C_{22}$ linear alkyl, $C_{23}$ linear alkyl, or $C_{24}$ linear alkyl.

In some embodiments, the invention provides a non naturally occurring microbial organism, wherein one or more enzymes of the FAACPE cycle are each selective for a compound of Formula (II) wherein $R_1$ is $C_{1-24}$ linear alkyl, or alternatively $R_1$ is $C_{1-17}$ linear alkyl, or alternatively $R_1$ is $C_{9-13}$ linear alkyl. In some aspects of the invention, $R_1$ is $C_1$ linear alkyl, $C_2$ linear alkyl, $C_3$ linear alkyl, $C_4$ linear alkyl, $C_5$ linear alkyl, $C_6$ linear alkyl, $C_7$ linear alkyl, $C_8$ linear alkyl, $C_9$ linear alkyl, $C_{10}$ linear alkyl, $C_{11}$, linear alkyl, $C_{12}$ linear alkyl, $C_{13}$ linear alkyl, $C_{14}$ linear alkyl, $C_{15}$ linear alkyl, $C_{16}$ linear alkyl, $C_{17}$ linear alkyl, $C_{18}$ linear alkyl, $C_{19}$ linear alkyl, $C_{20}$ linear alkyl, $C_{21}$ linear alkyl, $C_{22}$ linear alkyl, $C_{23}$ linear alkyl, or $C_{24}$ linear alkyl.

In some embodiments, the invention provides a non naturally occurring microbial organism, wherein one or more enzymes of the termination pathway are each selective for a compound of Formula (II) wherein $R_1$ is $C_{1-24}$ linear alkyl, or alternatively $R_1$ is $C_{1-17}$ linear alkyl, or alternatively $R_1$ is $C_{9-13}$ linear alkyl. In some aspects of the invention, $R_1$ is $C_1$ linear alkyl, $C_2$ linear alkyl, $C_3$ linear alkyl, $C_4$ linear alkyl, $C_5$ linear alkyl, $C_6$ linear alkyl, $C_7$ linear alkyl, $C_8$ linear alkyl, $C_9$ linear alkyl, $C_{10}$ linear alkyl, $C_{11}$, linear alkyl, $C_{12}$ linear alkyl, $C_{13}$ linear alkyl, $C_{14}$ linear alkyl, $C_{15}$ linear alkyl, $C_{16}$ linear alkyl, $C_{17}$ linear alkyl, $C_{18}$ linear alkyl, $C_{19}$ linear alkyl, $C_{20}$ linear alkyl, $C_{21}$ linear alkyl, $C_{22}$ linear alkyl, $C_{23}$ linear alkyl, or $C_{24}$ linear alkyl.

Figure 11:
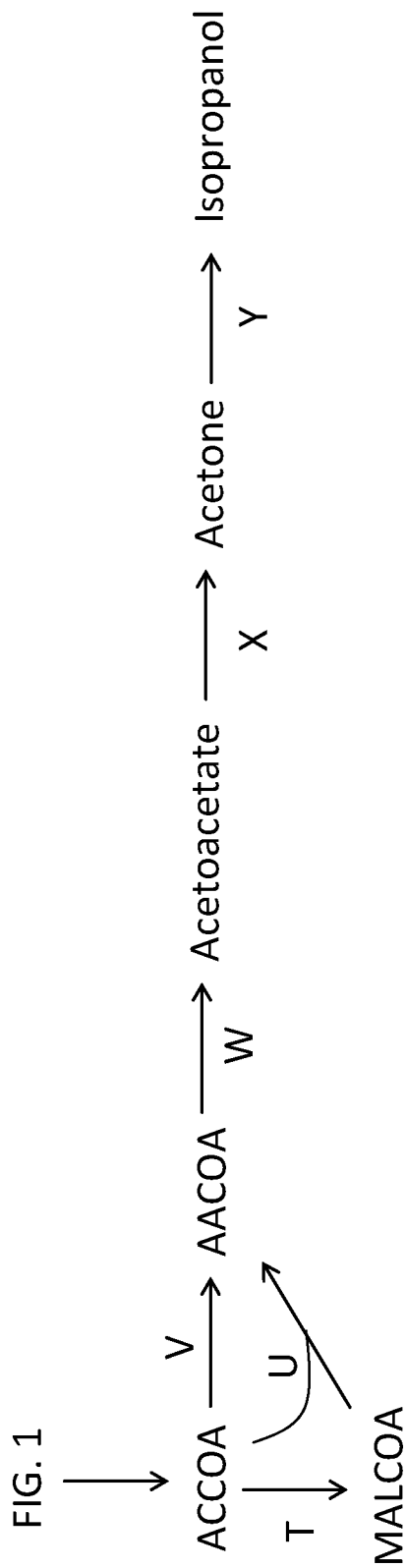
FIG. 11 shows exemplary metabolic pathways enabling the conversion of acetyl-CoA to isopropanol. Enzymes are: T) acetyl-CoA carboxylase, U) acetoacetyl-CoA synthase, V) acetyl-CoA:acetyl-CoA acyltransferase, W) acetoacetyl-CoA hydrolase, acetoacetyl-CoA transferase, acetoacetyl-CoA ligase, phosphotransacetoacetylase/acetoacetate kinase, X) acetoacetate decarboxylase, Y) acetone reductase (or isopropanol dehydrogenase). See abbreviation list below for compound names.

In some embodiments, the invention provides a non-naturally occurring microbial organism having: (i) a formaldehyde fixation pathway; (ii) a formate assimilation pathway; and/or (iii) a methanol metabolic pathway as depicted in FIGS. 1 and 10, and an isopropanol pathway as depicted in FIG. 11, wherein said formaldehyde fixation pathway comprises: (1) 1B and 1C; (2) 1D; or (3) 1D and 1Z, wherein 1B is a 3-hexulose-6-phosphate synthase, wherein 1C is a 6-phospho-3-hexuloisomerase, wherein 1D is a dihydroxyacetone synthase, wherein 1Z is a fructose-6-phosphate aldolase, wherein said formate assimilation pathway comprises a pathway selected from: (4) 1E; (5) 1F, and 1G; (6) 1H, 1I, 1J, and 1K; (7) 1H, 1I, 1J, 1L, 1M, and 1N; (8) 1E, 1H, 1I, 1J, 1L, 1M, and 1N; (9) 1F, 1G, 1H, 1I, 1J, 1L, 1M, and 1N; (10) 1K, 1H, 1I, 1J, 1L, 1M, and 1N; and (11) 1H, 1I, 1J, 1O, and 1P, wherein 1E is a formate reductase, 1F is a formate ligase, a formate transferase, or a formate synthetase, wherein 1G is a formyl-CoA reductase, wherein 1H is a formyltetrahydrofolate synthetase, wherein 1I is a methenyltetrahydrofolate cyclohydrolase, wherein 1J is a methylenetetrahydrofolate dehydrogenase, wherein 1K is a formaldehyde-forming enzyme or spontaneous, wherein 1L is a glycine cleavage system, wherein 1M is a serine hydroxymethyltransferase, wherein 1N is a serine deaminase, wherein 1O is a methylenetetrahydrofolate reductase, wherein 1P is an acetyl-CoA synthase, wherein said methanol metabolic pathway comprises a pathway selected from: (12) 10J; (13) 10A, (14) 10A and 10B; (15) 10A, 10B and 10C; (16) 10J, 10K and 10C; (17) 10J, 10M, and 10N; (18) 10J and 10L; (19) 10J, 10L and 10G; (20) 10J, 10L, and 10I; (21) 10A, 10B, 10C, 10D, and 10E; (22) 10A, 10B, 10C, 10D, and 10F; (23) 10J, 10K, 10C, 10D, and 10E; (24) 10J, 10K, 10C, 10D, and 10F; (25) 10J, 10M, 10N, and 10O; (26) 10A, 10B, 10C, 10D, 10E, and 10G; (27) 10A, 10B, 10C, 10D, 10F, and 10G; (28) 10J, 10K, 10C, 10D, 10E, and 10G; (29) 10J, 10K, 10C, 10D, 10F, and 10G; (30) 10J, 10M, 10N, 10O, and 10G; (31) 10A, 10B, 10C, 10D, 10E, and 10I; (32) 10A, 10B, 10C, 10D, 10F, and 10I; (33) 10J, 10K, 10C, 10D, 10E, and 10I; (34) 10J, 10K, 10C, 10D, 10F, and 10I; and (35) 10J, 10M, 10N, 10O, and 10I, wherein 10A is a methanol methyltransferase, wherein 10B is a methylenetetrahydrofolate reductase, wherein 10C is a methylenetetrahydrofolate dehydrogenase, wherein 10D is a methenyltetrahydrofolate cyclohydrolase, wherein 10E is a formyltetrahydrofolate deformylase, wherein 10F is a formyltetrahydrofolate synthetase, wherein 10G is a formate hydrogen lyase, wherein 10I is a formate dehydrogenase, wherein 10J is a methanol dehydrogenase, wherein 10K is a formaldehyde activating enzyme or spontaneous, wherein 10L is a formaldehyde dehydrogenase, wherein 10M is a S-(hydroxymethyl)glutathione synthase or spontaneous, wherein 10N is a glutathione-dependent formaldehyde dehydrogenase, wherein 10O is a S-formylglutathione hydrolase, wherein said isopanol pathway comprises: (36) 11V, 11W, 11X, and 11Y; or (37) 11T, 11U, 11W, 11X, and 11Y, wherein 11T is an acetyl-CoA carboxylase, wherein 11U is an acetoacetyl-CoA synthase, wherein 11V is an acetyl-CoA:acetyl-CoA acyltransferase, wherein 11W is an acetoacetyl-CoA hydrolase, an acetoacetyl-CoA transferase, an acetoacetyl-CoA ligase, or a phosphotransacetoacetylase/acetoacetate kinase, wherein 11X is an acetoacetate decarboxylase, wherein 11Y is an acetone reductase or isopropanol dehydrogenase, wherein an enzyme of the formaldehyde fixation pathway, formate assimilation pathway, methanol metabolic pathway, or isopropanol pathway is encoded by at least one exogenous nucleic acid and is expressed in a sufficient amount to produce isopropanol.

In some embodiments, the non-naturally occurring microbial organism of the invention has a combination of one or more pathways for generating substrates, intermediates and/or reducing equivalents that can be used with isopropanol pathways described herein for producing isopropanol of the invention. Accordingly, in some embodiments, the microbial organism has a formaldehyde fixation pathway and an isopropanol pathway. In some embodiments, the microbial organism has a formate assimilation pathway and an isopropanol pathway. In some embodiments, the microbial organism has a formaldehyde fixation pathway, a formate assimilation pathway, and an isopropanol pathway. In some embodiments, the microbial organism has a methanol metabolic pathway and an isopropanol pathway. In some embodiments, the microbial organism has a formaldehyde fixation pathway, a methanol metabolic pathway and an isopropanol pathway. In some embodiments, the microbial organism has a formate assimilation pathway, a methanol metabolic pathway and an isopropanol pathway. In some embodiments, the microbial organism has a formaldehyde fixation pathway, a formate assimilation pathway, a methanol metabolic pathway and an isopropanol pathway.

In some aspects of the invention, the microbial organism includes two, three, four, five or six exogenous nucleic acids each encoding an enzyme of the isopropanol pathway. In some aspects of the invention, the microbial organism includes one, two, three, four, five, six, seven, or eight exogenous nucleic acids each encoding a formaldehyde fixation pathway enzyme, a formate assimilation pathway enzyme, or a methanol metabolic pathway enzyme. In some aspects of the invention, the microbial organism includes exogenous nucleic acids encoding each of the enzymes of at least one of the pathways selected from (1)-(37) for a microbial organism having an isopropanol pathway as depicted in FIGS. 1, 10 and 11.

In some embodiments, a non-naturally occurring microbial organism of the invention having a formate assimilation pathway further includes wherein the formate assimilation pathway comprises: (1) 1Q; (2) 1R, and 1S; (3) 1Y and 1Q; (4) 1Y, 1R and 1S, wherein 1Q is a pyruvate formate lyase, wherein 1R is a pyruvate dehydrogenase, a pyruvate ferredoxin oxidoreductase, or a pyruvate:NADP+ oxidoreductase, wherein 1S is a formate dehydrogenase, wherein 1Y is a glyceraldehydes-3-phosphate dehydrogenase or an enzyme of lower glycolysis. In addition to a glyceraldehyde-3-phosphate dehydrogenase, lower glycolysis includes a phosphoglycerate kinase, a phosphoglyceromutase, an enolase, a pyruvate kinase or a PTS-dependant substrate import. Accordingly, in some embodiments, the formate assimilation pathway comprising 1Y includes an enzyme selected from a phosphoglycerate kinase, a phosphoglyceromutase, an enolase, a pyruvate kinase and a PTS-dependant substrate import.

In some embodiments, a non-naturally occurring micoribial organism of the invention includes a methanol oxidation pathway. Such a pathway can include at least one exogenous nucleic acid encoding a methanol oxidation pathway enzyme expressed in a sufficient amount to produce formaldehyde in the presence of methanol. An exemplary methanol oxidation pathway enzyme is a methanol dehydrogenase. Accordingly, in some embodiments, a non-naturally occurring micoribial organism of the invention includes at least one exogenous nucleic acid encoding a methanol dehydrogenase expressed in a sufficient amount to produce formaldehyde in the presence of methanol.

In some embodiments, the exogenous nucleic acid encoding an methanol dehydrogenase is expressed in a sufficient amount to produce an amount of formaldehyde greater than or equal to 1 µM, 10 µM, 20 µM, or 50 µM, or a range thereof, in culture medium or intracellularly. In other embodiments, the exogenous nucleic acid encoding an methanol dehydrogenase is capable of producing an amount of formaldehyde greater than or equal to 1 µM, 10 µM, 20 µM, or 50 µM, or a range thereof, in culture medium or intracellularly. In some embodiments, the range is from 1 µM to 50 µM or greater. In other embodiments, the range is from 10 µM to 50 µM or greater. In other embodiments, the range is from 20 µM to 50 µM or greater. In other embodiments, the amount of formaldehyde production is 50 µM or greater. In specific embodiments, the amount of formaldehyde production is in excess of, or as compared to, that of a negative control, e.g., the same species of organism that does not comprise the exogenous nucleic acid, such as a wild-type microbial organism or a control microbial organism thereof. In certain embodiments, the methanol dehydrogenase is selected from those provided herein, e.g., as exemplified in Example II (see FIG. 1, Step A, or FIG. 10, Step J). In certain embodiments, the amount of formaldehyde production is determined by a whole cell assay, such as that provided in Example II (see FIG. 1, Step A, or FIG. 10, Step J), or by another assay provided herein or otherwise known in the art. In certain embodiments, formaldehyde utilization activity is absent in the whole cell.

In certain embodiments, the exogenous nucleic acid encoding an methanol dehydrogenase is expressed in a sufficient amount to produce at least 1×, 2×, 3×, 4×, 5×, 6×, 7×, 8×, 9×, 10×, 15×, 20×, 30×, 40×, 50×, 100× or more formaldehyde in culture medium or intracellularly. In other embodiments, the exogenous nucleic acid encoding an methanol dehydrogenase is capable of producing an amount of formaldehyde at least 1×, 2×, 3×, 4×, 5×, 6×, 7×, 8×, 9×, 10×, 15×, 20×, 30×, 40×, 50×, 100×, or a range thereof, in culture medium or intracellularly. In some embodiments, the range is from 1× to 100×. In other embodiments, the range is from 2× to 100×. In other embodiments, the range is from 5× to 100×. In other embodiments, the range is from 10× to 100×. In other embodiments, the range is from 50× to 100×. In some embodiments, the amount of formaldehyde production is at least 20×. In other embodiments, the amount of formaldehyde production is at least 50×. In specific embodiments, the amount of formaldehyde production is in excess of, or as compared to, that of a negative control, e.g., the same species of organism that does not comprise the exogenous nucleic acid, such as a wild-type microbial organism or a control microbial organism thereof. In certain embodiments, the methanol dehydrogenase is selected from those provided herein, e.g., as exemplified in Example II (see FIG. 1, Step A, or FIG. 10, Step J). In certain embodiments, the amount of formaldehyde production is determined by a whole cell assay, such as that provided in Example II (see FIG. 1, Step A, or FIG. 10, Step J), or by another assay provided herein or otherwise known in the art. In certain embodiments, formaldehyde utilization activity is absent in the whole cell.

In some embodiments, a non-naturally occurring microbial organism of the invention includes one or more enzymes for generating reducing equivalents. For example, the microbial organism can further include a hydrogenase and/or a carbon monoxide dehydrogenase. In some aspects, the organism comprises an exogenous nucleic acid encoding the hydrogenase or the carbon monoxide dehydrogenase.

A reducing equivalent can also be readily obtained from a glycolysis intermediate by any of several central metabolic reactions including glyceraldehyde-3-phosphate dehydrogenase, pyruvate dehydrogenase, pyruvate formate lyase and NAD(P)-dependant formate dehydrogenase, isocitrate dehydrogenase, alpha-ketoglutarate dehydrogenase, succinate dehydrogenase, and malate dehydrogenase. Additionally, reducing equivalents can be generated from glucose 6-phosphate-1-dehydrogenase and 6-phosphogluconate dehydrogenase of the pentose phosphate pathway. Overall, at most twelve reducing equivalents can be obtained from a $C_6$ glycolysis intermediate (e.g., glucose-6-phosphate, fructose-6-phosphate, fructose-1,6-diphosphate) and at most six reducing equivalents can be generated from a $C_3$ glycolysis intermediate (e.g., dihydroxyacetone phosphate, glyceraldehyde-3-phosphate).

In some embodiments, the at least one exogenous nucleic acid included in the non-naturally occurring microbial organism of the invention is a heterologous nucleic acid. Accordingly, in some embodiments, the at least one exogenous nucleic acid encoding a formaldehyde fixation pathway enzyme described herein is a heterologous nucleic acid. In some embodiments, the at least one exogenous nucleic acid encoding a formate assimilation pathway enzyme described herein is a heterologous nucleic acid. In some embodiments, the at least one exogenous nucleic acid encoding a methanol metabolic pathway enzyme described herein is a heterologous nucleic acid. In some embodiments, the at least one exogenous nucleic acid encoding a MI-FAE cycle enzyme described herein is a heterologous nucleic acid. In some embodiments, the at least one exogenous nucleic acid encoding a MD-FAE cycle enzyme described herein is a heterologous nucleic acid. In some embodiments, the at least one exogenous nucleic acid encoding a FAACPE cycle enzyme described herein is a heterologous nucleic acid. In some embodiments, the at least one exogenous nucleic acid encoding a termination pathway enzyme described herein is a heterologous nucleic acid. In some embodiments, the at least one exogenous nucleic acid encoding an acetoacetyl-ACP pathway enzyme described herein is a heterologous nucleic acid. In some embodiments, the at least one exogenous nucleic acid encoding a 3-oxovalery-ACP pathway enzyme described herein is a heterologous nucleic acid. In some embodiments, the at least one exogenous nucleic acid encoding an isopropanol pathway enzyme described herein is a heterologous nucleic acid. In some embodiments, the at least one exogenous nucleic acid encoding a methanol oxidation pathway enzyme described herein is a heterologous nucleic acid. In some embodiments, the at least one exogenous nucleic acid encoding a hydrogenase or a carbon monoxide dehydrogenase is a heterologous nucleic acid.

In some embodiments, the non-naturally occurring microbial organism of the invention is in a substantially anaerobic culture medium.

In some embodiments, the invention provides a non-naturally occurring microbial organism as described herein, wherein the microbial organism further includes an acetyl-CoA pathway and at least one exogenous nucleic acid encoding an acetyl-CoA pathway enzyme expressed in a sufficient amount to produce or enhance carbon flux through acetyl-CoA, wherein the acetyl-CoA pathway includes a pathway shown in FIG. 1, 3, 4, 5 or 6 selected from: (1) 3A and 3B; (2) 3A, 3C, and 3D; (3) 3H; (4) 3G and 3D; (5) 3E, 3F and 3B; (6) 3E and 3I; (7) 3J, 3F and 3B; (8) 3J and 3I; (9) 4A, 4B, and 4C; (10) 4A, 4B, 4J, 4K, and 4D; (11) 4A, 4B, 4G, and 4D; (12) 4A, 4F, and 4D; (13) 4N, 4H, 4B and 4C; (14) 4N, 4H, 4B, 4J, 4K, and 4D; (15) 4N, 4H, 4B, 4G, and 4D; (16) 4N, 4H, 4F, and 4D; (17) 4L, 4M, 4B and 4C; (18) 4L, 4M, 4B, 4J, 4K, and 4D; (19) 4L, 4M, 4B, 4G, and 4D; (20) 4L, 4M, 4F, and 4D; (21) 5A, 5B, 5D, 5H, 5I, and 5J; (22) 5A, 5B, 5E, 5F, 5H, 5I, and 5J; (23) 5A, 5B, 5E, 5K, 5L, 5H, 5I, and 5J; (24) 5A, 5C, 5D, 5H, and 5J; (25) 5A, 5C, 5E, 5F, 5H, and 5J; (26) 5A, 5C, 5E, 5K, 5L, 5H, and 5J; (27) 6A, 6B, 6D, and 6G; (28) 6A, 6B, 6E, 6F, and 6G; (29) 6A, 6B, 6E, 6K, 6L, and 6G; (30) 6A, 6C, and 6D; (31) 6A, 6C, 6E, and 6F; (32) 6A, 6C, 6E, 6K, and 6L, (33) 1T and 1V; (34) 1T, 1W, and 1X; (35) 1U and 1V; and (36) 1U, 1W, and 1X, wherein 3A is a pyruvate oxidase (acetate-forming), wherein 3B is an acetyl-CoA synthetase, an acetyl-CoA ligase or an acetyl-CoA transferase, wherein 3C is an acetate kinase, wherein 3D is a phosphotransacetylase, wherein 3E is a pyruvate decarboxylase, wherein 3F is an acetaldehyde dehydrogenase, wherein 3G is a pyruvate oxidase (acetyl-phosphate forming), wherein 3H is a pyruvate dehydrogenase, a pyruvate:ferredoxin oxidoreductase, a pyruvate:NAD(P)H oxidoreductase or a pyruvate formate lyase, wherein 3I is an acetaldehyde dehydrogenase (acylating), wherein 3J is a threonine aldolase, wherein 4A is a phosphoenolpyruvate (PEP) carboxylase or a PEP carboxykinase, wherein 4B is an oxaloacetate decarboxylase, wherein 4C is a malonate semialdehyde dehydrogenase (acetylating), wherein 4D is an acetyl-CoA carboxylase or a malonyl-CoA decarboxylase, wherein 4F is an oxaloacetate dehydrogenase or an oxaloacetate oxidoreductase, wherein 4G is a malonate semialdehyde dehydrogenase (acylating), wherein 4H is a pyruvate carboxylase, wherein 4J is a malonate semialdehyde dehydrogenase, wherein 4K is a malonyl-CoA synthetase or a malonyl-CoA transferase, wherein 4L is a malic enzyme, wherein 4M is a malate dehydrogenase or a malate oxidoreductase, wherein 4N is a pyruvate kinase or a PEP phosphatase, wherein 5A is a citrate synthase, wherein 5B is a citrate transporter, wherein 5C is a citrate/malate transporter, wherein 5D is an ATP citrate lyase, wherein 5E is a citrate lyase, wherein 5F is an acetyl-CoA synthetase or an acetyl-CoA transferase, wherein 5H is a cytosolic malate dehydrogenase, wherein 5I is a malate transporter, wherein 5J is a mitochondrial malate dehydrogenase, wherein 5K is an acetate kinase, wherein 5L is a phosphotransacetylase, wherein 6A is a citrate synthase, wherein 6B is a citrate transporter, wherein 6C is a citrate/oxaloacetate transporter, wherein 6D is an ATP citrate lyase, wherein 6E is a citrate lyase, wherein 6F is an acetyl-CoA synthetase or an acetyl-CoA transferase, wherein 6G is an oxaloacetate transporter, wherein 6K is an acetate kinase, wherein 6L is a phosphotransacetylase, wherein 1T is a fructose-6-phosphate phosphoketolase, wherein 1U is a xylulose-5-phosphate phosphoketolase, wherein 1V is a phosphotransacetylase, wherein 1W is an acetate kinase, wherein 1X is an acetyl-CoA transferase, an acetyl-CoA synthetase, or an acetyl-CoA ligase.

In some aspects, the microbial organism of the invention can include two, three, four, five, six, seven or eight exogenous nucleic acids each encoding an acetyl-CoA pathway enzyme. In some aspects, the microbial organism includes exogenous nucleic acids encoding each of the acetyl-CoA pathway enzymes of at least one of the pathways selected from (1)-(36).

Figure 22:
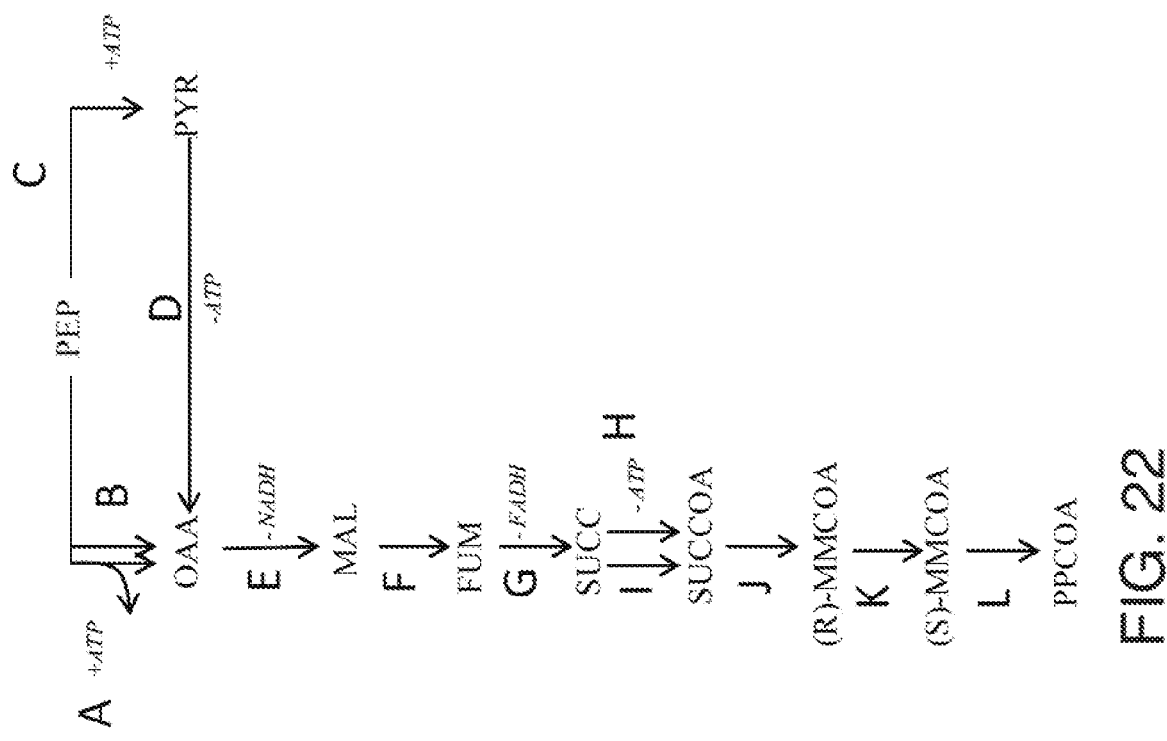
FIG. 22 depictes exemplary pathways for production of propionyl-CoA. Enzymes are: A) PEP carboxykinase, B) PEP carboxylase, C) Pyruvate kinase, D) Pyruvate carboxylase, E) Malate dehydrogenase, F) Fumarase, G) Fumarate reductase, H) Succinyl-CoA synthetase, I) Succinyl-CoA:3-ketoacid-CoA transferase, J) Methylmalonyl-CoA mutase, K) Methyl-malonyl-CoA epimerase, L) Methylmalonyl-CoA decarboxylase. See abbreviation list below for compound names.

In some embodiments, the invention provides a non-naturally occurring microbial organism as described herein, wherein the microbial organism further includes a propionyl-CoA pathway and at least one exogenous nucleic acid encoding a propionyl-CoA pathway enzyme expressed in a sufficient amount to produce propionyl-CoA, wherein the propionyl-CoA pathway includes a pathway shown in FIG. 22. For example, in some embodiments, the propionyl-CoA pathway comprises a pathway selected from: (1) 22A, 22E, 22F, 22G, 22I, 22J, 22K and 22L; (2) 22A, 22E, 22F, 22G, 22H, 22J, 22K and 22L; (3) 22B, 22E, 22F, 22G, 22I, 22J, 22K and 22L; (4) 22B, 22E, 22F, 22G, 22H, 22J, 22K and 22L; (5) 22C, 22D, 22E, 22F, 22G, 22I, 22J, 22K and 22L; and (6) 22C, 22D, 22E, 22F, 22G, 22H, 22J, 22K and 22L, wherein 22A is a PEP carboxykinase, wherein 22B is a PEP carboxylase, wherein 22C is a Pyruvate kinase, wherein 22D is a Pyruvate carboxylase, wherein 22E is a Malate dehydrogenase, wherein 22F is a Fumarase, wherein 22G is a Fumarate reductase, wherein 22H is a Succinyl-CoA synthetase, wherein 22I is a Succinyl-CoA:3-ketoacid-CoA transferase, wherein 22J is a Methylmalonyl-CoA mutase, wherein 22K is a Methyl-malonyl-CoA epimerase, and wherein 22L is a Methylmalonyl-CoA decarboxylase.

In an additional embodiment, the invention provides a non-naturally occurring microbial organism having a fatty alcohol, fatty aldehyde or fatty acid pathway, wherein the non-naturally occurring microbial organism comprises at least one exogenous nucleic acid encoding an enzyme or protein that converts a substrate to a product selected from the group consisting of MeOH to Fald, Fald to H6P, H6P to F6P, Fald to DHA and G3P, DHA and G3P to F6P, F6P to ACTP and E4P, ACTP to ACCOA, ACTP to acetate, acetate to ACCOA, Xu5P to ACTP and G3P, G3P to PYR, PYR to formate and ACCOA, PYR to CO2 and ACCOA, $CO_2$ to formate, formate to Fald, formate to Formyl-CoA, Formyl-CoA to Fald, Formate to FTHF, FTHF to methenyl-THF, methenyl-THF to methylene-THF, methylene-THF to Fald, methylene-THF to glycine, glycine to serine, serine to PYR, methylene-THF to methyl-THF, methyl-THF to ACCOA, two acetyl-CoA molecules to a 3-ketoacyl-CoA, acetyl-CoA plus propionyl-CoA to a ketoacyl-CoA, malonyl-CoA to 3-ketoacyl-CoA, a 3-ketoacyl-CoA to a 3-hydroxyacyl-CoA, a 3-hydroxyacyl-CoA to an enoyl-CoA, an enoyl-CoA to an acyl-CoA, an acyl-CoA plus an acetyl-CoA to a 3-ketoacyl-CoA, an acyl-CoA plus malonyl-CoA to a 3-ketoacyl-CoA, an acyl-CoA to a fatty aldehyde, a fatty aldehyde to a fatty alcohol, an acyl-CoA to a fatty alcohol, an acyl-CoA to an acyl-ACP, an acyl-ACP to a fatty acid, an acyl-CoA to a fatty acid, an acyl-ACP to a fatty aldehyde, a fatty acid to a fatty aldehyde, a fatty aldehyde to a fatty acid, formaldehyde to S-hydroxymethylglutathione, S-hydroxymethylglutathione to S-formylglutathione to formate, formaldehyde to formate, MeOH to methyl-THF, methyl-THF to methylene-THF, formaldehyde to methylene-THF, methylene-THF to methenyl-THF, methenyl-THF to formyl-THF, formyl-THF to formate, formaldehyde to formate, ACCOA to MALCOA, ACCOA to AACOA, MALCOA to AACOA, AACOA to acetoacetate, acetoacetate to acetone, acetone to isopropanol, malonyl-CoA to malonyl-ACP, malonyl-ACP and acetyl-CoA to acetoacetyl-ACP, malonyl-ACP and acetyl-ACP to acetoacetyl-ACP, malonyl-ACP and propionyl-CoA to 3-oxovalery-ACP, malonyl-ACP and an acyl-ACP to a β-ketoacyl-ACP, a β-ketoacyl-ACP to a β-hydroxyacyl-ACP, a β-hydroxyacyl-ACP to a trans-2-enoyl-ACP, a trans-2-enoyl-ACP to an acyl-ACP, an acyl-ACP to a fatty acid, an acyl-ACP to a fatty aldehyde, a fatty acid to a fatty aldehyde, a fatty acid to an acyl-CoA, an acyl-CoA to a fatty aldehyde, a fatty aldehyde to a fatty alcohol, a fatty aldehyde to a fatty alcohol, PEP to OAA, OAA to MAL, MAL to FUM, FUM to SUCC, SUCCOA to (R)-MMCOA, (R)-MMCOA to (S)-MMCOA, MMCOA to PPCOA, PEP to PYR, pyruvate to acetate, acetate to acetyl-CoA, pyruvate to acetyl-CoA, pyruvate to acetaldehyde, threonin to acetaldehyde, acetaldehyde to acetate, acetaldehyde to acetyl-CoA, pyruvate to acetyl-phosphate, acetate to acetyl-phosphate, acetyl-phosphate to acetyl-CoA, phosphoenolpyruvate (PEP) to pyruvate, pyruvate to malate, malate to oxaloacetate, pyruvate to oxaloacetate, PEP to oxaloacetate, oxaloacetate to malonate semialdehyde, oxaloacetate to malonyl-CoA, malonate semialdehyde to malonate, malonate to malonyl-CoA, malonate semialdehyde to malonyl-CoA, malonyl-CoA to acetyl-CoA, malonate semialdehyde to acetyl-CoA, oxaloacetate plus acetyl-CoA to citrate, citrate to oxaloacetate plus acetyl-CoA, citrate to oxaloacetate plus acetate, and oxaloacetate to malate. One skilled in the art will understand that these are merely exemplary and that any of the substrate-product pairs disclosed herein suitable to produce a desired product and for which an appropriate activity is available for the conversion of the substrate to the product can be readily determined by one skilled in the art based on the teachings herein. Thus, the invention provides a non-naturally occurring microbial organism containing at least one exogenous nucleic acid encoding an enzyme or protein, where the enzyme or protein converts the substrates and products of a fatty alcohol, fatty aldehyde, fatty acid, or isopropanol pathway, such as that shown in FIGS. 1-12 and 22.

While generally described herein as a microbial organism that contains a fatty alcohol, fatty aldehyde, fatty acid or isopropanol pathway, it is understood that the invention additionally provides a non-naturally occurring microbial organism comprising at least one exogenous nucleic acid encoding a fatty alcohol, fatty aldehyde, fatty acid or isopropanol pathway enzyme or protein expressed in a sufficient amount to produce an intermediate of a fatty alcohol, fatty aldehyde, fatty acid or isopropanol pathway. For example, as disclosed herein, a fatty alcohol, fatty aldehyde, fatty acid or isopropanol pathway is exemplified in FIGS. 1-12 and 22. Therefore, in addition to a microbial organism containing a fatty alcohol, fatty aldehyde, fatty acid or isopropanol pathway that produces fatty alcohol, fatty aldehyde, fatty acid or isopropanol, the invention additionally provides a non-naturally occurring microbial organism comprising at least one exogenous nucleic acid encoding a fatty alcohol, fatty aldehyde, fatty acid or isopropanol pathway enzyme, where the microbial organism produces a fatty alcohol, fatty aldehyde, fatty acid or isopropanol pathway intermediate, for example, pyruvate, formate, formaldehyde, H6P, DHA, G3P, F6P, ACTP, E4P, formyl-CoA, FTHF, methenyl-THF, methylene-THF, glycine, serine, methyl-THF, CO2, a 3-ketoacyl-CoA, a 3-hydroxyacyl-CoA, an enoyl-CoA, a β-ketoacyl-ACP, a β-hydroxyacyl-ACP, a trans-2-enoyl-ACP, an acyl-CoA, an acyl-ACP, acetoacetate, acetone, acetate, acetaldehyde, acetyl-phosphate, oxaloacetate, matate, malonate semialdehyde, malonate, malonyl-ACP, propionyl-CoA, malonyl-CoA, acetyl-CoA, or citrate.

It is understood that any of the pathways disclosed herein, as described in the Examples and exemplified in the Figures, including the pathways of FIGS. 1-12 and 22, can be utilized to generate a non-naturally occurring microbial organism that produces any pathway intermediate or product, as desired. As disclosed herein, such a microbial organism that produces an intermediate can be used in combination with another microbial organism expressing downstream pathway enzymes to produce a desired product. However, it is understood that a non-naturally occurring microbial organism that produces a fatty alcohol, fatty aldehyde, fatty acid or isopropanol pathway intermediate can be utilized to produce the intermediate as a desired product.

In some embodiments, the invention provides a non-naturally occurring microbial organism having an acetyl-CoA pathway, wherein said acetyl-CoA pathway comprises a pathway selected from: (1) 1T and 1V; (2) 1T, 1W, and 1X; (3) 1U and 1V; (4) 1U, 1W, and 1X; wherein 1T is a fructose-6-phosphate phosphoketolase, wherein 1U is a xylulose-5-phosphate phosphoketolase, wherein 1V is a phosphotransacetylase, wherein 1W is an acetate kinase, wherein 1X is an acetyl-CoA transferase, an acetyl-CoA synthetase, or an acetyl-CoA ligase, wherein said non-naturally occurring microbial organism further comprises a pathway capable of producing isopropanol and an exogenous nucleic acid encoding an isopropanol pathway enzyme expressed in a sufficient amount to produce isopropanol, wherein said isopropanol pathway comprises a pathway selected from: (1) 11V, 11W, 11X, and 11Y; or (2) 11T, 11U, 11W, 11X, and 11Y, wherein 11T is an acetyl-CoA carboxylase, wherein 11U is an acetoacetyl-CoA synthase, wherein 11V is an acetyl-CoA:acetyl-CoA acyltransferase, wherein 11W is an acetoacetyl-CoA hydrolase, an acetoacetyl-CoA transferase, an acetoacetyl-CoA ligase, or a phosphotransacetoacetylase/acetoacetate kinase, wherein 11X is an acetoacetate decarboxylase, wherein 11Y is an acetone reductase or isopropanol dehydrogenase.

The invention further provides non-naturally occurring microbial organisms that have elevated or enhanced synthesis or yields of acetyl-CoA (e.g. intracellular) or biosynthetic products such as a fatty alcohol, fatty aldehyde, fatty acid or isopropanol and methods of using these non-naturally occurring organisms to produce such biosynthetic products. The enhanced synthesis of intracellular acetyl-CoA enables enhanced production of a fatty alcohol, fatty aldehyde, fatty acid or isopropanol from which acetyl-CoA is an intermediate and further, may have been rate limiting.

The non-naturally occurring microbial organisms having enhanced yields of a biosynthetic product include one or more of the various pathway configurations employing a methanol dehydrogenase for methanol oxidation, a formaldehyde fixation pathway and/or an acetyl-CoA enhancing pathway, e.g. phosphoketolase, for directing the carbon from methanol into acetyl-CoA and other desired products via formaldehyde fixation. The various different methanol oxidation and formaldehyde fixation configurations exemplified below can be engineered in conjunction with any or each of the various methanol oxidation, formaldehyde fixation, formate reutilization, fatty alcohol, fatty aldehyde, fatty acid and/or isopropanol pathways exemplified previously and herein. The metabolic modifications exemplified below increase biosynthetic product yields over, for example, endogenous methanol utilization pathways because they further focus methanol derived carbon into the assimilation pathways described herein, decrease inefficient use of methanol carbon through competing methanol utilization and/or formaldehyde fixation pathways and/or increase the production of reducing equivalents.

In this regard, methylotrophs microbial organisms utilize methanol as the sole source of carbon and energy. In such methylotrophic organisms, the oxidation of methanol to formaldehyde is catalyzed by one of three different enzymes: NADH dependent methanol dehydrogenase (MeDH), PQQ-dependent methanol dehydrogenase (MeDH-PQQ) and alcohol oxidase (AOX). Methanol oxidase is a specific type of AOX with activity on methanol. Gram positive bacterial methylotrophs such as *Bacillus methanolicus* utilize a cytosolic MeDH which generates reducing equivalents in the form of NADH. Gram negative bacterial methylotrophs utilize periplasmic PQQ-containing methanol dehydrogenase enzymes which transfer electrons from methanol to specialized cytochromes CL, and subsequently to a cytochrome oxidase (Afolabi et al, *Biochem* 40:9799-9809 (2001)). Eukaryotic methylotrophs employ a peroxisomal oxygen-consuming and hydrogen-peroxide producing alcohol oxidase.

Bacterial methylotrophs are found in in the genera *Bacillus, Methylobacterium, Methyloversatilis, Methylococcus, Methylocystis* and *Hyphomicrobium*. These organisms utilize either the serine cycle (type II) or the RuMP cycle (type I) to further assimilate formaldehyde into central metabolism (Hanson and Hanson, *Microbiol Rev* 60:439-471 (1996)). As described previously, the RuMP pathway combines formaldehyde with ribulose monophosphate to form hexulose-6-phosphate, which is further converted to fructose-6-phosphate (see FIG. 1, step C). In the serine cycle formaldehyde is initially converted to 5,10-methylene-THF, which is combined with glycine to form serine. Overall, the reactions of the serine cycle produce one equivalent of acetyl-CoA from three equivalents of methanol (Anthony, *Science Prog* 94:109-37 (2011)). The RUMP cycle also yields one equivalent of acetyl-CoA from three equivalents methanol in the absence of phosphoketolase activity or a formate assimilation pathway. Genetic tools are available for numerous prokaryotic methylotrophs and methanotrophs.

Eukaryotic methylotrophs are found in the genera *Candida, Pichia, Ogataea, Kuraishia* and *Komagataella*. Particularly useful methylotrophic host organisms are those with well-characterized genetic tools and gene expression systems such as *Hansenula polymorpha, Pichia pastoris, Candida boidinii* and *Pichia methanolica* (for review see Yurimoto et al, *Int J Microbiol* (2011)). The initial step of methanol assimilation in eukaryotic methylotrophs occurs in the peroxisomes, where methanol and oxygen are oxidized to formaldehyde and hydrogen peroxide by alcohol oxidase (AOX). Formaldehyde assimilation with xylulose-5-phosphate via DHA synthase also occurs in the peroxisomes. During growth on methanol, the two enzymes DHA synthase and AOX together comprise 80% of the total cell protein (Horiguchi et al, *J Bacteriol* 183:6372-83 (2001)). DHA synthase products, DHA and glyceraldehyde-3-phosphate, are secreted into the cytosol where they undergo a series of rearrangements catalyzed by pentose phosphate pathway enzymes, and are ultimately converted to cellular constituents and xylulose-5-phosphate, which is transported back into the peroxisomes. The initial step of formaldehyde dissimilation, catalyzed by S-(hydroxymethyl)-glutathione synthase, also occurs in the peroxisomes. Like the bacterial methylotrophic pathways described above, eukaryotic methylotrophic pathways convert three equivalents of methanol to at most one equivalent of acetyl-CoA because they lack phosphoketolase activity or a formate assimilation pathway.

As exemplified further below, the various configurations of metabolic modifications disclosed herein for enhancing product yields via methanol derived carbon include enhancing methanol oxidation and production of reducing equivalents using either an endogenous NADH dependent methanol dehydrogenase, an exogenous NADH dependent methanol dehydrogenase, both an endogenous NADH dependent methanol dehydrogenase and exogenous NADH dependent methanol dehydrogenase alone or in combination with one or more metabolic modifications that attenuate, for example, DHA synthase and/or AOX. In addition, other metabolic modifications as exemplified below that reduce carbon flux away from methanol oxidation and formaldehyde fixation also can be included, alone or in combination, with the methanol oxidation and formaldehyde fixation pathway configurations disclosed herein that enhance carbon flux into product precursors such as acetyl-CoA and, therefore, enhance product yields.

Accordingly, the microbial organisms of the invention having one or more of any of the above and/or below metabolic modifications to a methanol utilization pathway and/or formaldehyde assimilation pathway configurations for enhancing product yields can be combined with any one or more, including all of the previously described methanol oxidation, formaldehyde fixation, formate reutilization, fatty alcohol, fatty aldehyde, acid and/or isopropanol pathways to enhance the yield and/or production of a product such as any of the fatty alcohol, fatty aldehyde, fatty acids and/or isopropanol described herein.

Given the teachings and guidance provided herein, the methanol oxidation and formaldehyde fixation pathway configurations can be equally engineered into both prokaryotic and eukaryotic organisms. In prokaryotic microbial organisms, for example, one skilled in the art will understand that utilization of an endogenous methanol oxidation pathway enzyme or expression of an exogenous nucleic acid encoding a methanol oxidation pathway enzyme will naturally occur cytosolically because prokaryotic organisms lack peroxisomes. In eukaryotic microbial organisms one skilled in the art will understand that certain methanol oxidation pathways occur in the peroxisome as described above and that cytosolic expression of the methanol oxidation pathway or pathways described herein to enhance product yields can be beneficial. The peroxisome located pathways and competing pathways remain or, alternatively, attenuated as described below to further enhance methanol oxidation and formaldehyde fixation.

With respect to eukaryotic microbial host organisms, those skilled in the art will know that yeasts and other eukaryotic microorganisms exhibit certain characteristics distinct from prokaryotic microbial organisms. When such characteristics are desirable, one skilled in the art can choose to use such eukaryotic microbial organisms as a host for engineering the various different methanol oxidation and formaldehyde fixation configurations exemplified herein for enhancing product yields. For example, yeast are robust organisms, able to grow over a wide pH range and able to tolerate more impurities in the feedstock. Yeast also ferment under low growth conditions and are not susceptible to infection by phage. Less stringent aseptic design requirements can also reduce production costs. Cell removal, disposal and propagation are also cheaper, with the added potential for by-product value for animal feed applications. The potential for cell recycle and semi-continuous fermentation offers benefits in increased overall yields and rates. Other benefits include: potential for extended fermentation times under low growth conditions, lower viscosity broth (vs *E. coli*) with insoluble hydrophobic products, the ability to employ large fermenters with external loop heat exchangers.

Eukaryotic host microbial organisms suitable for engineering carbon efficient methanol utilization capability can be selected from, and the non-naturally occurring microbial organisms generated in, for example, yeast, fungus or any of a variety of other microorganisms applicable to fermentation processes. As described previously, exemplary yeasts or fungi include species selected from the genera *Saccharomyces, Schizosaccharomyces, Schizochytrium, Rhodotorula, Thraustochytrium, Aspergillus, Kluyveromyces, Issatchenkia, Yarrowia, Candida, Pichia, Ogataea, Kuraishia, Hansenula* and *Komagataella*. Useful host organisms include *Saccharomyces cerevisiae, Schizosaccharomyces pombe, Hansenula polymorpha, Pichia methanolica, Candida boidinii, Kluyveromyces lactis, Kluyveromyces marxianus, Aspergillus terreus, Aspergillus niger, Pichia pastoris, Rhizopus arrhizus, Rhizobus oryzae, Yarrowia lipolytica, Issatchenkia orientalis* and the like.

The methanol oxidation and/or formaldehyde assimilation pathway configurations described herein for enhancing product yields include, for example, a NADH-dependent methanol dehydrogenase (MeDH), one or more formaldehyde assimilation pathways and/or one or more phosphoketolases. Such engineered pathways provide a yield advantage over endogenous pathways found in methylotrophic organisms. For example, methanol assimilation via methanol dehydrogenase provides reducing equivalents in the useful form of NADH, whereas alcohol oxidase and PQQ-dependent methanol dehydrogenase do not. Several product pathways described herein have several NADH-dependant enzymatic steps. In addition, deletion of redox-inefficient methanol oxidation enzymes as described further below, combined with increased cytosolic or peroxisomal expression of an NADH-dependent methanol dehydrogenase, improves the ability of the organism to extract useful reducing equivalents from methanol. In some aspects, if NADH-dependent methanol dehydrogenase is engineered into the peroxisome, an efficient means of shuttling redox in the form of NADH out of the peroxisome and into the cytosol can be included. Further employment of a formaldehyde assimilation pathway in combination with a phosphoketolase or formate assimilation pathway enables high yield conversion of methanol to acetyl-CoA, and subsequently to acetyl-CoA derived products.

For example, in a eukaryotic organism such as *Pichia pastoris*, deleting the endogenous alcohol oxidase and peroxisomal formaldehyde assimilation and dissimilation pathways, and expressing redox and carbon-efficient cytosolic methanol utilization pathways significantly improves the yield of dodecanol, an acetyl-CoA derived product. The maximum docidecanol yield of *Pichia pastoris* from methanol using endogenous methanol oxidase and formaldehyde assimilation enzymes is 0.256 g dodecanol/g methanol. Adding one or more heterologous cytosolic phosphoketolase enzymes, in combination with a formaldehyde assimilation pathway such as the DHA pathway or the RUMP pathway, boosts the dodecanol yield to 0.306 g dodecanol/g methanol. Deletion of peroxisomal methanol oxidase and formaldehyde assimilation pathway enzymes (alcohol oxidase, DHA synthase), and replacement with cytosolic methanol dehydrogenase (NADH dependent) and formaldehyde assimilation pathways, together with a phosphoketolase, provides a significant boost of yield to 0.422 g/g.

| Strain design (assumes DHA pathway) | Max FA yield (g dodecanol/g MeOH) |
|---|---|
| Pichia + AOX + fatty acid pathway | 0.256 |
| Pichia + AOX + PK | 0.306 |
| Pichia + MeDH + PK | 0.422 |

Metabolic modifications for enabling redox- and carbon-efficient cytosolic methanol utilization in a eukaryotic or prokaryotic organism are exemplified in further detail below.

In one embodiment, the invention provides cytosolic expression of one or more methanol oxidation and/or formaldehyde assimilation pathways. Engineering into a host microbial organism carbon- and redox-efficient cytosolic formaldehyde assimilation can be achieved by expression of one or more endogenous or exogenous methanol oxidation pathways and/or one or more endogenous or exogenous formaldehyde assimilation pathway enzymes in the cytosol. An exemplary pathway for methanol oxidation includes NADH dependent methanol dehydrogenase as shown in FIG. 1. Exemplary pathways for converting cytosolic formaldehyde into glycolytic intermediates also are shown in FIG. 1. Such pathways include methanol oxidation via expression of an cytosolic NADH dependent methanol dehydrogenase, formaldehyde fixation via expression of cytosolic DHA synthase, both methanol oxidation via expression of an cytosolic NADH dependent methanol dehydrogenase and formaldehyde fixation via expression of cytosolic DHA synthase alone or together with the metabolic modifications exemplified below that attenuate less beneficial methanol oxidation and/or formaldehyde fixation pathways. Such attenuating metabolic modifications include, for example, attenuation of alcohol oxidase, attenuation of DHA kinase and/or when utilization of ribulose-5-phosphate (Ru5P) pathway for formaldehyde fixation attenuation of DHA synthase For example, in the carbon-efficient DHA pathway of formaldehyde assimilation shown in FIG. 1, step D, formaldehyde is converted to dihydroxyacetone (DHA) and glyceraldehyde-3-phosphate (GAP) by DHA synthase (FIG. 1D). DHA and G3P are then converted to fructose-6-phosphate in one step by F6P aldolase (FIG. 1C) or in three steps by DHA kinase, FBP aldolase and fructose-1,6-bisphosphatase (not shown). Formation of F6P from DHA and G3P by F6P aldolase is more ATP-efficient than using DHA kinase, FBP aldolase and fructose-1,6-bisphosphatase. Rearrangement of F6P and E4P by enzymes of the pentose phosphate pathway (transaldolase, transketolase, $R_5P$ epimerase and Ru5P epimerase) regenerates xylulose-5-phosphate, the DHA synthase substrate. Conversion of F6P to acetyl-phosphate and E4P (FIG. 11), or Xu5P to G3P and acetyl-phosphate (FIGS. 1T and 1U) by one or more phosphoketolase enzymes results in the carbon-efficient generation of cytosolic acetyl-CoA. Exemplary enzymes catalyzing each step of the carbon efficient DHA pathway are described elsewhere herein.

An alternate carbon efficient pathway for formaldehyde assimilation proceeding through ribulose-5-phosphate (Ru5P) is shown in FIG. 1, step B. The formaldehyde assimilation enzyme of this pathway is 3-hexulose-6-phosphate synthase, which combines ru5p and formaldehyde to form hexulose-6-phosphate (FIG. 1B). 6-Phospho-3-hexuloisomerase converts H6P to F6P (FIG. 1C). Regeneration of Ru5P from F6P proceeds by pentose phosphate pathway enzymes. Carbon-efficient phosphoketolase enzymes catalyze the conversion of F6P and/or Xu5P to acetyl-phosphate and pentose phosphate intermediates. Exemplary enzymes catalyzing each step of the carbon efficient RUMP pathway are described elsewhere herein.

Thus, in this embodiment, conversion of cytosolic formaldehyde into glycolytic intermediates can occur via expression of a cytosolic 3-hexulose-6-phosphate (3-Hu6P) synthase and 6-phospho-3-hexuloisomerase. Thus, exemplary pathways that can be engineered into a microbial organism of the invention can include methanol oxidation via expression of a cytosolic NADH dependent methanol dehydrogenase, formaldehyde fixation via expression of cytosolic 3-Hu6P synthase and 6-phospho-3-hexuloisomerase, both methanol oxidation via expression of an cytosolic NADH dependent dehydrogenase and formaldehyde fixation via expression of cytosolic 3-Hu6P synthase and 6-phospho-3-hexuloisomerase alone or together with the metabolic modifications exemplified below that attenuate less beneficial methanol oxidation and/or formaldehyde fixation pathways. Such attenuating metabolic modifications include, for example, attenuation of alcohol oxidase, attenuation of DHA kinase and/or when utilization of ribulose-5-phosphate (Ru5P) pathway for formaldehyde fixation attenuation of DHA synthase.

In yet another embodiment increased product yields can be accomplished by engineering into the host microbial organism of the invention both the RUMP and DHA pathways as shown in FIG. 1. In this embodiment, the microbial organisms can have cytosolic expression of one or more methanol oxidation and/or formaldehyde assimilation pathways. The formaldehyde assimilation pathways can include both assimilation through cytosolic DHA synthase and 3-Hu6P synthase Such pathways include methanol oxidation via expression of a cytosolic NADH dependent methanol dehydrogenase, formaldehyde fixation via expression of cytosolic DHA synthase and 3-Hu6P synthase, both methanol oxidation via expression of an cytosolic NADH dependent dehydrogenase and formaldehyde fixation via expression of cytosolic DHA synthase and 3-Hu6P synthase alone or together with the metabolic modifications exemplified previously and also below that attenuate less beneficial methanol oxidation and/or formaldehyde fixation pathways. Such attenuating metabolic modifications include, for example, attenuation of alcohol oxidase, attenuation of DHA kinase and/or attenuation of DHA synthase (e.g. when ribulose-5-phosphate (Ru5P) pathway for formaldehyde fixation is utilized).

Increasing the expression and/or activity of one or more formaldehyde assimilation pathway enzymes in the cytosol can be utilized to assimilate formaldehyde at a high rate. Increased activity can be achieved by increased expression, altering the ribosome binding site, altering the enzyme activity, or altering the sequence of the gene to ensure, for example, that codon usage is balanced with the needs of the host organism, or that the enzyme is targeted to the cytosol as disclosed herein.

In some embodiments, the invention provides a non-naturally occurring microbial organism as described herein, wherein the microbial organism further includes attenuation of one or more endogenous enzymes, which enhances carbon flux through acetyl-CoA. For example, in some aspects, the endogenous enzyme can be selected from DHA kinase, methanol oxidase, PQQ-dependent methanol dehydrogenase, DHA synthase or any combination thereof. Accordingly, in some aspects, the attenuation is of the endogenous enzyme DHA kinase In some aspects, the attenuation is of the endogenous enzyme methanol oxidase. In some aspects, the attenuation is of the endogenous enzyme PQQ-dependent methanol dehydrogenase. In some aspects, the attenuation is of the endogenous enzyme DHA synthase. The invention also provides a microbial organism wherein attenuation is of any combination of two or three endogenous enzymes described herein. For example, a microbial organism of the invention can include attenuation of DHA kinase and DHA synthase, or alternatively methanol oxidase and PQQ-dependent methanol dehydrogenase, or alternatively DHA kinase, methanol oxidase, and PQQ-dependent methanol dehydrogenase, or alternatively DHA kinase, methanol oxidase, and DHA synthase. The invention also provides a microbial organism wherein attenuation is of all endogenous enzymes described herein. For example, in some aspects, a microbial organism described herein includes attenuation of DHA kinase, methanol oxidase, PQQ-dependent methanol dehydrogenase and DHA synthase.

In some embodiments, the invention provides a non-naturally occurring microbial organism as described herein, wherein the microbial organism further includes attenuation of one or more endogenous enzymes of a competing formaldehyde assimilation or dissimilation pathway. Examples of these endogenous enzymes are disclosed in FIG. 1 and described in Example XXIII. It is understood that a person skilled in the art would be able to readily identify enzymes of such competing pathways. Competing pathways can be dependent upon the host microbial organism and/or the exogenous nucleic acid introduced into the microbial organism as described herein. Accordingly, in some aspects of the invention, the microbial organism includes attenuation of one, two, three, four, five, six, seven, eight, nine, ten or more endogenous enzymes of a competing formaldehyde assimilation or dissimilation pathway.

In some embodiments, the invention provides a non-naturally occurring microbial organism as described herein, wherein the microbial organism further includes a gene disruption of one or more endogenous nucleic acids encoding enzymes, which enhances carbon flux through acetyl-CoA. For example, in some aspects, the endogenous enzyme can be selected from DHA kinase, methanol oxidase, PQQ-dependent methanol dehydrogenase, DHA synthase or any combination thereof. According, in some aspects, the gene disruption is of an endogenous nucleic acid encoding the enzyme DHA kinase In some aspects, the gene disruption is of an endogenous nucleic acid encoding the enzyme methanol oxidase. In some aspects, the gene disruption is of an endogenous nucleic acid encoding the enzyme PQQ-dependent methanol dehydrogenase. In some aspects, the gene disruption is of an endogenous nucleic acid encoding the enzyme DHA synthase. The invention also provides a microbial organism wherein the gene disruption is of any combination of two or three nucleic acids encoding endogenous enzymes described herein. For example, a microbial organism of the invention can include a gene disruption of DHA kinase and DHA synthase, or alternatively methanol oxidase and PQQ-dependent methanol dehydrogenase, or alternatively DHA kinase, methanol oxidase, and PQQ-dependent methanol dehydrogenase, or alternatively DHA kinase, methanol oxidase, and DHA synthase. The invention also provides a microbial organism wherein all endogenous nucleic acids encoding enzymes described herein are disrupted. For example, in some aspects, a microbial organism described herein includes disruption of DHA kinase, methanol oxidase, PQQ-dependent methanol dehydrogenase and DHA synthase.

In some embodiments, the invention provides a non-naturally occurring microbial organism as described herein, wherein the microbial organism further includes a gene disruption of one or more endogenous enzymes of a competing formaldehyde assimilation or dissimilation pathway. Examples of these endogenous enzymes are disclosed in FIG. 1 and described in Example XXIII. It is understood that a person skilled in the art would be able to readily identify enzymes of such competing pathways. Competing pathways can be dependent upon the host microbial organism and/or the exogenous nucleic acid introduced into the microbial organism as described herein. Accordingly, in some aspects of the invention, the microbial organism includes a gene disruption of one, two, three, four, five, six, seven, eight, nine, ten or more endogenous nucleic acids encoding enzymes of a competing formaldehyde assimilation or dissimilation pathway.

The invention is described herein with general reference to the metabolic reaction, reactant or product thereof, or with specific reference to one or more nucleic acids or genes encoding an enzyme associated with or catalyzing, or a protein associated with, the referenced metabolic reaction, reactant or product. Unless otherwise expressly stated herein, those skilled in the art will understand that reference to a reaction also constitutes reference to the reactants and products of the reaction. Similarly, unless otherwise expressly stated herein, reference to a reactant or product also references the reaction, and reference to any of these metabolic constituents also references the gene or genes encoding the enzymes that catalyze or proteins involved in the referenced reaction, reactant or product. Likewise, given the well known fields of metabolic biochemistry, enzymology and genomics, reference herein to a gene or encoding nucleic acid also constitutes a reference to the corresponding encoded enzyme and the reaction it catalyzes or a protein associated with the reaction as well as the reactants and products of the reaction.

The non-naturally occurring microbial organisms of the invention can be produced by introducing expressible nucleic acids encoding one or more of the enzymes or proteins participating in one or more fatty alcohol, fatty aldehyde, fatty acid or isopropanol biosynthetic pathways. Depending on the host microbial organism chosen for biosynthesis, nucleic acids for some or all of a particular fatty alcohol, fatty aldehyde, fatty acid or isopropanol biosynthetic pathway can be expressed. For example, if a chosen host is deficient in one or more enzymes or proteins for a desired biosynthetic pathway, then expressible nucleic acids for the deficient enzyme(s) or protein(s) are introduced into the host for subsequent exogenous expression. Alternatively, if the chosen host exhibits endogenous expression of some pathway genes, but is deficient in others, then an encoding nucleic acid is needed for the deficient enzyme(s) or protein(s) to achieve fatty alcohol, fatty aldehyde, fatty acid or isopropanol biosynthesis. Thus, a non-naturally occurring microbial organism of the invention can be produced by introducing exogenous enzyme or protein activities to obtain a desired biosynthetic pathway or a desired biosynthetic pathway can be obtained by introducing one or more exogenous enzyme or protein activities that, together with one or more endogenous enzymes or proteins, produces a desired product such as fatty alcohol, fatty aldehyde, fatty acid or isopropanol.

Host microbial organisms can be selected from, and the non-naturally occurring microbial organisms generated in, for example, bacteria, yeast, fungus or any of a variety of other microorganisms applicable or suitable to fermentation processes. Exemplary bacteria include any species selected from the order Enterobacteriales, family Enterobacteriaceae, including the genera *Escherichia* and *Klebsiella*; the order Aeromonadales, family Succinivibrionaceae, including the genus *Anaerobiospirillum*; the order Pasteurellales, family Pasteurellaceae, including the genera *Actinobacillus* and *Mannheimia*; the order Rhizobiales, family Bradyrhizobiaceae, including the genus *Rhizobium*; the order Bacillales, family Bacillaceae, including the genus *Bacillus*; the order Actinomycetales, families Corynebacteriaceae and Streptomycetaceae, including the genus *Corynebacterium* and the genus *Streptomyces*, respectively; order Rhodospirillales, family Acetobacteraceae, including the genus *Gluconobacter*; the order Sphingomonadales, family Sphingomonadaceae, including the genus *Zymomonas*; the order Lactobacillales, families Lactobacillaceae and Streptococcaceae, including the genus *Lactobacillus* and the genus *Lactococcus*, respectively; the order Clostridiales, family Clostridiaceae, genus *Clostridium*; and the order Pseudomonadales, family Pseudomonadaceae, including the genus *Pseudomonas*. Non-limiting species of host bacteria include *Escherichia coli, Klebsiella oxytoca, Anaerobiospirillum succiniciproducens, Actinobacillus succinogenes, Mannheimia succiniciproducens, Rhizobium etli, Bacillus subtilis, Corynebacterium glutamicum, Gluconobacter oxydans, Zymomonas mobilis, Lactococcus lactis, Lactobacillus plantarum, Streptomyces coelicolor, Clostridium acetobutylicum, Pseudomonas fluorescens,* and *Pseudomonas putida*. Exemplary bacterial methylotrophs include, for example, *Bacillus, Methylobacterium, Methyloversatilis, Methylococcus, Methylocystis* and *Hyphomicrobium*.

Similarly, exemplary species of yeast or fungi species include any species selected from the order Saccharomycetales, family Saccaromycetaceae, including the genera *Saccharomyces, Kluyveromyces* and *Pichia*; the order Saccharomycetales, family Dipodascaceae, including the genus *Yarrowia*; the order Schizosaccharomycetales, family Schizosaccaromycetaceae, including the genus *Schizosaccharomyces*; the order Eurotiales, family Trichocomaceae, including the genus *Aspergillus*; and the orderMucorales, family Mucoraceae, including the genus *Rhizopus*. Non-limiting species of host yeast or fungi include *Saccharomyces cerevisiae, Schizosaccharomyces pombe, Kluyveromyces lactis, Kluyveromyces marxianus, Aspergillus terreus, Aspergillus niger, Pichia pastoris, Rhizopus arrhizus, Rhizobus oryzae, Yarrowia lipolytica*, and the like. *E. coli* is a particularly useful host organism since it is a well characterized microbial organism suitable for genetic engineering. Other particularly useful host organisms include yeast such as *Saccharomyces cerevisiae* and yeasts or fungi selected from the genera *Saccharomyces, Schizosaccharomyces, Schizochytrium, Rhodotorula, Thraustochytrium, Aspergillus, Kluyveromyces, Issatchenkia, Yarrowia, Candida, Pichia, Ogataea, Kuraishia, Hansenula* and *Komagataella*. Useful host organisms include *Saccharomyces cerevisiae, Schizosaccharomyces pombe, Hansenula polymorpha, Pichia methanolica, Candida boidinii, Kluyveromyces lactis, Kluyveromyces marxianus, Aspergillus terreus, Aspergillus niger, Pichia pastoris, Rhizopus arrhizus, Rhizobus oryzae, Yarrowia lipolytica, Issatchenkia orientalis* and the like. Exemplary eukaryotic methylotrophs include, for example, eukaryotic methylotrophs found in the genera *Candida, Pichia, Ogataea, Kuraishia* and *Komagataella*. Particularly useful methylotrophic host organisms include, for example, *Hansenula polymorpha, Pichia pastoris, Candida boichnii* and *Pichia methanolica*. It is understood that any suitable microbial host organism can be used to introduce metabolic and/or genetic modifications to produce a desired product.

Depending on the fatty alcohol, fatty aldehyde, fatty acid or isopropanol biosynthetic pathway constituents of a selected host microbial organism, the non-naturally occurring microbial organisms of the invention will include at least one exogenously expressed fatty alcohol, fatty aldehyde, fatty acid or isopropanol pathway-encoding nucleic acid and up to all encoding nucleic acids for one or more fatty alcohol, fatty aldehyde, fatty acid or isopropanol biosynthetic pathways. For example, fatty alcohol, fatty aldehyde, fatty acid or isopropanol biosynthesis can be established in a host deficient in a pathway enzyme or protein through exogenous expression of the corresponding encoding nucleic acid. In a host deficient in all enzymes or proteins of a fatty alcohol, fatty aldehyde, fatty acid or isopropanol pathway, exogenous expression of all enzyme or proteins in the pathway can be included, although it is understood that all enzymes or proteins of a pathway can be expressed even if the host contains at least one of the pathway enzymes or proteins. For example, exogenous expression of all enzymes or proteins in a pathway for production of fatty alcohol, fatty aldehyde, fatty acid or isopropanol can be included, such as a thiolase, a 3-oxoacyl-CoA reductase, a 3-hydroxyacyl-CoA dehydratase, an enoyl-CoA redutase, an acyl-CoA reductase (aldehyde forming) and an alcohol dehydrogenase, for production of a fatty alcohol.

Given the teachings and guidance provided herein, those skilled in the art will understand that the number of encoding nucleic acids to introduce in an expressible form will, at least, parallel the fatty alcohol, fatty aldehyde, fatty acid or isopropanol pathway deficiencies of the selected host microbial organism. Therefore, a non-naturally occurring microbial organism of the invention can have one, two, three, four, five, six, seven or eight up to all nucleic acids encoding the enzymes or proteins constituting a fatty alcohol, fatty aldehyde, fatty acid or isopropanol biosynthetic pathway disclosed herein. In some embodiments, the non-naturally occurring microbial organisms also can include other genetic modifications that facilitate or optimize fatty alcohol, fatty aldehyde, fatty acid or isopropanol biosynthesis or that confer other useful functions onto the host microbial organism. One such other functionality can include, for example, augmentation of the synthesis of one or more of the fatty alcohol, fatty aldehyde, fatty acid or isopropanol pathway precursors such as acetyl-CoA, malonyl-ACP, malonyl-CoA or propionyl-CoA.

Generally, a host microbial organism is selected such that it produces the precursor of a fatty alcohol, fatty aldehyde, fatty acid or isopropanol pathway, either as a naturally produced molecule or as an engineered product that either provides de novo production of a desired precursor or increased production of a precursor naturally produced by the host microbial organism. For example, acetyl-CoA is produced naturally in a host organism such as *E. coli*. A host organism can be engineered to increase production of a precursor, as disclosed herein. In addition, a microbial organism that has been engineered to produce a desired precursor can be used as a host organism and further engineered to express enzymes or proteins of a fatty alcohol, fatty aldehyde, fatty acid or isopropanol pathway.

In some embodiments, a non-naturally occurring microbial organism of the invention is generated from a host that contains the enzymatic capability to synthesize fatty alcohol, fatty aldehyde, fatty acid or isopropanol. In this specific embodiment it can be useful to increase the synthesis or accumulation of a fatty alcohol, fatty aldehyde, fatty acid or isopropanol pathway product to, for example, drive fatty alcohol, fatty aldehyde, fatty acid or isopropanol pathway reactions toward fatty alcohol, fatty aldehyde, fatty acid or isopropanol production. Increased synthesis or accumulation can be accomplished by, for example, overexpression of nucleic acids encoding one or more of the above-described fatty alcohol, fatty aldehyde, fatty acid or isopropanol pathway enzymes or proteins. Overexpression of the enzyme or enzymes and/or protein or proteins of the fatty alcohol, fatty aldehyde, fatty acid or isopropanol pathway can occur, for example, through exogenous expression of the endogenous gene or genes, or through exogenous expression of the heterologous gene or genes. Therefore, naturally occurring organisms can be readily generated to be non-naturally occurring microbial organisms of the invention, for example, producing fatty alcohol, fatty aldehyde, fatty acid or isopropanol, through overexpression of one, two, three, four, five, six, seven, or eight, that is, up to all nucleic acids encoding fatty alcohol, fatty aldehyde, fatty acid or isopropanol biosynthetic pathway enzymes or proteins. In addition, a non-naturally occurring organism can be generated by mutagenesis of an endogenous gene that results in an increase in activity of an enzyme in the fatty alcohol, fatty aldehyde, fatty acid or isopropanol biosynthetic pathway.

In particularly useful embodiments, exogenous expression of the encoding nucleic acids is employed. Exogenous expression confers the ability to custom tailor the expression and/or regulatory elements to the host and application to achieve a desired expression level that is controlled by the user. However, endogenous expression also can be utilized in other embodiments such as by removing a negative regulatory effector or induction of the gene's promoter when linked to an inducible promoter or other regulatory element. Thus, an endogenous gene having a naturally occurring inducible promoter can be up-regulated by providing the appropriate inducing agent, or the regulatory region of an endogenous gene can be engineered to incorporate an inducible regulatory element, thereby allowing the regulation of increased expression of an endogenous gene at a desired time. Similarly, an inducible promoter can be included as a regulatory element for an exogenous gene introduced into a non-naturally occurring microbial organism.

It is understood that, in methods of the invention, any of the one or more exogenous nucleic acids can be introduced into a microbial organism to produce a non-naturally occurring microbial organism of the invention. The nucleic acids can be introduced so as to confer, for example, a fatty alcohol, fatty aldehyde, fatty acid or isopropanol biosynthetic pathway onto the microbial organism. Alternatively, encoding nucleic acids can be introduced to produce an intermediate microbial organism having the biosynthetic capability to catalyze some of the required reactions to confer fatty alcohol, fatty aldehyde, fatty acid or isopropanol biosynthetic capability. For example, a non-naturally occurring microbial organism having a fatty alcohol, fatty aldehyde, fatty acid or isopropanol biosynthetic pathway can comprise at least two exogenous nucleic acids encoding desired enzymes or proteins, such as the combination of a thiolase and an acyl-CoA reductase (alcohol forming), or alternatively a 2-oxoacyl-CoA reductase and an acyl-CoA hydrolase, or alternatively a enoyl-CoA reductase and an acyl-CoA reductase (aldehyde forming), or alternatively a methanol methyltransferase and an acetone reductase, or alternatively a 3-hexulose-6-phosphate synthase and an enoyl ACP-reductase, and the like. Thus, it is understood that any combination of two or more enzymes or proteins of a biosynthetic pathway can be included in a non-naturally occurring microbial organism of the invention. Similarly, it is understood that any combination of three or more enzymes or proteins of a biosynthetic pathway can be included in a non-naturally occurring microbial organism of the invention, for example, a thiolase, an enoyl-CoA reductase and a aldehyde dehydrogenase (acid forming), or alternatively a 3-hydroxyacyl-coA dehydratase, an acyl-CoA:ACP acyltransferase and a thioesterase, or alternatively a 3-oxoacyl-CoA reductase, an acyl-CoA hydrolase and a carboxylic acid reductase, or alternatively a dihydroxyacetone synthase, a S-formylglutathione hydrolase and an acetoacetyl-CoA ligase, or alternatively a 6-phospho-3-hexuloisomerase, a β-hydroxyacyl-ACP reductase and a fatty alcohol forming acyl-CoA reductase, and so forth, as desired, so long as the combination of enzymes and/or proteins of the desired biosynthetic pathway results in production of the corresponding desired product. Similarly, any combination of four, five, six, seven, eight, nine, ten, eleven, twelve, thirteen, fourteen, fifteen, sixteen, seventeen, eighteen, nineteen, twenty or more enzymes or proteins of a biosynthetic pathway as disclosed herein can be included in a non-naturally occurring microbial organism of the invention, as desired, so long as the combination of enzymes and/or proteins of the desired biosynthetic pathway results in production of the corresponding desired product.

In addition to the biosynthesis of fatty alcohol, fatty aldehyde, fatty acid or isopropanol as described herein, the non-naturally occurring microbial organisms and methods of the invention also can be utilized in various combinations with each other and/or with other microbial organisms and methods well known in the art to achieve product biosynthesis by other routes. For example, one alternative to produce fatty alcohol, fatty aldehyde, fatty acid or isopropanol other than use of the fatty alcohol, fatty aldehyde, fatty acid or isopropanol producers is through addition of another microbial organism capable of converting a fatty alcohol, fatty aldehyde, fatty acid or isopropanol pathway intermediate to fatty alcohol, fatty aldehyde, fatty acid or isopropanol. One such procedure includes, for example, the fermentation of a microbial organism that produces a fatty alcohol, fatty aldehyde, fatty acid or isopropanol pathway intermediate. The fatty alcohol, fatty aldehyde, fatty acid or isopropanol pathway intermediate can then be used as a substrate for a second microbial organism that converts the fatty alcohol, fatty aldehyde, fatty acid or isopropanol pathway intermediate to fatty alcohol, fatty aldehyde, fatty acid or isopropanol. The fatty alcohol, fatty aldehyde, fatty acid or isopropanol pathway intermediate can be added directly to another culture of the second organism or the original culture of the fatty alcohol, fatty aldehyde, fatty acid or isopropanol pathway intermediate producers can be depleted of these microbial organisms by, for example, cell separation, and then subsequent addition of the second organism to the fermentation broth can be utilized to produce the final product without intermediate purification steps.

In other embodiments, the non-naturally occurring microbial organisms and methods of the invention can be assembled in a wide variety of subpathways to achieve biosynthesis of, for example, fatty alcohol, fatty aldehyde, fatty acid or isopropanol. In these embodiments, biosynthetic pathways for a desired product of the invention can be segregated into different microbial organisms, and the different microbial organisms can be co-cultured to produce the final product. In such a biosynthetic scheme, the product of one microbial organism is the substrate for a second microbial organism until the final product is synthesized. For example, the biosynthesis of fatty alcohol, fatty aldehyde, fatty acid or isopropanol can be accomplished by constructing a microbial organism that contains biosynthetic pathways for conversion of one pathway intermediate to another pathway intermediate or the product. Alternatively, fatty alcohol, fatty aldehyde, fatty acid or isopropanol also can be biosynthetically produced from microbial organisms through co-culture or co-fermentation using two organisms in the same vessel, where the first microbial organism produces a fatty alcohol, fatty aldehyde, fatty acid or isopropanol intermediate and the second microbial organism converts the intermediate to fatty alcohol, fatty aldehyde, fatty acid or isopropanol.

Given the teachings and guidance provided herein, those skilled in the art will understand that a wide variety of combinations and permutations exist for the non-naturally occurring microbial organisms and methods of the invention together with other microbial organisms, with the co-culture of other non-naturally occurring microbial organisms having subpathways and with combinations of other chemical and/or biochemical procedures well known in the art to produce fatty alcohol, fatty aldehyde, fatty acid or isopropanol.

Similarly, it is understood by those skilled in the art that a host organism can be selected based on desired characteristics for introduction of one or more gene disruptions to increase production of fatty alcohol, fatty aldehyde, fatty acid or isopropanol. Thus, it is understood that, if a genetic modification is to be introduced into a host organism to disrupt a gene, any homologs, orthologs or paralogs that catalyze similar, yet non-identical metabolic reactions can similarly be disrupted to ensure that a desired metabolic reaction is sufficiently disrupted. Because certain differences exist among metabolic networks between different organisms, those skilled in the art will understand that the actual genes disrupted in a given organism may differ between organisms. However, given the teachings and guidance provided herein, those skilled in the art also will understand that the methods of the invention can be applied to any suitable host microorganism to identify the cognate metabolic alterations needed to construct an organism in a species of interest that will increase fatty alcohol, fatty aldehyde, fatty acid or isopropanol biosynthesis. In a particular embodiment, the increased production couples biosynthesis of fatty alcohol, fatty aldehyde, fatty acid or isopropanol to growth of the organism, and can obligatorily couple production of fatty alcohol, fatty aldehyde, fatty acid or isopropanol to growth of the organism if desired and as disclosed herein.

Sources of encoding nucleic acids for a fatty alcohol, fatty aldehyde, fatty acid or isopropanol pathway enzyme or protein can include, for example, any species where the encoded gene product is capable of catalyzing the referenced reaction. Such species include both prokaryotic and eukaryotic organisms including, but not limited to, bacteria, including archaea and eubacteria, and eukaryotes, including yeast, plant, insect, animal, and mammal, including human. Exemplary species for such sources include, for example, *Escherichia coli* 255956237, *Penicillium chrysogenum* Wisconsin 54-1255, *Acetobacter pasteurians, Acidaminococcus fermentans, Acinetobacter baumannii* Naval-82 *Acinetobacter baylyi, Acinetobacter calcoaceticus, Acinetobacter* sp. ADP1, *Acinetobacter* sp. Strain M-1, *Actinobacillus succinogenes, Actinobacillus succinogenes* 130Z *Aedes aegypti, Allochromatium vinosum* DWl 180, *Aminomonas aminovorus, Anabaena variabilis* ATCC 29413, *Anaerobiospirillum succiniciproducens, Aquifex aeolicus, Arabidopsis thaliana, Archaeoglobus fulgidus, Archaeoglobus fulgidus* DSM 4304, *Arthrobacter globiformis, Ascaris suum, Aspergillus fumigatus, Aspergillus nidulans, Aspergillus niger, Aspergillus niger* CBS 513.88, *Aspergillus terreus* NIH2624, *Aspergillus Synechococcus elongatus* PCC 6301, *Azotobacter vinelandii* DT *B. subtilis* 168, *Bacillus alcalophilus* ATCC 27647, *Bacillus anthracis, Bacillus azotoformans* LMG 9581, *Bacillus cereus, Bacillus cereus* ATCC 14579, *Bacillus coagulans* 36D1, *Bacillus megaterium, Bacillus methanolicus* MGA3, *Bacillus methanolicus* PB1, *Bacillus selenitireducens* MLS10, *Bacillus* sp. SG-1, *Bacillus sphaericus, Bacillus subtilis, Bacteroides fragilis, Bifidobacterium bifidum, Bifidobacterium longum* NCC2705, *Bombyx mori, Bos taurus, Bradyrhizobium japonicum, Bradyrhizobium japonicum* USDA110, *Brassica juncea, Brassica napsus, Burkholderia ambifaria* AMMD, *Burkholderia cenocepacia, Burkholderia cepacia, Burkholderia multivorans, Burkholderia phymatum, Burkholderia pyrrocinia, Burkholderia stabilis, Burkholderia thailandensis* E264, *Burkholderiales bacterium* Joshi_001, butyrate-producing bacterium L2-50, *Caenorhabditis elegans, Campylobacter curvus* 525.92, *Campylobacter jejuni, Candida albicans, Candida boidlnii, Candida methylica, Candida parapsilosis, Candida tropicalis, Candida tropicalis* MYA-3404, *Candida tropicalis* MYA-3404, *Candida tropicalis, Carboxydothermus hydrogenoformans, Carboxydothermus hydrogenoformans* Z-2901, *Carthamus tinctorius, Caulobacter* sp. AP07, *Chlamydomonas reinhardtii, Chlorobium limicola, Chlorobium phaeobacteroides* DSM266, *Chlorobium tepidum, Chloroflexus aurantiacus, Cinnamomum camphorum, Citrobacter koseri* ATCC BAA-895, *Citrus junos, Clostridium acetobutylicum, Clostridium acetobutylicum* ATCC 824, *Clostridium aminoburicum, Clostridium beijerinckii, Clostridium beijerinckii* NCIMB 8052, *Clostridium carboxidivorans* P7, *Clostridium cellulolyticum* H10, *Clostridium cellulovorans* 743B, *Clostridium kluyveri, Clostridium kluyveri* DSM 555, *Clostridium ljungdahli, Clostridium ljungdahlii* DSM 13528, *Clostridium pasteurianum, Clostridium pasteurianum* DSM525, *Clostridium perfringens, Clostridium perfringens* ATCC 13124, *Clostridium perfringers* str. 13, *Clostridium phytofermentans* ISDg, *Clostridium saccharoperbulacetonicum, Clostridium symbiosum, Corynebacterium glutamicum, Corynebacterium glutamicum* ATCC 14067, *Corynebacterium glutamicum* R, *Corynebacterium* sp., *Corynebacterium* sp. U-96, *Corynebacterium ulcerans, Corynebacterium variabile, Cryptosporidium parvum* Iowa II, *Cuphea hookeriana, Cuphea palustris, Cupriavidus necator, Cupriavidus necator* N-1, *Cupriavidus taiwanensis, Cyanobium* PCC7001, *Cyanothece* sp. PCC 7425, *Danio rerio, Desulfatibacillum alkenivorans* AK-01, *Desulfitobacterium hafniense, Desulfitobacterium metallireducens* DSM 15288, *Desulfococcus oleovorans* Hxd3, *Desulfotomaculum reducens* MI-1, *Desulfovibrio africanus, Desulfovibrio africanus* str. *Walvis Bay, Desulfovibrio alaskensis, Desulfovibrio desulfuricans* subsp. *desulfuricans* str. ATCC 27774, *Desulfovibrio fructosovorans* JJ, *Desulfovibrio vulgaris* str. 'Miyazaki F' *Desulfovibrio vulgaris* str. Hildenborough, *Dictyostelium discoideum* AX4, *E. coli, Erythrobacter* sp. NAP1, *Escherichia coli* DH1, *Escherichia coli* K-12, *Escherichia coli* K-12 MG1655, *Escherichia coli* K-12 MG1655 *niger* CBS 513.88, *Escherichia coli* LW1655F+, *Escherichia coli* MG1655, *Escherichia coli* str. K-12 substr. MG1655, *Euglena gracilis, Flavobacterium frigoris, Fusobacterium nucleatum, Geobacillus* sp. GHH01, *Geobacillus* sp. M10EXG, *Geobacillus* sp. Y4.1MC1, *Geobacillus themodenitrificans* NG80-2, *Geobacillus thermodenitrificans, Geobacter bemidjiensis* Bem, *Geobacter metallireducens* GS-15, *Geobacter sulfurreducens, Geobacter sulfurreducens* PCA, *Haemophilus influenza, Haloarcula marismortui, Haloarcula marismortui* ATCC 43049, *Halomonas* sp.

HTNK1, *Helianthus annuus, Helicobacter pylori, Helicobacter pylori* 26695, *Homo sapiens*, human gut metagenome, *Hydrogenobacter thermophilus, Hyphomicrobium denitrificans* ATCC 51888, *Hyphomicrobium zavarzinii, Kineococcus radiotolerans, Klebsiella pneumonia, Klebsiella pneumoniae, Klebsiella pneumoniae* subsp. *pneumoniae* MGH 78578, *Kluyveromyces lactis, Kluyveromyces lactis* NRRL Y-1140, *Lactobacillus acidophilus, Lactobacillus brevis* ATCC 367, *Lactobacillus casei, Lactobacillus plantarum, Lactobacillus reuteri, Lactococcus lactis, Lactococcus lactis* subsp. *lactis, Leifsonia* sp. S749, *Leuconostoc mesenteroides, Listeria monocytogenes, Lyngbya* sp. PCC 8106, *Lysinibacillus fusiformis, Lysinibacillus sphaericus, Mannheimia succiniciproducens*, marine gamma proteobacterium HTCC2080, *Marinobacter aquaeolei, Megathyrsus maximus, Mesorhizobium loti, Mesorhizobium loti* MAFF303099, *Metallosphaera sedula, Metallosphaera sedula, Metarhizium acridum* CQMa 102, *Methanosarcina acetivorans, Methanosarcina acetivorans* C2A, *Methanosarcina barkeri, Methanosarcina mazei* Tuc01, *Methanosarcina thermophila, Methanothermobacter thermautotrophicus, Methylobacillus flagellates, Methylobacillus flagellatus* KT, *Methylobacter marinus, Methylobacterium extorquens, Methylobacterium extorquens* AM1, *Methylococcus capsulatis, Methylomicrobium album* BG8, *Methylomonas aminofaciens, Methylovorus glucosetrophus* SIP3-4, *Methylovorus* sp. MP688, *Moorella thermoacetica, Moorella thermoacetica* ATCC 39073, *Mus musculus; Mycobacter* sp. strain JC1 DSM3803, *Mycobacterium avium* subsp. *paratuberculosis* K-10, *Mycobacterium bovis* BCG, *Mycobacterium gastri, Mycobacterium kansasii* ATCC 12478, *Mycobacterium marinum* M, *Mycobacterium smegmatis, Mycobacterium smegmatis* MC2 155, *Mycobacterium smegmatis* str. MC2 155, *Mycobacterium* sp. strain JLS, *Mycobacterium tuberculosis, Mycobacterium tuberculosis* H37Rv, *Neurospora crassa* OR 74A, *Nicotiana tabacum, Nitrosopumilus salaria* BD31, *Nitrososphaera gargensis* Ga9.2, *Nocardia brasiliensis, Nocardia farcinica* IFM10152 *Nocardia iowensis, Nocardia iowensis* (sp. NRRL 5646), *Nodularia spumigena* CCY9414, *Nostoc azollae, Nostoc* sp. PCC 7120, *Ogataea parapolymorpha* DL-1 (*Hansenula polymorpha* DL-1), *Oxalobacter formigenes, Paenibacillus peoriae* KCTC 3763, *Paracoccus denitrficans, Pelobacter carbinolicus* DSM 2380, *Penicillium chrysogenum, Perkinsus marinus* ATCC 50983, *Photobacterium leiognathi* PL741, *Photobacterium phosphoreum, Photobacterium profundum* 3TCK *Phtomonas* sp., *Pichia pastoris, Pichia pastoris* GS115, *Picrophilus torridus* DSM9790, *Plasmodium falciparum, Porphyromonas gingivalis, Porphyromonas gingivalis* W83, *Prochlorococcus marinus* MIT 9312, *Propionibacterium acnes, Propionibacterium fredenreichii* sp. *shennanii, Propionibacterium freudenreichii, Propionibacterium freundenreichii* subsp. *Shermanii, Propionigenium modestum, Pseudomonas aeruginosa, Pseudomonas aeruginosa* PA01, *Pseudomonas fluorescens, Pseudomonas fluorescens* Pf0-1, *Pseudomonas knackmussii, Pseudomonas knackmussii* (B13), *Pseudomonas mendocina, Pseudomonas putida, Pseudomonas putida* GB-1, *Pseudomonas putida* GB-1 *Trypanosoma brucei, Pseudomonas* sp, *Pseudomonas* sp. CF600, *Pseudomonas stutzeri, Pseudomonas syringae, Pseudomonas syringae* pv. *syringae* B728a, *Pyrobaculum aerophilum* str. IM2, *Pyrococcus abyssi, Pyrococcus furiosus, Pyrococcus horikoshii* OT3, *Ralstonia eutropha, Ralstonia eutropha* H16, *Ralstonia metallidurans, Rattus norvegicus, Rhizobium leguminosarum, Rhizopus oryzae, Rhodobacter capsulatus, Rhodobacter sphaeroides, Rhodobacter sphaeroides* ATCC 17025, *Rhodococcus erythropolis* SK121, *Rhodococcus opacus* B4, *Rhodopseudomonas palustris, Rhodopseudomonas palustris* CGA009, *Rhodopseudomonas palustris* DX-1, *Rhodospirillum rubrum, Roseiflexus castenholzii, Saccahromyces cerevisiae, Saccharomyces cerevisiae* S288c, *Salmonella enteric, Salmonella enterica, Salmonella enterica* LT2, *Salmonella enterica* subsp. *enterica* serovar *Typhimurium* str. LT2, *Salmonella enterica Typhimurium, Salmonella typhimurium, Salmonella typhimurium* LT2, *Schizosaccharomyces pombe, Sebaldella termitidis* ATCC 33386, *Shewanella oneidensis* MR-1, *Shigella dysenteriae, Shigella flexneri, Shigella sonnei, Simmondsia chinensis, Sinorhizobium meliloti* 1021, *Solanum lycopersicum, Sordaria macrospora, Staphylococcus aureus, Staphylococcus aureus* MW2, *Streptococcus mutans, Streptococcus mutans* UA159, *Streptococcus pneumoniae, Streptococcus sanguinis, Streptomyces anulatus, Streptomyces avermitilis* MA-4680, *Streptomyces avermitillis, Streptomyces cinnamonensis, Streptomyces coelicolor, Streptomyces glaucescens, Streptomyces griseus* subsp. *griseus* NBRC 13350, *Streptomyces luridus, Streptomyces* sp CL190, *Streptomyces* sp CL190, *Streptomyces* sp. KO-3988, *Streptomyces viridochromogenes, Streptomyces wedmorensis, Sulfolobus acidocaldarius, Sulfolobus solfataricus, Sulfolobus solfataricus* P-2, *Sulfolobus tokodaii, Sulfurihydrogenibium subterraneum, Sulfurimonas denitrificans, Sus scrofa, Synechococcus elongatus* PCC 6301, *Synechococcus elongatus* PCC7942, *Synechococcus* sp. PCC 7002, *Synechocystis* str. PCC 6803, *Syntrophobacter fumaroxidans, Syntrophus aciditrophicus, Thauera aromatic, Thermoanaerobacter ethanolicus* JW 200, *Thermoanaerobacter pseudethanolicus* ATCC 33223, *Thermoanaerobacter* sp. X514, *Thermoanaerobacter tengcongensis* MB4, *Thermoanaerobobacter brockii, Thermococcus kodakaraensis, Thermococcus litoralis, Thermomyces lanuginosus, Thermoplasma acidophilum, Thermoproteus neutrophilus, Thermotoga maritime, Thiocapsa roseopersicina, Treponema denticola, Trichomonas vaginalis* G3, *Triticum aestivum, Trypanosoma brucei, Trypanosoma cruzi* strain CL Brener, *Tsukamurella paurometabola* DSM 20162, *Umbellularia californica*, uncultured organism, *Veillonella parvula, Vibrio harveyi* ATCC BAA-1116, *Xanthobacter autotrophicus* Py2, *Xenopus tropicalis, Yarrowia lipolytica, Yersinia frederiksenii, Zea mays, Zoogloea ramigera, Zymomonas mobilis, Zymomonas mobilis* subsp. *mobilis* ZM4, *Clostridium beijerinickii, Deinococcus radiodurans* R1, *Aquifex aeolicus* VF5, *Methanocaldococcus janaschii, Yersinia pestis, Bifidobacterium animalis lactis, Bifidobacterium dentium* ATCC 27678, *Bifidobacterium pseudolongum* subsp. *globosum, Bifidobacterium breve, Lactobacillus paraplantarum, Corynebacterium glutamicum* ATCC 13032, as well as other exemplary species disclosed herein or available as source organisms for corresponding genes. However, with the complete genome sequence available for now more than 550 species (with more than half of these available on public databases such as the NCBI), including 395 microorganism genomes and a variety of yeast, fungi, plant, and mammalian genomes, the identification of genes encoding the requisite fatty alcohol, fatty aldehyde, fatty acid or isopropanol biosynthetic activity for one or more genes in related or distant species, including for example, homologues, orthologs, paralogs and nonorthologous gene displacements of known genes, and the interchange of genetic alterations between organisms is routine and well known in the art. Accordingly, the metabolic alterations allowing biosynthesis of fatty alcohol, fatty aldehyde, fatty acid or isopropanol described herein with reference to a particular organism such as *E. coli* can be readily applied to other microorganisms, including prokaryotic and eukaryotic organisms alike. Given the teachings and guidance provided herein, those skilled in the art will know that a metabolic alteration exemplified in one organism can be applied equally to other organisms.

In some instances, such as when an alternative fatty alcohol, fatty aldehyde, fatty acid or isopropanol biosynthetic pathway exists in an unrelated species, fatty alcohol, fatty aldehyde, fatty acid or isopropanol biosynthesis can be conferred onto the host species by, for example, exogenous expression of a paralog or paralogs from the unrelated species that catalyzes a similar, yet non-identical metabolic reaction to replace the referenced reaction. Because certain differences among metabolic networks exist between different organisms, those skilled in the art will understand that the actual gene usage between different organisms may differ. However, given the teachings and guidance provided herein, those skilled in the art also will understand that the teachings and methods of the invention can be applied to all microbial organisms using the cognate metabolic alterations to those exemplified herein to construct a microbial organism in a species of interest that will synthesize fatty alcohol, fatty aldehyde, fatty acid or isopropanol. A nucleic acid molecule encoding a fatty alcohol, fatty aldehyde, fatty acid or isopropanol pathway enzyme or protein of the invention can also include a nucleic acid molecule that hybridizes to a nucleic acid disclosed herein by SEQ ID NO, GenBank and/or GI number or a nucleic acid molecule that hybridizes to a nucleic acid molecule that encodes an amino acid sequence disclosed herein by SEQ ID NO, GenBank and/or GI number. Hybridization conditions can include highly stringent, moderately stringent, or low stringency hybridization conditions that are well known to one of skill in the art such as those described herein. Similarly, a nucleic acid molecule that can be used in the invention can be described as having a certain percent sequence identity to a nucleic acid disclosed herein by SEQ ID NO, GenBank and/or GI number or a nucleic acid molecule that hybridizes to a nucleic acid molecule that encodes an amino acid sequence disclosed herein by SEQ ID NO, GenBank and/or GI number. For example, the nucleic acid molecule can have at least 65%, 70%, 75%, 80%, 85%, 90%, 91%, 92%, 93%, 94%, 95%, 96%, 97%, 98% or 99% sequence identity to a nucleic acid described herein.

Stringent hybridization refers to conditions under which hybridized polynucleotides are stable. As known to those of skill in the art, the stability of hybridized polynucleotides is reflected in the melting temperature ($T_m$) of the hybrids. In general, the stability of hybridized polynucleotides is a function of the salt concentration, for example, the sodium ion concentration and temperature. A hybridization reaction can be performed under conditions of lower stringency, followed by washes of varying, but higher, stringency. Reference to hybridization stringency relates to such washing conditions. Highly stringent hybridization includes conditions that permit hybridization of only those nucleic acid sequences that form stable hybridized polynucleotides in 0.018M NaCl at 65° C., for example, if a hybrid is not stable in 0.018M NaCl at 65° C., it will not be stable under high stringency conditions, as contemplated herein. High stringency conditions can be provided, for example, by hybridization in 50% formamide, 5× Denhart's solution, 5× SSPE, 0.2% SDS at 42° C., followed by washing in 0.1× SSPE, and 0.1% SDS at 65° C. Hybridization conditions other than highly stringent hybridization conditions can also be used to describe the nucleic acid sequences disclosed herein. For example, the phrase moderately stringent hybridization refers to conditions equivalent to hybridization in 50% formamide, 5× Denhart's solution, 5× SSPE, 0.2% SDS at 42° C., followed by washing in 0.2×SSPE, 0.2% SDS, at 42° C. The phrase low stringency hybridization refers to conditions equivalent to hybridization in 10% formamide, 5× Denhart's solution, 6× SSPE, 0.2% SDS at 22° C., followed by washing in 1× SSPE, 0.2% SDS, at 37° C. Denhart's solution contains 1% Ficoll, 1% polyvinylpyrolidone, and 1% bovine serum albumin (BSA). 20× SSPE (sodium chloride, sodium phosphate, ethylene diamide tetraacetic acid (EDTA)) contains 3M sodium chloride, 0.2M sodium phosphate, and 0.025 M (EDTA). Other suitable low, moderate and high stringency hybridization buffers and conditions are well known to those of skill in the art and are described, for example, in Sambrook et al., *Molecular Cloning: A Laboratory Manual*, Third Ed., Cold Spring Harbor Laboratory, New York (2001); and Ausubel et al., *Current Protocols in Molecular Biology*, John Wiley and Sons, Baltimore, MD (1999).

A nucleic acid molecule encoding a fatty alcohol, fatty aldehyde, fatty acid or isopropanol pathway enzyme or protein of the invention can have at least a certain sequence identity to a nucleotide sequence disclosed herein. Accordingly, in some aspects of the invention, a nucleic acid molecule encoding a fatty alcohol, fatty aldehyde, fatty acid or isopropanol pathway enzyme or protein has a nucleotide sequence of at least 65% identity, at least 70% identity, at least 75% identity, at least 80% identity, at least 85% identity, at least 90% identity, at least 91% identity, at least 92% identity, at least 93% identity, at least 94% identity, at least 95% identity, at least 96% identity, at least 97% identity, at least 98% identity, or at least 99% identity to a nucleic acid disclosed herein by SEQ ID NO, GenBank and/or GI number or a nucleic acid molecule that hybridizes to a nucleic acid molecule that encodes an amino acid sequence disclosed herein by SEQ ID NO, GenBank and/or GI number.

Sequence identity (also known as homology or similarity) refers to sequence similarity between two nucleic acid molecules or between two polypeptides. Identity can be determined by comparing a position in each sequence, which may be aligned for purposes of comparison. When a position in the compared sequence is occupied by the same base or amino acid, then the molecules are identical at that position. A degree of identity between sequences is a function of the number of matching or homologous positions shared by the sequences. The alignment of two sequences to determine their percent sequence identity can be done using software programs known in the art, such as, for example, those described in Ausubel et al., *Current Protocols in Molecular Biology*, John Wiley and Sons, Baltimore,MD. (1999). Preferably, default parameters are used for the alignment. One alignment program well known in the art that can be used is BLAST set to default parameters. In particular, programs are BLASTN and BLASTP, using the following default parameters: Genetic code=standard; filter=none; strand=both; cutoff=60; expect=10; Matrix=BLOSUM62; Descriptions=50 sequences; sort by=HIGH SCORE; Databases=non-redundant, GenBank+ EMBL+DDBJ+PDB+GenBank CDS translations+ SwissProtein+SPupdate+PIR. Details of these programs can be found at the National Center for Biotechnology Information.

Methods for constructing and testing the expression levels of a non-naturally occurring fatty alcohol, fatty aldehyde, fatty acid or isopropanol-producing host can be performed, for example, by recombinant and detection methods well known in the art. Such methods can be found described in, for example, Sambrook et al., *Molecular Cloning: A Laboratory Manual*, Third Ed., Cold Spring Harbor Laboratory, New York (2001); and Ausubel et al., *Current Protocols in Molecular Biology*, John Wiley and Sons, Baltimore,MD. (1999).

Exogenous nucleic acid sequences involved in a pathway for production of fatty alcohol, fatty aldehyde, fatty acid or isopropanol can be introduced stably or transiently into a host cell using techniques well known in the art including, but not limited to, conjugation, electroporation, chemical transformation, transduction, transfection, and ultrasound transformation. For exogenous expression in *E. coli* or other prokaryotic cells, some nucleic acid sequences in the genes or cDNAs of eukaryotic nucleic acids can encode targeting signals such as an N-terminal mitochondrial or other targeting signal, which can be removed before transformation into prokaryotic host cells, if desired. For example, removal of a mitochondrial leader sequence led to increased expression in *E. coli* (Hoffmeister et al., *J. Biol. Chem.* 280:4329-4338 (2005)). For exogenous expression in yeast or other eukaryotic cells, genes can be expressed in the cytosol without the addition of leader sequence, or can be targeted to mitochondrion or other organelles, or targeted for secretion, by the addition of a suitable targeting sequence such as a mitochondrial targeting or secretion signal suitable for the host cells. Thus, it is understood that appropriate modifications to a nucleic acid sequence to remove or include a targeting sequence can be incorporated into an exogenous nucleic acid sequence to impart desirable properties. Furthermore, genes can be subjected to codon optimization with techniques well known in the art to achieve optimized expression of the proteins.

An expression vector or vectors can be constructed to include one or more fatty alcohol, fatty aldehyde, fatty acid or isopropanol biosynthetic pathway encoding nucleic acids as exemplified herein operably linked to expression control sequences functional in the host organism. Expression vectors applicable for use in the microbial host organisms of the invention include, for example, plasmids, phage vectors, viral vectors, episomes and artificial chromosomes, including vectors and selection sequences or markers operable for stable integration into a host chromosome. Additionally, the expression vectors can include one or more selectable marker genes and appropriate expression control sequences. Selectable marker genes also can be included that, for example, provide resistance to antibiotics or toxins, complement auxotrophic deficiencies, or supply critical nutrients not in the culture media. Expression control sequences can include constitutive and inducible promoters, transcription enhancers, transcription terminators, and the like which are well known in the art. When two or more exogenous encoding nucleic acids are to be co-expressed, both nucleic acids can be inserted, for example, into a single expression vector or in separate expression vectors. For single vector expression, the encoding nucleic acids can be operationally linked to one common expression control sequence or linked to different expression control sequences, such as one inducible promoter and one constitutive promoter. The transformation of exogenous nucleic acid sequences involved in a metabolic or synthetic pathway can be confirmed using methods well known in the art. Such methods include, for example, nucleic acid analysis such as Northern blots or polymerase chain reaction (PCR) amplification of mRNA, or immunoblotting for expression of gene products, or other suitable analytical methods to test the expression of an introduced nucleic acid sequence or its corresponding gene product. It is understood by those skilled in the art that the exogenous nucleic acid is expressed in a sufficient amount to produce the desired product, and it is further understood that expression levels can be optimized to obtain sufficient expression using methods well known in the art and as disclosed herein.

In some embodiments, the invention provides a method for producing a compound of Formula (I):

wherein $R_1$ is $C_{1-24}$ linear alkyl; $R_2$ is $CH_2OH$, CHO, or COOH; $R_3$ is H, OH, or oxo (=O); and ====== represents a single or double bond with the proviso that the valency of the carbon atom to which $R_3$ is attached is four, comprising culturing a non-naturally occurring microbial organism of the invention under conditions and for a sufficient period of time to produce the compound of Formula (I).

In some aspects of the invention, the microbial organism used in a method of the invention includes a non-naturally occurring having: (i) a formaldehyde fixation pathway; (ii) a formate assimilation pathway; and/or (iii) a methanol metabolic pathway as depicted in FIGS. 1 and 10, and a MI-FAE cycle or a MD-FAE cycle in combination with a termination pathway as depicted in FIGS. 2, 7 and 8, wherein said formaldehyde fixation pathway comprises: (1) 1B and 1C; (2) 1D; or (3) 1D and 1Z, wherein 1B is a 3-hexulose-6-phosphate synthase, wherein 1C is a 6-phospho-3-hexuloisomerase, wherein 1D is a dihydroxyacetone synthase, wherein 1Z is a fructose-6-phosphate aldolase, wherein said formate assimilation pathway comprises a pathway selected from: (4) 1E; (5) 1F, and 1G; (6) 1H, 1I, 1J, and 1K; (7) 1H, 1I, 1J, 1L, 1M, and 1N; (8) 1E, 1H, 1I, 1J, 1L, 1M, and 1N; (9) 1F, 1G, 1H, 1I, 1J, 1L, 1M, and 1N; (10) 1K, 1H, 1I, 1J, 1L, 1M, and 1N; and (11) 1H, 1I, 1J, 1O, and 1P, wherein 1E is a formate reductase, 1F is a formate ligase, a formate transferase, or a formate synthetase, wherein 1G is a formyl-CoA reductase, wherein 1H is a formyltetrahydrofolate synthetase, wherein 1I is a methenyltetrahydrofolate cyclohydrolase, wherein 1J is a methylenetetrahydrofolate dehydrogenase, wherein 1K is a formaldehyde-forming enzyme or spontaneous, wherein 1L is a glycine cleavage system, wherein 1M is a serine hydroxymethyltransferase, wherein 1N is a serine deaminase, wherein 1O is a methylenetetrahydrofolate reductase, wherein 1P is an acetyl-CoA synthase, wherein said methanol metabolic pathway comprises a pathway selected from: (12) 10J; (13) 10A, (14) 10A and 10B; (15) 10A, 10B and 10C; (16) 10J, 10K and 10C; (17) 10J, 10M, and 10N; (18) 10J and 10L; (19) 10J, 10L and 10G; (20) 10J, 10L, and 10I; (21) 10A, 10B, 10C, 10D, and 10E; (22) 10A, 10B, 10C, 10D, and 10F; (23) 10J, 10K, 10C, 10D, and 10E; (24) 10J, 10K, 10C, 10D, and 10F; (25) 10J, 10M, 10N, and 10O; (26) 10A, 10B, 10C, 10D, 10E, and 10G; (27) 10A, 10B, 10C, 10D, 10F, and 10G; (28) 10J, 10K, 10C, 10D, 10E, and 10G; (29) 10J, 10K, 10C, 10D, 10F, and 10G; (30) 10J, 10M, 10N, 10O, and 10G; (31) 10A, 10B, 10C, 10D, 10E, and 10I; (32) 10A, 10B, 10C, 10D, 10F, and 10I; (33) 10J, 10K, 10C, 10D, 10E, and 10I; (34) 10J, 10K, 10C, 10D, 10F, and 10I; and (35) 10J, 10M, 10N, 10O, and 10I, wherein 10A is a methanol methyltransferase, wherein 10B is a methylenetetrahydrofolate reductase, wherein 10C is a methylenetetrahydrofolate dehydrogenase, wherein 10D is a methenyltetrahydrofolate cyclohydrolase, wherein 10E is a formyltetrahydrofolate deformylase, wherein 10F is a formyltetrahydrofolate synthetase, wherein 10G is a formate hydrogen lyase, wherein 10I is a formate dehydrogenase, wherein 10J is a methanol dehydrogenase, wherein 10K is a formaldehyde activating enzyme or spontaneous, wherein 10L is a formaldehyde dehydrogenase, wherein 10M is a S-(hydroxymethyl)glutathione synthase or spontaneous, wherein 10N is a glutathione-dependent formaldehyde dehydrogenase, wherein 10O is a S-formylglutathione hydrolase, wherein the MI-FAE cycle includes one or more thiolase, one or more 3-oxoacyl-CoA reductase, one or more 3-hydroxyacyl-CoA dehydratase, and one or more enoyl-CoA reductase, wherein the MD-FAE cycle includes one or more elongase, one or more 3-oxoacyl-CoA reductase, one or more 3-hydroxyacyl-CoA dehydratase, and one or more enoyl-CoA reductase, wherein the termination pathway includes a pathway selected from: (36) 2H; (37) 2K and 2L; (38) 2E and 2N; (39) 2K, 2J, and 2N; (40) 2E; (41) 2K and 2J; (42) 2H and 2N; (43) 2K, 2L, and 2N; (44) 2E and 2F; (45) 2K, 2J, and 2F; (46) 2H, 2N, and 2F; (47) 2K, 2L, 2N, and 2F; (48) 2G; and (49) 2P, wherein 2E is an acyl-CoA reductase (aldehyde forming), wherein 2F is an alcohol dehydrogenase, wherein 2G is an acyl-CoA reductase (alcohol forming), wherein 2H is an acyl-CoA hydrolase, acyl-CoA transferase or acyl-CoA synthase, wherein 2J is an acyl-ACP reductase, wherein 2K is an acyl-CoA:ACP acyltransferase, wherein 2L is a thioesterase, wherein 2N is an aldehyde dehydrogenase (acid forming) or a carboxylic acid reductase, wherein 2P is an acyl-ACP reductase (alcohol forming) wherein an enzyme of the formaldehyde fixation pathway, the formate assimilation pathway, the methanol metabolic pathway, the MI-FAE cycle, MD-FAE cycle or termination pathway is encoded by at least one exogenous nucleic acid and is expressed in a sufficient amount to produce a compound of Formula (I):

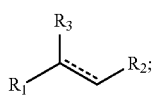

(I)

wherein $R_1$ is $C_{1-24}$ linear alkyl; $R_2$ is $CH_2OH$, CHO, or COOH; $R_3$ is H, OH, or oxo (=O); and ------ represents a single or double bond with the proviso that the valency of the carbon atom to which $R_3$ is attached is four, wherein the substrate of each of said enzymes of the MI-FAE cycle, the MD-FAE cycle and the termination pathway are independently selected from a compound of Formula (II), malonyl-CoA, propionyl-CoA or acetyl-CoA:

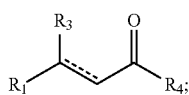

(II)

wherein $R_1$ is $C_{1-24}$ linear alkyl; $R_3$ is H, OH, or oxo (=O); $R_4$ is S-CoA, ACP, OH or H; and ------ represents a single or double bond with the proviso that the valency of the carbon atom to which $R_3$ is attached is four; wherein said one or more enzymes of the MI-FAE cycle are each selective for a compound of Formula (II) having a number of carbon atoms at $R_1$ that is no greater than the number of carbon atoms at $R_1$ of said compound of Formula (I), wherein said one or more enzymes of the MD-FAE cycle are each selective for a compound of Formula (II) having a number of carbon atoms at $R_1$ that is no greater than the number of carbon atoms at $R_1$ of said compound of Formula (I), and wherein said one or more enzymes of the termination pathway are each selective for a compound of Formula (II) having a number of carbon atoms at $R_1$ that is no less than the number of carbon atoms at $R_1$ of said compound of Formula (I).

In some aspects of the invention, the microbial organism used in a method of the invention includes a non-naturally occurring having: (i) a formaldehyde fixation pathway; (ii) a formate assimilation pathway; and/or (iii) a methanol metabolic pathway as depicted in FIGS. 1 and 10, and a FAACPE cycle in combination with a termination pathway as depicted in FIG. 12, wherein said formaldehyde fixation pathway comprises: (1) 1B and 1C; (2) 1D; (3) 1D and 1Z, wherein 1B is a 3-hexulose-6-phosphate synthase, wherein 1C is a 6-phospho-3-hexuloisomerase, wherein 1D is a dihydroxyacetone synthase, wherein 1Z is a fructose-6-phosphate aldolase, wherein said formate assimilation pathway comprises a pathway selected from: (4) 1E; (5) 1F, and 1G; (6) 1H, 1I, 1J, and 1K; (7) 1H, 1I, 1J, 1L, 1M, and 1N; (8) 1E, 1H, 1I, 1J, 1L, 1M, and 1N; (9) 1F, 1G, 1H, 1I, 1J, 1L, 1M, and 1N; (10) 1K, 1H, 1I, 1J, 1L, 1M, and 1N; and (11) 1H, 1I, 1J, 1O, and 1P, wherein 1E is a formate reductase, 1F is a formate ligase, a formate transferase, or a formate synthetase, wherein 1G is a formyl-CoA reductase, wherein 1H is a formyltetrahydrofolate synthetase, wherein 1I is a methenyltetrahydrofolate cyclohydrolase, wherein 1J is a methylenetetrahydrofolate dehydrogenase, wherein 1K is a formaldehyde-forming enzyme or spontaneous, wherein 1L is a glycine cleavage system, wherein 1M is a serine hydroxymethyltransferase, wherein 1N is a serine deaminase, wherein 1O is a methylenetetrahydrofolate reductase, wherein 1P is an acetyl-CoA synthase, wherein said methanol metabolic pathway comprises a pathway selected from: (12) 10J; (13) 10A, (14) 10A and 10B; (15) 10A, 10B and 10C; (16) 10J, 10K and 10C; (17) 10J, 10M, and 10N; (18) 10J and 10L; (19) 10J, 10L and 10G; (20) 10J, 10L, and 10I; (21) 10A, 10B, 10C, 10D, and 10E; (22) 10A, 10B, 10C, 10D, and 10F; (23) 10J, 10K, 10C, 10D, and 10E; (24) 10J, 10K, 10C, 10D, and 10F; (25) 10J, 10M, 10N, and 10O; (26) 10A, 10B, 10C, 10D, 10E, and 10G; (27) 10A, 10B, 10C, 10D, 10F, and 10G; (28) 10J, 10K, 10C, 10D, 10E, and 10G; (29) 10J, 10K, 10C, 10D, 10F, and 10G; (30) 10J, 10M, 10N, 10O, and 10G; (31) 10A, 10B, 10C, 10D, 10E, and 10I; (32) 10A, 10B, 10C, 10D, 10F, and 10I; (33) 10J, 10K, 10C, 10D, 10E, and 10I; (34) 10J, 10K, 10C, 10D, 10F, and 10I; and (35) 10J, 10M, 10N, 10O, and 10I, wherein 10A is a methanol methyltransferase, wherein 10B is a methylenetetrahydrofolate reductase, wherein 10C is a methylenetetrahydrofolate dehydrogenase, wherein 10D is a methenyltetrahydrofolate cyclohydrolase, wherein 10E is a formyltetrahydrofolate deformylase, wherein 10F is a formyltetrahydrofolate synthetase, wherein 10G is a formate hydrogen lyase, wherein 10I is a formate dehydrogenase, wherein 10J is a methanol dehydrogenase, wherein 10K is a formaldehyde activating enzyme or spontaneous, wherein 10L is a formaldehyde dehydrogenase, wherein 10M is a S-(hydroxymethyl)glutathione synthase or spontaneous, wherein 10N is a glutathione-dependent formaldehyde dehydrogenase, wherein 10O is a S-formylglutathione hydrolase, wherein said FAACPE cycle comprises one or more β-ketoacyl-ACP synthase, one or more β-ketoacyl-ACP reductase, one or more β-hydroxyacyl-ACP reductase, and one or more enoyl ACP-reductase, wherein said termination pathway comprises a pathway selected from: (36) 12I; (37) 12J; (38) 12I, 12K, and 12L; (39) 12I and 12O; (40) 12J and 12M; (41) 12I, 12K, 12L, and 12M; (42) 12I, 12O, and 12M; (43) 12I, 12K and 12N, and (44) 12P, wherein 12I is a thioesterase, wherein 12J is a fatty acyl-ACP reductase, wherein 12K is an acyl-CoA synthase, wherein 12L is an acyl-CoA reductase, wherein 12M is a fatty aldehyde reductase, wherein 12N is a fatty alcohol forming acyl-CoA reductase (FAR), wherein 12O is a carboxylic acid reductase (CAR), wherein 12P is an acyl-ACP reductase (alcohol forming),wherein an enzyme of the formaldehyde fixation pathway, the formate assimilation pathway, the methanol metabolic pathway, the FAACPE cycle or the termination pathway is encoded by at least one exogenous nucleic acid and is expressed in a sufficient amount to produce a compound of Formula (I):

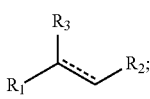
(I)

wherein $R_1$ is $C_{1-24}$ linear alkyl; $R_2$ is $CH_2OH$, CHO, or COOH; $R_3$ is H, OH, or oxo (=O); and ------ represents a single or double bond with the proviso that the valency of the carbon atom to which $R_3$ is attached is four, wherein the substrate of each of said enzymes of the FAACPE cycle and the termination pathway are independently selected from a compound of Formula (II) or malonyl-ACP:

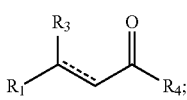
(II)

wherein $R_1$ is $C_{1-24}$ linear alkyl; $R_3$ is H, OH, or oxo (=O); $R_4$ is S-CoA, ACP, OH or H; and ------ represents a single or double bond with the proviso that the valency of the carbon atom to which $R_3$ is attached is four; wherein said one or more enzymes of the FAACPE cycle are each selective for a compound of Formula (II) having a number of carbon atoms at $R_1$ that is no greater than the number of carbon atoms at $R_1$ of said compound of Formula (I), and wherein said one or more enzymes of the termination pathway are each selective for a compound of Formula (II) having a number of carbon atoms at $R_1$ that is no less than the number of carbon atoms at $R_1$ of said compound of Formula (I).

In some aspects of the invention, the microbial organism used in a method of the invention includes a non-naturally occurring having a combination of one or more pathways for generating substrates, intermediates and/or reducing equivalents that can be used with elongation cycles and termination pathways described herein for producing a fatty alcohol, fatty acid or fatty aldehyde of the invention. Accordingly, in some embodiments, the microbial organism has a formaldehyde fixation pathway and a MI-FAE cycle in combination with a termination pathway. In some embodiments, the microbial organism has a formate assimilation pathway and a MI-FAE cycle in combination with a termination pathway. In some embodiments, the microbial organism has a formaldehyde fixation pathway, a formate assimilation pathway, and a MI-FAE cycle in combination with a termination pathway. In some embodiments, the microbial organism has a formaldehyde fixation pathway and a MD-FAE cycle in combination with a termination pathway. In some embodiments, the microbial organism has a formate assimilation pathway and a MD-FAE cycle in combination with a termination pathway. In some embodiments, the microbial organism has a formaldehyde fixation pathway, a formate assimilation pathway, and a MD-FAE cycle in combination with a termination pathway. In some embodiments, the microbial organism has a methanol metabolic pathway and a MI-FAE cycle in combination with a termination pathway. In some embodiments, the microbial organism has a methanol metabolic pathway and a MD-FAE cycle in combination with a termination pathway. In some embodiments, the microbial organism has a formaldehyde fixation pathway, a methanol metabolic pathway and a MI-FAE cycle in combination with a termination pathway. In some embodiments, the microbial organism has a formate assimilation pathway, a methanol metabolic pathway and a MI-FAE cycle in combination with a termination pathway. In some embodiments, the microbial organism has a formaldehyde fixation pathway, a formate assimilation pathway, a methanol metabolic pathway and a MI-FAE cycle in combination with a termination pathway. In some embodiments, the microbial organism has a formaldehyde fixation pathway, a methanol metabolic pathway and a MD-FAE cycle in combination with a termination pathway. In some embodiments, the microbial organism has a formate assimilation pathway, a methanol metabolic pathway and a MD-FAE cycle in combination with a termination pathway. In some embodiments, the microbial organism has a formaldehyde fixation pathway, a formate assimilation pathway, a methanol metabolic pathway and MD-FAE cycle in combination with a termination pathway. In some embodiments, the microbial organism has a formaldehyde fixation pathway and an FAACPE cycle in combination with a termination pathway. In some embodiments, the microbial organism has a formate assimilation pathway and an FAACPE cycle in combination with a termination pathway. In some embodiments, the microbial organism has a formaldehyde fixation pathway, a formate assimilation pathway, and an FAACPE cycle in combination with a termination pathway. In some embodiments, the microbial organism has a methanol metabolic pathway and an FAACPE cycle in combination with a termination pathway. In some embodiments, the microbial organism has a formaldehyde fixation pathway, a methanol metabolic pathway and an FAACPE cycle in combination with a termination pathway. In some embodiments, the microbial organism has a formate assimilation pathway, a methanol metabolic pathway and an FAACPE cycle in combination with a termination pathway. In some embodiments, the microbial organism has a formaldehyde fixation pathway, a formate assimilation pathway, a methanol metabolic pathway and an FAACPE cycle in combination with a termination pathway.

In some aspects of the invention, the microbial organism used in a method of the invention that includes a FAACPE cycle in combination with a termination pathway as described herein, can further include a pathway for production of substrates for the FAACPE cycle, such as acetoacetyl-ACP or 3-oxovalery-ACP. Accordingly, in some embodiments, the microbial organism further comprises an acetoacetyl-ACP pathway of: (1) 12A, 12B, and 12C; or (2) 12A, 12B, and 12D, wherein 12A is an acetyl-CoA carboxylase, wherein 12B is malonyl-CoA ACP transacylase, wherein 12C is an acetoacetyl-ACP synthase, and wherein 12D is a β-ketoacyl-ACP synthase In some embodiments, the microbial organism further comprises a 3-oxovalery-ACP pathway comprising an acetyl-CoA carboxylase, a malonyl-CoA ACP transacylase, and a β-ketoacyl-ACP synthase. In some aspects of the invention, an enzyme of the acetoacetyl-ACP pathway is encoded by at least one exogenous nucleic acid and is expressed in a sufficient amount to produce acetoacetyl-ACP wherein the acetoacetyl-ACP is a β-ketoacyl-ACP of the FAACPE cycle. In some aspects of the invention, an enzyme of the 3-oxovalery-ACP pathway is encoded by at least one exogenous nucleic acid and is expressed in a sufficient amount to produce 3-oxovalery-ACP, wherein the 3-oxovalery-ACP is a β-ketoacyl-ACP of the FAACPE cycle.

In some embodiments, the invention provides a method for producing a compound of Formula (I) wherein $R_1$ is $C_{1-17}$ linear alkyl. In another aspect of the invention, the $R_1$ of the compound of Formula (I) is $C_1$ linear alkyl, $C_2$ linear alkyl, $C_3$ linear alkyl, $C_4$ linear alkyl, $C_5$ linear alkyl, $C_6$ linear alkyl, $C_7$ linear alkyl, $C_8$ linear alkyl, $C_9$ linear alkyl, $C_{10}$ linear alkyl, $C_{11}$, linear alkyl, $C_{12}$ linear alkyl or $C_{13}$ linear alkyl, $C_{14}$ linear alkyl, $C_{15}$ linear alkyl, $C_{16}$ linear alkyl, $C_{17}$ linear alkyl, $C_{18}$ linear alkyl, $C_{19}$ linear alkyl, $C_{20}$ linear alkyl, $C_{21}$ linear alkyl, $C_{22}$ linear alkyl, $C_{23}$ linear alkyl, or $C_{24}$ linear alkyl.

In some aspects of the invention, the microbial organism used in a method of the invention includes two, three, or four exogenous nucleic acids each encoding an enzyme of the MI-FAE cycle, the MD-FAE cycle, or the FAACPE cycle. In some aspects of the invention, the microbial organism includes two, three, or four exogenous nucleic acids each encoding an enzyme of the termination pathway. In some aspects of the invention, the microbial organism includes one, two, three, four, five, six, seven, or eight exogenous nucleic acids each encoding a formaldehyde fixation pathway enzyme, a formate assimilation pathway enzyme, or a methanol metabolic pathway enzyme. In some aspects of the invention, the microbial organism includes exogenous nucleic acids encoding each of the enzymes of at least one of the pathways selected from (1)-(49) for a microbial organism having a MI-FAE cycle or a MD-FAE cycle in combination with a termination pathway as depicted in FIGS. 1, 2, 7, 8 and 10. In some aspects of the invention, the microbial organism includes exogenous nucleic acids encoding each of the enzymes of at least one of the pathways selected from (1)-(44) for a microbial organism having a fatty acyl-ACP elongation (FAACPE) cycle in combination with a termination pathway as depicted in FIGS. 1, 10 and 12.

In some embodiments, the invention provides a method for producing a fatty alcohol selected from the Formulas (III)—(VI):

(III)
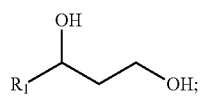

(IV)
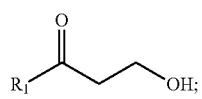

-continued (V)
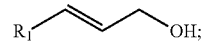

(VI)
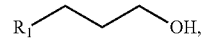

wherein $R_1$ is $C_{1-24}$ linear alkyl, or alternatively $R_1$ is $C_{1-17}$ linear alkyl, or alternatively $R_1$ is $C_{9-13}$ linear alkyl. In some aspects of the invention, $R_1$ is $C_1$ linear alkyl, $C_2$ linear alkyl, $C_3$ linear alkyl, $C_4$ linear alkyl, $C_5$ linear alkyl, $C_6$ linear alkyl, $C_7$ linear alkyl, $C_8$ linear alkyl, $C_9$ linear alkyl, $C_{10}$ linear alkyl, $C_{11}$, linear alkyl, $C_{12}$ linear alkyl or $C_{13}$ linear alkyl, $C_{14}$ linear alkyl, $C_{15}$ linear alkyl, $C_{16}$ linear alkyl, $C_{17}$ linear alkyl, $C_{18}$ linear alkyl, $C_{19}$ linear alkyl, $C_{20}$ linear alkyl, $C_{21}$ linear alkyl, $C_{22}$ linear alkyl, $C_{23}$ linear alkyl, or $C_{24}$ linear alkyl.

In some embodiments, the invention provides a method for producing a fatty aldehyde selected from the Formulas (VII)—(X):

(VII)
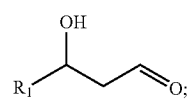

(VIII)
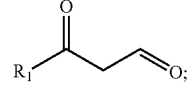

(IX)
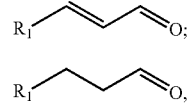

(X)

wherein $R_1$ is $C_{1-24}$ linear alkyl, or alternatively $R_1$ is $C_{1-17}$ linear alkyl, or alternatively $R_1$ is $C_{9-13}$ linear alkyl. In some aspects of the invention, $R_1$ is $C_1$ linear alkyl, $C_2$ linear alkyl, $C_3$ linear alkyl, $C_4$ linear alkyl, $C_5$ linear alkyl, $C_6$ linear alkyl, $C_7$ linear alkyl, $C_8$ linear alkyl, $C_9$ linear alkyl, $C_{10}$ linear alkyl, $C_{11}$, linear alkyl, $C_{12}$ linear alkyl or $C_{13}$ linear alkyl, $C_{14}$ linear alkyl, $C_{15}$ linear alkyl, $C_{16}$ linear alkyl, $C_{17}$ linear alkyl, $C_{18}$ linear alkyl, $C_{19}$ linear alkyl, $C_{20}$ linear alkyl, $C_{21}$ linear alkyl, $C_{22}$ linear alkyl, $C_{23}$ linear alkyl, or $C_{24}$ linear alkyl.

In some embodiments, the invention provides a method for producing a fatty acid selected from the Formulas (XI)—(XIV):

(XI)
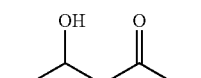

(XII)
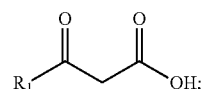

(XIII)
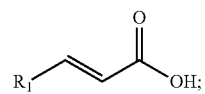

-continued

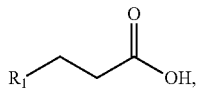
(XIV)

wherein $R_1$ is $C_{1-24}$ linear alkyl, or alternatively $R_1$ is $C_{1-17}$ linear alkyl, or alternatively $R_1$ is $C_{9-13}$ linear alkyl. In some aspects of the invention, $R_1$ is $C_1$ linear alkyl, $C_2$ linear alkyl, $C_3$ linear alkyl, $C_4$ linear alkyl, $C_5$ linear alkyl, $C_6$ linear alkyl, $C_7$ linear alkyl, $C_8$ linear alkyl, $C_9$ linear alkyl, $C_{10}$ linear alkyl, $C_{11}$, linear alkyl, $C_{12}$ linear alkyl or $C_{13}$ linear alkyl, $C_{14}$ linear alkyl, $C_{15}$ linear alkyl, $C_{16}$ linear alkyl, $C_{17}$ linear alkyl, $C_{18}$ linear alkyl, $C_{19}$ linear alkyl, $C_{20}$ linear alkyl, $C_{21}$ linear alkyl, $C_{22}$ linear alkyl, $C_{23}$ linear alkyl, or $C_{24}$ linear alkyl.

In some embodiments, the invention provides a method for producing isopropanol comprising culturing the non-naturally occurring a microbial organism of the invention under conditions for a sufficient period of time to produce isopropanol.

In some aspects of the invention, the microbial organism used in a method of the invention includes a non-naturally occurring having: (i) a formaldehyde fixation pathway; (ii) a formate assimilation pathway; and/or (iii) a methanol metabolic pathway as depicted in FIGS. 1 and 10, and an isopropanol pathway as depicted in FIG. 11, wherein said formaldehyde fixation pathway comprises: (1) 1B and 1C; (2) 1D; or (3) 1D and 1Z, wherein 1B is a 3-hexulose-6-phosphate synthase, wherein 1C is a 6-phospho-3-hexuloisomerase, wherein 1D is a dihydroxyacetone synthase, wherein 1Z is a fructose-6-phosphate aldolase, wherein said formate assimilation pathway comprises a pathway selected from: (4) 1E; (5) 1F, and 1G; (6) 1H, 1I, 1J, and 1K; (7) 1H, 1I, 1J, 1L, 1M, and 1N; (8) 1E, 1H, 1I, 1J, 1L, 1M, and 1N; (9) 1F, 1G, 1H, 1I, 1J, 1L, 1M, and 1N; (10) 1K, 1H, 1I, 1J, 1L, 1M, and 1N; and (11) 1H, 1I, 1J, 1O, and 1P, wherein 1E is a formate reductase, 1F is a formate ligase, a formate transferase, or a formate synthetase, wherein 1G is a formyl-CoA reductase, wherein 1H is a formyltetrahydrofolate synthetase, wherein 1I is a methenyltetrahydrofolate cyclohydrolase, wherein 1J is a methylenetetrahydrofolate dehydrogenase, wherein 1K is a formaldehyde-forming enzyme or spontaneous, wherein 1L is a glycine cleavage system, wherein 1M is a serine hydroxymethyltransferase, wherein 1N is a serine deaminase, wherein 1O is a methylenetetrahydrofolate reductase, wherein 1P is an acetyl-CoA synthase, wherein said methanol metabolic pathway comprises a pathway selected from: (12) 10J; (13) 10A, (14) 10A and 10B; (15) 10A, 10B and 10C; (16) 10J, 10K and 10C; (17) 10J, 10M, and 10N; (18) 10J and 10L; (19) 10J, 10L and 10G; (20) 10J, 10L, and 10I; (21) 10A, 10B, 10C, 10D, and 10E; (22) 10A, 10B, 10C, 10D, and 10F; (23) 10J, 10K, 10C, 10D, and 10E; (24) 10J, 10K, 10C, 10D, and 10F; (25) 10J, 10M, 10N, and 10O; (26) 10A, 10B, 10C, 10D, 10E, and 10G; (27) 10A, 10B, 10C, 10D, 10F, and 10G; (28) 10J, 10K, 10C, 10D, 10E, and 10G; (29) 10J, 10K, 10C, 10D, 10F, and 10G; (30) 10J, 10M, 10N, 10O, and 10G; (31) 10A, 10B, 10C, 10D, 10E, and 10I; (32) 10A, 10B, 10C, 10D, 10F, and 10I; (33) 10J, 10K, 10C, 10D, 10E, and 10I; (34) 10J, 10K, 10C, 10D, 10F, and 10I; and (35) 10J, 10M, 10N, 10O, and 10I, wherein 10A is a methanol methyltransferase, wherein 10B is a methylenetetrahydrofolate reductase, wherein 10C is a methylenetetrahydrofolate dehydrogenase, wherein 10D is a methenyltetrahydrofolate cyclohydrolase, wherein 10E is a formyltetrahydrofolate deformylase, wherein 10F is a formyltetrahydrofolate synthetase, wherein 10G is a formate hydrogen lyase, wherein 10I is a formate dehydrogenase, wherein 10J is a methanol dehydrogenase, wherein 10K is a formaldehyde activating enzyme or spontaneous, wherein 10L is a formaldehyde dehydrogenase, wherein 10M is a S-(hydroxymethyl)glutathione synthase or spontaneous, wherein 10N is a glutathione-dependent formaldehyde dehydrogenase, wherein 10O is a S-formylglutathione hydrolase, wherein said isopanol pathway comprises: (36) 11V, 11W, 11X, and 11Y; or (37) 11T, 11U, 11W, 11X, and 11Y, wherein 11T is an acetyl-CoA carboxylase, wherein 11U is an acetoacetyl-CoA synthase, wherein 11V is an acetyl-CoA:acetyl-CoA acyltransferase, wherein 11W is an acetoacetyl-CoA hydrolase, an acetoacetyl-CoA transferase, an acetoacetyl-CoA ligase, or a phosphotransacetoacetylase/acetoacetate kinase, wherein 11X is an acetoacetate decarboxylase, wherein 11Y is an acetone reductase or isopropanol dehydrogenase, wherein an enzyme of the formaldehyde fixation pathway, formate assimilation pathway, methanol metabolic pathway, or isopropanol pathway is encoded by at least one exogenous nucleic acid and is expressed in a sufficient amount to produce isopropanol. In some embodiments, the non-naturally occurring microbial organism described herein comprises an acetyl-CoA pathway that comprises 1T and 1V and a formaldehyde fixation pathway that comprises 1D and 1Z. In some embodiments, the non-naturally occurring microbial organism described herein comprises an acetyl-CoA pathway that comprises 1T and 1V and a formaldehyde fixation pathway comprises 1B and 1C.

In some aspects of the invention, the microbial organism used in a method of the invention has a combination of one or more pathways for generating substrates, intermediates and/or reducing equivalents that can be used with isopropanol pathways described herein for producing isopropanol of the invention. Accordingly, in some embodiments, the microbial organism has a formaldehyde fixation pathway and an isopropanol pathway. In some embodiments, the microbial organism has a formate assimilation pathway and an isopropanol pathway. In some embodiments, the microbial organism has a formaldehyde fixation pathway, a formate assimilation pathway, and an isopropanol pathway. In some embodiments, the microbial organism has a methanol metabolic pathway and an isopropanol pathway. In some embodiments, the microbial organism has a formaldehyde fixation pathway, a methanol metabolic pathway and an isopropanol pathway. In some embodiments, the microbial organism has a formate assimilation pathway, a methanol metabolic pathway and an isopropanol pathway. In some embodiments, the microbial organism has a formaldehyde fixation pathway, a formate assimilation pathway, a methanol metabolic pathway and an isopropanol pathway.

In some aspects of the invention, the microbial organism used in a method of the invention includes two, three, four, five or six exogenous nucleic acids each encoding an enzyme of the isopropanol pathway. In some aspects of the invention, the microbial organism includes one, two, three, four, five, six, seven, or eight exogenous nucleic acids each encoding a formaldehyde fixation pathway enzyme, a formate assimilation pathway enzyme, or a methanol metabolic pathway enzyme. In some aspects of the invention, the microbial organism includes exogenous nucleic acids encoding each of the enzymes of at least one of the pathways selected from (1)-(37) for a microbial organism having an isopropanol pathway as depicted in FIGS. 1, 10 and 11.

In some aspects of the invention, the microbial organism used in a method of the invention having a formate assimilation pathway further includes wherein the formate assimilation pathway comprises: (1) 1Q; (2) 1R, and 1S; (3) 1Y and 1Q; or (4) 1Y, 1R, and 1S, wherein 1Q is a pyruvate formate lyase, wherein 1R is a pyruvate dehydrogenase, a pyruvate ferredoxin oxidoreductase, or a pyruvate:NADP+ oxidoreductase, wherein 1S is a formate dehydrogenase wherein 10Y is a glyceraldehydes-3-phosphate dehydrogenase or an enzyme of lower glycolysis. In addition to a glyceraldehyde-3-phosphate dehydrogenase, lower glycolysis includes a phosphoglycerate kinase, a phosphoglyceromutase, an enolase, a pyruvate kinase or a PTS-dependant substrate import. Accordingly, in some embodiments, the formate assimilation pathway comprising 1Y includes an enzyme selected from a phosphoglycemte kinase, a phosphoglyceromutase, an enolase, a pyruvate kinase and a PTS-dependant substrate import.

In some aspects of the invention, the microbial organism used in a method of the invention includes a methanol oxidation pathway. Such a pathway can include at least one exogenous nucleic acid encoding a methanol oxidation pathway enzyme expressed in a sufficient amount to produce formaldehyde in the presence of methanol. An exemplary methanol oxidation pathway enzyme is a methanol dehydrogenase. Accordingly, in some aspects, the microbial organism used in the method of the invention includes a non-naturally occurring having at least one exogenous nucleic acid encoding a methanol dehydrogenase expressed in a sufficient amount to produce formaldehyde in the presence of methanol.

In some aspects of the invention, the microbial organism used in a method of the invention includes one or more enzymes for generating reducing equivalents. For example, the microbial organism can further include a hydrogenase and/or a carbon monoxide dehydrogenase. In some aspects, the microbial organism used in the method of the invention includes a non-naturally occurring having an exogenous nucleic acid encoding the hydrogenase or the carbon monoxide dehydrogenase.

In some aspects of the invention, the microbial organism used in a method of the invention includes a non-naturally occurring having at least one exogenous nucleic acid that is a heterologous nucleic acid. Accordingly, in some embodiments, the at least one exogenous nucleic acid encoding a formaldehyde fixation pathway enzyme described herein is a heterologous nucleic acid. In some embodiments, the at least one exogenous nucleic acid encoding a formate assimilation pathway enzyme described herein is a heterologous nucleic acid. In some embodiments, the at least one exogenous nucleic acid encoding a methanol metabolic pathway enzyme described herein is a heterologous nucleic acid. In some embodiments, the at least one exogenous nucleic acid encoding a MI-FAE cycle enzyme described herein is a heterologous nucleic acid. In some embodiments, the at least one exogenous nucleic acid encoding a MD-FAE cycle enzyme described herein is a heterologous nucleic acid. In some embodiments, the at least one exogenous nucleic acid encoding a FAACPE cycle enzyme described herein is a heterologous nucleic acid. In some embodiments, the at least one exogenous nucleic acid encoding a termination pathway enzyme described herein is a heterologous nucleic acid. In some embodiments, the at least one exogenous nucleic acid encoding an acetoacetyl-ACP pathway enzyme described herein is a heterologous nucleic acid. In some embodiments, the at least one exogenous nucleic acid encoding a 3-oxovalery-ACP pathway enzyme described herein is a heterologous nucleic acid. In some embodiments, the at least one exogenous nucleic acid encoding an isopropanol pathway enzyme described herein is a heterologous nucleic acid. In some embodiments, the at least one exogenous nucleic acid encoding a methanol oxidation pathway enzyme described herein is a heterologous nucleic acid. In some embodiments, the at least one exogenous nucleic acid encoding a hydrogenase or a carbon monoxide dehydrogenase is a heterologous nucleic acid.

In some embodiments, the method for producing a fatty alcohol, fatty aldehyde, fatty acid or isopropanol described herein includes using a non-naturally occurring microbial organism as described herein, wherein the microbial organism further includes an acetyl-CoA pathway and at least one exogenous nucleic acid encoding an acetyl-CoA pathway enzyme expressed in a sufficient amount to produce or enhance carbon flux through acetyl-CoA, wherein the acetyl-CoA pathway includes a pathway shown in FIG. 1, 3, 4, 5 or 6 selected from: (1) 3A and 3B; (2) 3A, 3C, and 3D; (3) 3H; (4) 3G and 3D; (5) 3E, 3F and 3B; (6) 3E and 31; (7) 3J, 3F and 3B; (8) 3J and 3I; (9) 4A, 4B, and 4C; (10) 4A, 4B, 4J, 4K, and 4D; (11) 4A, 4B, 4G, and 4D; (12) 4A, 4F, and 4D; (13) 4N, 4H, 4B and 4C; (14) 4N, 4H, 4B, 4J, 4K, and 4D; (15) 4N, 4H, 4B, 4G, and 4D; (16) 4N, 4H, 4F, and 4D; (17) 4L, 4M, 4B and 4C; (18) 4L, 4M, 4B, 4J, 4K, and 4D; (19) 4L, 4M, 4B, 4G, and 4D; (20) 4L, 4M, 4F, and 4D; (21) 5A, 5B, 5D, 5H, 5I, and 5J; (22) 5A, 5B, 5E, 5F, 5H, 5I, and 5J; (23) 5A, 5B, 5E, 5K, 5L, 5H, 51, and 5J; (24) 5A, 5C, 5D, 5H, and 5J; (25) 5A, 5C, 5E, 5F, 5H, and 5J; (26) 5A, 5C, 5E, 5K, 5L, 5H, and 5J; (27) 6A, 6B, 6D, and 6G; (28) 6A, 6B, 6E, 6F, and 6G; (29) 6A, 6B, 6E, 6K, 6L, and 6G, (30) 6A, 6C, and 6D; (31) 6A, 6C, 6E, and 6F; (32) 6A, 6C, 6E, 6K, and 6L; (33) 1T and 1V; (34) 1T, 1W, and 1X; (35) 1U and 1V; and (36) 1U, 1W, and 1X, wherein 3A is a pyruvate oxidase (acetate-forming), wherein 3B is an acetyl-CoA synthetase, an acetyl-CoA ligase or an acetyl-CoA transfemse, wherein 3C is an acetate kinase, wherein 3D is a phosphotransacetylase, wherein 3E is a pyruvate decarboxylase, wherein 3F is an acetaldehyde dehydrogenase, wherein 3G is a pyruvate oxidase (acetyl-phosphate forming), wherein 3H is a pyruvate dehydrogenase, a pyruvate:fenedoxin oxidoreductase, a pyruvate:NAD(P)H oxidoreductase or a pyruvate formate lyase, wherein 3I is an acetaldehyde dehydrogenase (acylating), wherein 3J is a threonine aldolase, wherein 4A is a phosphoenolpyruvate (PEP) carboxylase or a PEP carboxykinase, wherein 4B is an oxaloacetate decarboxylase, wherein 4C is a malonate semialdehyde dehydrogenase (acetylating), wherein 4D is an acetyl-CoA carboxylase or a malonyl-CoA decarboxylase, wherein 4F is an oxaloacetate dehydrogenase or an oxaloacetate oxidoreductase, wherein 4G is a malonate semialdehyde dehydrogenase (acylating), wherein 4H is a pyruvate carboxylase, wherein 4J is a malonate semialdehyde dehydrogenase, wherein 4K is a malonyl-CoA synthetase or a malonyl-CoA transfemse, wherein 4L is a malic enzyme, wherein 4M is a malate dehydrogenase or a malate oxidoreductase, wherein 4N is a pyruvate kinase or a PEP phosphatase, wherein 5A is a citrate synthase, wherein 5B is a citrate transporter, wherein 5C is a citrate/malate transporter, wherein 5D is an ATP citrate lyase, wherein 5E is a citrate lyase, wherein 5F is an acetyl-CoA synthetase or an acetyl-CoA transferase, wherein 5H is a cytosolic malate dehydrogenase, wherein 5I is a malate transporter, wherein 5J is a mitochondrial malate dehydrogenase, wherein 5K is an acetate kinase, wherein 5L is a phosphotransacetylase, wherein 6A is a citrate synthase, wherein 6B is a citrate transporter, wherein 6C is a citrate/oxaloacetate transporter, wherein 6D is an ATP citrate lyase, wherein 6E is a citrate lyase, wherein 6F is an acetyl-CoA synthetase or an acetyl- CoA transfemse, wherein 6G is an oxaloacetate transporter, wherein 6K is an acetate kinase, and wherein 6L is a phosphotransacetylase, wherein 1T is a fructose-6-phosphate phosphoketolase, wherein 1U is a xylulose-5-phosphate phosphoketolase, wherein 1V is a phosphotransacetylase, wherein 1W is an acetate kinase, wherein 1X is an acetyl-CoA transfemse, an acetyl-CoA synthetase, or an acetyl-CoA ligase.

In some aspects, the microbial organism used in a method of the invention includes two, three, four, five, six, seven or eight exogenous nucleic acids each encoding an acetyl-CoA pathway enzyme. In some aspects, the microbial organism used in a method of the invention includes exogenous nucleic acids encoding each of the acetyl-CoA pathway enzymes of at least one of the pathways selected from (1)-(36).

In some aspects, the microbial organism used in a method of the invention includes further includes a propionyl-CoA pathway and at least one exogenous nucleic acid encoding a propionyl-CoA pathway enzyme expressed in a sufficient amount to produce propionyl-CoA, wherein the propionyl-CoA pathway includes a pathway shown in FIG. 22. For example, in some embodiments, the propionyl-CoA pathway comprises a pathway selected from: (1) 22A, 22E, 22F, 22G, 22I, 22J, 22K and 22L; (2) 22A, 22E, 22F, 22G, 22H, 22J, 22K and 22L; (3) 22B, 22E, 22F, 22G, 22I, 22J, 22K and 22L; (4) 22B, 22E, 22F, 22G, 22H, 22J, 22K and 22L; (5) 22C, 22D, 22E, 22F, 22G, 22I, 22J, 22K and 22L; and (6) 22C, 22D, 22E, 22F, 22G, 22H, 22J, 22K and 22L, wherein 22A is a PEP carboxykinase, wherein 22B is a PEP carboxylase, wherein 22C is a Pyruvate kinase, wherein 22D is a Pyruvate carboxylase, wherein 22E is a Malate dehydrogenase, wherein 22F is a Fumarase, wherein 22G is a Fumamte reductase, wherein 22H is a Succinyl-CoA synthetase, wherein 22I is a Succinyl-CoA:3-ketoacid-CoA transferase, wherein 22J is a Methylmalonyl-CoA mutase, wherein 22K is a Methyl-malonyl-CoA epimerase, and wherein 22L is a Methylmalonyl-CoA decarboxylase.

In some embodiments, the invention provides a method for producing isopropanol, wherein the method includes culturing a non-naturally occurring microbial organism described herin under conditions and for a sufficient period of time to produce isopropanol, wherein the microbial organism comprises an acetyl-CoA pathway, wherein said acetyl-CoA pathway comprises a pathway selected from: (1) 1T and 1V; (2) 1T, 1W, and 1X; (3) 1U and 1V; (4) 1U, 1W, and 1X; wherein 1T is a fructose-6-phosphate phosphoketolase, wherein 1U is a xylulose-5-phosphate phosphoketolase, wherein 1V is a phosphotransacetylase, wherein 1W is an acetate kinase, wherein 1X is an acetyl-CoA transferase, an acetyl-CoA synthetase, or an acetyl-CoA ligase, wherein said non-naturally occurring microbial organism further comprises a pathway capable of producing isopropanol and an exogenous nucleic acid encoding an isopropanol pathway enzyme expressed in a sufficient amount to produce isopropanol, wherein said isopropanol pathway comprises a pathway selected from: (1) 11V, 11W, 11X, and 11Y; or (2) 11T, 11U, 11W, 11X, and 11Y, wherein 11T is an acetyl-CoA carboxylase, wherein 11U is an acetoacetyl-CoA synthase, wherein 11V is an acetyl-CoA:acetyl-CoA acyltransferase, wherein 11W is an acetoacetyl-CoA hydrolase, an acetoacetyl-CoA transferase, an acetoacetyl-CoA ligase, or a phosphotransacetoacetylase/acetoacetate kinase, wherein 11X is an acetoacetate decarboxylase, wherein 11Y is an acetone reductase or isopropanol dehydrogenase.

In other aspects, the invention further provides methods for producing elevated or enhanced yields of biosynthetic products such as a fatty alcohol, fatty aldehyde, fatty acid and/or isopropanol.

The methods for producing enhanced yields of a fatty alcohol, fatty aldehyde, fatty acid and/or isopropanol described herein include using a non-naturally occurring microbial organisms having one or more of the various pathway configurations employing a methanol dehydrogenase for methanol oxidation, a formaldehyde fixation pathway, and/or a phosphoketolase for directing the carbon from methanol into acetyl-CoA and other desired products via formaldehyde fixation as described previously. The methods include using a non-naturally occurring microbial organism of the invention having one or more of the various different methanol oxidation and formaldehyde fixation configurations exemplified previously and below engineered in conjunction with any or each of the various methanol oxidation, formaldehyde fixation, formate reutilization, fatty alcohol, fatty aldehyde, fatty acid and/or isopropanol pathway exemplified previously. Accordingly, the methods of the invention can use a microbial organism having one or more of the metabolic modifications exemplified previously and also below that increase biosynthetic product yields over, for example, endogenous methanol utilization pathways because they further focus methanol derived carbon into the assimilation pathways described herein, decrease inefficient use of methanol carbon through competing methanol utilization and/or formaldehyde fixation pathways and/or increase the production of reducing equivalents.

In some aspects, the methods of the invention can use microbial organisms containing or engineered to contain one or more of the various configurations of metabolic modifications disclosed herein for enhancing product yields via methanol derived carbon include enhancing methanol oxidation and production of reducing equivalents using either an endogenous NADH dependent methanol dehydrogenase, an exogenous NADH dependent methanol dehydrogenase, both an endogenous NADH dependent methanol dehydrogenase and exogenous NADH dependent methanol dehydrogenase alone or in combination with one or more metabolic modifications that attenuate, for example, DHA synthase and/or AOX. In addition, other metabolic modifications as exemplified previously and further below that reduce carbon flux away from methanol oxidation and formaldehyde fixation also can be included, alone or in combination, with the methanol oxidation and formaldehyde fixation pathway configurations disclosed herein that enhance carbon flux into product precursors such as acetyl-CoA and, therefore, enhance product yields.

Accordingly, in some embodiments, the microbial organisms used in a method of the invention can include one or more of any of the above and/or below metabolic modifications to a methanol utilization pathway and/or formaldehyde assimilation pathway configurations for enhancing product yields can be combined with any one or more, including all of the previously described methanol oxidation, formaldehyde fixation, formate reutilization, fatty alcohol, fatty aldehyde, fatty acid and/or isopropanol pathway to enhance the yield and/or production of a product such as any of the fatty alcohol, fatty aldehyde, fatty acids and/or isopropanol described herein.

Given the teachings and guidance provided herein, both prokaryotic and eukaryotic microbial organisms engineered to have methanol oxidation and/or formaldehyde fixation pathway configurations for enhancing product yields can be used in the methods of the invention. As exemplified herein and well known in the art, those skilled in the art will know which organism to select for a particular application. For example, with respect to eukaryotic microbial host organisms, those skilled in the art will know that yeasts and other eukaryotic microorganisms exhibit certain characteristics distinct from prokaryotic microbial organisms. When such characteristics are desirable, one skilled in the art can choose to use such eukaryotic microbial organisms having one or more of the various different methanol oxidation and formaldehyde fixation configurations exemplified herein for enhancing product yields in a method of the invention. Such characteristics have been described previously.

In some embodiments, the microbial organism used in a method of the invention and having a methanol oxidation and/or formaldehyde assimilation pathway configurations described herein for enhancing product yields can include, for example, a NADH-dependent methanol dehydrogenase (MeDH), one or more formaldehyde assimilation pathways and/or one or more phosphoketolases.

In one embodiment, the methods of the invention use microbial organisms that have cytosolic expression of one or more methanol oxidation and/or formaldehyde assimilation pathways. As described previously, exemplary pathways for converting cytosolic formaldehyde into glycolytic intermediates are shown in FIG. 1. Such pathways include methanol oxidation via expression of a cytosolic NADH dependent methanol dehydrogenase, formaldehyde fixation via expression of cytosolic DHA synthase, both methanol oxidation via expression of an cytosolic NADH dependent methanol dehydrogenase and formaldehyde fixation via expression of cytosolic DHA synthase alone or together with the metabolic modifications exemplified previously and also below that attenuate less beneficial methanol oxidation and/or formaldehyde fixation pathways. Such attenuating metabolic modifications include, for example, attenuation of alcohol oxidase, attenuation of DHA kinase and/or attenuation of DHA synthase (e.g. when ribulose-5-phosphate (Ru5P) pathway for formaldehyde fixation is utilized).

In another embodiment, conversion of cytosolic formaldehyde into glycolytic intermediates can occur via expression of a cytosolic 3-hexulose-6-phosphate (3-Hu6P) synthase Thus, exemplary pathways that can be engineered into a microbial organism used in a method of the invention can include methanol oxidation via expression of a cytosolic NADH dependent methanol dehydrogenase, formaldehyde fixation via expression of cytosolic 3-Hu6P synthase, both methanol oxidation via expression of an cytosolic NADH dependent dehydrogenase and formaldehyde fixation via expression of cytosolic 3-Hu6P synthase alone or together with the metabolic modifications exemplified previously and also below that attenuate less beneficial methanol oxidation and/or formaldehyde fixation pathways. Such attenuating metabolic modifications include, for example, attenuation of alcohol oxidase, attenuation of DHA kinase and/or attenuation of DHA synthase (e.g. when ribulose-5-phosphate (Ru5P) pathway for formaldehyde fixation is utilized).

In yet another embodiment, the methods of the invention use microbial organisms that have cytosolic expression of one or more methanol oxidation and/or formaldehyde assimilation pathways. The formaldehyde assimilation pathways can include both assimilation through cytosolic DHA synthase and 3-Hu6P synthase In this specific embodiment, such pathways include methanol oxidation via expression of a cytosolic NADH dependent methanol dehydrogenase, formaldehyde fixation via expression of cytosolic DHA synthase and 3-Hu6P synthase, both methanol oxidation via expression of an cytosolic NADH dependent dehydrogenase and formaldehyde fixation via expression of cytosolic DHA synthase and 3-Hu6P synthase alone or together with the metabolic modifications exemplified previously and also below that attenuate less beneficial methanol oxidation and/or formaldehyde fixation pathways. Such attenuating metabolic modifications include, for example, attenuation of alcohol oxidase, attenuation of DHA kinase and/or attenuation of DHA synthase (e.g. when ribulose-5-phosphate (Ru5P) pathway for formaldehyde fixation is utilized).

In some embodiments, the method for producing a fatty alcohol, fatty aldehyde, fatty acid or isopropanol described herein includes using a non-naturally occurring microbial organism as described herein, wherein the microbial organism further includes attenuation of one or more endogenous enzymes, which enhances carbon flux through acetyl-CoA. For example, in some aspects, the endogenous enzyme can be selected from DHA kinase, methanol oxidase, PQQ-dependent methanol dehydrogenase, DHA synthase or any combination thereof. Accordingly, in some aspects, the attenuation is of the endogenous enzyme DHA kinase In some aspects, the attenuation is of the endogenous enzyme methanol oxidase. In some aspects, the attenuation is of the endogenous enzyme PQQ-dependent methanol dehydrogenase. In some aspects, the attenuation is of the endogenous enzyme DHA synthase. The invention also provides a method wherein the microbial organism used includes attenuation of any combination of two or three endogenous enzymes described herein. For example, a microbial organism can include attenuation of DHA kinase and DHA synthase, or alternatively methanol oxidase and PQQ-dependent methanol dehydrogenase, or alternatively DHA kinase, methanol oxidase, and PQQ-dependent methanol dehydrogenase, or alternatively DHA kinase, methanol oxidase, and DHA synthase. The invention also provides a method wherein the microbial organism used includes attenuation of all endogenous enzymes described herein. For example, in some aspects, a microbial organism includes attenuation of DHA kinase, methanol oxidase, PQQ-dependent methanol dehydrogenase and DHA synthase.

In some embodiments, the method for producing a fatty alcohol, fatty aldehyde, fatty acid or isopropanol described herein includes using a non-naturally occurring microbial organism as described herein, wherein the microbial organism further includes attenuation of one or more endogenous enzymes of a competing formaldehyde assimilation or dissimilation pathway. Examples of these endogenous enzymes are disclosed in FIG. 1 and described in Example XXIII. It is understood that a person skilled in the art would be able to readily identify enzymes of such competing pathways. Competing pathways can be dependent upon the host microbial organism and/or the exogenous nucleic acid introduced into the microbial organism as described herein. Accordingly, in some aspects of the invention, the method includes a microbial organism having attenuation of one, two, three, four, five, six, seven, eight, nine, ten or more endogenous enzymes of a competing formaldehyde assimilation or dissimilation pathway.

In some embodiments, the method for producing a fatty alcohol, fatty aldehyde, fatty acid or isopropanol described herein includes using a non-naturally occurring microbial organism as described herein, wherein the microbial organism further includes a gene disruption of one or more endogenous nucleic acids encoding enzymes, which enhances carbon flux through acetyl-CoA. For example, in some aspects, the endogenous enzyme can be selected from DHA kinase, methanol oxidase, PQQ-dependent methanol dehydrogenase, DHA synthase or any combination thereof.

According, in some aspects, the gene disruption is of an endogenous nucleic acid encoding the enzyme DHA kinase. In some aspects, the gene disruption is of an endogenous nucleic acid encoding the enzyme methanol oxidase. In some aspects, the gene disruption is of an endogenous nucleic acid encoding the enzyme PQQ-dependent methanol dehydrogenase. In some aspects, the gene disruption is of an endogenous nucleic acid encoding the enzyme DHA synthase. The invention also provides a method wherein the microbial organism used includes the gene disruption of any combination of two or three nucleic acids encoding endogenous enzymes described herein. For example, a microbial organism of the invention can include a gene disruption of DHA kinase and DHA synthase, or alternatively methanol oxidase and PQQ-dependent methanol dehydrogenase, or alternatively DHA kinase, methanol oxidase, and PQQ-dependent methanol dehydrogenase, or alternatively DHA kinase, methanol oxidase, and DHA synthase. The invention also provides a method wherein the microbial organism used includes wherein all endogenous nucleic acids encoding enzymes described herein are disrupted. For example, in some aspects, a microbial organism described herein includes disruption of DHA kinase, methanol oxidase, PQQ-dependent methanol dehydrogenase and DHA synthase.

In some embodiments, the method for producing a fatty alcohol, fatty aldehyde, fatty acid or isopropanol described herein includes using a non-naturally occurring microbial organism as described herein, wherein the microbial organism further includes a gene disruption of one or more endogenous enzymes of a competing formaldehyde assimilation or dissimilation pathway. Examples of these endogenous enzymes are disclosed in FIG. 1 and described in Example XXIII. It is understood that a person skilled in the art would be able to readily identify enzymes of such competing pathways. Competing pathways can be dependent upon the host microbial organism and/or the exogenous nucleic acid introduced into the microbial organism as described herein. Accordingly, in some aspects of the invention, the microbial organism used in the method includes a gene disruption of one, two, three, four, five, six, seven, eight, nine, ten or more endogenous nucleic acids encoding enzymes of a competing formaldehyde assimilation or dissimilation pathway.

Suitable purification and/or assays to test for the production of fatty alcohol, fatty aldehyde, fatty acid or isopropanol can be performed using well known methods. Suitable replicates such as triplicate cultures can be grown for each engineered strain to be tested. For example, product and byproduct formation in the engineered production host can be monitored. The final product and intermediates, and other organic compounds, can be analyzed by methods such as HPLC (High Performance Liquid Chromatography), GC-MS (Gas Chromatography-Mass Spectroscopy) and LC-MS (Liquid Chromatography-Mass Spectroscopy) or other suitable analytical methods using routine procedures well known in the art. The release of product in the fermentation broth can also be tested with the culture supernatant. Byproducts and residual glucose can be quantified by HPLC using, for example, a refractive index detector for glucose and alcohols, and a UV detector for organic acids (Lin et al., *Biotechnol. Bioeng.* 90:775-779 (2005)), or other suitable assay and detection methods well known in the art. The individual enzyme or protein activities from the exogenous DNA sequences can also be assayed using methods well known in the art.

The fatty alcohol, fatty aldehyde, fatty acid or isopropanol can be separated from other components in the culture using a variety of methods well known in the art. Such separation methods include, for example, extraction procedures as well as methods that include continuous liquid-liquid extraction, pervaporation, membrane filtration, membrane separation, reverse osmosis, electrodialysis, distillation, crystallization, centrifugation, extractive filtration, ion exchange chromatography, size exclusion chromatography, adsorption chromatography, and ultrafiltration. All of the above methods are well known in the art.

Any of the non-naturally occurring microbial organisms described herein can be cultured to produce and/or secrete the biosynthetic products of the invention. For example, the fatty alcohol, fatty aldehyde, fatty acid or isopropanol producers can be cultured for the biosynthetic production of fatty alcohol, fatty aldehyde, fatty acid or isopropanol. Accordingly, in some embodiments, the invention provides culture medium having the fatty alcohol, fatty aldehyde, fatty acid or isopropanol pathway intermediate described herein. In some aspects, the culture medium can also be separated from the non-naturally occurring microbial organisms of the invention that produced the fatty alcohol, fatty aldehyde, fatty acid or isopropanol pathway intermediate. Methods for separating a microbial organism from culture medium are well known in the art. Exemplary methods include filtration, flocculation, precipitation, centrifugation, sedimentation, and the like.

For the production of fatty alcohol, fatty aldehyde, fatty acid or isopropanol, the recombinant strains are cultured in a medium with carbon source and other essential nutrients. It is sometimes desirable and can be highly desirable to maintain anaerobic conditions in the fermenter to reduce the cost of the overall process. Such conditions can be obtained, for example, by first sparging the medium with nitrogen and then sealing the flasks with a septum and crimp-cap. For strains where growth is not observed anaerobically, microaerobic or substantially anaerobic conditions can be applied by perforating the septum with a small hole for limited aeration. Exemplary anaerobic conditions have been described previously and are well-known in the art. Exemplary aerobic and anaerobic conditions are described, for example, in United State publication 2009/0047719, filed Aug. 10, 2007. Fermentations can be performed in a batch, fed-batch or continuous manner, as disclosed herein. Fermentations can also be conducted in two phases, if desired. The first phase can be aerobic to allow for high growth and therefore high productivity, followed by an anaerobic phase of high fatty alcohol, fatty aldehyde, fatty acid or isopropanol yields.

If desired, the pH of the medium can be maintained at a desired pH, in particular neutral pH, such as a pH of around 7 by addition of a base, such as NaOH or other bases, or acid, as needed to maintain the culture medium at a desirable pH. The growth rate can be determined by measuring optical density using a spectrophotometer (600 nm), and the glucose uptake rate by monitoring carbon source depletion over time.

The growth medium, can include, for example, any carbohydrate source which can supply a source of carbon to the non-naturally occurring microbial organism of the invention. Such sources include, for example, sugars such as glucose, xylose, arabinose, galactose, mannose, fructose, sucrose and starch; or glycerol, alone as the sole source of carbon or in combination with other carbon sources described herein or known in the art. In one embodiment, the carbon source is a sugar. In one embodiment, the carbon source is a sugar-containing biomass. In some embodiments, the sugar is glucose. In one embodiment, the sugar is xylose.

In another embodiment, the sugar is arabinose. In one embodiment, the sugar is galactose. In another embodiment, the sugar is fructose. In other embodiments, the sugar is sucrose. In one embodiment, the sugar is starch. In certain embodiments, the carbon source is glycerol. In some embodiments, the carbon source is crude glycerol. In one embodiment, the carbon source is crude glycerol without treatment. In other embodiments, the carbon source is glycerol and glucose. In another embodiment, the carbon source is methanol and glycerol. In one embodiment, the carbon source is carbon dioxide. In one embodiment, the carbon source is formate. In one embodiment, the carbon source is methane. In one embodiment, the carbon source is methanol. In certain embodiments, methanol is used alone as the sole source of carbon or in combination with other carbon sources described herein or known in the art. In a specific embodiment, the methanol is the only (sole) carbon source. In one embodiment, the carbon source is chemoelectro-generated carbon (see, e.g., Liao et al. (2012) Science 335:1596). In one embodiment, the chemoelectro-generated carbon is methanol. In one embodiment, the chemoelectro-generated carbon is formate. In one embodiment, the chemo-electro-generated carbon is formate and methanol. In one embodiment, the carbon source is a carbohydrate and methanol. In one embodiment, the carbon source is a sugar and methanol. In another embodiment, the carbon source is a sugar and glycerol. In other embodiments, the carbon source is a sugar and crude glycerol. In yet other embodiments, the carbon source is a sugar and crude glycerol without treatment. In one embodiment, the carbon source is a sugar-containing biomass and methanol. In another embodiment, the carbon source is a sugar-containing biomass and glycerol. In other embodiments, the carbon source is a sugar-containing biomass and crude glycerol. In yet other embodiments, the carbon source is a sugar-containing biomass and crude glycerol without treatment. In some embodiments, the carbon source is a sugar-containing biomass, methanol and a carbohydrate. Other sources of carbohydrate include, for example, renewable feedstocks and biomass. Exemplary types of biomasses that can be used as feedstocks in the methods provided herein include cellulosic biomass, hemi-cellulosic biomass and lignin feedstocks or portions of feedstocks. Such biomass feedstocks contain, for example, carbohydrate substrates useful as carbon sources such as glucose, xylose, arabinose, galactose, mannose, fructose and starch. Given the teachings and guidance provided herein, those skilled in the art will understand that renewable feedstocks and biomass other than those exemplified above also can be used for culturing the microbial organisms provided herein for the production of succinate and other pathway intermediates.

In one embodiment, the carbon source is glycerol. In certain embodiments, the glycerol carbon source is crude glycerol or crude glycerol without further treatment. In a further embodiment, the carbon source comprises glycerol or crude glycerol, and also sugar or a sugar-containing biomass, such as glucose. In a specific embodiment, the concentration of glycerol in the fermentation broth is maintained by feeding crude glycerol, or a mixture of crude glycerol and sugar (e.g., glucose). In certain embodiments, sugar is provided for sufficient strain growth. In some embodiments, the sugar (e.g., glucose) is provided at a molar concentration ratio of glycerol to sugar of from 200:1 to 1:200. In some embodiments, the sugar (e.g., glucose) is provided at a molar concentration ratio of glycerol to sugar of from 100:1 to 1:100. In some embodiments, the sugar (e.g., glucose) is provided at a molar concentration ratio of glycerol to sugar of from 100:1 to 5:1. In some embodiments, the sugar (e.g., glucose) is provided at a molar concentration ratio of glycerol to sugar of from 50:1 to 5:1. In certain embodiments, the sugar (e.g., glucose) is provided at a molar concentration ratio of glycerol to sugar of 100:1. In one embodiment, the sugar (e.g., glucose) is provided at a molar concentration ratio of glycerol to sugar of 90:1. In one embodiment, the sugar (e.g., glucose) is provided at a molar concentration ratio of glycerol to sugar of 80:1. In one embodiment, the sugar (e.g., glucose) is provided at a molar concentration ratio of glycerol to sugar of 70:1. In one embodiment, the sugar (e.g., glucose) is provided at a molar concentration ratio of glycerol to sugar of 60:1. In one embodiment, the sugar (e.g., glucose) is provided at a molar concentration ratio of glycerol to sugar of 50:1. In one embodiment, the sugar (e.g., glucose) is provided at a molar concentration ratio of glycerol to sugar of 40:1. In one embodiment, the sugar (e.g., glucose) is provided at a molar concentration ratio of glycerol to sugar of 30:1. In one embodiment, the sugar (e.g., glucose) is provided at a molar concentration ratio of glycerol to sugar of 20:1. In one embodiment, the sugar (e.g., glucose) is provided at a molar concentration ratio of glycerol to sugar of 10:1. In one embodiment, the sugar (e.g., glucose) is provided at a molar concentration ratio of glycerol to sugar of 5:1. In one embodiment, the sugar (e.g., glucose) is provided at a molar concentration ratio of glycerol to sugar of 2:1. In one embodiment, the sugar (e.g., glucose) is provided at a molar concentration ratio of glycerol to sugar of 1:1. In certain embodiments, the sugar (e.g., glucose) is provided at a molar concentration ratio of glycerol to sugar of 1:100. In one embodiment, the sugar (e.g., glucose) is provided at a molar concentration ratio of glycerol to sugar of 1:90. In one embodiment, the sugar (e.g., glucose) is provided at a molar concentration ratio of glycerol to sugar of 1:80. In one embodiment, the sugar (e.g., glucose) is provided at a molar concentration ratio of glycerol to sugar of 1:70. In one embodiment, the sugar (e.g., glucose) is provided at a molar concentration ratio of glycerol to sugar of 1:60. In one embodiment, the sugar (e.g., glucose) is provided at a molar concentration ratio of glycerol to sugar of 1:50. In one embodiment, the sugar (e.g., glucose) is provided at a molar concentration ratio of glycerol to sugar of 1:40. In one embodiment, the sugar (e.g., glucose) is provided at a molar concentration ratio of glycerol to sugar of 1:30. In one embodiment, the sugar (e.g., glucose) is provided at a molar concentration ratio of glycerol to sugar of 1:20. In one embodiment, the sugar (e.g., glucose) is provided at a molar concentration ratio of glycerol to sugar of 1:10. In one embodiment, the sugar (e.g., glucose) is provided at a molar concentration ratio of glycerol to sugar of 1:5. In one embodiment, the sugar (e.g., glucose) is provided at a molar concentration ratio of glycerol to sugar of 1:2. In certain embodiments of the ratios provided above, the sugar is a sugar-containing biomass. In certain other embodiments of the ratios provided above, the glycerol is a crude glycerol or a crude glycerol without further treatment. In other embodiments of the ratios provided above, the sugar is a sugar-containing biomass, and the glycerol is a crude glycerol or a crude glycerol without further treatment.

Crude glycerol can be a by-product produced in the production of biodiesel, and can be used for fermentation without any further treatment. Biodiesel production methods include (1) a chemical method wherein the glycerol-group of vegetable oils or animal oils is substituted by low-carbon alcohols such as methanol or ethanol to produce a corresponding fatty acid methyl esters or fatty acid ethyl esters by transesterification in the presence of acidic or basic catalysts; (2) a biological method where biological enzymes or cells are used to catalyze transesterification reaction and the corresponding fatty acid methyl esters or fatty acid ethyl esters are produced; and (3) a supercritical method, wherein transesterification reaction is carried out in a supercritical solvent system without any catalysts. The chemical composition of crude glycerol can vary with the process used to produce biodiesel, the transesterification efficiency, recovery efficiency of the biodiesel, other impurities in the feedstock, and whether methanol and catalysts were recovered. For example, the chemical compositions of eleven crude glycerol collected from seven Australian biodiesel producers reported that glycerol content ranged between 38% and 96%, with some samples including more than 14% methanol and 29% ash. In certain embodiments, the crude glycerol comprises from 5% to 99% glycerol. In some embodiments, the crude glycerol comprises from 10% to 90% glycerol. In some embodiments, the crude glycerol comprises from 10% to 80% glycerol. In some embodiments, the crude glycerol comprises from 10% to 70% glycerol. In some embodiments, the crude glycerol comprises from 10% to 60% glycerol. In some embodiments, the crude glycerol comprises from 10% to 50% glycerol. In some embodiments, the crude glycerol comprises from 10% to 40% glycerol. In some embodiments, the crude glycerol comprises from 10% to 30% glycerol. In some embodiments, the crude glycerol comprises from 10% to 20% glycerol. In some embodiments, the crude glycerol comprises from 80% to 90% glycerol. In some embodiments, the crude glycerol comprises from 70% to 90% glycerol. In some embodiments, the crude glycerol comprises from 60% to 90% glycerol. In some embodiments, the crude glycerol comprises from 50% to 90% glycerol. In some embodiments, the crude glycerol comprises from 40% to 90% glycerol. In some embodiments, the crude glycerol comprises from 30% to 90% glycerol. In some embodiments, the crude glycerol comprises from 20% to 90% glycerol. In some embodiments, the crude glycerol comprises from 20% to 40% glycerol. In some embodiments, the crude glycerol comprises from 40% to 60% glycerol. In some embodiments, the crude glycerol comprises from 60% to 80% glycerol. In some embodiments, the crude glycerol comprises from 50% to 70% glycerol. In one embodiment, the glycerol comprises 5% glycerol. In one embodiment, the glycerol comprises 10% glycerol. In one embodiment, the glycerol comprises 15% glycerol. In one embodiment, the glycerol comprises 20% glycerol. In one embodiment, the glycerol comprises 25% glycerol. In one embodiment, the glycerol comprises 30% glycerol. In one embodiment, the glycerol comprises 35% glycerol. In one embodiment, the glycerol comprises 40% glycerol. In one embodiment, the glycerol comprises 45% glycerol. In one embodiment, the glycerol comprises 50% glycerol. In one embodiment, the glycerol comprises 55% glycerol. In one embodiment, the glycerol comprises 60% glycerol. In one embodiment, the glycerol comprises 65% glycerol. In one embodiment, the glycerol comprises 70% glycerol. In one embodiment, the glycerol comprises 75% glycerol. In one embodiment, the glycerol comprises 80% glycerol. In one embodiment, the glycerol comprises 85% glycerol. In one embodiment, the glycerol comprises 90% glycerol. In one embodiment, the glycerol comprises 95% glycerol. In one embodiment, the glycerol comprises 99% glycerol.

In one embodiment, the carbon source is methanol or formate. In certain embodiments, methanol is used as a carbon source in a formaldehyde fixation pathway provided herein. In one embodiment, the carbon source is methanol or formate. In other embodiments, formate is used as a carbon source in a formaldehyde fixation pathway provided herein. In specific embodiments, methanol is used as a carbon source in a methanol oxidation pathway provided herein, either alone or in combination with the fatty alcohol, fatty aldehyde, fatty acid or isopropanol pathways provided herein. In one embodiment, the carbon source is methanol. In another embodiment, the carbon source is formate.

In one embodiment, the carbon source comprises methanol, and sugar (e.g., glucose) or a sugar-containing biomass. In another embodiment, the carbon source comprises formate, and sugar (e.g., glucose) or a sugar-containing biomass. In one embodiment, the carbon source comprises methanol, formate, and sugar (e.g., glucose) or a sugar-containing biomass. In specific embodiments, the methanol or formate, or both, in the fermentation feed is provided as a mixture with sugar (e.g., glucose) or sugar-comprising biomass. In certain embodiments, sugar is provided for sufficient strain growth.

In certain embodiments, the carbon source comprises methanol and a sugar (e.g., glucose). In some embodiments, the sugar (e.g., glucose) is provided at a molar concentration ratio of methanol to sugar of from 200:1 to 1:200. In some embodiments, the sugar (e.g., glucose) is provided at a molar concentration ratio of methanol to sugar of from 100:1 to 1:100. In some embodiments, the sugar (e.g., glucose) is provided at a molar concentration ratio of methanol to sugar of from 100:1 to 5:1. In some embodiments, the sugar (e.g., glucose) is provided at a molar concentration ratio of methanol to sugar of from 50:1 to 5:1. In certain embodiments, the sugar (e.g., glucose) is provided at a molar concentration ratio of methanol to sugar of 100:1. In one embodiment, the sugar (e.g., glucose) is provided at a molar concentration ratio of methanol to sugar of 90:1. In one embodiment, the sugar (e.g., glucose) is provided at a molar concentration ratio of methanol to sugar of 80:1. In one embodiment, the sugar (e.g., glucose) is provided at a molar concentration ratio of methanol to sugar of 70:1. In one embodiment, the sugar (e.g., glucose) is provided at a molar concentration ratio of methanol to sugar of 60:1. In one embodiment, the sugar (e.g., glucose) is provided at a molar concentration ratio of methanol to sugar of 50:1. In one embodiment, the sugar (e.g., glucose) is provided at a molar concentration ratio of methanol to sugar of 40:1. In one embodiment, the sugar (e.g., glucose) is provided at a molar concentration ratio of methanol to sugar of 30:1. In one embodiment, the sugar (e.g., glucose) is provided at a molar concentration ratio of methanol to sugar of 20:1. In one embodiment, the sugar (e.g., glucose) is provided at a molar concentration ratio of methanol to sugar of 10:1. In one embodiment, the sugar (e.g., glucose) is provided at a molar concentration ratio of methanol to sugar of 5:1. In one embodiment, the sugar (e.g., glucose) is provided at a molar concentration ratio of methanol to sugar of 2:1. In one embodiment, the sugar (e.g., glucose) is provided at a molar concentration ratio of methanol to sugar of 1:1. In certain embodiments, the sugar (e.g., glucose) is provided at a molar concentration ratio of methanol to sugar of 1:100. In one embodiment, the sugar (e.g., glucose) is provided at a molar concentration ratio of methanol to sugar of 1:90. In one embodiment, the sugar (e.g., glucose) is provided at a molar concentration ratio of methanol to sugar of 1:80. In one embodiment, the sugar (e.g., glucose) is provided at a molar concentration ratio of methanol to sugar of 1:70. In one embodiment, the sugar (e.g., glucose) is provided at a molar concentration ratio of methanol to sugar of 1:60. In one embodiment, the sugar (e.g., glucose) is provided at a molar concentration ratio of methanol to sugar of 1:50. In one embodiment, the sugar (e.g., glucose) is provided at a molar concentration ratio of methanol to sugar of 1:40. In one embodiment, the sugar (e.g., glucose) is provided at a molar concentration ratio of methanol to sugar of 1:30. In one embodiment, the sugar (e.g., glucose) is provided at a molar concentration ratio of methanol to sugar of 1:20. In one embodiment, the sugar (e.g., glucose) is provided at a molar concentration ratio of methanol to sugar of 1:10. In one embodiment, the sugar (e.g., glucose) is provided at a molar concentration ratio of methanol to sugar of 1:5. In one embodiment, the sugar (e.g., glucose) is provided at a molar concentration ratio of methanol to sugar of 1:2. In certain embodiments of the ratios provided above, the sugar is a sugar-containing biomass.

In certain embodiments, the carbon source comprises formate and a sugar (e.g., glucose). In some embodiments, the sugar (e.g., glucose) is provided at a molar concentration ratio of formate to sugar of from 200:1 to 1:200. In some embodiments, the sugar (e.g., glucose) is provided at a molar concentration ratio of formate to sugar of from 100:1 to 1:100. In some embodiments, the sugar (e.g., glucose) is provided at a molar concentration ratio of formate to sugar of from 100:1 to 5:1. In some embodiments, the sugar (e.g., glucose) is provided at a molar concentration ratio of formate to sugar of from 50:1 to 5:1. In certain embodiments, the sugar (e.g., glucose) is provided at a molar concentration ratio of formate to sugar of 100:1. In one embodiment, the sugar (e.g., glucose) is provided at a molar concentration ratio of formate to sugar of 90:1. In one embodiment, the sugar (e.g., glucose) is provided at a molar concentration ratio of formate to sugar of 80:1. In one embodiment, the sugar (e.g., glucose) is provided at a molar concentration ratio of formate to sugar of 70:1. In one embodiment, the sugar (e.g., glucose) is provided at a molar concentration ratio of formate to sugar of 60:1. In one embodiment, the sugar (e.g., glucose) is provided at a molar concentration ratio of formate to sugar of 50:1. In one embodiment, the sugar (e.g., glucose) is provided at a molar concentration ratio of formate to sugar of 40:1. In one embodiment, the sugar (e.g., glucose) is provided at a molar concentration ratio of formate to sugar of 30:1. In one embodiment, the sugar (e.g., glucose) is provided at a molar concentration ratio of formate to sugar of 20:1. In one embodiment, the sugar (e.g., glucose) is provided at a molar concentration ratio of formate to sugar of 10:1. In one embodiment, the sugar (e.g., glucose) is provided at a molar concentration ratio of formate to sugar of 5:1. In one embodiment, the sugar (e.g., glucose) is provided at a molar concentration ratio of formate to sugar of 2:1. In one embodiment, the sugar (e.g., glucose) is provided at a molar concentration ratio of formate to sugar of 1:1. In certain embodiments, the sugar (e.g., glucose) is provided at a molar concentration ratio of formate to sugar of 1:100. In one embodiment, the sugar (e.g., glucose) is provided at a molar concentration ratio of formate to sugar of 1:90. In one embodiment, the sugar (e.g., glucose) is provided at a molar concentration ratio of formate to sugar of 1:80. In one embodiment, the sugar (e.g., glucose) is provided at a molar concentration ratio of formate to sugar of 1:70. In one embodiment, the sugar (e.g., glucose) is provided at a molar concentration ratio of formate to sugar of 1:60. In one embodiment, the sugar (e.g., glucose) is provided at a molar concentration ratio of formate to sugar of 1:50. In one embodiment, the sugar (e.g., glucose) is provided at a molar concentration ratio of formate to sugar of 1:40. In one embodiment, the sugar (e.g., glucose) is provided at a molar concentration ratio of formate to sugar of 1:30. In one embodiment, the sugar (e.g., glucose) is provided at a molar concentration ratio of formate to sugar of 1:20. In one embodiment, the sugar (e.g., glucose) is provided at a molar concentration ratio of formate to sugar of 1:10. In one embodiment, the sugar (e.g., glucose) is provided at a molar concentration ratio of formate to sugar of 1:5. In one embodiment, the sugar (e.g., glucose) is provided at a molar concentration ratio of formate to sugar of 1:2. In certain embodiments of the ratios provided above, the sugar is a sugar-containing biomass.

In certain embodiments, the carbon source comprises a mixture of methanol and formate, and a sugar (e.g., glucose). In certain embodiments, sugar is provided for sufficient strain growth. In some embodiments, the sugar (e.g., glucose) is provided at a molar concentration ratio of methanol and formate to sugar of from 200:1 to 1:200. In some embodiments, the sugar (e.g., glucose) is provided at a molar concentration ratio of methanol and formate to sugar of from 100:1 to 1:100. In some embodiments, the sugar (e.g., glucose) is provided at a molar concentration ratio of methanol and formate to sugar of from 100:1 to 5:1. In some embodiments, the sugar (e.g., glucose) is provided at a molar concentration ratio of methanol and formate to sugar of from 50:1 to 5:1. In certain embodiments, the sugar (e.g., glucose) is provided at a molar concentration ratio of methanol and formate to sugar of 100:1. In one embodiment, the sugar (e.g., glucose) is provided at a molar concentration ratio of methanol and formate to sugar of 90:1. In one embodiment, the sugar (e.g., glucose) is provided at a molar concentration ratio of methanol and formate to sugar of 80:1. In one embodiment, the sugar (e.g., glucose) is provided at a molar concentration ratio of methanol and formate to sugar of 70:1. In one embodiment, the sugar (e.g., glucose) is provided at a molar concentration ratio of methanol and formate to sugar of 60:1. In one embodiment, the sugar (e.g., glucose) is provided at a molar concentration ratio of methanol and formate to sugar of 50:1. In one embodiment, the sugar (e.g., glucose) is provided at a molar concentration ratio of methanol and formate to sugar of 40:1. In one embodiment, the sugar (e.g., glucose) is provided at a molar concentration ratio of methanol and formate to sugar of 30:1. In one embodiment, the sugar (e.g., glucose) is provided at a molar concentration ratio of methanol and formate to sugar of 20:1. In one embodiment, the sugar (e.g., glucose) is provided at a molar concentration ratio of methanol and formate to sugar of 10:1. In one embodiment, the sugar (e.g., glucose) is provided at a molar concentration ratio of methanol and formate to sugar of 5:1. In one embodiment, the sugar (e.g., glucose) is provided at a molar concentration ratio of methanol and formate to sugar of 2:1. In one embodiment, the sugar (e.g., glucose) is provided at a molar concentration ratio of methanol and formate to sugar of 1:1. In certain embodiments, the sugar (e.g., glucose) is provided at a molar concentration ratio of methanol and formate to sugar of 1:100. In one embodiment, the sugar (e.g., glucose) is provided at a molar concentration ratio of methanol and formate to sugar of 1:90. In one embodiment, the sugar (e.g., glucose) is provided at a molar concentration ratio of methanol and formate to sugar of 1:80. In one embodiment, the sugar (e.g., glucose) is provided at a molar concentration ratio of methanol and formate to sugar of 1:70. In one embodiment, the sugar (e.g., glucose) is provided at a molar concentration ratio of methanol and formate to sugar of 1:60. In one embodiment, the sugar (e.g., glucose) is provided at a molar concentration ratio of methanol and formate to sugar of 1:50. In one embodiment, the sugar (e.g., glucose) is provided at a molar concentration ratio of methanol and formate to sugar of 1:40. In one embodiment, the sugar (e.g., glucose) is provided at a molar concentration ratio of methanol and formate to sugar of 1:30. In one embodiment, the sugar (e.g., glucose) is provided at a molar concentration ratio of methanol and formate to sugar of 1:20. In one embodiment, the sugar (e.g., glucose) is provided at a molar concentration ratio of methanol and formate to sugar of 1:10. In one embodiment, the sugar (e.g., glucose) is provided at a molar concentration ratio of methanol and formate to sugar of 1:5. In one embodiment, the sugar (e.g., glucose) is provided at a molar concentration ratio of methanol and formate to sugar of 1:2. In certain embodiments of the ratios provided above, the sugar is a sugar-containing biomass.

In addition to renewable feedstocks such as those exemplified above, the fatty alcohol, fatty aldehyde, fatty acid or isopropanol producing microbial organisms of the invention also can be modified for growth on syngas as its source of carbon. In this specific embodiment, one or more proteins or enzymes are expressed in the fatty alcohol, fatty aldehyde, fatty acid or isopropanol producing organisms to provide a metabolic pathway for utilization of syngas or other gaseous carbon source.

Synthesis gas, also known as syngas or producer gas, is the major product of gasification of coal and of carbonaceous materials such as biomass materials, including agricultural crops and residues. Syngas is a mixture primarily of $H_2$ and CO and can be obtained from the gasification of any organic feedstock, including but not limited to coal, coal oil, natural gas, biomass, and waste organic matter. Gasification is generally carried out under a high fuel to oxygen ratio. Although largely $H_2$ and CO, syngas can also include $CO_2$ and other gases in smaller quantities. Thus, synthesis gas provides a cost effective source of gaseous carbon such as CO and, additionally, $CO_2$.

Accordingly, given the teachings and guidance provided herein, those skilled in the art will understand that a non-naturally occurring microbial organism can be produced that secretes the biosynthesized compounds of the invention when grown on a carbon source such as a carbohydrate. Such compounds include, for example, fatty alcohol, fatty aldehyde, fatty acid or isopropanol and any of the intermediate metabolites in the fatty alcohol, fatty aldehyde, fatty acid or isopropanol pathway. All that is required is to engineer in one or more of the required enzyme or protein activities to achieve biosynthesis of the desired compound or intermediate including, for example, inclusion of some or all of the fatty alcohol, fatty aldehyde, fatty acid or isopropanol biosynthetic pathways. Accordingly, the invention provides a non-naturally occurring microbial organism that produces and/or secretes fatty alcohol, fatty aldehyde, fatty acid or isopropanol when grown on a carbohydrate or other carbon source and produces and/or secretes any of the intermediate metabolites shown in the fatty alcohol, fatty aldehyde, fatty acid or isopropanol pathway when grown on a carbohydrate or other carbon source. The fatty alcohol, fatty aldehyde, fatty acid or isopropanol producing microbial organisms of the invention can initiate synthesis from an intermediate, for example, a 3-ketoacyl-CoA, a 3-hydroxyacyl-CoA, an enoyl-CoA, an acyl-CoA, an acyl-ACP, acetate, acetaldehyde, acetyl-phosphate, oxaloacetate, matate, malonate semialdehyde, malonate, malonyl-CoA, acetyl-CoA, or citrate.

The non-naturally occurring microbial organisms of the invention are constructed using methods well known in the art as exemplified herein to exogenously express at least one nucleic acid encoding a fatty alcohol, fatty aldehyde, fatty acid or isopropanol pathway enzyme or protein in sufficient amounts to produce fatty alcohol, fatty aldehyde, fatty acid or isopropanol. It is understood that the microbial organisms of the invention are cultured under conditions sufficient to produce fatty alcohol, fatty aldehyde, fatty acid or isopropanol. Following the teachings and guidance provided herein, the non-naturally occurring microbial organisms of the invention can achieve biosynthesis of fatty alcohol, fatty aldehyde, fatty acid or isopropanol resulting in intracellular concentrations between about 0.1-200 mM or more. Generally, the intracellular concentration of fatty alcohol, fatty aldehyde, fatty acid or isopropanol is between about 3-150 mM, particularly between about 5-125 mM and more particularly between about 8-100 mM, including about 10 mM, 20 mM, 50 mM, 80 mM, or more. Intracellular concentrations between and above each of these exemplary ranges also can be achieved from the non-naturally occurring microbial organisms of the invention.

In some embodiments, culture conditions include anaerobic or substantially anaerobic growth or maintenance conditions. Exemplary anaerobic conditions have been described previously and are well known in the art. Exemplary anaerobic conditions for fermentation processes are described herein and are described, for example, in U.S. publication 2009/0047719, filed Aug. 10, 2007. Any of these conditions can be employed with the non-naturally occurring microbial organisms as well as other anaerobic conditions well known in the art. Under such anaerobic or substantially anaerobic conditions, the fatty alcohol, fatty aldehyde, fatty acid or isopropanol producers can synthesize fatty alcohol, fatty aldehyde, fatty acid or isopropanol at intracellular concentrations of 5-10 mM or more as well as all other concentrations exemplified herein. It is understood that, even though the above description refers to intracellular concentrations, fatty alcohol, fatty aldehyde, fatty acid or isopropanol producing microbial organisms can produce fatty alcohol, fatty aldehyde, fatty acid or isopropanol intracellularly and/or secrete the product into the culture medium.

Exemplary fermentation processes include, but are not limited to, fed-batch fermentation and batch separation; fed-batch fermentation and continuous separation; and continuous fermentation and continuous separation. In an exemplary batch fermentation protocol, the production organism is grown in a suitably sized bioreactor sparged with an appropriate gas. Under anaerobic conditions, the culture is sparged with an inert gas or combination of gases, for example, nitrogen, $N_2/CO_2$ mixture, argon, helium, and the like. As the cells grow and utilize the carbon source, additional carbon source(s) and/or other nutrients are fed into the bioreactor at a rate approximately balancing consumption of the carbon source and/or nutrients. The temperature of the bioreactor is maintained at a desired temperature, generally in the range of 22-37 degrees C., but the temperature can be maintained at a higher or lower temperature depending on the the growth characteristics of the production organism and/or desired conditions for the fermentation process. Growth continues for a desired period of time to achieve desired characteristics of the culture in the fermenter, for example, cell density, product concentration, and the like. In a batch fermentation process, the time period for the fermentation is generally in the range of several hours to several days, for example, 8 to 24 hours, or 1, 2, 3, 4 or 5 days, or up to a week, depending on the desired culture conditions. The pH can be controlled or not, as desired, in which case a culture in which pH is not controlled will typically decrease to pH 3-6 by the end of the run. Upon completion of the cultivation period, the fermenter contents can be passed through a cell separation unit, for example, a centrifuge, filtration unit, and the like, to remove cells and cell debris. In the case where the desired product is expressed intracellularly, the cells can be lysed or disrupted enzymatically or chemically prior to or after separation of cells from the fermentation broth, as desired, in order to release additional product. The fermentation broth can be transferred to a product separations unit. Isolation of product occurs by standard separations procedures employed in the art to separate a desired product from dilute aqueous solutions. Such methods include, but are not limited to, liquid-liquid extraction using a water immiscible organic solvent (e.g., toluene or other suitable solvents, including but not limited to diethyl ether, ethyl acetate, tetrahydrofuran (THF), methylene chloride, chloroform, benzene, pentane, hexane, heptane, petroleum ether, methyl tertiary butyl ether (MTBE), dioxane, dimethylformamide (DMF), dimethyl sulfoxide (DMSO), and the like) to provide an organic solution of the product, if appropriate, standard distillation methods, and the like, depending on the chemical characteristics of the product of the fermentation process.

In an exemplary fully continuous fermentation protocol, the production organism is generally first grown up in batch mode in order to achieve a desired cell density. When the carbon source and/or other nutrients are exhausted, feed medium of the same composition is supplied continuously at a desired rate, and fermentation liquid is withdrawn at the same rate. Under such conditions, the product concentration in the bioreactor generally remains constant, as well as the cell density. The temperature of the fermenter is maintained at a desired temperature, as discussed above. During the continuous fermentation phase, it is generally desirable to maintain a suitable pH range for optimized production. The pH can be monitored and maintained using routine methods, including the addition of suitable acids or bases to maintain a desired pH range. The bioreactor is operated continuously for extended periods of time, generally at least one week to several weeks and up to one month, or longer, as appropriate and desired. The fermentation liquid and/or culture is monitored periodically, including sampling up to every day, as desired, to assure consistency of product concentration and/or cell density. In continuous mode, fermenter contents are constantly removed as new feed medium is supplied. The exit stream, containing cells, medium, and product, are generally subjected to a continuous product separations procedure, with or without removing cells and cell debris, as desired. Continuous separations methods employed in the art can be used to separate the product from dilute aqueous solutions, including but not limited to continuous liquid-liquid extraction using a water immiscible organic solvent (e.g., toluene or other suitable solvents, including but not limited to diethyl ether, ethyl acetate, tetrahydrofuran (THF), methylene chloride, chloroform, benzene, pentane, hexane, heptane, petroleum ether, methyl tertiary butyl ether (MTBE), dioxane, dimethylformamide (DMF), dimethyl sulfoxide (DMSO), and the like), standard continuous distillation methods, and the like, or other methods well known in the art.

In addition to the culturing and fermentation conditions disclosed herein, growth condition for achieving biosynthesis of fatty alcohol, fatty aldehyde, fatty acid or isopropanol can include the addition of an osmoprotectant to the culturing conditions. In certain embodiments, the non-naturally occurring microbial organisms of the invention can be sustained, cultured or fermented as described herein in the presence of an osmoprotectant. Briefly, an osmoprotectant refers to a compound that acts as an osmolyte and helps a microbial organism as described herein survive osmotic stress. Osmoprotectants include, but are not limited to, betaines, amino acids, and the sugar trehalose. Non-limiting examples of such are glycine betaine, praline betaine, dimethylthetin, dimethylslfoniopoprionate, 3-dimethylsulfonio-2-methylproprionate, pipecolic acid, dimethylsulfonioacetate, choline, L-carnitine and ectoine. In one aspect, the osmoprotectant is glycine betaine. It is understood to one of ordinary skill in the art that the amount and type of osmoprotectant suitable for protecting a microbial organism described herein from osmotic stress will depend on the microbial organism used. The amount of osmoprotectant in the culturing conditions can be, for example, no more than about 0.1 mM, no more than about 0.5 mM, no more than about 1.0 mM, no more than about 1.5 mM, no more than about 2.0 mM, no more than about 2.5 mM, no more than about 3.0 mM, no more than about 5.0 mM, no more than about 7.0 mM, no more than about 10 mM, no more than about 50 mM, no more than about 100 mM or no more than about 500 mM.

In some embodiments, the carbon feedstock and other cellular uptake sources such as phosphate, ammonia, sulfate, chloride and other halogens can be chosen to alter the isotopic distribution of the atoms present in fatty alcohol, fatty aldehyde, fatty acid or isopropanol or any fatty alcohol, fatty aldehyde, fatty acid or isopropanol pathway intermediate. The various carbon feedstock and other uptake sources enumerated above will be referred to herein, collectively, as "uptake sources." Uptake sources can provide isotopic enrichment for any atom present in the product fatty alcohol, fatty aldehyde, fatty acid or isopropanol or fatty alcohol, fatty aldehyde, fatty acid or isopropanol pathway intermediate, or for side products generated in reactions diverging away from a fatty alcohol, fatty aldehyde, fatty acid or isopropanol pathway. Isotopic enrichment can be achieved for any target atom including, for example, carbon, hydrogen, oxygen, nitrogen, sulfur, phosphorus, chloride or other halogens.

In some embodiments, the uptake sources can be selected to alter the carbon-12, carbon-13, and carbon-14 ratios. In some embodiments, the uptake sources can be selected to alter the oxygen-16, oxygen-17, and oxygen-18 ratios. In some embodiments, the uptake sources can be selected to alter the hydrogen, deuterium, and tritium ratios. In some embodiments, the uptake sources can be selected to alter the nitrogen-14 and nitrogen-15 ratios. In some embodiments, the uptake sources can be selected to alter the sulfur-32, sulfur-33, sulfur-34, and sulfur-35 ratios. In some embodiments, the uptake sources can be selected to alter the phosphorus-31, phosphorus-32, and phosphorus-33 ratios. In some embodiments, the uptake sources can be selected to alter the chlorine-35, chlorine-36, and chlorine-37 ratios.

In some embodiments, the isotopic ratio of a target atom can be varied to a desired ratio by selecting one or more uptake sources. An uptake source can be derived from a natural source, as found in nature, or from a man-made source, and one skilled in the art can select a natural source, a man-made source, or a combination thereof, to achieve a desired isotopic ratio of a target atom. An example of a man-made uptake source includes, for example, an uptake source that is at least partially derived from a chemical synthetic reaction. Such isotopically enriched uptake sources can be purchased commercially or prepared in the laboratory and/or optionally mixed with a natural source of the uptake source to achieve a desired isotopic ratio. In some embodiments, a target atom isotopic ratio of an uptake source can be achieved by selecting a desired origin of the uptake source as found in nature. For example, as discussed herein, a natural source can be a biobased derived from or synthesized by a biological organism or a source such as petroleum-based products or the atmosphere. In some such embodiments, a source of carbon, for example, can be selected from a fossil fuel-derived carbon source, which can be relatively depleted of carbon-14, or an environmental or atmospheric carbon source, such as $CO_2$, which can possess a larger amount of carbon-14 than its petroleum-derived counterpart.

The unstable carbon isotope carbon-14 or radiocarbon makes up for roughly 1 in $10^{12}$ carbon atoms in the earth's atmosphere and has a half-life of about 5700 years. The stock of carbon is replenished in the upper atmosphere by a nuclear reaction involving cosmic rays and ordinary nitrogen ($^{14}N$). Fossil fuels contain no carbon-14, as it decayed long ago. Burning of fossil fuels lowers the atmospheric carbon-14 fraction, the so-called "Suess effect".

Methods of determining the isotopic ratios of atoms in a compound are well known to those skilled in the art. Isotopic enrichment is readily assessed by mass spectrometry using techniques known in the art such as accelerated mass spectrometry (AMS), Stable Isotope Ratio Mass Spectrometry (SIRMS) and Site-Specific Natural Isotopic Fractionation by Nuclear Magnetic Resonance (SNIF-NMR). Such mass spectral techniques can be integrated with separation techniques such as liquid chromatography (LC), high performance liquid chromatography (HPLC) and/or gas chromatography, and the like.

In the case of carbon, ASTM D6866 was developed in the United States as a standardized analytical method for determining the biobased content of solid, liquid, and gaseous samples using radiocarbon dating by the American Society for Testing and Materials (ASTM) International. The standard is based on the use of radiocarbon dating for the determination of a product's biobased content. ASTM D6866 was first published in 2004, and the current active version of the standard is ASTM D6866-11 (effective Apr. 1, 2011). Radiocarbon dating techniques are well known to those skilled in the art, including those described herein.

The biobased content of a compound is estimated by the ratio of carbon-14 ($^{14}C$) to carbon-12 ($^{12}C$). Specifically, the Fraction Modem (Fm) is computed from the expression: Fm=(S−B)/(M−B), where B, S and M represent the $^{14}C/^{12}C$ ratios of the blank, the sample and the modern reference, respectively. Fraction Modem is a measurement of the deviation of the $^{14}C/^{12}C$ ratio of a sample from "Modem." Modem is defined as 95% of the radiocarbon concentration (in AD 1950) of National Bureau of Standards (NBS) Oxalic Acid I (i.e., standard reference materials (SRM) 4990b) normalized to $\delta^{13}C_{VPDB}$=−19 per mil (Olsson, *The use of Oxalic acid as a Standard.* in, *Radiocarbon Variations and Absolute Chronology*, Nobel Symposium, 12th Proc., John Wiley & Sons, New York (1970)). Mass spectrometry results, for example, measured by ASM, are calculated using the internationally agreed upon definition of 0.95 times the specific activity of NBS Oxalic Acid I (SRM 4990b) normalized to $\delta^{13}C_{VPBD}$=−19 per mil. This is equivalent to an absolute (AD 1950) $^{14}C/^{12}C$ ratio of $1.176\pm0.010\times10^{-12}$ (Karlen et al., *Arkiv Geofisik*, 4:465-471 (1968)). The standard calculations take into account the differential uptake of one isotope with respect to another, for example, the preferential uptake in biological systems of $C^{12}$ over $C^{13}$ over $C^{14}$, and these corrections are reflected as a Fm corrected for $\delta^{13}$.

An oxalic acid standard (SRM 4990b or HOx 1) was made from a crop of 1955 sugar beet. Although there were 1000 lbs made, this oxalic acid standard is no longer commercially available. The Oxalic Acid II standard (HOx 2; N.I.S.T designation SRM 4990 C) was made from a crop of 1977 French beet molasses. In the early 1980's, a group of 12 laboratories measured the ratios of the two standards. The ratio of the activity of Oxalic acid II to 1 is 1.2933±0.001 (the weighted mean). The isotopic ratio of HOx II is −17.8 per mil. ASTM D6866-11 suggests use of the available Oxalic Acid II standard SRM 4990 C (Hox2) for the modern standard (see discussion of original vs. currently available oxalic acid standards in Mann, *Radiocarbon*, 25(2):519-527 (1983)). A Fm=0% represents the entire lack of carbon-14 atoms in a material, thus indicating a fossil (for example, petroleum based) carbon source. A Fm=100%, after correction for the post-1950 injection of carbon-14 into the atmosphere from nuclear bomb testing, indicates an entirely modern carbon source. As described herein, such a "modern" source includes biobased sources.

As described in ASTM D6866, the percent modern carbon (pMC) can be greater than 100% because of the continuing but diminishing effects of the 1950s nuclear testing programs, which resulted in a considerable enrichment of carbon-14 in the atmosphere as described in ASTM D6866-11. Because all sample carbon-14 activities are referenced to a "pre-bomb" standard, and because nearly all new biobased products are produced in a post-bomb environment, all pMC values (after correction for isotopic fraction) must be multiplied by 0.95 (as of 2010) to better reflect the true biobased content of the sample A biobased content that is greater than 103% suggests that either an analytical error has occurred, or that the source of biobased carbon is more than several years old.

ASTM D6866 quantifies the biobased content relative to the material's total organic content and does not consider the inorganic carbon and other non-carbon containing substances present. For example, a product that is 50% starch-based material and 50% water would be considered to have a Biobased Content=100% (50% organic content that is 100% biobased) based on ASTM D6866. In another example, a product that is 50% starch-based material, 25% petroleum-based, and 25% water would have a Biobased Content=66.7% (75% organic content but only 50% of the product is biobased). In another example, a product that is 50% organic carbon and is a petroleum-based product would be considered to have a Biobased Content=0% (50% organic carbon but from fossil sources). Thus, based on the well known methods and known standards for determining the biobased content of a compound or material, one skilled in the art can readily determine the biobased content and/or prepared downstream products that utilize of the invention having a desired biobased content.

Applications of carbon-14 dating techniques to quantify bio-based content of materials are known in the art (Currie et al., *Nuclear Instruments and Methods in Physics Research B*, 172:281-287 (2000)). For example, carbon-14 dating has been used to quantify bio-based content in terephthalate-containing materials (Colonna et al., *Green Chemistry*, 13:2543-2548 (2011)). Notably, polypropylene terephthalate (PPT) polymers derived from renewable 1,3-propanediol and petroleum-derived terephthalic acid resulted in Fm values near 30% (i.e., since 3/11 of the polymeric carbon derives from renewable 1,3-propanediol and 8/11 from the fossil end member terephthalic acid) (Currie et al., supra, 2000). In contrast, polybutylene terephthalate polymer derived from both renewable 1,4-butanediol and renewable terephthalic acid resulted in bio-based content exceeding 90% (Colonna et al., supra, 2011).

Accordingly, in some embodiments, the present invention provides fatty alcohol, fatty aldehyde, fatty acid or isopropanol or a fatty alcohol, fatty aldehyde, fatty acid or isopropanol pathway intermediate that has a carbon-12, carbon-13, and carbon-14 ratio that reflects an atmospheric carbon, also referred to as environmental carbon, uptake source. For example, in some aspects the fatty alcohol, fatty aldehyde, fatty acid or isopropanol or a fatty alcohol, fatty aldehyde, fatty acid or isopropanol pathway intermediate can have an Fm value of at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 98% or as much as 100%. In some such embodiments, the uptake source is CO2. In some embodiments, the present invention provides fatty alcohol, fatty aldehyde, fatty acid or isopropanol or a fatty alcohol, fatty aldehyde, fatty acid or isopropanol pathway intermediate that has a carbon-12, carbon-13, and carbon-14 ratio that reflects petroleum-based carbon uptake source. In this aspect, the fatty alcohol, fatty aldehyde, fatty acid or isopropanol or a fatty alcohol, fatty aldehyde, fatty acid or isopropanol pathway intermediate can have an Fm value of less than 95%, less than 90%, less than 85%, less than 80%, less than 75%, less than 70%, less than 65%, less than 60%, less than 55%, less than 50%, less than 45%, less than 40%, less than 35%, less than 30%, less than 25%, less than 20%, less than 15%, less than 10%, less than 5%, less than 2% or less than 1%. In some embodiments, the present invention provides fatty alcohol, fatty aldehyde, fatty acid or isopropanol or a fatty alcohol, fatty aldehyde, fatty acid or isopropanol pathway intermediate that has a carbon-12, carbon-13, and carbon-14 ratio that is obtained by a combination of an atmospheric carbon uptake source with a petroleum-based uptake source. Using such a combination of uptake sources is one way by which the carbon-12, carbon-13, and carbon-14 ratio can be varied, and the respective ratios would reflect the proportions of the uptake sources.

Further, the present invention relates to the biologically produced fatty alcohol, fatty aldehyde, fatty acid or isopropanol or fatty alcohol, fatty aldehyde, fatty acid or isopropanol pathway intermediate as disclosed herein, and to the products derived therefrom, wherein the fatty alcohol, fatty aldehyde, fatty acid or isopropanol or a fatty alcohol, fatty aldehyde, fatty acid or isopropanol pathway intermediate has a carbon-12, carbon-13, and carbon-14 isotope ratio of about the same value as the $CO_2$ that occurs in the environment. For example, in some aspects the invention provides bioderived fatty alcohol, fatty aldehyde, fatty acid or isopropanol or a bioderived fatty alcohol, fatty aldehyde, fatty acid or isopropanol intermediate having a carbon-12 versus carbon-13 versus carbon-14 isotope ratio of about the same value as the $CO_2$ that occurs in the environment, or any of the other ratios disclosed herein. It is understood, as disclosed herein, that a product can have a carbon-12 versus carbon-13 versus carbon-14 isotope ratio of about the same value as the $CO_2$ that occurs in the environment, or any of the ratios disclosed herein, wherein the product is generated from bioderived fatty alcohol, fatty aldehyde, fatty acid or isopropanol or a bioderived fatty alcohol, fatty aldehyde, fatty acid or isopropanol pathway intermediate as disclosed herein, wherein the bioderived product is chemically modified to generate a final product. Methods of chemically modifying a bioderived product of fatty alcohol, fatty aldehyde, fatty acid or isopropanol, or an intermediate thereof, to generate a desired product are well known to those skilled in the art, as described herein. The invention further provides biofuels, chemicals, polymers, surfactants, soaps, detergents, shampoos, lubricating oil additives, fragrances, flavor materials or acrylates having a carbon-12 versus carbon-13 versus carbon-14 isotope ratio of about the same value as the $CO_2$ that occurs in the environment, wherein the biofuels, chemicals, polymers, surfactants, soaps, detergents, shampoos, lubricating oil additives, fragrances, flavor materials or acrylates are generated directly from or in combination with bioderived fatty alcohol, fatty aldehyde, fatty acid or isopropanol or a bioderived fatty alcohol, fatty aldehyde, fatty acid or isopropanol pathway intermediate as disclosed herein.

Fatty alcohol, fatty aldehyde or fatty acid is a chemical used in commercial and industrial applications. Non-limiting examples of such applications include production of biofuels, chemicals, polymers, surfactants, soaps, detergents, shampoos, lubricating oil additives, fragrances, flavor materials and acrylates. Accordingly, in some embodiments, the invention provides biobased biofuels, chemicals, polymers, surfactants, soaps, detergents, shampoos, lubricating oil additives, fragrances, flavor materials and acrylates comprising one or more bioderived fatty alcohol, fatty aldehyde or fatty acid or bioderived fatty alcohol, fatty aldehyde or fatty acid pathway intermediate produced by a non-naturally occurring microorganism of the invention or produced using a method disclosed herein.

Isopropanol is a chemical used in commercial and industrial applications. Non-limiting examples of such applications include production of solvents, including rubbing alcohol. As a solvent, isopropanol is found in products such as paints, lacquers, thinners, inks, adhesives, general-purpose cleaners, disinfectants, cosmetics, toiletries, de-icers, and pharmaceuticals. Low-grade isoproapnol is also used in motor oils. Isopropanol is also used as a chemical intermediate for the production of isopropylamines, isopropylethers, and isopropyl esters. Isopropanol can potentially be dehydrated to form propylene, a polymer precursor. Accordingly, in some embodiments, the invention provides biobased solvents, rubbing alcohol, paints, lacquers, thinners, inks, adhesives, general-purpose cleaners, disinfectants, cosmetics, toiletries, de-icers, pharmaceuticals, motor oils, isopropylamines, isopropylethers, isopropyl esters, propylene and polymers, comprising bioderived isopropanol produced by a non-naturally occurring microorganism of the invention or produced using a method disclosed herein.

As used herein, the term "bioderived" means derived from or synthesized by a biological organism and can be considered a renewable resource since it can be generated by a biological organism. Such a biological organism, in particular the microbial organisms of the invention disclosed herein, can utilize feedstock or biomass, such as, sugars or carbohydrates obtained from an agricultural, plant, bacterial, or animal source. Alternatively, the biological organism can utilize atmospheric carbon. As used herein, the term "biobased" means a product as described above that is composed, in whole or in part, of a bioderived compound of the invention. A biobased or bioderived product is in contrast to a petroleum derived product, wherein such a product is derived from or synthesized from petroleum or a petrochemical feedstock.

In some embodiments, the invention provides a biofuel, chemical, polymer, surfactant, soap, detergent, shampoo, lubricating oil additive, fragrance, flavor material or acrylate comprising bioderived fatty alcohol, fatty aldehyde or fatty acid or bioderived fatty alcohol, fatty aldehyde or fatty acid pathway intermediate, wherein the bioderived fatty alcohol, fatty aldehyde or fatty acid or bioderived fatty alcohol, fatty aldehyde or fatty acid pathway intermediate includes all or part of the fatty alcohol, fatty aldehyde or fatty acid or fatty alcohol, fatty aldehyde or fatty acid pathway intermediate used in the production of a biofuel, chemical, polymer, surfactant, soap, detergent, shampoo, lubricating oil additive, fragrance, flavor material or acrylate. For example, the final biofuel, chemical, polymer, surfactant, soap, detergent, shampoo, lubricating oil additive, fragrance, flavor material or acrylate can contain the bioderived fatty alcohol, fatty aldehyde or fatty acid, fatty alcohol, fatty aldehyde or fatty acid pathway intermediate, or a portion thereof that is the result of the manufacturing of the biofuel, chemical, polymer, surfactant, soap, detergent, shampoo, lubricating oil additive, fragrance, flavor material or acrylate. Such manufacturing can include chemically reacting the bioderived fatty alcohol, fatty aldehyde or fatty acid, or bioderived fatty alcohol, fatty aldehyde or fatty acid pathway intermediate (e.g. chemical conversion, chemical functionalization, chemical coupling, oxidation, reduction, polymerization, copolymerization and the like) with itself or another compound in a reaction that produces the final biofuel, chemical, polymer, surfactant, soap, detergent, shampoo, lubricating oil additive, fragrance, flavor material or acrylate. Thus, in some aspects, the invention provides a biobased biofuel, chemical, polymer, surfactant, soap, detergent, shampoo, lubricating oil additive, fragrance, flavor material or acrylate comprising at least 2%, at least 3%, at least 5%, at least 10%, at least 15%, at least 20%, at least 25%, at least 30%, at least 35%, at least 40%, at least 50%, at least 60%, at least 70%, at least 80%, at least 90%, at least 95%, at least 98% or 100% bioderived fatty alcohol, fatty aldehyde or fatty acid or bioderived fatty alcohol, fatty aldehyde or fatty acid pathway intermediate as disclosed herein. In some aspects, when the product is a biobased polymer that includes or is obtained from a bioderived fatty alcohol, fatty aldehyde or fatty acid, or or fatty alcohol, fatty aldehyde or fatty acid pathway intermediate described herein, the biobased polymer can be molded using methods well known in the art. Accordingly, in some embodiments, provided herein is a molded product comprising the biobased polymer described herein.

Additionally, in some embodiments, the invention provides a composition having a bioderived fatty alcohol, fatty aldehyde or fatty acid, or fatty alcohol, fatty aldehyde or fatty acid pathway intermediate disclosed herein and a compound other than the bioderived fatty alcohol, fatty aldehyde or fatty acid or fatty alcohol, fatty aldehyde or fatty acid pathway intermediate. For example, in some aspects, the invention provides a biobased biofuel, chemical, polymer, surfactant, soap, detergent, shampoo, lubricating oil additive, fragrance, flavor material or acrylate wherein the fatty alcohol, fatty aldehyde or fatty acid or fatty alcohol, fatty aldehyde or fatty acid pathway intermediate used in its production is a combination of bioderived and petroleum derived fatty alcohol, fatty aldehyde or fatty acid or fatty alcohol, fatty aldehyde or fatty acid pathway intermediate. For example, a biobased biofuel, chemical, polymer, surfactant, soap, detergent, shampoo, lubricating oil additive, fragrance, flavor material or acrylate can be produced using 50% bioderived fatty alcohol, fatty aldehyde or fatty acid and 50% petroleum derived fatty alcohol, fatty aldehyde or fatty acid or other desired ratios such as 60%/40%, 70%/30%, 80%/20%, 90%/10%, 95%/5%, 100%/0%, 40%/60%, 30%/70%, 20%/80%, 10%/90% of bioderived/petroleum derived precursors, so long as at least a portion of the product comprises a bioderived product produced by the microbial organisms disclosed herein. It is understood that methods for producing a biofuel, chemical, polymer, surfactant, soap, detergent, shampoo, lubricating oil additive, fragrance, flavor material or acrylate using the bioderived fatty alcohol, fatty aldehyde or fatty acid or bioderived fatty alcohol, fatty aldehyde or fatty acid pathway intermediate of the invention are well known in the art.

In some embodiments, the invention provides a solvent, a paint, lacquer, thinner, ink, adhesive, cleaner, disinfectant, cosmetic, toiletry, de-icer, pharmaceutical, motor oil, isopropylamine, isopropylether, isopropyl ester, propylene or a polymer comprising bioderived isopropanol or bioderived isopropanol pathway intermediate, wherein the bioderived isopropanol or bioderived isopropanol pathway intermediate includes all or part of the isopropanol or isopropanol pathway intermediate used in the production of a solvent, a paint, lacquer, thinner, ink, adhesive, cleaner, disinfectant, cosmetic, toiletry, de-icer, pharmaceutical, motor oil, isopropylamine, isopropylether, isopropyl ester, propylene or a polymer. For example, the final solvent, paint, lacquer, thinner, ink, adhesive, cleaner, disinfectant, cosmetic, toiletry, de-icer, pharmaceutical, motor oil, isopropylamine, isopropylether, isopropyl ester, propylene or polymer can contain the bioderived isopropanol, isopropanol pathway intermediate, or a portion thereof that is the result of the manufacturing of a solvent, paint, lacquer, thinner, ink, adhesive, cleaner, disinfectant, cosmetic, toiletry, de-icer, pharmaceutical, motor oil, isopropylamine, isopropylether, isopropyl ester, propylene or a polymer. Such manufacturing can include chemically reacting the bioderived isopropanol or bioderived isopropanol pathway intermediate (e.g. chemical conversion, chemical functionalization, chemical coupling, oxidation, reduction, polymerization, copolymerization and the like) into the final solvent, paint, lacquer, thinner, ink, adhesive, cleaner, disinfectant, cosmetic, toiletry, de-icer, pharmaceutical, motor oil, isopropylamine, isopropylether, isopropyl ester, propylene or polymer. Thus, in some aspects, the invention provides a biobased solvent, paint, lacquer, thinner, ink, adhesive, cleaner, disinfectant, cosmetic, toiletry, de-icer, pharmaceutical, motor oil, isopropylamine, isopropylether, isopropyl ester, propylene or polymer comprising at least 2%, at least 3%, at least 5%, at least 10%, at least 15%, at least 20%, at least 25%, at least 30%, at least 35%, at least 40%, at least 50%, at least 60%, at least 70%, at least 80%, at least 90%, at least 95%, at least 98% or 100% bioderived isopropanol or bioderived isopropanol pathway intermediate as disclosed herein.

Additionally, in some embodiments, the invention provides a composition having a bioderived isopropanol or isopropanol pathway intermediate disclosed herein and a compound other than the bioderived isopropanol or isopropanol pathway intermediate. For example, in some aspects, the invention provides a biobased solvent, paint, lacquer, thinner, ink, adhesive, cleaner, disinfectant, cosmetic, toiletry, de-icer, pharmaceutical, motor oil, isopropylamine, isopropylether, isopropyl ester, propylene or polymer wherein the isopropanol or isopropanol pathway intermediate used in its production is a combination of bioderived and petroleum derived isopropanol or isopropanol pathway intermediate. For example, a biobased solvent, paint, lacquer, thinner, ink, adhesive, cleaner, disinfectant, cosmetic, toiletry, de-icer, pharmaceutical, motor oil, isopropylamine, isopropylether, isopropyl ester, propylene or polymer can be produced using 50% bioderived isopropanol and 50% petroleum derived isopropanol or other desired ratios such as 60%/40%, 70%/30%, 80%/20%, 90%/10%, 95%/5%, 100%/0%, 40%/60%, 30%/70%, 20%/80%, 10%/90% of bioderived/petroleum derived precursors, so long as at least a portion of the product comprises a bioderived product produced by the microbial organisms disclosed herein. It is understood that methods for producing a solvent, paint, lacquer, thinner, ink, adhesive, cleaner, disinfectant, cosmetic, toiletry, de-icer, pharmaceutical, motor oil, isopropylamine, isopropylether, isopropyl ester, propylene or polymer using the bioderived isopropanol or bioderived isopropanol pathway intermediate of the invention are well known in the art.

The invention further provides a composition comprising bioderived fatty alcohol, fatty aldehyde, fatty acid or isopropanol, and a compound other than the bioderived fatty alcohol, fatty aldehyde, fatty acid or isopropanol. The compound other than the bioderived product can be a cellular portion, for example, a trace amount of a cellular portion of, or can be fermentation broth or culture medium, or a purified or partially purified fraction thereof produced in the presence of, a non-naturally occurring microbial organism of the invention having a fatty alcohol, fatty aldehyde, fatty acid or isopropanol pathway. The composition can comprise, for example, a reduced level of a byproduct when produced by an organism having reduced byproduct formation, as disclosed herein. The composition can comprise, for example, bioderived fatty alcohol, fatty aldehyde, fatty acid or isopropanol, or a cell lysate or culture supernatant of a microbial organism of the invention.

In certain embodiments, provided herein is a composition comprising a bioderived fatty alcohol, fatty aldehyde or fatty acid provided herein, for example, a bioderived fatty alcohol, fatty aldehyde or fatty acid produced by culturing a non-naturally occurring microbial organism having a formaldehyde fixation pathway, a formate assimilation pathway and/or a methanol metabolic pathway, and a MI-FAE cycle, a MD-FAE cycle, and/or a FAACPE cycle in combination with a termination pathway, as provided herein. In some embodiments, the composition further comprises a compound other than said bioderived fatty alcohol, fatty aldehyde or fatty acid. In certain embodiments, the compound other than said bioderived fatty alcohol, fatty aldehyde or fatty acid is a trace amount of a cellular portion of a non-naturally occurring microbial organism having a formaldehyde fixation pathway, a formate assimilation pathway and/or a methanol metabolic pathway, and a MI-FAE cycle, a MD-FAE cycle, and/or a FAACPE cycle in combination with a termination pathway, as provided herein.

In certain embodiments, provided herein is a composition comprising bioderived isopropanol provided herein, for example, bioderived isopropanol produced by culturing a non-naturally occurring microbial organism having a formaldehyde fixation pathway, a formate assimilation pathway and/or a methanol metabolic pathway, and an isopropanol pathway, as provided herein. In some embodiments, the composition further comprises a compound other than said bioderived isopropanol. In certain embodiments, the compound other than said bioderived isopropanol is a trace amount of a cellular portion of a non-naturally occurring microbial organism having a formaldehyde fixation pathway, a formate assimilation pathway and/or a methanol metabolic pathway, and a isopropanol pathway, as provided herein.

In some embodiments, provided herein is a biobased product comprising a bioderived fatty alcohol, fatty aldehyde, fatty acid or isopropanol provided herein. In certain embodiments, the biobased product is a biofuel, chemical, polymer, surfactant, soap, detergent, shampoo, lubricating oil additive, fragrance, flavor material or acrylate. In certain embodiments, the biobased product is a solvent, paint, lacquer, thinner, ink, adhesive, cleaner, disinfectant, cosmetic, toiletry, de-icer, pharmaceutical, motor oil, isopropylamine, isopropylether, isopropyl ester, propylene or polymer. In certain embodiments, the biobased product comprises at least 5% bioderived fatty alcohol, fatty aldehyde, fatty acid or isopropanol. In certain embodiments, the biobased product comprises at least 10% bioderived fatty alcohol, fatty aldehyde, fatty acid or isopropanol. In some embodiments, the biobased product comprises at least 20% bioderived fatty alcohol, fatty aldehyde, fatty acid or isopropanol. In other embodiments, the biobased product comprises at least 30% bioderived fatty alcohol, fatty aldehyde, fatty acid or isopropanol. In some embodiments, the biobased product comprises at least 40% bioderived fatty alcohol, fatty aldehyde, fatty acid or isopropanol. In other embodiments, the biobased product comprises at least 50% bioderived fatty alcohol, fatty aldehyde, fatty acid or isopropanol. In one embodiment, the biobased product comprises a portion of said bioderived fatty alcohol, fatty aldehyde, fatty acid or isopropanol as a repeating unit. In another embodiment, provided herein is a molded product obtained by molding the biobased product provided herein. In other embodiments, provided herein is a process for producing a biobased product provided herein, comprising chemically reacting said bioderived fatty alcohol, fatty aldehyde, fatty acid or isopropanol with itself or another compound in a reaction that produces said biobased product. In certain embodiments, provided herein is a polymer comprising or obtained by converting the bioderived fatty alcohol, fatty aldehyde, fatty acid or isopropanol. In other embodiments, provided herein is a method for producing a polymer, comprising chemically of enzymatically converting the bioderived fatty alcohol, fatty aldehyde, fatty acid or isopropanol to the polymer. In yet other embodiments, provided herein is a composition comprising the bioderived fatty alcohol, fatty aldehyde, fatty acid or isopropanol, or a cell lysate or culture supernatant thereof.

The culture conditions can include, for example, liquid culture procedures as well as fermentation and other large scale culture procedures. As described herein, particularly useful yields of the biosynthetic products of the invention can be obtained under anaerobic or substantially anaerobic culture conditions.

As described herein, one exemplary growth condition for achieving biosynthesis of fatty alcohol, fatty aldehyde, fatty acid or isopropanol includes anaerobic culture or fermentation conditions. In certain embodiments, the non-naturally occurring microbial organisms of the invention can be sustained, cultured or fermented under anaerobic or substantially anaerobic conditions. Briefly, an anaerobic condition refers to an environment devoid of oxygen. Substantially anaerobic conditions include, for example, a culture, batch fermentation or continuous fermentation such that the dissolved oxygen concentration in the medium remains between 0 and 10% of saturation. Substantially anaerobic conditions also includes growing or resting cells in liquid medium or on solid agar inside a sealed chamber maintained with an atmosphere of less than 1% oxygen. The percent of oxygen can be maintained by, for example, sparging the culture with an $N_2/CO_2$ mixture or other suitable non-oxygen gas or gases.

The culture conditions described herein can be scaled up and grown continuously for manufacturing of fatty alcohol, fatty aldehyde, fatty acid or isopropanol. Exemplary growth procedures include, for example, fed-batch fermentation and batch separation; fed-batch fermentation and continuous separation, or continuous fermentation and continuous separation. All of these processes are well known in the art. Fermentation procedures are particularly useful for the biosynthetic production of commercial quantities of fatty alcohol, fatty aldehyde, fatty acid or isopropanol. Generally, and as with non-continuous culture procedures, the continuous and/or near-continuous production of fatty alcohol, fatty aldehyde, fatty acid or isopropanol will include culturing a non-naturally occurring fatty alcohol, fatty aldehyde, fatty acid or isopropanol producing organism of the invention in sufficient nutrients and medium to sustain and/or nearly sustain growth in an exponential phase. Continuous culture under such conditions can include, for example, growth or culturing for 1 day, 2, 3, 4, 5, 6 or 7 days or more. Additionally, continuous culture can include longer time periods of 1 week, 2, 3, 4 or 5 or more weeks and up to several months. Alternatively, organisms of the invention can be cultured for hours, if suitable for a particular application. It is to be understood that the continuous and/or near-continuous culture conditions also can include all time intervals in between these exemplary periods. It is further understood that the time of culturing the microbial organism of the invention is for a sufficient period of time to produce a sufficient amount of product for a desired purpose.

Fermentation procedures are well known in the art. Briefly, fermentation for the biosynthetic production of fatty alcohol, fatty aldehyde, fatty acid or isopropanol can be utilized in, for example, fed-batch fermentation and batch separation; fed-batch fermentation and continuous separation, or continuous fermentation and continuous separation. Examples of batch and continuous fermentation procedures are well known in the art.

In addition to the above fermentation procedures using the fatty alcohol, fatty aldehyde, fatty acid or isopropanol producers of the invention for continuous production of substantial quantities of fatty alcohol, fatty aldehyde, fatty acid or isopropanol, the fatty alcohol, fatty aldehyde, fatty acid or isopropanol producers also can be, for example, simultaneously subjected to chemical synthesis and/or enzymatic procedures to convert the product to other compounds or the product can be separated from the fermentation culture and sequentially subjected to chemical and/or enzymatic conversion to convert the product to other compounds, if desired.

To generate better producers, metabolic modeling can be utilized to optimize growth conditions. Modeling can also be used to design gene knockouts that additionally optimize utilization of the pathway (see, for example, U.S. patent publications US 2002/0012939, US 2003/0224363, US 2004/0029149, US 2004/0072723, US 2003/0059792, US 2002/0168654 and US 2004/0009466, and U.S. Pat. No. 7,127,379). Modeling analysis allows reliable predictions of the effects on cell growth of shifting the metabolism towards more efficient production of fatty alcohol, fatty aldehyde, fatty acid or isopropanol.

In addition to active and selective enzymes producing fatty alcohols, fatty aldehydes, fatty acid or isopropanols at high yield, titer and productivity, a robust host organism that can efficiently direct carbon and reducing equivalents to fatty alcohol, fatty aldehyde and fatty acid biosynthesis can be beneficial. Host modifications described herein are particularly useful in combination with selective enzymes described herein that favor formation of the desired fatty alcohol, fatty aldehyde, fatty acid or isopropanol product. Several host modifications described herein entail introducing heterologous enzyme activities into the host organism.

Other modifications involve overexpressing or elevating enzyme activity relative to wild type levels. Yet other modifications include disrupting endogenous genes or attenuating endogenous enzyme activities.

In one embodiment of the invention, the microbial organisms efficiently directs carbon and energy sources into production of acetyl-CoA, which is used as both a primer and extension unit in the MI-FAE cycle. In one embodiment of the invention, the microbial organisms efficiently directs carbon and energy sources into production of malonyl-CoA, which is used as both a primer and extension unit in the MD-FAE cycle. In unmodified microbial organism, fatty alcohol, fatty aldehyde and fatty acid production in the cytosol relies on the native cell machinery to provide the necessary precursors. Thus, high concentrations of cytosolic acetyl-CoA and/or malonyl-CoA are desirable for facilitating deployment of a cytosolic fatty alcohol, fatty aldehyde or fatty acid production pathway that originates from acetyl-CoA or malonyl-CoA. Metabolic engineering strategies for increasing cytosolic acetyl-CoA and malonyl-CoA are disclosed herein.

Figures 3, 4:
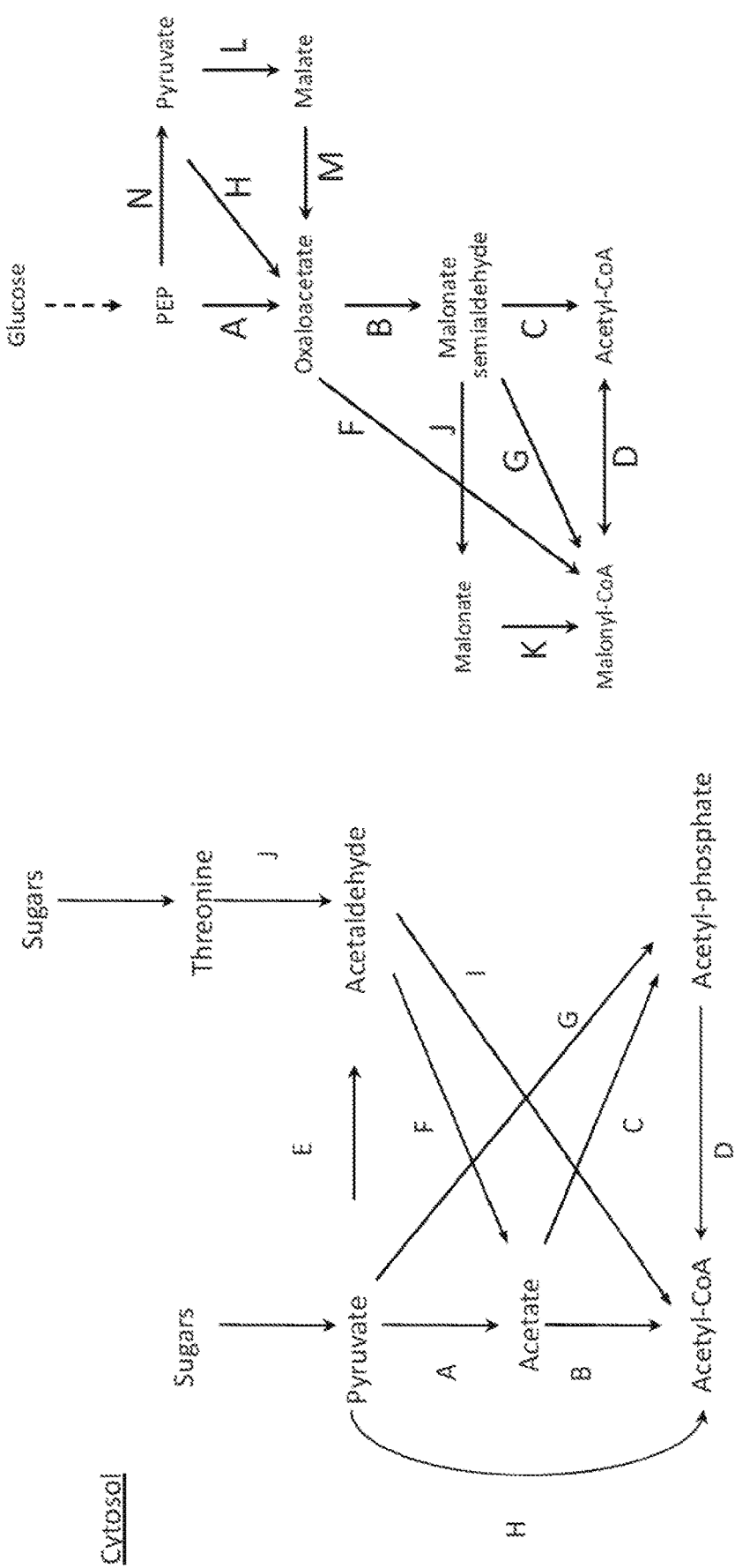
FIG. 3 shows exemplary pathways for production of cytosolic acetyl-CoA from pyruvate or threonine. Enzymes are: A. pyruvate oxidase (acetate-forming); B. acetyl-CoA synthetase, ligase or transferase; C. acetate kinase; D. phosphotransacetylase; E. pyruvate decarboxylase; F. acetaldehyde dehydrogenase; G. pyruvate oxidase (acetyl-phosphate forming); H. pyruvate dehydrogenase, pyruvate:fenedoxin oxidoreductase, pyruvate:NAD(P)H oxidoreductase or pyruvate formate lyase; I. acetaldehyde dehydrogenase (acylating); and J. threonine aldolase.
FIG. 4 shows exemplary pathways for production of acetyl-CoA from phosphoenolpyruvate (PEP). Enzymes are: A. PEP carboxylase or PEP carboxykinase; B. oxaloacetate decarboxylase; C. malonate semialdehyde dehydrogenase (acetylating); D. acetyl-CoA carboxylase or malonyl-CoA decarboxylase; F. oxaloacetate dehydrogenase or oxaloacetate oxidoreductase; G. malonate semialdehyde dehydrogenase (acylating); H. pyruvate carboxylase; J. malonate semialdehyde dehydrogenase; K. malonyl-CoA synthetase or transferase; L. malic enzyme; M. malate dehydrogenase or oxidoreductase; and N. pyruvate kinase or PEP phosphatase.

Since many eukaryotic organisms synthesize most of their acetyl-CoA in the mitochondria during growth on glucose, increasing the availability of acetyl-CoA in the cytosol can be obtained by introduction of a cytosolic acetyl-CoA biosynthesis pathway. Accordingly, acetyl-CoA biosynthesis pathways are described herein. In one embodiment, utilizing the pathways shown in FIG. 3, acetyl-CoA can be synthesized in the cytosol from a pyruvate or threonine precursor. In other embodiment, acetyl-CoA can be synthesized in the cytosol from phosphoenolpyruvate (PEP) or pyruvate (FIG. 4). In yet another embodiment acetyl-CoA can be synthesized in cellular compartments and transported to the cytosol. For example, one mechanism involves converting mitochondrial acetyl-CoA to a metabolic intermediate such as citrate or citramalate, transporting those intermediates to the cytosol, and then regenerating the acetyl-CoA (see FIGS. 5 and 6). Exemplary acetyl-CoA pathways and corresponding enzymes are further described in Examples V-VII.

In another embodiment, increasing cytosolic acetyl-CoA availability for fatty alcohol, fatty aldehyde, fatty acid or isopropanol biosynthesis is to disrupt or attenuate competing enzymes and pathways that utilize acetyl-CoA or its precursors. Exemplary competing enzyme activities include, but are not limited to, pyruvate decarboxylase, lactate dehydrogenase, short-chain aldehyde and alcohol dehydrogenases, acetate kinase, phosphotransacetylase, glyceraldehyde-3-phosphate dehydrogenases, pyruvate oxidase and acetyl-CoA carboxylase. Exemplary acetyl-CoA consuming pathways whose disruption or attenuation can improve fatty alcohol, fatty aldehyde, fatty acid or isopropanol production include the mitochondrial TCA cycle, fatty acid biosynthesis, ethanol production and amino acid biosynthesis. These enzymes and pathways are further described herein.

Yet another strategy for increasing cytosolic acetyl-CoA production is to increase the pool of CoA available in the cytoplasm. This can be accomplished by overexpression of CoA biosynthetic enzymes in the cytosol. In particular, expression of pantothenate kinase (EC 2.7.1.33) can be used. This enzyme catalyzes the first step and rate-limiting enzyme of CoA biosynthesis. Exemplary pantothenate kinase variants resistant to feedback inhibition by CoA are well known in the art (Rock et al, *J Bacteriol* 185: 3410-5 (2003)) and are described in the below table.

| Protein | Accession # | GI number | Organism |
|---|---|---|---|
| coaA | AAC76952 | 1790409 | Escherichia coli |
| CAB1 | NP_010820.3 | 398366683 | Saccharomyces cerevisiae |
| KLLA0C00869g | XP_452233.1 | 50304555 | Kluyveromyces lactis |
| YALI0D25476g | XP_503275.1 | 50551601 | Yarrowia lipolytica |
| ANI_1_3272024 | XP_001400486.2 | 317028058 | Aspergillus niger |

Competing enzymes and pathways that divert acyl-CoA substrates from production of fatty alcohols, fatty aldehydes or fatty acids of the invention can also be attenuated or disrupted. Exemplary enzymes for attenuation include acyltransferases, carnitine shuttle enzymes and negative regulators of MI-FAE cycle, MD-FAE cycle, FAACPE cycle or termination pathway enzymes.

Disruption or attenuation of acyltransferases that transfer acyl moieties from CoA to other acceptors such as ACP, glycerol, ethanol and others, can increase the availability of acyl-CoA for fatty alcohol, fatty aldehyde or fatty acid production. For example, Acyl-CoA:ACP transacylase (EC 2.3.1.38; 2.3.1.39) enzymes such as fabH (KASIII) of E. coli transfer acyl moieties from CoA to ACP. FabH is active on acetyl-CoA and butyryl-CoA (Prescott et al, Adv. Enzymol. Relat. Areas Mol, 36:269-311(1972)). Acetyl-CoA:ACP transacylase enzymes from Plasmodium falciparum and Streptomyces avermitillis have been heterologously expressed in E. coli (Lobo et al, Biochem 40:11955-64 (2001)). A synthetic KASIII (FabH) from P. falciparum expressed in a fabH-deficient Lactococcus lactis host was able to complement the native fadH activity (Du et al, AEM 76:3959-66 (2010)). The acetyl-CoA:ACP transacylase enzyme from Spinacia oleracea accepts other acyl-ACP molecules as substrates, including butyryl-ACP (Shimakata et al, Methods Enzym 122:53-9 (1986)). Malonyl-CoA:ACP transacylase enzymes include FabD of E. coil and Brassica napsus (Verwoert et al, J Bacteriol, 174:2851-7 (1992); Simon et al, FEBS Lett 435:204-6 (1998)). FabD of B. napsus was able to complementfabD-deficient E. coli. The multifunctional eukaryotic fatty acid synthase enzyme complexes (described herein) also catalyze this activity. Other exemplary acyltransferases include diacylglycerol acyltransferases such as LRO1 and DGA1 of S. cerevisiae and DGA1 and DGA2 of Yarrowia lipolytica, glycerolipid acyltransferase enzymes such as plsB of E. coli (GenBank: AAC77011.2, GI:87082362; Heath and Rock, J Bacteriol 180:1425-30 (1998)), sterol acyltransferases such as ARE1 and ARE2 of S. cerevisiae, ethanol acyltransferases (EEB1, EHT1), putative acyltransferases (YMR210W) and others.

| Protein | GenBank ID | GI Number | Organism |
|---|---|---|---|
| fabH | AAC74175.1 | 1787333 | Escherichia coli |
| fadA | NP_824032.1 | 29829398 | Streptomyces avermitillis |
| fabH | AAC63960.1 | 3746429 | Plasmodium falciparum |
| Synthetic construct | ACX34097.1 | 260178848 | Plasmodium falciparum |
| fabH | CAL98359.1 | 124493385 | Lactococcus lactis |
| fabD | AAC74176.1 | 1787334 | Escherichia coli |
| fabD | CAB45522.1 | 5139348 | Brassica napsus |
| LRO1 | NP_014405.1 | 6324335 | Saccharomyces cerevisiae |
| DGA1 | NP_014888.1 | 6324819 | Saccharomyces cerevisiae |
| DGA1 | CAG79269.1 | 49649549 | Yarrowia lipolytica |
| DGA2 | XP_504700.1 | 50554583 | Yarrowia lipolytica |
| ARE1 | NP_009978.1 | 6319896 | Saccharomyces cerevisiae |
| ARE2 | NP_014416.1 | 6324346 | Saccharomyces cerevisiae |
| EEB1 | NP_015230.1 | 6325162 | Saccharomyces cerevisiae |
| EHT1 | NP_009736.3 | 398365307 | Saccharomyces cerevisiae |
| YMR210W | NP_013937.1 | 6323866 | Saccharomyces cerevisiae |
| ALE1 | NP_014818.1 | 6324749 | Saccharomyces cerevisiae |

Increasing production of fatty alcohols, fatty aldehydes or fatty acids may necessitate disruption or attenuation of enzymes involved in the trafficking of acetyl-CoA and acyl-CoA molecules from the cytosol to other compartments of the organism such as mitochondria, endoplasmic reticulum, proteoliposomes and peroxisomes. In these compartments, the acyl-CoA intermediate can be degraded or used as building blocks to synthesize fatty acids, cofactors and other byproducts.

Acetyl-CoA and acyl-CoA molecules localized in the cytosol can be transported into other cellular compartments with the aid of the carrier molecule carnitine via carnitine shuttles (van Roermund et al., EMBO J 14:3480-86 (1995)). Acyl-carnitine shuttles between cellular compartments have been characterized in yeasts such as Candida albicans (Strijbis et al, J Biol Chem 285:24335-46 (2010)). In these shuttles, the acyl moiety of acyl-CoA is reversibly transferred to carnitine by acylcarnitine transferase enzymes. Acetylcarnitine can then be transported across the membrane by organelle-specific acylcarnitine/carnitine translocase enzymes. After translocation, the acyl-CoA is regenerated by acetylcarnitine transferase. Enzymes suitable for disruption or attenuation include carnitine acyltransferase enzymes, acylcarnitine translocases, acylcarnitine carrier proteins and enzymes involved in carnitine biosynthesis.

Carnitine acetyltransferase (CAT, EC 2.3.1.7) reversibly links acetyl units from acetyl-CoA to the carrier molecule, carnitine. Candida albicans encodes three CAT isozymes: Cat2, Yat1 and Yat2 (Strijbis et al., J Biol Chem 285:24335-46 (2010)). Cat2 is expressed in both the mitochondrion and the peroxisomes, whereas Yat1 and Yat2 are cytosolic. The Cat2 transcript contains two start codons that are regulated under different carbon source conditions. The longer transcript contains a mitochondrial targeting sequence whereas the shorter transcript is targeted to peroxisomes. Cat2 of Saccharomyces cerevisiae and AcuJ of Aspergillus nidulans employ similar mechanisms of dual localization (Elgersma et al., EMBO J14:3472-9 (1995); Hynes et al., Euk Cell 10:547-55 (2011)). The cytosolic CAT of A. nidulans is encoded byfacC. Other exemplary CAT enzymes are found in Rattus norvegicus and Homo sapiens (Cordente et al., Biochem 45:6133-41(2006)). Exemplary carnitine acyltransferase enzymes (EC 2.3.1.21) are the Cpt1 and Cpt2 gene products of Rattus norvegicus (de Vries et al., Biochem 36:5285-92 (1997)).

| Protein | Accession # | GI number | Organism |
|---|---|---|---|
| Cat2 | AAN31660.1 | 23394954 | Candida albicans |
| Yat1 | AAN31659.1 | 23394952 | Candida albicans |
| Yat2 | XP_711005.1 | 68490355 | Candida albicans |
| Cat2 | CAA88327.1 | 683665 | Saccharomyces cerevisiae |
| Yat1 | AAC09495.1 | 456138 | Saccharomyces cerevisiae |
| Yat2 | NP_010941.1 | 6320862 | Saccharomyces cerevisiae |
| AcuJ | CBF69795.1 | 259479509 | Aspergillus nidulans |
| FacC | AAC82487.1 | 2511761 | Aspergillus nidulans |
| Crat | AAH83616.1 | 53733439 | Rattus norvegicus |
| Crat | P43155.5 | 215274265 | Homo sapiens |
| Cpt1 | AAB48046.1 | 1850590 | Rattus norvegicus |
| Cpt2 | AAB02339.1 | 1374784 | Rattus norvegicus |

Carnitine-acylcarnitine translocases can catalyze the bidirectional transport of carnitine and carnitine-fatty acid complexes. The Cact gene product provides a mechanism for transporting acyl-carnitine substrates across the mitochondrial membrane (Ramsay et al Biochim Biophys Acta 1546: 21-42 (2001)). A similar protein has been studied in humans (Sekoguchi et al., *J Biol Chem* 278:38796-38802 (2003)). The *Saccharomyces cerevisiae* mitochondrial carnitine carrier is Crc1 (van Roermund et al., supra; Palmieri et al., *Biochimica et Biophys Acta* 1757:1249-62 (2006)). The human carnitine translocase was able to complement a Crc1-deficient strain of *S. cerevisiae* (van Roermund et al., supra). Two additional carnitine translocases found in *Drosophila melanogaster* and *Caenorhabditis elegans* were also able to complement Crc1-deficient yeast (Oey et al., *Mol Genet Metab* 85:121-24 (2005)). Four mitochondrial carnitine/acetylcarnitine carriers were identified in *Trypanosoma brucei* based on sequence homology to the yeast and human transporters (Colasante et al., *Mol Biochem Parasit* 167:104-117 (2009)). The carnitine transporter of *Candida albicans* was also identified by sequence homology. An additional mitochondrial carnitine transporter is the acuH gene product of *Aspergillus nidulans*, which is exclusively localized to the mitochondrial membrane (Lucas et al., FEMS Microbiol Lett 201:193-8 (2006)).

| Protein | GenBank ID | GI Number | Organism |
|---|---|---|---|
| Cact | P97521.1 | 2497984 | *Rattus norvegicus* |
| Cacl | NP_001034444.1 | 86198310 | *Homo sapiens* |
| CaO19.2851 | XP_715782.1 | 68480576 | *Candida albicans* |
| Crc1 | NP_014743.1 | 6324674 | *Saccharomyces cerevisiae* |
| Dif-1 | CAA88283.1 | 829102 | *Caenorhabditis elegans* |
| colt | CAA73099.1 | 1944534 | *Drosophila melanogaster* |
| Tb11.02.2960 | EAN79492.1 | 70833990 | *Trypanosoma brucei* |
| Tb11.03.0870 | EAN79007.1 | 70833505 | *Trypanosoma brucei* |
| Tb11.01.5040 | EAN80288.1 | 70834786 | *Trypanosoma brucei* |
| Tb927.8.5810 | AAX69329.1 | 62175181 | *Trypanosoma brucei* |
| acuH | CAB44434.1 | 5019305 | *Aspergillus nidulans* |

Transport of carnitine and acylcarnitine across the peroxisomal membrane has not been well-characterized. Specific peroxisomal acylcarnitine carrier proteins in yeasts have not been identified to date. However, mitochonidrial carnitine translocases can also function in the peroxisomal transport of carnitine and acetylcarnitine. Experimental evidence suggests that the OCTN3 protein of Mus musculus is a peroxisomal carnitine/acylcarnitine translocase.

Yet another possibility is that acyl-CoA or acyl-carnitine are transported across the peroxisomal or mitochondrial membranes by an acyl-CoA transporter such as the Pxa1 and Pxa2 ABC transporter of *Saccharomyces cerevisiae* or the ALDP ABC transporter of *Homo sapiens* (van Roermund et al., *FASEB J* 22:4201-8 (2008)). Pxa1 and Pxa2 (Pat1 and Pat2) form a heterodimeric complex in the peroxisomal membrane and catalyze the ATP-dependent transport of fatty acyl-CoA esters into the peroxisome (Verleur et al., *Eur J Biochem* 249: 657-61(1997)). The mutant phenotype of a pxa1/pxa2 deficient yeast can be rescued by heterologous expression of ALDP, which was shown to transport a range of acyl-CoA substrates (van Roermund et al., *FASEB J* 22:4201-8 (2008)). Deletion of the Pxa12 transport system, in tandem with deletion of the peroxisomal fatty acyl-CoA synthetase (Faa7) abolished peroxisomal beta-oxidation in *S. cerevisiae*. Yet another strategy for reducing transport of pathway intermediates or products into the peroxisome is to attenuate or eliminate peroxisomal function, by interfering with systems involved in peroxisomal biogenesis. An exemplary target is Pex10 of *Yarrowia lipolytica* and homologs.

| Protein | Accession # | GI number | Organism |
|---|---|---|---|
| OCTN3 | BAA78343.1 | 4996131 | *Mus musculus* |
| Pxa1 | AAC49009.1 | 619668 | *Saccharomyces cerevisiae* |
| Pxa2 | AAB51597.1 | 1931633 | *Saccharomyces cerevisiae* |
| Faa2 | NP_010931.3 | 398364331 | *Saccharomyces cerevisiae* |
| ALDP | NP_000024.2 | 7262393 | *Homo sapiens* |
| Pex10 | BAA99413.1 | 9049374 | *Yarrowia lipolytica* |

Carnitine biosynthetic pathway enzymes are also suitable candidates for disruption or attenuation. In *Candida albicans*, for example, carnitine is synthesized from trimethyl-L-lysine in four enzymatic steps (Strijbis et al., *FASEB J* 23:2349-59 (2009)). The carnitine pathway precursor, trimethyllysine (TML), is produced during protein degradation. TML dioxygenase (CaO13.4316) hydroxylates TML to form 3-hydroxy-6-N-trimethyllysine. A pyridoxal-5'-phoshpate dependent aldolase (CaO19.6305) then cleaves HTML into 4-trimethylaminobutyraldehyde. The 4-trimethylaminobutyraldehyde is subsequently oxidized to 4-trimethylaminobutyrate by a dehydrogenase (CaO19.6306). In the final step, 4-trimethylaminobutymte is hydroxylated to form carnitine by the gene product of CaO19.7131. Flux through the carnitine biosynthesis pathway is limited by the availability of the pathway substrate and very low levels of carnitine seem to be sufficient for normal carnitine shuttle activity (Strejbis et al., *IUBMB Life* 62:357-62 (2010)).

| Protein | Accession # | GI number | Organism |
|---|---|---|---|
| CaO19.4316 | XP_720623.1 | 68470755 | *Candida albicans* |
| CaO19.6305 | XP_711090.1 | 68490151 | *Candida albicans* |
| CaO19.6306 | XP_711091.1 | 68490153 | *Candida albicans* |
| CaO19.7131 | XP_715182.1 | 68481628 | *Candida albicans* |

Carbon flux towards production of fatty alcohols, fatty aldehydes or fatty acids can be improved by deleting or attenuating competing pathways. Typical fermentation products of yeast include ethanol, glycerol and $CO_2$. The elimination or reduction of these byproducts can be accomplished by approaches described herein. For example, carbon loss due to respiration can be reduced. Other potential byproducts include lactate, acetate, formate, fatty acids and amino acids.

The conversion of acetyl-CoA into ethanol can be detrimental to the production of fatty alcohols, fatty aldehyes, fatty acids or isopropanol because the conversion process can draw away both carbon and reducing equivalents from the MI-FAE cycle, MD-FAE cycle, FAACPE cycle, termination pathway or isopropanol pathway. Ethanol can be formed from pyruvate in two enzymatic steps catalyzed by pyruvate decarboxylase and ethanol dehydrogenase. *Saccharomyces cerevisiae* has three pyruvate decarboxylases (PDC1, PDC5 and PDC6). PDC1 is the major isozyme and is strongly expressed in actively fermenting cells. PDC5 also functions during glycolytic fermentation, but is expressed only in the absence of PDC1 or under thiamine limiting conditions. PDC6 functions during growth on nonfermentable carbon sources. Deleting PDC1 and PDC5 can reduce ethanol production significantly; however these deletions can lead to mutants with increased PDC6 expression. Deletion of all three eliminates ethanol formation completely but also can cause a growth defect because of inability of the cells to form sufficient acetyl-CoA for biomass formation.

This, however, can be overcome by evolving cells in the presence of reducing amounts of C2 carbon source (ethanol or acetate) (van Mans et al, *AEM* 69:2094-9 (2003)). It has also been reported that deletion of the positive regulator PDC2 of pyruvate decarboxylases PDC1 and PDC5, reduced ethanol formation to ~10% of that made by wild-type (Hohmann et al, *Mol Gen Genet* 241:657-66 (1993)). Protein sequences and identifiers of PDC enzymes are listed in Example V.

Alternatively, alcohol dehydrogenases that convert acetaldehyde into ethanol and/or other short chain alcohol dehydrogenases can be disrupted or attenuated to provide carbon and reducing equivalents for the MI-FAE cycle, MD-FAE cycle, FAACPE cycle, termination pathway or isopropanol pathway. To date, seven alcohol dehydrogenases, ADHI-ADHVII, have been reported in *S. cerevisiae* (de Smidt et al, *FEMS Yeast Res* 8:967-78 (2008)). ADH1 (GI:1419926) is the key enzyme responsible for reducing acetaldehyde to ethanol in the cytosol under anaerobic conditions. It has been reported that a yeast strain deficient in ADH1 cannot grow anaerobically because an active respiratory chain is the only alternative path to regenerate NADH and lead to a net gain of ATP (Drewke et al, *J Bacteriol* 172:3909-17 (1990)). This enzyme is an ideal candidate for downregulation to limit ethanol production. ADH2 is severely repressed in the presence of glucose. In *K. lactis*, two NAD-dependent cytosolic alcohol dehydrogenases have been identified and characterized. These genes also show activity for other aliphatic alcohols. The genes ADH1 (GI:113358) and ADHII (GI:51704293) are preferentially expressed in glucose-grown cells (Bozzi et al, *Biochim Biophys Acta* 1339:133-142 (1997)). Cytosolic alcohol dehydrogenases are encoded by ADH1 (GI:608690) in *C. albicans*, ADH1 (GI:3810864) in *S. pombe*, ADH1 (GI:5802617) in *Y. lipolytica*, ADH1 (GI:2114038) and ADHII (GI:2143328) in *Pichia stipitis* or *Scheffersomyces stipitis* (Passoth et al, *Yeast* 14:1311-23 (1998)). Candidate alcohol dehydrogenases are shown the table below.

| Protein | GenBank ID | GI number | Organism |
|---|---|---|---|
| SADH | BAA24528.1 | 2815409 | *Candida parapsilosis* |
| ADH1 | NP_014555.1 | 6324486 | *Saccharomyces cerevisiae* s288c |
| ADH2 | NP_014032.1 | 6323961 | *Saccharomyces cerevisiae* s288c |
| ADH3 | NP_013800.1 | 6323729 | *Saccharomyces cerevisiae* s288c |
| ADH4 | NP_011258.2 | 269970305 | *Saccharomyces cerevisiae* s288c |
| ADH5 (SFA1) | NP_010113.1 | 6320033 | *Saccharomyces cerevisiae* s288c |
| ADH6 | NP_014051.1 | 6323980 | *Saccharomyces cerevisiae* s288c |
| ADH7 | NP_010030.1 | 6319949 | *Saccharomyces cerevisiae* s288c |
| adhP | CAA44614.1 | 2810 | *Kluyveromyces lactis* |
| ADH1 | P20369.1 | 113358 | *Kluyveromyces lactis* |
| ADH2 | CAA45739.1 | 2833 | *Kluyveromyces lactis* |
| ADH3 | P49384.2 | 51704294 | *Kluyveromyces lactis* |
| ADH1 | CAA57342.1 | 608690 | *Candida albicans* |
| ADH2 | CAA21988.1 | 3859714 | *Candida albicans* |
| SAD | XP_712899.1 | 68486457 | *Candida albicans* |
| ADH1 | CAA21782.1 | 3810864 | *Schizosaccharomyces pombe* |
| ADH1 | AAD51737.1 | 5802617 | *Yarrowia lipolytica* |
| ADH2 | AAD51738.1 | 5802619 | *Yarrowia lipolytica* |
| ADH3 | AAD51739.1 | 5802621 | *Yarrowia lipolytica* |
| AlcB | AAX53105.1 | 61696864 | *Aspergillus niger* |
| ANI_1_282024 | XP_001399347.1 | 145231748 | *Aspergillus niger* |
| ANI_1_126164 | XP_001398574.2 | 317037131 | *Aspergillus niger* |
| ANI_1_1756104 | XP_001395505.2 | 317033815 | *Aspergillus niger* |
| ADH2 | CAA73827.1 | 2143328 | *Scheffersomyces stipitis* |

Attenuation or disruption of one or more glycerol-3-phosphatase or glycerol-3-phosphate (G3P) dehydrogenase enzymes can eliminate or reduce the formation of glycerol, and thereby conserving carbon and reducing equivalents for production of fatty alcohols, fatty aldehydes, fatty acids or isopropnaol.

G3P phosphatase catalyzes the hydrolysis of G3P to glycerol. Enzymes with this activity include the glycerol-1-phosphatase (EC 3.1.3.21) enzymes of *Saccharomyces cerevisiae* (GPP1 and GPP2), *Candida albicans* and *Dunaleilla parva* (Popp et al, *Biotechnol Bioeng* 100:497-505 (2008); Fan et al, *FEMS Microbiol Lett* 245:107-16 (2005)). The *D. parva* gene has not been identified to date. These and additional G3P phosphatase enzymes are shown in the table below.

| Protein | GenBank ID | GI Number | Organism |
|---|---|---|---|
| GPP1 | DAA08494.1 | 285812595 | *Saccharomyces cerevisiae* |
| GPP2 | NP_010984.1 | 6320905 | *Saccharomyces cerevisiae* |
| GPP1 | XP_717809.1 | 68476319 | *Candida albicans* |
| KLLA0C08217g | XP_452565.1 | 50305213 | *Kluyveromyces lactis* |
| KLLA0C11143g | XP_452697.1 | 50305475 | *Kluyveromyces lactis* |
| ANI_1_380074 | XP_001392369.1 | 145239445 | *Aspergillus niger* |
| ANI_1_444054 | XP_001390913.2 | 317029125 | *Aspergillus niger* |

*S. cerevisiae* has three G3P dehydrogenase enzymes encoded by GPD1 and GDP2 in the cytosol and GUT2 in the mitochondrion. GPD2 is known to encode the enzyme responsible for the majority of the glycerol formation and is responsible for maintaining the redox balance under anaerobic conditions. GPD1 is primarily responsible for adaptation of *S. cerevisiae* to osmotic stress (Bakker et al., *FEMS Microbiol Rev* 24:15-37 (2001)). Attenuation of GPD1, GPD2 and/or GUT2 will reduce glycerol formation. GPD1 and GUT2 encode G3P dehydrogenases in *Yarrowia lipolytica* (Beopoulos et al, *AEM* 74:7779-89 (2008)). GPD1 and GPD2 encode for G3P dehydrogenases in *S. pombe*. Similarly, G3P dehydrogenase is encoded by CTRL_02011 in *Candida tropicalis* and a gene represented by GI:20522022 in *Candida albicans*.

| Protein | GenBank ID | GI number | Organism |
|---|---|---|---|
| GPD1 | CAA98582.1 | 1430995 | *Saccharomyces cerevisiae* |
| GPD2 | NP_014582.1 | 6324513 | *Saccharomyces cerevisiae* |
| GUT2 | NP_012111.1 | 6322036 | *Saccharomyces cerevisiae* |
| GPD1 | CAA22119.1 | 6066826 | *Yarrowia lipolytica* |
| GUT2 | CAG83113.1 | 49646728 | *Yarrowia lipolytica* |
| GPD1 | CAA22119.1 | 3873542 | *Schizosaccharomyces pombe* |

-continued

| Protein | GenBank ID | GI number | Organism |
|---|---|---|---|
| GPD2 | CAA91239.1 | 1039342 | Schizosaccharomyces pombe |
| ANI_1_786014 | XP_001389035.2 | 317025419 | Aspergillus niger |
| ANI_1_1768134 | XP_001397265.1 | 145251503 | Aspergillus niger |
| KLLA0C04004g | XP_452375.1 | 50304839 | Kluyveromyces lactis |
| CTRG_02011 | XP_002547704.1 | 255725550 | Candida tropicalis |
| GPD1 | XP_714362.1 | 68483412 | Candida albicans |
| GPD2 | XP_713824.1 | 68484586 | Candida albicans |

Enzymes that form acid byproducts such as acetate, formate and lactate can also be attenuated or disrupted. Such enzymes include acetate kinase, phosphotransacetylase and pyruvate oxidase. Disruption or attenuation of pyruvate formate lyase and formate dehydrogenase could limit formation of formate and carbon dioxide. These enzymes are described in further detail in Example V.

Alcohol dehydrogenases that convert pyruvate to lactate are also candidates for disruption or attenuation. Lactate dehydrogenase enzymes include ldhA of *E. coli* and ldh from *Ralstonia eutropha* (Steinbuchel and Schlegel, *Eur. J. Biochem.* 130:329-334 (1983)). Other alcohol dehydrogenases listed above may also exhibit LDH activity.

| Protein | GenBank ID | GI number | Organism |
|---|---|---|---|
| ldhA | NP_415898.1 | 16129341 | Escherichia coli |
| Ldh | YP_725182.1 | 113866693 | Ralstonia eutropha |

Tuning down activity of the mitochondrial pyruvate dehydrogenase complex will limit flux into the mitochondrial TCA cycle. Under anaerobic conditions and in conditions where glucose concentrations are high in the medium, the capacity of this mitochondrial enzyme is very limited and there is no significant flux through it. However, in some embodiments, this enzyme can be disrupted or attenuated to increase fatty alcohol, fatty aldehyde or fatty acid production. Exemplary pyruvate dehydrogenase genes include PDB1, PDA1, LAT1 and LPD1. Accession numbers and homologs are listed in Example V.

Another strategy for reducing flux into the TCA cycle is to limit transport of pyruvate into the mitochondria by tuning down or deleting the mitochondrial pyruvate carrier. Transport of pyruvate into the mitochondria in *S. cerevisiae* is catalyzed by a heterocomplex encoded by MPC1 and MPC2 (Herzig et al, *Science* 337:93-6 (2012); Bricker et al, *Science* 337:96-100 (2012)). *S. cerevisiae* encodes five other putative monocarboxylate transporters (MCH1-5), several of which may be localized to the mitochondrial membrane (Makuc et al, *Yeast* 18:1131-43 (2001)). NDT1 is another putative pyruvate transporter, although the role of this protein is disputed in the literature (Todisco et al, *J Biol Chem* 20:1524-31(2006)). Exemplary pyruvate and monocarboxylate transporters are shown in the table below:

| Protein | GenBank ID | GI number | Organism |
|---|---|---|---|
| MPC1 | NP_011435.1 | 6321358 | Saccharomyces cerevisiae |
| MPC2 | NP_012032.1 | 6321956 | Saccharomyces cerevisiae |
| MPC1 | XP_504811.1 | 50554805 | Yarrowia lipolytica |
| MPC2 | XP_501390.1 | 50547841 | Yarrowia lipolytica |
| MPC1 | XP_719951.1 | 68471816 | Candida albicans |
| MPC2 | XP_716190.1 | 68479656 | Candida albicans |
| MCH1 | NP_010229.1 | 6320149 | Saccharomyces cerevisiae |
| MCH2 | NP_012701.2 | 330443640 | Saccharomyces cerevisiae |
| MCH3 | NP_014274.1 | 6324204 | Saccharomyces cerevisiae |
| MCH5 | NP_014951.2 | 330443742 | Saccharomyces cerevisiae |
| NDT1 | NP_012260.1 | 6322185 | Saccharomyces cerevisiae |
| ANI_1_1592184 | XP_001401484.2 | 317038471 | Aspergillus niger |
| CaJ7_0216 | XP_888808.1 | 77022728 | Candida albicans |
| YALI0E16478g | XP_504023.1 | 50553226 | Yarrowia lipolytica |
| KLLA0D14036g | XP_453688.1 | 50307419 | Kluyveromyces lactis |

Disruption or attenuation of enzymes that synthesize malonyl-CoA and fatty acids can increase the supply of carbon available for fatty alcohol, fatty aldehyde or fatty acid biosynthesis from acetyl-CoA. Exemplary enzymes for disruption or attenuation include fatty acid synthase, acetyl-CoA carboxylase, biotin:apoenzyme ligase, acyl carrier protein, thioesterase, acyltransferases, ACP malonyltransferase, fatty acid elongase, acyl-CoA synthetase, acyl-CoA transferase and acyl-CoA hydrolase.

Another strategy to reduce fatty acid biosynthesis is expression or overexpression of regulatory proteins which repress fatty acid forming genes. Acetyl-CoA carboxylase (EC 6.4.1.2) catalyzes the first step of fatty acid biosynthesis in many organisms: the ATP-dependent carboxylation of acetyl-CoA to malonyl-CoA. This enzyme utilizes biotin as a cofactor. Exemplary ACC enzymes are encoded by accABCD of *E. coli* (Davis et al, *J Biol Chem* 275:28593-8 (2000)), ACC1 of *Saccharomyces cerevisiae* and homologs (Sumper et al, *Methods Enzym* 71:34-7 (1981)). The mitochondrial acetyl-CoA carboxylase of *S. cerevisiae* is encoded by HFA1. Acetyl-CoA carboxylase holoenzyme formation requires attachment of biotin by a biotin:apoprotein ligase such as BPL1 of *S. cerevisiae*.

| Protein | GenBank ID | GI Number | Organism |
|---|---|---|---|
| ACC1 | CAA96294.1 | 1302498 | Saccharomyces cerevisiae |
| KLLA0F06072g | XP_455355.1 | 50310667 | Kluyveromyces lactis |
| ACC1 | XP_718624.1 | 68474502 | Candida albicans |
| YALI0C11407p | XP_501721.1 | 50548503 | Yarrowia lipolytica |
| ANI_1_1724104 | XP_001395476.1 | 145246454 | Aspergillus niger |
| accA | AAC73296.1 | 1786382 | Escherichia coli |
| accB | AAC76287.1 | 1789653 | Escherichia coli |
| accC | AAC76288.1 | 1789654 | Escherichia coli |
| accD | AAC75376.1 | 1788655 | Escherichia coli |
| HFA1 | NP_013934.1 | 6323863 | Saccharomyces cerevisiae |
| BPL1 | NP_010140.1 | 6320060 | Saccharomyces cerevisiae |

Proteins participating in the synthesis of fatty acids are shown below. The fatty acid synthase enzyme complex of yeast is composed of two multifunctional subunits, FAS1 and FAS2, which together catalyze the net conversion of acetyl-CoA and malonyl-CoA to fatty acids (Lomakin et al, *Cell* 129: 319-32 (2007)). Additional proteins associated with mitochondrial fatty acid synthesis include OAR1, Mct1, ETR1, ACP1 and PPT2. ACP1 is the mitochondrial acyl carrier protein and PPT2 encodes a phosphopantetheine transferase, which pantetheinylates mitochondrial ACP and is required for fatty acid biosynthesis in the mitochondria (Stuible et al, *J Biol Chem:* 273: 22334-9 (1998)). A non-genetic strategy for reducing activity of fatty acid synthases is to add an inhibitor such as cerulenin. Global regulators of lipid biosynthesis can also be altered to tune down endogenous fatty acid biosynthesis pathways during production of long chain alcohols or related products. An exemplary global regulator is SNF1 of *Yarrowia lipolyfica* and *Saccharomyces cerevisiae*.

| Protein | GenBank ID | GI Number | Organism |
|---|---|---|---|
| FAS1 | NP_012739.1 | 6322666 | *Saccharomyces cerevisiae* |
| FAS2 | NP_015093.1 | 6325025 | *Saccharomyces cerevisiae* |
| FAS1 | XP_451653.1 | 50303423 | *Kluyveromyces lactis* |
| FAS2 | XP_452914.1 | 50305907 | *Kluyveromyces lactis* |
| FAS1 | XP_716817.1 | 68478392 | *Candida albicans* |
| FAS2 | XP_723014.1 | 68465892 | *Candida albicans* |
| FAS1 | XP_500912.1 | 50546885 | *Yarrowia lipolytica* |
| FAS2 | XP_501096.1 | 50547253 | *Yarrowia lipolytica* |
| FAS1 | XP_001393490.2 | 317031809 | *Aspergillus niger* |
| FAS2 | XP_001388458.1 | 145228299 | *Aspergillus niger* |
| OAR1 | NP_012868.1 | 6322795 | *Saccharomyces cerevisiae* |
| MCT1 | NP_014864.4 | 398365823 | *Saccharomyces cerevisiae* |
| ETR1 | NP_009582.1 | 6319500 | *Saccharomyces cerevisiae* |
| ACP1 | NP_012729.1 | 6322656 | *Saccharomyces cerevisiae* |
| PPT2 | NP_015177.2 | 37362701 | *Saccharomyces cerevisiae* |
| SNF1 | CAG80498.1 | 49648180 | *Yarrowia lipolytica* |
| SNF1 | P06782.1 | 134588 | *Saccharomyces cerevisiae* |

Disruption or attenuation of elongase enzymes which convert acyl-CoA substrates to longer-chain length fatty acid derivatives longer than the product of interest can also be used to increase fatty alcohol, fatty aldehyde or fatty acid production. Elongase enzymes are found in compartments such as the mitochondria, endoplasmic reticulum, proteoliposomes and peroxisomes. For example, some yeast such as *S. cerevisiae* are able to synthesize long-chain fatty acids of chain length C16 and higher via a mitochondrial elongase which accepts exogenous or endogenous acyl-CoA substrates (Bessoule et al, *FEBS Lett* 214: 158-162 (1987)). This system requires ATP for activity. The endoplasmic reticulum also has an elongase system for synthesizing very long chain fatty acids (C18+) from acyl-CoA substrates of varying lengths (Kohlwein et al, *Mol Cell Biol* 21:109-25 (2001)). Genes involved in this system include TSC13, ELO2 and ELO3. ELO1 catalyzes the elongation of C12 acyl-CoAs to C16-C18 fatty acids.

| Protein | Accession # | GI number | Organism |
|---|---|---|---|
| ELO2 | NP_009963.1 | 6319882 | *Saccharomyces cerevisiae* |
| ELO3 | NP_013476.3 | 398366027 | *Saccharomyces cerevisiae* |
| TSC13 | NP_010269.1 | 6320189 | *Saccharomyces cerevisiae* |
| ELO1 | NP_012339.1 | 6322265 | *Saccharomyces cerevisiae* |

Native enzymes converting acyl-CoA pathway intermediates to acid byproducts can also reduce fatty alcohol, fatty aldehyde or fatty acid yield. For example, CoA hydrolases, transferases and synthetases can act on acyl-CoA intermediates to form short-, medium- or long chain acids. Disruption or attenuation of endogenous CoA hydrolases, CoA transerases and/or reversible CoA synthetases can be used to increase fatty alcohol, fatty aldehyde or fatty acid yield. Exempahy enzymes are shown in the table below.

| Protein | GenBank ID | GI number | Organism |
|---|---|---|---|
| Tes1 | NP_012553.1 | 6322480 | *Saccharomyces cerevisiae* s288c |
| ACH1 | NP_009538.1 | 6319456 | *Saccharomyces cerevisiae* s288c |
| EHD3 | NP_010321.1 | 6320241 | *Saccharomyces cerevisiae* s288c |
| YALI0F14729p | XP_505426.1 | 50556036 | *Yarrowia lipolytica* |
| YALI0E30965p | XP_504613.1 | 50554409 | *Yarrowia lipolytica* |
| KLLA0E16523g | XP_454694.1 | 50309373 | *Kluyveromyces lactis* |
| KLLA0E10561g | XP_454427.1 | 50308845 | *Kluyveromyces lactis* |
| ACH1 | P83773.2 | 229462795 | *Candida albicans* |
| CaO19.10681 | XP_714720.1 | 68482646 | *Candida albicans* |
| ANI_1_318184 | XP_001401512.1 | 145256774 | *Aspergillus niger* |
| ANI_1_1594124 | XP_001401252.2 | 317035188 | *Aspergillus niger* |
| tesB | NP_414986.1 | 16128437 | *Escherichia coli* |
| tesB | NP_355686.2 | 159185364 | *Agrobacterium tumefaciens* |
| atoA | 2492994 | P76459.1 | *Escherichia coli* |
| atoD | 2492990 | P76458.1 | *Escherichia coli* |

Enzymes that favor the degradation of products, MI-FAE cycle intermediates, MD-FAE cycle intermediates, FAACPE cycle intermediates, termination pathway intermediates, or isopropanol pathway intermediates can also be disrupted or attenuated. Examples include aldehyde dehydrogenases, aldehyde decarbonylases, oxidative alcohol dehydrogenases, and irreversible fatty acyl-CoA degrading enzymes.

For production of fatty alcohols, fatty aldehydes, fatty acids or isopropanol of the invention, deletion or attenuation of non-specific aldehyde dehydrogenases can improve yield. For production of fatty acids, expression of such an enzyme may improve product formation. Such enzymes can, for example, convert acetyl-CoA into acetaldehyde, fatty aldehydes to fatty acids, or fatty alcohols to fatty acids. Acylating aldehyde dehydrogenase enzymes are described in Example IV. Acid-forming aldehyde dehydrogenase are described in Examples VI and XII.

The pathway enzymes that favor the reverse direction can also be disrupted or attenuated, if they are detrimental to fatty alcohol, fatty aldehyde, fatty acid or isopropanol production. An example is long chain alcohol dehydrogenases (EC 1.1.1.192) that favor the oxidative direction. Exemplary long chain alcohol dehydrogenases are ADH1 and ADH2 of *Geobacillus thermodenitrificans*, which oxidize alcohols up to a chain length of C30 (Liu et al, *Physiol Biochem* 155:2078-85 (2009)). These and other exemplary fatty alcohol dehydrogenase enzymes are listed in Examples IV and V. If an alcohol-forming acyl-CoA reductase is utilized for fatty alcohol, fatty aldehyde or fatty acid biosynthesis, deletion of endogenous fatty alcohol dehydrogenases will substantially reduce back lux.

Beta-oxidation enzymes may be reversible and operate in the direction of acyl-CoA synthesis. However, if they are irreversible or strongly favored in the degradation direction they are candidates for disruption or attenuation. An enzyme that fall into this category includes FOX2 of *S. cerevisiae*, a multifunctional enzyme with 3-hydroxyacyl-CoA dehydrogenase and enoyl-CoA hydratase activity (Hiltunen et al, *J Biol Chem* 267: 6646-6653 (1992)). Additional genes include degradative thiolases such as POT1 and acyl-CoA dehydrogenases that utilize cofactors other than NAD(P)H (EG. EC 1.3.8.) such as fadE of *E. coli*.

| Protein | GenBank ID | GI Number | Organism |
|---|---|---|---|
| POT1 | NP_012106.1 | 6322031 | *Saccharomyces cerevisiae* |
| FOX2 | NP_012934.1 | 6322861 | *Saccharomyces cerevisiae* |
| fadE | AAC73325.2 | 87081702 | *Escherichia coli* |

Fatty acyl-CoA oxidase enzymes such as PDX1 of *S. cerevisiae* catalyze the oxygen-dependent oxidation of fatty acyl-CoA substrates. Enzymes with this activity can be disrupted or attenuated, if they are expressed under fatty alcohol, fatty aldehyde or fatty acid producing conditions. PDX1 (EC 1.3.3.6) genes and homologs are shown in the table below. PDX1 is subject to regulation by OAF1, which also activates genes involved in peroxisomal beta-oxidation, organization and biogenesis (Luo et al, *J Biol Chem* 271: 12068-75 (1996)). Regulators with functions similar to OAFL and neroxisomal fatty acid transporters PXA1 and PXA2 are also candidates for deletion.

| Protein | GenBank ID | GI Number | Organism |
|---|---|---|---|
| POX1 | NP_011310.1 | 6321233 | *Saccharomyces cerevisiae* |
| OAF1 | NP_009349.3 | 330443370 | *Saccharomyces cerevisiae* |
| PXA1 | NP_015178.1 | 6325110 | *Saccharomyces cerevisiae* |
| PXA2 | NP_012733.1 | 6322660 | *Saccharomyces cerevisiae* |
| YALI0F10857g | XP_505264.1 | 50555712 | *Yarrowia lipolytica* |
| YALI0D24750p | XP_503244.1 | 50551539 | *Yarrowia lipolytica* |
| YALI0E32835p | XP_504703.1 | 50554589 | *Yarrowia lipolytica* |
| YALI0E06567p | XP_503632.1 | 50552444 | *Yarrowia lipolytica* |
| YALI0E27654p | XP_504475.1 | 50554133 | *Yarrowia lipolytica* |
| YALI0C23859p | XP_502199.1 | 50549457 | *Yarrowia lipolytica* |
| POX | XP_455532.1 | 50311017 | *Kluyveromyces lactis* |
| POX104 | XP_721610.1 | 68468582 | *Candida albicans* |
| POX105 | XP_717995.1 | 68475844 | *Candida albicans* |
| POX102 | XP_721613.1 | 68468588 | *Candida albicans* |

Another candidate for disruption or attenuation is an acyl-CoA binding protein. The acyl binding protein ACB1 of *S. cerevisiae*, for example, binds acyl-CoA esters and shuttles them to acyl-CoA utilizing processes (Schjerling et al, J Biol Chem 271: 22514-21(1996)). Deletion of this protein did not impact growth rate and lead to increased accumulation of longer-chain acyl-CoA molecules. Acyl-CoA esters are involved in diverse cellular processes including lipid biosynthesis and homeostatis, signal transduction, growth regulation and cell differentiation (Rose et al, PNAS USA 89: 11287-11291(1992)).

| Protein | GenBank ID | GI Number | Organism |
|---|---|---|---|
| ACB1 | P31787.3 | 398991 | *Saccharomyces cerevisiae* |
| KLLA0B05643g | XP_451787.2 | 302309983 | *Kluyveromyces lactis* |
| YALI0E23185g | XP_002143080.1 | 210076210 | *Yarrowia lipolytica* |
| ANI_1_1084034 | XP_001390082.1 | 145234867 | *Aspergillus niger* |

To achieve high yields of fatty alcohols, fatty aldehydes fatty acids or isopropanol, it is desirable that the host organism can supply the cofactors required by the MI-FAE cycle, MD-FAE cycle, FAACPE cycle, the termination pathway and/or isopropanol pathway in sufficient quantities. In several organisms, in particular eukaryotic organisms, such as several *Saccharomyces, Kluyveromyces, Candida, Aspergillus*, and *Yarrowia* species, NADH is more abundant than NADPH in the cytosol as it is produced in large quantities by glycolysis. NADH can be made even more abundant by converting pyruvate to acetyl-CoA by means of heterologous or native NAD-dependant enzymes such as NAD-dependant pyruvate dehydrogenase, NAD-dependant formate dehydrogenase, NADH:ferredoxin oxidoreductase, or NAD-dependant acylating acetylaldehyde dehydrogenase in the cytosol. Given the abundance of NADH in the cytosol of most organisms, it can be beneficial for all reduction steps of the MI-FAE cycle, MD-FAE cycle, FAACPE cycle, terminatio pathway and/or isopropanol pathway to accept NADH as the reducing agent preferentially over other reducing agents such as NADPH. High yields of fatty alcohols, fatty aldehydes or fatty acids can thus be accomplished by, for example: 1) identifying and implementing endogenous or exogenous MI-FAE cycle, MD-FAE cycle and/or termination pathway enzymes with a stronger preference for NADH than other reducing equivalents such as NADPH; 2) attenuating one or more endogenous MI-FAE cycle, MD-FAE cycle or termination pathway enzymes that contribute NADPH-dependant reduction activity; 3) altering the cofactor specificity of endogenous or exogenous MI-FAE cycle, MD-FAE cycle, FAACPE cycle, termination pathway or isopropanol pathway enzymes so that they have a stronger preference for NADH than their natural versions; or 4) altering the cofactor specificity of endogenous or exogenous MI-FAE cycle, MD-FAE cycle, FAACPE cycle, termination pathway or isopropanol pathway enzymes so that they have a weaker preference for NADPH than their natural versions.

Strategies for engineering NADH-favoring MI-FAE cycle, MD-FAE cycle, FAACPE cycle termination pathways and/or isopropanol pathways are described in further detail in Example VIII. Methods for changing the cofactor specificity of an enzyme are well known in the art, and an example is described in Example IX.

If one or more of the MI-FAE cycle, MD-FAE cycle, FAACPE cycle, termination pathway and/or isopropanol pathway enzymes utilizes NADPH as the cofactor, it can be beneficial to increase the production of NADPH in the host organism. In particular, if the MI-FAE cycle, MD-FAE cycle, FAACPE cycle, termination pathway and/or isopropanol pathway is present in the cytosol of the host organism, methods for increasing NADPH production in the cytosol can be beneficial. Several approaches for increasing cytosolic production of NADPH can be implemented including channeling an increased amount of flux through the oxidative branch of the pentose phosphate pathway relative to wild-type, channeling an increased amount of flux through the Entner Doudoroff pathway relative to wild-type, introducing a soluble or membrane-bound transhydrogenase to convert NADH to NADPH, or employing NADP-dependant versions of the following enzymes: phosphorylating or non-phosphorylating glyceraldehyde-3-phosphate dehydrogenase, pyruvate dehydrogenase, formate dehydrogenase, or acylating acetylaldehyde dehydrogenase. These activities can be augmented by disrupting or attenuating native NAD-dependant enzymes including glyceraldehyde-3-phosphate dehydrogenase, pyruvate dehydrogenase, formate dehydrogenase, or acylating acetylaldehyde dehydrogenase. Strategies for engineering increased NADPH availability are described in Example X.

Synthesis of fatty alcohols, fatty aldehyes, fatty acids or isopropanol in the cytosol can be dependent upon the availability of sufficient carbon and reducing equivalents. Therefore, without being bound to any particular theory of operation, increasing the redox ratio of NAD(P)H to NAD (P) can help drive the MI-FAE cycle, MD-FAE cycle, FAACPE cycle, termination pathway and/or isopropanol pathway in the forward direction. Methods for increasing the redox ratio of NAD(P)H to NAD(P) include limiting respiration, attenuating or disrupting competing pathways that produce reduced byproducts such as ethanol and glycerol, attenuating or eliminating the use of NADH by NADH dehydrogenases, and attenuating or eliminating redox shuttles between compartments.

One exemplary method to provide an increased number of reducing equivalents, such as NAD(P)H, for enabling the formation of fatty alcohols, fatty aldehydes, fatty acids or isopropanol is to constrain the use of such reducing equivalents during respiration. Respiration can be limited by: reducing the availability of oxygen, attenuating NADH dehydrogenases and/or cytochrome oxidase activity, attenuating G3P dehydrogenase, and/or providing excess glucose to Crabtree positive organisms.

Restricting oxygen availability by culturing the non-naturally occurring eukaryotic organisms in a fermenter is one exmaple for limiting respiration and thereby increasing the ratio of NAD(P)H to NAD(P). The ratio of NAD(P)H/NAD(P) increases as culture conditions become more anaerobic, with completely anaerobic conditions providing the highest ratios of the reduced cofactors to the oxidized ones. For example, it has been reported that the ratio of NADH/NAD=0.02 in aerobic conditions and 0.75 in anaerobic conditions in E. coli (de Graes et al, J Bacteriol 181: 2351-57 (1999)).

Respiration can also be limited by reducing expression or activity of NADH dehydrogenases and/or cytochrome oxidases in the cell under aerobic conditions. In this case, respiration can be limited by the capacity of the electron transport chain. Such an approach has been used to enable anaerobic metabolism of E. coli under completely aerobic conditions (Portnoy et al, AEM 74:7561-9 (2008)). S. cerevisiae can oxidize cytosolic NADH directly using external NADH dehydrogenases, encoded by NDE1 and NDE2. One such NADH dehydrogenase in Yarrowia lipolytica is encoded by NDH2 (Kerscher et al, J Cell Sci 112:2347-54 (1999)). These and other NADH dehydrogenase enzymes are listed in the table below.

| Protein | GenBank ID | GI number | Organism |
| --- | --- | --- | --- |
| NDE1 | NP_013865.1 | 6323794 | Saccharomyces cerevisiae s288c |
| NDE2 | NP_010198.1 | 6320118 | Saccharomyces cerevisiae s288c |
| NDH2 | AJ006852.1 | 3718004 | Yarrowia lipolytica |
| ANI_1_610074 | XP_001392541.2 | 317030427 | Aspergillus niger |
| ANI_1_2462094 | XP_001394893.2 | 317033119 | Aspergillus niger |
| KLLA0E21891g | XP_454942.1 | 50309857 | Kluyveromyces lactis |
| KLLA0C06336g | XP_452480.1 | 50305045 | Kluyveromyces lactis |
| NDE1 | XP_720034.1 | 68471982 | Candida albicans |
| NDE2 | XP_717986.1 | 68475826 | Candida albicans |

Cytochrome oxidases of Saccharomyces cerevisiae include the COX gene products. COX1-3 are the three core subunits encoded by the mitochondrial genome, whereas COX4-13 are encoded by nuclear genes. Attenuation or disruption of any of the cytochrome genes results in a decrease or block in respiratory growth (Hermann and Funes, Gene 354:43-52 (2005)). Cytochrome oxidase genes in other organisms can be inferred by sequence homology.

| Protein | GenBank ID | GI number | Organism |
| --- | --- | --- | --- |
| COX1 | CAA09824.1 | 4160366 | Saccharomyces cerevisiae s288c |
| COX2 | CAA09845.1 | 4160387 | Saccharomyces cerevisiae s288c |
| COX3 | CAA09846.1 | 4160389 | Saccharomyces cerevisiae s288c |
| COX4 | NP_011328.1 | 6321251 | Saccharomyces cerevisiae s288c |
| COX5A | NP_014346.1 | 6324276 | Saccharomyces cerevisiae s288c |
| COX5B | NP_012155.1 | 6322080 | Saccharomyces cerevisiae s288c |
| COX6 | NP_011918.1 | 6321842 | Saccharomyces cerevisiae s288c |
| COX7 | NP_013983.1 | 6323912 | Saccharomyces cerevisiae s288c |
| COX8 | NP_013499.1 | 6323427 | Saccharomyces cerevisiae s288c |
| COX9 | NP_010216.1 | 6320136 | Saccharomyces cerevisiae s288c |
| COX12 | NP_013139.1 | 6323067 | Saccharomyces cerevisiae s288c |
| COX13 | NP_011324.1 | 6321247 | Saccharomyces cerevisiae s288c |

Cytosolic NADH can also be oxidized by the respiratory chain via the G3P dehydrogenase shuttle, consisting of cytosolic NADH-linked G3P dehydrogenase and a membrane-bound G3P:ubiquinone oxidoreductase. The deletion or attenuation of G3P dehydrogenase enzymes will also prevent the oxidation of NADH for respiration. Enzyme candidates encoding these enzymes are described herein.

Additionally, in Crabtree positive organisms, fermentative metabolism can be achieved in the presence of excess of glucose. For example, S. cerevisiae makes ethanol even under aerobic conditions. The formation of ethanol and glycerol can be reduced/eliminated and replaced by the production of fatty alcohol, fatty aldehyde, fatty acid or isopropanol in a Crabtree positive organism by feeding excess glucose to the Crabtree positive organism. In another aspect, provided herein is a method for producing fatty alcohols, fatty aldehydes, fatty acids, isopropanol comprising culturing a non-naturally occurring eukaryotic organism under conditions and for a sufficient period of time to produce fatty alcohol, fatty aldehyde, fatty acid or isopropanol, wherein the eukaryotic organism is a Crabtree positive organism, and wherein the eukaryotic organism is in a culture medium comprising excess glucose.

Preventing formation of reduced fermentation byproducts will increase the availability of both carbon and reducing equivalents for fatty alcohol, fatty aldehyde, fatty acid or isopropanol production. The two key reduced byproducts under anaerobic and microaerobic conditions are ethanol and glycerol. Ethanol is typically formed from pyruvate in two enzymatic steps catalyzed by pyruvate decarboxylase and ethanol dehydrogenase. Glycerol is formed from the glycolytic intermediate dihydroxyacetone phosphate by the enzymes glycerol-3-phsophate dehydrogenase and glycerol-3-phosphate phosphatase. Attenuation of one or more of these enzyme activities will increase the yield of fatty alcohols, fatty aldehydes, fatty acids or isopropanol. Strain engineering strategies for reducing or eliminating ethanol and glycerol formation are described herein.

Yeast such as S. cerevisiae can produce glycerol to allow for regeneration of NAD(P) under anaerobic conditions. Another way to reduce or eliminate glycerol production is by oxygen-limited cultivation (Bakker et al, supra). Glycerol formation only sets in when the specific oxygen uptake rates of the cells decrease below the rate that is required to reoxidize the NADH formed in biosynthesis.

In addition to the redox sinks listed above, malate dehydrogenase can potentially draw away reducing equivalents when it functions in the reductive direction. Several redox shuttles believed to be functional in S. cerevisiae utilize this enzyme to transfer reducing equivalents between the cytosol and the mitochondria. This transfer of redox can be prevented by attenuating malate dehydrogenase and/or malic enzyme activity. The redox shuttles that can be blocked by the attenuation of mdh include (i) malate-asparate shuttle, (ii) malate-oxaloacetate shuttle, and (iii) malate-pyruvate shuttle. Genes encoding malate dehydrogenase and malic enzymes are listed in the table below.

| Protein | GenBank ID | GI Number | Organism |
|---|---|---|---|
| MDH1 | NP_012838.1 | 6322765 | Saccharomyces cerevisiae |
| MDH2 | NP_014515.2 | 116006499 | Saccharomyces cerevisiae |
| MDH3 | NP_010205.1 | 6320125 | Saccharomyces cerevisiae |
| MAE1 | NP_012896.1 | 6322823 | Saccharomyces cerevisiae |
| MDH1 | XP_722674.1 | 68466384 | Candida albicans |
| MDH2 | XP_718638.1 | 68474530 | Candida albicans |
| MAE1 | XP_716669.1 | 68478574 | Candida albicans |
| KLLA0F25960g | XP_456236.1 | 50312405 | Kluyveromyces lactis |
| KLLA0E18635g | XP_454793.1 | 50309563 | Kluyveromyces lactis |
| KLLA0E07525g | XP_454288.1 | 50308571 | Kluyveromyces lactis |
| YALI0D16753p | XP_502909.1 | 50550873 | Yarrowia lipolytica |
| YALI0E18634p | XP_504112.1 | 50553402 | Yarrowia lipolytica |
| ANI_1_268064 | XP_001391302.1 | 145237310 | Aspergillus niger |
| ANI_1_12134 | XP_001396546.1 | 145250065 | Aspergillus niger |
| ANI_1_22104 | XP_001395105.2 | 317033225 | Aspergillus niger |

Overall, disruption or attenuation of the aforementioned sinks for redox either individually or in combination with the other redox sinks can eliminate or lower the use of reducing power for respiration or byproduct formation. It has been reported that the deletion of the external NADH dehydrogenases (NDE1 and NDE2) and the mitochondrial G3P dehydrogenase (GUT2) almost completely eliminates cytosolic NAD+ regeneration in S. cerevisiae (Overkamp et al, J Bacterial 182:2823-30 (2000)).

Microorganisms of the invention produce fatty alcohols, fatty aldehydes fatty acids or isopropanol and optionally secrete the fatty alcohols, fatty aldehydes fatty acids or isopropanol into the culture medium. S. cerevisiae, Yarrowia lipolytica and E. coli harboring heterologous fatty alcohol forming activities accululated fatty alcohols intracellularly; however fatty alcohols were not detected in the culture medium (Behrouzian et al, United States Patent Application 20100298612). The introduction of fatty acyl-CoA reductase enzymes with improved activity resulted in higher levels of fatty alcohol secreted into the culture media. Alternately, introduction of a fatty alcohol, fatty aldehyde, fatty acid or isopropanol transporter or transport system can improve extracellular accumulation of fatty alcohols, fatty aldehydes or fatty acids. Exemplary transporters are listed in the table below.

| Protein | GenBank ID | GI Number | Organism |
|---|---|---|---|
| Fatp | NP_524723.2 | 24583463 | Drosophila melanogaster |
| AY161280.1:45..1757 | AAN73268.1 | 34776949 | Rhodococcus erythropolis |
| acrA | CAF23274.1 | 46399825 | Candidatus Protochlamydia amoebophila |
| acrB | CAF23275.1 | 46399826 | Candidatus Protochlamydia amoebophila |
| CER5 | AY734542.1 | 52354013 | Arabidopsis thaliana |
| AmiS2 | JC5491 | 7449112 | Rhodococcus sp. |
| ANI_1_1160064 | XP_001391993.1 | 145238692 | Aspergillus niger |
| YALI0E1601g | XP_504004.1 | 50553188 | Yarrowia lipolytica |

Thus, in some embodiments, the invention provides a non-naturally occurring microbial organism as disclosed herein having one or more gene disruptions, wherein the one or more gene disruptions occurr in endogenous genes encoding proteins or enzymes involved in: native production of ethanol, glycerol, acetate, formate, lactate, $CO_2$, fatty acids, or malonyl-CoA by said microbial organism; transfer of pathway intermediates to cellular compartments other than the cytosol; or native degradation of a MI-FAE cycle intermediate, a MD-FAE cycle intermediate, a FAACPE cycle intermediate or a termination pathway intermediate by the microbial organism, the one or more gene disruptions confer increased production of a fatty alcohol, fatty aldehyde or fatty acid in the microbial organism. Accordingly, the protein or enzyme can be a fatty acid synthase, an acetyl-CoA carboxylase, a biotin:apoenzyme ligase, an acyl carrier protein, a thioesterase, an acyltransferase, an ACP malonyltransfemse, a fatty acid elongase, an acyl-CoA synthetase, an acyl-CoA transferase, an acyl-CoA hydrolase, a pyruvate decarboxylase, a lactate dehydrogenase, an alcohol dehydrogenase, an acid-forming aldehyde dehydrogenases, an acetate kinase, a phosphotransacetylase, a pyruvate oxidase, a glycerol-3-phosphate dehydrogenase, a glycerol-3-phosphate phosphatase, a mitochondrial pyruvate carrier, a peroxisomal fatty acid transporter, a peroxisomal acyl-CoA transporter, a peroxisomal camitine/acylcamitine transferase, an acyl-CoA oxidase, or an acyl-CoA binding protein. In some aspects, the one or more gene disruptions include a deletion of the one or more genes.

In some embodiments, the invention provides a non-naturally occurring microbial organism as described herein, wherein one or more enzymes of the MI-FAE cycle, the MD-FAE cycle, the FAACPE cycle or the termination pathway preferentially react with an NADH cofactor or have reduced preference for reacting with an NAD(P)H cofactor. For example, the one or more enzymes of the MI-FAE cycle can be a 3-ketoacyl-CoA reductase or an enoyl-CoA reductase. As another example, the one or more enzymes of the FAACPE cycle can be a 3-ketoacyl-ACP reductase or an enoyl-ACP reductase. For the termination pathway, the one or more enzymes can be an acyl-CoA reductase (aldehyde forming), an alcohol dehydrogenase, an acyl-CoA reductase (alcohol forming), an aldehyde decarbonylase, an acyl-ACP reductase, an aldehyde dehydrogenase (acid forming) or a carboxylic acid reductase.

In some embodiments, the invention provides a non-naturally occurring microbial organism as described herein having one or more gene disruptions in genes encoding proteins or enzymes that result in an increased mtio of NAD(P)H to NAD(P) present in the cytosol of the microbial organism following the disruptions. Accordingly, the gene encoding a protein or enzyme that results in an increased mtio of NAD(P)H to NAD(P) present in the cytosol of the microbial organism following the disruptions can be an NADH dehydrogenase, a cytochrome oxidase, a G3P dehydrogenase, G3P phosphatase, an alcohol dehydrogenase, a pyruvate decarboxylase, an aldehyde dehydrogenase (acid forming), a lactate dehydrogenase, a glycerol-3-phosphate dehydrogenase, a glycerol-3-phosphate:quinone oxidoreductase, a malic enzyme and a malate dehydrogenase. In some aspects, the one or more gene disruptions include a deletion of the one or more genes.

In some embodiments, the non-naturally occurring microbial organism of the invention is Crabtree positive and is in culture medium comprising excess glucose. In such conditions, as described herein, the microbial organism can result in increasing the ratio of NAD(P)H to NAD(P) present in the cytosol of the microbial organism.

In some embodiments, the invention provides a non-naturally occurring microbial organism as described herein having at least one exogenous nucleic acid encoding an extracellular transporter or an extracellular transport system for a fatty alcohol, fatty aldehyde or fatty acid of the invention.

In some embodiments, the invention provides a non-naturally occurring microbial organism as described herein, wherein one or more endogenous enzymes involved in: native production of ethanol, glycerol, acetate, formate, lactate, $CO_2$, fatty acids, or malonyl-CoA by said microbial organism; transfer of pathway intermediates to cellular compartments other than the cytosol; or native degradation of a MI-FAE cycle intermediate, a MD-FAE cycle intermediate, a FAACPE cycle intermediate or a termination pathway intermediate by said microbial organism, has attenuated enzyme activity or expression levels. Accordingly, the endogenous enzyme can be a fatty acid synthase, an acetyl-CoA carboxylase, a biotin:apoenzyme ligase, an acyl carrier protein, a thioesterase, an acyltransferase, an ACP malonyltransferase, a fatty acid elongase, an acyl-CoA synthetase, an acyl-CoA transferase, an acyl-CoA hydrolase, a pyruvate decarboxylase, a lactate dehydrogenase, an alcohol dehydrogenase, an acid-forming aldehyde dehydrogenases, an acetate kinase, a phosphotransacetylase, a pyruvate oxidase, a glycerol-3-phosphate dehydrogenase, a glycerol-3-phosphate phosphatase, a mitochondrial pyruvate carrier, a peroxisomal fatty acid transporter, a peroxisomal acyl-CoA transporter, a peroxisomal carnitine/acykarnitine transferase, an acyl-CoA oxidase, or an acyl-CoA binding protein.

In some embodiments, the invention provides a non-naturally occurring microbial organism as described herein, wherein one or more endogenous enzymes involved in the oxidation of NAD(P)H or NADH, has attenuated enzyme activity or expression levels. Accordingly, the one or more endogenous enzymes can be a NADH dehydrogenase, a cytochrome oxidase, a G3P dehydrogenase, G3P phosphatase, an alcohol dehydrogenase, a pyruvate decarboxylase, an aldehyde dehydrogenase (acid forming), a lactate dehydrogenase, a glycerol-3-phosphate dehydrogenase, a glycerol-3-phosphate:quinone oxidoreductase, a malic enzyme and a malate dehydrogenase.

The non-naturally occurring microbal organisms of the invention can contain stable genetic alterations, which refers to microorganisms that can be cultured for greater than five generations without loss of the alteration. Generally, stable genetic alterations include modifications that persist greater than 10 generations, particularly stable modifications will persist more than about 25 generations, and more particularly, stable genetic modifications will be greater than 50 generations, including indefinitely.

In the case of gene disruptions, a particularly useful stable genetic alteration is a gene deletion. The use of a gene deletion to introduce a stable genetic alteration is particularly useful to reduce the likelihood of a reversion to a phenotype prior to the genetic alteration. For example, stable growth-coupled production of a biochemical can be achieved, for example, by deletion of a gene encoding an enzyme catalyzing one or more reactions within a set of metabolic modifications. The stability of growth-coupled production of a biochemical can be further enhanced through multiple deletions, significantly reducing the likelihood of multiple compensatory reversions occurring for each disrupted activity.

Also provided is a method of producing a non-naturally occurring microbial organisms having stable growth-coupled production of fatty alcohol, fatty aldehyde, fatty acid or isopropanol. The method can include identifying in silico a set of metabolic modifications that increase production of fatty alcohol, fatty aldehyde, fatty acid or isopropanol, for example, increase production during exponential growth; genetically modifying an organism to contain the set of metabolic modifications that increase production of fatty alcohol, fatty aldehyde, fatty acid or isopropanol, and culturing the genetically modified organism. If desired, culturing can include adaptively evolving the genetically modified organism under conditions requiring production of fatty alcohol, fatty aldehyde, fatty acid or isopropanol. The methods of the invention are applicable to bacterium, yeast and fungus as well as a variety of other cells and microorganism, as disclosed herein.

Thus, the invention provides a non-naturally occurring microbial organism comprising one or more gene disruptions that confer increased production of fatty alcohol, fatty aldehyde, fatty acid or isopropanol. In one embodiment, the one or more gene disruptions confer growth-coupled production of fatty alcohol, fatty aldehyde, fatty acid or isopropanol, and can, for example, confer stable growth-coupled production of fatty alcohol, fatty aldehyde, fatty acid or isopropanol. In another embodiment, the one or more gene disruptions can confer obligatory coupling of fatty alcohol, fatty aldehyde, fatty acid or isopropanol production to growth of the microbial organism. Such one or more gene disruptions reduce the activity of the respective one or more encoded enzymes.

The non-naturally occurring microbial organism can have one or more gene disruptions included in a gene encoding a enzyme or protein disclosed herein. As disclosed herein, the one or more gene disruptions can be a deletion. Such non-naturally occurring microbial organisms of the invention include bacteria, yeast, fungus, or any of a variety of other microorganisms applicable to fermentation processes, as disclosed herein.

Thus, the invention provides a non-naturally occurring microbial organism, comprising one or more gene disruptions, where the one or more gene disruptions occur in genes encoding proteins or enzymes where the one or more gene disruptions confer increased production of fatty alcohol, fatty aldehyde, fatty acid or isopropanol in the organism. The production of fatty alcohol, fatty aldehyde, fatty acid or isopropanol can be growth-coupled or not growth-coupled. In a particular embodiment, the production of fatty alcohol, fatty aldehyde, fatty acid or isopropanol can be obligatorily coupled to growth of the organism, as disclosed herein.

The invention provides non naturally occurring microbial organisms having genetic alterations such as gene disruptions that increase production of fatty alcohol, fatty aldehyde, fatty acid or isopropanol, for example, growth-coupled production of fatty alcohol, fatty aldehyde, fatty acid or isopropanol. Product production can be, for example, obligatorily linked to the exponential growth phase of the microorganism by genetically altering the metabolic pathways of the cell, as disclosed herein. The genetic alterations can increase the production of the desired product or even make the desired product an obligatory product during the growth phase. Metabolic alterations or transformations that result in increased production and elevated levels of fatty alcohol, fatty aldehyde, fatty acid or isopropanol biosynthesis are exemplified herein. Each alteration corresponds to the requisite metabolic reaction that should be functionally disrupted. Functional disruption of all reactions within one or more of the pathways can result in the increased production of fatty alcohol, fatty aldehyde, fatty acid or isopropanol by the engineered strain during the growth phase.

Each of these non-naturally occurring alterations result in increased production and an enhanced level of fatty alcohol, fatty aldehyde, fatty acid or isopropanol production, for example, during the exponential growth phase of the microbial organism, compared to a strain that does not contain such metabolic alterations, under appropriate culture conditions. Appropriate conditions include, for example, those disclosed herein, including conditions such as particular carbon sources or reactant availabilities and/or adaptive evolution.

Given the teachings and guidance provided herein, those skilled in the art will understand that to introduce a metabolic alteration such as attenuation of an enzyme, it can be necessary to disrupt the catalytic activity of the one or more enzymes involved in the reaction. Alternatively, a metabolic alteration can include disrupting expression of a regulatory protein or cofactor necessary for enzyme activity or maximal activity. Furthermore, genetic loss of a cofactor necessary for an enzymatic reaction can also have the same effect as a disruption of the gene encoding the enzyme. Disruption can occur by a variety of methods including, for example, deletion of an encoding gene or incorporation of a genetic alteration in one or more of the encoding gene sequences. The encoding genes targeted for disruption can be one, some, or all of the genes encoding enzymes involved in the catalytic activity. For example, where a single enzyme is involved in a targeted catalytic activity, disruption can occur by a genetic alteration that reduces or eliminates the catalytic activity of the encoded gene product. Similarly, where the single enzyme is multimeric, including heteromeric, disruption can occur by a genetic alteration that reduces or destroys the function of one or all subunits of the encoded gene products. Destruction of activity can be accomplished by loss of the binding activity of one or more subunits required to form an active complex, by destruction of the catalytic subunit of the multimeric complex or by both. Other functions of multimeric protein association and activity also can be targeted in order to disrupt a metabolic reaction of the invention. Such other functions are well known to those skilled in the art. Similarly, a target enzyme activity can be reduced or eliminated by disrupting expression of a protein or enzyme that modifies and/or activates the target enzyme, for example, a molecule required to convert an apoenzyme to a holoenzyme. Further, some or all of the functions of a single polypeptide or multimeric complex can be disrupted according to the invention in order to reduce or abolish the catalytic activity of one or more enzymes involved in a reaction or metabolic modification of the invention. Similarly, some or all of enzymes involved in a reaction or metabolic modification of the invention can be disrupted so long as the targeted reaction is reduced or eliminated.

Given the teachings and guidance provided herein, those skilled in the art also will understand that an enzymatic reaction can be disrupted by reducing or eliminating reactions encoded by a common gene and/or by one or more orthologs of that gene exhibiting similar or substantially the same activity. Reduction of both the common gene and all orthologs can lead to complete abolishment of any catalytic activity of a targeted reaction. However, disruption of either the common gene or one or more orthologs can lead to a reduction in the catalytic activity of the targeted reaction sufficient to promote coupling of growth to product biosynthesis. Exemplified herein are both the common genes encoding catalytic activities for a variety of metabolic modifications as well as their orthologs. Those skilled in the art will understand that disruption of some or all of the genes encoding a enzyme of a targeted metabolic reaction can be practiced in the methods of the invention and incorporated into the non-naturally occurring microbial organisms of the invention in order to achieve the increased production of fatty alcohol, fatty aldehyde, fatty acid or isopropanol or growth-coupled product production.

Given the teachings and guidance provided herein, those skilled in the art also will understand that enzymatic activity or expression can be attenuated using well known methods. Reduction of the activity or amount of an enzyme can mimic complete disruption of a gene if the reduction causes activity of the enzyme to fall below a critical level that is normally required for a pathway to function. Reduction of enzymatic activity by various techniques rather than use of a gene disruption can be important for an organism's viability. Methods of reducing enzymatic activity that result in similar or identical effects of a gene disruption include, but are not limited to: reducing gene transcription or translation; destabilizing mRNA, protein or catalytic RNA; and mutating a gene that affects enzyme activity or kinetics (See, Sambrook et al., *Molecular Cloning: A Laboratory Manual*, Third Ed., Cold Spring Harbor Laboratory, New York (2001); and Ausubel et al., *Current Protocols in Molecular Biology*, John Wiley and Sons, Baltimore, MD (1999). Natural or imposed regulatory controls can also accomplish enzyme attenuation including: promoter replacement (See, Wang et al., *Mol. Biotechnol.* 52(2):300-308 (2012)); loss or alteration of transcription factors (Dietrick et al., *Annu. Rev. Biochem.* 79:563-590 (2010); and Simicevic et al., *Mol. Biosyst.* 6(3):462-468 (2010)); introduction of inhibitory RNAs or peptides such as siRNA, antisense RNA, RNA or peptide/small-molecule binding aptamers, ribozymes, aptazymes and riboswitches (Wieland et al., *Methods* 56(3): 351-357 (2012); O'Sullivan, *Anal. Bioanal. Chem.* 372(1): 44-48 (2002); and Lee et al., *Curr. Opin. Biotechnol.* 14(5): 505-511(2003)); and addition of drugs or other chemicals that reduce or disrupt enzymatic activity such as an enzyme inhibitor, an antibiotic or a target-specific drug.

One skilled in the art will also understand and recognize that attenuation of an enzyme can be done at various levels. For example, at the gene level, a mutation causing a partial or complete null phenotype, such as a gene disruption, or a mutation causing epistatic genetic effects that mask the activity of a gene product (Miko, *Nature Education* 1(1) (2008)), can be used to attenuate an enzyme. At the gene expression level, methods for attenuation include: coupling transcription to an endogenous or exogenous inducer, such as isopropylthio-β-galactoside (IPTG), then adding low amounts of inducer or no inducer during the production phase (Donovan et al., *J. Ind. Microbiol.* 16(3):145-154 (1996); and Hansen et al., *Curr. Microbiol.* 36(6):341-347 (1998)); introducing or modifying a positive or a negative regulator of a gene; modify histone acetylation/deacetylation in a eukaryotic chromosomal region where a gene is integrated (Yang et al., *Curr. Opin. Genet. Dev.* 13(2):143-153 (2003) and Kurdistani et al., *Nat. Rev. Mol. Cell Biol.* 4(4):276-284 (2003)); introducing a transposition to disrupt a promoter or a regulatory gene (Bleykasten-Brosshans et al., *C. R. Biol.* 33(8-9):679-686 (2011); and McCue et al., *PLoS Genet.* 8(2):e1002474 (2012)); flipping the orientation of a transposable element or promoter region so as to modulate gene expression of an adjacent gene (Wang et al., Genetics 120(4):875-885 (1988); Hayes, Annu. Rev. Genet. 37:3-29 (2003); in a diploid organism, deleting one allele resulting in loss of heterozygosity (Daigaku et al., *Mutation Research/Fundamental and Molecular Mechanisms of Mutagenesis* 600(1-2)177-183 (2006)); introducing nucleic acids that increase RNA degradation (Houseley et al., *Cell*, 136(4):763-776 (2009); or in bacteria, for example, introduction of a transfer-messenger RNA (tmRNA) tag, which can lead to RNA degradation and ribosomal stalling (Sunohara et al., *RNA* 10(3):378-386 (2004); and Sunohara et al., *J. Biol. Chem.* 279:15368-15375 (2004)). At the translational level, attenuation can include: introducing rare codons to limit translation (Angov, *Biotechnol. J.* 6(6):650-659 (2011)); introducing RNA interference molecules that block translation (Castel et al., *Nat. Rev. Genet.* 14(2):100-112 (2013); and Kawasaki et al., *Curr. Opin. Mol. Ther.* 7(2): 125-131(2005); modifying regions outside the coding sequence, such as introducing secondary structure into an untranslated region (UTR) to block translation or reduce efficiency of translation (Ringner et al., *PLoS Comput. Biol.* 1(7):e72 (2005)); adding RNAase sites for rapid transcript degradation (Pasquinelli, *Nat. Rev. Genet.* 13(4):271-282 (2012); and Arraiano et al., *FEMS Microbiol. Rev.* 34(5): 883-932 (2010); introducing antisense RNA oligomers or antisense transcripts (Nashizawa et al., *Front. Biosci.* 17:938-958 (2012)); introducing RNA or peptide aptamers, ribozymes, aptazymes, riboswitches (Wieland et al., *Methods* 56(3):351-357 (2012); O'Sullivan, *Anal. Bioanal. Chem.* 372(1):44-48 (2002); and Lee et al., *Curr. Opin. Biotechnol.* 14(5):505-511(2003)); or introducing translational regulatory elements involving RNA structure that can prevent or reduce translation that can be controlled by the presence or absence of small molecules (Araujo et al., *Comparative and Functional Genomics*, Article ID 475731, 8 pages (2012)). At the level of enzyme localization and/or longevity, enzyme attenuation can include: adding a degradation tag for faster protein turnover (Hochstrasser, *Annual Rev. Genet.* 30:405-439 (1996); and Yuan et al., *PLoS One* 8(4):e62529 (2013)); or adding a localization tag that results in the enzyme being secreted or localized to a subcellular compartment in a eukaryotic cell, where the enzyme would not be able to react with its normal substrate (Nakai et al. *Genomics* 14(4):897-911 (1992); and Russell et al., *J. Bact.* 189(21)7581-7585 (2007)). At the level of post-translational regulation, enzyme attenuation can include: increasing intracellular concentration of known inhibitors; or modifying post-translational modified sites (Mann et al., *Nature Biotech.* 21:255-261 (2003)). At the level of enzyme activity, enzyme attenuation can include: adding an endogenous or an exogenous inhibitor, such as an enzyme inhibitor, an antibiotic or a target-specific drug, to reduce enzyme activity; limiting availability of essential cofactors, such as vitamin B12, for an enzyme that requires the cofactor; chelating a metal ion that is required for enzyme activity; or introducing a dominant negative mutation. The applicability of a technique for attenuation described above can depend upon whether a given host microbial organism is prokaryotic or eukaryotic, and it is understand that a determination of what is the appropriate technique for a given host can be readily made by one skilled in the art.

In some embodiments, microaerobic designs can be used based on the growth-coupled formation of the desired product. To examine this, production cones can be constructed for each strategy by first maximizing and, subsequently minimizing the product yields at different rates of biomass formation feasible in the network. If the rightmost boundary of all possible phenotypes of the mutant network is a single point, it implies that there is a unique optimum yield of the product at the maximum biomass formation rate possible in the network. In other cases, the rightmost boundary of the feasible phenotypes is a vertical line, indicating that at the point of maximum biomass the network can make any amount of the product in the calculated range, including the lowest amount at the bottommost point of the vertical line. Such designs are given a low priority.

The fatty alcohol, fatty aldehyde, fatty acid or isopropanol-production strategies identified in the various tables disclosed herein can be disrupted to increase production of fatty alcohol, fatty aldehyde, fatty acid or isopropanol. Accordingly, the invention also provides a non-naturally occurring microbial organism having metabolic modifications coupling fatty alcohol, fatty aldehyde, fatty acid or isopropanol production to growth of the organism, where the metabolic modifications includes disruption of one or more genes selected from the genes encoding proteins and/or enzymes shown in the various tables disclosed herein.

Each of the strains can be supplemented with additional deletions if it is determined that the strain designs do not sufficiently increase the production of fatty alcohol, fatty aldehyde, fatty acid or isopropanol and/or couple the formation of the product with biomass formation. Alternatively, some other enzymes not known to possess significant activity under the growth conditions can become active due to adaptive evolution or random mutagenesis. Such activities can also be knocked out. However, the list of gene deletion disclosed herein allows the construction of strains exhibiting high-yield production of fatty alcohol, fatty aldehyde, fatty acid or isopropanol, including growth-coupled production of fatty alcohol, fatty aldehyde, fatty acid or isopropanol.

In some embodiments, the invention provides a method for producing a compound of Formula (I):

(I)

wherein $R_1$ is $C_{1-24}$ linear alkyl; $R_2$ is $CH_2OH$, CHO, or COOH; $R_3$ is H, OH, or oxo (=O); and ‾‾‾‾‾ represents a single or double bond with the proviso that the valency of the carbon atom to which $R_3$ is attached is four, comprising culturing a non-naturally occurring microbial organism described herein under conditions and for a sufficient period of time to produce the compound of Formula (I), wherein the non-naturally occurring microbial organism has one or more gene disruptions, wherein the one or more gene disruptions occurr in endogenous genes encoding proteins or enzymes involved in: native production of ethanol, glycerol, acetate, formate, lactate, $CO_2$, fatty acids, or malonyl-CoA by said microbial organism; transfer of pathway intermediates to cellular compartments other than the cytosol; or native degradation of a MI-FAE cycle intermediate, a MD-FAE cycle intermediate or a termination pathway intermediate by the microbial organism, the one or more gene disruptions confer increased production of a fatty alcohol, fatty aldehyde or fatty acid in the microbial organism. Accordingly, the protein or enzyme can be a fatty acid synthase, an acetyl-CoA carboxylase, a biotin:apoenzyme ligase, an acyl carrier protein, a thioesterase, an acyltransferases, an ACP malonyltransferase, a fatty acid elongase, an acyl-CoA synthetase, an acyl-CoA transferase, an acyl-CoA hydrolase, a pyruvate decarboxylase, a lactate dehydrogenase, an alcohol dehydrogenase, an acid-forming aldehyde dehydrogenases, an acetate kinase, a phosphotransacetylase, a pyruvate oxidase, a glycerol- 3-phosphate dehydrogenase, a glycerol-3-phosphate phosphatase, a mitochondrial pyruvate carrier, a peroxisomal fatty acid transporters, a peroxisomal acyl-CoA transporters, a peroxisomal camitine/acykarnitine transferases, an acyl-CoA oxidase, or an acyl-CoA binding protein. In some aspects, the one or more gene disruptions include a deletion of the one or more genes.

In some embodiments, the invention provides a method for producing a fatty alcohol, fatty aldehyde or fatty acid using a non-naturally occurring microbial organism as described herein, wherein one or more enzymes of the MI-FAE cycle, MD-FAE cycle, FAACPE cycle or the termination pathway preferentially react with an NADH cofactor or have reduced preference for reacting with an NAD(P)H cofactor. For example, the one or more enzymes of the MI-FAE cycle or MD-FAE cycle can be a 3-ketoacyl-CoA reductase or an enoyl-CoA reductase. As another example, the one or more enzymes of the FAACPE cycle can be a 3-ketoacyl-ACP reductase or an enoyl-ACP reductase. For the termination pathway, the one or more enzymes can be an acyl-CoA reductase (aldehyde forming), an alcohol dehydrogenase, an acyl-CoA reductase (alcohol forming), an aldehyde decarbonylase, an acyl-ACP reductase, an aldehyde dehydrogenase (acid forming) or a carboxylic acid reductase.

In some embodiments, the invention provides a method for producing a fatty alcohol, fatty aldehyde or fatty acid using a non-naturally occurring microbial organism as described herein having one or more gene disruptions in genes encoding proteins or enzymes that result in an increased ratio of NAD(P)H to NAD(P) present in the cytosol of the microbial organism following the disruptions. Accordingly, the gene encoding a protein or enzyme that results in an increased ratio of NAD(P)H to NAD(P) present in the cytosol of the microbial organism following the disruptions can be an NADH dehydrogenase, a cytochrome oxidase, a glycerol-3-phosphate (G3P) dehydrogenase, a glycerol-3-phosphate (G3P) phosphatase, an alcohol dehydrogenase, a pyruvate decarboxylase, an aldehyde dehydrogenase (acid forming), a lactate dehydrogenase, a glycerol-3-phosphate dehydrogenase, a glycerol-3-phosphate:quinone oxidoreductase, a malic enzyme and a malate dehydrogenase. In some aspects, the one or more gene disruptions include a deletion of the one or more genes.

In some embodiments, the invention provides a method for producing a fatty alcohol, fatty aldehyde or fatty acid using a non-naturally occurring microbial organism of the invention that is Crabtree positive and is in culture medium comprising excess glucose. In such conditions, as described herein, the microbial organism can result in increasing the ratio of NAD(P)H to NAD(P) present in the cytosol of the microbial organism.

In some embodiments, the invention provides a method for producing a fatty alcohol, fatty aldehyde or fatty acid using a non-naturally occurring microbial organism as described herein having at least one exogenous nucleic acid encoding an extracellular transporter or an extracellular transport system for a fatty alcohol, fatty aldehyde or fatty acid of the invention.

In some embodiments, the invention provides a method for producing a fatty alcohol, fatty aldehyde or fatty acid using a non-naturally occurring microbial organism as described herein, wherein one or more endogenous enzymes involved in: native production of ethanol, glycerol, acetate, formate, lactate, $CO_2$, fatty acids, or malonyl-CoA by said microbial organism; transfer of pathway intermediates to cellular compartments other than the cytosol; or native degradation of a MI-FAE cycle intermediate, a MD-FAE cycle intermediate, a FAACPE cycle intermediate or a termination pathway intermediate by said microbial organism, has attenuated enzyme activity or expression levels. Accordingly, the endogenous enzyme can be a fatty acid synthase, an acetyl-CoA carboxylase, a biotin:apoenzyme ligase, an acyl carrier protein, a thioesterase, an acyltransferase, an ACP malonyltransferase, a fatty acid elongase, an acyl-CoA synthetase, an acyl-CoA transferase, an acyl-CoA hydrolase, a pyruvate decarboxylase, a lactate dehydrogenase, an alcohol dehydrogenase, an acid-forming aldehyde dehydrogenases, an acetate kinase, a phosphotransacetylase, a pyruvate oxidase, a glycerol-3-phosphate dehydrogenase, a glycerol-3-phosphate phosphatase, a mitochondrial pyruvate carrier, a peroxisomal fatty acid transporter, a peroxisomal acyl-CoA transporter, a peroxisomal carnitine/acylcarnitine transferase, an acyl-CoA oxidase, and an acyl-CoA binding protein.

In some embodiments, the invention provides a method for producing a fatty alcohol, fatty aldehyde or fatty acid using a non-naturally occurring microbial organism as described herein, wherein one or more endogenous enzymes involved in the oxidation of NAD(P)H or NADH, has attenuated enzyme activity or expression levels. Accordingly, the one or more endogenous enzymes can be NADH dehydrogenase, a cytochrome oxidase, a glycerol-3-phosphate dehydrogenase, glycerol-3-phosphate phosphatase, an alcohol dehydrogenase, a pyruvate decarboxylase, an aldehyde dehydrogenase (acid forming), a lactate dehydrogenase, a glycerol-3-phosphate dehydrogenase, a glycerol-3-phosphate:quinone oxidoreductase, a malic enzyme and a malate dehydrogenase.

A fatty alcohol, fatty aldehyde or fatty acid can be harvested or isolated at any time point during the culturing of the microbial organism, for example, in a continuous and/or near-continuous culture period, as disclosed herein. Generally, the longer the microorganisms are maintained in a continuous and/or near-continuous growth phase, the proportionally greater amount of fatty alcohol, fatty aldehyde or fatty acid can be produced.

Therefore, the invention additionally provides a method for producing fatty alcohol, fatty aldehyde or fatty acid that includes culturing a non-naturally occurring microbial organism having one or more gene disruptions, as disclosed herein. The disruptions can occur in one or more genes encoding an enzyme that increases production of fatty alcohol, fatty aldehyde or fatty acid, including optionally coupling fatty alcohol, fatty aldehyde or fatty acid production to growth of the microorganism when the gene disruption reduces or eliminates an activity of the enzyme. For example, the disruptions can confer stable growth-coupled production of fatty alcohol, fatty aldehyde or fatty acid onto the non-naturally microbial organism.

In some embodiments, the gene disruption can include a complete gene deletion. In some embodiments other methods to disrupt a gene include, for example, frameshifting by omission or addition of oligonucleotides or by mutations that render the gene inoperable. One skilled in the art will recognize the advantages of gene deletions, however, because of the stability it confers to the non-naturally occurring organism from reverting to a parental phenotype in which the gene disruption has not occurred. In particular, the gene disruptions are selected from the gene sets as disclosed herein.

Once computational predictions are made of gene sets for disruption to increase production of fatty alcohol, fatty aldehyde or fatty acid, the strains can be constructed, evolved, and tested. Gene disruptions, including gene deletions, are introduced into host organism by methods well known in the art. A particularly useful method for gene disruption is by homologous recombination, as disclosed herein.

The engineered strains can be characterized by measuring the growth mte, the substrate uptake mte, and/or the product/byproduct secretion mte. Cultures can be grown and used as inoculum for a fresh batch culture for which measurements are taken during exponential growth. The growth mte can be determined by measuring optical density using a spectrophotometer (A600). Concentrations of glucose and other organic acid byproducts in the culture supernatant can be determined by well known methods such as HPLC, GC-MS or other well known analytical methods suitable for the analysis of the desired product, as disclosed herein, and used to calculate uptake and secretion rates.

Strains containing gene disruptions can exhibit suboptimal growth mtes until their metabolic networks have adjusted to their missing functionalities. To assist in this adjustment, the strains can be adaptively evolved. By subjecting the strains to adaptive evolution, cellular growth rate becomes the primary selection pressure and the mutant cells are compelled to reallocate their metabolic fluxes in order to enhance their rates of growth. This reprogramming of metabolism has been recently demonstrated for several *E. coli* mutants that had been adaptively evolved on various substrates to reach the growth rates predicted a priori by an in silico model (Fong and Palsson, *Nat. Genet.* 36:1056-1058 (2004)). The growth improvements brought about by adaptive evolution can be accompanied by enhanced rates of fatty alcohol, fatty aldehyde or fatty acid production. The strains are generally adaptively evolved in replicate, running in parallel, to account for differences in the evolutionary patterns that can be exhibited by a host organism (Fong and Palsson, *Nat. Genet.* 36:1056-1058 (2004); Fong et al., *J. Bacteriol.* 185:6400-6408 (2003); Ibarra et al., *Nature* 420: 186-189 (2002)) that could potentially result in one strain having superior production qualities over the others. Evolutions can be run for a period of time, typically 2-6 weeks, depending upon the rate of growth improvement attained. In general, evolutions are stopped once a stable phenotype is obtained.

Following the adaptive evolution process, the new strains are characterized again by measuring the growth rate, the substrate uptake rate, and the product/byproduct secretion rate. These results are compared to the theoretical predictions by plotting actual growth and production yields alongside the production envelopes from metabolic modeling. The most successful design/evolution combinations are chosen to pursue further, and are characterized in lab-scale batch and continuous fermentations. The growth-coupled biochemical production concept behind the methods disclosed herein such as OptKnock approach should also result in the generation of genetically stable overproducers. Thus, the cultures are maintained in continuous mode for an extended period of time, for example, one month or more, to evaluate long-term stability. Periodic samples can be taken to ensure that yield and productivity are maintained.

Adaptive evolution is a powerful technique that can be used to increase growth rates of mutant or engineered microbial strains, or of wild-type strains growing under unnatural environmental conditions. It is especially useful for strains designed via methods such as OptKnock, which results in growth-coupled product formation. Therefore, evolution toward optimal growing strains will indirectly optimize production as well. Unique strains of *E. coli* K-12 MG1655 were created through gene knockouts and adaptive evolution. (Fong and Palsson, *Nat. Genet.* 36:1056-1058 (2004)). In this work, all adaptive evolutionary cultures were maintained in prolonged exponential growth by serial passage of batch cultures into fresh medium before the stationary phase was reached, thus rendering growth rate as the primary selection pressure. Knockout strains were constructed and evolved on minimal medium supplemented with different carbon substrates (four for each knockout strain). Evolution cultures were carried out in duplicate or triplicate, giving a total of 50 evolution knockout strains. The evolution cultures were maintained in exponential growth until a stable growth rate was reached. The computational predictions were accurate (within 10%) at predicting the post-evolution growth rate of the knockout strains in 38 out of the 50 cases examined. Furthermore, a combination of OptKnock design with adaptive evolution has led to improved lactic acid production strains. (Fong et al., *Biotechnol. Bioeng.* 91:643-648 (2005)). Similar methods can be applied to the strains disclosed herein and applied to various host strains.

There are a number of developed technologies for carrying out adaptive evolution. Exemplary methods are disclosed herein. In some embodiments, optimization of a non-naturally occurring organism of the present invention includes utilizing adaptive evolution techniques to increase fatty alcohol, fatty aldehyde, fatty acid or isopropanol production and/or stability of the producing strain.

Serial culture involves repetitive transfer of a small volume of grown culture to a much larger vessel containing fresh growth medium. When the cultured organisms have grown to saturation in the new vessel, the process is repeated. This method has been used to achieve the longest demonstrations of sustained culture in the literature (Lenski and Travisano, *Proc. Natl. Acad. Sci. USA* 91:6808-6814 (1994)) in experiments which clearly demonstrated consistent improvement in reproductive rate over a period of years. Typically, transfer of cultures is usually performed during exponential phase, so each day the transfer volume is precisely calculated to maintain exponential growth through the next 24 hour period. Manual serial dilution is inexpensive and easy to parallelize.

In continuous culture the growth of cells in a chemostat represents an extreme case of dilution in which a very high fraction of the cell population remains. As a culture grows and becomes saturated, a small proportion of the grown culture is replaced with fresh media, allowing the culture to continually grow at close to its maximum population size. Chemostats have been used to demonstrate short periods of rapid improvement in reproductive rate (Dykhuizen, *Methods Enzymol.* 613-631 (1993)). The potential usefulness of these devices was recognized, but traditional chemostats were unable to sustain long periods of selection for increased reproduction rate, due to the unintended selection of dilution-resistant (static) variants. These variants are able to resist dilution by adhering to the surface of the chemostat, and by doing so, outcompete less adherent individuals, including those that have higher reproductive rates, thus obviating the intended purpose of the device (Chao and Ramsdell, *J. Gen. Microbiol* 20:132-138 (1985)). One possible way to overcome this drawback is the implementation of a device with two growth chambers, which periodically undergo transient phases of sterilization, as described previously (Marliere and Mutzel, U.S. Pat. No. 6,686,194).

Evolugator™ is a continuous culture device developed by Evolugate, LLC (GainesvilleFLa.) and exhibits significant time and effort savings over traditional evolution techniques (de Crecy et al., *Appl. Microbiol. Biotechnol.* 77:489-496 (2007)). The cells are maintained in prolonged exponential growth by the serial passage of batch cultures into fresh medium before the stationary phase is attained. By automating optical density measurement and liquid handling, the Evolugator™ can perform serial transfer at high rates using large culture volumes, thus approaching the efficiency of a chemostat in evolution of cell fitness. For example, a mutant of *Acinetobacter* sp ADP1 deficient in a component of the translation apparatus, and having severely hampered growth, was evolved in 200 generations to 80% of the wild-type growth rate. However, in contrast to the chemostat which maintains cells in a single vessel, the machine operates by moving from one "reactor" to the next in subdivided regions of a spool of tubing, thus eliminating any selection for wall-growth. The transfer volume is adjustable, and normally set to about 50%. A drawback to this device is that it is large and costly, thus running large numbers of evolutions in parallel is not practical. Furthermore, gas addition is not well regulated, and strict anaerobic conditions are not maintained with the current device configuration. Nevertheless, this is an alternative method to adaptively evolve a production strain.

As disclosed herein, a nucleic acid encoding a desired activity of a fatty alcohol, fatty aldehyde, fatty acid or isopropanol pathway can be introduced into a host organism. In some cases, it can be desirable to modify an activity of a fatty alcohol, fatty aldehyde, fatty acid or isopropanol pathway enzyme or protein to increase production of fatty alcohol, fatty aldehyde, fatty acid or isopropanol. For example, known mutations that increase the activity of a protein or enzyme can be introduced into an encoding nucleic acid molecule. Additionally, optimization methods can be applied to increase the activity of an enzyme or protein and/or decrease an inhibitory activity, for example, decrease the activity of a negative regulator.

One such optimization method is directed evolution. Directed evolution is a powerful approach that involves the introduction of mutations targeted to a specific gene in order to improve and/or alter the properties of an enzyme. Improved and/or altered enzymes can be identified through the development and implementation of sensitive high-throughput screening assays that allow the automated screening of many enzyme variants (for example, >$10^4$). Iterative rounds of mutagenesis and screening typically are performed to afford an enzyme with optimized properties. Computational algorithms that can help to identify areas of the gene for mutagenesis also have been developed and can significantly reduce the number of enzyme variants that need to be generated and screened. Numerous directed evolution technologies have been developed (for reviews, see Hibbert et al., *Biomol. Eng* 22:11-19 (2005); Huisman and Lalonde, In Biocatalysis in the pharmaceutical and biotechnology industries pgs. 717-742 (2007), Patel (ed.), CRC Press; Often and Quax. *Biomol. Eng* 22:1-9 (2005); and Sen et al., *Appl Biochem. Biotechnol* 143:212-223 (2007)) to be effective at creating diverse variant libraries, and these methods have been successfully applied to the improvement of a wide range of properties across many enzyme classes. Enzyme characteristics that have been improved and/or altered by directed evolution technologies include, for example: selectivity/specificity, for conversion of non-natural substrates; temperature stability, for robust high temperature processing; pH stability, for bioprocessing under lower or higher pH conditions; substrate or product tolerance, so that high product titers can be achieved; binding ($K_m$), including broadening substrate binding to include non-natural substrates; inhibition ($K_i$), to remove inhibition by products, substrates, or key intermediates; activity (kcat), to increases enzymatic reaction rates to achieve desired flux; expression levels, to increase protein yields and overall pathway flux; oxygen stability, for operation of air sensitive enzymes under aerobic conditions; and anaerobic activity, for operation of an aerobic enzyme in the absence of oxygen.

Described below in more detail are exemplary methods that have been developed for the mutagenesis and diversification of genes to target desired properties of specific enzymes. Such methods are well known to those skilled in the art. Any of these can be used to alter and/or optimize the activity of a fatty alcohol, fatty aldehyde, fatty acid or isopropanol pathway enzyme or protein.

EpPCR (Pritchard et al., *J Theor. Biol.* 234:497-509 (2005)) introduces random point mutations by reducing the fidelity of DNA polymerase in PCR reactions by the addition of $Mn^{2+}$ ions, by biasing dNTP concentrations, or by other conditional variations. The five step cloning process to confine the mutagenesis to the target gene of interest involves: 1) error-prone PCR amplification of the gene of interest; 2) restriction enzyme digestion; 3) gel purification of the desired DNA fragment 4) ligation into a vector; 5) transformation of the gene variants into a suitable host and screening of the library for improved performance. This method can generate multiple mutations in a single gene simultaneously, which can be useful to screen a larger number of potential variants having a desired activity. A high number of mutants can be generated by EpPCR, so a high-throughput screening assay or a selection method, for example, using robotics, is useful to identify those with desirable characteristics.

Error-prone Rolling Circle Amplification (epRCA) (Fujii et al., *Nucleic Acids Res.* 32:e145 (2004); and Fujii et al., *Nat. Protoc.* 1:2493-2497 (2006)) has many of the same elements as epPCR except a whole circular plasmid is used as the template and random 6-mers with exonuclease resistant thiophosphate linkages on the last 2 nucleotides are used to amplify the plasmid followed by transformation into cells in which the plasmid is re-circularized at tandem repeats. Adjusting the $Mn^{2+}$ concentration can vary the mutation rate somewhat. This technique uses a simple error-prone, single-step method to create a full copy of the plasmid with 3-4 mutations/kbp. No restriction enzyme digestion or specific primers are required. Additionally, this method is typically available as a commercially available kit.

DNA or Family Shuffling (Stemmer, *Proc Natl Acad Sci USA* 91:10747-10751(1994)); and Stemmer, *Nature* 370: 389-391(1994)) typically involves digestion of two or more variant genes with nucleases such as Dnase I or EndoV to generate a pool of random fragments that are reassembled by cycles of annealing and extension in the presence of DNA polymerase to create a library of chimeric genes. Fragments prime each other and recombination occurs when one copy primes another copy (template switch). This method can be used with >1 kbp DNA sequences. In addition to mutational recombinants created by fragment reassembly, this method introduces point mutations in the extension steps at a rate similar to error-prone PCR. The method can be used to remove deleterious, random and neutral mutations.

Staggered Extension (StEP) (Zhao et al., *Nat. Biotechnol.* 16:258-261(1998)) entails template priming followed by repeated cycles of 2 step PCR with denaturation and very short duration of annealing/extension (as short as 5 sec). Growing fragments anneal to different templates and extend further, which is repeated until full-length sequences are made. Template switching means most resulting fragments have multiple parents. Combinations of low-fidelity polymerases (Taq and Mutazyme) reduce error-prone biases because of opposite mutational spectra.

In Random Priming Recombination (RPR) random sequence primers are used to generate many short DNA fragments complementary to different segments of the template (Shao et al., *Nucleic Acids Res* 26:681-683 (1998)). Base misincorporation and mispriming via epPCR give point mutations. Short DNA fragments prime one another based on homology and are recombined and reassembled into full-length by repeated thermocycling. Removal of templates prior to this step assures low parental recombinants. This method, like most others, can be performed over multiple iterations to evolve distinct properties. This technology avoids sequence bias, is independent of gene length, and requires very little parent DNA for the application.

In Heteroduplex Recombination linearized plasmid DNA is used to form heteroduplexes that are repaired by mismatch repair (Volkov et al, *Nucleic Acids Res.* 27:e18 (1999); and Volkov et al., *Methods Enzymol.* 328:456-463 (2000)). The mismatch repair step is at least somewhat mutagenic. Heteroduplexes transform more efficiently than linear homoduplexes. This method is suitable for large genes and whole operons.

Random Chimeragenesis on Transient Templates (RACHITT) (Coco et al., *Nat. Biotechnol.* 19:354-359 (2001)) employs Dnase I fragmentation and size fractionation of single stranded DNA (ssDNA). Homologous fragments are hybridized in the absence of polymerase to a complementary ssDNA scaffold. Any overlapping unhybridized fragment ends are trimmed down by an exonuclease. Gaps between fragments are filled in and then ligated to give a pool of full-length diverse strands hybridized to the scaffold, which contains U to preclude amplification. The scaffold then is destroyed and is replaced by a new strand complementary to the diverse strand by PCR amplification. The method involves one strand (scaffold) that is from only one parent while the priming fragments derive from other genes, and the parent scaffold is selected against. Thus, no reannealing with parental fragments occurs. Overlapping fragments are trimmed with an exonuclease. Otherwise, this is conceptually similar to DNA shuffling and StEP. Therefore, there should be no siblings, few inactives, and no unshuffled parentals. This technique has advantages in that few or no parental genes are created and many more crossovers can result relative to standard DNA shuffling.

Recombined Extension on Truncated templates (RETT) entails template switching of unidirectionally growing strands from primers in the presence of unidirectional ssDNA fragments used as a pool of templates (Lee et al., *J. Molec. Catalysis* 26:119-129 (2003)). No DNA endonucleases are used. Unidirectional ssDNA is made by DNA polymerase with random primers or serial deletion with exonuclease. Unidirectional ssDNA are only templates and not primers Random priming and exonucleases do not introduce sequence bias as true of enzymatic cleavage of DNA shuffling/RACHITT. RETT can be easier to optimize than StEP because it uses normal PCR conditions instead of very short extensions. Recombination occurs as a component of the PCR steps, that is, no direct shuffling. This method can also be more random than StEP due to the absence of pauses.

In Degenerate Oligonucleotide Gene Shuffling (DOGS) degenerate primers are used to control recombination between molecules; (Bergquist and Gibbs, *Methods Mol. Biol* 352:191-204 (2007); Bergquist et al., *Biomol.Eng* 22:63-72 (2005); Gibbs et al., *Gene* 271:13-20 (2001)) this can be used to control the tendency of other methods such as DNA shuffling to regenerate parental genes. This method can be combined with random mutagenesis (epPCR) of selected gene segments. This can be a good method to block the reformation of parental sequences. No endonucleases are needed. By adjusting input concentrations of segments made, one can bias towards a desired backbone. This method allows DNA shuffling from unrelated parents without restriction enzyme digests and allows a choice of random mutagenesis methods.

Incremental Truncation for the Creation of Hybrid Enzymes (ITCHY) creates a combinatorial library with 1 base pair deletions of a gene or gene fragment of interest (Ostermeier et al., *Proc. Natl. Acad. Sci. USA* 96:3562-3567 (1999); and Ostermeier et al., *Nat. Biotechnol.* 17:1205-1209 (1999)). Truncations are introduced in opposite direction on pieces of 2 different genes. These are ligated together and the fusions are cloned. This technique does not require homology between the 2 parental genes. When ITCHY is combined with DNA shuffling, the system is called SCRATCHY (see below). A major advantage of both is no need for homology between parental genes; for example, functional fusions between an *E. coli* and a human gene were created via ITCHY. When ITCHY libraries are made, all possible crossovers are captured.

Thio-Incremental Truncation for the Creation of Hybrid Enzymes (THIO-ITCHY) is similar to ITCHY except that phosphothioate dNTPs are used to generate truncations (Lutz et al., *Nucleic Acids Res* 29:E16 (2001)). Relative to ITCHY, THIO-ITCHY can be easier to optimize, provide more reproducibility, and adjustability.

SCRATCHY combines two methods for recombining genes, ITCHY and DNA shuffling (Lutz et al., *Proc. Natl. Acad. Sci. USA* 98:11248-11253 (2001)). SCRATCHY combines the best features of ITCHY and DNA shuffling. First, ITCHY is used to create a comprehensive set of fusions between fragments of genes in a DNA homology-independent fashion. This artificial family is then subjected to a DNA-shuffling step to augment the number of crossovers. Computational predictions can be used in optimization. SCRATCHY is more effective than DNA shuffling when sequence identity is below 80%.

In Random Drift Mutagenesis (RNDM) mutations are made via epPCR followed by screening/selection for those retaining usable activity (Bergquist et al., *Biomol. Eng* 22:63-72 (2005)). Then, these are used in DOGS to generate recombinants with fusions between multiple active mutants or between active mutants and some other desirable parent. Designed to promote isolation of neutral mutations; its purpose is to screen for retained catalytic activity whether or not this activity is higher or lower than in the original gene. RNDM is usable in high throughput assays when screening is capable of detecting activity above background. RNDM has been used as a front end to DOGS in generating diversity. The technique imposes a requirement for activity prior to shuffling or other subsequent steps; neutral drill libraries are indicated to result in higher/quicker improvements in activity from smaller libraries. Though published using epPCR, this could be applied to other large-scale mutagenesis methods.

Sequence Saturation Mutagenesis (SeSaM) is a random mutagenesis method that: 1) generates a pool of random length fragments using random incorporation of a phosphothioate nucleotide and cleavage; this pool is used as a template to 2) extend in the presence of "universal" bases such as inosine; 3) replication of an inosine-containing complement gives random base incorporation and, consequently, mutagenesis (Wong et al., *Biotechnol. J.* 3:74-82 (2008); Wong et al., *Nucleic Acids Res.* 32:e26 (2004); and Wong et al., *Anal. Biochem.* 341:187-189 (2005)). Using this technique it can be possible to generate a large library of mutants within 2 to 3 days using simple methods. This technique is non-directed in comparison to the mutational bias of DNA polymerases. Differences in this approach makes this technique complementary (or an alternative) to epPCR.

In Synthetic Shuffling, overlapping oligonucleotides are designed to encode "all genetic diversity in targets" and allow a very high diversity for the shuffled progeny (Ness et al., *Nat. Biotechnol.* 20:1251-1255 (2002)). In this technique, one can design the fragments to be shuffled. This aids in increasing the resulting diversity of the progeny. One can design sequence/codon biases to make more distantly related sequences recombine at rates approaching those observed with more closely related sequences. Additionally, the technique does not require physically possessing the template genes.

Nucleotide Exchange and Excision Technology NexT exploits a combination of dUTP incorporation followed by treatment with uracil DNA glycosylase and then piperidine to perform endpoint DNA fragmentation (Muller et al., *Nucleic Acids Res.* 33:e117 (2005)). The gene is reassembled using internal PCR primer extension with proofreading polymerase. The sizes for shuffling are directly controllable using varying dUPT::dTTP ratios. This is an end point reaction using simple methods for uracil incorporation and cleavage. Other nucleotide analogs, such as 8-oxo-guanine, can be used with this method. Additionally, the technique works well with very short fragments (86 bp) and has a low error rate. The chemical cleavage of DNA used in this technique results in very few unshuffled clones.

In Sequence Homology-Independent Protein Recombination (SHIPREC), a linker is used to facilitate fusion between two distantly related or unrelated genes. Nuclease treatment is used to generate a range of chimeras between the two genes. These fusions result in libraries of single-crossover hybrids (Sieber et al., *Nat. Biotechnol.* 19:456-460 (2001)). This produces a limited type of shuffling and a separate process is required for mutagenesis. In addition, since no homology is needed, this technique can create a library of chimeras with varying fractions of each of the two unrelated parent genes. SHIPREC was tested with a heme-binding domain of a bacterial CP450 fused to N-terminal regions of a mammalian CP450; this produced mammalian activity in a more soluble enzyme.

In Gene Site Saturation Mutagenesis™ (GSSM™) the starting materials are a supercoiled dsDNA plasmid containing an insert and two primers which are degenerate at the desired site of mutations (Kretz et al., *Methods Enzymol.* 388:3-11 (2004)). Primers carrying the mutation of interest, anneal to the same sequence on opposite strands of DNA. The mutation is typically in the middle of the primer and flanked on each side by approximately 20 nucleotides of correct sequence. The sequence in the primer is NNN or NNK (coding) and MNN (noncoding) (N=all 4, K=G, T, M=A, C). After extension, DpnI is used to digest dam-methylated DNA to eliminate the wild-type template. This technique explores all possible amino acid substitutions at a given locus (that is, one codon). The technique facilitates the generation of all possible replacements at a single-site with no nonsense codons and results in equal to near-equal representation of most possible alleles. This technique does not require prior knowledge of the structure, mechanism, or domains of the target enzyme. If followed by shuffling or Gene Reassembly, this technology creates a diverse library of recombinants containing all possible combinations of single-site up-mutations. The usefulness of this technology combination has been demonstrated for the successful evolution of over 50 different enzymes, and also for more than one property in a given enzyme.

Combinatorial Cassette Mutagenesis (CCM) involves the use of short oligonucleotide cassettes to replace limited regions with a large number of possible amino acid sequence alterations (Reidhaar-Olson et al. *Methods Enzymol.* 208: 564-586 (1991); and Reidhaar-Olson et al. *Science* 241:53-57 (1988)). Simultaneous substitutions at two or three sites are possible using this technique. Additionally, the method tests a large multiplicity of possible sequence changes at a limited range of sites. This technique has been used to explore the information content of the lambda repressor DNA-binding domain.

Combinatorial Multiple Cassette Mutagenesis (CMCM) is essentially similar to CCM except it is employed as part of a larger program: 1) use of epPCR at high mutation rate to 2) identify hot spots and hot regions and then 3) extension by CMCM to cover a defined region of protein sequence space (Reetz et al., *Angew. Chem. Int. Ed Engl.* 40:3589-3591 (2001)). As with CCM, this method can test virtually all possible alterations over a target region. If used along with methods to create random mutations and shuffled genes, it provides an excellent means of generating diverse, shuffled proteins. This approach was successful in increasing, by 51-fold, the enantioselectivity of an enzyme.

In the Mutator Strains technique, conditional ts mutator plasmids allow increases of 20 to 4000-X in random and natural mutation frequency during selection and block accumulation of deleterious mutations when selection is not required (Selifonova et al., *Appl. Environ. Microbiol.* 67:3645-3649 (2001)). This technology is based on a plasmid-derived mutD5 gene, which encodes a mutant subunit of DNA polymerase III. This subunit binds to endogenous DNA polymerase III and compromises the proofreading ability of polymerase III in any strain that harbors the plasmid. A broad-spectrum of base substitutions and frameshift mutations occur. In order for effective use, the mutator plasmid should be removed once the desired phenotype is achieved; this is accomplished through a temperature sensitive (ts) origin of replication, which allows for plasmid curing at 41° C. It should be noted that mutator strains have been explored for quite some time (see Low et al., *J. Mol. Biol.* 260:359-3680 (1996)). In this technique, very high spontaneous mutation rates are observed. The conditional property minimizes non-desired background mutations. This technology could be combined with adaptive evolution to enhance mutagenesis rates and more rapidly achieve desired phenotypes.

Look-Through Mutagenesis (LTM) is a multidimensional mutagenesis method that assesses and optimizes combinatorial mutations of selected amino acids (Rajpal et al., *Proc. Natl. Acad. Sci. USA* 102:8466-8471 (2005)). Rather than saturating each site with all possible amino acid changes, a set of nine is chosen to cover the range of amino acid R-group chemistry. Fewer changes per site allows multiple sites to be subjected to this type of mutagenesis. A>800-fold increase in binding affinity for an antibody from low nanomolar to picomolar has been achieved through this method. This is a rational approach to minimize the number of random combinations and can increase the ability to find improved traits by greatly decreasing the numbers of clones to be screened. This has been applied to antibody engineering, specifically to increase the binding affinity and/or reduce dissociation. The technique can be combined with either screens or selections.

Gene Reassembly is a DNA shuffling method that can be applied to multiple genes at one time or to create a large library of chimeras (multiple mutations) of a single gene (Tunable GeneReassembly™ (TGR™) Technology supplied by Verenium Corporation). Typically this technology is used in combination with ultra-high-throughput screening to query the represented sequence space for desired improvements. This technique allows multiple gene recombination independent of homology. The exact number and position of cross-over events can be pre-determined using fragments designed via bioinformatic analysis. This technology leads to a very high level of diversity with virtually no parental gene reformation and a low level of inactive genes. Combined with GSSM™, a large range of mutations can be tested for improved activity. The method allows "blending" and "fine tuning" of DNA shuffling, for example, codon usage can be optimized.

In Silico Protein Design Automation (PDA) is an optimization algorithm that anchors the structurally defined protein backbone possessing a particular fold, and searches sequence space for amino acid substitutions that can stabilize the fold and overall protein energetics (Hayes et al., Proc. Natl. Acad Sci. USA 99:15926-15931(2002)). This technology uses in silico structure-based entropy predictions in order to search for structural tolerance toward protein amino acid variations. Statistical mechanics is applied to calculate coupling interactions at each position. Structural tolerance toward amino acid substitution is a measure of coupling. Ultimately, this technology is designed to yield desired modifications of protein properties while maintaining the integrity of structural characteristics. The method computationally assesses and allows filtering of a very large number of possible sequence variants ($10^{50}$). The choice of sequence variants to test is related to predictions based on the most favorable thermodynamics. Ostensibly only stability or properties that are linked to stability can be effectively addressed with this technology. The method has been successfully used in some therapeutic proteins, especially in engineering immunoglobulins. In silico predictions avoid testing extraordinarily large numbers of potential variants. Predictions based on existing three-dimensional structures are more likely to succeed than predictions based on hypothetical structures. This technology can readily predict and allow targeted screening of multiple simultaneous mutations, something not possible with purely experimental technologies due to exponential increases in numbers.

Iterative Saturation Mutagenesis (ISM) involves: 1) using knowledge of structure/function to choose a likely site for enzyme improvement; 2) performing saturation mutagenesis at chosen site using a mutagenesis method such as Stratagene QuikChange (Stratagene; San DiegCAf.); 3) screening/selecting for desired properties; and 4) using improved clone(s), start over at another site and continue repeating until a desired activity is achieved (Reetz et al., Nat. Protoc. 2:891-903 (2007); and Reetz et al., Angew. Chem. Int. Ed Engl. 45:7745-7751 (2006)). This is a proven methodology, which assures all possible replacements at a given position are made for screening/selection.

Any of the aforementioned methods for mutagenesis can be used alone or in any combination. Additionally, any one or combination of the directed evolution methods can be used in conjunction with adaptive evolution techniques, as described herein.

It is understood that modifications which do not substantially affect the activity of the various embodiments of this invention are also provided within the definition of the invention provided herein. Accordingly, the following examples are intended to illustrate but not limit the present invention.

Example I

Formate Assimilation Pathways

This example describes enzymatic pathways for converting pyruvate to formaldehyde, and optionally in combination with producing acetyl-CoA and/or reproducing pyruvate.

Step E, FIG. 1: Formate Reductase

The conversion of formate to formaldehyde can be carried out by a formate reductase (step E, FIG. 1). A suitable enzyme for these transformations is the aryl-aldehyde dehydrogenase, or equivalently a carboxylic acid reductase, from Nocardia iowensis. Carboxylic acid reductase catalyzes the magnesium, ATP and NADPH-dependent reduction of carboxylic acids to their corresponding aldehydes (Venkitasubramanian et al., J. Biol. Chem. 282:478-485 (2007)). This enzyme, encoded by car, was cloned and functionally expressed in E. coli (Venkitasubramanian et al., J. Biol. Chem. 282:478-485 (2007)). Expression of the npt gene product improved activity of the enzyme via post-transcriptional modification. The npt gene encodes a specific phosphopantetheine transferase (PPTase) that converts the inactive apo-enzyme to the active holo-enzyme. The natural substrate of this enzyme is vanillic acid, and the enzyme exhibits broad acceptance of aromatic and aliphatic substrates (Venkitasubramanian et al., in Biocatalysis in the Pharmaceutical and Biotechnology Industires, ed. R. N. Patel, Chapter 15, pp. 425-440, CRC Press LLC, Boca RatonFLa. (2006)). Information related to these proteins and genes is shown below.

| Protein | GenBank ID | GI number | Organism |
|---|---|---|---|
| Car | AAR91681.1 | 40796035 | Nocardia iowensis (sp. NRRL 5646) |
| Npt | ABI83656.1 | 114848891 | Nocardia iowensis (sp. NRRL 5646) |

Additional car and npt genes can be identified based on sequence homology.

| Protein | GenBank ID | GI number | Organism |
|---|---|---|---|
| fadD9 | YP_978699.1 | 121638475 | Mycobacterium bovis BCG |
| BCG_2812c | YP_978898.1 | 121638674 | Mycobacterium bovis BCG |
| nfa20150 | YP_118225.1 | 54023983 | Nocardia farcinica IFM 10152 |
| nfa40540 | YP_120266.1 | 54026024 | Nocardia farcinica IFM 10152 |
| SGR_6790 | YP_001828302.1 | 182440583 | Streptomyces griseus subsp. griseus NBRC 13350 |
| SGR_665 | YP_001822177.1 | 182434458 | Streptomyces griseus subsp. griseus NBRC 13350 |
| MSMEG 2956 | YP_887275.1 | 118473501 | Mycobacterium smegmatis MC2155 |

-continued

| Protein | GenBank ID | GI number | Organism |
|---|---|---|---|
| MSMEG 5739 | YP_889972.1 | 118469671 | Mycobacterium smegmatis MC2155 |
| MSMEG 2648 | YP_886985.1 | 118471293 | Mycobacterium smegmatis MC2155 |
| MAP1040c | NP_959974.1 | 41407138 | Mycobacterium avium subsp. paratuberculosis K-10 |
| MAP2899c | NP_961833.1 | 41408997 | Mycobacterium avium subsp. paratuberculosis K-10 |
| MMAR_2117 | YP_001850422.1 | 183982131 | Mycobacterium marinum M |
| MM4R_2936 | YP_001851230.1 | 183982939 | Mycobacterium marinum M |
| MMAR_1916 | YP_001850220.1 | 183981929 | Mycobacterium marinum M |
| TpauDRAFT_33060 | ZP_04027864.1 | 227980601 | Tsukamwella paurometabola DSM 20162 |
| TpauDRAFT_20920 | ZP_04026660.1 | 227979396 | Tsukamwella paurometabola DSM 20162 |
| CPCC7001 1320 | ZP_05045132.1 | 254431429 | Cyanobium PCC7001 |
| DDBDRAFT 0187729 | XP_636931.1 | 66806417 | Dictyostelium discoideum AX4 |

An additional enzyme candidate found in *Streptomyces griseus* is encoded by the griC and griD genes. This enzyme is believed to convert 3-amino-4-hydroxybenzoic acid to 3-amino-4-hydroxybenzaldehyde as deletion of either griC or griD led to accumulation of extracellular 3-acetylamino-4-hydroxybenzoic acid, a shunt product of 3-amino-4-hydroxybenzoic acid metabolism (Suzuki, et al., *J. Antibiot.* 60(6):380-387 (2007)). Co-expression of griC and griD with SGR 665, an enzyme similar in sequence to the *Nocardia iowensis* npt, can be beneficial. Information related to these proteins and genes is shown below.

| Protein | GenBank ID | GI number | Organism |
|---|---|---|---|
| griC | YP_001825755.1 | 182438036 | Streptomyces griseus subsp. griseus NBRC 13350 |
| griD | YP_001825756.1 | 182438037 | Streptomyces griseus subsp. griseus NBRC 13350 |

An enzyme with similar characteristics, alpha-aminoadipate reductase (AAR, EC 1.2.1.31), participates in lysine biosynthesis pathways in some fungal species. This enzyme naturally reduces alpha-aminoadipate to alpha-aminoadipate semialdehyde. The carboxyl group is first activated through the ATP-dependent formation of an adenylate that is then reduced by NAD(P)H to yield the aldehyde and AMP. Like CAR, this enzyme utilizes magnesium and requires activation by a PPTase. Enzyme candidates for AAR and its corresponding PPTase are found in *Saccharomyces cerevisiae* (Morris et al., *Gene* 98:141-145 (1991)), *Candida albicans* (Guo et al., *Mol. Genet. Genomics* 269:271-279 (2003)), and *Schizosaccharomyces pombe* (Ford et al., *Curr. Genet.* 28:131-137 (1995)). The AAR from *S. pombe* exhibited significant activity when expressed in *E. coli* (Guo et al., *Yeast* 21:1279-1288 (2004)). The AAR from *Penicillium chrysogenum* accepts S-carboxymethyl-L-cysteine as an alternate substrate, but did not react with adipate, L-glutamate or diaminopimelate (Hijarrubia et al., *J. Biol. Chem.* 278:8250-8256 (2003)). The gene encoding the *P. chrysogenum* PPTase has not been identified to date. Information related to these proteins and genes is shown below.

| Protein | GenBank ID | GI number | Organism |
|---|---|---|---|
| LYS2 | AAA34747.1 | 171867 | Saccharomyces cerevisiae |
| LYS5 | P50113.1 | 1708896 | Saccharomyces cerevisiae |
| LYS2 | AAC02241.1 | 2853226 | Candida albicans |
| LYS5 | AAO26020.1 | 28136195 | Candida albicans |
| Lys1p | P40976.3 | 13124791 | Schizosaccharomyces pombe |
| Lys7p | Q10474.1 | 1723561 | Schizosaccharomyces pombe |
| Lys2 | CAA74300.1 | 3282044 | Penicillium chrysogenum |

Tani et al (Agric Biol Chem, 1978, 42: 63-68; Agric Biol Chem, 1974, 38: 2057-2058) showed that purified enzymes from *Escherichia* coli strain B could reduce the sodium salts of different organic acids (e.g. formate, glycolate, acetate, etc.) to their respective aldehydes (e.g. formaldehyde, glycoaldehyde, acetaldehyde, etc.). Of three purified enzymes examined by Tani et al (1978), only the "A" isozyme was shown to reduce formate to formaldehyde. Collectively, this group of enzymes was originally termed glycoaldehyde dehydrogenase; however, their novel reductase activity led the authors to propose the name glycolate reductase as being more appropriate (Morita et al, Agric Biol Chem, 1979, 43: 185-186). Morita et al (Agric Biol Chem, 1979, 43: 185-186) subsequently showed that glycolate reductase activity is relatively widespread among microorganisms, being found for example in: *Pseudomonas, Agrobacterium, Escherichia, Flavobacterium, Micrococcus, Staphylococcus, Bacillus*, and others. Without wishing to be bound by any particular theory, it is believed that some of these glycolate reductase enzymes are able to reduce formate to formaldehyde.

Any of these CAR or CAR-like enzymes can exhibit formate reductase activity or can be engineered to do so.

Step F, FIG. 1 Formate Ligase, Formate Transferase, Formate Synthetase

The acylation of formate to formyl-CoA is catalyzed by enzymes with formate transferase, synthetase, or ligase activity (Step F, FIG. 1). Formate transferase enzymes have been identified in several organisms including *Escherichia coli* (Toyota, et al., *J Bacteriol.* 2008 April; 190(7):2556-64), *Oxalobacter formigenes* (Toyota, et al., *J Bacteriol.* 2008 April; 190(7):2556-64; Baetz et al., *J Bacteriol.* 1990 July; 172(7):3537-40; Ricagno, et al., *EMBO J.* 2003 Jul. 1; 22(13):3210-9)), and *Lactobacillus acidophilus* (Azcarate-Peril, et al., *Appl. Environ. Microbiol.* 2006 72(3) 1891-1899). Homologs exist in several other organisms. Enzymes acting on the CoA-donor for formate transferase may also be expressed to ensure efficient regeneration of the CoA-donor. For example, if oxalyl-CoA is the CoA donor substrate for formate transferase, an additional transferase, synthetase, or ligase may be required to enable efficient regeneration of oxalyl-CoA from oxalate. Similarly, if succinyl-CoA or acetyl-CoA is the CoA donor substrate for formate transferase, an additional transferase, synthetase, or ligase may be required to enable efficient regeneration of succinyl-CoA from succinate or acetyl-CoA from acetate, respectively.

| Protein | GenBank ID | GI number | Organism |
|---|---|---|---|
| YfdW | NP_416875.1 | 16130306 | Escherichia coli |
| frc | O06644.3 | 21542067 | Oxalobacter formigenes |
| frc | ZP_04021099.1 | 227903294 | Lactobacillus acidophilus |

Suitable CoA-donor regeneration or formate transferase enzymes are encoded by the gene products of cat1, cat2, and cats of *Clostridium kluyveri*. These enzymes have been shown to exhibit succinyl-CoA, 4-hydroxybutyryl-CoA, and butyryl-CoA acetyltransferase activity, respectively (Seedorf et al., *Proc. Natl. Acad Sci. USA* 105:2128-2133 (2008); Sohling and Gottschalk, *J Bacteriol* 178:871-880 (1996)). Similar CoA transferase activities are also present in *Trichomonas vaginalis* (van Grinsven et al., *J. Biol. Chem.* 283:1411-1418 (2008)) and *Trypanosoma brucei* (Riviere et al., *J. Biol. Chem.* 279:45337-45346 (2004)). Yet another transferase capable of the desired conversions is butyryl-CoA:acetoacetate CoA-transferase. Exemplary enzymes can be found in *Fusobacterium nucleatum* (Barker et al., *J. Bacteriol.* 152(1):201-7 (1982)), *Clostridium* SB4 (Barker et al., *J. Biol. Chem.* 253(4):1219-25 (1978)), and *Clostridium acetobutylicum* (Wiesenbom et al., *Appl. Environ. Microbiol.* 55(2):323-9 (1989)). Although specific gene sequences were not provided for butyryl-CoA:acetoacetate CoA-transferase in these references, the genes FN0272 and FN0273 have been annotated as a butyrate-acetoacetate CoA-transferase (Kapatral et al., *J. Bact.* 184(7) 2005-2018 (2002)). Homologs in *Fusobacterium nucleatum* such as FN1857 and FN1856 also likely have the desired acetoacetyl-CoA transferase activity. FN1857 and FN1856 are located adjacent to many other genes involved in lysine fermentation and are thus very likely to encode an acetoacetate:butyrate CoA transferase (Kreimeyer, et al., *J. Biol. Chem.* 282 (10) 7191-7197 (2007)). Additional candidates from *Porphyrmonas gingivalis* and *Thermoanaerobacter tengcongensis* can be identified in a similar fashion (Kreimeyer, et al., *J. Biol. Chem.* 282 (10) 7191-7197 (2007)). Information related to these proteins and genes is shown below.

| Protein | GenBank ID | GI number | Organism |
|---|---|---|---|
| Cat1 | P38946.1 | 729048 | Clostridium kluyveri |
| Cat2 | P38942.2 | 1705614 | Clostridium kluyveri |
| Cat3 | EDK35586.1 | 146349050 | Clostridium kluyveri |
| TVAG_395550 | XP_001330176 | 123975034 | Trichomonas vaginalis G3 |
| Tb11.02.0290 | XP_828352 | 71754875 | Trypanosoma brucei |
| FN0272 | NP_603179.1 | 19703617 | Fusobacterium nucleatum |
| FN0273 | NP_603180.1 | 19703618 | Fusobacterium nucleatum |
| FN1857 | NP_602657.1 | 19705162 | Fusobacterium nucleatum |
| FN1856 | NP_602656.1 | 19705161 | Fusobacterium nucleatum |
| PG1066 | NP_905281.1 | 34540802 | Porphyromonas gingivalis W83 |
| PG1075 | NP_905290.1 | 34540811 | Porphyromonas gingivalis W83 |
| TTE0720 | NP_622378.1 | 20807207 | Thermoanaerobacter tengcongensis MB4 |
| TTE0721 | NP_622379.1 | 20807208 | Thermoanaerobacter tengcongensis MB4 |

Additional transferase enzymes of interest include the gene products of atoAD from *E. coli* (Hanai et al., *Appl Environ Microbiol* 73:7814-7818 (2007)), cffAB from *C. acetobutylicum* (Jojima et al., *Appl Microbiol Biotechnol* 77:1219-1224 (2008)), and cffAB from *Clostridium saccharoperbutylacetonicum* (Kosaka et al., *Biosci.Biotechnol Biochem.* 71:58-68 (2007)). Information related to these proteins and genes is shown below.

| Protein | GenBank ID | GI number | Organism |
|---|---|---|---|
| AtoA | P76459.1 | 2492994 | Escherichia coli |
| AtoD | P76458.1 | 2492990 | Escherichia coli |
| CtfA | NP_149326.1 | 15004866 | Clostridium acetobutylicum |
| CtfB | NP_149327.1 | 15004867 | Clostridium acetobutylicum |
| CtfA | AAP42564.1 | 31075384 | Clostridium saccharoperbutylacetonicum |
| CtfB | AAP42565.1 | 31075385 | Clostridium saccharoperbutylacetonicum |

Succinyl-CoA:3-ketoacid-CoA transferase naturally converts succinate to succinyl-CoA while converting a 3-ketoacyl-CoA to a 3-ketoacid. Exemplary succinyl-CoA:3:ketoacid-CoA transferases are present in *Helicobacter pylori* (Corthesy-Theulaz et al., *J.Biol.Chem.* 272:25659-25667 (1997)), *Bacillus subtilis* (Stols et al., *Protein.Expr.Punf.* 53:396-403 (2007)), and *Homo sapiens* (Fukao et al., *Genomics* 68:144-151(2000); Tanaka et al., *Mol.Hum.Reprod* 8:16-23 (2002)). Information related to these proteins and genes is shown below.

| Protein | GenBank ID | GI number | Organism |
|---|---|---|---|
| HPAG1_0676 | YP_627417 | 108563101 | Helicobacter pylori |
| HPAG1_0677 | YP_627418 | 108563102 | Helicobacter pylori |
| ScoA | NP_391778 | 16080950 | Bacillus subtilis |
| ScoB | NP_391777 | 16080949 | Bacillus subtilis |
| OXCT1 | NP_000427 | 4557817 | Homo sapiens |
| OXCT2 | NP_071403 | 11545841 | Homo sapiens |

Two additional enzymes that catalyze the activation of formate to formyl-CoA reaction are AMP-forming formyl-CoA synthetase and ADP-forming formyl-CoA synthetase. Exemplary enzymes, known to function on acetate, are found in *E. coli* (Brown et Gen. *Microbiol.* 102:327-336 (1977)), *Ralstonia eutropha* (Priefert and Steinbuchel, *J. Bacteriol.* 174:6590-6599 (1992)), *Methanothermobacter thermautotrophicus* (Ingram-Smith and Smith, *Archaea* 2:95-107 (2007)), *Salmonella enterica* (Gulick et al., *Biochemistry* 42:2866-2873 (2003)) and *Saccharomyces cerevisiae* (Jogl and Tong, *Biochemistry* 43:1425-1431(2004)). Such enzymes may also acylate formate naturally or can be engineered to do so.

| Protein | Gen Bank ID | GI Number | Organism |
|---|---|---|---|
| acs | AAC77039.1 | 1790505 | Escherichia coli |
| acoE | AAA21945.1 | 141890 | Ralstonia eutropha |
| acs1 | ABC87079.1 | 86169671 | Methanothermobacter thermautotrophicus |
| acs1 | AAL23099.1 | 16422835 | Salmonella enterica |
| ACS1 | Q01574.2 | 257050994 | Saccharomyces cerevisiae |

ADP forming acetyl-CoA synthetase (ACD, EC 6.2.1.13) is another candidate enzyme that couples the conversion of acyl-CoA esters to their corresponding acids with the concurrent synthesis of ATP. Several enzymes with broad substrate specificities have been described in the literature. ACD I from *Archaeoglobus fulgidus*, encoded by AF1211, was shown to operate on a variety of linear and branched-chain substrates including acetyl-CoA, propionyl-CoA, butyryl-CoA, acetate, propionate, butyrate, isobutyryate, isovakrate, succinate, fumarate, phenylacetate, indoleacetate (Musfeldt et *J. Bacteriol.* 184:636-644 (2002)). The enzyme from *Haloarcula marismortui* (annotated as a succinyl-CoA synthetase) accepts propionate, butyrate, and branched-chain acids (isovalerate and isobutyrate) as substrates, and was shown to operate in the forward and reverse directions (Brasen et al., *Arch. Microbiol.* 182:277-287 (2004)). The ACD encoded by PAE3250 from hyperthermophilic crenarchaeon *Pyrobaculum aerophilum* showed the broadest substrate range of all characterized ACDs, reacting with acetyl-CoA, isobutyryl-CoA (preferred substrate) and phenylacetyl-CoA (Brasen et al., supra (2004)). The enzymes from *A. filgidus, H. marismortui* and *P. aerophilum* have all been cloned, functionally expressed, and characterized in *E. coli* (Musfeldt et al., supra; Brasen et al., supra (2004)). Additional candidates include the succinyl-CoA synthetase encoded by sucCD in *E. coli* (Buck et al., *Biochemistry* 24:6245-6252 (1985)) and the acyl-CoA ligase from *Pseudomonas putida* (Fernandez-Valverde et al., *Appl. Environ. Microbiol.* 59:1149-1154 (1993)). Such enzymes may also acylate formate naturally or can be engineered to do so. Information related to these proteins and genes is shown below.

| Protein | GenBank ID | GI number | Organism |
| --- | --- | --- | --- |
| AF1211 | NP_070039.1 | 11498810 | *Archaeoglobus fulgidus* DSM4304 |
| AF1983 | NP_070807.1 | 11499565 | *Archaeoglobus fulgidus* DSM4304 |
| scs | YP_135572.1 | 55377722 | *Haloarcula marismortui* ATCC 43049 |
| PAE3250 | NP_560604.1 | 18313937 | *Pyrobaculum aerophilum* str. IM2 |
| sucC | NP_415256.1 | 16128703 | *Escherichia coli* |
| sueD | AAC73823.1 | 1786949 | *Escherichia coli* |
| paaF | AAC24333.2 | 22711873 | *Pseudomonas putida* |

An alternative method for adding the CoA moiety to formate is to apply a pair of enzymes such as a phosphate-transferring acyltransferase and a kinase. These activities enable the net formation of formyl-CoA with the simultaneous consumption of ATP. An exemplary phosphate-transferring acyltransferase is phosphotransacetylase, encoded by pta. The pta gene from *E. coli* encodes an enzyme that can convert acetyl-CoA into acetyl-phosphate, and vice versa (Suzuki, T. *Biochim.Biophys.Acta* 191:559-569 (1969)). This enzyme can also utilize propionyl-CoA instead of acetyl-CoA forming propionate in the process (Hesslinger et al. *Mol.Microbiol* 27:477-492 (1998)). Homologs exist in several other organisms including *Salmonella enterica* and *Chlamydomonas reinhardtii*. Such enzymes may also phosphorylate formate naturally or can be engineered to do so.

| Protein | GenBank ID | GI number | Organism |
| --- | --- | --- | --- |
| Pta | NP_416800.1 | 16130232 | *Escherichia coli* |
| Pta | NP_461280.1 | 16765665 | *Salmonella enterica* subsp. *enterica serovar Typhimurium* str. LT2 |
| PAT2 | XP_001694504.1 | 159472743 | *Chlamydomonas reinhardtii* |
| PAT1 | XP_001691787.1 | 159467202 | *Chlamydomonas reinhardtii* |

An exemplary acetate kinase is the *E. coli* acetate kinase, encoded by ackA (Skarstedt and Silverstein *J.Biol.Chem.* 251:6775-6783 (1976)). Homologs exist in several other organisms including *Salmonella enterica* and *Chlamydomonas reinhardtii*. It is likely that such enzymes naturally possess formate kinase activity or can be engineered to have this activity. Information related to these proteins and genes is shown below:

| Protein | GenBank ID | GI number | Organism |
| --- | --- | --- | --- |
| AckA | NP_416799.1 | 16130231 | *Escherichia coli* |
| AckA | NP_461279.1 | 16765664 | *Salmonella enterica* subsp. *enterica serovar Typhimurium* str. LT2 |
| ACK1 | XP_001694505.1 | 159472745 | *Chlamydomonas reinhardtii* |
| ACK2 | XP_001691682.1 | 159466992 | *Chlamydomonas reinhardtii* |

The acylation of formate to formyl-CoA can also be carried out by a formate ligase. For example, the product of the LSC1 and LSC2 genes of *S. cerevisiae* and the sucC and sucD genes of *E. coli* naturally form a succinyl-CoA ligase complex that catalyzes the formation of succinyl-CoA from succinate with the concomitant consumption of one ATP, a reaction which is reversible in vivo (Grays et al., U.S. Pat. No. 5,958,745, filed Sep. 28, 1999). Such enzymes may also acylate formate naturally or can be engineered to do so. Information related to these proteins and genes is shown below.

| Protein | GenBank ID | GI number | Organism |
| --- | --- | --- | --- |
| SucC | NP_415256.1 | 16128703 | *Escherichia coli* |
| SucD | AAC73823.1 | 1786949 | *Escherichia coli* |
| LSC1 | NP_014785 | 6324716 | *Saccharomyces cerevisiae* |
| LSC2 | NP_011760 | 6321683 | *Saccharomyces cerevisiae* |

Additional exemplary CoA-ligases include the rat dicarboxylate-CoA ligase for which the sequence is yet uncharacterized (Vamecq et al., *Biochemical J.* 230:683-693 (1985)), either of the two characterized phenylacetate-CoA ligases from *P. chrysogenum* (Lamas-Maceiras et al., *Biochem. J.* 395:147-155 (2005); Wang et al., *Biochem Biophy Res Commun* 360(2):453-458 (2007)), the phenylacetate-CoA ligase from *Pseudomonas putida* (Martinez-Blanco et al., *J. Biol. Chem.* 265:7084-7090 (1990)), and the 6-carboxyhexanoate-CoA ligase from *Bacilis subtilis* (Bower et al., *J. Bacteriol.* 178(14):4122-4130 (1996)). Additional candidate enzymes are acetoacetyl-CoA synthetases from Mus musculus (Hasegawa et al., *Biochim. Biophys. Acta* 1779:414-419 (2008)) and Homo sapiens (Ohgami et al., *Biochem. Pharmacol.* 65:989-994 (2003)), which naturally catalyze the ATP-dependant conversion of acetoacetate into acetoacetyl-CoA. 4-Hydroxybutyryl-CoA synthetase activity has been demonstrated in *Metallosphaera sedula* (Berg et al., *Science* 318:1782-1786 (2007)). This function has been tentatively assigned to the Msed_1422 gene. Such enzymes may also acylate formate naturally or can be engineered to do so. Information related to these proteins and genes is shown below.

| Protein | GenBank ID | GI number | Organism |
| --- | --- | --- | --- |
| Phl | CAJ15517.1 | 77019264 | *Penicillium chrysogenum* |
| PhlB | ABS19624.1 | 152002983 | *Penicillium chrysogenum* |
| PaaF | AAC24333.2 | 22711873 | *Pseudomonas putida* |
| BioW | NP_390902.2 | 50812281 | *Bacillus subtilis* |
| AACS | NP_084486.1 | 21313520 | *Mus musculus* |
| AACS | NP_076417.2 | 31982927 | *Homo sapiens* |
| Msed 1422 | YP_001191504 | 146304188 | *Metallosphaera sedula* |

Step G, FIG. 1: Formyl-CoA reductase

Several acyl-CoA dehydrogenases are capable of reducing an acyl-CoA (e.g., formyl-CoA) to its corresponding aldehyde (e.g., formaldehyde) (Steps F, FIG. 1). Exemplary genes that encode such enzymes include the *Acinetobacter calcoaceticus* acr1 encoding a fatty acyl-CoA reductase (Reiser and Somerville, *J. Bacteriol.* 179:2969-2975 (1997), the *Acinetobacter* sp. M-1 fatty acyl-CoA reductase (Ishige et al., *Appl. Environ. Microbiol.* 68:1192-1195 (2002), and a CoA- and NADP-dependent succinate semialdehyde dehydrogenase encoded by the sucD gene in *Clostridium kluyveri* (Sohling and Gottschalk, *J. Bacteriol.* 178:871-880 (1996); Sohling and Gottschalk, *J. Bacteriol.* 1778:871-880 (1996)). SucD of *P. gingivalis* is another succinate semialdehyde dehydrogenase (Takahashi et al., *J. Bacteriol.* 182:4704-4710 (2000). The enzyme acylating acetaldehyde dehydrogenase in *Pseudomonas* sp, encoded by bphG, is yet another candidate as it has been demonstrated to oxidize and acylate acetaldehyde, propionaldehyde, butyraldehyde, isobutyraldehyde and formaldehyde (Powlowski et al., *J. Bacteriol.* 175:377-385 (1993)). In addition to reducing acetyl-CoA to ethanol, the enzyme encoded by adhE in *Leuconostoc mesenteroides* has been shown to oxidize the branched chain compound isobutyraldehyde to isobutyryl-CoA (Kazahaya et al., *J. Gen. Appl. Microbiol.* 18:45-55 (1972); Koo et al., *Biotechnol. Lett.* 27:505-510 (2005)). Butyraldehyde dehydrogenase catalyzes a similar reaction, conversion of butyryl-CoA to butyraldehyde, in solventogenic organisms such as *Clostridium saccharoperbulylacetonicum* (Kosaka et al., *Biosci. Biotechnol. Biochem.* 71:58-68 (2007)). Additional aldehyde dehydrogenase enzyme candidates are found in *Desulfatibacillum alkenivorans, Citrobacter koseri, Salmonella enterica, Lactobacillus brevis* and *Bacillus selenitireducens*. Such enzymes may be capable of naturally converting formyl-CoA to formaldehyde or can be engineered to do so.

| Protein | GenBank ID | GI number | Organism |
|---|---|---|---|
| acr1 | YP_047869.1 | 50086355 | *Acinetobacter calcoaceticus* |
| acr1 | AAC45217 | 1684886 | *Acinetobacter baylyi* |
| acr1 | BAB85476.1 | 18857901 | *Acinetobacter* sp. Strain M-1 |
| sucD | P38947.1 | 172046062 | *Clostridium kluyveri* |
| sucD | NP_904963.1 | 34540484 | *Porphyromonas gingivalis* |
| bphG | BAA03892.1 | 425213 | *Pseudomonas* sp |
| adhE | AAV66076.1 | 55818563 | *Leuconostoc mesenteroides* |
| Bld | AAP42563.1 | 31075383 | *Clostridium saccharoperbutylacetonicum* |
| Ald | ACL06658.1 | 218764192 | *Desulfatibacillum alkenivorans* AK-01 |
| Ald | YP_001452373 | 157145054 | *Citrobacter koseri* ATCC BAA-895 |
| pduP | NP_460996.1 | 16765381 | *Salmonella enterica Typhimurium* |
| pduP | ABJ64680.1 | 116099531 | *Lactobacillus brevis* ATCC 367 |
| BselDRAFT_1651 | ZP_02169447 | 163762382 | *Bacillus selenitireducens* MLS10 |

An additional enzyme type that converts an acyl-CoA to its corresponding aldehyde is malonyl-CoA reductase which transforms malonyl-CoA to malonic semialdehyde. Malonyl-CoA reductase is a key enzyme in autotrophic carbon fixation via the 3-hydroxypropionate cycle in thermoacidophilic archaeal bacteria (Berg et al., *Science* 318:1782-1786 (2007); Thauer, *Science* 318:1732-1733 (2007)). The enzyme utilizes NADPH as a cofactor and has been characterized in *Metallosphaera* and *Sulfolobus* spp (Alber et al. *J. Bacteriol.* 188:8551-8559 (2006); Hugler et al *J. Bacteriol.* 184:2404-2410 (2002)). The enzyme is encoded by Msed_0709 in *Metallosphaera sedula* (Alber et al., supra (2006); Berg et al., *Science* 318:1782-1786 (2007)). A gene encoding a malonyl-CoA reductase from *Sulfolobus tokodaii* was cloned and heterologously expressed in *E. coli* (Alber et J. *Bacteriol.* 188:8551-8559 (2006)). This enzyme has also been shown to catalyze the conversion of methylmalonyl-CoA to its corresponding aldehyde (WO 2007/141208 (2007)). Although the aldehyde dehydrogenase functionality of these enzymes is similar to the bifunctional dehydrogenase from *Chloroflexus aurantiacus*, there is little sequence similarity. Both malonyl-CoA reductase enzyme candidates have high sequence similarity to aspartate-semialdehyde dehydrogenase, an enzyme catalyzing the reduction and concurrent dephosphorylation of aspartyl-4-phosphate to aspartate semialdehyde. Additional gene candidates can be found by sequence homology to proteins in other organisms including *Sulfolobus solfataricus* and *Sulfolobus acidocaldarius* and have been listed below. Yet another candidate for CoA-acylating aldehyde dehydrogenase is the ald gene from *Clostridium beijerinckii* (Toth et al., *Appl. Environ. Microbiol.* 65:4973-4980 (1999). This enzyme has been reported to reduce acetyl-CoA and butyryl-CoA to their corresponding aldehydes. This gene is very similar to eutE that encodes acetaldehyde dehydrogenase of *Salmonella typhimurium* and *E. coli* (Toth et al., supra). Such enzymes may be capable of naturally converting formyl-CoA to formaldehyde or can be engineered to do so.

| Protein | GenBank ID | GI number | Organism |
|---|---|---|---|
| Msed_0709 | YP_001190808.1 | 146303492 | *Metallosphaera sedula* |
| Mcr | NP_378167.1 | 15922498 | *Sulfolobus tokodaii* |
| asd-2 | NP_343563.1 | 15898958 | *Sulfolobus solfataricus* |
| Saci 2370 | YP_256941.1 | 70608071 | *Sulfolobus acidocaldarius* |
| Ald | AAT66436 | 9473535 | *Clostridium beijerinckii* |
| eutE | AAA80209 | 687645 | *Salmonella typhimurium* |
| eutE | P77445 | 2498347 | *Escherichia coli* |

Step H, FIG. 1: Formyltetrahydrofolate Synthetase

Formyltetrahydrofolate synthetase ligates formate to tetrahydrofolate at the expense of one ATP. This reaction is catalyzed by the gene product of Moth_0109 in *M. thermoacetica* (O'brien et al., *Experientia Suppl.* 26:249-262 (1976); Lovell et al., *Arch. Microbiol.* 149:280-285 (1988); Lovell et al., *Biochemistry* 29:5687-5694 (1990)), FHS in *Clostridium acidurici* (Whitehead and Rabinowitz, *J. Bacteriol.* 167:203-209 (1986); Whitehead and Rabinowitz, *J. Bacteriol.* 170:3255-3261 (1988), and CHY_2385 in *C. hydrogenoformans* (Wu et al., *PLoS Genet.* 1:e65 (2005). Homologs exist in *C. carboxicbvorans* P7. This enzyme is found in several other organisms as listed below.

| Protein | Gen Bank ID | GI number | Organism |
|---|---|---|---|
| Moth_0109 | YP_428991.1 | 83588982 | *Moorella thermoacetica* |
| CHY_2385 | YP_361182.1 | 78045024 | *Carboxydothermus hydrogenoformans* |
| FHS | P13419.1 | 120562 | *Clostridium acidurici* |
| CcarbDRAFT_1913 | ZP_05391913.1 | 255524966 | *Clostridium carboxidivorans* P7 |
| CcarbDRAFT_2946 | ZP_05392946.1 | 255526022 | *Clostridium carboxidivorans* P7 |
| Dhaf_0555 | ACL18622.1 | 219536883 | *Desulfitobacterium hafniense* |
| fhs | YP_001393842.1 | 153953077 | *Clostridium kluyveri* DSM 555 |

| Protein | Gen Bank ID | GI number | Organism |
|---|---|---|---|
| fhs | YP_003781893.1 | 300856909 | Clostridium ljunydahlii DSM 13528 |
| MGA3_08300 | EIJ83208.1 | 387590889 | Bacillus methanolicus MGA3 |
| PB1_13509 | ZP_10132113.1 | 387929436 | Bacillus methanolicus PB1 |

Steps I and J, FIG. 1: Formyltetrahydrofolate Synthetase and Methylenetetrahydrofolate Dehydrogenase In *M. thermoacetica*, *E. coli*, and *C. hydrogenoformans*, methenyltetrahydrofolate cyclohydrolase and methylenetetrahydrofolate dehydrogenase are carried out by the bifunctional gene products of Moth_1516,folD, and CHY_1878, respectively (Pierce et al., *Environ. Microbiol* 10:2550-2573 (2008); Wu et al., *PLoS Genet.* 1:e65 (2005); D'Ari and Rabinowitz, *J. Biol. Chem.* 266:23953-23958 (1991)). A homolog exists in *C. carboxidivorans P7*. Several other organisms also encode for this bifunctional protein as tabulated below.

| Protein | Gen Bank ID | GI number | Organism |
|---|---|---|---|
| Moth_1516 | YP_430368.1 | 83590359 | Moorella thermoacetica |
| folD | NP_415062.1 | 16128513 | Escherichia coli |
| CHY_1878 | YP_360698.1 | 78044829 | Carboxydothermus hydrogenoformans |
| CcarbDRAFT_2948 | ZP_05392948.1 | 255526024 | Clostridium carboxidivorans P7 |
| folD | ADK16789.1 | 300437022 | Clostridium ljungdahlii DSM 13528 |
| folD-2 | NP_951919.1 | 39995968 | Geobacter sulfurreducens PCA |
| folD | YP_725874.1 | 113867385 | Ralstonia eutropha H16 |
| folD | NP_348702.1 | 15895353 | Clostridium acetobutylicum ATCC 824 |
| folD | YP_696506.1 | 110800457 | Clostridium perfringens |
| MGA3_09460 | EIJ83438.1 | 387591119 | Bacillus methanolicus MGA3 |
| PB1_14689 | ZP_10132349.1 | 387929672 | Bacillus methanolicus PB1 |

Steps K, FIG. 1: Formaldehyde-Forming Enzyme or Spontaneous

Methylene-THF, or active formaldehyde, will spontaneously decompose to formaldehyde and THF (Thorndike and Beck, *Cancer Res.* 1977, 37(4) 1125-32; Ordonez and Caraballo, *Psychophannacol Commun.* 1975 1(3) 253-60; Kallen and Jencks, 1966, *J Biol Chem* 241(24) 5851-63). To achieve higher rates, a formaldehyde-forming enzyme can be applied. Such an activity can be obtained by engineering an enzyme that reversibly forms methylene-THF from THF and a formaldehyde donor, to release free formaldehyde. Such enzymes include glycine cleavage system enzymes which naturally transfer a formaldehyde group from methylene-THF to glycine (see Step L, FIG. 1 for candidate enzymes). Additional enzymes include serine hydroxymethyltransferase (see Step M, FIG. 1 for candidate enzymes), dimethylglycine dehydrogenase (Porter, et al., *Arch Biochem Biophys.* 1985, 243(2) 396-407; Brizio et al., 2004, (37) 2, 434-442), sarcosine dehydrogenase (Porter, et al., *Arch Biochem Biophys.* 1985, 243(2) 396-407), and dimethylglycine oxidase (Leys, et al., 2003, *The EMBO Journal* 22(16) 4038-4048).

| Protein | GenBank ID | GI number | Organism |
|---|---|---|---|
| dmgo | ZP_09278452.1 | 359775109 | Arthrobacter globiformis |
| dmgo | YP_002778684.1 | 226360906 | Rhodococcus opacus B4 |
| dmgo | EFY87157.1 | 322695347 | Metarhizium acridum CQMa 102 |
| shd | AAD53398.2 | 5902974 | Homo sapiens |
| shd | NP_446116.1 | GI: 25742657 | Rattus norvegicus |
| dmgdh | NP_037523.2 | 24797151 | Homo sapiens |
| dmgdh | Q63342.1 | 2498527 | Rattus norvegicus |

Step L, FIG. 1: Glycine Cleavage System

The reversible NAD(P)H-dependent conversion of 5,10-methylenetetrahydrofolate and $CO_2$ to glycine is catalyzed by the glycine cleavage complex, also called glycine cleavage system, composed of four protein components; P, H, T and L. The glycine cleavage complex is involved in glycine catabolism in organisms such as *E. coli* and glycine biosynthesis in eukaryotes (Kikuchi et al, *Proc Jpn Acad Ser* 84:246 (2008)). The glycine cleavage system of *E. coli* is encoded by four genes: gcvPHT and lpdA (Okamura et al, Eur J Biochem 216:539-48 (1993); Heil et al, Microbiol 148:2203-14 (2002)). Activity of the glycine cleavage system in the direction of glycine biosynthesis has been demonstrated in vivo in *Saccharomyces cerevisiae* (Maaheimo et al, Eur J Biochem 268:2464-79 (2001)). The yeast GCV is encoded by GCV1, GCV2, GCV3 and LPD1.

| Protein | GenBank ID | GI Number | Organism |
|---|---|---|---|
| gcvP | AAC75941.1 | 1789269 | Escherichia coli |
| gcvT | AAC75943.1 | 1789272 | Escherichia coli |
| gcvH | AAC75942.1 | 1789271 | Escherichia coli |
| lpdA | AAC73227.1 | 1786307 | Escherichia coli |
| GCV1 | NP_010302.1 | 6320222 | Saccharomyces cerevisiae |
| GCV2 | NP_013914.1 | 6323843 | Saccharomyces cerevisiae |
| GCV3 | NP_009355.3 | 269970294 | Saccharomyces cerevisiae |
| LPD1 | NP_116635.1 | 14318501 | Saccharomyces cerevisiae |

Step M, FIG. 1: Serine hydroxymethyltransferase

Conversion of glycine to serine is catalyzed by serine hydroxymethyltransferase, also called glycine hydroxymethyltranferase. This enzyme reversibly converts glycine and 5,10-methylenetetrahydrofolate to serine and THF. Serine methyltransferase has several side reactions including the reversible cleavage of 3-hydroxyacids to glycine and an aldehyde, and the hydrolysis of 5,10-methenyl-THF to 5-formyl-THF. This enzyme is encoded by glyA of *E. coli* (Plamann et al, *Gene* 22:9-18 (1983)). Serine hydroxymethyltranferase enzymes of *S. cerevisiae* include SHM1 (mitochondrial) and SHM2 (cytosolic) (McNeil et al, *J Biol Chem* 269:9155-65 (1994)). Similar enzymes have been studied in *Corynebacterium glutamicum* and *Methylobacterium extorquens* (Chistoserdova et al, *J Bacteriol* 176:6759-62 (1994); Schweitzer et al, *J Biotechnol* 139:214-21 (2009)).

| Protein | GenBank ID | GI Number | Organism |
|---|---|---|---|
| glyA | AAC75604.1 | 1788902 | *Escherichia coli* |
| SHM1 | NP_009822.2 | 37362622 | *Saccharomyces cerevisiae* |
| SHM2 | NP_013159.1 | 6323087 | *Saccharomyces cerevisiae* |
| glyA | AAA64456.1 | 496116 | *Methylobacterium extorquens* |
| gly | AAK60516.1 | 14334055 | *Corynebacterium glutamicum* |

Step N, FIG. 1: Serine Deaminase

Serine can be deaminated to pyruvate by serine deaminase Serine deaminase enzymes are present in several organisms including *Clostridium acidurici* (Carter, et al., 1972, *J Bacteriol.*, 109(2) 757-763), *Escherichia coli* (Cicchillo et al., 2004, *J Biol Chem.*, 279(31) 32418-25), and *Corneybacterium* sp. (Netzer et al., *Appl Environ Microbiol.* 2004 December; 70(12):7148-55).

| Protein | GenBank ID | GI Number | Organism |
|---|---|---|---|
| sdaA | YP_490075.1 | 388477887 | *Escherichia coli* |
| sdaB | YP_491005.1 | 388478813 | *Escherichia coli* |
| tdcG | YP_491301.1 | 388479109 | *Escherichia coli* |
| tdcB | YP_491307.1 | 388479115 | *Escherichia coli* |
| sdaA | YP_225930.1 | 62390528 | *Corynebacterium* sp. |

Step O, FIG. 1: Methylenetetrahydrofolate Reductase

In *M. thermoacetica*, this enzyme is oxygen-sensitive and contains an iron-sulfur cluster (Clark and Ljungdahl, *J. Biol. Chem.* 259:10845-10849 (1984). This enzyme is encoded by metF in *E. coli* (Sheppard et al., *J. Bacteriol.* 181:718-725 (1999) and CHY_1233 in *C. hydrogenoformans* (Wu et al., *PLoS Genet.* 1:e65 (2005). The *M. thermoacetica* genes, and its *C. hydrogenoformans* counterpart, are located near the CODH/ACS gene cluster, separated by putative hydrogenase and heterodisulfide reductase genes. Some additional gene candidates found bioinformatically are listed below. In *Acetobacterium woodii* metF is coupled to the Rnf complex through RnfC2 (Poehlein et al, PLoS One. 7:e33439). Homologs of RnfC are found in other organisms by blast search. The Rnf complex is known to be a reversible complex (Fuchs (2011) Annu. Rev. Microbiol. 65:631-658).

Step P, FIG. 1: Acetyl-CoA Synthase

Acetyl-CoA synthase is the central enzyme of the carbonyl branch of the Wood-Ljungdahl pathway. It catalyzes the synthesis of acetyl-CoA from carbon monoxide, coenzyme A, and the methyl group from a methylated corrinoid-iron-sulfur protein. The corrinoid-iron-sulfur-protein is methylated by methyltetrahydrofolate via a methyltransferase. Expression in a foreign host entails introducing one or more of the following proteins and their corresponding activities: Methyltetrahydrofolate:corrinoid protein methyltransferase (AcsE), Corrinoid iron-sulfur protein (AcsD), Nickel-protein assembly protein (AcsF), Ferredoxin (Orf7), Acetyl-CoA synthase (AcsB and AcsC), Carbon monoxide dehydrogenase (AcsA), and Nickel-protein assembly protein (CooC).

The genes used for carbon-monoxide dehydrogenase/acetyl-CoA synthase activity typically reside in a limited region of the native genome that can be an extended operon (Ragsdale, S. W., *Crit. Rev. Biochem. Mol. Biol.* 39:165-195 (2004); Morton et al., *J. Biol. Chem.* 266:23824-23828 (1991); Roberts et al., *Proc. Natl. Acad Sci. U.S.A.* 86:32-36 (1989). Each of the genes in this operon from the acetogen, *M. thermoacetica*, has already been cloned and expressed actively in *E. coli* (Morton et al. supra; Roberts et al. supra; Lu et al., *J. Biol. Chem.* 268:5605-5614 (1993). The protein sequences of these genes can be identified by the following GenBank accession numbers.

| Protein | GenBank ID | GI number | Organism |
|---|---|---|---|
| AcsE | YP_430054 | 83590045 | *Moorella thermoacetica* |
| AcsD | YP_430055 | 83590046 | *Moorella thermoacetica* |
| AcsF | YP_430056 | 83590047 | *Moorella thermoacetica* |
| Orf7 | YP_430057 | 83590048 | *Moorella thermoacetica* |
| AcsC | YP_430058 | 83590049 | *Moorella thermoacetica* |
| AcsB | YP_430059 | 83590050 | *Moorella thermoacetica* |
| AcsA | YP_430060 | 83590051 | *Moorella thermoacetica* |
| CooC | YP_430061 | 83590052 | *Moorella thermoacetica* |

The hydrogenic bacterium, *Carboxydothermus hydrogenoformans*, can utilize carbon monoxide as a growth substrate by means of acetyl-CoA synthase (Wu et al., *PLoS Genet.* 1:e65 (2005)). In strain Z-2901, the acetyl-CoA synthase enzyme complex lacks carbon monoxide dehydrogenase due to a frameshift mutation (Wu et al. supra (2005)), whereas in strain DSM 6008, a functional unframeshifted full-length version of this protein has been purified (Svetlitchnyi et al., *Proc. Natl. Acad. Sci. U.S.A.* 101:446-451 (2004)). The protein sequences of the *C. hydrogenoformans* genes from strain Z-2901 can be identified by the following GenBank accession numbers.

| Protein | GenBank ID | GI number | Organism |
|---|---|---|---|
| Moth_1191 | YP_430048.1 | 83590039 | *Moorella thermoacetica* |
| Moth_1192 | YP_430049.1 | 83590040 | *Moorella thermoacetica* |
| metF | NP_418376.1 | 16131779 | *Escherichia coli* |
| CH_1233 | YP_360071.1 | 78044792 | *Carboxydothermus hydrogenoformans* |
| CLJU_c37610 | YP_003781889.1 | 300856905 | *Clostridium ljungdahlii* DSM 13528 |
| DesfrDRAFT_3717 | ZP_07335241.1 | 303248996 | *Desulfovibrio fructosovorans* JJ |
| CcarbDRAFT_2950 | ZP_05392950.1 | 255526026 | *Clostridium carboxidivorans*P7 |
| Ccel74_010100023124 | ZP_07633513.1 | 307691067 | *Clostridium cellulovorans* 743B |
| Cphy_3110 | YP_001560205.1 | 160881237 | *Clostridium phytofermentans* ISDg |

| Protein | GenBank ID | GI number | Organism |
|---|---|---|---|
| AcsE | YP_360065 | 78044202 | Carboxydothermus hydrogenoformans |
| AcsD | YP_360064 | 78042962 | Carboxydothermus hydrogenoformans |
| AcsF | YP_360063 | 78044060 | Carboxydothermus hydrogenoformans |
| Orf7 | YP_360062 | 78044449 | Carboxydothermus hydrogenoformans |
| AcsC | YP_360061 | 78043584 | Carboxydothermus hydrogenoformans |
| AcsB | YP_360060 | 78042742 | Carboxydothermus hydrogenoformans |
| CooC | YP_360059 | 78044249 | Carboxydothermus hydrogenoformans |

Homologous ACS/CODH genes can also be found in the draft genome assembly of Clostridium carboxidivorans P7.

| Protein | GenBank ID | GI Number | Organism |
|---|---|---|---|
| AcsA | ZP_05392944.1 | 255526020 | Clostridium carboxidivorans P7 |
| CooC | ZP_05392945.1 | 255526021 | Clostridium carboxidivorans P7 |
| AcsF | ZP_05392952.1 | 255526028 | Clostridium carboxidivorans P7 |
| AcsD | ZP_05392953.1 | 255526029 | Clostridium carboxidivorans P7 |
| AcsC | ZP_05392954.1 | 255526030 | Clostridium carboxidivorans P7 |
| AcsE | ZP_05392955.1 | 255526031 | Clostridium carboxidivorans P7 |
| AcsB | ZP_05392956.1 | 255526032 | Clostridium carboxidivorans P7 |
| Orf7 | ZP_05392958.1 | 255526034 | Clostridium carboxidivorans P7 |

The methanogenic archaeon, Methanosarcina acetivorans, can also grow on carbon monoxide, exhibits acetyl-CoA synthase/carbon monoxide dehydrogenase activity, and produces both acetate and formate (Lessner et al., Proc. Natl. Acad Sci. U.S.A. 103:17921-17926 (2006)). This organism contains two sets of genes that encode ACS/CODH activity (Rother and Metcalf, Proc. Natl. Acad Sci. U.S.A. 101:16929-16934 (2004)). The protein sequences of both sets of M acetivorans genes are identified by the following GenBank accession numbers.

| Protein | GenBank ID | GI number | Organism |
|---|---|---|---|
| AcsC | NP_618736 | 20092661 | Methanosarcina acetivorans |
| AcsD | NP_618735 | 20092660 | Methanosarcina acetivorans |
| AcsF, CooC | NP_618734 | 20092659 | Methanosarcina acetivorans |
| AcsB | NP_618733 | 20092658 | Methanosarcina acetivorans |
| AcsEps | NP_618732 | 20092657 | Methanosarcina acetivorans |
| AcsA | NP_618731 | 20092656 | Methanosarcina acetivorans |
| AcsC | NP_615961 | 20089886 | Methanosarcina acetivorans |
| AcsD | NP_615962 | 20089887 | Methanosarcina acetivorans |
| AcsF, CooC | NP_615963 | 20089888 | Methanosarcina acetivorans |
| AcsB | NP_615964 | 20089889 | Methanosarcina acetivorans |
| AcsEps | NP_615965 | 20089890 | Methanosarcina acetivorans |
| AcsA | NP_615966 | 20089891 | Methanosarcina acetivorans |

The AcsC, AcsD, AcsB, AcsEps, and AcsA proteins are commonly referred to as the gamma, delta, beta, epsilon, and alpha subunits of the methanogenic CODH/ACS. Homologs to the epsilon encoding genes are not present in acetogens such as M. thermoacetica or hydrogenogenic bacteria such as C. hydrogenoformans. Hypotheses for the existence of two active CODH/ACS operons in M acetivorans include catalytic properties (i.e., $K_m$, $V_{max}$, $k_{cat}$) that favor carboxidotrophic or aceticlastic growth or differential gene regulation enabling various stimuli to induce CODH/ACS expression (Rother et al., Arch. Microbiol. 188:463-472 (2007)).

Step Y, FIG. 1: Glyceraldehydes-3-phosphate Dehydrogenase and Enzymes of Lower Glycolysis Enzymes comprising Step Y, G3P to PYR include: Glyceraldehyde-3-phosphate dehydrogenase; Phosphoglycemte kinase; Phosphoglyceromutase; Enolase; Pyruvate kinase or PTS-dependant substrate import.

Glyceraldehyde-3-phosphate dehydrogenase enzymes include:

NADP-dependant glyceraldehyde-3-phosphate dehydrogenase, exemplary enzymes are:

| Protein | GenBank ID | GI Number | Organism |
|---|---|---|---|
| gapN | AAA91091.1 | 642667 | Streptococcus mutans |
| NP-GAPDH | AEC07555.1 | 330252461 | Arabidopsis thaliana |
| GAPN | AAM77679.2 | 82469904 | Triticum aestivum |
| gapN | CAI56300.1 | 87298962 | Clostridium acetobutylicum |
| NADP-GAPDH | 2D2I_A | 112490271 | Synechococcus elongatus PCC 7942 |

| Protein | GenBank ID | GI Number | Organism |
| --- | --- | --- | --- |
| NADP-GAPDH | CAA62619.1 | 4741714 | Synechococcus elongatus PCC 7942 |
| GDP1 | XP_455496.1 | 50310947 | Kluyveromyces lactis NRRL Y-1140 |
| HP1346 | NP_208138.1 | 15645959 | Helicobacter pylori 26695 | and NAD-dependant glyceraldehyde-3-phosphate dehydrogenase, exemplary enzymes are:

| Protein | GenBank ID | GI Number | Organism |
| --- | --- | --- | --- |
| TDH1 | NP_012483.1 | 6322409 | Saccharomyces cerevisiae s288c |
| TDH2 | NP_012542.1 | 6322468 | Saccharomyces cerevisiae s288c |
| TDH3 | NP_011708.1 | 632163 | Saccharomyces cerevisiae s288c |
| KLLA0A11858g | XP_451516.1 | 50303157 | Kluyveromyces lactis NRRL Y-1140 |
| KLLA0F20988g | XP_456022.1 | 50311981 | Kluyveromyces lactis NRRL Y-1140 |
| ANI_1_256144 | XP_001397496.1 | 145251966 | Aspergillus niger CBS 513.88 |
| YALI0C06369g | XP_501515.1 | 50548091 | Yarrowia lipolytica |
| CTRG_05666 | XP_002551368.1 | 255732890 | Candida tropicalis MYA-3404 |
| HPODL 1089 | EFW97311.1 | 320583095 | Hansenula polymorpha DL-1 |
| gapA | YP_490040.1 | 388477852 | Escherichia coli |

Phosphoglycemte kinase enzymes include:

| Protein | GenBank ID | GI Number | Organism |
| --- | --- | --- | --- |
| PGK1 | NP_009938.2 | 10383781 | Saccharomyces cerevisiae s288c |
| PGK | BAD83658.1 | 57157302 | Candida boidinii |
| PGK | EFW98395.1 | 320584184 | Hansenula polymorpha DL-1 |
| pgk | EIJ77825.1 | 387585500 | Bacillus methanolicus MGA3 |
| pgk | YP_491126.1 | 388478934 | Escherichia coli |

Phosphoglyceromutase (aka phosphoglycemte mutase) enzymes include;

| Protein | GenBank ID | GI Number | Organism |
| --- | --- | --- | --- |
| GPM1 | NP_012770.1 | 6322697 | Saccharomyces cerevisiae s288c |
| GPM2 | NP_010263.1 | 6320183 | Saccharomyces cerevisiae s288c |
| GPM3 | NP_014585.1 | 6324516 | Saccharomyces cerevisiae s288c |
| HPODL_1391 | EFW96681.1 | 320582464 | Hansenula polymorpha DL-1 |
| HPODL_0376 | EFW97746.1 | 320583533 | Hansenula polymorpha DL-1 |
| gpmI | EIJ77827.1 | 387585502 | Bacillus methanolicus MGA3 |
| gpmA | YP_489028.1 | 388476840 | Escherichia coli |
| gpmM | AAC76636.1 | 1790041 | Escherichia coli |

Enolase (also known as phosphopyruvate hydratase and 2-phosphoglycemte dehydratase) enzymes include:

| Protein | GenBank ID | GI Number | Organism |
| --- | --- | --- | --- |
| ENO1 | NP_011770.3 | 398366315 | Saccharomyces cerevisiae s288c |
| ENO2 | AAB68019.1 | 458897 | Saccharomyces cerevisiae s288c |
| HPODL_2596 | EFW95743.1 | 320581523 | Hansenula polymorpha DL-1 |
| eno | EIJ77828.1 | 387585503 | Bacillus methanolicus MGA3 |
| eno | AAC75821.1 | 1789141 | Escherichia coli |

Pyruvate kinase (also known as phosphoenolpyruvate kinase and phosphoenolpyruvate kinase) or PTS-dependant substrate import enzymes include those below. Pyruvate kinase, also known as phosphoenolpyruvate synthase (EC 2.7.9.2), converts pyruvate and ATP to PEP and AMP. This enzyme is encoded by the PYK1 (Burke et al., J. Biol. Chem. 258:2193-2201 (1983)) and PYK2 (Boles et al., J. Bacteriol. 179:2987-2993 (1997)) genes in S. cerevisiae. In E. coli, this activity is catalyzed by the gene products of pykF and pykA. Note that pykA and pykF are genes encoding separate enzymes potentially capable of carrying out the PYK reaction. Selected homologs of the S. cerevisiae enzymes are also shown in the table below.

| Protein | GenBank ID | GI Number | Organism |
|---|---|---|---|
| PYK1 | NP_009362 | 6319279 | Saccharomyces cerevisiae |
| PYK2 | NP_014992 | 6324923 | Saccharomyces cerevisiae |
| pykF | NP_416191.1 | 16129632 | Escherichia coli |
| pykA | NP_416368.1 | 16129807 | Escherichia coli |
| KLLA0F23397g | XP_456122.1 | 50312181 | Kluyveromyces lactis |
| CaO19.3575 | XP_714934.1 | 68482353 | Candida albicans |
| CaO19.11059 | XP_714997.1 | 68482226 | Candida albicans |
| YALI0F09185p | XP_505195 | 210075987 | Yarrowia lipolytica |
| ANI_1_1126064 | XP_001391973 | 145238652 | Aspergillus niger |
| MGA3_03005 | EIJ84220.1 | 387591903 | Bacillus methanolicus MGA3 |
| HPODL_1539 | EFW96829.1 | 320582612 | Hansenula polymorpha DL-1 |

Alternatively, Phosphoenolpyruvate phosphatase (EC 3.1.3.60) catalyzes the hydrolysis of PEP to pyruvate and phosphate. Numerous phosphatase enzymes catalyze this activity, including alkaline phosphatase (EC 3.1.3.1), acid phosphatase (EC 3.1.3.2), phosphoglycerate phosphatase (EC 3.1.3.20) and PEP phosphatase (EC 3.1.3.60). PEP phosphatase enzymes have been characterized in plants such as Vignia radiate, Bruguiera sexangula and Brassica nigra. The phytase from Aspergillus fumigates, the acid phosphatase from Homo sapiens and the alkaline phosphatase of E. coli also catalyze the hydrolysis of PEP to pyruvate (Brugger et al, Appl Microbiol Biotech 63:383-9 (2004); Hayman et al, Biochem J 261:601-9 (1989); et al, The Enzymes 3rd Ed. 4:373-415 (1971))). Similar enzymes have been characterized in Campylobacter jejuni (van Mourik et al., Microbiol. 154:584-92 (2008)), Saccharomyces cerevisiae (Oshima et al., Gene 179:171-7 (1996)) and Staphylococcus aureus (Shah and Blobel, J. Bacteriol. 94:780-1 (1967)). Enzyme engineering and/or removal of targeting sequences may be required for alkaline phosphatase enzymes to function in the cytoplasm.

| Protein | GenBank ID | GI Number | Organism |
|---|---|---|---|
| phyA | O00092.1 | 41017447 | Aspergillus fumigatus |
| Acp5 | P13686.3 | 56757583 | Homo sapiens |
| phoA | NP_414917.2 | 49176017 | Escherichia coli |
| phoX | ZP_01072054.1 | 86153851 | Campylobacter jejuni |
| PHO8 | AAA34871.1 | 172164 | Saccharomyces cerevisiae |
| SaurJH1_2706 | YP_001317815.1 | 150395140 | Staphylococcus aureus |

Step Q, FIG. 1: Pyruvate Formate Lyase

Pyruvate formate-lyase (PFL, EC 2.3.1.54), encoded by pflB in E. coli, can convert pyruvate into acetyl-CoA and formate. The activity of PFL can be enhanced by an activating enzyme encoded by pflA (Knappe et al., Proc.Natl.Acad.Sci USA 81:1332-1335 (1984); Wong et al., Biochemistry 32:14102-14110 (1993)). Keto-acid formate-lyase (EC 2.3.1.-), also known as 2-ketobutyrate formate-lyase (KFL) and pyruvate formate-lyase 4, is the gene product of tdcE in E. coli. This enzyme catalyzes the conversion of 2-ketobutyrate to propionyl-CoA and formate during anaerobic threonine degradation, and can also substitute for pyruvate formate-lyase in anaerobic catabolism (Simanshu et al., J Biosci. 32:1195-1206 (2007)). The enzyme is oxygen-sensitive and, like PflB, can require post-translational modification by PFL-AE to activate a glycyl radical in the active site (Hesslinger et al., Mol.Microbiol 27:477-492 (1998)). A pyruvate formate-lyase from Archaeglubus fulgidus encoded by pflD has been cloned, expressed in E. coli and characterized (Lehtio et al., Protein Eng Des Sel 17:545-552 (2004)). The crystal structures of the A. fulgidus and E. coli enzymes have been resolved (Lehtio et al., J Mol.Biol. 357:221-235 (2006); Leppanen et al., Structure. 7:733-744 (1999)). Additional PFL and PFL-AE candidates are found in Lactococcus lactis (Melchiorsen et al., Appl Microbiol Biotechnol 58:338-344 (2002)), and Streptococcus mutans (Takahashi-Abbe et al., Oral.Microbiol Immunol. 18:293-297 (2003)), Chlamydomonas reinhardtli (Hemschemeier et al., Eukaryot. Cell 7:518-526 (2008b); Atteia et al., J.Biol.Chem. 281:9909-9918 (2006)) and Clostridium pasteurianum (Weidner et al., J Bacteriol. 178:2440-2444 (1996)).

| Protein | GenBank ID | GI Number | Organism |
|---|---|---|---|
| pflB | NP_415423 | 16128870 | Escherichia coli |
| pflA | NP_415422.1 | 16128869 | Escherichia coli |
| tdcE | AAT48170.1 | 48994926 | Escherichia coli |
| pflD | NP_070278.1 | 11499044 | Archaeglubus fulgidus |
| Pfl | CAA03993 | 2407931 | Lactococcus lactis |
| Pfl | BAA09085 | 1129082 | Streptococcus mutans |
| PFL1 | XP_001689719.1 | 159462978 | Chlamydomonas reinhardtii |

-continued

| Protein | GenBank ID | GI Number | Organism |
|---|---|---|---|
| pflA1 | XP_001700657.1 | 159485246 | Chlamydomonas reinhardtii |
| Pfl | Q46266.1 | 2500058 | Clostridium pasteurianum |
| Act | CAA63749.1 | 1072362 | Clostridium pasteurianum |

Step R, FIG. 1: Pyruvate Dehydrogenase, Pyruvate Ferredoxin Oxidoreductase, Pyruvate:nadp+Oxidoreductase The pyruvate dehydrogenase (PDH) complex catalyzes the conversion of pyruvate to acetyl-CoA (FIG. 3H). The E. coli PDH complex is encoded by the genes aceEF and lpdA. Enzyme engineering efforts have improved the E. coli PDH enzyme activity under anaerobic conditions (Kim et al., J.Bacteriol. 190:3851-3858 (2008); Kim et al., Appl.Environ.Microbiol. 73:1766-1771 (2007); Zhou et al., Biotechnol.Lett. 30:335-342 (2008)). In contrast to the E. coli PDH, the B. subtilis complex is active and required for growth under anaerobic conditions (Nakano et al., 179:6749-6755 (1997)). The *Klebsiella pneumoniae* PDH, characterized during growth on glycerol, is also active under anaerobic conditions (Menzel et al., 56:135-142 (1997)). Crystal structures of the enzyme complex from bovine kidney (Zhou et al., 98:14802-14807 (2001)) and the E2 catalytic domain from *Azotobacter vinelandii* are available (Mattevi et al., *Science.* 255:1544-1550 (1992)). Some mammalian PDH enzymes complexes can react on alternate substrates such as 2-oxobutanoate. Comparative kinetics of *Rattus norvegicus* PDH and BCKAD indicate that BCKAD has higher activity on 2-oxobutanoate as a substrate (Paxton et al., *Biochem.J.* 234:295-303 (1986)). The *S. cerevisiae* PDH complex can consist of an E2 (LAT1) core that binds E1 (PDA1, PDB1), E3 (LPD1), and Protein X (PDX1) components (Pronk et al., *Yeast* 12:1607-1633 (1996)). The PDH complex of *S. cerevisiae* is regulated by phosphorylation of E1 involving PKP1 (PDH kinase I), PTCS (PDH phosphatase I), PKP2 and PTC6. Modification of these regulators may also enhance PDH activity. Coexpression of lipoyl ligase (LpiA of *E. coli* and AIM22 in *S. cerevisiae*) with PDH in the cytosol may be necessary for activating the PDH enzyme complex. Increasing the supply of cytosolic lipoate, either by modifying a metabolic pathway or media supplementation with lipoate, may also improve PDH activity.

| Gene | Accession No. | GI Number | Organism |
| --- | --- | --- | --- |
| aceE | NP_414656.1 | 16128107 | *Escherichia coli* |
| aceF | NP_414657.1 | 16128108 | *Escherichia coli* |
| lpd | NP_414658.1 | 16128109 | *Escherichia coli* |
| lplA | NP_418803.1 | 16132203 | *Escherichia coli* |
| pdhA | P21881.1 | 3123238 | *Bacillus subtilis* |
| pdhB | P21882.1 | 129068 | *Bacillus subtilis* |
| pdhC | P21883.2 | 129054 | *Bacillus subtilis* |
| pdhD | P21880.1 | 118672 | *Bacillus subtilis* |
| aceE | YP_001333808.1 | 152968699 | *Klebsiella pneumoniae* |
| aceF | YP_001333809.1 | 152968700 | *Klebsiella pneumoniae* |
| lpdA | YP_001333810.1 | 152968701 | *Klebsiella pneumoniae* |
| Pdha1 | NP_001004072.2 | 124430510 | *Rattus norvegicus* |
| Pdha2 | NP_446446.1 | 16758900 | *Rattus norvegicus* |
| Dlat | NP_112287.1 | 78365255 | *Rattus norvegicus* |
| Dld | NP_955417.1 | 40786469 | *Rattus norvegicus* |
| LAT1 | NP_014328 | 6324258 | *Saccharomyces cerevisiae* |
| PDA1 | NP_011105 | 37362644 | *Saccharomyces cerevisiae* |
| PDB1 | NP_009780 | 6319698 | *Saccharomyces cerevisiae* |
| LPD1 | NP_116635 | 14318501 | *Saccharomyces cerevisiae* |
| PDX1 | NP_011709 | 6321632 | *Saccharomyces cerevisiae* |
| AIM22 | NP_012489.2 | 83578101 | *Saccharomyces cerevisiae* |

As an alternative to the large multienzyme PDH complexes described above, some organisms utilize enzymes in the 2-ketoacid oxidoreductase family (OFOR) to catalyze acylating oxidative decarboxylation of 2-keto-acids. Unlike the PDH complexes, PFOR enzymes contain iron-sulfur clusters, utilize different cofactors and use fenedoxin or flavodixin as electron acceptors in lieu of NAD(P)H. Pyruvate ferredoxin oxidoreductase (PFOR) can catalyze the oxidation of pyruvate to form acetyl-CoA (FIG. 3H). The PFOR from *Desulfovibrio africanus* has been cloned and expressed in *E. coli* resulting in an active recombinant enzyme that was stable for several days in the presence of oxygen (Pieulle et al., *J Bacteriol.* 179:5684-5692 (1997)). Oxygen stability is relatively uncommon in PFORs and is believed to be conferred by a 60 residue extension in the polypeptide chain of the *D. africanus* enzyme. The *M. thermoacetica* PFOR is also well characterized (Menon et al., *Biochemistry* 36:8484-8494 (1997)) and was even shown to have high activity in the direction of pyruvate synthesis during autotrophic growth (Furdui et al., *J Biol Chem.* 275:28494-28499 (2000)). Further, *E. coli* possesses an uncharacterized open reading frame, ydbK that encodes a protein that is 51% identical to the *M. thermoacetica* PFOR. Evidence for pyruvate oxidoreductase activity in *E. coli* has been described (Blaschkowski et al., *Eur.J Biochem.* 123: 563-569 (1982)). Several additional PFOR enzymes are described in Ragsdale, *Chem.Rev.* 103:2333-2346 (2003). Finally, flavodoxin reductases (e.g., fqrB from *Helicobacter pylori* or *Campylobacter jejuni* (St Maurice et al., *J.Bacteriol.* 189:4764-4773 (2007))) or Rnf-type proteins (Seedorf et al., *Proc.Natl.AcadSci.USA.* 105:2128-2133 (2008); Her nann et al., *J.Bacteriol.* 190:784-791 (2008)) provide a means to generate NADH or NADPH from the reduced ferredoxin generated by PFOR. These proteins are identified below.

| Protein | GenBank ID | GI Number | Organism |
| --- | --- | --- | --- |
| Por | CAA70873.1 | 1770208 | *Desulfovibrio africanus* |
| Por | YP_428946.1 | 83588937 | *Moorella thermoacetica* |
| ydbK | NP_415896.1 | 16129339 | *Escherichia coli* |
| fqrB | NP_207955.1 | 15645778 | *Helicobacter pylori* |
| fqrB | YP_001482096.1 | 157414840 | *Campylobacter jejuni* |
| RnfC | EDK33306.1 | 146346770 | *Clostridium kluyveri* |
| RnfD | EDK33307.1 | 146346771 | *Clostridium kluyveri* |
| RnfG | EDK33308.1 | 146346772 | *Clostridium kluyveri* |
| RnfE | EDK33309.1 | 146346773 | *Clostridium kluyveri* |
| RnfA | EDK33310.1 | 146346774 | *Clostridium kluyveri* |
| RnfB | EDK33311.1 | 146346775 | *Clostridium kluyveri* |

Pyruvate:NADP oxidoreductase (PNO) catalyzes the conversion of pyruvate to acetyl-CoA. This enzyme is encoded by a single gene and the active enzyme is a homodimer, in contrast to the multi-subunit PDH enzyme complexes described above. The enzyme from *Euglena* gracilis is stabilized by its cofactor, thiamin pyrophosphate (Nakazawa et al, *Arch Biochem Biophys* 411:183-8 (2003)). The mitochondrial targeting sequence of this enzyme should be removed for expression in the cytosol. The PNO protein of *E. gracilis* and other NADP-dependant pyruvate:NADP+ oxidoreductase enzymes are listed in the table below.

| Protein | GenBank ID | GI Number | Organism |
| --- | --- | --- | --- |
| PNO | Q94IN5.1 | 33112418 | *Euglena gracilis* |
| cgd4_690 | XP_625673.1 | 66356990 | *Cryptosporidium parvum* Iowa II |
| TPP_PFOR_PNO | XP_002765111.11 | 294867463 | *Perkinsus marinus* ATCC 50983 |

Step S, FIG. 1: Formate Dehydrogenase

Formate dehydrogenase (FDH) catalyzes the reversible transfer of electrons from formate to an acceptor. Enzymes with FDH activity utilize various electron carriers such as, for example, NADH (EC 1.2.1.2), NADPH (EC 1.2.1.43), quinols (EC 1.1.5.6), cytochromes (EC 1.2.2.3) and hydrogenases (EC 1.1.99.33). FDH enzymes have been characterized from *Moorella thermoacetica* (Andreesen and Ljungdahl, *J Bacteriol* 116:867-873 (1973); Li et al., *J*

Bacteriol 92:405-412 (1966); Yamamoto et al., *J Biol Chem.* 258:1826-1832 (1983). The loci, Moth_2312 is responsible for encoding the alpha subunit of formate dehydrogenase while the beta subunit is encoded by Moth_2314 (Pierce et al., *Environ Microbiol* (2008)). Another set of genes encoding formate dehydrogenase activity with a propensity for $CO_2$ reduction is encoded by Sfum_2703 through Sfum_2706 in *Syntrophobacter fumaroxidans* (de Bok et al., *Eur J Biochem.* 270:2476-2485 (2003)); Reda et al., *PNAS* 105:10654-10658 (2008)). A similar set of genes presumed to carry out the same function are encoded by CHY_0731, CHY_0732, and CHY 0733 in *C. hydrogenoformans* (Wu et al., *PLoS Genet* 1:e65 (2005)). Formate dehydrogenases are also found many additional organisms including *C. carboxidivorans* P7, *Bacillus methanolicus, Burkholderia stabilis, Moorella thermoacetica* ATCC 39073, *Candida boidinii, Candida methylica,* and *Saccharomyces cerevisiae* S288c. The soluble formate dehydrogenase from *Ralstonia eutropha* reduces $NAD^+$ (fdsG, —B, -A, —C, -D) (Oh and Bowien, 1998)

Several EM8 enzymes have been identified that have higher specificity for NADP as the cofactor as compared to NAD. This enzyme has been deemed as the NADP-dependent formate dehydrogenase and has been reported from 5 species of the *Burkholderia cepacia* complex. It was tested and verified in multiple strains of *Burkholderia multivorans, Burkholderia stabilis, Burkholderia pyrrocinia,* and *Burkholderia cenocepacia* (Hatrongjit et al., *Enzyme and Microbial Tech.,* 46: 557-561 (2010)). The enzyme from *Burkholderia stabilis* has been characterized and the apparent $K_m$ of the enzyme were reported to be 55.5 mM, 0.16 mM and 1.43 mM for formate, NADP, and NAD respectively. More gene candidates can be identified using sequence homology of proteins deposited in Public databases such as NCBI, JGI and the metagenomic databases.

Example II

Production of Reducing Equivalents

This example describes methanol metabolic pathways and other additional enzymes generating reducing equivalents as shown in FIG. 10.

FIG. 10, Step A—Methanol Methyltransferase

A complex of 3-methyltransferase proteins, denoted MtaA, MtaB, and MtaC, perform the desired methanol methyltransferase activity (Sauer et al., *Eur. Biochem.* 243: 670-677 (1997); Naidu and Ragsdale, *J. Bacteriol.* 183: 3276-3281 (2001); Tallant and Krzycki, *J. Biol. Chem.* 276:4485-4493 (2001); Tallant and Krzycki, *J. Bacteriol.* 179:6902-6911 (1997); Tallant and Krzycki, *J. Bacteriol.* 178:1295-1301 (1996); Ragsdale, S. W., *Crit. Rev. Biochem. Mol. Biol.* 39:165-195 (2004)).

MtaB is a zinc protein that can catalyze the transfer of a methyl group from methanol to MtaC, a corrinoid protein. Exemplary genes encoding MtaB and MtaC can be found in methanogenic archaea such as *Methanosarcina barkeri* (Maeder et al., *J. Bacteriol.* 188:7922-7931 (2006) and *Methanosarcina acetivorans* (Galagan et al., *Genome Res.* 12:532-542 (2002), as well as the acetogen, *Moorella thermoacetica* (Das et al., *Proteins* 67:167-176 (2007). In general, the MtaB and MtaC genes are adjacent to one another on the chromosome as their activities are tightly interdependent. The protein sequences of various MtaB and MtaC encoding genes in *M. barkeri, M. acetivorans,* and *M. thennoaceticum* can be identified by their following GenBank accession numbers.

| Protein | GenBank ID | GI Number | Organism |
| --- | --- | --- | --- |
| Moth_2312 | YP_431142 | 148283121 | *Moorella thermoacetica* |
| Moth_2314 | YP_431144 | 83591135 | *Moorella thermoacetica* |
| Sfum_2703 | YP_846816.1 | 116750129 | *Syntrophobacter fimaroxidans* |
| Sfum_2704 | YP_846817.1 | 116750130 | *Syntrophobacter fimaroxidans* |
| Sfum_2705 | YP_846818.1 | 116750131 | *Syntrophobacter fimaroxidans* |
| Sfum_2706 | YP_846819.1 | 116750132 | *Syntrophobacter fimaroxidans* |
| CHY_0731 | YP_359585.1 | 78044572 | *Carboxydothermus hydroyenoformans* |
| CHY_0732 | YP_359586.1 | 78044500 | *Carboxydothermus hydroyenoformans* |
| CHY_0733 | YP_359587.1 | 78044647 | *Carboxydothermus hydroyenoformans* |
| CcarbDRAFT_0901 | ZP_05390901.1 | 255523938 | *Clostridium carboxidivorans* P7 |
| CcarbDRAFT_4380 | ZP_05394380.1 | 255527512 | *Clostridium carboxidivorans* P7 |
| fdhA, MGA3_06625 | EIJ82879.1 | 387590560 | *Bacillus methanolicus* MGA3 |
| fdhA, PB1_11719 | ZP_10131761.1 | 387929084 | *Bacillus methanolicus* PB1 |
| fdhD, MGA3_06630 | EIJ82880.1 | 387590561 | *Bacillus methanolicus* MGA3 |
| fdhD, PB1_11724 | ZP_10131762.1 | 387929085 | *Bacillus methanolicus* PB1 |
| fdh | ACF35003.1 | 194220249 | *Burkholderia stabilis* |
| fdh | ACF35004.1 | 194220251 | *Burkholderia pyrrocinia* |
| fdh | ACF35002.1 | 194220247 | *Burkholderia cenocepacia* |
| fdh | ACF35001.1 | 194220245 | *Burkholderia multivorans* |
| fdh | ACF35000.1 | 194220243 | *Burkholderia cepacia* |
| FDH1 | AAC49766.1 | 2276465 | *Candida boidinii* |
| fdh | CAA57036.1 | 1181204 | *Candida methylica* |
| FDH2 | P0CF35.1 | 294956522 | *Saccharomyces cerevisiae* S288c |
| FDH1 | NP_015033.1 | 6324964 | *Saccharomyces cerevisiae* S288c |
| fdsG | YP_725156.1 | 113866667 | *Ralstonia eutropha* |
| fdsB | YP_725157.1 | 113866668 | *Ralstonia eutropha* |
| fdsA | YP_725158.1 | 113866669 | *Ralstonia eutropha* |
| fdsC | YP_725159.1 | 113866670 | *Ralstonia eutropha* |
| fdsD | YP_725160.1 | 113866671 | *Ralstonia eutropha* |

| Protein | GenBank ID | GI number | Organism |
|---------|------------|-----------|----------|
| MtaB1 | YP_304299 | 73668284 | *Methanosarcina barkeri* |
| MtaC1 | YP_304298 | 73668283 | *Methanosarcina barkeri* |
| MtaB2 | YP_307082 | 73671067 | *Methanosarcina barkeri* |
| MtaC2 | YP_307081 | 73671066 | *Methanosarcina barkeri* |
| MtaB3 | YP_304612 | 73668597 | *Methanosarcina barkeri* |
| MtaC3 | YP_304611 | 73668596 | *Methanosarcina barkeri* |
| MtaB1 | NP_615421 | 20089346 | *Methanosarcina acetivorans* |
| MtaB1 | NP_615422 | 20089347 | *Methanosarcina acetivorans* |
| MtaB2 | NP_619254 | 20093179 | *Methanosarcina acetivorans* |
| MtaC2 | NP_619253 | 20093178 | *Methanosarcina acetivorans* |
| MtaB3 | NP_616549 | 20090474 | *Methanosarcina acetivorans* |
| MtaC3 | NP_616550 | 20090475 | *Methanosarcina acetivorans* |
| MtaB | YP_430066 | 83590057 | *Moorella thermoacetica* |
| MtaC | YP_430065 | 83590056 | *Moorella thermoacetica* |
| MtaA | YP_430064 | 83590056 | *Moorella thermoacetica* |

The MtaB1 and MtaC1 genes, YP_304299 and YP_304298, from *M. barkeri* were cloned into *E. coli* and sequenced (Sauer et al., *Eur. J. Biochem.* 243:670-677 (1997)). The crystal structure of this methanol-cobalamin methyltransferase complex is also available (Hagemeier et al., *Proc. Natl. Acad. Sci. U.S.A.* 103:18917-18922 (2006)). The MtaB genes, YP_307082 and YP_304612, in *M. barkeri* were identified by sequence homology to YP_304299. In general, homology searches are an effective means of identifying methanol methyltransferases because MtaB encoding genes show little or no similarity to methyltransferases that act on alternative substrates such as trimethylamine, dimethylamine, monomethylamine, or dimethylsulfide. The MtaC genes, YP_307081 and YP_304611 were identified based on their proximity to the MtaR genes and also their homology to YP_304298. The three sets of MtaB and MtaC genes from *M. acetivorans* have been genetically, physiologically, and biochemically characterized (Pritchett and Metcalf, *Mol. Microbiol.* 56:1183-1194 (2005)). Mutant strains lacking two of the sets were able to grow on methanol, whereas a strain lacking all three sets of MtaB and MtaC genes sets could not grow on methanol. This suggests that each set of genes plays a role in methanol utilization. The *M. thermoacetica* MtaB gene was identified based on homology to the methanogenic MtaB genes and also by its adjacent chromosomal proximity to the methanol-induced corrinoid protein, MtaC, which has been crystallized (Zhou et al., *Acta Crystallogr. Sect. F. Struct. Biol. Cyrst. Commun.* 61:537-540 (2005) and further characterized by Northern hybridization and Western Blotting ((Das et al., *Proteins* 67:167-176 (2007)).

MtaA is zinc protein that catalyzes the transfer of the methyl group from MtaC to either Coenzyme M in methanogens or methyltetrahydrofolate in acetogens. MtaA can also utilize methylcobalamin as the methyl donor. Exemplary genes encoding MtaA can be found in methanogenic archaea such as *Methanosarcina barkeri* (Maeder et al., *J. Bacteriol.* 188:7922-7931(2006) and *Methanosarcina acetivorans* (Galagan et al., *Genome Res.* 12:532-542 (2002), as well as the acetogen, *Moorella thermoacetica* ((Das et al., *Proteins* 67:167-176 (2007)). In general, MtaA proteins that catalyze the transfer of the methyl group from $CH_3$-MtaC are difficult to identify bioinformatically as they share similarity to other corrinoid protein methyltransferases and are not oriented adjacent to the MtaB and MtaC genes on the chromosomes. Nevertheless, a number of MtaA encoding genes have been characterized. The protein sequences of these genes in *M. barkeri* and *M. acetivorans* can be identified by the following GenBank accession numbers.

| Protein | GenBank ID | GI number | Organism |
|---------|------------|-----------|----------|
| MtaA | YP_304602 | 73668587 | *Methanosarcina barkeri* |
| MtaA1 | NP_619241 | 20093166 | *Methanosarcina acetivorans* |
| MtaA2 | NP_616548 | 20090473 | *Methanosarcina acetivorans* |

The MtaA gene, YP_304602, from *M. barkeri* was cloned, sequenced, and functionally overexpressed in *E. coli* (Harms and Thauer, *Eur. J. Biochem.* 235:653-659 (1996)). In *M. acetivorans*, MtaA1 is required for growth on methanol, whereas MtaA2 is dispensable even though methane production from methanol is reduced in MtaA2 mutants (Bose et al., *J. Bacteriol.* 190:4017-4026 (2008)). There are multiple additional MtaA homologs in *M. barkeri* and *M. acetivorans* that are as yet uncharacterized, but may also catalyze corrinoid protein methyltransferase activity.

Putative MtaA encoding genes in *M. thermoacetica* were identified by their sequence similarity to the characterized methanogenic MtaA genes. Specifically, three *M. thermoacetica* genes show high homology (>30% sequence identity) to YP_304602 from *M. barkeri*. Unlike methanogenic MtaA proteins that naturally catalyze the transfer of the methyl group from $CH_3$-MtaC to Coenzyme M, anM thermoacetica MtaA is likely to transfer the methyl group to methyltetrahydrofolate given the similar roles of methyltetrahydrofolate and Coenzyme M in methanogens and acetogens, respectively. The protein sequences of putative MtaA encoding genes from *M. thermoacetica* can be identified by the following GenBank accession numbers.

| Protein | GenBank ID | GI number | Organism |
|---------|------------|-----------|----------|
| MtaA | YP_430937 | 83590928 | *Moorella thermoacetica* |
| MtaA | YP_431175 | 83591166 | *Moorella thermoacetica* |
| MtaA | YP_430935 | 83590926 | *Moorella thermoacetica* |
| MtaA | YP_430064 | 83590056 | *Moorella thermoacetica* |

FIG. 10, Step B—Methylenetetrahydrofolate Reductase

The conversion of methyl-THF to methylenetetrahydrofolate is catalyzed by methylenetetrahydrofolate reductase. In *M. thermoacetica*, this enzyme is oxygen-sensitive and contains an iron-sulfur cluster (Clark and Ljungdahl, *J. Biol. Chem.* 259:10845-10849 (1984). This enzyme is encoded by metF in *E. coli* (Sheppard et al., *J. Bacteriol.* 181:718-725 (1999) and CHY_1233 in *C. hydrogenoformans* (Wu et al., *PLoS Genet.* 1:e65 (2005). The *M. thermoacetica* genes, and its *C. hydrogenoformans* counterpart, are located near the CODH/ACS gene cluster, separated by putative hydrogenase and heterodisulfide reductase genes. Some additional gene candidates found bioinformatically are listed below. In *Acetobacterium woodii* metF is coupled to the Rnf complex through RnfC2 (Poehlein et al, *PLoS One.* 7:e33439). Homologs of RnfC are found in other organisms by blast search. The Rnf complex is known to be a reversible complex (Fuchs (2011) *Annu. Rev. Microbiol.* 65:631-658).

| Protein | GenBank ID | GI number | Organism |
| --- | --- | --- | --- |
| Moth_1191 | YP_430048.1 | 83590039 | Moorella thermoacetica |
| Moth_1192 | YP_430049.1 | 83590040 | Moorella thermoacetica |
| metF | NP_418376.1 | 16131779 | Escherichia coli |
| CHY_1233 | YP_360071.1 | 78044792 | Carboxydothermus hydrogenoformans |
| CLJU_c37610 | YP_003781889.1 | 300856905 | Clostridium ljunydahlii DSM 13528 |
| DesfrDRAFT_3717 | ZP_07335241.1 | 303248996 | Desulfovibrio fructosovorans JJ |
| CcarbDRAFT_2950 | ZP_05392950.1 | 255526026 | Clostridium carboxidivorans P7 |
| Ccel74_010100023124 | ZP_07633513.1 | 307691067 | Clostridium cellulovorans 743B |
| Cphy_3110 | YP_001560205.1 | 160881237 | Clostridium phytofermentans ISDg |

FIG. 10, Steps C and D—Methylenetetrahydrofolate Dehydrogenase, Methenyltetrahydrofolate Cyclohydrolase In *M. thermoacetica, E. coli*, and *C. hydrogenoformans*, methenyltetrahydrofolate cyclohydrolase and methylenetetrahydrofolate dehydrogenase are carried out by the bifunctional gene products of Moth_1516,folD, and CHY_1878, respectively (Pierce et al., *Environ. Microbiol.* 10:2550-2573 (2008); Wu et al., *PLoS Genet.* 1:e65 (2005); D'Ari and Rabinowitz, *J. Biol. Chem.* 266:23953-23958 (1991)). A homolog exists in *C. carboxidivorans* P7. Several other organisms also encode for this bifunctional protein as tabulated below.

| Protein | GenBank ID | GI number | Organism |
| --- | --- | --- | --- |
| Moth_1516 | YP_430368.1 | 83590359 | Moorella thermoacetica |
| folD | NP_415062.1 | 16128513 | Escherichia coli |
| CHY_1878 | YP_360698.1 | 78044829 | Carboxydothermus hydrogenoformans |
| CcarbDRAFT_2948 | ZP_05392948.1 | 255526024 | Clostridium carboxidivorans P7 |
| folD | ADK16789.1 | 300437022 | Clostridium ljunydahlii DSM 13528 |
| folD-2 | NP_951919.1 | 39995968 | Geobacter sulfurreducens PCA |
| folD | YP_725874.1 | 113867385 | Ralstonia eutropha H16 |
| folD | NP_348702.1 | 15895353 | Clostridium acetobutylicum ATCC 824 |
| folD | YP_696506.1 | 110800457 | Clostridium perfringens |
| MGA3_09460 | EIJ83438.1 | 387591119 | Bacillus methanolicus MGA3 |
| PB1_14689 | ZP_10132349.1 | 387929672 | Bacillus methanolicus PB1 |

FIG. 10, Step E—Formyltetrahydrofolate Deformylase

This enzyme catalyzes the hydrolysis of 10-formyltetrahydrofolate (formyl-THF) to THF and formate. In *E. coli*, this enzyme is encoded by purU and has been overproduced, purified, and characterized (Nagy, et al., *J. Bacteriol.* 3:1292-1298 (1995)). Homologs exist in *Corynebacterium* sp. U-96 (Suzuki, et al., Biosci. Biotechnol. Biochem. 69(5): 952-956 (2005)), *Corynebacterium glutamicum* ATCC 14067, *Salmonella enterica*, and several additional organisms.

| Protein | GenBank ID | GI number | Organism |
| --- | --- | --- | --- |
| purU | AAC74314.1 | 1787483 | Escherichia coli K-12 MG1655 |
| purU | BAD97821.1 | 63002616 | Corynebacterium sp. U-96 |
| purU | EHE84645.1 | 354511740 | Corynebacterium glutamicum ATCC 14067 |
| purU | NP_460715.1 | 16765100 | Salmonella enterica subsp. enterica serovar Typhimurium str. LT2 |

FIG. 10, Step F—Formyltetrahydrofolate Synthetase

Formyltetrahydrofolate synthetase ligates formate to tetrahydrofolate at the expense of one ATP. This reaction is catalyzed by the gene product of Moth_0109 in *M. thermoacetica* (O'brien et al., *Experientia Suppl.* 26:249-262 (1976); Lovell et al., *Arch. Microbiol.* 149:280-285 (1988); Lovell et al., *Biochemistry* 29:5687-5694 (1990)), FHS in *Clostridium acidurici* (Whitehead and Rabinowitz, *J. Bacteriol.* 167:203-209 (1986); Whitehead and Rabinowitz, *J. Bacteriol.* 170:3255-3261 (1988), and CHY_2385 in *C. hydrogenoformans* (Wu et al., *PLoS Genet.* 1:e65 (2005). Homologs exist in *C. carboxidivorans* P7. This enzyme is found in several other organisms as listed below.

| Protein | GenBank ID | GI number | Organism |
| --- | --- | --- | --- |
| Moth_0109 | YP_428991.1 | 83588982 | *Moorella thermoacetica* |
| CHY_2385 | YP_361182.1 | 78045024 | *Carboxydothermus hydrogenoformans* |
| FHS | P13419.1 | 120562 | *Clostridium acidurici* |
| CcarbDRAFT_1913 | ZP_05391913.1 | 255524966 | *Clostridium carboxidivorans* P7 |
| CcarbDRAFT_2946 | ZP_05392946.1 | 255526022 | *Clostridium carboxidivorans* P7 |
| Dhaf_0555 | ACL18622.1 | 219536883 | *Desulfitobacterium hafniense* |
| fhs | YP_001393842.1 | 153953077 | *Clostridium kluyveri* DSM 555 |
| fhs | YP_003781893.1 | 300856909 | *Clostridium ljungdahlii* DSM 13528 |
| MGA3_08300 | EIJ83208.1 | 387590889 | *Bacillus methanolicus* MGA3 |
| PB1_13509 | ZP_10132113.1 | 387929436 | *Bacillus methanolicus* PB1 |

FIG. 10, Step G— Formate Hydrogen Lyase

A formate hydrogen lyase enzyme can be employed to convert formate to carbon dioxide and hydrogen. An exemplary formate hydrogen lyase enzyme can be found in *Escherichia coli*. The *E. coli* formate hydrogen lyase consists of hydrogenase 3 and formate dehydrogenase-H (Maeda et al., *Appl Microbiol Biotechnol* 77:879-890 (2007)). It is activated by the gene product of fhlA. (Maeda et al., *Appl Microbiol Biotechnol* 77:879-890 (2007)). The addition of the trace elements, selenium, nickel and molybdenum, to a fermentation broth has been shown to enhance formate hydrogen lyase activity (Soini et al., *Microb. Cell Fact.* 7:26 (2008)). Various hydrogenase 3, formate dehydrogenase and transcriptional activator genes are shown below.

| Protein | GenBank ID | GI number | Organism |
| --- | --- | --- | --- |
| hycA | NP_417205 | 16130632 | *Escherichia coli* K-12 MG1655 |
| hycB | NP_417204 | 16130631 | *Escherichia coli* K-12 MG1655 |
| hycC | NP_417203 | 16130630 | *Escherichia coli* K-12 MG1655 |
| hycD | NP_417202 | 16130629 | *Escherichia coli* K-12 MG1655 |
| hycE | NP_417201 | 16130628 | *Escherichia coli* K-12 MG1655 |
| hycF | NP_417200 | 16130627 | *Escherichia coli* K-12 MG1655 |
| hycG | NP_417199 | 16130626 | *Escherichia coli* K-12 MG1655 |
| hycH | NP_417198 | 16130625 | *Escherichia coli* K-12 MG1655 |
| hycI | NP_417197 | 16130624 | *Escherichia coli* K-12 MG1655 |
| fdhF | NP_418503 | 16131905 | *Escherichia coli* K-12 MG1655 |
| fhlA | NP_417211 | 16130638 | *Escherichia coli* K-12 MG1655 |

A formate hydrogen lyase enzyme also exists in the hyperthermophilic archaeon, *Thermococcus litoralis* (Takacs et al., *BMC.Microbiol* 8:88 (2008)).

| Protein | GenBank ID | GI number | Organism |
| --- | --- | --- | --- |
| mhyC | ABW05543 | 157954626 | *Thermococcus litoralis* |
| mhyD | ABW05544 | 157954627 | *Thermococcus litoralis* |
| mhyE | ABW05545 | 157954628 | *Thermococcus litoralis* |
| myhF | ABW05546 | 157954629 | *Thermococcus litoralis* |
| myhG | ABW05547 | 157954630 | *Thermococcus litoralis* |
| myhH | ABW05548 | 157954631 | *Thermococcus litoralis* |
| fdhA | AAB94932 | 2146136 | *Thermococcus litoralis* |
| fdhB | AAB94931 | 157954625 | *Thermococcus litoralis* |

Additional formate hydrogen lyase systems have been found in *Salmonella typhimurium, Klebsiella pneumoniae, Rhodospirillum rubrum, Methanobacterium formicicum* (Vardar-Schara et al., Microbial Biotechnology 1:107-125 (2008)).

FIG. 10, Step H—Hydrogenase

Hydrogenase enzymes can convert hydrogen gas to protons and transfer electrons to acceptors such as ferredoxins, NAD+, or NADP+. *Ralstonia eutropha* H16 uses hydrogen as an energy source with oxygen as a terminal electron acceptor. Its membrane-bound uptake [NiFe]-hydrogenase is an "O2-tolerant" hydrogenase (Cracknell, et al. Proc Nat Acad Sci, 106(49) 20681-20686 (2009)) that is periplasmically-oriented and connected to the respiratory chain via a b-type cytochrome (Schink and Schlegel, *Biochim. Biophys. Acta,* 567, 315-324 (1979); Bernhard et al., *Eur. J. Biochem.* 248, 179-186 (1997)). *R. eutropha* also contains an $O_2$-tolerant soluble hydrogenase encoded by the Hox operon which is cytoplasmic and directly reduces NAD+ at the expense of hydrogen (Schneider and Schlegel, *Biochim. Biophys. Acta* 452, 66-80 (1976); Burgdorf, *J. Bact.* 187(9) 3122-3132(2005)). Soluble hydrogenase enzymes are additionally present in several other organisms including *Geobacter sulfurreducens* (Coppi, *Microbiology* 151, 1239-1254 (2005)), *Synechocystis* str. PCC 6803 (Germer, *J. Biol. Chem.,* 284(52), 36462-36472 (2009)), and *Thiocapsa roseopersicina* (Rakhely, *Appl. Environ. Microbiol.* 70(2) 722-728 (2004)). The *Synechocystis* enzyme is capable of generating NADPH from hydrogen. Overexpression of both the Hox operon from *Synechocystis* str. PCC 6803 and the accessory genes encoded by the Hyp operon from *Nostoc* sp. PCC 7120 led to increased hydrogenase activity compared to expression of the Hox genes alone (Germer, *J. Biol. Chem.* 284(52), 36462-36472 (2009)).

| Protein | Gen Bank ID | GI Number | Organism |
| --- | --- | --- | --- |
| HoxF | NP_942727.1 | 38637753 | *Ralstonia eutropha* HI 6 |
| HoxU | NP_942728.1 | 38637754 | *Ralstonia eutropha* HI 6 |
| HoxY | NP_942729.1 | 38637755 | *Ralstonia eutropha* HI 6 |
| HoxH | NP_942730.1 | 38637756 | *Ralstonia eutropha* HI 6 |
| HoxW | NP_942731.1 | 38637757 | *Ralstonia eutropha* HI 6 |
| HoxI | NP_942732.1 | 38637758 | *Ralstonia eutropha* HI 6 |
| HoxE | NP_953767.1 | 39997816 | *Geobacter sulfurreducens* |
| HoxF | NP_953766.1 | 39997815 | *Geobacter sulfurreducens* |

-continued

| Protein | Gen Bank ID | GI Number | Organism |
|---|---|---|---|
| HoxU | NP_953765.1 | 39997814 | Geobacter sulfurreducens |
| HoxY | NP_953764.1 | 39997813 | Geobacter sulfurreducens |
| HoxH | NP_953763.1 | 39997812 | Geobacter sulfurreducens |
| GSU2717 | NP_953762.1 | 39997811 | Geobacter sulfurreducens |
| HoxE | NP_441418.1 | 16330690 | Synechocystis str. PCC 6803 |
| HoxF | NP_441417.1 | 16330689 | Synechocystis str. PCC 6803 |
| Unknown function | NP_441416.1 | 16330688 | Synechocystis str. PCC 6803 |
| HoxU | NP_441415.1 | 16330687 | Synechocystis str. PCC 6803 |
| HoxY | NP_441414.1 | 16330686 | Synechocystis str. PCC 6803 |
| Unknown function | NP_441413.1 | 16330685 | Synechocystis str. PCC 6803 |
| Unknown function | NP_441412.1 | 16330684 | Synechocystis str. PCC 6803 |
| HoxH | NP_441411.1 | 16330683 | Synechocystis str. PCC 6803 |
| HypF | NP_484737.1 | 17228189 | Nostoc sp. PCC 7120 |
| HypC | NP_484738.1 | 17228190 | Nostoc sp. PCC 7120 |
| HypD | NP_484739.1 | 17228191 | Nostoc sp. PCC 7120 |
| Unknown function | NP_484740.1 | 17228192 | Nostoc sp. PCC 7120 |
| HypE | NP_484741.1 | 17228193 | Nostoc sp. PCC 7120 |
| HypA | NP_484742.1 | 17228194 | Nostoc sp. PCC 7120 |
| HypB | NP_484743.1 | 17228195 | Nostoc sp. PCC 7120 |
| Hox1E | AAP50519.1 | 37787351 | Thiocapsa roseopersicina |
| Hox1F | AAP50520.1 | 37787352 | Thiocapsa roseopersicina |
| Hox1U | AAP50521.1 | 37787353 | Thiocapsa roseopersicina |
| Hox1Y | AAP50522.1 | 37787354 | Thiocapsa roseopersicina |
| Hox1H | AAP50523.1 | 37787355 | Thiocapsa roseopersicina |

The genomes of E. coli and other enteric bacteria encode up to four hydrogenase enzymes (Sawers, G., Antonie Van Leeuwenhoek 66:57-88 (1994); Sawers et al., J Bacteriol. 164:1324-1331(1985); Sawers and Boxer, Eur J Biochem. 156:265-275 (1986); Sawers et al., J Bacteriol. 168:398-404 (1986)). Given the multiplicity of enzyme activities E. coli or another host organism can provide sufficient hydrogenase activity to split incoming molecular hydrogen and reduce the corresponding acceptor. Endogenous hydrogen-lyase enzymes of E. coli include hydrogenase 3, a membrane-bound enzyme complex using ferredoxin as an acceptor, and hydrogenase 4 that also uses a ferredoxin acceptor. Hydrogenase 3 and 4 are encoded by the hyc and hyfgene clusters, respectively. Hydrogenase activity in E. coli is also dependent upon the expression of the hyp genes whose corresponding proteins are involved in the assembly of the hydrogenase complexes (Jacobi et al., Arch.Microbiol 158: 444-451(1992); Rangarajan et al., J Bacteriol. 190:1447-1458 (2008)). The M. thermoacetica and Clostridium ljungdahli hydrogenases are suitable for a host that lacks sufficient endogenous hydrogenase activity. M. thermoacetica and C. ljungdahli can grow with $CO_2$ as the exclusive carbon source indicating that reducing equivalents are extracted from $H_2$ to enable acetyl-CoA synthesis via the Wood-Ljungdahl pathway (Drake, H. L., J Bacteriol. 150: 702-709 (1982); Drake and Daniel, Res Microbiol 155:869-883 (2004); Kellum and Drake, J Bacteriol. 160:466-469 (1984)). M. thermoacetica has homologs to several hyp, hyc, and hyfgenes from E. coli. These protein sequences encoded for by these genes are identified by the following GenBank accession numbers. In addition, several gene clusters encoding hydrogenase functionality are present in M. thermoacetica and C. ljungdahli (see for example US 2012/0003652).

| Protein | GenBank ID | GI Number | Organism |
|---|---|---|---|
| HypA | NP_417206 | 16130633 | Escherichia coli |
| HypB | NP_417207 | 16130634 | Escherichia coli |
| HypC | NP_417208 | 16130635 | Escherichia coli |
| HypD | NP_417209 | 16130636 | Escherichia coli |
| HypE | NP_417210 | 226524740 | Escherichia coli |
| HypF | NP_417192 | 16130619 | Escherichia coli |
| HycA | NP_417205 | 16130632 | Escherichia coli |
| HycB | NP_417204 | 16130631 | Escherichia coli |
| HycC | NP_417203 | 16130630 | Escherichia coli |
| HycD | NP_417202 | 16130629 | Escherichia coli |
| HycE | NP_417201 | 16130628 | Escherichia coli |
| HycF | NP_417200 | 16130627 | Escherichia coli |
| HycG | NP_417199 | 16130626 | Escherichia coli |
| HycH | NP_417198 | 16130625 | Escherichia coli |
| HycI | NP_417197 | 16130624 | Escherichia coli |
| HyfA | NP_416976 | 90111444 | Escherichia coli |
| HyfB | NP_416977 | 16130407 | Escherichia coli |
| HyfC | NP_416978 | 90111445 | Escherichia coli |
| HyfD | NP_416979 | 16130409 | Escherichia coli |
| HyfE | NP_416980 | 16130410 | Escherichia coli |
| HyfF | NP_416981 | 16130411 | Escherichia coli |
| HyfG | NP_416982 | 16130412 | Escherichia coli |
| HyfH | NP_416983 | 16130413 | Escherichia coli |
| HyfI | NP_416984 | 16130414 | Escherichia coli |
| HyfJ | NP_416985 | 90111446 | Escherichia coli |
| HyfR | NP_416986 | 90111447 | Escherichia coli |

Proteins in M. thermoacetica whose genes are homologous to the E. coli hydrogenase genes are shown below.

| Protein | GenBank ID | GI Number | Organism |
|---|---|---|---|
| Moth_2175 | YP_431007 | 83590998 | Moorella thermoacetica |
| Moth_2176 | YP_431008 | 83590999 | Moorella thermoacetica |
| Moth_2177 | YP_431009 | 83591000 | Moorella thermoacetica |
| Moth_2178 | YP_431010 | 83591001 | Moorella thermoacetica |
| Moth_2179 | YP_431011 | 83591002 | Moorella thermoacetica |
| Moth_2180 | YP_431012 | 83591003 | Moorella thermoacetica |
| Moth_2181 | YP_431013 | 83591004 | Moorella thermoacetica |
| Moth_2182 | YP_431014 | 83591005 | Moorella thermoacetica |
| Moth_2183 | YP_431015 | 83591006 | Moorella thermoacetica |
| Moth_2184 | YP_431016 | 83591007 | Moorella thermoacetica |
| Moth_2185 | YP_431017 | 83591008 | Moorella thermoacetica |
| Moth_2186 | YP_431018 | 83591009 | Moorella thermoacetica |
| Moth_2187 | YP_431019 | 83591010 | Moorella thermoacetica |
| Moth_2188 | YP_431020 | 83591011 | Moorella thermoacetica |
| Moth_2189 | YP_431021 | 83591012 | Moorella thermoacetica |
| Moth_2190 | YP_431022 | 83591013 | Moorella thermoacetica |
| Moth_2191 | YP_431023 | 83591014 | Moorella thermoacetica |
| Moth_2192 | YP_431024 | 83591015 | Moorella thermoacetica |
| Moth_0439 | YP_429313 | 83589304 | Moorella thermoacetica |
| Moth_0440 | YP_429314 | 83589305 | Moorella thermoacetica |
| Moth_0441 | YP_429315 | 83589306 | Moorella thermoacetica |
| Moth_0442 | YP_429316 | 83589307 | Moorella thermoacetica |
| Moth_0809 | YP_429670 | 83589661 | Moorella thermoacetica |
| Moth_0810 | YP_429671 | 83589662 | Moorella thermoacetica |
| Moth_0811 | YP_429672 | 83589663 | Moorella thermoacetica |
| Moth_0812 | YP_429673 | 83589664 | Moorella thermoacetica |
| Moth_0814 | YP_429674 | 83589665 | Moorella thermoacetica |
| Moth_0815 | YP_429675 | 83589666 | Moorella thermoacetica |
| Moth_0816 | YP_429676 | 83589667 | Moorella thermoacetica |
| Moth_1193 | YP_430050 | 83590041 | Moorella thermoacetica |
| Moth_1194 | YP_430051 | 83590042 | Moorella thermoacetica |
| Moth_1195 | YP_430052 | 83590043 | Moorella thermoacetica |
| Moth_1196 | YP_430053 | 83590044 | Moorella thermoacetica |
| Moth_1717 | YP_430562 | 83590553 | Moorella thermoacetica |
| Moth_1718 | YP_430563 | 83590554 | Moorella thermoacetica |
| Moth_1719 | YP_430564 | 83590555 | Moorella thermoacetica |
| Moth_1883 | YP_430726 | 83590717 | Moorella thermoacetica |
| Moth_1884 | YP_430727 | 83590718 | Moorella thermoacetica |

| Protein | GenBank ID | GI Number | Organism |
|---|---|---|---|
| Moth_1885 | YP_430728 | 83590719 | Moorella thermoacetica |
| Moth_1886 | YP_430729 | 83590720 | Moorella thermoacetica |
| Moth_1887 | YP_430730 | 83590721 | Moorella thermoacetica |
| Moth_1888 | YP_430731 | 83590722 | Moorella thermoacetica |
| Moth_1452 | YP_430305 | 83590296 | Moorella thermoacetica |
| Moth_1453 | YP_430306 | 83590297 | Moorella thermoacetica |
| Moth_1454 | YP_430307 | 83590298 | Moorella thermoacetica |

Genes encoding hydrogenase enzymes from *C. ljungdahli* are shown below.

| Protein | GenBank ID | GI Number | Organism |
|---|---|---|---|
| CLJU_c20290 | ADK15091.1 | 300435324 | Clostridium ljungdahli |
| CLJU_c07030 | ADK13773.1 | 300434006 | Clostridium ljungdahli |
| CLJU_c07040 | ADK13774.1 | 300434007 | Clostridium ljungdahli |
| CLJU_c07050 | ADK13775.1 | 300434008 | Clostridium ljungdahli |
| CLJU_c07060 | ADK13776.1 | 300434009 | Clostridium ljungdahli |
| CLJU_c07070 | ADK13777.1 | 300434010 | Clostridium ljungdahli |
| CLJU_c07080 | ADK13778.1 | 300434011 | Clostridium ljungdahli |
| CLJU_c14730 | ADK14541.1 | 300434774 | Clostridium ljungdahli |
| CLJU_c14720 | ADK14540.1 | 300434773 | Clostridium ljungdahli |
| CLJU_c14710 | ADK14539.1 | 300434772 | Clostridium ljungdahli |
| CLJU_c14700 | ADK14538.1 | 300434771 | Clostridium ljungdahli |
| CLJU_c28670 | ADK15915.1 | 300436148 | Clostridium ljungdahli |
| CLJU_c28660 | ADK15914.1 | 300436147 | Clostridium ljungdahli |
| CLJU_c28650 | ADK15913.1 | 300436146 | Clostridium ljungdahli |
| CLJU_c28640 | ADK15912.1 | 300436145 | Clostridium ljungdahli |

In some cases, hydrogenase encoding genes are located adjacent to a CODH. In *Rhodospirillum rubrum*, the encoded CODH/hydrogenase proteins form a membrane-bound enzyme complex that has been indicated to be a site where energy, in the form of a proton gradient, is generated from the conversion of CO and $H_2O$ to $CO_2$ and H2 (Fox et al., *J Bacteriol.* 178:6200-6208 (1996)). The CODH-I of *C. hydrogenoformans* and its adjacent genes have been proposed to catalyze a similar functional role based on their similarity to the *R. rubrum* CODH/hydrogenase gene cluster (Wu et al., *PLoS Genet.* 1:e65 (2005)). The *C. hydrogenoformans* CODH-I was also shown to exhibit intense CO oxidation and $CO_2$ reduction activities when linked to an electrode (Parkin et al., *J Am.Chem.Soc.* 129:10328-10329 (2007)).

| Protein | GenBank ID | GI Number | Organism |
|---|---|---|---|
| CooL | AAC45118 | 1515468 | Rhodospirillum rubrum |
| CooX | AAC45119 | 1515469 | Rhodospirillum rubrum |
| CooU | AAC45120 | 1515470 | Rhodospirillum rubrum |
| CooH | AAC45121 | 1498746 | Rhodospirillum rubrum |
| CooF | AAC45122 | 1498747 | Rhodospirillum rubrum |
| CODH(CooS) | AAC45123 | 1498748 | Rhodospirillum rubrum |
| CooC | AAC45124 | 1498749 | Rhodospirillum rubrum |
| CooT | AAC45125 | 1498750 | Rhodospirillum rubrum |
| CooJ | AAC45126 | 1498751 | Rhodospirillum rubrum |
| CODH-I (CooS-I) | YP_360644 | 78043418 | Carboxydothermus hydropenoformans |
| CooF | YP_360645 | 78044791 | Carboxydothermus hydrogenoformans |
| HypA | YP_360646 | 78044340 | Carboxydothermus hydrogenoformans |
| CooH | YP_360647 | 78043871 | Carboxydothermus hydrogenoformans |
| CooU | YP_360648 | 78044023 | Carboxydothermus hydrogenoformans |
| CooX | YP_360649 | 78043124 | Carboxydothermus hydrogenoformans |
| CooL | YP_360650 | 78043938 | Carboxydothermus hydrogenoformans |
| CooK | YP_360651 | 78044700 | Carboxydothermus hydrogenoformans |
| CooM | YP_360652 | 78043942 | Carboxydothermus hydrogenoformans |
| CooC | YP_360654.1 | 78043296 | Carboxydothermus hydrogenoformans |
| CooA-1 | YP_360655.1 | 78044021 | Carboxydothermus hydrogenoformans |

Some hydrogenase and CODH enzymes transfer electrons to ferredoxins. Ferredoxins are small acidic proteins containing one or more iron-sulfur clusters that function as intracellular electron carriers with a low reduction potential. Reduced ferredoxins donate electrons to Fe-dependent enzymes such as ferredoxin-$NADP^+$ oxidoreductase, pyruvate:fenedoxin oxidoreductase (PFOR) and 2-oxoglutarate:fenedoxin oxidoreductase (OFOR). The *H. thermophilus* gene fdx1 encodes a [4Fe-4S]-type ferredoxin that is required for the reversible carboxylation of 2-oxoglutarate and pyruvate by OFOR and PFOR, respectively (Yamamoto et al., *Extremophiles* 14:79-85 (2010)). The ferredoxin associated with the *Sulfolobus solfataricus* 2-oxoacid:ferredoxin reductase is a monomeric dicluster [3Fe-4S][4Fe-4S] type ferredoxin (Park et al. 2006). While the gene associated with this protein has not been fully sequenced, the N-terminal domain shares 93% homology with the zfx ferredoxin from *S. acidocaldarius*. The *E. coli* genome encodes a soluble fenedoxin of unknown physiological function, fdx. Some evidence indicates that this protein can function in iron-sulfur cluster assembly (Takahashi and Nakamura, 1999). Additional ferredoxin proteins have been characterized in *Helicobacter pylori* (Mukhopadhyay et al. 2003) and *Campylobacter jejuni* (van Vliet et al. 2001). A 2Fe-2S ferredoxin from *Clostridium pasteurianum* has been cloned and expressed in *E. coli* (Fujinaga and Meyer, Biochemical and Biophysical Research Communications, 192(3): (1993)). Acetogenic bacteria such as *Moorella thermoacetica, Clostridium carboxidivorans* P7, *Clostridium ljungdahli* and *Rhodospirillum rubrum* are predicted to encode several ferredoxins, listed below.

| Protein | GenBank ID | GI Number | Organism |
|---|---|---|---|
| fdx1 | BAE02673.1 | 68163284 | Hydrogenobacter thermophilus |
| M11214.1 | AAA83524.1 | 144806 | Clostridium pasteurianum |
| Zfx | AAY79867.1 | 68566938 | Sulfolobus acidocalarius |
| Fdx | AAC75578.1 | 1788874 | Escherichia coli |
| hp_0277 | AAD07340.1 | 2313367 | Helicobacter pylori |
| fdxA | CAL34484.1 | 112359698 | Campylobacter jejuni |
| Moth_0061 | ABC18400.1 | 83571848 | Moorella thermoacetica |
| Moth_1200 | ABC19514.1 | 83572962 | Moorella thermoacetica |
| Moth_1888 | ABC20188.1 | 83573636 | Moorella thermoacetica |
| Moth_2112 | ABC20404.1 | 83573852 | Moorella thermoacetica |
| Moth_1037 | ABC19351.1 | 83572799 | Moorella thermoacetica |
| CcarbDRAFT_4383 | ZP_05394383.1 | 255527515 | Clostridium carboxidivorans P7 |
| CcarbDRAFT_2958 | ZP_05392958.1 | 255526034 | Clostridium carboxidivorans P7 |
| CcarbDRAFT_2281 | ZP_05392281.1 | 255525342 | Clostridium carboxidivorans P7 |
| CcarbDRAFT_5296 | ZP_05395295.1 | 255528511 | Clostridium carboxidivorans P7 |
| CcarbDRAFT_1615 | ZP_05391615.1 | 255524662 | Clostridium carboxidivorans P7 |
| CcarbDRAFT_1304 | ZP_05391304.1 | 255524347 | Clostridium carboxidivorans P7 |
| cooF | AAG29808.1 | 11095245 | Carboxydothermus hydroygenoformans |
| fdxN | CAA35699.1 | 46143 | Rhodobacter capsulatus |
| Rru_A2264 | ABC23064.1 | 83576513 | Rhodospirillum rubrum |
| Rru_A1916 | ABC22716.1 | 83576165 | Rhodospirillum rubrum |
| Rru_A2026 | ABC22826.1 | 83576275 | Rhodospirillum rubrum |
| cooF | AAC45122.1 | 1498747 | Rhodospirillum rubrum |
| fdxN | AAA26460.1 | 152605 | Rhodospirillum rubrum |
| Alvin_2884 | ADC63789.1 | 288897953 | Allochromatium vinosum DSM 180 |
| Fdx | YP_002801146.1 | 226946073 | Azotobacter vinelandii DJ |
| CKL_3790 | YP_001397146.1 | 153956381 | Clostridium kluyveri DSM 555 |
| fer1 | NP_949965.1 | 39937689 | Rhodopseudomonas palustris CGA009 |
| Fdx | CAA12251.1 | 3724172 | Thauera aromatica |
| CHY_2405 | YP_361202.1 | 78044690 | Carboxydothermus hydroyenoformans |
| Fer | YP_359966.1 | 78045103 | Carboxydothermus hydroyenoformans |
| Fer | AAC83945.1 | 1146198 | Bacillus subtilis |
| fdx1 | NP_249053.1 | 15595559 | Pseudomonas aeruyinosa PA01 |
| yfhL | AP_003148.1 | 89109368 | Escherichia coli K-12 |
| CLJU_c00930 | ADK13195.1 | 300433428 | Clostridium ljungdahli |
| CLJU_c00010 | ADK13115.1 | 300433348 | Clostridium ljungdahli |
| CLJU_c01820 | ADK13272.1 | 300433505 | Clostridium ljungdahli |
| CLJU_cl 7980 | ADK14861.1 | 300435094 | Clostridium ljungdahli |
| CLJU_c17970 | ADK14860.1 | 300435093 | Clostridium ljungdahli |
| CLJU_c22510 | ADK15311.1 | 300435544 | Clostridium ljungdahli |
| CLJU_c26680 | ADK15726.1 | 300435959 | Clostridium ljungdahli |
| CLJU_c29400 | ADK15988.1 | 300436221 | Clostridium ljungdahli |

Ferredoxin oxidoreductase enzymes transfer electrons from ferredoxins or flavodoxins to NAD(P)H. Two enzymes catalyzing the reversible transfer of electrons from reduced ferredoxins to NAD(P)+ are ferredoxin:NAD+ oxidoreductase (EC 1.18.1.3) and ferredoxin:NADP+ oxidoreductase (FNR, EC 1.18.1.2). Ferredoxin:NADP+ oxidoreductase (FNR, EC 1.18.1.2) has a noncovalently bound FAD cofactor that facilitates the reversible transfer of electrons from NADPH to low-potential acceptors such as ferredoxins or flavodoxins (Blaschkowski et al., Eur. J. Biochem. 123:563-569 (1982); Fujii et al., 1977). The Helicobacter pylori FNR, encoded by HP1164 (fqrB), is coupled to the activity of pyruvate:ferredoxin oxidoreductase (PFOR) resulting in the pyruvate-dependent production of NADPH (St et al. 2007). An analogous enzyme is found in Campylobacter jejuni (St Maurice et al., J. Bacteriol. 189: 4764-4773 (2007)). A ferredoxin:NADP+ oxidoreductase enzyme is encoded in the E. coli genome by fpr (Bianchi et al. 1993). Ferredoxin:NAD+ oxidoreductase utilizes reduced ferredoxin to genemte NADH from NAD+. In several organisms, including E. coli, this enzyme is a component of multifunctional dioxygenase enzyme complexes. The ferredoxin:NAD+ oxidoreductase of E. coli, encoded by hcaD, is a component of the 3-phenylproppionate dioxygenase system involved in involved in aromatic acid utilization (Diaz et al. 1998). NADH:fenedoxin reductase activity was detected in cell extracts of Hydrogenobacter thermophilus, although a gene with this activity has not yet been indicated (Yoon et al. 2006). Additional ferredoxin:NAD(P)+ oxidoreductases have been annotated in Clostridium carboxydivorans P7. The NADH-dependent reduced ferredoxin: NADP oxidoreductase of C. kluyveri, encoded by nfnAB, catalyzes the concomitant reduction of ferredoxin and NAD+ with two equivalents of NADPH (Wang et al, J Bacteriol 192: 5115-5123 (2010)). Finally, the energy-conserving membrane-associated Rnf-type proteins (Seedorf et al, PNAS 105:2128-2133 (2008); and Hermann, J. Bacteriol 190:784-791 (2008)) provide a means to genemte NADH or NADPH from reduced fenedoxin.

| Protein | GenBank ID | GI Number | Organism |
|---|---|---|---|
| fqrB | NP_207955.1 | 15645778 | Helicobacter pylori |
| fqrB | YP_001482096.1 | 157414840 | Campylobacter jejuni |
| RPA3954 | CAE29395.1 | 39650872 | Rhodopseudomonas palustris |
| Fpr | BAH29712.1 | 225320633 | Hydrogenobacter thermophilus |
| yumC | NP_391091.2 | 255767736 | Bacillus subtilis |

-continued

| Protein | GenBank ID | GI Number | Organism |
|---|---|---|---|
| Fpr | P28861.4 | 399486 | Escherichia coli |
| hcaD | AAC75595.1 | 1788892 | Escherichia coli |
| LOC100282643 | NP_001149023.1 | 226497434 | Zea mays |
| NfnA | YP_001393861.1 | 153953096 | Clostridium kluyveri |
| NfnB | YP_001393862.1 | 153953097 | Clostridium kluyveri |
| CcarbDRAFT_2639 | ZP_05392639.1 | 255525707 | Clostridium carboxidivorans P7 |
| CcarbDRAFT_2638 | ZP_05392638.1 | 255525706 | Clostridium carboxidivorans P7 |
| CcarbDRAFT_2636 | ZP_05392636.1 | 255525704 | Clostridium carboxidivorans P7 |
| CcarbDRAFT_5060 | ZP_05395060.1 | 255528241 | Clostridium carboxidivorans P7 |
| CcarbDRAFT_2450 | ZP_05392450.1 | 255525514 | Clostridium carboxidivorans P7 |
| CcarbDRAFT_1084 | ZP_05391084.1 | 255524124 | Clostridium carboxidivorans P7 |
| RnfC | EDK33306.1 | 146346770 | Clostridium kluyveri |
| RnfD | EDK33307.1 | 146346771 | Clostridium kluyveri |
| RnfG | EDK33308.1 | 146346772 | Clostridium kluyveri |
| RnfE | EDK33309.1 | 146346773 | Clostridium kluyveri |
| RnfA | EDK33310.1 | 146346774 | Clostridium kluyveri |
| RnfB | EDK33311.1 | 146346775 | Clostridium kluyveri |
| CLJU_c11410 (RnfB) | ADK14209.1 | 300434442 | Clostridium ljungdahli |
| CLJU_c11400 (RnfA) | ADK14208.1 | 300434441 | Clostridium ljungdahli |
| CLJU_c11390 (RnfE) | ADK14207.1 | 300434440 | Clostridium ljungdahli |
| CLJU_c11380 (RnfG) | ADK14206.1 | 300434439 | Clostridium ljungdahli |
| CLJU_c11370 (RnfD) | ADK14205.1 | 300434438 | Clostridium ljungdahli |
| CLJU_c11360 (RnfC) | ADK14204.1 | 300434437 | Clostridium ljungdahli |
| MOTH_1518 (NfnA) | YP_430370.1 | 83590361 | Moorella thermoacetica |
| MOTH_1517(NfnB) | YP_430369.1 | 83590360 | Moorella thermoacetica |
| CHY 1992 (NfnA) | YP_360811.1 | 78045020 | Carboxydothermus hydrogenoformans |
| CHY 1993 (NfnB) | YP_360812.1 | 78044266 | Carboxydothermus hydrogenoformans |
| CLJU_c37220(NfnAB) | YP_003781850.1 | 300856866 | Clostridium ljungdahli |

FIG. 10, Step I—Formate Dehydrogenase

Formate dehydrogenase (FDH) catalyzes the reversible transfer of electrons from formate to an acceptor. Enzymes with FDH activity utilize various electron carriers such as, for example, NADH (EC 1.2.1.2), NADPH (EC 1.2.1.43), quinols (EC 1.1.5.6), cytochromes (EC 1.2.2.3) and hydrogenases (EC 1.1.99.33). FDH enzymes have been characterized from Moorella thermoacetica (Andreesen and Ljungdahl, J Bacteriol 116:867-873 (1973); Li et al., J Bacteriol 92:405-412 (1966); Yamamoto et al., J Biol Chem. 258:1826-1832 (1983). The loci, Moth_2312 is responsible for encoding the alpha subunit of formate dehydrogenase while the beta subunit is encoded by Moth_2314 (Pierce et al., Environ Microbiol (2008)). Another set of genes encoding formate dehydrogenase activity with a propensity for $CO_2$ reduction is encoded by Sfum_2703 through Sfum_2706 in Syntrophobacter fumaroxidans (de Bok et al., Eur J Biochem. 270:2476-2485 (2003)); Reda et al., PNAS 105:10654-10658 (2008)). A similar set of genes presumed to carry out the same function are encoded by CHY_0731, CHY 0732, and CHY 0733 in C. hydrogenoformans (Wu et al., PLoS Genet 1:e65 (2005)). Formate dehydrogenases are also found many additional organisms including C. carboxidivorans P7, Bacillus methanolicus, Burkholderia stabilis, Moorella thermoacetica ATCC 39073, Candida boidinii, Candida methylica, and Saccharomyces cerevisiae S288c. The soluble formate dehydrogenase from Ralstonia eutropha reduces $NAD^+$ (fdsG, —B, -A, —C, -D) (Oh and Bowien, 1998)

| Protein | GenBank ID | GI Number | Organism |
|---|---|---|---|
| Moth_2312 | YP_431142 | 148283121 | Moorella thermoacetica |
| Moth_2314 | YP_431144 | 83591135 | Moorella thermoacetica |
| Sfum_2703 | YP_846816.1 | 116750129 | Syntrophobacter fumaroxidans |
| Sfum_2704 | YP_846817.1 | 116750130 | Syntrophobacter fumaroxidans |
| Sfum_2705 | YP_846818.1 | 116750131 | Syntrophobacter fumaroxidans |
| Sfum_2706 | YP_846819.1 | 116750132 | Syntrophobacter fumaroxidans |
| CHY_0731 | YP_359585.1 | 78044572 | Carboxydothermus hydrogenoformans |
| CHY_0732 | YP_359586.1 | 78044500 | Carboxydothermus hydrogenoformans |
| CHY_0733 | YP_359587.1 | 78044647 | Carboxydothermus hydrogenoformans |
| CcarbDRAFT_0901 | ZP_05390901.1 | 255523938 | Clostridium carboxidivorans P7 |
| CcarbDRAFT_4380 | ZP_05394380.1 | 255527512 | Clostridium carboxidivorans P7 |
| fdhA,MGA3_06625 | EIJ82879.1 | 387590560 | Bacillus methanolicus MGA3 |
| fdhA,PB1_11719 | ZP_10131761.1 | 387929084 | Bacillus methanolicus PB1 |
| fdhD, MGA3_06630 | EIJ82880.1 | 387590561 | Bacillus methanolicus MGA3 |
| fdhD, PB1_11724 | ZP_10131762.1 | 387929085 | Bacillus methanolicus PB1 |
| fdh | ACF35003. | 194220249 | Burkholderia stabilis |
| FDH1 | AAC49766.1 | 2276465 | Candida boidinii |
| fdh | CAA57036.1 | 1181204 | Candida methylica |
| FDH2 | P0CF35.1 | 294956522 | Saccharomyces cerevisiae S288c |
| FDH1 | NP_015033.1 | 6324964 | Saccharomyces cerevisiae S288c |
| fdsG | YP_725156.1 | 113866667 | Ralstonia eutropha |
| fdsB | YP_725157.1 | 113866668 | Ralstonia eutropha |

-continued

| Protein | GenBank ID | GI Number | Organism |
|---|---|---|---|
| fdsA | YP_725158.1 | 113866669 | Ralstonia eutropha |
| fdsC | YP_725159.1 | 113866670 | Ralstonia eutropha |
| fdsD | YP_725160.1 | 113866671 | Ralstonia eutropha |

FIG. 10, Step J—Methanol Dehydrogenase

NAD+ dependent methanol dehydrogenase enzymes (EC 1.1.1.244) catalyze the conversion of methanol and NAD+ to formaldehyde and NADH. An enzyme with this activity was first characterized in *Bacillus methanolicus* (Heggeset, et al., *Applied and Environmental Microbiology*, 78(15): 5170-5181 (2012)). This enzyme is zinc and magnesium dependent, and activity of the enzyme is enhanced by the activating enzyme encoded by act (Kloosterman et al, *J Biol Chem* 277:34785-92 (2002)). The act is a Nudix hydrolase. Several of these candidates have been identified and shown to have activity on methanol. Additional NAD(P)+ dependent enzymes can be identified by sequence homology. Methanol dehydrogenase enzymes utilizing different electron acceptors are also known in the art. Examples include cytochrome dependent enzymes such as mxaIF of the methylotroph *Methylobacterium extorquens* (Nunn et al, Nucl Acid Res 16:7722 (1988)). Methanol dehydrogenase enzymes of methanotrophs such as *Methylococcus capsulatis* function in a complex with methane monooxygenase (MMO) (Myronova et al, Biochem 45:11905-14 (2006)). Methanol can also be oxidized to formaldehyde by alcohol oxidase enzymes such as methanol oxidase (EC 1.1.3.13) of *Candida boidinii* (Sakai et al, Gene 114: 67-73 (1992)).

| Protein | GenBank ID | GI Number | Organism |
|---|---|---|---|
| mdh, MGA3_17392 | EIJ77596.1 | 387585261 | Bacillus methanolicus MGA3 |
| mdh2, MGA3_07340 | EIJ83020.1 | 387590701 | Bacillus methanolicus MGA3 |
| mdh3, MGA3_10725 | EIJ80770.1 | 387588449 | Bacillus methanolicus MGA3 |
| act, MGA3_09170 | EIJ83380.1 | 387591061 | Bacillus methanolicus MGA3 |
| mdh,PB1_17533 | ZP_10132907.1 | 387930234 | Bacillus methanolicus PB1 |
| mdh1, PB1_14569 | ZP_10132325.1 | 387929648 | Bacillus methanolicus PB1 |
| mdh2, PB1_12584 | ZP_10131932.1 | 387929255 | Bacillus methanolicus PB1 |
| act, PB1_14394 | ZP_10132290.1 | 387929613 | Bacillus methanolicus PB1 |
| BFZC1_05383 | ZP_07048751.1 | 299535429 | Lysinibacillus fusiformis |
| BFZC1_20163 | ZP_07051637.1 | 299538354 | Lysinibacillus fusiformis |
| Bsph_4187 | YP_001699778.1 | 169829620 | Lysinibacillus sphaericus |
| Bsph_1706 | YP_001697432.1 | 169827274 | Lysinibacillus sphaericus |
| mdh2 | YP_004681552.1 | 339322658 | Cupriavidus necator N-1 |
| nudF1 | YP_004684845.1 | 339325152 | Cupriavidus necator N-1 |
| BthaA_010200007655 | ZP_05587334.1 | 257139072 | Burkholderia thailandensis E264 |
| BTH_I1076 (MutT/NUDIX NTP pyrophosphatase) | YP_441629.1 | 83721454 | Burkholderia thailandensis E264 |
| BalcAV_11743 | ZP_10819291.1 | 402299711 | Bacillus alcalophilus ATCC 27647 |
| BalcAV_05251 | ZP_10818002.1 | 402298299 | Bacillus alcalophilus ATCC 27647 |
| alcohol dehydrogenase | YP_001447544 | 156976638 | Vibrio harveyi ATCC BAA-1116 |
| P3TCK_27679 | ZP_01220157.1 | 90412151 | Photobacterium profundum 3TCK |
| alcohol dehydrogenase | YP_694908 | 110799824 | Clostridium perfringens ATCC 13124 |
| adhB | NP_717107 | 24373064 | Shewanella oneidensis MR-1 |
| alcohol dehydrogenase | YP_237055 | 66047214 | Pseudomonas syringae pv. syringae B728a |
| alcohol dehydrogenase | YP_359772 | 78043360 | Carboxydothermus hydrogenoformans Z-2901 |
| alcohol dehydrogenase | YP_003990729 | 312112413 | Geobacillus sp. Y4.1MC1 |
| PpeoK3_010100018471 | ZP_10241531.1 | 390456003 | Paenibacillus peoriae KCTC 3763 |
| OBE_12016 | EKC54576 | 406526935 | human gut metaypnome |
| alcohol dehydrogenase | YP_001343716 | 152978087 | Actinobacillus succinopenes 130Z |
| dhaT | AAC45651 | 2393887 | Clostridium pastewianum DSM 525 |
| alcohol dehydrogenase | NP_561852 | 18309918 | Clostridium perfringens str. 13 |
| BAZO_10081 | ZP_11313277.1 | 410459529 | Bacillus azotoformans LMG 9581 |
| alcohol dehydrogenase | YP_007491369 | 452211255 | Methanosarcina mazei Tuc01 |
| alcohol dehydrogenase | YP_004860127 | 347752562 | Bacillus coagulans 36D1 |
| alcohol dehydrogenase | YP_002138168 | 197117741 | Geobacter bemidjiensis Bem |
| DesmeDRAFT_1354 | ZP_08977641.1 | 354558386 | Desulfitobacterium metallireducens DSM 15288 |
| alcohol dehydrogenase | YP_001337153 | 152972007 | Klebsiella pneumoniae subsp. pneumoniae MGH 78578 |
| alcohol dehydrogenase | YP_001113612 | 134300116 | Desulfotomaculum reducens MI-1 |
| alcohol dehydrogenase | YP_001663549 | 167040564 | Thermoanaerobacter sp. X514 |
| ACINNAV82_2382 | ZP_16224338.1 | 421788018 | Acinetobacter baumannii Naval-82 |
| alcohol dehydrogenase | YP_005052855 | 374301216 | Desulfovibrio africanus str. Walvis Bay |
| alcohol dehydrogenase | AGF87161 | 451936849 | uncultured organism |
| DesfrDRAFT_3929 | ZP_07335453.1 | 303249216 | Desulfovibrio fructosovorans JJ |
| alcohol dehydrogenase | NP_617528 | 20091453 | Methanosarcina acetivorans C2A |
| alcohol dehydrogenase | NP_343875.1 | 15899270 | Sulfolobus solfataricus P-2 |
| adh4 | YP_006863258 | 408405275 | Nitrososphaera parpensis Ga9.2 |
| Ta0841 | NP_394301.1 | 16081897 | Thermoplasma acidophilum |
| PTO1151 | YP_023929.1 | 48478223 | Picrophilus torridus DSM9790 |

| Protein | GenBank ID | GI Number | Organism |
|---|---|---|---|
| alcohol dehydrogenase | ZP_10129817.1 | 387927138 | *Bacillus methanolicus* PB-1 |
| cgR_2695 | YP_001139613.1 | 145296792 | *Corynebacterium glutamicum* R |
| alcohol dehydrogenase | YP_004758576.1 | 340793113 | *Corynebacterium variabile* |
| HMPREF1015_01790 | ZP_09352758.1 | 365156443 | *Bacillus smithii* |
| ADH1 | NP_014555.1 | 6324486 | *Saccharomyces cerevisiae* |
| NADH-dependent butanol dehydrogenase A | YP_001126968.1 | 138896515 | *Geobacillus thermodenitrificans* NG80-2 |
| alcohol dehydrogenase | WP_007139094.1 | 494231392 | *Flavobacterium frigoris* |
| methanol dehydrogenase | WP_003897664.1 | 489994607 | *Mycobacterium smegmatis* |
| ADH1B | NP_000659.2 | 34577061 | *Homo sapiens* |
| PMI01_01199 | ZP_10750164.1 | 399072070 | *Caulobacter* sp. AP07 |
| YiaY | YP_026233.1 | 49176377 | *Escherichia coli* |
| MCA0299 | YP_112833.1 | 53802410 | *Methylococcus capsulatus* |
| MCA0782 | YP_113284.1 | 53804880 | *Methylococcus capsulatus* |
| mxaI | YP_002965443.1 | 240140963 | *Methylobacterium extorquens* |
| mxaF | YP_002965446.1 | 240140966 | *Methylobacterium extorquens* |
| AOD1 | AAA34321.1 | 170820 | *Candida boidinii* |
| hypothetical protein GOS_1920437 | EDA87976.1 | 142827286 | Marine metagenome JCVI_SCAF_1096627185304 |
| alcohol dehydrogenase | CAA80989.1 | 580823 | *Geobacillus stearothermophilus* |

An in vivo assay was developed to determine the activity of methanol dehydrogenases. This assay relies on the detection of formaldehyde (HCHO), thus measuring the forward activity of the enzyme (oxidation of methanol). To this end, a strain comprising a BDOP and lacking frmA, frmB, frmR was created using Lamba Red recombinase technology (Datsenko and Wanner, *Proc. Natl. Acad Sci. USA*, 6 97(12): 6640-5 (2000) Plasmids expressing methanol dehydrogenases were transformed into the strain, then grown to saturation in LB medium+antibiotic at 37° C. with shaking. Transformation of the strain with an empty vector served as a negative control. Cultures were adjusted by O.D. and then diluted 1:10 into M9 medium+0.5% glucose+antibiotic and cultured at 37° C. with shaking for 6-8 hours until late log phase. Methanol was added to 2% v/v and the cultures were further incubated for 30 min. with shaking at 37° C. Cultures were spun down and the supernatant was assayed for formaldehyde produced using DEFECTX Formaldehyde Detection kit (Arbor Assays; Ann ArborMIh.) according to manufacturer's instructions. The frmA, frmB, frmR deletions resulted in the native formaldehyde utilization pathway to be deleted, which enables the formation of formaldehyde that can be used to detect methanol dehydrogenase activity in the NNOMO.

The activity of several enzymes was measured using the assay described above. The results of four independent experiments are provided in Table 5 below.

TABLE 5

Results of in vivo assays showing formaldehyde (HCHO) production by various NNOMO comprising a plasmid expressing a methanol dehydrogenase.

| Accession number | HCHO ($\mu$M) |
|---|---|
| Experiment 1 | |
| EIJ177596.1 | >50 |
| EIJ83020.1 | >20 |
| EIJ80770.1 | >50 |
| ZP_10132907.1 | >20 |
| ZP_10132325.1 | >20 |
| ZP_10131932.1 | >50 |
| ZP_07048751.1 | >50 |
| YP_001699778.1 | >50 |
| YP_004681552.1 | >10 |
| ZP_10819291.1 | <1 |
| Empty vector | 2.33 |
| Experiment 2 | |
| EIJ77596.1 | >50 |
| NP_00659.2 | >50 |
| YP_004758576.1 | >20 |
| ZP_09352758.1 | >50 |
| ZP_10129817.1 | >20 |
| YP_001139613.1 | >20 |
| NP_014555.1 | >10 |
| WP_007139094.1 | >10 |
| NP_343875.1 | >1 |
| YP_006863258 | >1 |
| NP_394301.1 | >1 |
| ZP_10750164.1 | >1 |
| YP_023929.1 | >1 |
| ZP_08977641.1 | <1 |
| ZP_10117398.1 | <1 |
| YP_004108045.1 | <1 |
| ZP_09753449.1 | <1 |
| Empty vector | 0.17 |
| Experiment 3 | |
| EIJ77596.1 | >50 |
| NP_561852 | >50 |
| YP_002138168 | >50 |
| YP_026233.1 | >50 |
| YP_001447544 | >50 |
| Metalibrary | >50 |
| YP_359772 | >50 |
| ZP_01220157.1 | >50 |
| ZP_07335453.1 | >20 |
| YP_001337153 | >20 |
| YP_694908 | >20 |
| NP_717107 | >20 |
| AAC45651 | >10 |
| ZP_11313277.1 | >10 |
| ZP_16224338.1 | >10 |
| YP_001113612 | >10 |

TABLE 5-continued

Results of in vivo assays showing formaldehyde (HCHO) production by various NNOMO comprising a plasmid expressing a methanol dehydrogenase.

| Accession number | HCHO (μM) |
|---|---|
| YP_004860127 | >10 |
| YP_003310546 | >10 |
| YP_001343716 | >10 |
| NP_717107 | >10 |
| YP_002434746 | >10 |
| Empty vector | 0.11 |
| Experiment 4 | |
| EIJ77596.1 | >20 |
| ZP_11313277.1 | >50 |
| YP_001113612 | >50 |
| YP_001447544 | >20 |
| AGF87161 | >50 |
| EDA87976.1 | >20 |
| Empty vector | −0.8 |

FIG. 10, Step K—Spontaneous or Formaldehyde Activating Enzyme

The conversion of formaldehyde and THF to methylenetetrahydrofolate can occur spontaneously. It is also possible that the rate of this reaction can be enhanced by a formaldehyde activating enzyme. A formaldehyde activating enzyme (Fae) has been identified in *Methylobacterium extorquens* AM1 which catalyzes the condensation of formaldehyde and tetrahydromethanopterin to methylene tetrahydromethanopterin (Vorholt, et al., J. Bacteriol., 182(23), 6645-6650 (2000)). It is possible that a similar enzyme exists or can be engineered to catalyze the condensation of formaldehyde and tetrahydrofolate to methylenetetrahydrofolate. Homologs exist in several organisms including *Xanthobacter autotrophicus* Py2 and *Hyphomicrobium denitrificans* ATCC 51888.

| Protein | GenBank ID | GI Number | Organism |
|---|---|---|---|
| MexAM1_META1p1766 | Q9FA38.3 | 17366061 | *Methylobacterium extorquens* AM1 |
| Xaut_0032 | YP_001414948.1 | 154243990 | *Xanthobacter autotrophicus* Py2 |
| Hden_1474 | YP_003755607.1 | 300022996 | *Hyphomicrobium denitrificans* ATCC 51888 |

FIG. 10, Step L—Formaldehyde Dehydrogenase

Oxidation of formaldehyde to formate is catalyzed by formaldehyde dehydrogenase. An NAD+ dependent formaldehyde dehydrogenase enzyme is encoded by fdhA of *Pseudomonas putida* (Ito et al, J Bacteriol 176: 2483-2491 (1994)). Additional formaldehyde dehydrogenase enzymes include the NAD+ and glutathione independent formaldehyde dehydrogenase from *Hyphomicrobium zavarzinii* (Jerome et al, Appl Microbiol Biotechnol 77:779-88 (2007)), the glutathione dependent formaldehyde dehydrogenase of *Pichia* pastoris (Sunga et al, Gene 330:39-47 (2004)) and the NAD(P)+ dependent formaldehyde dehydrogenase of *Methylobacter marinus* (Speer et al, FEMS Microbiol Lett, 121(3):349-55 (1994)).

| Protein | GenBank ID | GI Number | Organism |
|---|---|---|---|
| fdhA | P46154.3 | 1169603 | *Pseudomonas putida* |
| faoA | CAC85637.1 | 19912992 | *Hyphomicrobium zavarzinii* |
| Fld1 | CCA39112.1 | 328352714 | *Pichia pastoris* |
| fdh | P47734.2 | 221222447 | *Methylobacter marinus* |

In addition to the formaldehyde dehydrogenase enzymes listed above, alternate enzymes and pathways for converting formaldehyde to formate are known in the art. For example, many organisms employ glutathione-dependent formaldehyde oxidation pathways, in which formaldehyde is converted to formate in three steps via the intermediates S-hydroxymethylglutathione and S-formylglutathione (Vorholt et al, J Bacteriol 182:6645-50 (2000)). The enzymes of this pathway are S-(hydroxymethyl)glutathione synthase (EC 4.4.1.22), glutathione-dependent formaldehyde dehydrogenase (EC 1.1.1.284) and S-formylglutathione hydrolase (EC 3.1.2.12).

FIG. 10, Step M—Spontaneous or S-(hydroxymethyl)glutathione Synthase

While conversion of formaldehyde to S-hydroxymethylglutathione can occur spontaneously in the presence of glutathione, it has been shown by Goenrich et al (Goenrich, et al., J Biol Chem 277(5); 3069-72 (2002)) that an enzyme from *Paracoccus denitrificans* can accelerate this spontaneous condensation reaction. The enzyme catalyzing the conversion of formaldehyde and glutathione was purified and named glutathione-dependent formaldehyde-activating enzyme (Gfa). The gene encoding it, which was named gfa, is located directly upstream of the gene for glutathione-dependent formaldehyde dehydrogenase, which catalyzes the subsequent oxidation of S-hydroxymethylglutathione. Putative proteins with sequence identity to Gfa from *P. denitrificans* are present also in *Rhodobacter sphaeroides*, *Sinorhizobium meliloti*, and *Mesorhizobium loti*.

| Protein | GenBank ID | GI Number | Organism |
|---|---|---|---|
| Gfa | Q51669.3 | 38257308 | *Paracoccus denitrificans* |
| Gfa | ABP71667.1 | 145557054 | *Rhodobacter sphaeroides* ATCC 17025 |
| Gfa | Q92WX6.1 | 38257348 | *Sinorhizobium meliloti* 1021 |
| Gfa | Q98LU4.2 | 38257349 | *Mesorhizobium loti* MAFF303099 |

FIG. 10, Step N—Glutathione-Dependent Formaldehyde Dehydrogenase

Glutathione-dependent formaldehyde dehydrogenase (GS-FDH) belongs to the family of class III alcohol dehydrogenases. Glutathione and formaldehyde combine non-enzymatically to form hydroxymethylglutathione, the true substrate of the GS-FDH catalyzed reaction. The product, S-formylglutathione, is further metabolized to formic acid.

| Protein | GenBank ID | GI Number | Organism |
|---|---|---|---|
| fmA | YP_488650.1 | 388476464 | Escherichia coli K-12MG1655 |
| SFA1 | NP_010113.1 | 6320033 | Saccharomyces cerevisiae S288c |
| fhA | AAC44551.1 | 1002865 | Paracoccus denitrificans |
| adhI | AAB09774.1 | 986949 | Rhodobacter sphaeroides |

FIG. 10, Step O—S-formylglutathione Hydrolase

S-formylglutathione hydrolase is a glutathione thiol esterase found in bacteria, plants and animals. It catalyzes conversion of S-formylglutathione to formate and glutathione. The fghA gene of *P. denitnficans* is located in the same operon with gfa and fhA, two genes involved in the oxidation of formaldehyde to formate in this organism. In *E. coli*, FrmB is encoded in an operon with FrmR and FnnA, which are proteins involved in the oxidation of formaldehyde. YeiG of *E. coli* is a promiscuous serine hydrolase; its highest specific activity is with the substrate S-formylglutathione.

| Protein | GenBankID | GI Number | Organism |
|---|---|---|---|
| frmB | NP_414889.1 | 16128340 | Escherichia coli K-12MG1655 |
| yeiG | AAC75215.1 | 1788477 | Escherichia coli K-12MG1655 |
| fghA | AAC44554.1 | 1002868 | Paracoccus denitrificans | encoding genes are located outside of the ACS/CODH operons. These enzymes provide a means for extracting electrons (or reducing equivalents) from the conversion of carbon monoxide to carbon dioxide. The *M. thermoacetica* gene (Genbank Accession Number: YP_430813) is expressed by itself in an operon and is believed to transfer electrons from CO to an external mediator like ferredoxin in a "Ping-pong" reaction. The reduced mediator then couples to other reduced nicolinamide adenine dinucleotide phosphate (NAD(P)H) carriers or ferredoxin-dependent cellular processes (Ragsdale, *Annals of the New York Academy ofSciences* 1125: 129-136 (2008)). The genes encoding the *C. hydrogenoformans* CODH-II and CooF, a neighboring protein, were cloned and sequenced (Gonzalez and Robb, *FEMS Microbiol Lett.* 191:243-247 (2000)). The resulting complex was membrane-bound, although cytoplasmic fractions of CODH-II were shown to catalyze the formation of NADPH suggesting an anabolic role (Svetlitchnyi et al., *J Bacteriol.* 183:5134-5144 (2001)). The crystal structure of the CODH-II is also available (Dobbek et al., *Science* 293:1281-1285 (2001)). Similar ACS-free CODH enzymes can be found in a diverse array of organisms including *Geobacter metallireducens* GS-15, *Chlorobium phaeobacteroides* DSM 266, *Clostridium cellulolyticum* H10, *Desulfovibrio desuifuricans* subsp. *desuifuricans* str. ATCC 27774, *Pelobacter carbinolicus* DSM 2380, *C. ijungdahli* and *Campylobacter curvus* 525.92.

| Protein | Gen Bank ID | GI Number | Organism |
|---|---|---|---|
| CODH (putative) | YP_430813 | 83590804 | Moorella thermoacetica |
| CODH-II (CooS-II) | YP_358957 | 78044574 | Carboxydothermus hydrogenoformans |
| CooF | YP_358958 | 78045112 | Carboxydothermus hydrogenoformans |
| CODH (putative) | ZP_05390164.1 | 255523193 | Clostridium carboxidivorans P7 |
| CcarbDRAFT_0341 | ZP_05390341.1 | 255523371 | Clostridium carboxidivorans P7 |
| CcarbDRAFT_1756 | ZP_05391756.1 | 255524806 | Clostridium carboxidivorans P7 |
| CcarbDRAFT_2944 | ZP_05392944.1 | 255526020 | Clostridium carboxidivorans P7 |
| CODH | YP_384856.1 | 78223109 | Geobacter metallireducens GS-15 |
| Cpha266_0148 (cytochrome c) | YP_910642.1 | 119355998 | Chlorobium phaeobacteroides DSM 266 |
| Cpha266_0149 (CODH) | YP_910643.1 | 119355999 | Chlorobium phaeobacteroides DSM 266 |
| Ccel 0438 | YP_002504800.1 | 220927891 | Clostridium cellulolyticum H10 |
| Ddes_0382 (CODH) | YP_002478973.1 | 220903661 | Desulfovibrio desulfuricans subsp. desulfuricans str. ATCC 27774 |
| Ddes_0381 (CooC) | YP_002478972.1 | 220903660 | Desulfovibrio desulfuricans subsp. desulfuricans str. ATCC 27774 |
| Pcar_0057 (CODH) | YP_355490.1 | 7791767 | Pelobacter carbinolicus DSM2380 |
| Pcear_0058 (CooC) | YP_355491.1 | 7791766 | Pelobacter carbinolicus DSM2380 |
| Pcar_0058 (HypA) | YP_355492.1 | 7791765 | Pelobacter carbinolicus DSM2380 |
| CooS(CODH) | YP_001407343.1 | 154175407 | Campylobacter curvus 525.92 |
| CLJU_c09110 | ADK13979.1 | 300434212 | Clostridium ljungdahli |
| CLJU_C09100 | ADK13978.1 | 300434211 | Clostridium ljungdahli |
| CLJU_C09090 | ADK13977.1 | 300434210 | Clostridium ljungdahli |

FIG. 10, Step P—Carbon Monoxide Dehydrogenase (CODH)

CODH is a reversible enzyme that interconverts CO and $CO_2$ at the expense or gain of electrons. The natural physiological role of the CODH in ACS/CODH complexes is to convert $CO_2$ to CO for incorporation into acetyl-CoA by acetyl-CoA synthase Nevertheless, such CODH enzymes are suitable for the extraction of reducing equivalents from CO due to the reversible nature of such enzymes. Expressing such CODH enzymes in the absence of ACS allows them to operate in the direction opposite to their natural physiological role (i.e., CO oxidation).

In *M. thermoacetica, C. hydrogenoformans, C. carboxidivorans* P7, and several other organisms, additional CODH Example III Methods for Formaldehyde Fixation Provided herein are exemplary pathways, which utilize formaldehyde produced from the oxidation of methanol (see, e.g., FIG. 1, step A, or FIG. 10, step J) or from formate assimilation pathways described in Example I (see, e.g., FIG. 1) in the formation of intermediates of certain central metabolic pathways that can be used for the production of compounds disclosed herein.

One exemplary pathway that can utilize formaldehyde produced from the oxidation of methanol is shown in FIG. 1, which involves condensation of formaldehyde and D-ribulose-5-phosphate to form hexulose-6-phosphate (h6p) by hexulose-6-phosphate synthase (FIG. 1, step B). The enzyme can use $Mg^{2+}$ or $Mn^{2+}$ for maximal activity, although other metal ions are useful, and even non-metal-ion-dependent mechanisms are contemplated. H6p is converted into fructose-6-phosphate by 6-phospho-3-hexuloisomerase (FIG. 1, step C).

Another exemplary pathway that involves the detoxification and assimilation of formaldehyde produced from the oxidation of methanol is shown in FIG. 1 and proceeds through dihydroxyacetone. Dihydroxyacetone synthase is a special transketolase that first transfers a glycoaldehyde group from xylulose-5-phosphate to formaldehyde, resulting in the formation of dihydroxyacetone (DHA) and glyceraldehyde-3-phosphate (G3P), which is an intermediate in glycolysis (FIG. 1). The DHA obtained from DHA synthase can be further phosphorylated to form DHA phosphate and assimilated into glycolysis and several other pathways (FIG. 1). Alternatively, or in addition, a fructose-6-phosphate aldolase can be used to catalyze the conversion of DHA and G3P to fructose-6-phosphate (FIG. 1, step Z).

FIG. 1, Steps B and C—Hexulose-6-phosphate synthase (Step B) and 6-phospho-3-hexuloisomerase (Step C)

Both of the hexulose-6-phosphate synthase and 6-phospho-3-hexuloisomerase enzymes are found in several organisms, including methanotrops and methylotrophs where they have been purified (Kato et al., 2006, BioSci Biotechnol Biochem. 70(1):10-21. In addition, these enzymes have been reported in heterotrophs such as *Bacillus subtilis* also where they are reported to be involved in formaldehyde detoxification (Mitsui et al., 2003, AEM 69(10):6128-32, Yasueda et al., 1999. J Bac 181(23):7154-60. Genes for these two enzymes from the methylotrophic bacterium *Mycobacterium gastri* MB19 have been fused and *E. coli* strains harboring the hps-phi construct showed more efficient utilization of fomialdehyde (Orita et A. 2007. Appl Microbiol Biotechnol. 76:439-445). In some organisms, these two enzymes naturally exist as a fused version that is bifunctional.

Exemplary candidate genes for hexulose-6-phopshate synthase are:

| Protein | GenBank ID | GI number | Organism |
|---|---|---|---|
| Hps | AAR39392.1 | 40074227 | *Bacillus methanolicus* MGA3 |
| Hps | EIJ81375.1 | 387589055 | *Bacillus methanolicus* PB1 |
| RmpA | BAA83096.1 | 5706381 | *Methylomonas aminofaciens* |
| RmpA | BAA90546.1 | 6899861 | *Mycobacterium gastri* |

-continued

| Protein | GenBank ID | GI number | Organism |
|---|---|---|---|
| YckG | BAA08980.1 | 1805418 | *Bacillus subtilis* |
| Hps | YP_544362.1 | 91774606 | *Methylobacillus flagellatus* |
| Hps | YP_545763.1 | 91776007 | *Methylobacillus flagellatus* |
| Hps | AAG29505.1 | 11093955 | *Aminomonas aminovorus* |
| SgbH | YP_004038706.1 | 313200048 | *Methylovorus* sp. MP688 |
| Hps | YP_003050044.1 | 253997981 | *Methylovorus glucosetrophus* SIP3-4 |
| Hps | YP_003990382.1 | 312112066 | *Geobacillus* sp. Y4.1MC1 |
| Hps | gb\|AAR91478.1 | 40795504 | *Geobacillus* sp. M10EXG |
| Hps | YP_007402409.1 | 448238351 | *Geobacillus* sp. GHH01 |

Exemplary gene candidates for 6-phospho-3-hexuloisomerase are:

| Protein | GenBank ID | GI number | Organism |
|---|---|---|---|
| Phi | AAR39393.1 | 40074228 | *Bacillus methanolicus* MGA3 |
| Phi | EIJ81376.1 | 387589056 | *Bacillus methanolicus* PB1 |
| Phi | BAA83098.1 | 5706383 | *Methylomonas aminofaciens* |
| RmpB | BAA90545.1 | 6899860 | *Mycobacterium gastri* |
| Phi | YP_545762.1 | 91776006 | *Methylobacillus flagellatus* KT |
| Phi | YP_003051269.1 | 253999206 | *Methylovorus glucosetrophus* SIP3-4 |
| Phi | YP_003990383.1 | 312112067 | *Geobacillus* sp. Y4.1MC1 |
| Phi | YP_007402408.1 | 448238350 | *Geobacillus* sp. GHH01 |

Candidates for enzymes where both of these functions have been fused into a single open reading frame include the following.

| Protein | GenBank ID | GI number | Organism |
|---|---|---|---|
| PH1938 | NP_143767.1 | 14591680 | *Pyrococcus horikoshii* OT3 |
| PF0220 | NP_577949.1 | 18976592 | *Pyrococcus furiosus* |
| TK0475 | YP_182888.1 | 57640410 | *Thermococcus kodakaraensis* |
| PAB1222 | NP_127388.1 | 14521911 | *Pyrococcus abyssi* |
| MCA2738 | YP_115138.1 | 53803128 | *Methylococcus capsulatas* |
| Metal_3152 | EIC30826.1 | 380884949 | *Methylomicrobium album* BG8 |

FIG. 1, Step D—Dihydroxyacetone Synthase

The dihydroxyacetone synthase enzyme in *Candida boidinii* uses thiamine pyrophosphate and $Mg^{2+}$ as cofactors and is localized in the peroxisome. The enzyme from the methanol-growing carboxydobacterium, *Mycobacter* sp. strain JC1 DSM 3803, was also found to have DHA synthase and kinase activities (Ro et al., 1997, JBac 179(19):6041-7). DHA synthase from this organism also has similar cofactor requirements as the enzyme from *C. boidinii*. The $K_m$s for formaldehyde and xylulose 5-phosphate were reported to be 1.86 mM and 33.3 microM, respectively. Several other mycobacteria, excluding only *Mycobacterium tuberculosis*, can use methanol as the sole source of carbon and energy and are reported to use dihydroxyacetone synthase (Part et al., 2003, JBac 185(1):142-7.

| Protein | GenBank ID | GI number | Organism |
| --- | --- | --- | --- |
| DAS1 | AAC83349.1 | 3978466 | Candida boidinii |
| HPODL_2613 | EFW95760.1 | 320581540 | Ogataea parapolymorpha DL-1 (Hansenula polymorpha DL-1) |
| | AAG12171.2 | 18497328 | Mycobacter sp. strain JC1 DSM 3803 |

FIG. 1, Step Z—Fructose-6-phosphate aldolase

Fructose-6-phosphate aldolase (F6P aldolase) can catalyze the combination of dihydroxyacetone (DHA) and glyceraldehyde-3-phosphate (G3P) to form fructose-6-phosphate. This activity was recently discovered in E. coli and the corresponding gene candidate has been termed fsa (Schunnann and Sprenger, J. Biol. Chem., 2001, 276(14), 11055-11061). The enzyme has narrow substrate specificity and cannot utilize fructose, fructose 1-phosphate, fructose 1,6-bisphosphate, or dihydroxyacetone phosphate. It can however use hydroxybutanone and acetol instead of DHA. The purified enzyme displayed a $V_{max}$ of 7 units/mg of protein for fructose 6-phosphate cleavage (at 30 degrees C., pH 8.5 in 50 mm glycylglycine buffer). For the aldolization reaction a $V_{max}$ of 45 units/mg of protein was found; $K_m$ values for the substrates were 9 mM for fructose 6-phosphate, 35 mM for dihydroxyacetone, and 0.8 mM for glyceraldehyde 3-phosphate. The enzyme prefers the aldol formation over the cleavage reaction.

The selectivity of the E. coli enzyme towards DHA can be improved by introducing point mutations. For example, the mutation A129S improved reactivity towards DHA by over 17 fold in terms of $K_{Cat}/K_m$ (Gutierrez et al., Chem Commun (Carob), 2011, 47(20), 5762-5764). The same mutation reduced the catalytic efficiency on hydroxyacetone by more than 3 fold and reduced the affinity for glycoaldehyde by more than 3 fold compared to that of the wild type enzyme (Castillo et al., Advanced Synthesis & Catalysis, 352(6), 1039-1046). Genes similar to fsa have been found in other genomes by sequence homology. Some exemplary gene candidates have been listed below.

| Gene | Protein accession number | GI number | Organism |
| --- | --- | --- | --- |
| fsa | AAC73912.2 | 87081788 | Escherichia coli K12 |
| talC | AAC76928.1 | 1790382 | Escherichia coli K12 |
| fsa | WP_017209835.1 | 515777235 | Clostridium beijerinickii |
| DR_1337 | AAF10909.1 | 6459090 | Deinococcus radiodurans R1 |
| talC | NP_213080.1 | 15605703 | Aquifex aeolicus VF5 |
| MJ_0960 | NP_247955.1 | 15669150 | Methanocaldococcus janaschii |
| mipB | NP_993370.2 | 161511381 | Yersinia pestis |

As described below, there is an energetic advantage to using F6P aldolase in the DHA pathway.

The assimilation of formaldehyde formed by the oxidation of methanol can proceed either via the dihydroxyacetone (DHA) pathway (step D, FIG. 1) or the Ribulose monophosphate (RuMP) pathway (steps B and C, FIG. 1). In the RUMP pathway, formaldehyde combines with ribulose-5-phosphate to form F6P. F6P is then either metabolized via glycolysis or used for regeneration of ribulose-5-phosphate to enable further formaldehyde assimilation. Notably, ATP hydrolysis is not required to form F6P from formaldehyde and ribulose-5-phosphate via the RuMP pathway.

In contrast, in the DHA pathway, formaldehyde combines with xylulose-5-phosphate (X5P) to form dihydroxyacetone (DHA) and glyceraldehyde-3-phosphate (G3P). Some of the DHA and G3P must be metabolized to F6P to enable regeneration of xylulose-5-phosphate. In the standard DHA pathway, DHA and G3P are converted to F6P by three enzymes: DHA kinase, fructose bisphosphate aldolase, and fructose bisphosphatase. The net conversion of DHA and G3P to F6P requires ATP hydrolysis as described below. First, DHA is phosphorylated to form DHA phosphate (DHAP) by DHA kinase at the expense of an ATP. DHAP and G3P are then combined by fructose bisphosphate aldolase to form fructose-1,6-diphosphate (FDP). FDP is converted to F6P by fructose bisphosphatase, thus wasting a high energy phosphate bond.

A more ATP efficient sequence of reactions is enabled if DHA synthase functions in combination with F6P aldolase as opposed to in combination with DHA kinase, fructose bisphosphate aldolase, and fructose bisphosphatase. F6P aldolase enables direct conversion of DHA and G3P to F6P, bypassing the need for ATP hydrolysis. Overall, DHA synthase when combined with F6P aldolase is identical in energy demand to the RuMP pathway. Both of these formaldehyde assimilation options (i.e., RuMP pathway, DHA synthase+F6P aldolase) are superior to DHA synthase combined with DHA kinase, fructose bisphosphate aldolase, and fructose bisphosphatase in terms of ATP demand.

Example IV

Production of Fatty Alcohols and Fatty Aldehydes by MI-FAE Cycle, MD-FAE Cycle and Acyl-CoA Termination Pathways Encoding nucleic acids and species that can be used as sources for conferring fatty alcohol and fatty aldehyde production capability onto a host microbial organism are exemplified further below.

Multienzyme Complexes

In one exemplary embodiment, the genes fadA and fadB encode a multienzyme complex that exhibits three constituent activities of the malonyl-CoA independent FAS pathway, namely, ketoacyl-CoA thiolase, 3-hydroxyacyl-CoA dehydrogenase, and enoyl-CoA hydratase activities (Nakahigashi, K. and H. Inokuchi, *Nucleic Acids Research* 18:4937 (1990); Yang et al., *Journal of Bacteriology* 173:7405-7406 (1991); Yang et al, *Journal of Biological Chemistry* 265: 10424-10429 (1990); Yang et al., *Biochemistry* 30:6788-6795 (1990)). The fadI and fadJ genes encode similar activities which can substitute for the above malonyl-CoA independent FAS conferring genes fadA and fadB. The acyl-CoA dehydrogenase of *E. coli* is encoded by fadE (Campbell et al, *J Bacteriol* 184: 3759-64)). This enzyme catalyzes the rate-limiting step of beta-oxidation (O'Brien et al, *J Bacteriol* 132:532-40 (1977)). The nucleic acid sequences for each of the above fad genes are well known in the art and can be accessed in the public databases such as Genbank using the following accession numbers.

| Protein | GenBank ID | GI Number | Organism |
| --- | --- | --- | --- |
| fadA | YP_026272.1 | 49176430 | *Escherichia coli* |
| fadB | NP_418288.1 | 16131692 | *Escherichia coli* |
| fadI | NP_416844.1 | 16130275 | *Escherichia coli* |
| fadJ | NP_416843.1 | 16130274 | *Escherichia coli* |
| fadR | NP_415705.1 | 16129150 | *Escherichia coli* |
| fadE | AAC73325.2 | 87081702 | *Escherichia coli* |

Step A. Thiolase

Thiolase enzymes, also know as beta-keto thiolase, acyl-CoA C-acetyltransferase, acyl-CoA:acetyl-CoA C-acyltransferase, 3-oxoacyl-CoA thiolase, 3-ketoacyl-CoA thiolase, beta-ketoacyl-CoA thiolase, and acyl-CoA thiolase, that are suitable for fatty alcohol, fatty aldehyde or fatty acid production are described herein (FIGS. 2A and 7A). Exemplary acetoacetyl-CoA thiolase enzymes include the gene products of atoB and homologyqeF from *E. coli* (Martin et al., *Nat.Biotechnol* 21:796-802 (2003)), thlA and thlB from *C. acetobutylicum* (Hanai et al., *Appl Environ Microbiol* 73:7814-7818 (2007); Winzer et al., *J.Mol.Microbiol Biotechnol* 2:531-541(2000)), and ERG10 from *S. cerevisiae* (Hiser et al., *J.Biol.Chem.* 269:31383-31389 (1994)). A degradative thiolase of *S. cerevisiae* is encoded by POT1. Another candidate thiolase is the phaA gene product of *R.* eutropha (Jenkins et al, *Journal of Bacteriology* 169:42-52 (1987)). The acetoacetyl-CoA thiolase from *Zoogloea ramigera* is irreversible in the biosynthetic direction and a crystal structure is available (Merilainen et al, *Biochem* 48: 11011-25 (2009)). Accession numbers for these thiolases and homologs are included in the table below.

| Protein | GenBank ID | GI Number | Organism |
| --- | --- | --- | --- |
| atoB | NP_416728 | 16130161 | *Escherichia coli* |
| yqeF | NP_417321.2 | 90111494 | *Escherichia coli* |
| thlA | NP_349476.1 | 15896127 | *Clostridium acetobutylicum* |
| thlB | NP_149242.1 | 15004782 | *Clostridium acetobutylicum* |
| ERG10 | NP_015297 | 6325229 | *Saccharomyces cerevisiae* |
| POT1 | NP_012106.1 | 6322031 | *Saccharomyces cerevisiae* |
| phaA | YP_725941 | 113867452 | *Ralstonia eutropha* |
| phbA | P07097.4 | 135759 | *Zoogloea ramigera* |
| h16_A1713 | YP_726205.1 | 113867716 | *Ralstonia eutropha* |
| pcaF | YP_728366.1 | 116694155 | *Ralstonia eutropha* |
| h16_B1369 | YP_840888.1 | 116695312 | *Ralstonia eutropha* |
| h16_A0170 | YP_724690.1 | 113866201 | *Ralstonia eutropha* |
| h16_A0462 | YP_724980.1 | 113866491 | *Ralstonia eutropha* |
| h16_A1528 | YP_726028.1 | 113867539 | *Ralstonia eutropha* |
| h16_B0381 | YP_728545.1 | 116694334 | *Ralstonia eutropha* |
| h16_B0662 | YP_728824.1 | 116694613 | *Ralstonia eutropha* |
| h16_B0759 | YP_728921.1 | 116694710 | *Ralstonia eutropha* |
| h16_B0668 | YP_728830.1 | 116694619 | *Ralstonia eutropha* |
| h16_A1720 | YP_726212.1 | 113867723 | *Ralstonia eutropha* |
| h16_A1887 | YP_726356.1 | 113867867 | *Ralstonia eutropha* |
| bktB | YP_002005382.1 | 194289475 | *Cupriavidus taiwanensis* |
| Rmet_1362 | YP_583514.1 | 94310304 | *Ralstonia metallidurans* |
| Bphy_0975 | YP_001857210.1 | 186475740 | *Burkholderia phymatum* |

Many thiolase enzymes catalyze the formation of longer-chain acyl-CoA products. Exemplary thiolases include, for example, 3-oxoadipyl-CoA thiolase (EC 2.3.1.174) and acyl-CoA thiolase (EC 2.3.1.16). 3-Oxoadipyl-CoA thiolase converts succinyl-CoA and acetyl-CoA to 3-oxoadipyl-CoA, and is a key enzyme of the beta-ketoadipate pathway for aromatic compound degradation. The enzyme is widespread in soil bacteria and fungi including *Pseudomonas putida* (Harwood et al., *J Bacteriol*. 176:6479-6488 (1994)) and *Acinetobacter calcoaceticus* (Doten et al., *J Bacteriol*. 169: 3168-3174 (1987)). The gene products encoded by pcaF in *Pseudomonas* strain B13 (Kaschabek et al., *J Bactenol*. 184:207-215 (2002)), phaD in *Pseudomonas putida* U (Olivera et al., *Proc.Natl.AcadSci USA* 95:6419-6424 (1998)), paaE in *Pseudomonas fluorescens* ST (Di et al., *Arch.Microbiol* 188:117-125 (2007)), and paaJ from *E. coli* (Nogales et al., *Microbiology* 153:357-365 (2007)) also catalyze this transformation. Several beta-ketothiolases exhibit significant and selective activities in the oxoadipyl-CoA forming direction including bkt from *Pseudomonas putida*, pcaF and bkt from *Pseudomonas aeruginosa* PAO1, bkt from *Burkholderia ambifaria* AMMD, paaJ from *E. coli*, and phaD from *P. putida*. Two gene products of *Ralstonia eutropha* (formerly known as *Alcaligenes eutrophus*), encoded by genes bktB and bktC, catalyze the formation of 3-oxopimeloyl-CoA (Slater et al., *J.Bacteriol*. 180:1979-1987 (1998); Haywood et al., *FEMS Microbiology Letters* 52:91-96 (1988)). The sequence of the BktB protein is known; however, the sequence of the BktC protein has not been reported. BktB is also active on substrates of length C6 and C8 (Machado et al, Met Eng in press (2012)). The pim operon of *Rhodopsendomonas palustris* also encodes a beta-ketothiolase, encoded by pimB, predicted to catalyze this transformation in the degradative direction during benzoyl-CoA degradation (Harrison et al., *Microbiology* 151: 727-736 (2005)). A beta-ketothiolase enzyme candidate in *S. aciditrophicus* was identified by sequence homology to bktB (43% identity, evalue=1e-93).

| Gene name | GI# | GenBank Accession # | Organism |
|---|---|---|---|
| paaJ | 16129358 | NP_415915.1 | *Escherichia coli* |
| pcaF | 17736947 | AAL02407 | *Pseudomonas knackmussii* (B13) |
| phaD | 3253200 | AAC24332.1 | *Pseudomonas putida* |
| pcaF | 506695 | AAA85138.1 | *Pseudomonas putida* |
| pcaF | 141777 | AAC37148.1 | *Acinetobacter calcoaceticus* |
| paaE | 106636097 | ABF82237.1 | *Pseudomonas fluorescens* |
| bkt | 115360515 | YP_777652.1 | *Burkholderia ambifaria* AMMD |
| bkt | 9949744 | AAG06977.1 | *Pseudomonas aeruginosa* PAO1 |
| pcaF | 9946065 | AAG03617.1 | *Pseudomonas aeruginosa* PAO1 |
| bktB | YP_725948 | 11386745 | *Ralstonia eutropha* |
| pimB | CAE29156 | 39650633 | *Rhodopseudomonas palustris* |
| syn_02642 | YP_462685.1 | 85860483 | *Syntrophus aciditrophicus* |

Acyl-CoA thiolase (EC 2.3.1.16) enzymes involved in the beta-oxidation cycle of fatty acid degradation exhibit activity on a broad range of acyl-CoA substrates of varying chain length. Exemplary acyl-CoA thiolases are found in *Arabidopsis thaliana* (Cruz et al, Plant Physiol 135:85-94 (2004)), *Homo sapiens* (Mannaerts et al, Cell Biochem Biphys 32:73-87 (2000)), *Helianthus annuus* (Schiedel et al, Prot Expr Purif 33:25-33 (2004)). The chain length specificity of thiolase enzymes can be assayed by methods well known in the art (Wrensford et al, *Anal Biochem* 192:49-54 (1991)). A peroxisomal thiolase found in rat liver catalyze the acetyl-CoA dependent formation of longer chain acyl-CoA products from octanoyl-CoA (Horie et al, *Arch Biochem Biophys* 274: 64-73 (1989); Hijikata et al, *J Biol Chem* 265, 4600-4606 (1990)).

Chain length selectivity of selected thiolase enzymes described above is summarized in the table below.

| Chain length | Gene | Organism |
|---|---|---|
| C4 | atoB | *Escherichia coli* |
| C6 | phaD | *Pseudomonas putida* |
| C6-C8 | bktB | *Ralstonia eutropha* |
| C10-C16 | Acaa1a | *Rattus norvegicus* |

Step B. 3-Oxoacyl-CoA Reductase

3-Oxoacyl-CoA reductases (also known as 3-hydroxyacyl-CoA dehydrogenases, 3-ketoacyl-CoA reductases, beta-

| Protein | GenBank ID | GI Number | Organism |
|---|---|---|---|
| AY308827.1:1 . . . 1350 | AAQ77242.1 | 34597334 | *Helianthus annuus* |
| KAT2 | Q56WD9.2 | 73919871 | *Arabidopsis thaliana* |
| KAT1 | Q8LF48.2 | 73919870 | *Arabidopsis thaliana* |
| KAT5 | Q570C8.2 | 73919872 | *Arabidopsis thaliana* |
| ACAA1 | P09110.2 | 135751 | *Homo sapiens* |
| LCTHIO | AAF04612.1 | 6165556 | *Sus scrofa* |
| Acaa1a | NP_036621.1 | 6978429 | *Rattus norvegicus* |
| Acaa1b | NP_001035108.1 | 90968642 | *Rattus norvegicus* |
| Acaa2 | NP_569117.1 | 18426866 | *Rattus norvegicus* |

Acetoacetyl-CoA can also be synthesized from acetyl-CoA and malonyl-CoA by acetoacetyl-CoA synthase (EC 2.3.1.194). This enzyme (FhsA) has been characterized in the soil bacterium Streptomyces sp. CL190 where it participates in mevalonate biosynthesis (Okamura et al, *PNAS USA* 107:11265-70 (2010)). As this enzyme catalyzes an essentially irreversible reaction, it is particularly useful for metabolic engineering applications for overproducing metabolites, fuels or chemicals derived from acetoacetyl-CoA such as long chain alcohols. Other acetoacetyl-CoA synthase genes can be identified by sequence homology to fhsA. Acyl-CoA synthase enzymes such as fhsA and homologs can be engineered or evolved to accept longer acyl-CoA substrates by methods known in the art.

ketoacyl-CoA reductases, beta-hydroxyacyl-CoA dehydrogenases, hydroxyacyl-CoA dehydrogenases, and ketoacyl-CoA reductases) catalyze the reduction of 3-oxoacyl-CoA substrates to 3-hydroxyacyl-CoA products (FIG. 2B and FIG. 7B). These enzymes are often involved in fatty acid beta-oxidation and aromatic degradation pathways. For example, subunits of two fatty acid oxidation complexes in *E. coli*, encoded by fadB and fadJ, function as 3-hydroxyacyl-CoA dehydrogenases (Binstock et al., *Methods Enzymol.* 71 Pt C:403-411 (1981)). Knocking out a negative regulator encoded by fadR can be utilized to activate the fadB gene product (Sato et al., *J Biosci.Bioeng* 103:38-44 (2007)). Another 3-hydroxyacyl-CoA dehydrogenase from *E. coli* is paaH (Ismail et al., *European Journal of Biochemistry* 270:3047-3054 (2003)). Additional 3-oxoacyl-CoA

| Protein | GenBank ID | GI Number | Organism |
|---|---|---|---|
| fhsA | BAJ83474.1 | 325302227 | *Streptomyces* sp CL190 |
| AB183750.1:11991 . . . 12971 | BAD86806.1 | 57753876 | *Streptomyces* sp. KO-3988 |
| epzT | ADQ43379.1 | 312190954 | *Streptomyces cinnamonensis* |
| ppzT | CAX48662.1 | 238623523 | *Streptomyces anulatus* |
| O3I_22085 | ZP_09840373.1 | 378817444 | *Nocardia brasiliensis* | enzymes include the gene products of phaC in *Pseudomonas putida* (Olives et al., *Proc.Natl.Acad.Sci USA* 95:6419-6424 (1998)) and paaC in *Pseudomonas fluorescens* (Di et al., 188:117-125 (2007)). These enzymes catalyze the reversible oxidation of 3-hydroxyadipyl-CoA to 3-oxoadipyl-CoA during the catabolism of phenylacetate or styrene. Other suitable enzyme candidates include AAO72312.1 from *E. gracilis* (Winkler et al., *Plant Physiology* 131:753-762 (2003)) and paaC from *Pseudomonas putida* (Olivera et al., *PNAS USA* 95:6419-6424 (1998)). Enzymes catalyzing the reduction of acetoacetyl-CoA to 3-hydroxybutyiyl-CoA include hbd of *Clostridium acetobutylicum* (Youngleson et al., *J Bacteriol.* 171:6800-6807 (1989)), phbB from *Zoogloea ramigera* (Ploux et al., *Eur.JBiochem.* 174:177-182 (1988)), phaB from *Rhodobacter sphaeroides* (Alber et al., *Mol.Microbiol* 61:297-309 (2006)) and paaH1 of *Ralstonia eutropha* (Machado et al, *Met Eng*, In Press (2012)). The *Z. ramigera* enzyme is NADPH-dependent and also accepts 3-oxopropionyl-CoA as a substrate (Ploux et al., *Eur.J Biochem.* 174:177-182 (1988)). Additional genes include phaB in *Paracoccus denitrificans*, Hbd1 (C-terminal domain) and Hbd2 (N-terminal domain) in *Clostridium kluyveri* (Hilimer and Gottschalk, *Biochim. Biophys. Acta* 3334:12-23 (1974)) and HSD17B10 in *Bos taurus* (Wakil et al., *J Biol.Chem.* 207:631-638 (1954)). The enzyme from *Paracoccus denitrificans* has been functionally expressed and characterized in *E. coli* (Yabutani et al., *FEMS Microbiol Lett.* 133:85-90 (1995)). A number of similar enzymes have been found in other species of *Clostridia* and in *Metallosphaera sedula* (Berg et al., *Science.* 318:1782-1786 (2007)). The enzyme from *Candida tropicalis* is a component of the peroxisomal fatty acid beta-oxidation multifunctional enzyme type 2 (MFE-2). The dehydrogenase B domain of this protein is catalytically active on acetoacetyl-CoA. The domain has been functionally expressed in *E. coli*, a crystal structure is available, and the catalytic mechanism is well-understood (Ylianttila et al., *Biochem Biophys Res Commun* 324:25-30 (2004); Ylianttila et al., *J Mol Biol* 358:1286-1295 (2006)). 3-Hydroxyacyl-CoA dehydrogenases that accept longer acyl-CoA substrates (eg. EC 1.1.1.35) are typically involved in beta-oxidation. An example is HSD17B10 in *Bos taurus* (Wakil et al., *J Biol.Chem.* 207:631-638 (1954)). The pig liver enzyme is preferentially active on short and medium chain acyl-CoA substrates whereas the heart enzyme is less selective (He et al, Biochim Biophys Acta 1392:119-26 (1998)). The *S. cerevisiae* enzyme FOX2 is active in beta-degradation pathways and also has enoyl-CoA hydratase activity (Hiltunen et al, *J Biol Chem* 267: 6646-6653 (1992)).

| Protein | Genbank ID | GI number | Organism |
| --- | --- | --- | --- |
| fadB | P21177.2 | 119811 | *Escherichia coli* |
| fadJ | P77399.1 | 3334437 | *Escherichia coli* |
| paaH | NP_415913.1 | 16129356 | *Escherichia coli* |
| Hbd2 | EDK34807.1 | 146348271 | *Clostridium kluyveri* |
| Hbd1 | EDK32512.1 | 146345976 | *Clostridium kluyveri* |
| phaC | NP_745425.1 | 26990000 | *Pseudomonas putida* |
| paaC | ABF82235.1 | 106636095 | *Pseudomonas fluorescens* |
| HSD17B10 | O02691.3 | 3183024 | *Bos taurus* |
| phbB | P23238.1 | 130017 | *Zoogloea ramigera* |
| phaB | YP_353825.1 | 77464321 | *Rhodobacter sphaeroides* |
| paaH1 | CAJ91433.1 | 113525088 | *Ralstonia eutropha* |
| phaB | BAA08358 | 675524 | *Paracoccus denitrificans* |
| Hbd | NP_349314.1 | 15895965 | *Clostridium acetobutylicum* |
| Hbd | AAM14586.1 | 20162442 | *Clostridium beijerinckii* |
| Msed_1423 | YP_001191505 | 146304189 | *Metallosphaera sedula* |
| Msed_0399 | YP_001190500 | 146303184 | *Metallosphaera sedula* |
| Msed_0389 | YP_001190490 | 146303174 | *Metallosphaera sedula* |
| Msed_1993 | YP_001192057 | 146304741 | *Metallosphaera sedula* |
| Fox2 | Q02207 | 399508 | *Candida tropicalis* |
| HSD17B10 | O02691.3 | 3183024 | *Bos taurus* |
| HADH | NP_999496.1 | 47523722 | *Bos taurus* |
| 3HCDH | AAO72312.1 | 29293591 | *Euglena gracilis* |
| FOX2 | NP_012934.1 | 6322861 | *Saccharomyces cerevisiae* |

Chain length specificity of selected hydroxyacyl-CoA dehydrogenase enzymes is shown below. Directed evolution can enhance selectivity of enzymes for longer-chain substrates. For example, Machado and coworkers developed a selection platform for directed evolution of chain elongation enzymes that favor longer acyl-CoA substrates. This group evolved paaH1 of *Ralstonia eutropha* for improved activity on 3-oxo-hexanoyl-CoA (Machado et al, *Met Eng*, In Press (2012)).

| Chain length | Gene | Organism |
| --- | --- | --- |
| C4 | hbd | *Clostridium acetobutylicum* |
| C5 | phbB | *Zoogloea ramigera* |
| C4-C6 | paaH1 | *Ralstonia eutropha* |
| C4-C10 | HADH | *Sus scrofa* |
| C4-C18 | fadB | *Escherichia coli* |

Step C. 3-Hydroxyacyl-CoA Dehydratase

3-Hydroxyacyl-CoA dehydratases (eg. EC 4.2.1.17, also known as enoyl-CoA hydratases) catalyze the dehydration of a range of 3-hydroxyacyl-CoA substrates (Roberts et al., *Arch.Microbiol* 117:99-108 (1978); Agnihotri et al., *Bioorg.Med.Chem.* 11:9-20 (2003); Conrad et al., *J Bacteriol.* 118:103-111(1974)) and can be used in the conversion of 3-hydroxyacyl-CoA to enoyl-CoA (FIGS. 2C and 7C). The ech gene product of *Pseudomonas putida* catalyzes the conversion of 3-hydroxybutyryl-CoA to crotonyl-CoA (Roberts et al., *Arch.Microbiol* 117:99-108 (1978)). This transformation is also catalyzed by the crt gene product of *Clostridium acetobutylicum*, the crt1 gene product of *C. kluyveri*, and other clostridial organisms Atsumi et al., *Metab Eng* 10:305-311(2008); Boynton et al., *J Bacteriol.* 178:3015-3024 (1996); Hillmer et al., *FEBS Lett.* 21:351-354 (1972)). Additional enoyl-CoA hydratase candidates are phaA and phaB, of *P. putida*, and paaA and paaB from *P. fluorescens* (Olives et al., *Proc.Natl.Acad.Sci U.S.A* 95:6419-6424 (1998)). The gene product of pimF in *Rhodopseudomonas palustris* is predicted to encode an enoyl-CoA hydratase that participates in pimeloyl-CoA degradation (Harrison et al., *Microbiology* 151:727-736 (2005)). Lastly, a number of *Escherichia coli* genes have been shown to demonstrate enoyl-CoA hydratase functionality including maoC (Park et al., *J Bacteriol.* 185:5391-5397 (2003)), paaF (Ismail et al., *Eur.J Biochem.* 270:3047-3054 (2003); Park et al., *Appl.Biochem.Biotechnol* 113-116:335-346 (2004); Park et al., *Biotechnol Bioeng* 86:681-686 (2004)) and paaG (Ismail et al., *Eur.J Biochem.* 270:3047-3054 (2003); Park and Lee, *Appl.Biochem.Biotechnol* 113-116:335-346 (2004); Park and Yup, *Biotechnol Bioeng* 86:681-686 (2004)). Enzymes with 3-hydroxyacyl-CoA dehydratase activity in *S. cerevisiae* include PHS1 and FOX2.

| Gene | GenBank Accession No. | GI No. | Organism |
|---|---|---|---|
| ech | NP_745498.1 | 26990073 | *Pseudomonas putida* |
| crt | NP_349318.1 | 15895969 | *Clostridium acetobutylicum* |
| crt1 | YP_001393856 | 153953091 | *Clostridium kluyveri* |
| phaA | ABF82233.1 | 26990002 | *Pseudomonas putida* |
| phaB | ABF82234.1 | 26990001 | *Pseudomonas putida* |
| paaA | NP_745427.1 | 106636093 | *Pseudomonas fluorescens* |
| paaB | NP_745426.1 | 106636094 | *Pseudomonas fluorescens* |
| pimF | CAE29158.1 | 39650635 | *Rhodopseudomonas palustris* |
| maoC | NP_415905.1 | 16129348 | *Escherichia coli* |
| paaF | NP_415911.1 | 16129354 | *Escherichia coli* |
| paaG | NP_415912.1 | 16129355 | *Escherichia coli* |
| FOX2 | NP_012934.1 | 6322861 | *Saccharomyces cerevisiae* |
| PHS1 | NP_012438.1 | 6322364 | *Saccharomyces cerevisiae* |

Enoyl-CoA hydratases involved in beta-oxidation can also be used in an fatty alcohol, fatty aldehyde and fatty acid biosynthetic pathway. For example, the multifunctional MFP2 gene product of *Arabidopsis thaliana* exhibits an enoyl-CoA reductase activity selective for chain lengths less than or equal to C14 (Arent et al, *J Biol Chem* 285:24066-77 (2010)). Alternatively, the *E. coli* gene products of fadA and fadB encode a multienzyme complex involved in fatty acid oxidation that exhibits enoyl-CoA hydratase activity (Yang et al., Biochemistry 30:6788-6795 (1991); Yang, *J Bacteriol.* 173:7405-7406 (1991); Nakahigashi et al., *Nucleic Acids Res.* 18:4937 (1990)). The fadI and fadJ genes encode similar functions and are naturally expressed under anaerobic conditions (Campbell et al., *Mol.Microbiol* 47:793-805 (2003)).

| Protein | GenBank ID | GI Number | Organism |
|---|---|---|---|
| MFP2 | AAD18042.1 | 4337027 | *Arabidopsis thaliana* |
| fadA | YP_026272.1 | 49176430 | *Escherichia coli* |
| fadB | NP_418288.1 | 16131692 | *Escherichia coli* |
| fadI | NP_416844.1 | 16130275 | *Escherichia coli* |
| fadJ | NP_416843.1 | 16130274 | *Escherichia coli* |
| fadR | NP_415705.1 | 16129150 | *Escherichia coli* |

Chain length specificity of selected 3-hydroxyacyl-CoA dehydratase enzymes is shown below.

| Chain length | Gene | Organism |
|---|---|---|
| C4-C6 | crt | *Clostridium acetobutylicum* |
| C4-C7 | pimF | *Rhodopseudomonas palustris* |
| C4-C14 | MFP2 | *Arabidopsis thaliana* |

Step D. Enoyl-CoA Reductase

Enoyl-CoA reductases (also known as acyl-CoA dehydrogenases, trans-2-enoyl-CoA reductases, or acyl-CoA oxidoreductases) catalyze the conversion of an enoyl-CoA to an acyl-CoA (step D of FIGS. 2 and 7). Exemplary acyl-CoA dehydrogenase or enoyl-CoA reductase (ECR) enzymes are the gene products of fadE of *E. coli* and *Salmonella enterica* (Tram et al, J Bacteriol 188:599-608 (2006)). YdiO of *E. coli* encodes a ferridoxin-dependent enoyl-CoA reductase (Dellomonaco et al *Nature* 476:355 (2011)). The bcd gene product from *Clostridium acetobutylicum* (Atsumi et al., 10:305-311(2008); Boynton et al., *J Bacteriol.* 178:3015-3024 (1996)) catalyzes the reduction of crotonyl-CoA to butyryl-CoA (EC 1.3.99.2). This enzyme participates in the acetyl-CoA fermentation pathway to butyrate in *Clostridial* species (Jones et al., *Microbiol Rev.* 50:484-524 (1986)). Activity of butyryl-CoA reductase can be enhanced by expressing bcd in conjunction with expression of the *C. acetobutylicum* effAB genes, which encode an electron transfer flavoprotein. An additional candidate for the enoyl-CoA reductase step is the enoyl-CoA reductase (EC 1.3.1.44) TER from *E. gracilis* (Hoffmeister et al., *J Biol.Chem* 280:4329-4338 (2005)). A construct derived from this sequence following the removal of its mitochondrial targeting leader sequence was cloned in *E. coil* resulting in an active enzyme. A close homolog of the ECR protein from the prokaryote *Treponema denticola*, encoded by TDE0597, has also been cloned and expressed in *E. coli* (Tucci et al., FEBS Lett, 581:1561-1566 (2007)). Six genes in *Syntrophus aciditrophicus* were identified by sequence homology to the *C. acetobutylicum* bcd gene product. The *S. aciditrophicus* genes syn_02637 and syn_02636 bear high sequence homology to the effAB genes of *C. acetobutylicum*, and are predicted to encode the alpha and beta subunits of an electron transfer flavoprotein.

| Protein | GenBank ID | GI Number | Organism |
|---|---|---|---|
| fadE | AAC73325.2 | 87081702 | *Escherichia coli* |
| ydiO | YP_489957.1 | 4E+08 | *Escherichia coli* |
| fadE | YP_005241256.1 | 379699528 | *Salmonella enterica* |
| bcd | NP_349317.1 | 15895968 | *Clostridium acetobutylicum* |
| etfA | NP_349315.1 | 15895966 | *Clostridium acetobutylicum* |
| etfB | NP_349316.1 | 15895967 | *Clostridium acetobutylicum* |
| TER | Q5EU90.1 | 62287512 | *Euglena gracilis* |
| TER | NP_612558.1 | 19924091 | *Rattus norvegicus* |
| TDE0597 | NP_971211.1 | 42526113 | *Treponema denticola* |
| syn_02587 | ABC76101 | 85721158 | *Syntrophus aciditrophicus* |

-continued

| Protein | GenBank ID | GI Number | Organism |
|---|---|---|---|
| syn_02586 | ABC76100 | 85721157 | Syntrophus aciditrophicus |
| syn_01146 | ABC76260 | 85721317 | Syntrophus aciditrophicus |
| syn_00480 | ABC77899 | 85722956 | Syntrophus aciditrophicus |
| syn_02128 | ABC76949 | 85722006 | Syntrophus aciditrophicus |
| syn_01699 | ABC78863 | 85723920 | Syntrophus aciditrophicus |
| syn_02637 | ABC78522.1 | 85723579 | Syntrophus aciditrophicus |
| syn_02636 | ABC78523.1 | 85723580 | Syntrophus aciditrophicus |

Additional enoyl-CoA reductase enzyme candidates are found in organisms that degrade aromatic compounds. *Rhodopseudomonas palustris*, a model organism for benzoate degradation, has the enzymatic capability to degrade pimelate via beta-oxidation of pimeloyl-CoA. Adjacent genes in the pim operon, pimC and pimD, bear sequence homology to *C. acetobutylicum* bcd and are predicted to encode a flavin-containing pimeloyl-CoA dehydrogenase (Harrison et al., 151:727-736 (2005)). The genome of nitrogen-fixing soybean symbiont *Bradyrhizobium japonicum* also contains a pim operon composed of genes with high sequence similarity to pimC and pimD of *R. palustris* (Harrison and Harwood, *Microbiology* 151:727-736 (2005)).

| Protein | GenBank ID | GI Number | Organism |
|---|---|---|---|
| pimC | CAE29155 | 39650632 | Rhodopseudomonas palustris |
| pimD | CAE29154 | 39650631 | Rhodopseudomonas palustris |
| pimC | BAC53083 | 27356102 | Bradyrhizobium japonicum |
| pimD | BAC53082 | 27356101 | Bradyrhizobium japonicum |

An additional candidate is 2-methyl-branched chain enoyl-CoA reductase (EC 1.3.1.52 and EC 1.3.99.12), an enzyme catalyzing the reduction of sterically hindered trans-enoyl-CoA substrates. This enzyme participates in branched-chain fatty acid synthesis in the nematode *Ascaris suum* and is capable of reducing a variety of linear and branched chain substrates including 2-methylvalelyl-CoA, 2-methylbutanoyl-CoA, 2-methylpentanoyl-CoA, octanoyl-CoA and pentanoyl-CoA (Duran et al., 268:22391-22396 (1993)). Two isoforms of the enzyme, encoded by genes acad1 and acad, have been characterized.

| Protein | GenBank ID | GI Number | Organism |
|---|---|---|---|
| acad1 | AAC48316.1 | 2407655 | Ascaris suum |
| acad | AAA16096.1 | 347404 | Ascaris suum |

At least three mitochondrial enoyl-CoA reductase enzymes exist in *E. gracilis* and are applicable for use in the invention. Three mitochondrial enoyl-CoA reductase enzymes of *E. gracilis* (ECR1-3) exhibit different chain length preferences (Inui et al., *European Journal of Biochemistry* 142:121-126 (1984)), which is particularly useful for dictating the chain length of the desired fatty alcohol, fatty aldehyde or fatty acid products. EST's ELL00002199, ELL00002335, and ELL00002648, which are all annotated as mitochondrial trans-2-enoyl-CoA reductases, can be used to isolate these additional enoyl-CoA reductase genes by methods known in the art. Two ECR enzymes from rat liver microsomes also exhibit different substrate specificities (Nagi et al, *Arch Biochem Biophys* 226:50-64 (1983)). The sequences of these enzymes have not been identified to date. The *Mycobacterium smegmatis* enoyl-CoA reductase accepts acyl-CoA substrates of chain lengths between C10-C16 (Shimakata et al, *J Biochem* 89:1075-80 (1981)).

| Protein | GenBank ID | GI Number | Organism |
|---|---|---|---|
| acad | WP_015308343.1 | 5E+08 | Mycobacterium smegmatis |
| caiA | WP_015308454.1 | 5E+08 | Mycobacterium smegmatis |

Enoyl-CoA reductases and their chain length specificities are shown in the table below.

| Chain length | Gene | Organism |
|---|---|---|
| C4-C6 | ECR1 | Euglena gracilis |
| C6-C8 | ECR3 | Euglena gracilis |
| C8-10 | ECR2 | Euglena gracilis |
| C8-C16 | Long chain ECR | Rattus norvegicus |
| C10-C16 | ECR (acad; caiA) | Mycobacterium smegmatis |
| C2-C18 | fadE | Salmonella enterica |

Step E. Acyl-CoA Reductase (Aldehyde Forming)

Reduction of an acyl-CoA to a fatty alcohol is catalyzed by either a single enzyme or pair of enzymes that exhibit acyl-CoA reductase and alcohol dehydrogenase activities. Acyl-CoA dehydrogenases that reduce an acyl-CoA to its corresponding aldehyde include fatty acyl-CoA reductase (EC 1.2.1.42, 1.2.1.50), succinyl-CoA reductase (EC 1.2.1.76), acetyl-CoA reductase, butyryl-CoA reductase and propionyl-CoA reductase (EC 1.2.1.3). Aldehyde forming acyl-CoA reductase enzymes with demonstrated activity on acyl-CoA, 3-hydroxyacyl-CoA and 3-oxoacyl-CoA substrates are known in the literature. Several acyl-CoA reductase enzymes are active on 3-hydroxyacyl-CoA substrates. For example, some butyryl-CoA reductases from Clostridial organisms, are active on 3-hydroxybutyryl-CoA and propionyl-CoA reductase of *L. reuteri* is active on 3-hydroxypropionyl-CoA. An enzyme for converting 3-oxoacyl-CoA substrates to their corresponding aldehydes is malonyl-CoA reductase. Enzymes in this class that demonstrate activity on enoyl-CoA substrates have not been identified to date. Specificity for a particular substrate can be refined using evolution or enzyme engineering methods known in the art.

Exemplary fatty acyl-CoA reductases enzymes are encoded by acrl of *Acinetobacter calcoaceticus* (Reiser, *Journal of Bacteriology* 179:2969-2975 (1997)) and *Acinetobacter* sp. M-1 (Ishige et al., *Appl. Environ. Microbiol.* 68:1192-1195 (2002)). Two gene products from *Mycobacterium tuberculosis* accept longer chain fatty acyl-CoA substrates of length C16-C18 (Harminder Singh, U. Central Florida (2007)). Yet another fatty acyl-CoA reductase is LuxC of *Photobacterium phosphoreum* (Lee et al, *Biochim Biohys Acta* 1388:215-22 (1997)). Enzymes with succinyl- CoA reductase activity are encoded by sucD of *Clostridium kluyveri* (Sohling, *J. Bacteriol.* 178:871-880 (1996)) and sucD of *P. gingivalis* (Takahashi, *J. Bacteriol* 182:4704-4710 (2000)). Additional succinyl-CoA reductase enzymes participate in the 3-hydroxypropionate/4-hydroxybutyrate cycle of thermophilic archaea including *Metallosphaera sedula* (Berg et al., *Science* 318:1782-1786 (2007)) and *Thermoproteus neutrophilus* (Ramos-Vera et al., *J Bacteriol,* 191:4286-4297 (2009)). The *M. sedula* enzyme, encoded by Msed_0709, is strictly NADPH-dependent and also has malonyl-CoA reductase activity. The *T. neutrophilus* enzyme is active with both NADPH and NADH. The enzyme acylating acetaldehyde dehydrogenase in *Pseudomonas* sp, encoded by bphG, is yet another as it has been demonstrated to oxidize and acylate acetaldehyde, propionaldehyde, butyraldehyde, isobutyraldehyde and formaldehyde (Powlowski, *J. Bacteriol.* 175:377-385 (1993)). In addition to reducing acetyl-CoA to ethanol, the enzyme encoded by adhE in *Leuconostoc mesenteroides* has been shown to oxidize the branched chain compound isobutyraldehyde to isobutyryl-CoA (Kazahaya, *J. Gen. Appl. Microbiol.* 18:43-55 (1972); and Koo et al., *Biotechnol Lett.* 27:505-510 (2005)). Butyraldehyde dehydrogenase catalyzes a similar reaction, conversion of butyryl-CoA to butyraldehyde, in solventogenic organisms such as *Clostridium saccharoperbulacetonicum* (Kosaka et al., *Biosci Biotechnol Biochem.,* 71:58-68 (2007)). Exemplary propionyl-CoA reductase enzymes include pduP of *Salmonella typhimurium* LT2 (Leal, Arch. Microbiol. 180:353-361 (2003)) and eutE from *E. coli* (Skmly, WO Patent No. 2004/024876). The propionyl-CoA reductase of *Salmonella typhimurium* LT2, which naturally converts propionyl-CoA to propionaldehyde, also catalyzes the reduction of 5-hydroxyvaleryl-CoA to 5-hydroxypentanal (WO 2010/068953A2). The propionaldehyde dehydrogenase of *Lactobacillus reuteri*, PduP, has a broad substrate range that includes butyraldehyde, valeraldehyde and 3-hydroxypropionaldehyde (Luo et al, *Appl Microbiol Biotech*, 89: 697-703 (2011). Additional FAR enzymes are encoded by wax2 of *Arabidopsis thaliana* and $FAR_1$ and FAR2 of Mus musculus (Chen et al, Plant Cell 15:1170-85 (2003); Cheng and Russel, J Biol Chem 279:37789-97 (2004)). Both mouse FAR enzymes accept substrates with a chain length of C16-18. Additionally, some acyl-ACP reductase enzymes such as the orf1594 gene product of *Synechococcus elongatus* PCC7942 also exhibit aldehyde-forming acyl-CoA reductase activity (Schirmer et al, *Science,* 329: 559-62 (2010)). Acyl-ACP reductase enzymes and homologs are described in further detail in Example XII.

| Protein | GenBank ID | GI Number | Organism |
|---|---|---|---|
| acr1 | YP_047869.1 | 50086359 | *Acinetobacter calcoaceticus* |
| acr1 | AAC45217 | 1684886 | *Acinetobacter baylyi* |
| acr1 | BAB85476.1 | 18857901 | *Acinetobacter* sp. Strain M-1 |
| Rv1543 | NP_216059.1 | 15608681 | *Mycobacterium tuberculosis* |
| Rv3391 | NP_217908.1 | 15610527 | *Mycobacterium tuberculosis* |
| LuxC | Q03324 | 547874 | *Photobacterium leiognathi* PL741 |
| LuxC | AAT00788.1 | 46561111 | *Photobacterium phosphoreum* |
| Msed_0709 | YP_001190808.1 | 146303492 | *Metallosphaera sedula* |
| Tneu_0421 | ACB39369.1 | 170934108 | *Thermoproteus neutrophilus* |
| sucD | P38947.1 | 172046062 | *Clostridium kluyveri* |
| sucD | NP_904963.1 | 34540484 | *Porphyromonas gingivalis* |
| bphG | BAA03892.1 | 425213 | *Pseudomonas* sp |
| adhE | AAV66076.1 | 55818563 | *Leuconostoc mesenteroides* |
| bld | AAP42563.1 | 31075383 | *Clostridium saccharoperbutylacetonicum* |
| pduP | NP_460996 | 16765381 | *Salmonella typhimurium* LT2 |
| eutE | NP_416950 | 16130380 | *Escherichia coli* |
| pduP | CCC03595.1 | 337728491 | *Lactobacillus reuteri* |
| wax2 | AAN06975.1 | 22900949 | *Arabidopsis thaliana* |
| FAR1 | AAH07178.1 | 13938126 | *Mus musculus* |
| FAR2 | AAH55759 | 33416982 | *Mus musculus* |

An additional enzyme type that converts an acyl-CoA to its corresponding aldehyde is malonyl-CoA reductase which transforms malonyl-CoA to malonic semialdehyde. Malonyl-CoA reductase is a key enzyme in autotrophic carbon fixation via the 3-hydroxypropionate cycle in thermoacidophilic archaeal bacteria (Berg, *Science* 318:1782-1786 (2007); and Thauer, *Science* 318:1732-1733 (2007)). The enzyme utilizes NADPH as a cofactor and has been characterized in *Metallosphaera* and *Sulfolobus* sp. (Alber et al., *J. Bacteriol.* 188:8551-8559 (2006); and Hugler, *J. Bacteriol.* 184:2404-2410 (2002)). The enzyme is encoded by Msed_0709 in *Metallosphaera sedula* (Alber et al., *J. Bacteriol.* 188:8551-8559 (2006); and Berg, Science 318:1782-1786 (2007)). A gene encoding a malonyl-CoA reductase from *Sulfolobus tokodaii* was cloned and heterologously expressed in *E. coli* (Alber et al., *J. Bacteriol* 188:8551-8559 (2006). This enzyme has also been shown to catalyze the conversion of methylmalonyl-CoA to its corresponding aldehyde (WO2007141208 (2007)). Although the aldehyde dehydrogenase functionality of these enzymes is similar to the bifunctional dehydrogenase from *Chlorollexus aurantiacus*, there is little sequence similarity. Both malonyl-CoA reductase enzyme candidates have high sequence similarity to aspartate-semialdehyde dehydrogenase, an enzyme catalyzing the reduction and concurrent dephosphorylation of aspartyl-4-phosphate to aspartate semialdehyde. Additional gene candidates can be found by sequence homology to proteins in other organisms including *Sulfolobus solfataricus* and *Sulfolobus acidocaldarius* and have been listed below. Yet another candidate for CoA-acylating aldehyde dehydrogenase is the ald gene from *Clostridium beijerinckii* (Toth, *Appl. Environ. Microbiol.* 65:4973-4980 (1999). This enzyme has been reported to reduce acetyl-CoA and butyryl-CoA to their corresponding aldehydes. This gene is very similar to eutE that encodes acetaldehyde dehydrogenase of *Salmonella typhimurium* and *E. coli* (Toth, *Appl. Environ. Microbiol.* 65:4973-4980 (1999).

| Gene | GenBank ID | GI Number | Organism |
| --- | --- | --- | --- |
| Msed_0709 | YP_001190808.1 | 146303492 | *Metallosphaera sedula* |
| mcr | NP_378167.1 | 15922498 | *Sulfolobus tokodaii* |
| asd-2 | NP_343563.1 | 15898958 | *Sulfolobus solfataricus* |
| Saci_2370 | YP_256941.1 | 70608071 | *Sulfolobus acidocaldarius* |
| Ald | AAT66436 | 49473535 | *Clostridium beijerinckii* |
| eutE | AAA80209 | 687645 | *Salmonella typhimurium* |
| eutE | NP_416950 | 16130380 | *Escherichia coli* |

Chain length specificity ranges of selected aldehyde-forming acyl-CoA reductase enzymes are show in the table below.

| Chain length | Gene | Organism |
| --- | --- | --- |
| C2-C4 | bphG | *Pseudomonas* sp |
| C4 | Bld | *Clostridium saccharoperbutylacetonicum* |
| C12-C20 | ACR | *Acinetobacter calcoaceticus* |
| C14-C18 | Acr1 | *Acinetobacter* sp. Strain M-1 |
| C16-C18 | Rv1543, Rv3391 | *Mycobacterium tuberculosis* |
| C16-C18 | FAR1, FAR2 | *Mus musculus* |
| C18 | Wax2 | *Arabidopsis thaliana* |

Step G. Acyl-CoA Reductase (Alcohol Forming)

Bifunctional alcohol-forming acyl-CoA reductase enzymes catalyze step G (i.e. step E and F) of FIGS. 2 and 7. Enzymes with this activity include adhE of *E. coli* (Kessler et al., *FEBS.Lett.* 281:59-63 (1991))) and adhE2 of *Clostridium acetobutylicum* (Fontaine et al., *J.Bacteriol.* 184:821-830 (2002))). The *E. coli* enzyme is active on C2 substrates, whereas the *C. acetobutylicum* enzyme has a broad substrate range that spans C2-C8 (Dekishima et al, *J Am Chem Soc* 133:11399-11401(2011)). The *C. acetobutylicum* enzymes encoded by bdh I and bdh II (Walter, et *J. Bacteriol.* 174:7149-7158 (1992)), reduce acetyl-CoA and butyryl-CoA to ethanol and butanol, respectively. The adhE gene produce from *Leuconostoc mesenteroides* is active on acetyl-CoA and isobutyryl-CoA (Kazahaya et al., *J.Gen.Appl.Microbiol.* 18:43-55 (1972); Koo et al., *Biotechnol Lett,* 27:505-510 (2005)). Enzyme candidates in other organisms including *Roseiflexus castenholzii, Erythrobacter* sp. NAP1 and marine gamma proteobacterium HTCC2080 can be inferred by sequence similarity. Longer chain acyl-CoA molecules can be reduced to their corresponding alcohols by enzymes such as the jojoba (*Simmondsia chinensis*) FAR which encodes an alcohol-forming fatty acyl-CoA reductase. Its overexpression in *E. coli* resulted in FAR activity and the accumulation of C16-C18 fatty alcohols (Metz et al., *Plant Physiol,* 122:635-644 (2000)). FAR enzymes in *Arabidopsis thaliana* include the gene products of At3g11980, At3g44560 and CER4 (Doan et al, *J Plant Physiol* 166 (2006); Rowland et al, Plant Physiol 142:866-77 (2006)). Bifunctional prokaryotic FAR enzymes are found in *Marinobacter aquaeolei* VT8 (Hofvander et al, FEBS Lett 3538-43 (2011)), *Marinobacter algicola* and *Oceanobacter* strain RED65 (US Pat Appl 20110000125). Other suitable enzymes include bfar from *Bombyx mori*, mfar1 and mfar2 from Mus musculus; mfar2 from Mus musculus; acrM1 from *Acinetobacter* sp. M1; and hfar from *H. sapiens*.

| Protein | GenBank ID | GI Number | Organism |
| --- | --- | --- | --- |
| adhE | NP_415757.1 | 16129202 | *Escherichia coli* |
| adhE2 | AAK09379.1 | 12958626 | *Clostridium acetobutylicum* |
| bdh I | NP_349892.1 | 15896543 | *Clostridium acetobutylicum* |
| bdh II | NP_349891.1 | 15896542 | *Clostridium acetobutylicum* |
| adhE | AAV66076.1 | 55818563 | *Leucoriostoc mesenteroides* |
| mcr | AAS20429.1 | 42561982 | *Chloroflexus aurantiacus* |
| Rcas_2929 | YP_001433009.1 | 156742880 | *Roseiflexus castenholzii* |
| NAP1_02720 | ZP_01039179.1 | 85708113 | *Erythrobacter* sp. NAP1 |
| MGP2080_00535 | ZP_01626393.1 | 119504313 | marine gamma proteobacterium HTCC2080 |
| FAR | AAD38039.1 | 5020215 | *Simmondsia chinensis* |
| At3g11980 | NP_191229.1 | 15228993 | *Arabidopsis thaliana* |
| At3g44560 | NP_190042.2 | 145339120 | *Arabidopsis thaliana* |
| CER4 | AEE86278.1 | 332660878 | *Arabidopsis thaliana* |
| FAR | YP_959486.1 | 120555135 | *Marinobacter aquaeolei* |
| bfar | Q8R079 | 81901336 | *Bombyx mori* |

Chain length specificity ranges of selected alcohol-forming acyl-CoA reductase enzymes are show in the table below.

| Chain length | Gene | Organism |
| --- | --- | --- |
| C2 | adhE | *Escherichia coli* |
| C2-C8 | adhe2 | *Clostridium acetobutylicum* |
| C14-C16 | At3g11980 | *Arabidopsis thaliana* |
| C16 | At3g44560 | *Arabidopsis thaliana* |

-continued

| Chain length | Gene | Organism |
|---|---|---|
| C16-C18 | FAR | *Simmondsia chinensis* |
| C14-C18 | FAR | *Marinobacter aquaeolei* |
| C24-C26 | CER4 | *Arabidopsis thaliana* |

Step F. Fatty Aldehyde Reductase

Exemplary genes encoding enzymes that catalyze the conversion of an aldehyde to alcohol (i.e., alcohol dehydrogenase or equivalently aldehyde reductase) include alrA encoding a medium-chain alcohol dehydrogenase for C2-C14 (Tani et al., *Appl.Environ.Microbiol.* 66:5231-5235 (2000)), yqhD and fucO from *E. coli* (Sulzenbacher et al., 342:489-502 (2004)), and bdh I and bdh II from *C. acetobutylicum* which converts butylyaldehyde into butanol (Walter et al., *J Bacteriol* 174:7149-7158 (1992)). The alrA gene product showed no activity on aldehydes longer than C14, and favored the reductive direction (Tani et al, supra). YqhD catalyzes the reduction of a wide range of aldehydes using NADPH as the cofactor, with a preference for chain lengths longer than C(3) (Sulzenbacher et al, *J Mol Biol* 342:489-502 (2004); Perez et al., *J Biol.Chem.* 283:7346-7353 (2008)). The adhA gene product from *Zymomonas mobilis* has been demonstrated to have activity on a number of aldehydes including formaldehyde, acetaldehyde, propionaldehyde, butyraldehyde, and acrolein (Kinoshita et al., *Appl Microbiol Biotechnol* 22:249-254 (1985)). Additional aldehyde reductase candidates are encoded by bdh in *C. saccharoperbulacetonicum* and Cbei_1722, Cbei_2181 and Cbei_2421 in *C. beijerinckii*. The alcohol dehydrogenase from *Leifsonia* sp. S749 shows maximal activity on medium chain-length substrates of length C6-C7 (Inoue et al, *AEM* 71: 3633-3641 (2005). The adh gene product of *Pseudomonas putida* is active on substrates of length C3-C10 (Nagashima et al, *J Ferment Bioeng* 82:328-33(1996)). The alcohol dehydrogenase enzymes ADH1 and ADH2 of *Geobacillus thermodenitrificans* oxidize alcohols up to a chain length of C30 (Liu et al, *Physiol Biochem* 155:2078-85 (2009)). Three additional alcohol dehydrogenase enzymes from *Geobacillus thermodenitrificans* are active on C2-C14 substrates (Liu et al, supra).

| Protein | GenBank ID | GI Number | Organism |
|---|---|---|---|
| alrA | BAB12273.1 | 9967138 | *Acinetobacter* sp. strain M-1 |
| ADH2 | NP_014032.1 | 6323961 | *Saccharomyces cerevisiae* |
| yqhD | NP_417484.1 | 16130909 | *Escherichia coli* |
| fucO | NP_417279.1 | 16130706 | *Escherichia coli* |
| bdh I | NP_349892.1 | 15896543 | *Clostridium acetobutylicum* |
| bdh II | NP_349891.1 | 15896542 | *Clostridium acetobutylicum* |
| adhA | YP_162971.1 | 56552132 | *Zymomonas mobilis* |
| bdh | BAF45463.1 | 124221917 | *Clostridium saccharoperbutylacetonicum* |
| Cbei_1722 | YP_001308850 | 150016596 | *Clostridium beijerinckii* |
| Cbei_2181 | YP_001309304 | 150017050 | *Clostridium beijerinckii* |
| Cbei_2421 | YP_001309535 | 150017281 | *Clostridium beijerinckii* |
| lsadh | BAD99642.1 | 67625613 | *Leifsonia* sp. S749 |
| adh | | | *Pseudomonas putida* |
| ADH1 | YP_001126968.1 | 138896515 | *Geobacillus thermodenitrificans* |
| ADH2 | YP_001125863.1 | 138895410 | *Geobacillus thermodenitrificans* |
| GTNG_0872 | YP_001124995.1 | 138894542 | *Geobacillus thermodenitrificans* |
| GTNG_1287 | YP_001125402.1 | 138894949 | *Geobacillus thermodenitrificans* |
| GTNG_1851 | YP_001125956.1 | 138895503 | *Geobacillus thermodenitrificans* |

Native alcohol dehydrogenases also convert aldehyde substrates to alcohol products. To date, seven alcohol dehydrogenases, ADHI-ADHVII, have been reported in *S. cerevisiae* (de Smidt et al, FEMS Yeast Res 8:967-78 (2008)). ADH1 (GI:1419926) is the key enzyme responsible for reducing acetaldehyde to ethanol in the cytosol under anaerobic conditions. In *K. lactis*, two NAD-dependent cytosolic alcohol dehydrogenases have been identified and characterized. These genes also show activity for other aliphatic alcohols. The genes ADH1 (GI:113358) and ADHII (GI:51704293) are preferentially expressed in glucose-grown cells (Bozzi et al, *Biochim Biophys Acta* 1339: 133-142 (1997)). Cytosolic alcohol dehydrogenases are encoded by ADH1 (GI:608690) in *C. albicans*, ADH1 (GI:3810864) in *S. pombe*, ADH1 (GI:5802617) in *Y. lipolytica*, ADH1 (GI:2114038) and ADHII (GI:2143328) in *Pichia stipitis* or *Scheffersomyces stipitis* (Passoth et al, Yeast 14:1311-23 (1998)). Candidate alcohol dehydrogenases are shown the table below.

| Protein | GenBank ID | GI number | Organism |
|---|---|---|---|
| SADH | BAA24528.1 | 2815409 | *Candida parapsilosis* |
| ADH1 | NP_014555.1 | 6324486 | *Saccharomyces cerevisiae* s288c |
| ADH2 | NP_014032.1 | 6323961 | *Saccharomyces cerevisiae* s288c |
| ADH3 | NP_013800.1 | 6323729 | *Saccharomyces cerevisiae* s288c |

-continued

| Protein | GenBank ID | GI number | Organism |
|---|---|---|---|
| ADH4 | NP_011258.2 | 269970305 | Saccharomyces cerevisiae s288c |
| ADH5 (SFA1) | NP_010113.1 | 6320033 | Saccharomyces cerevisiae s288c |
| ADH6 | NP_014051.1 | 6323980 | Saccharomyces cerevisiae s288c |
| ADH7 | NP_010030.1 | 6319949 | Saccharomyces cerevisiae s288c |
| adhP | CAA44614.1 | 2810 | Kluyveromyces lactis |
| ADH1 | P20369.1 | 113358 | Kluyveromyces lactis |
| ADH2 | CAA45739.1 | 2833 | Kluyveromyces lactis |
| ADH3 | P49384.2 | 51704294 | Kluyveromyces lactis |

Substrate specificity ranges of selected alcohol dehydrogenase enzymes are show in the table below.

| Chain length | Gene | Organism |
|---|---|---|
| C6-C7 | lsadh | Leifsonia sp. S749 |
| C2-C8 | yqhD | Escherichia coli |
| C3-C10 | Adh | Pseudomonas putida |
| C2-C14 | alrA | Acinetobacter sp. strain M-1 |
| C2-C14 | ADH | Geobacillus thermodenitrificans |
| C2-C30 | ADH1 | Geobacillus thermodenitrificans |

Step O. Elongase

Elongase (ELO) enzymes utilize malonyl-CoA to add a C2 unit to a growing acyl-CoA chain. This process also involves decarboxylation and is thus largely irreversible. *Trypanosoma brucei*, a eukaryotic human parasite, is known to produce long chain fatty acids using an elongase system. The process is initiated by butyryl-CoA. In particular, the ELO system esterifies the growing fatty acid chain to CoA intermediates rather than ACP intermediates like the bacterial and other microbial counterparts (Lee et al, Cell 126, 691-699, 2006; Cronan, Cell, 126, 2006). This is in contrast to typical bacterial fatty acid elongation which is initiated following the formation of acetoacetyl acyl-ACP from malonyl-ACP. So far, four ELOs (encoded by ELO1-4) that are homologous to their animal counterparts have been found in *T. brucei* (Lee et al, Nature Reviews Microbiology, Vol 5, 287-297, 2007). ELO1-3 together account for synthesis of saturated fatty acids up to a chain length of C18. ELO1 converts C4 to C10, ELO2 extends the chain length from C10 to myristate (C14), and ELO3 extends myristate to C18. There is some overlap in ELO specificity; for example, ELO1 can extend a C10 primer to C12, albeit with low activity. ELO4 is an example of an ELO that is specific for poly unsaturated fatty acids (PUFAs). It extends arachidonate (C20:4) by two carbon atoms. Several additional ELO enzymes can be found by sequence homology (see Lee et al, Nature Reviews Microbiology, Vol 5, 287-297, 2007).

Elongase enzymes are found in several compartments including the mitochondria, endoplasmic reticulum, proteoliposomes and peroxisomes. For example, some yeast such as *S. cerevisiae* are able to synthesize long-chain fatty acids of chain length C16 and higher via a mitochondrial elongase which accepts exogenous or endogenous acyl-CoA substrates (Bessoule et al, FEBS Lett 214: 158-162 (1987)). This system requires ATP for activity. The endoplasmic reticulum also has an elongase system for synthesizing very long chain fatty acids (C18+) from acyl-CoA substrates of varying lengths (Kohlwein et al, Mol Cell Biol 21:109-25 (2001)). Genes involved in this system include TSC13, ELO2 and ELO3. ELO1 catalyzes the elongation of C12 acyl-CoAs to C16-C18 fatty acids.

| Protein | Accession # | GI number | Organism |
|---|---|---|---|
| ELO2 | NP_009963.1 | 6319882 | Saccharomyces cerevisiae |
| ELO3 | NP_013476.3 | 398366027 | Saccharomyces cerevisiae |
| TSC13 | NP_010269.1 | 6320189 | Saccharomyces cerevisiae |
| ELO1 | NP_012339.1 | 6322265 | Saccharomyces cerevisiae |
| ELO1 | AAX70671.1 | 62176566 | Trypanosoma brucei |
| ELO2 | AAX70672.1 | 62176567 | Trypanosoma brucei |
| ELO3 | AAX70673.1 | 62176568 | Trypanosoma brucei |
| ELO4 | AAX70768.1 | 62176665 | Trypanosoma brucei |
| ELO4 | AAX69821.1 | 62175690 | Trypanosoma brucei |

Those skilled in the art also can obtain nucleic acids encoding any or all of the malonyl-CoA independent FAS pathway or acyl-reduction pathway enzymes by cloning using known sequences from available sources. For example, any or all of the encoding nucleic acids for the malonyl-CoA independent FAS pathway can be readily obtained using methods well known in the art from *E. gracilis* as this pathway has been well characterized in this organism. *E. gracilis* encoding nucleic acids can be isolated from, for example, an *E. gracilis* cDNA library using probes of known sequence. The probes can be designed with whole or partial DNA sequences from the following EST sequences from the publically available sequence database TBestDB (http://tbestdb.bcm.umontreal.ca). The nucleic acids generated from this process can be inserted into an appropriate expression vector and transformed into *E. coli* or other microorganisms to generate fatty alcohols, fatty aldehydes or fatty acids production organisms of the invention.

Thiolase (FIG. 2A): ELL00002550, ELL00002493, ELL00000789

3-Hydroxyacyl-CoA dehydrogenase (FIG. 2B): ELL00000206, ELL00002419, ELL00006286, ELL00006656

Enoyl-CoA hydratase (FIG. 2C): ELL00005926, ELL00001952, ELL00002235, ELL00006206

Enoyl-CoA reductase (FIG. 2D): ELL00002199, ELL00002335, ELL00002648

Acyl-CoA reductase (FIG. 2E; 2E/F): ELL00002572, ELL00002581, ELL00000108

Alternatively, the above EST sequences can be used to identify homologue polypeptides in GenBank through BLAST search. The resulting homologue polypeptides and their corresponding gene sequences provide additional encoding nucleic acids for transformation into *E. coli* or other microorganisms to generate the fatty alcohols, fatty aldehydes or fatty acids producing organisms of the invention. Listed below are exemplary homologue polypeptide and their gene accession numbers in GenBank which are applicable for use in the non-naturally occurring organisms of the invention.

Ketoacyl-CoA Acyltransferase (or Ketoacyl-CoA Thiolase)

| Protein | GenBank ID | GI number | Organism |
|---|---|---|---|
| Dole_2160 | YP_001530041 | 158522171 | *Desulfococcus oleovorans* Hxd3 |
| DalkDRAFT_1939 | ZP_02133627 | 163726110 | *Desulfatibacillum alkenivorans* AK-01 |
| BSG1_09488 | ZP_01860900 | 149182424 | *Bacillus* sp. SG-1 |

3-Hydroxyacyl-CoA Dehydrogenase

| Protein | GenBank ID | GI number | Organism |
|---|---|---|---|
| AaeL_AAEL002841 | XP_001655993 | 157132312 | *Aedes aegypti* |
| hadh | NP_001011073 | 58331907 | *Xenopus tropicalis* |
| hadh | NP_001003515 | 51011113 | *Danio rerio* |

Enoyl-CoA Hydratase

| Protein | GenBank ID | GI number Organism |
|---|---|---|
| Tb927.3.4850 | XP_844077 | 72387305 *Trypanosoma brucei* |
| Tc00.1047053509701.10 | XP_802711 | 71399112 *Trypanosoma cruzi* strain CL Brener |
| PputGB1_3629 | YP_001669856 | 167034625 *Pseudomonas putida* GB-1 |

Enoyl-CoA Reductase

| Protein | GenBank ID | GI number Organism |
|---|---|---|
| mecr | XP_642118 | 66816217 *Dictyostelium discoideum* AX4 |
| NEMVEDRAFT_v1g228294 | XP_001639469 | 156402181 *Nematostella vectensis* |
| AaeL_AAEL003995 | XP_001648220 | 157104018 *Aedes aegypti* |

In addition to the above exemplary encoding nucleic acids, nucleic acids other than those within the MI-FAE cycle, MD-FAE and/or termination pathways of the invention also can be introduced into a host organism for further production of fatty alcohols, fatty aldehydes or fatty acids. For example, the *Ralstonia eutropha* BktB and PhbB genes catalyze the condensation of butyryl-CoA and acetyl-CoA to form β-keto-hexanoyl-CoA and the reduction of β-keto-hexanoyl-CoA to 3-hydroxy-hexanoyl-CoA (Fukui et al., *Biomacromolecules* 3:618-624 (2002)). To improve the production of fatty alcohols, exogenous DNA sequences encoding for these specific enzymes can be expressed in the production host of interest. Furthermore, the above described enzymes can be subjected to directed evolution to generate improved versions of these enzymes with high activity and high substrate specificity. A similar approach also can be utilized with any or all other enzymatic steps in the fatty alcohol, fatty aldehyde or fatty acid producing pathways of the invention to, for example, improve enzymatic activity and/or specificity and/or to generate a fatty alcohol, a fatty aldehyde or a fatty acid of a predetermined chain length or lengths.

Example V

Pathways For Producing Cytosolic Acetyl-CoA from Cytosolic Pyruvate

The following example describes exemplary pathways for the conversion of cytosolic pyruvate and threonine to cytosolic acetyl-CoA, as shown in FIG. 3.

Pathways for the conversion of cytosolic pyruvate and threonine to cytosolic acetyl-CoA could enable deployment of a cytosolic fatty alcohol, fatty aldehyde or fatty acid production pathway that originates from acetyl-CoA. Several pathways for converting cytosolic pyruvate to cytosolic acetyl-CoA are shown in FIG. 3. Direct conversion of pyruvate to acetyl-CoA can be catalyzed by pyruvate dehydrogenase, pyruvate formate lyase, pyruvate:NAD(P) oxidoreductase or pyruvate:fenedoxin oxidoreductase. If a pyruvate formate lyase is utilized, the formate byproduct can be further converted to $CO_2$ by formate dehydrogenase or formate hydrogen lyase.

Indirect conversion of pyruvate to acetyl-CoA can proceed through several alternate routes. Pyruvate can be converted to acetaldehyde by a pyruvate decarboxylase. Acetaldehyde can then converted to acetyl-CoA by an acylating (CoA-dependent) acetaldehyde dehydrogenase. Alternately, acetaldehyde generated by pyruvate decarboxylase can be converted to acetyl-CoA by the "PDH bypass" pathway. In this pathway, acetaldehyde is oxidized by acetaldehyde dehydrogenase to acetate, which is then converted to acetyl-CoA by a CoA ligase, synthetase or transferase. In another embodiment, the acetate intermediate is converted by an acetate kinase to acetyl-phosphate that is then converted to acetyl-CoA by a phosphotransacetylase. In yet another embodiment, pyruvate is directly converted to acetyl-phosphate by a pyruvate oxidase (acetyl-phosphate forming). Conversion of pyruvate to acetate is also catalyzed by acetate-forming pyruvate oxidase.

Cytosolic acetyl-CoA can also be synthesized from threonine by expressing a native or heterologous threonine aldolase (FIG. 6J) (van Mans et al, *AEM* 69:2094-9 (2003)). Threonine aldolase converts threonine into acetaldehyde and glycine. The acetaldehyde product is subsequently converted to acetyl-CoA by various pathways described above.

Gene candidates for the acetyl-CoA forming enzymes shown in FIG. 3 are described below.

Pyruvate oxidase (acetate-forming) (FIG. 3A) or pyruvate:quinone oxidoreductase (PQO) can catalyze the oxidative decarboxylation of pyruvate into acetate, using ubiquione (EC 1.2.5.1) or quinone (EC 1.2.2.1) as an electron acceptor. The *E. coli* enzyme, PoxB, is localized on the inner membrane (Abdel-Hamid et al., *Microbiol* 147:1483-98 (2001)). The enzyme has thiamin pyrophosphate and flavin adenine dinucleotide (FAD) cofactors (Koland and Gennis, *Biochemistry* 21:4438-4442 (1982)); O'Brien et al., *Biochemistry* 16:3105-3109 (1977); O'Brien and Gennis, *J. Biol. Chem.* 255:3302-3307 (1980)). PoxB has similarity to pyruvate decarboxylase of *S. cerevisiae* and *Zymomonas* mobilis. The pqo transcript of *Corynebacterium glutamicum* encodes a quinone-dependent and acetate-forming pyruvate oxidoreductase (Schreiner et al., *J Bacteriol* 188:1341-50 (2006)) Similar enzymes can be inferred by sequence homology.

| Protein | GenBank ID | GI Number | Organism |
|---------|------------|-----------|----------|
| poxB | NP_415392.1 | 16128839 | *Escherichia coli* |
| pqo | YP_226851.1 | 62391449 | *Corynebacterium glutamicum* |
| poxB | YP_309835.1 | 74311416 | *Shigella sonnei* |
| poxB | ZP_03065403.1 | 194433121 | *Shigella dysenteriae* |

The acylation of acetate to acetyl-CoA (FIG. 3B) can be catalyzed by enzymes with acetyl-CoA synthetase, ligase or transferase activity. Two enzymes that can catalyze this reaction are AMP-forming acetyl-CoA synthetase or ligase (EC 6.2.1.1) and ADP-forming acetyl-CoA synthetase (EC 6.2.1.13). AMP-forming acetyl-CoA synthetase (ACS) is the predominant enzyme for activation of acetate to acetyl-CoA. Exemplary ACS enzymes are found in *E. coli* (Brown et al., *J. Gen. Microbiol.* 102:327-336 (1977)), *Ralstonia eutropha* (Priefert and Steinbuchel, *J. Bacteriol.* 174:6590-6599 (1992)), *Methanothermobacter thermautotrophicus* (Ingram-Smith and Smith, *Archaea* 2:95-107 (2007)), *Salmonella enterica* (Gulick et al., *Biochemistry* 42:2866-2873 (2003)) and *Saccharomyces cerevisiae* (Jogl and Tong, *Biochemistry* 43:1425-1431 (2004)). ADP-forming acetyl-CoA synthetases are reversible enzymes with a generally broad substrate range (Musfeldt and Schonheit, *J. Bacteriol.* 184: 636-644 (2002)). Two isozymes of ADP-forming acetyl-CoA synthetases are encoded in the *Archaeoglobus fulgidus* genome by are encoded by AF1211 and AF1983 (Musfeldt and Schonheit, supra (2002)). The enzyme from *Haloarcula marismortui* (annotated as a succinyl-CoA synthetase) also accepts acetate as a substrate and reversibility of the enzyme was demonstrated (Brasen and Schonheit, *Arch. Microbiol.* 182:277-287 (2004)). The ACD encoded by PAE3250 from hyperthermophilic crenarchaeon *Pyrobaculum aerophilum* showed the broadest substrate range of all characterized ACDs, reacting with acetate, isobutyryl-CoA (preferred substrate) and phenylacetyl-CoA (Brasen and Schonheit, supra (2004)). Directed evolution or engineering can be used to modify this enzyme to operate at the physiological temperature of the host organism. The enzymes from *A. fulgidus, H. marismortui* and *P. aerophilum* have all been cloned, functionally expressed, and characterized in *E. coli* (Brasen and Schonheit, supra (2004); Musfeldt and Schonheit, supra (2002)). Additional candidates include the succinyl-CoA synthetase encoded by sucCD in *E. coli* (Buck et al., *Biochemistry* 24:6245-6252 (1985)) and the acyl-CoA ligase from *Pseudomonas putida* (Fernandez-Valverde et al., *Appl. Environ. Microbiol.* 59:1149-1154 (1993)). The aforementioned proteins are shown below.

| Protein | GenBank ID | GI Number | Organism |
|---------|------------|-----------|----------|
| acs | AAC77039.1 | 1790505 | *Escherichia coli* |
| acoE | AAA21945.1 | 141890 | *Ralstonia eutropha* |
| acs1 | ABC87079.1 | 86169671 | *Methanothermobacter thermautotrophicus* |
| acs1 | AAL23099.1 | 16422835 | *Salmonella enterica* |
| ACS1 | Q01574.2 | 257050994 | *Saccharomyces cerevisiae* |
| AF1211 | NP_070039.1 | 11498810 | *Archaeoglobus fulgidus* |
| AF1983 | NP_070807.1 | 11499565 | *Archaeoglobus fulgidus* |
| scs | YP_135572.1 | 55377722 | *Haloarcula marismortui* |
| PAE3250 | NP_560604.1 | 18313937 | *Pyrobaculum aerophilum* str. IM2 |

| Protein | GenBank ID | GI Number | Organism |
|---------|------------|-----------|----------|
| sucC | NP_415256.1 | 16128703 | *Escherichia coli* |
| sucD | AAC73823.1 | 1786949 | *Escherichia coli* |
| paaF | AAC24333.2 | 22711873 | *Pseudomonas putida* |

The acylation of acetate to acetyl-CoA can also be catalyzed by CoA transferase enzymes (FIG. 3B). Numerous enzymes employ acetate as the CoA acceptor, resulting in the formation of acetyl-CoA. An exemplary CoA transferase is acetoacetyl-CoA transferase, encoded by the *E. coli* atoA (alpha subunit) and atoD (beta subunit) genes (Korolev et al., *Acta Crystallogr.D.Biol.Crystallogr.* 58:2116-2121 (2002); Vanderwinkel et al., 33:902-908 (1968)). This enzyme has a broad substrate range (Sramek et al., *Arch Biochem Biophys* 171:14-26 (1975)) and has been shown to transfer the CoA moiety to acetate from a variety of branched and linear acyl-CoA substrates, including isobutyrate (Matthies et al., *Appl Environ.Microbiol* 58:1435-1439 (1992)), valerate (Vanderwinkel et al., *Biochem.Biophys.Res.Commun.* 33:902-908 (1968)) and butanoate (Vanderwinkel et al., *Biochem.Biophys.Res. Commun.* 33:902-908 (1968)). Similar enzymes exist in *Corynebacterium glutamicum* ATCC 13032 (Duncan et al., 68:5186-5190 (2002)), *Clostridium acetobutylicum* (Cary et al., *Appl Environ Microbiol* 56:1576-1583 (1990); Wiesenborn et al., *Appl Environ Microbiol* 55:323-329 (1989)), and *Clostridium saccharoperbutylacetonicum* (Kosaka et al., *Biosci.Biotechnol Biochem.* 71:58-68 (2007)).

| Gene | GI # | Accession No. | Organism |
|------|------|---------------|----------|
| atoA | 2492994 | P76459.1 | *Escherichia coli* |
| atoD | 2492990 | P76458.1 | *Escherichia coli* |
| actA | 62391407 | YP_226809.1 | *Corynebacterium glutamicum* |
| cg0592 | 62389399 | YP_224801.1 | *Corynebacterium glutamicum* |
| ctfA | 15004866 | NP_149326.1 | *Clostridium acetobutylicum* |
| ctfB | 15004867 | NP_149327.1 | *Clostridium acetobutylicum* |
| ctfA | 31075384 | AAP42564.1 | *Clostridium saccharoperbutylacetonicum* |
| ctfB | 31075385 | AAP42565.1 | *Clostridium saccharoperbutylacetonicum* |

Acetate kinase (EC 2.7.2.1) can catalyzes the reversible ATP-dependent phosphorylation of acetate to acetylphosphate (FIG. 3C). Exemplary acetate kinase enzymes have been characterized in many organisms including *E. coli, Clostridium acetobutylicum* and *Methanosarcina thermophila* (Ingram-Smith et al., *J. Bacteriol.* 187:2386-2394 (2005); Fox and Roseman, *J. Biol. Chem.* 261:13487-13497 (1986); Winzer et al., *Microbioloy* 143 (Pt 10):3279-3286 (1997)). Acetate kinase activity has also been demonstrated in the gene product of *E. coli* purT (Marolewski et al., *Biochemistry* 33:2531-2537 (1994). Some butyrate kinase enzymes (EC 2.7.2.7), for example buk1 and buk2 from *Clostridium acetobutylicum*, also accept acetate as a substrate (Hartmanis, M. G., *J. Biol. Chem.* 262:617-621 (1987)). Homologs exist in several other organisms including *Salmonella enterica* and *Chlamydomonas reinhardtii*.

| Protein | GenBank ID | GI Number | Organism |
|---------|------------|-----------|----------|
| ackA | NP_416799.1 | 16130231 | *Escherichia coli* |
| Ack | AAB18301.1 | 1491790 | *Clostridium acetobutylicum* |
| Ack | AAA72042.1 | 349834 | *Methanosarcina thermophila* |

| Protein | GenBank ID | GI Number | Organism |
|---|---|---|---|
| purT | AAC74919.1 | 1788155 | Escherichia coli |
| buk1 | NP_349675 | 15896326 | Clostridium acetobutylicum |
| buk2 | Q97II1 | 20137415 | Clostridium acetobutylicum |
| ackA | NP_461279.1 | 16765664 | Salmonella typhimurium |
| ACK1 | XP_001694505.1 | 159472745 | Chlamydomonas reinhardtii |
| ACK2 | XP_001691682.1 | 159466992 | Chlamydomonas reinhardtii |

The formation of acetyl-CoA from acetyl-phosphate can be catalyzed by phosphotransacetylase (EC 2.3.1.8) (FIG. 3D). The pta gene from *E. coli* encodes an enzyme that reversibly converts acetyl-CoA into acetyl-phosphate (Suzuki, T., *Biochim. Biophys. Acta* 191:559-569 (969)). Additional acetyltransferase enzymes have been characterized in *Bacillus subtilis* (Rado and Hoch, *Biochim. Biophys. Acta* 321:114-125 (1973), *Clostridium kluyveri* (Stadtman, E., *Methods Enzymol.* 1:5896-599 (1955), and *Thermotoga maritima* (Bock et al., *J. Bacteriol.* 181:1861-1867 (1999)). This reaction can also be catalyzed by some phosphotranbutyrylase enzymes (EC 2.3.1.19), including the ptb gene products from *Clostridium acetobutylicum* (Wiesenbom et al., *App. Environ. Microbiol.* 55:317-322 (1989); Walter et al., *Gene* 134:107-111(1993)). Additional ptb genes are found in butyrate-producing bacterium L2-50 (Louis et al., *J. Bacteriol.* 186:2099-2106 (2004) and *Bacillus megaterium* (Vazquez et al., *Curr. Microbiol.* 42:345-349 (2001). Homologs to the *E. coli* pta gene exist in several other organisms including *Salmonella enterica* and *Chlamydomonas reinhardtii*.

| Protein | GenBank ID | GI Number | Organism |
|---|---|---|---|
| Pta | NP_416800.1 | 71152910 | Escherichia coli |
| Pta | P39646 | 730415 | Bacillus subtilis |
| Pta | A5N801 | 146346896 | Clostridium kluyveri |
| Pta | Q9X0L4 | 6685776 | Thermotoga maritime |
| Ptb | NP_349676 | 34540484 | Clostridium acetobutylicum |
| Ptb | AAR19757.1 | 38425288 | butyrate-producing bacterium L2-50 |
| Ptb | CAC07932.1 | 10046659 | Bacillus megaterium |
| Pta | NP_461280.1 | 16765665 | Salmonella enterica subsp. enterica serovar Typhimurium str. LT2 |
| PAT2 | XP_001694504.1 | 159472743 | Chlamydomonas reinhardtii |
| PAT1 | XP_001691787.1 | 159467202 | Chlamydomonas reinhardtii |

Pyruvate decarboxylase (PDC) is a key enzyme in alcoholic fermentation, catalyzing the decarboxylation of pyruvate to acetaldehyde (FIG. 3E). The PDC1 enzyme from *Saccharomyces cerevisiae* has been extensively studied (Killenberg-Jabs et al., *Eur.J.Biochem.* 268:1698-1704 (2001); Li et al., *Biochemistry.* 38:10004-10012 (1999); ter Schure et al., *Appl.Environ.Microbiol.* 64:1303-1307 (1998)). Other well-characterized PDC enzymes are found in *Zymomonas mobilus* (Siegert et al., *Protein Eng Des Sel* 18:345-357 (2005)), *Acetobacter pasteurians* (Chandra et al., 176:443-451(2001)) and *Kluyveromyces lactis* (Krieger et al., 269: 3256-3263 (2002)). The PDC1 and PDC5 enzymes of *Saccharomyces cerevisiae* are subject to positive transcriptional regulation by PDC2 (Hohmann et al, *Mol Gen Genet* 241: 657-66 (1993)). Pyruvate decarboxylase activity is also possessed by a protein encoded by CTRL_03826 (GI: 255729208) in *Candida tropicalis*, PDC1 (GI number: 1226007) in *Kluyveromyces lactis*, YALI0D10131g (GI: 50550349) in *Yarrowia lipolytica*, PAS_chr3_0188 (GI: 254570575) in *Pichia pastoris*, pyruvate decarboxylase (GI: GI:159883897) in *Schizosaccharomyces pombe*, ANI_1_1024084 (GI:145241548), ANI_1_796114 (GI: 317034487), ANI_1_936024 (GI:317026934) and ANI_1_2276014 (GI:317025935) in *Aspergillus niger*.

| Protein | GenBank ID | GI Number | Organism |
|---|---|---|---|
| pdc | P06672.1 | 118391 | Zymomonas mobilis |
| pdc1 | P06169 | 30923172 | Saccharomyces cerevisiae |
| Pdc2 | NP_010366.1 | 6320286 | Saccharomyces cerevisiae |
| Pdc5 | NP_013235.1 | 6323163 | Saccharomyces cerevisiae |
| CTRG_03826 | XP_002549529 | 255729208 | Candida tropicalis, |
| CU329670.1: 585597.587312 | CAA90807 | 159883897 | Schizosaccharomyces pombe |
| YALI0D10131g | XP_502647 | 50550349 | Yarrowia lipolytica |
| PAS_chr3_0188 | XP_002492397 | 254570575 | Pichia pastoris |
| pdc | Q8L388 | 20385191 | Acetobacter pasteurians |
| pdc1 | Q12629 | 52788279 | Kluyveromyces lactis |
| ANI_1_1024084 | XP_001393420 | 145241548 | Aspergillus niger |
| ANI_1_796114 | XP_001399817 | 317026934 | Aspergillus niger |
| ANI_1_936024 | XP_001396467 | 317034487 | Aspergillus niger |
| ANI_1_2276014 | XP_001388598 | 317025935 | Aspervillus niger |

Aldehyde dehydrogenase enzymes in EC class 1.2.1 catalyze the oxidation of acetaldehyde to acetate (FIG. 3F). Exemplary genes encoding this activity were described above. The oxidation of acetaldehyde to acetate can also be catalyzed by an aldehyde oxidase with acetaldehyde oxidase activity. Such enzymes can convert acetaldehyde, water and $O_2$ to acetate and hydrogen peroxide. Exemplary aldehyde oxidase enzymes that have been shown to catalyze this transformation can be found in *Bos taurus* and *Mus musculus* (Garattini et al., Cell Mol Life Sci 65:109-48 (2008); Cabre et al., Biochem Soc Trans 15:882-3 (1987)). Additional aldehyde oxidase gene candidates include the two flavin- and molybdenum-containing aldehyde oxidases of *Zea mays*, encoded by zmAO-1 and zmAO-2 (Sekimoto et al., *J Biol Chem* 272:15280-85 (1997)).

| Gene | GenBank Accession No. | GI No. | Organism |
|---|---|---|---|
| zmAO-1 | NP_001105308.1 | 162458742 | Zea mays |
| zmAO-2 | BAA23227.1 | 2589164 | Zea mays |
| Aox1 | O54754.2 | 20978408 | Mus musculus |
| XDH | DAA24801.1 | 296482686 | Bos taurus |

Pyruvate oxidase (acetyl-phosphate forming) can catalyze the conversion of pyruvate, oxygen and phosphate to acetyl-phosphate and hydrogen peroxide (FIG. 3G). This type of pyruvate oxidase is soluble and requires the cofactors thiamin diphosphate and flavin adenine dinucleotide (FAD). Acetyl-phosphate forming pyruvate oxidase enzymes can be found in lactic acid bacteria *Lactobacillus delbrueckii* and *Lactobacillus plantarum* (Lorquet et al., *J Bacteriol* 186: 3749-3759 (2004); Hager et al., *Fed Proc* 13:734-38 (1954)). A crystal structure of the *L. plantarum* enzyme has been solved (Muller et al., (1994)). In *Streptococcus sanguinis* and *Streptococcus pneumonia*, acetyl-phosphate forming pyruvate oxidase enzymes are encoded by the spxB gene (Spellerberg et al., *Mol Micro* 19:803-13 (1996); Ramos-Montanez et al., *Mol Micro* 67:729-46 (2008)). The SpxR was shown to positively regulate the transcription of spxB in *S. pneumoniae* (Ramos-Montanez et al., supra). A similar regulator in *S. sanguinis* was identified by sequence homology. Introduction or modification of catalase activity can reduce accumulation of the hydrogen peroxide product.

| Gene | GenBank Accession No. | GI No. | Organism |
|---|---|---|---|
| poxB | NP_786788.1 | 28379896 | Lactobacillus plantarum |
| spxB | L39074.1 | 1161269 | Streptococcus pneumoniae |
| Spd_0969 (spxR) | YP_816445.1 | 116517139 | Streptococcus pneumoniae |
| spxB | ZP_07887723.1 | 315612812 | Streptococcus sanguinis |
| spxR | ZP_07887944.1 GI: | 315613033 | Streptococcus sanguinis |

The pyruvate dehydrogenase (PDH) complex catalyzes the conversion of pyruvate to acetyl-CoA (FIG. 3H). The *E. coli* PDH complex is encoded by the genes aceEF and 1pdA. Enzyme engineering efforts have improved the *E. coli* PDH enzyme activity under anaerobic conditions (Kim et al., *J. Bacteriol.* 190:3851-3858 (2008); Kim et al., *Appl.Environ..Microbiol.* 73:1766-1771 (2007); Zhou et al., *Biotechnol..Lett.* 30:335-342 (2008)). In contrast to the *E. coli* PDH, the *B. subtilis* complex is active and required for growth under anaerobic conditions (Nakano et al., 179:6749-6755 (1997)). The *Klebsiella pneumoniae* PDH, characterized during growth on glycerol, is also active under anaerobic conditions (Menzel et al., 56:135-142 (1997)). Crystal structures of the enzyme complex from bovine kidney (Zhou et al., 98:14802-14807 (2001)) and the E2 catalytic domain from *Azotobacter vinelandii* are available (Mattevi et al., *Science.* 255:1544-1550 (1992)). Some mammalian PDH enzymes complexes can react on alternate substrates such as 2-oxobutanoate. Comparative kinetics ofRattus norvegicus PDH and BCKAD indicate that BCKAD has higher activity on 2-oxobutanoate as a substrate (Paxton et al., *Biochem.J.* 234:295-303 (1986)). The *S. cerevisiae* PDH complex can-consist of an E2 (LAT1) core that binds E1 (PDA1, PDB1), E3 (LPD1), and Protein X (PDX1) components (Pronk et al., *Yeast* 12:1607-1633 (1996)). The PDH complex of *S. cerevisiae* is regulated by phosphorylation of E1 involving PKP1 (PDH kinase I), PTCS (PDH phosphatase I), PKP2 and PTC6. Modification of these regulators may also enhance PDH activity. Coexpression of lipoyl ligase (Lp/A of *E. coli* and AIM22 in *S. cerevisiae*) with PDH in the cytosol may be necessary for activating the PDH enzyme complex. Increasing the supply of cytosolic lipoate, either by modifying a metabolic pathway or media supplementation with lipoate, may also improve PDH activity.

| Gene | Accession No. | GI Number | Organism |
|---|---|---|---|
| aceE | NP_414656.1 | 16128107 | Escherichia coli |
| aceF | NP_414657.1 | 16128108 | Escherichia coli |
| lpd | NP_414658.1 | 16128109 | Escherichia coli |
| lplA | NP_418803.1 | 16132203 | Escherichia coli |
| pdhA | P21881.1 | 3123238 | Bacillus subtilis |
| pdhB | P21882.1 | 129068 | Bacillus subtilis |
| pdhC | P21883.2 | 129054 | Bacillus subtilis |
| pdhD | P21880.1 | 118672 | Bacillus subtilis |
| aceE | YP_001333808.1 | 152968699 | Klebsiella pneumoniae |
| aceF | YP_001333809.1 | 152968700 | Klebsiella pneumoniae |
| lpdA | YP_001333810.1 | 152968701 | Klebsiella pneumoniae |
| Pdha1 | NP_001004072.2 | 124430510 | Rattus norvegicus |
| Pdha2 | NP_446446.1 | 16758900 | Rattus norvegicus |
| Dlat | NP_112287.1 | 78365255 | Rattus norvegicus |
| Dld | NP_955417.1 | 40786469 | Rattus norvegicus |
| LAT1 | NP_014328 | 6324258 | Saccharomyces cerevisiae |
| PDA1 | NP_011105 | 37362644 | Saccharomyces cerevisiae |
| PDB1 | NP_009780 | 6319698 | Saccharomyces cerevisiae |
| LPD1 | NP_116635 | 14318501 | Saccharomyces cerevisiae |
| PDX1 | NP_011709 | 6321632 | Saccharomyces cerevisiae |
| AIM22 | NP_012489.2 | 83578101 | Saccharomyces cerevisiae |

As an alternative to the large multienzyme PDH complexes described above, some organisms utilize enzymes in the 2-ketoacid oxidoreductase family (OFOR) to catalyze acylating oxidative decarboxylation of 2-keto-acids. Unlike the PDH complexes, PFOR enzymes contain iron-sulfur clusters, utilize different cofactors and use fenedoxin or flavodixin as electron acceptors in lieu of NAD(P)H. Pyruvate ferredoxin oxidoreductase (PFOR) can catalyze the oxidation of pyruvate to form acetyl-CoA (FIG. 3H). The PFOR from *Desulfovibrio africanus* has been cloned and expressed in *E. coli* resulting in an active recombinant enzyme that was stable for several days in the presence of oxygen (Pieulle et al., *J Bacteriol.* 179:5684-5692 (1997)). Oxygen stability is relatively uncommon in PFORs and is believed to be conferred by a 60 residue extension in the polypeptide chain of the *D. africanus* enzyme. The *M. thermoacetica* PFOR is also well characterized (Menon et al., *Biochemistry* 36:8484-8494 (1997)) and was even shown to have high activity in the direction of pyruvate synthesis during autotrophic growth (Furdui et al., *J Biol Chem.* 275:28494-28499 (2000)). Further, *E. coli* possesses an uncharacterized open reading frame, ydbK that encodes a protein that is 51% identical to the *M thermoacetica* PFOR. Evidence for pyruvate oxidoreductase activity in *E. coli* has been described (Blaschkowski et al., *Eur.J.Biochem.* 123:563-569 (1982)). Several additional PFOR enzymes are described in Ragsdale, *Chem.Rev.* 103:2333-2346 (2003). Finally, flavodoxin reductases (e.g., fqrB from *Helicobacter pylori* or *Campylobacter jejuni* (St Maurice et al., *J.Bacteriol.* 189:4764-4773 (2007))) or Rnf-type proteins (Seedorf et al., *Proc.Natl.AcadSci.U.S.A.* 105:2128-2133 (2008); Herrmnann et al., *J.Bacteriol.* 190:784-791 (2008)) provide a means to generate NADH or NADPH from the reduced ferredoxin generated by PFOR. These proteins are identified below.

| Protein | GenBank ID | GI Number | Organism |
|---|---|---|---|
| Por | CAA70873.1 | 1770208 | Desulfovibrio africanus |
| Por | YP_428946.1 | 83588937 | Moorella thermoacetica |
| ydbK | NP_415896.1 | 16129339 | Escherichia coli |
| fqrB | NP_207955.1 | 15645778 | Helicobacter pylori |
| fqrB | YP_001482096.1 | 157414840 | Campylobacter jejuni |
| RnfC | EDK33306.1 | 146346770 | Clostridium kluyveri |
| RnfD | EDK33307.1 | 146346771 | Clostridium kluyveri |
| RnfG | EDK33308.1 | 146346772 | Clostridium kluyveri |
| RnfE | EDK33309.1 | 146346773 | Clostridium kluyveri |
| RnfA | EDK33310.1 | 146346774 | Clostridium kluyveri |
| RnfB | EDK33311.1 | 146346775 | Clostridium kluyveri |

Pyruvate formate-lyase (PFL, EC 2.3.1.54) (FIG. 3H), encoded by pflB in *E. coli*, can convert pyruvate into acetyl-CoA and formate. The activity of PFL can be enhanced by an activating enzyme encoded by pflA (Knappe et al., *Proc.Natl.AcadSci U.S.A* 81:1332-1335 (1984); Wong et al., *Biochemistry* 32:14102-14110 (1993)). Keto-acid formate-lyase (EC 2.3.1.-), also known as 2-ketobutymte formate-lyase (KFL) and pyruvate formate-lyase 4, is the gene product of tdcE in *E. coli*. This enzyme catalyzes the conversion of 2-ketobutyrate to propionyl-CoA and formate during anaerobic threonine degradation, and can also substitute for pyruvate formate-lyase in anaerobic catabolism (Simanshu et al., *J Biosci.* 32:1195-1206 (2007)). The enzyme is oxygen-sensitive and, like NIB, can require post-translational modification by PFL-AE to activate a glycyl radical in the active site (Hesslinger et al., *Mol.Microbiol* 27:477-492 (1998)). A pyruvate formate-lyase from *Archaeoglobus fulgidus* encoded by pflD has been cloned, expressed in *E. coli* and characterized (Lehtio et al., *Protein Eng Des Sel* 17:545-552 (2004)). The crystal structures of the *A. fulgidus* and *E. coli* enzymes have been resolved (Lehtio et al., *J Mol.Biol.* 357:221-235 (2006); Leppanen et al., *Structure.* 7:733-744 (1999)). Additional PFL and PFL-AE candidates are found in *Lactococcus lactis* (Melchiorsen et al., *Appl Microbiol Biotechnol* 58:338-344 (2002)), and *Streptococcus mutans* (Takahashi-Abbe et al., *Oral.Microbiol Immunol.* 18:293-297 (2003)), *Chlamydomonas reinhardtii* (Hemschemeier et al., *Eukaryot.Cell* 7:518-526 (2008b); Atteia et al., *J.Biol.Chem.* 281:9909-9918 (2006)) and *Clostridium pasteurianum* (Weidner et al., *J Bacteriol.* 178:2440-2444 (1996)).

Sfum_2703 through Sfum_2706 in *Syntrophobacter fumaroxidans* (de Bok et al., *Eur J Biochem.* 270:2476-2485 (2003)); Reda et al., *PNAS* 105:10654-10658 (2008)). A similar set of genes presumed to carry out the same function are encoded by CHY_0731, CHY_0732, and CHY_0733 in *C. hydrogenoformans* (Wu et al., *PLoS Genet* 1:e65 (2005)). Formate dehydrogenases are also found many additional organisms including *C. carboxidivorans* P7, *Bacillus methanolicus, Burkholderia stabilis, Moorella thermoacetica* ATCC 39073, *Candida boidinii, Candida methylica,* and *Saccharomyces cerevisiae* S288c.

| Protein | GenBank ID | GI Number | Organism |
|---|---|---|---|
| Moth_2312 | YP_431142 | 148283121 | *Moorella thermoacetica* |
| Moth_2314 | YP_431144 | 83591135 | *Moorella thermoacetica* |
| Sfum_2703 | YP_846816.1 | 116750129 | *Syntrophobacter fumaroxidans* |
| Sfum_2704 | YP_846817.1 | 116750130 | *Syntrophobacter fumaroxidans* |
| Sfum_2705 | YP_846818.1 | 116750131 | *Syntrophobacter fumaroxidans* |
| Sfum_2706 | YP_846819.1 | 116750132 | *Syntrophobacter fumaroxidans* |
| CHY_0731 | YP_359585.1 | 78044572 | *Carboxydothermus hydrogenoformans* |
| CHY_0732 | YP_359586.1 | 78044500 | *Carboxydothermus hydrogenoformans* |
| CHY_0733 | YP_359587.1 | 78044647 | *Carboxydothermus hydrogenoformans* |
| CcarbDRAFT_0901 | ZP_05390901.1 | 255523938 | *Clostridium carboxidivorans* P7 |
| CcarbDRAFT_4380 | ZP_05394380.1 | 255527512 | *Clostridium carboxidivorans* P7 |
| fdhA, MGA3_06625 | EIJ82879.1 | 387590560 | *Bacillus methanolicus* MGA3 |
| fdhA, PB1_11719 | ZP_10131761.1 | 387929084 | *Bacillus methanolicus* PB1 |
| fdhD, MGA3_06630 | EIJ82880.1 | 387590561 | *Bacillus methanolicus* MGA3 |
| fdhD, PB1_11724 | ZP_10131762.1 | 387929085 | *Bacillus methanolicus* PB1 |
| fdh | ACF35003. | 194220249 | *Burkholderia stabilis* |
| FDH1 | AAC49766.1 | 2276465 | *Candida boidinii* |
| fdh | CAA57036.1 | 1181204 | *Candida methylica* |
| FDH2 | P0CF35.1 | 294956522 | *Saccharomyces cerevisiae* S288c |
| FDH1 | NP_015033.1 | 6324964 | *Saccharomyces cerevisiae* S288c |

| Protein | GenBank ID | GI Number | Organism |
|---|---|---|---|
| pflB | NP_415423 | 16128870 | *Escherichia coli* |
| pflA | NP_415422.1 | 16128869 | *Escherichia coli* |
| tdcE | AAT48170.1 | 48994926 | *Escherichia coli* |
| pflD | NP_070278.1 | 11499044 | *Archaeoglobus fulgidus* |
| pfl | CAA03993 | 2407931 | *Lactococcus lactis* |
| pfl | BAA09085 | 1129082 | *Streptococcus mutans* |
| PFL1 | XP_001689719.1 | 159462978 | *Chlamydomonas reinhardtii* |
| pflA1 | XP_001700657.1 | 159485246 | *Chlamydomonas reinhardtii* |
| pfl | Q46266.1 | 2500058 | *Clostridium pasteurianum* |
| act | CAA63749.1 | 1072362 | *Clostridium pasteurianum* |

If a pyruvate formate lyase is utilized to convert pyruvate to acetyl-CoA, coexpression of a formate dehydrogenase or formate hydrogen lyase enzyme will converte formate to carbon dioxide. Formate dehydrogenase (FDH) catalyzes the reversible transfer of electrons from formate to an acceptor. Enzymes with FDH activity utilize various electron carriers such as, for example, NADH (EC 1.2.1.2), NADPH (EC 1.2.1.43), quinols (EC 1.1.5.6), cytochromes (EC 1.2.2.3) and hydrogenases (EC 1.1.99.33). FDH enzymes have been characterized from *Moorella thermoacetica* (Andreesen and Ljungdahl, *J Bacteriol* 116:867-873 (1973); Li et al., *J Bacteriol* 92:405-412 (1966); Yamamoto et al., *J Biol Chem.* 258:1826-1832 (1983). The loci, Moth_2312 is responsible for encoding the alpha subunit of formate dehydrogenase while the beta subunit is encoded by Moth_2314 (Pierce et al., *Environ Microbiol* (2008)). Another set of genes encoding formate dehydrogenase activity with a propensity for $CO_2$ reduction is encoded by Alternately, a formate hydrogen lyase enzyme can be employed to convert formate to carbon dioxide and hydrogen. An exemplary formate hydrogen lyase enzyme can be found in *Escherichia coli*. The *E. coli* formate hydrogen lyase consists of hydrogenase 3 and formate dehydrogenase-H (Maeda et al., *Appl Microbiol Biotechnol* 77:879-890 (2007)). It is activated by the gene product of fhlA. (Maeda et al., *Appl Microbiol Biotechnol* 77:879-890 (2007)). The addition of the trace elements, selenium, nickel and molybdenum, to a fermentation broth has been shown to enhance formate hydrogen lyase activity (Soini et al., *Microb.Cell Fact.* 7:26 (2008)). Various hydrogenase 3, formate dehydrogenase and transcriptional activator genes are shown below. A formate hydrogen lyase enzyme also exists in the hyperthermophilic archaeon, *Thermococcus litoralis* (Takacs et al., *BMC.Microbiol* 8:88 (2008)). Additional formate hydrogen lyase systems have been found in *Salmonella typhimurium, Klebsiella pneumoniae, Rhodospirillum rubrum, Methanobacterium formicicum* (Vardar-Schara et al., Microbial Biotechnology 1:107-125 (2008)).

| Protein | GenBank ID | GI number | Organism |
|---|---|---|---|
| hycA | NP_417205 | 16130632 | *Escherichia coli* K-12MG1655 |
| hycB | NP_417204 | 16130631 | *Escherichia coli* K-12MG1655 |
| hycC | NP_417203 | 16130630 | *Escherichia coli* K-12MG1655 |
| hycD | NP_417202 | 16130629 | *Escherichia coli* K-12MG1655 |
| hycE | NP_417201 | 16130628 | *Escherichia coli* K-12MG1655 |
| hycF | NP_417200 | 16130627 | *Escherichia coli* K-12MG1655 |
| hycG | NP 417199 | 16130626 | *Escherichia coli* K-12MG1655 |
| hycH | NP_417198 | 16130625 | *Escherichia coli* K-12MG1655 |
| hycI | NP_417197 | 16130624 | *Escherichia coli* K-12MG1655 |
| fdhF | NP_418503 | 16131905 | *Escherichia coli* K-12MG1655 |
| fhA | NP_417211 | 16130638 | *Escherichia coli* K-12MG1655 |

-continued

| Protein | GenBank ID | GI number | Organism |
|---|---|---|---|
| mhyC | ABW05543 | 157954626 | Thermococcus litoralis |
| mhyD | ABW05544 | 157954627 | Thermococcus litoralis |
| mhyE | ABW05545 | 157954628 | Thermococcus litoralis |
| myhF | ABW05546 | 157954629 | Thermococcus litoralis |
| myhG | ABW05547 | 157954630 | Thermococcus litoralis |
| myhH | ABW05548 | 157954631 | Thermococcus litoralis |
| fdhA | AAB94932 | 2746736 | Thermococcus litoralis |
| fdhB | AAB94931 | 157954625 | Thermococcus litoralis |

Pyruvate:NADP oxidoreductase (PNO) catalyzes the conversion of pyruvate to acetyl-CoA. This enzyme is encoded by a single gene and the active enzyme is a homodimer, in contrast to the multi-subunit PDH enzyme complexes described above. The enzyme from *Euglena gracilis* is stabilized by its cofactor, thiamin pyrophosphate (Nakazawa et al, *Arch Biochem Biophys* 411:183-8 (2003)). The mitochondrial targeting sequence of this enzyme should be removed for expression in the cytosol. The PNO protein of *E. gracilis* protein and other NADP-dependant pyruvate:NADP+ oxidoreductase enzymes are listed in the table below.

| Protein | GenBank ID | GI Number | Organism |
|---|---|---|---|
| PNO | Q94IN5.1 | 33112418 | Euglena gracilis |
| cgd_690 | XP_625673.1 | 66356990 | Cryptosporidium parvum Iowa II |
| TPP_PFOR_PNO | XP_002765111.11 | 294867463 | Perkinsus marinus ATCC 50983 |

The NAD(P)$^+$ dependent oxidation of acetaldehyde to acetyl-CoA (FIG. 31) can be catalyzed by an acylating acetaldehyde dehydrogenase (EC 1.2.1.10). Acylating acetaldehyde dehydrogenase enzymes of *E. coli* are encoded by adhE, eutE, and mhpF (Ferrandez et al, *J Bacteriol* 1179: 2573-81 (1997)). The *Pseudomonas* sp. CF600 enzyme, encoded by dmpF, participates in meta-cleavage pathways and forms a complex with 4-hydroxy-2-oxovalerate aldolase (Shingler et al, *J Bacteriol* 174:711-24 (1992)). Solventogenic organisms such as *Clostridium acetobutylicum* encode bifunctional enzymes with alcohol dehydrogenase and acetaldehyde dehydrogenase activities. The bifunctional *C. acetobutylicum* enzymes are encoded by bdh I and adhE2 (Walter, et al., *J. Bacteriol.* 174:7149-7158 (1992); Fontaine et al., *J.Bacteriol.* 184:821-830 (2002)). Yet another candidate for acylating acetaldehyde dehydrogenase is the ald gene from *Clostridium beijerinckii* (Toth, *Appl. Environ. Microbiol.* 65:4973-4980 (1999). This gene is very similar to the eutE acetaldehyde dehydrogenase genes of *Salmonella typhimurium* and *E. coli* (Toth, *Appl. Environ. Microbiol.* 65:4973-4980 (1999).

| Protein | Gen Bank ID | GI Number | Organism |
|---|---|---|---|
| adhE | NP_415757.1 | 16129202 | Escherichia coli |
| mhpF | NP_414885.1 | 16128336 | Escherichia coli |
| dmpF | CAA43226.1 | 45683 | Pseudomonas sp. CF600 |
| adhE2 | AAK09379.1 | 12958626 | Clostridium acetobutylicum |
| bdh I | NP_349892.1 | 15896543 | Clostridium acetobutylicum |
| Ald | AAT66436 | 49473535 | Clostridium beijerinckii |
| eutE | NP_416950 | 16130380 | Escherichia coli |
| eutE | AAA80209 | 687645 | Salmonella typhimurium |

Threonine aldolase (EC 4.1.2.5) catalyzes the cleavage of threonine to glycine and acetaldehyde (FIG. 3J). The *Saccharomyces cerevisiae* and *Candida albicans* enzymes are encoded by GLY1 (Liu et al, *Eur J Biochem* 245:289-93 (1997); McNeil et al, *Yeast* 16:167-75 (2000)). The ltaE and glyA gene products of *E. coli* also encode enzymes with this activity (Liu et al, *Eur J Biochem* 255:220-6 (1998)).

| Protein | GenBank ID | GI Number | Organism |
|---|---|---|---|
| GLY1 | NP_010868.1 | 6320789 | Saccharomyces cerevisiae |
| GLY1 | AAB64198.1 | 2282060 | Candida albicans |
| ltaE | AAC73957.1 | 1787095 | Escherichia coli |
| glyA | AAC75604.1 | 1788902 | Escherichia coli |

Example VI

Pathways for Producing Acetyl-CoA from PEP and Pyruvate

Pathways for the conversion of cytosolic phosphoenolpyruvate (PEP) and pyruvate to cytosolic acetyl-CoA can also enable deployment of a cytosolic fatty alcohol, fatty aldehyde or fatty acid production pathway from acetyl-CoA. FIG. 4 shows numerous pathways for converting PEP and pyruvate to acetyl-CoA.

The conversion of PEP to oxaloacetate is catalyzed in one, two or three enzymatic steps. Oxaloacetate is further converted to acetyl-CoA via malonate semialdehyde or malonyl-CoA intermediates. In one pathway, PEP carboxylase or PEP carboxykinase converts PEP to oxaloacetate (step A); oxaloacetate decarboxylase converts the oxaloacetate to malonate (step B); and malonate semialdehyde dehydrogenase (acetylating) converts the malonate semialdehyde to acetyl-CoA (step C). In another pathway pyruvate kinase or PEP phosphatase converts PEP to pyruvate (step N); pyruvate carboxylase converts the pyruvate to (step H); oxaloacetate decarboxylase converts the oxaloacetate to malonate (step B); and malonate semialdehyde dehydrogenase (acetylating) converts the malonate semialdehyde to acetyl-CoA (step C). In another pathway pyruvate kinase or PEP phosphatase converts PEP to pyruvate (step N); malic enzyme converts the pyruvate to malate (step L); malate dehydrogenase or oxidoreductase converts the malate to oxaloacetate (step M); oxaloacetate decarboxylase converts the oxaloacetate to malonate (step B); and malonate semialdehyde dehydrogenase (acetylating) converts the malonate semialdehyde to acetyl-CoA (step C). In another pathway, PEP carboxylase or PEP carboxykinase converts PEP to oxaloacetate (step A); oxaloacetate decarboxylase converts the oxaloacetate to malonate semialdehyde (step B); malonyl-CoA reductase converts the malonate semialdehyde to malonyl-CoA (step G); and malonyl-CoA decarboxylase converts the malonyl-CoA to acetyl-CoA (step D). In another pathway, pyruvate kinase or PEP phosphatase converts PEP to pyruvate (step N); pyruvate carboxylase converts the pyruvate to oxaloacetate (step H); (oxaloacetate decarboxylase converts the oxaloacetate to malonate semialdehyde (step B); malonyl-CoA reductase converts the malonate semialdehyde to malonyl-CoA (step G); and malonyl-CoA decarboxylase converts the malonyl-CoA to acetyl-CoA (step D). In another pathway, pyruvate kinase or PEP phosphatase converts PEP to pyruvate (step N); malic enzyme converts the pyruvate to malate (step L); malate dehydrogenase or oxidoreductase converts the malate to oxaloacetate (step M); oxaloacetate decarboxylase converts the oxaloacetate to malonate semialdehyde (step B); malonyl-CoA reductase converts the malonate semialdehyde to malonyl-CoA (step G); and malonyl-CoA decarboxylase converts the malonyl-CoA to acetyl-CoA (step D). In another pathway, PEP carboxylase or PEP carboxykinase converts PEP to oxaloacetate (step A); oxaloacetate decarboxylase converts the oxaloacetate to malonate semialdehyde (step B); malonate semialdehyde dehydrogenase converts the malonate semialdehyde to malonate (step J); malonyl-CoA synthetase or transferase converts the malonate to malonyl-CoA (step K); and malonyl-CoA decarboxylase converts the malonyl-CoA to acetyl-CoA (step D). In another pathway, pyruvate kinase or PEP phosphatase converts PEP to pyruvate (step N); pyruvate carboxylase converts the pyruvate to oxaloacetate (step H); oxaloacetate decarboxylase converts the oxaloacetate to malonate semialdehyde (step B); malonate semialdehyde dehydrogenase converts the malonate semialdehyde to malonate (step J); malonyl-CoA synthetase or transferase converts the malonate to malonyl-CoA (step K); and malonyl-CoA decarboxylase converts the malonyl-CoA to acetyl-CoA (step D). In another pathway, pyruvate kinase or PEP phosphatase converts PEP to pyruvate (step N); malic enzyme converts the pyruvate to malate (step L); malate dehydrogenase or oxidoreductase converts the malate to oxaloacetate (step M); oxaloacetate decarboxylase converts the oxaloacetate to malonate semialdehyde (step B); malonate semialdehyde dehydrogenase converts the malonate semialdehyde to malonate (step J); malonyl-CoA synthetase or transferase converts the malonate to malonyl-CoA (step K); and malonyl-CoA decarboxylase converts the malonyl-CoA to acetyl-CoA (step D). In another pathway, PEP carboxylase or PEP carboxykinase converts PEP to oxaloacetate (step A); oxaloacetate dehydrogenase or oxaloacetate oxidoreductase converts the oxaloacetate to malonyl-CoA (step F); and malonyl-CoA decarboxylase converts the malonyl-CoA to acetyl-CoA (step D). In another pathway, pyruvate kinase or PEP phosphatase converts PEP to pyruvate (step N); pyruvate carboxylase converts the pyruvate to oxaloacetate (step H); oxaloacetate dehydrogenase or oxaloacetate oxidoreductase converts the oxaloacetate to malonyl-CoA (step F); and malonyl-CoA decarboxylase converts the malonyl-CoA to acetyl-CoA (step D). In another pathway, pyruvate kinase or PEP phosphatase converts PEP to pyruvate (step N); malic enzyme converts the pyruvate to malate (step L); malate dehydrogenase or oxidoreductase converts the malate to oxaloacetate (step M); oxaloacetate dehydrogenase or oxaloacetate oxidoreductase converts the oxaloacetate to malonyl-CoA (step F); and malonyl-CoA decarboxylase converts the malonyl-CoA to acetyl-CoA (step D).

Enzymes candidates for the reactions shown in FIG. 4 are described below.

| | | |
|---|---|---|
| 1.1.n.a | Oxidoreductase (alcohol to oxo) | M |
| 1.1.1.d | Malic enzyme | L |
| 1.2.1.a | Oxidoreductase (aldehyde to acid) | J |
| 1.2.1.b | Oxidoreductase (acyl-CoA to aldehyde) | G |
| 1.2.1.f | Oxidoreductase (decarboxylating acyl-CoA to aldehyde) | C |
| 2.7.2.a | Kinase | N |
| 2.8.3.a | CoA transferase | K |
| 3.1.3.a | Phosphatase | N |
| 4.1.1.a | Decarboxylase | A, B, D |
| 6.2.1.a | CoA synthetase | K |
| 6.4.1.a | Carboxylase | D, H |

Enzyme candidates for several enzymes in FIG. 4 have been described elsewhere herein. These include acetyl-CoA carboxylase, acetoacetyl-CoA synthase, acetoacetyl-CoA thiolase, malonyl-CoA reductase (also called malonate semialdehyde dehydrogenase (acylating), malate dehydrogenase.

1.1.n.a Oxidoreductase (Alcohol to Oxo)

Malate dehydrogenase or oxidoreductase catalyzes the oxidation of malate to oxaloacetate. Different carriers can act as electron acceptors for enzymes in this class. Malate dehydrogenase enzymes utilize NADP or NAD as electron acceptors. Malate dehydrogenase (Step M) enzyme candidates are described herein. Malate:quinone oxidoreductase enzymes (EC 1.1.5.4) are membrane-associated and utilize quinones, flavoproteins or vitamin K as electron acceptors. Malate:quinone oxidoreductase enzymes of *E. coli*, *Helicobacter pylori* and *Pseudomonas syringae* are encoded by mqo (Kather et al, J Bacteriol 182:3204-9 (2000); Mellgren et al, J Bacteriol 191:3132-42 (2009)). The Cgl2001 gene of *C. gluamicum* also encodes an MQO enzyme (Mitsuhashi et al, Biosci Biotechnol Biochem 70:2803-6 (2006)).

| Protein | GenBank ID | GI Number | Organism |
|---|---|---|---|
| mqo | NP_416714.1 | 16130147 | Escherichia coli |
| mqo | NP_206886.1 | 15644716 | Helicobacter pylori |
| mqo | NP_790970.1 | 28868351 | Pseudomonas syringae |
| Cgl2001 | NP_601207.1 | 19553205 | Corynebacterium glutamicum |

1.1.1.d Malic Enzyme

Malic enzyme (malate dehydrogenase) catalyzes the reversible oxidative carboxylation of pyruvate to malate. *E. coli* encodes two malic enzymes, MaeA and MaeB (Takeo, *J. Biochem.* 66:379-387 (1969)). Although malic enzyme is typically assumed to operate in the direction of pyruvate formation from malate, the NAD-dependent enzyme, encoded by maeA, has been demonstrated to operate in the carbon-fixing direction (Stols and Donnelly, *Appl. Environ. Microbiol* 63(7) 2695-2701(1997)). A similar observation was made upon overexpressing the malic enzyme from *Ascaris suum* in *E. coli* (Stols et al., *Appl. Biochem. Biotechnol.* 63-65(1), 153-158 (1997)). The second *E. coli* malic enzyme, encoded by maeB, is NADP-dependent and also decarboxylates oxaloacetate and other alpha-keto acids (Iwakura et al., *J. Biochem.* 85(5):1355-65 (1979)). Another suitable enzyme candidate is me1 from *Zea mays* (Furumoto et al, *Plant Cell Physiol* 41:1200-1209 (2000)).

| Protein | GenBank ID | GI Number | Organism |
|---|---|---|---|
| maeA | NP_415996 | 90111281 | Escherichia coli |
| maeB | NP_416958 | 16130388 | Escherichia coli |
| NAD-ME | P27443 | 126732 | Ascaris suum |
| Me1 | P16243.1 | 126737 | Zea mays |

1.2.1.a Oxidoreductase (Aldehyde to Acid)

The oxidation of malonate semialdehyde to malonate is catalyzed by malonate semialdehyde dehydrogenase (EC 1.2.1.15). This enzyme was characterized in *Pseudomonas aeruginosa* (Nakamura et al, *Biochim Biophys Acta* 50:147-52 (1961)). The NADP and NAD-dependent succinate semialdehyde dehydrogenase enzymes of *Euglena gracilas* accept malonate semialdehyde as substrates (Tokunaga et al, Biochem Biophys Act 429:55-62 (1976)). Genes encoding these enzymes has not been identified to date. Aldehyde dehydrogenase enzymes from eukoryotic organisms such as *S. cerevisiae*, *C. albicans*, *Y. lipolytica* and *A. niger* typically have broad substrate specificity and are suitable candidates. These enzymes and other acid forming aldehyde dehydrogenase and aldehyde oxidase enzymes are described earlier and listed in Tables 9 and 30. Additional MSA dehydrogenase enzyme candidates include NAD(P)+-dependent aldehyde dehydrogenase enzymes (EC 1.2.1.3). Two aldehyde dehydrogenases found in human liver, ALDH-1 and ALDH-2, have broad substrate ranges for a variety of aliphatic, aromatic and polycyclic aldehydes (Klyosov, Biochemistry 35:4457-4467 (1996a)). Active ALDH-2 has been efficiently expressed in E. coli using the GroEL proteins as chaperonins (Lee et al., Biochem.Biophys.Res.Commun. 298:216-224 (2002)). The rat mitochondrial aldehyde dehydrogenase also has a broad substrate range (Siew et al., Arch.Biochem.Biophys. 176:638-649 (1976)). The E. coli genes astD and aldH encode NAD+-dependent aldehyde dehydrogenases. AstD is active on succinic semialdehyde (Kuznetsova et al., FEMS Microbiol Rev 29:263-279 (2005)) and aldH is active on a broad range of aromatic and aliphatic substrates (Jo et al, Appl Microbiol Biotechnol 81:51-60 (2008)).

| Gene | GenBank Accession No. | GI No. | Organism |
|---|---|---|---|
| astD | P76217.1 | 3913108 | Escherichia coli |
| aldH | AAC74382.1 | 1787558 | Escherichia coli |
| ALDH-2 | P05091.2 | 118504 | Homo sapiens |
| ALDH-2 | NP_115792.1 | 14192933 | Rattus norvegicus |

1.2.1.f Oxidoreductase (Decarboxylating acyl-CoA to Aldehyde)

Malonate semialdehyde dehydrogenase (acetylating) (EC 1.2.1.18) catalyzes the oxidative decarboxylation of malonate semialdehyde to acetyl-CoA. Exemplary enzymes are encoded by ddcC of Halomonas sp. HINK1 (Todd et al, Environ Microbiol 12:237-43 (2010)) and IolA of Lactobacillus casei (Yebra et al, AEM 73:3850-8 (2007)). The DdcC enzyme has homologs in A. niger and C. albicans, shown in the table below. The malonate semialdehyde dehydrogenase enzyme in Rattus norvegicus, Mmsdh, also converts malonate semialdehyde to acetyl-CoA (U.S. Pat. No. 8,048,624). A malonate semialdehyde dehydrogenase (acetylating) enzyme has also been characterized in Pseudomonas fluorescens, although the gene has not been identified to date (Hayaishi et al, J Biol Chem 236:781-90 (1961)). Methylmalonate semialdehyde dehydrogenase (acetylating) enzymes (EC 1.2.1.27) are also suitable candidates, as several enzymes in this class accept malonate semialdehyde as a substrate including Msdh of Bacillus subtilis (Stines-Chaumeil et al, Biochem J 395:107-15 (2006)) and the methylmalonate semialdehyde dehydrogenase of R. norvegicus (Kedishvii et al, Methods Enzymol 324:207-18 (2000)).

| Protein | GenBank ID | GI Number | Organism |
|---|---|---|---|
| ddcC | ACV84070.1 | 258618587 | Halomonas sp. HTNK1 |
| ANI_1_1120014 | XP_001389265.1 | 145229913 | Aspergillus niger |
| ALD6 | XP_710976.1 | 68490403 | Candida albicans |
| YALI0C01859g | XP_501343.1 | 50547747 | Yarrowia lipolytica |
| mmsA_1 | YP_257876.1 | 70734236 | Pseudomonas fluorescens |
| mmsA_2 | YP_257884.1 | 70734244 | Pseudomonas fluorescens |
| PA0130 | NP_248820.1 | 15595328 | Pseudomonas aeruginosa |
| Mmsdh | Q02253.1 | 400269 | Rattus norvegicus |
| msdh | NP_391855.1 | 16081027 | Bacillus subtilis |
| IolA | ABP57762.1 | 145309085 | Lactobacillus casei |

2.72.a Kinase

Pyruvate kinase (Step 10N), also known as phosphoenolpyruvate synthase (EC 2.7.9.2), converts pyruvate and ATP to PEP and AMP. This enzyme is encoded by the PYK1 (Burke et al., J. Biol. Chem. 258:2193-2201 (1983)) and PYK2 (Boles et al., J. Bacteriol 179:2987-2993 (1997)) genes in S. cerevisiae. In E. coli, this activity is catalyzed by the gene products of pykF and pykA. Selected homologs of the S. cerevisiae enzymes are also shown in the table below.

| Protein | GenBank ID | GI Number | Organism |
|---|---|---|---|
| PYK1 | NP_009362 | 6319279 | Saccharomyces cerevisiae |
| PYK2 | NP_014992 | 6324923 | Saccharomyces cerevisiae |
| pykF | NP_416191.1 | 16129632 | Escherichia coli |
| pykA | NP_416368.1 | 16129807 | Escherichia coli |
| KLLA0F23397g | XP_456122.1 | 50312181 | Kluyveromyces lactis |
| CaO19.3575 | XP_714934.1 | 68482353 | Candida albicans |
| CaO19.11059 | XP_714997.1 | 68482226 | Candida albicans |
| YALI0F09185p | XP_505195 | 210075987 | Yarrowia lipolytica |
| ANI_1_1126064 | XP_001391973 | 145238652 | Aspergillus niger |

2.83.a CoA Transferase

Activation of malonate to malonyl-CoA is catalyzed by a CoA transferase in EC class 2.8.3.a. Malonyl-CoA:acetate CoA transferase (EC 2.8.3.3) enzymes have been characterized in Pseudomonas species including Pseudomonas fluorescens and Pseudomonas putida (Takamura et al, Biochem Int 3:483-91 (1981); Hayaishi et al, J Biol Chem 215:125-36 (1955)). Genes associated with these enzymes have not been identified to date. A mitochondrial CoA transferase found in Rattus norvegicus liver also catalyzes this reaction and is able to utilize a range of CoA donors and acceptors (Deana et al, Biochem Int 26:767-73 (1992)). Several CoA transferase enzymes described herein can also be applied to catalyze step K of FIG. 4. These enzymes include acetyl-CoA transferase, 3-HB CoA transferase, acetoacetyl-CoA transferase, SCOT and other CoA transferases.

3.13.a Phosphatase

Phosphoenolpyruvate phosphatase (EC 3.1.3.60, FIG. 4, Step N) catalyzes the hydrolysis of PEP to pyruvate and phosphate. Numerous phosphatase enzymes catalyze this activity, including alkaline phosphatase (EC 3.1.3.1), acid phosphatase (EC 3.1.3.2), phosphoglycerate phosphatase (EC 3.1.3.20) and PEP phosphatase (EC 3.1.3.60). PEP phosphatase enzymes have been characterized in plants such as Vignia radiate, Bruguiera sexangula and Brassica nigra. The phytase from Aspergillus fumigates, the acid phosphatase from Homo sapiens and the alkaline phosphatase of E. coli also catalyze the hydrolysis of PEP to pyruvate (Bragger et al, Appl Microbiol Biotech 63:383-9 (2004); Hayman et al, Biochem J 261:601-9 (1989); et al, The Enzymes 3$^{rd}$ Ed. 4:373-415 (1971))) Similar enzymes have been characterized in Campylobacter jejuni (van Mourik et al., Microbiol. 154:584-92 (2008)), Saccharomyces cerevisiae (Oshima et al., Gene 179:171-7 (1996)) and Staphylococcus aureus (Shah and Blobel, J. Bacteriol. 94:780-1 (1967)). Enzyme engineering and/or removal of targeting sequences may be required for alkaline phosphatase enzymes to function in the cytoplasm.

| Protein | GenBank ID | GI Number | Organism |
|---|---|---|---|
| phyA | O00092.1 | 41017447 | Aspergillus fumigatus |
| Acp5 | P13686.3 | 56757583 | Homo sapiens |
| phoA | NP_414917.2 | 49176017 | Escherichia coli |
| phoX | ZP_01072054.1 | 86153851 | Campylobacter jejuni |

| Protein | GenBank ID | GI Number | Organism |
|---|---|---|---|
| PHO8 | AAA34871.1 | 172164 | Saccharomyces cerevisiae |
| SaurJH1_2706 | YP_001317815.1 | 150395140 | Staphylococcus aureus |

4.1.1.a Decarboxylase

Several reactions in FIG. 4 are catalyzed by decarboxylase enzymes in EC class 4.1.1, including oxaloacetate decarboxylase (Step B), malonyl-CoA decarboxylase (step D) and pyruvate carboxylase or carboxykinase (step A).

Carboxylation of phosphoenolpyruvate to oxaloacetate is catalyzed by phosphoenolpyruvate carboxylase (EC 4.1.1.31). Exemplary PEP carboxylase enzymes are encoded by ppc in E. coli (Kai et al., Arch. Biochem. Biophys. 414:170-179 (2003), ppcA in Methylobacterium extorquens AM1 (Arps et al., J. Bacteriol. 175:3776-3783 (1993), and ppc in Corynebacterium glutamicum (Eikmanns et al., Mol. Gen. Genet. 218:330-339 (1989).

| Protein | GenBank ID | GI Number | Organism |
|---|---|---|---|
| Ppc | NP_418391 | 16131794 | Escherichia coli |
| ppcA | AAB58883 | 28572162 | Methylobacterium extorquens |
| Ppc | ABB53270 | 80973080 | Corynebacterium glutamicum |

An alternative enzyme for carboxylating phosphoenolpyruvate to oxaloacetate is PEP carboxykinase (EC 4.1.1.32, 4.1.1.49), which simultaneously forms an ATP or GTP. In most organisms PEP carboxykinase serves a gluconeogenic function and converts oxaloacetate to PEP at the expense of one ATP. S. cerevisiae is one such organism whose native PEP carboxykinase, PCK1, serves a gluconeogenic role (Valdes-Hevia et al., FEBS Lett. 258:313-316 (1989). E. coli is another such organism, as the role of PEP carboxykinase in producing oxaloacetate is believed to be minor when compared to PEP carboxylase (Kim et al., Appl. Environ. Microbiol. 70:1238-1241 (2004)). Nevertheless, activity of the native E. coli PEP carboxykinase from PEP towards oxaloacetate has been recently demonstrated in ppc mutants of E. coli K-12 (Kwon et al., J. Microbiol. Biotechnol. 16:1448-1452 (2006)). These strains exhibited no growth defects and had increased succinate production at high $NaHCO_3$ concentrations. Mutant strains of E. coli can adopt Pck as the dominant $CO_2$-fixing enzyme following adaptive evolution (Zhang et al. 2009). In some organisms, particularly rumen bacteria, PEP carboxykinase is quite efficient in producing oxaloacetate from PEP and generating ATP. Examples of PEP carboxykinase genes that have been cloned into E. coli include those from Mannheimia succiniciproducens (Lee et al., Biotechnol. Bioprocess Eng 7:95-99 (2002)), Anaerobiospinllum succiniciproducens (Laive-nieks et al., Appl. Environ. Microbiol. 63:2273-2280 (1997), and Actinobacillus succinogenes (Kim et al. supra). The PEP carboxykinase enzyme encoded by Haemophilus influenza is effective at forming oxaloacetate from PEP. Another suitable candidate is the PEPCK enzyme from Megathyrsus maximus, which has a low Km for $CO_2$, a substrate thought to be rate-limiting in the E. coli enzyme (Chen et al., Plant Physiol 128:160-164 (2002); Cotelesage et al., Int.J Biochem.Cell Biol. 39:1204-1210 (2007)). The kinetics of the GTP-dependent pepck gene product from Cupriavidus necator favor oxaloacetate formation (U.S. Pat. No. 8,048,624 and Lea et al, Amino Acids 20:225-41(2001)).

| Protein | GenBank ID | GI Number | Organism |
|---|---|---|---|
| PCK1 | NP_013023 | 6322950 | Saccharomyces cerevisiae |
| pck | NP_417862.1 | 16131280 | Escherichia coli |
| pckA | YP_089485.1 | 52426348 | Mannheimia succiniciproducens |
| pckA | O09460.1 | 3122621 | Anaerobiospirillum succiniciproducens |
| pckA | Q6W6X5 | 75440571 | Actinobacillus succinogenes |
| pckA | P43923.1 | 1172573 | Haemophilus influenza |
| AF532733.1:1..1929 | AAQ10076.1 | 33329363 | Megathyrsus maximus |
| pepck | YP_728135.1 | 113869646 | Cupriavidus necator |

Oxaloacetate decarboxylase catalyzes the decarboxylation of oxaloacetate to malonate semialdehyde. Enzymes catalyzing this reaction include kgd of Mycobacterium tuberculosis (GenBank ID: 050463.4, GI: 160395583). Enzymes evolved from kgd with improved activity and/or substrate specificity for oxaloacetate have also been described (U.S. Pat. No. 8048624). Additional enzymes useful for catalyzing this reaction include keto-acid decarboxylases shown in the table below.

| EC number | Name |
|---|---|
| 4.1.1.1 | Pyruvate decarboxylase |
| 4.1.1.7 | Benzoylformate decarboxylase |
| 4.1.1.40 | Hydroxypyruvate decarboxylase |
| 4.1.1.43 | Ketophenylpyruvate decarboxylase |
| 4.1.1.71 | Alpha-ketoglutarate decarboxylase |
| 4.1.1.72 | Branched chain keto-acid decarboxylase |
| 4.1.1.74 | Indolepyruvate decarboxylase |
| 4.1.1.75 | 2-Ketoarginine decarboxylase |
| 4.1.1.79 | Sulfopyruvate decarboxylase |
| 4.1.1.80 | Hydroxyphenylpyruvate decarboxylase |
| 4.1.1.82 | Phosphonopyruvate decarboxylase |

The decarboxylation of keto-acids is catalyzed by a variety of enzymes with varied substrate specificities, including pyruvate decarboxylase (EC 4.1.1.1), benzoylformate decarboxylase (EC 4.1.1.7), alpha-ketoglutarate decarboxylase and branched-chain alpha-ketoacid decarboxylase. Pyruvate decarboxylase (PDC), also termed keto-acid decarboxylase, is a key enzyme in alcoholic fermentation, catalyzing the decarboxylation of pyruvate to acetaldehyde. The PDC1 enzyme from Saccharomyces cerevisiae has a broad substrate range for aliphatic 2-keto acids including 2-ketobutyrate, 2-ketovalemte, 3-hydroxypyruvate and 2-phenylpyruvate (22). This enzyme has been extensively studied, engineered for altered activity, and functionally expressed in E. coli (Killenberg-Jabs et al., Eur.J.Biochem. 268:1698-1704 (2001); Li et al., Biochemistry. 38:10004-10012 (1999); ter Schure et al., Appl.Environ.Microbiol. 64:1303-1307 (1998)). The PDC from Zymomonas mobilus, encoded by pdc, also has a broad substrate range and has been a subject of directed engineering studies to alter the affinity for different substrates (Siegert et al., Protein Eng Des Sel 18:345-357 (2005)). The crystal structure of this enzyme is available (Killenberg-Jabs et al., Eur.J.Biochem. 268:1698-1704 (2001)). Other well-characterized PDC candidates include the enzymes from Acetobacter pasteurians (Chandra et al., 176:443-451(2001)) and Kluyveromyces lactis (Krieger et al., 269:3256-3263 (2002)).

| Protein | GenBank ID | GI Number | Organism |
|---|---|---|---|
| pdc | P06672.1 | 118391 | Zymomonas mobilis |
| pdc1 | P06169 | 30923172 | Saccharomyces cerevisiae |

| Protein | GenBank ID | GI Number | Organism |
| --- | --- | --- | --- |
| pdc | Q8L388 | 20385191 | Acetobacter pasteurians |
| pdc1 | Q12629 | 52788279 | Kluyveromyces lactis |

Like PDC, benzoylformate decarboxylase (EC 4.1.1.7) has a broad substrate range and has been the target of enzyme engineering studies. The enzyme from *Pseudomonas putida* has been extensively studied and crystal structures of this enzyme are available (Polovnikova et al., 42:1820-1830 (2003); Hasson et al., 37:9918-9930 (1998)). Site-directed mutagenesis of two residues in the active site of the *Pseudomonas putida* enzyme altered the affinity (Km) of naturally and non-naturally occurring substrates (Siegert et al., *Protein Eng Des Sel* 18:345-357 (2005)). The properties of this enzyme have been further modified by directed engineering (Lingen et al., *Chembiochem.* 4:721-726 (2003); Lingen et al., *Protein Eng* 15:585-593 (2002)). The enzyme from *Pseudomonas aeruginosa*, encoded by mdlC, has also been characterized experimentally (Barrowman et al., 34:57-60 (1986)). Additional gene candidates from *Pseudomonas stutzeri, Pseudomonas fluorescens* and other organisms can be inferred by sequence homology or identified using a growth selection system developed in Pseudomonas putida (Henning et al., *Appl.Environ.Microbiol.* 72:7510-7517 (2006)).

| Protein | GenBank ID | GI Number | Organism |
| --- | --- | --- | --- |
| mdlC | P20906.2 | 3915757 | Pseudomonas putida |
| mdlC | Q9HUR2.1 | 81539678 | Pseudomonas aeruginosa |
| dpgB | ABN80423.1 | 126202187 | Pseudomonas stutzeri |
| ilvB-1 | YP_260581.1 | 70730840 | Pseudomonas fluorescens |

A third enzyme capable of decarboxylating 2-oxoacids is alpha-ketoglutarate decarboxylase (KGD, EC 4.1.1.71). The substrate range of this class of enzymes has not been studied to date. An exemplary KDC is encoded by kad in *Micobacterium tuberculosis* (Tian et al., *PNAS* 102:10670-10675 (2005)). KDC enzyme activity has also been detected in several species of rhizobia including *Bradyrhizobium japonicum* and *Mesorhizobium loti* (Green et al., *J Bacteriol* 182:2838-2844 (2000)). Although the KDC-encoding gene(s) have not been isolated in these organisms, the genome sequences are available and several genes in each genome are annotated as putative KDCs. A KDC from *Euglena gracilis* has also been characterized but the gene associated with this activity has not been identified to date (Shigeoka et al., *Arch.Biochem.Biophys.* 288:22-28 (1991)). The first twenty amino acids starting from the N-terminus were sequenced MTYKAPVKDVKFLLDKVFKV (SEQ ID NO: 24) (Shigeoka and Nakano, *Arch.Biochem.Biophys.* 288:22-28 (1991)). The gene could be identified by testing candidate genes containing this N-terminal sequence for KDC activity. A novel class of AKG decarboxylase enzymes has recently been identified in cyanobacteria such as *Synechococcus* sp. PCC 7002 and homologs (Zhang and Bryant, *Science* 334:1551-3 (2011)).

| Protein | GenBank ID | GI Number | Organism |
| --- | --- | --- | --- |
| kgd | O50463.4 | 160395583 | Mycobacterium tuberculosis |
| kgd | NP_767092.1 | 27375563 | Bradyrhizobium japonicum USDA110 |
| kgd | NP_105204.1 | 13473636 | Mesorhizobium loti |
| ilvB | ACB00744.1 | 169887030 | Synechococcus sp. PCC 7002 |

A fourth candidate enzyme for catalyzing this reaction is branched chain alpha-ketoacid decarboxylase (BCKA). This class of enzyme has been shown to act on a variety of compounds varying in chain length from 3 to 6 carbons (Oku et al., *J Biol Chem.* 263:18386-18396 (1988); Smit et al., *Appl Environ Microbiol* 71:303-311 (2005)). The enzyme in *Lactococcus lactis* has been characterized on a variety of branched and linear substrates including 2-oxobutanoate, 2-oxohexanoate, 2-oxopentanoate, 3-methyl-2-oxobutanoate, 4-methyl-2-oxobutanoate and isocaproate (Smit et al., *Appl Environ Microbiol* 71:303-311 (2005)). The enzyme has been structurally characterized (Berg et al., *Science.* 318:1782-1786 (2007)). Sequence alignments between the *Lactococcus lactis* enzyme and the pyruvate decarboxylase of *Zymomonas mobilus* indicate that the catalytic and substrate recognition residues are nearly identical (Siegert et al., *Protein Eng Des Sel* 18:345-357 (2005)), so this enzyme would be a promising candidate for directed engineering. Several ketoacid decarboxylases of Saccharomyces cerevisiae catalyze the decarboxylation of branched substrates, including ARO10, PDC6, PDC5, PDC1 and TH13 (Dickenson et al, *J Biol Chem* 275:10937-42 (2000)). Yet another BCKAD enzyme is encoded by rv0853c of *Mycobacterium tuberculosis* (Werther et al, *J Biol Chem* 283:5344-54 (2008)). This enzyme is subject to allosteric activation by alpha-ketoacid substrates. Decarboxylation of alpha-ketoglutarate by a BCKA was detected in *Bacillus subtilis*; however, this activity was low (5%) relative to activity on other branched-chain substrates (Oku and Kaneda, *J Biol Chem.* 263:18386-18396 (1988)) and the gene encoding this enzyme has not been identified to date. Additional BCKA gene candidates can be identified by homology to the *Lactococcus lactis* protein sequence. Many of the high-scoring BLASTp hits to this enzyme are annotated as indolepyruvate decarboxylases (EC 4.1.1.74). Indolepyruvate decarboxylase (IPDA) is an enzyme that catalyzes the decarboxylation of indolepyruvate to indoleacetaldehyde in plants and plant bacteria. Recombinant branched chain alpha-keto acid decarboxylase enzymes derived from the E1 subunits of the mitochondrial branched-chain keto acid dehydrogenase complex from *Homo sapiens* and *Bos taurus* have been cloned and functionally expressed in *E. coli* (Davie et al., *J.Biol.Chem.* 267:16601-16606 (1992); Wynn et al., *J.BiolChem.* 267:12400-12403 (1992); Wynn et al., *J.Biol.Chem.* 267:1881-1887 (1992)). In these studies, the authors found that co-expression of chaperonins GroEL and GroES enhanced the specific activity of the decarboxylase by 500-fold (Wynn et al., *J.Biol.Chem.* 267:12400-12403 (1992)). These enzymes are composed of two alpha and two beta subunits.

| Protein | GenBank ID | GI Number | Organism |
| --- | --- | --- | --- |
| kdcA | AAS49166.1 | 44921617 | Lactococcus lactis |
| PDC6 | NP_010366.1 | 6320286 | Saccharomyces cerevisiae |
| PDC5 | NP_013235.1 | 6323163 | Saccharomyces cerevisiae |
| PDC1 | P06169 | 30923172 | Saccharomyces cerevisiae |
| ARO10 | NP_010668.1 | 6320588 | Saccharomyces cerevisiae |
| THI3 | NP_010203.1 | 6320123 | Saccharomyces cerevisiae |
| rv0853c | O53865.1 | 81343167 | Mycobacterium tuberculosis |

| Protein | GenBank ID | GI Number | Organism |
|---|---|---|---|
| BCKDHB | NP_898871.1 | 34101272 | Homo sapiens |
| BCKDHA | NP_000700.1 | 11386135 | Homo sapiens |
| BCKDHB | P21839 | 115502434 | Bos taurus |
| BCKDHA | P11178 | 129030 | Bos taurus |

3-Phosphonopyruvate decarboxylase (EC 4.1.1.82) catalyzes the decarboxylation of 3-phosphonopyruvate to 2-phosphonoacetaldehyde. Exemplary phosphonopyruvate decarboxylase enzymes are encoded by dhpF of *Streptomyces luridus*, ppd of *Streptomyces viridochromogenes*, fom2 of *Streptomyces wedmorensis* and bcpC of *Streptomyces hygroscopius* (Circello et al, *Chem Biol* 17:402-11(2010); Blodgett et al, *FEMS Microbiol Lett* 163:149-57 (2005); Hidaka et al, *Mol Gen Genet* 249:274-80 (1995); Nakashita et al, *Biochim Biophys Acta* 1490:159-62 (2000)). The *Bacteroides fragilis* enzyme, encoded by aepY, also decarboxylates pyruvate and sulfopyruvate (Zhang et al, *J Biol Chem* 278:41302-8 (2003)).

| Protein | GenBank ID | GI Number | Organism |
|---|---|---|---|
| dhpF | ACZ13457.1 | 268628095 | Streptomyces luridus |
| Ppd | CAJ14045.1 | 68697716 | Streptomyces viridochromogenes |
| Fom2 | BAA32496.1 | 1061008 | Streptomyces wedmorensis |
| aepY | AAG26466.1 | 11023509 | Bacteroides fragilis |

Many oxaloacetate decarboxylase enzymes such as the eda gene product in *E. coli* (EC 4.1.1.3), act on the terminal acid of oxaloacetate to form pyruvate. Because decarboxylation at the 3-keto acid position competes with the malonate semialdehyde forming decarboxylation at the 2-keto-acid position, this enzyme activity can be knocked out in a host strain with a pathway proceeding through a malonate semilaldehyde intermediate.

Malonyl-CoA decarboxylase (EC 4.1.1.9) catalyzes the decarboxylation of malonyl-CoA to acetyl-CoA. Enzymes have been characterized in *Rhizobium legumMosarum* and *Acinetobacter calcoaceticus* (An et al, *Eur J Biochem* 257: 395-402 (1998); Koo et al, *Eur J Biochem* 266:683-90 (1999)). Similar enzymes have been characterized in *Streptomyces erythreus* (Hunaiti et al, *Arch Biochem Biophys* 229:426-39 (1984)). A recombinant human malonyl-CoA decarboxylase was overexpressed in *E. coli* (Zhou et al, *Prot Expr Pur* 34:261-9 (2004)). Methylmalonyl-CoA decarboxylase enzymes that decarboxylate malonyl-CoA are also suitable candidates. For example, the *Veillonella parvula* enzyme accepts malonyl-CoA as a substrate (Hilpert et al, *Nature* 296:584-5 (1982)). The *E. coli* enzyme is encoded by ygfG (Benning et al., *Biochemistry.* 39:4630-4639 (2000); Haller et al., *Biochemistry.* 39:4622-4629 (2000)). The stereo specificity of the *E. coli* enzyme was not reported, but the enzyme in *Propionigenium modestum* (Bott et al., *Eur.J.Biochem.* 250:590-599 (1997)) and *Veillonella parvula* (Huder et al., *J.Biol.Chem.* 268:24564-24571 (1993)) catalyzes the decarboxylation of the (S)-stereoisomer of methylmalonyl-CoA (Hoffmann et al., *FEBS.Lett.* 220:121-125 (1987)). The enzymes from *P. modestum* and *V. parvula* are comprised of multiple subunits that not only decarboxylate (S)-methylmalonyl-CoA, but also create a pump that transports sodium ions across the cell membrane as a means to generate energy.

| Protein | GenBank ID | GI Number | Organism |
|---|---|---|---|
| YgfG | NP_417394 | 90111512 | Escherichia coli |
| matA | Q9ZIP6 | 75424899 | Rhizobium leguminosarum |
| mdcD | AAB97628.1 | 2804622 | Acinetobacter calcoaceticus |
| mdcE | AAF20287.1 | 6642782 | Acinetobacter calcoaceticus |
| mdcA | AAB97627.1 | 2804621 | Acinetobacter calcoaceticus |
| mdcC | AAB97630.1 | 2804624 | Acinetobacter calcoaceticus |
| med | NP_036345.2 | 110349750 | Homo sapiens |
| mmdA | CAA05137 | 2706398 | Propionigenium modestum |
| mmdD | CAA05138 | 2706399 | Propionigenium modestum |
| mmdC | CAA05139 | 2706400 | Propionigenium modestum |
| mmdB | CAA05140 | 2706401 | Propionigenium modestum |
| mmdA | CAA80872 | 415915 | Veillonella parvula |
| mmdC | CAA80873 | 415916 | Veillonella parvula |
| mmdE | CAA80874 | 415917 | Veillonella parvula |
| mmdD | CAA80875 | 415918 | Veillonella parvula |
| mmdB | CAA80876 | 415919 | Veillonella parvula |

6.2.1.a CoA Synthetase

Activation of malonate to malonyl-CoA is catalyzed by a CoA synthetase in EC class 6.2.1.a. CoA synthetase enzymes that catalyze this reaction have not been described in the literature to date. Several CoA synthetase enzymes described above can also be applied to catalyze step K of FIG. 4. These enzymes include acetyl-CoA synthetase and ADP forming CoA synthetases.

6.4.1.a Carboxylase

Pyruvate carboxylase (EC 6.4.1.1) converts pyruvate to oxaloacetate at the cost of one ATP (step H). Exemplary pyruvate carboxylase enzymes are encoded by PYC1 (Walker et al., *Biochem. Biophys. Res. Commun.* 176:1210-1217 (1991) and PYC2 (Walker et al., supra) in *Saccharomyces cerevisiae*, and pyc in *Mycobacterium smegmatis* (Mukhopadhyay and Purwantini, *Biochim. Biophys. Acta* 1475:191-206 (2000)).

| Protein | GenBank ID | GI Number | Organism |
|---|---|---|---|
| PYC1 | NP_011453 | 6321376 | Saccharomyces cerevisiae |
| PYC2 | NP_009777 | 6319695 | Saccharomyces cerevisiae |
| Pyc | YP_890857.1 | 118470447 | Mycobacterium smegmatis |

Example VII

Pathways for Producing Cytosolic Acetyl-CoA from Mitochondrial Acetyl-CoA

A mechanism for transporting acetyl-CoA from the mitochondrion to the cytosol can facilitate deployment of a cytosolic fatty alcohol, fatty aldehyde or fatty acid production pathway that originates from acetyl-CoA. Exemplary mechanisms for exporting acetyl-CoA include those depicted in FIGS. 5 and 6, which can involve forming citrate from acetyl-CoA and oxaloacetate in the mitochondrion, exporting the citrate from the mitochondrion to the cytosol, and converting the citrate to oxaloacetate and either acetate or acetyl-CoA. In certain embodiments, provided herein are methods for engineering a eukaryotic organism to increase its availability of cytosolic acetyl-CoA by introducing enzymes capable of carrying out the transformations depicted in any one of FIGS. 5 and 6. Exemplary enzymes capable of carrying out the required transformations are also disclosed herein.

The production of cytosolic acetyl-CoA from mitochondrial acetyl-CoA can be accomplished by a number of pathways, for example, in three to five enzymatic steps. In one exemplary pathway, mitochondrial acetyl-CoA and oxaloacetate are combined into citrate by a citrate synthase and the citrate is exported out of the mitochondrion by a citrate or citrate/oxaloacetate transporter. Enzymatic conversion of the citrate in the cytosol results in cytosolic acetyl-CoA and oxaloacetate. The cytosolic oxaloacetate can then optionally be transported back into the mitochondrion by an oxaloacetate transporter and/or a citrate/oxaloacetate transporter. In another exemplary pathway, the cytosolic oxaloacetate is first enzymatically converted into malate in the cytosol and then optionally transferred into the mitochondrion by a malate transporter and/or a malate/citrate transporter. Mitochondrial malate can then be converted into oxaloacetate with a mitochondrial malate dehydrogenase.

In yet another exemplary pathway, mitochondrial acetyl-CoA can be converted to cytosolic acetyl-CoA via a citramalate intermediate. For example, mitochondrial acetyl-CoA and pyruvate are converted to citramalate by citramalate synthase Citramalate can then be transported into the cytosol by a citramalate or dicarboxylic acid transporter. Cytosolic acetyl-CoA and pyruvate are then regenerated from citramalate, directly or indirectly, and the pyruvate can re-enter the mitochondria.

Figure 5:
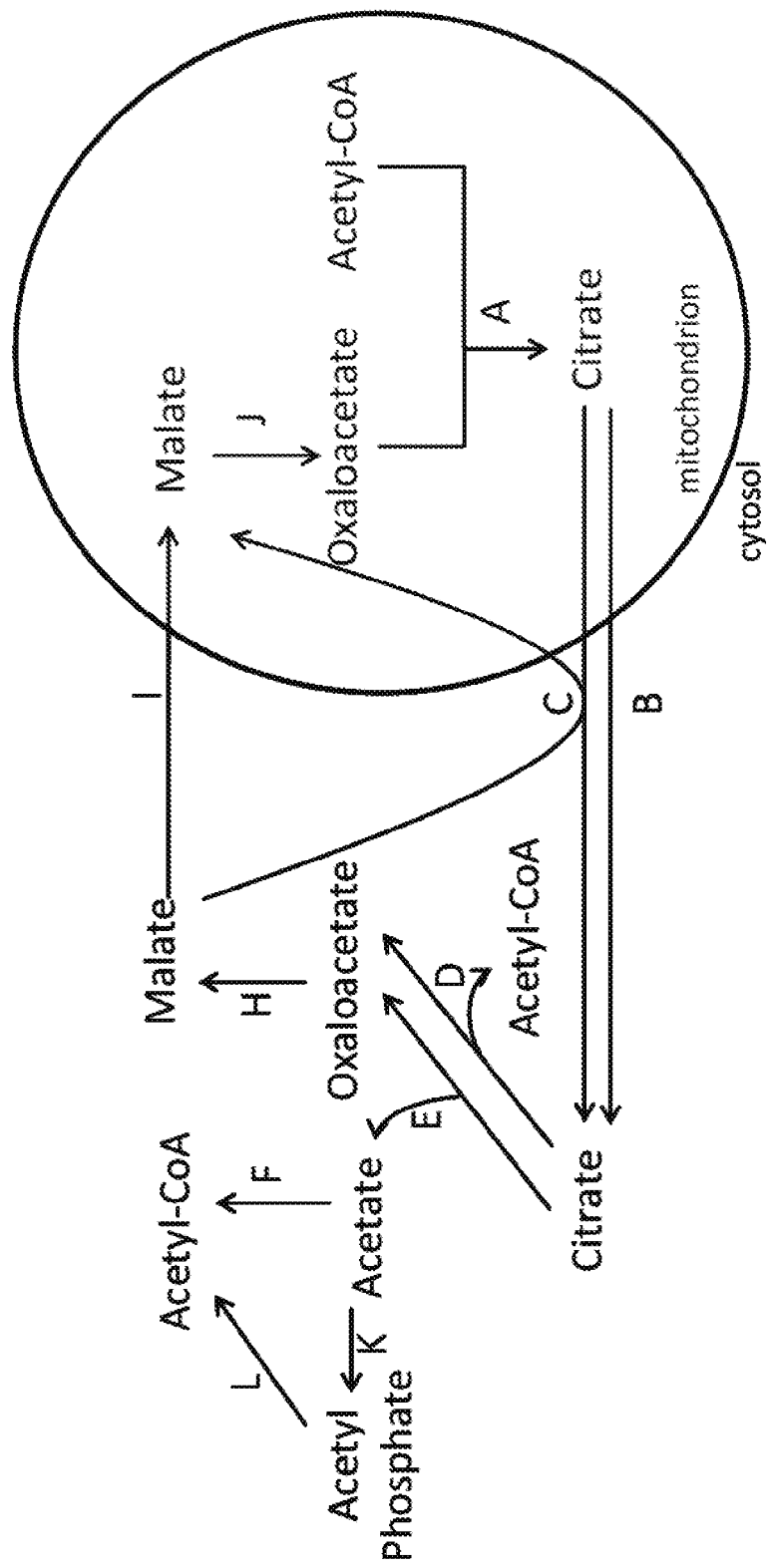
FIG. 5 shows exemplary pathways for production of cytosolic acetyl-CoA from mitochondrial acetyl-CoA using citrate and malate transporters. Enzymes are: A. citrate synthase; B. citrate transporter; C. citrate/malate transporter; D. ATP citrate lyase; E. citrate lyase; F. acetyl-CoA synthetase or transferase; H. cytosolic malate dehydrogenase; I. malate transporter; J. mitochondrial malate dehydrogenase; K. acetate kinase; and L. phosphotransacetylase.

Along these lines, several exemplary acetyl-CoA pathways for the production of cytosolic acetyl-CoA from mitochondrial acetyl-CoA are shown in FIGS. 5 and 6. In one embodiment, mitochondrial oxaloacetate is combined with mitochondrial acetyl-CoA to form citrate by a citrate synthase. The citrate is transported outside of the mitochondrion by a citrate transporter, a citrate/oxaloacetate transporter or a citrate/malate transporter. Cytosolic citrate is converted into cytosolic acetyl-CoA and oxaloacetate by an ATP citrate lyase. In another pathway, cytosolic citrate is converted into acetate and oxaloacetate by a citrate lyase. Acetate can then be converted into cytosolic acetyl-CoA by an acetyl-CoA synthetase or transferase. Alternatively, acetate can be converted by an acetate kinase to acetyl phosphate, and the acetyl phosphate can be converted to cytosolic acetyl-CoA by a phosphotransacetylase. Exemplary enzyme candidates for acetyl-CoA pathway enzymes are described below.

The conversion of oxaloacetate and mitochondrial acetyl-CoA is catalyzed by a citrate synthase (FIGS. 5 and 6, step A). In certain embodiments, the citrate synthase is expressed in a mitochondrion of a non-naturally occurring eukaryotic organism provided herein.

| Protein | GenBank ID | GI number | Organism |
|---|---|---|---|
| CIT1 | NP_014398.1 | 6324328 | Saccharomyces cerevisiae S288c |
| CIT2 | NP_009931.1 | 6319850 | Saccharomyces cerevisiae S288c |
| CIT3 | NP_015325.1 | 6325257 | Saccharomyces cerevisiae S288c |
| YALI0E02684p | XP_503469.1 | 50551989 | Yarrowia lipolytica |
| YALI0E00638p | XP_503380.1 | 50551811 | Yarrowia lipolytica |
| ANI_1_876084 | XP_001393983.1 | 145242820 | Aspergillus niger CBS 513.88 |
| ANI_1_1474074 | XP_001393195.2 | 317030721 | Aspergillus niger CBS 513.88 |
| ANI_1_2950014 | XP_001389414.2 | 317026339 | Aspergillus niger CBS 513.88 |
| ANI_1_1226134 | XP_001396731.1 | 145250435 | Aspergillus niger CBS 513.88 |
| gltA | NP_415248.1 | 16128695 | Escherichia coli K-12 MG1655 |

Transport of citrate from the mitochondrion to the cytosol can be carried out by several transport proteins. Such proteins either export citrate directly (i.e., citrate transporter, FIGS. 5 and 6, step B) to the cytosol or export citrate to the cytosol while simultaneously transporting a molecule such as malate (i.e., citrate/malate transporter, FIG. 5, step C) or oxaloacetate (i.e., citrate/oxaloacetate transporter FIG. 6, step C) from the cytosol into the mitochondrion as shown in FIGS. 5 and 6. Exemplary transport enzymes that carry out these transformations are provided in the table below.

| Protein | GenBank ID | GI number | Organism |
|---|---|---|---|
| CTP1 | NP_009850.1 | 6319768 | Saccharomyces cerevisiae S288c |
| YALI0F26323p | XP_505902.1 | 50556988 | Yarrowia lipolytica |
| ATEG_09970 | EAU29419.1 | 114187719 | Aspergillus terreus NIH2624 |
| KLLA0E18723g | XP_454797.1 | 50309571 | Kluyveromyces lactis NRRL Y-1140 |
| CTRG_02320 | XP_002548023.1 | 255726194 | Candida tropicalis MYA-3404 |
| ANI_1_1474094 | XP_001395080.1 | 145245625 | Aspergillus niger CBS 513.88 |
| YHM2 | NP_013968.1 | 6323897 | Saccharomyces cerevisiae S288c |
| DTC | CAC84549.1 | 19913113 | Arabidopsis thaliana |
| DTC1 | CAC84545.1 | 19913105 | Nicotiana tabacum |
| DTC2 | CAC84546.1 | 19913107 | Nicotiana tabacum |
| DTC3 | CAC84547.1 | 19913109 | Nicotiana tabacum |
| DTC4 | CAC84548.1 | 19913111 | Nicotiana tabacum |
| DTC | AAR06239.1 | 37964368 | Citrus junos |

ATP citrate lyase (ACL, EC 2.3.3.8, FIGS. 5 and 6, step D), also called ATP citrate synthase, catalyzes the ATP-dependent cleavage of citrate to oxaloacetate and acetyl-CoA. In certain embodiments, ATP citrate lyase is expressed in the cytosol of a eukaryotic organism. ACL is an enzyme of the RTCA cycle that has been studied in green sulfur bacteria *Chlorobium limicola* and *Chlorobium tepidum*. The alpha(4)beta(4) heteromeric enzyme from *Chlorobium limicola* was cloned and characterized in *E. coli* (Kanao et al., *Eur. J. Biochem.* 269:3409-3416 (2002). The *C. limicola* enzyme, encoded by aclAB, is irreversible and activity of the enzyme is regulated by the ratio of ADP/ATP. The *Chlorobium tepidum* a recombinant ACL from *Chlorobium tepidum* was also expressed in *E. coli* and the holoenzyme was reconstituted in vitro, in a study elucidating the role of the alpha and beta subunits in the catalytic mechanism (Kim and Tabita, *J. Bacteriol.* 188:6544-6552 (2006). ACL enzymes have also been identified in *Balnearium lithotrophicum, Sulfurihydrogenibium subterraneum* and other members of the bacterial phylum Aquificae (Hugler et al., *Environ. Microbiol.* 9:81-92 (2007)). This activity has been reported in some fungi as well. Exemplary organisms include *Sordaria macrospora* (Nowrousian et al., *Curr. Genet.* 37:189-93 (2000)), *Aspergillus nidulans* and *Yarrowia lipolytica* (Hynes and Murray, *Eukaryotic Cell*, July: 1039-1048, (2010), and *Aspergillus niger* (Meijer et al. *J. Ind. Microbiol. Biotechnol.* 36:1275-1280 (2009). Other candidates can be found based on sequence homology. Information related to these enzymes is tabulated below.

| Protein | GenBank ID | GI Number | Organism |
|---|---|---|---|
| aclA | BAB21376.1 | 12407237 | Chlorobium limicola |
| aclB | BAB21375.1 | 12407235 | Chlorobium limicola |
| aclA | AAM72321.1 | 21647054 | Chlorobium tepidum |
| aclB | AAM72322.1 | 21647055 | Chlorobium tepidum |
| aclB | ABI50084.1 | 114055039 | Sulfurihydrogenibium subterraneum |

-continued

| Protein | GenBank ID | GI Number | Organism |
|---|---|---|---|
| aclA | AAX76834.1 | 62199504 | Sulfurimonas denitrificans |
| aclB | AAX76835.1 | 62199506 | Sulfurimonas denitrificans |
| acl1 | XP_504787.1 | 50554757 | Yarrowia lipolytica |
| acl2 | XP_503231.1 | 50551515 | Yarrowia lipolytica |
| SPBC1703.07 | NP_596202.1 | 19112994 | Schizosaccharomyces pombe |
| SPAC22A12.16 | NP_593246.1 | 19114158 | Schizosaccharomyces pombe |
| acl1 | CAB76165.1 | 7160185 | Sordaria macrospora |
| acl2 | CAB76164.1 | 7160184 | Sordaria macrospora |
| aclA | CBF86850.1 | 259487849 | Aspergillus nidulans |
| aclB | CBF86848 | 259487848 | Aspergillus nidulans |

In some organisms the conversion of citrate to oxaloacetate and acetyl-CoA proceeds through a citryl-CoA intermediate and is catalyzed by two separate enzymes, ciftyl-CoA synthetase (EC 6.2.1.18) and citryl-CoA lyase (EC 4.1.3.34) (Aoshima, M., Appl. Microbiol. Biotechnol. 75:249-255 (2007). Ciftyl-CoA synthetase catalyzes the activation of citrate to ciftyl-CoA. The Hydrogenobacter thermophilus enzyme is composed of large and small subunits encoded by ccsA and ccsB, respectively (Aoshima et al., Mol. Micrbiol. 52:751-761(2004)). The citryl-CoA synthetase of Aquifex aeolicus is composed of alpha and beta subunits encoded by sucC1 and sucD1 (Hugler et al., Environ. Microbial. 9:81-92 (2007)). Ciftyl-CoA lyase splits ciftyl-CoA into oxaloacetate and acetyl-CoA. This enzyme is a homotrimer encoded by ccl in Hydrogenobacter thermophilus (Aoshima et al., Mol. Microbial. 52:763-770 (2004)) and aq_150 in Aquilex aeolicus (Hugler et al., supra (2007)). The genes for this mechanism of converting citrate to oxaloacetate and citryl-CoA have also been reported recently in Chlorobium tepidum (Eisen et al., PNAS 99(14): 9509-14 (2002)).

| Protein | GenBank ID | GI Number | Organism |
|---|---|---|---|
| ccsA | BAD17844.1 | 46849514 | Hydrogenobacter thermophilus |
| ccsB | BAD17846.1 | 46849517 | Hydrogenobacter thermophilus |
| sucC1 | AAC07285 | 2983723 | Aquifex aeolicus |
| sucD1 | AAC07686 | 2984152 | Aquifex aeolicus |
| ccl | BAD17841.1 | 46849510 | Hydrogenobacter thermophilus |
| aq_150 | AAC06486 | 2982866 | Aquifex aeolicus |
| CT0380 | NP_661284 | 21673219 | Chlorobium tepidum |
| CT0269 | NP_661173.1 | 21673108 | Chlorobium tepidum |
| CT1834 | AAM73055.1 | 21647851 | Chlorobium tepidum |

Citrate lyase (EC 4.1.3.6, FIGS. 5 and 6, step E) catalyzes a series of reactions resulting in the cleavage of citrate to acetate and oxaloacetate. In certain embodiments, citrate lyase is expressed in the cytosol of a eukaryotic organism. The enzyme is active under anaerobic conditions and is composed of three subunits: an acyl-carrier protein (ACP, gamma), an ACP transferase (alpha), and an acyl lyase (beta). Enzyme activation uses covalent binding and acetylation of an unusual prosthetic group, 2'-(5"-phosphoribosyl)-3-'-dephospho-CoA, which is similar in structure to acetyl-CoA. Acylation is catalyzed by CitC, a citrate lyase synthetase. Two additional proteins, CitG and CitX, are used to convert the apo enzyme into the active holo enzyme (Schneider et al., Biochemistry 39:9438-9450 (2000)). Wild type E. coli does not have citrate lyase activity; however, mutants deficient in molybdenum cofactor synthesis have an active citrate lyase (Clark, FEMS Microbiol. Lett. 55:245-249 (1990)). The E. coli enzyme is encoded by citEFD and the citrate lyase synthetase is encoded by citC (Nilekani and SivaRaman, Biochemistry 22:4657-4663 (1983)). The Leuconostoc mesenteroides citrate lyase has been cloned, characterized and expressed in E. coli (Bekal et al., J. Bacteriol. 180:647-654 (1998)). Citrate lyase enzymes have also been identified in enterobacteria that utilize citrate as a carbon and energy source, including Salmonella typhimurium and Klebsiella pneumoniae (Bott, Arch. Microbiol. 167: 78-88 (1997); Bott and Dimroth, Mol. Microbiol. 14:347-356 (1994)). The aforementioned proteins are tabulated below.

| Protein | GenBank ID | GI Number | Organism |
|---|---|---|---|
| citF | AAC73716.1 | 1786832 | Escherichia coli |
| cite | AAC73717.2 | 87081764 | Escherichia coli |
| citD | AAC73718.1 | 1786834 | Escherichia coli |
| citC | AAC73719.2 | 87081765 | Escherichia coli |
| citG | AAC73714.1 | 1786830 | Escherichia coli |
| citX | AAC73715.1 | 1786831 | Escherichia coli |
| citF | CAA71633.1 | 2842397 | Leuconostoc mesenteroides |
| citE | CAA71632.1 | 2842396 | Leuconostoc mesenteroides |
| citD | CAA71635.1 | 2842395 | Leuconostoc mesenteroides |
| citC | CAA71636.1 | 3413797 | Leuconostoc mesenteroides |
| citG | CAA71634.1 | 2842398 | Leuconostoc mesenteroides |
| citX | CAA71634.1 | 2842398 | Leuconostoc mesenteroides |
| citF | NP_459613.1 | 16763998 | Salmonella typhimurium |
| citE | AAL19573.1 | 16419133 | Salmonella typhimurium |
| citD | NP_459064.1 | 16763449 | Salmonella typhimurium |
| citC | NP_459616.1 | 16764001 | Salmonella typhimurium |
| citG | NP_459611.1 | 16763996 | Salmonella typhimurium |
| citX | NP_459612.1 | 16763997 | Salmonella typhimurium |
| citF | CAA56217.1 | 565619 | Klebsiella pneumoniae |
| citE | CAA56216.1 | 565618 | Klebsiella pneumoniae |
| citD | CAA56215.1 | 565617 | Klebsiella pneumoniae |
| citC | BAH66541.1 | 238774045 | Klebsiella pneumoniae |
| citG | CAA56218.1 | 565620 | Klebsiella pneumoniae |
| citX | AAL60463.1 | 18140907 | Klebsiella pneumoniae |

The acylation of acetate to acetyl-CoA is catalyzed by enzymes with acetyl-CoA synthetase activity (FIGS. 5 and 6, step F). In certain embodiments, acetyl-CoA synthetase is expressed in the cytosol of a eukaryotic organism. Two enzymes that catalyze this reaction are AMP-forming acetyl-CoA synthetase (EC 6.2.1.1) and ADP-forming acetyl-CoA synthetase (EC 6.2.1.13). AMP-forming acetyl-CoA synthetase (ACS) is the predominant enzyme for activation of acetate to acetyl-CoA. Exemplary ACS enzymes are found in E. coli (Brown et Gen. Microbiol. 102:327-336 (1977)), Ralstonia eutropha (Priefert and Steinbuchel, J. Bacteriol. 174:6590-6599 (1992)), Methanothermobacter thermautotrophicus (Ingram-Smith and Smith, Archaea 2:95-107 (2007)), Salmonella enterica (Gulick et al., Biochemistry 42:2866-2873 (2003)) and Saccharomyces cerevisiae (Jogl and Tong, Biochemistry 43:1425-1431(2004)).

| Protein | GenBank ID | GI Number | Organism |
|---|---|---|---|
| acs | AAC77039.1 | 1790505 | Escherichia coli |
| acoE | AAA21945.1 | 141890 | Ralstonia eutropha |
| acs1 | ABC87079.1 | 86169671 | Methanothermobacter thermautotrophicus |
| acs1 | AAL23099.1 | 16422835 | Salmonella enterica |
| ACS1 | Q01574.2 | 257050994 | Saccharomyces cerevisiae |

ADP forming acetyl-CoA synthetase (ACD, EC 6.2.1.13) is another candidate enzyme that couples the conversion of acyl-CoA esters to their corresponding acids with the concurrent synthesis of ATP. Several enzymes with broad substrate specificities have been described in the literature. ACD I from Archaeoglobus fulgidus, encoded by AF1211, was shown to operate on a variety of linear and branched-chain substrates including acetyl-CoA, propionyl-CoA, butyryl- CoA, acetate, propionate, butyrate, isobutyryate, isovalrate, succinate, fumarate, phenylacetate, indoleacetate (Musfeldt et al., *J. Bacteriol.* 184:636-644 (2002)). The enzyme from *Haloarcula marismortui* (annotated as a succinyl-CoA synthetase) accepts propionate, butyrate, and branched-chain acids (isovalerate and isobutyrate) as substrates, and was shown to operate in the forward and reverse directions (Brasen et al., *Arch. Microbiol.* 182:277-287 (2004)). The ACD encoded by PAE3250 from hyperthermophilic crenarchaeon *Pyrobaculum aerophilum* showed the broadest substrate range of all characterized ACDs, reacting with acetyl-CoA, isobutyryl-CoA (preferred substrate) and phenylacetyl-CoA (Brasen et al., supra (2004)). The enzymes from *A. fulgidus*, *H. marismortui* and *P. aerophilum* have all been cloned, functionally expressed, and characterized in *E. coli* (Musfeldt et al., supra; Brasen et al., supra (2004)). Additional candidates include the succinyl-CoA synthetase encoded by sucCD in *E. coli* (Buck et al., *Biochemistry* 24:6245-6252 (1985)) and the acyl-CoA ligase from *Pseudomonas putida* (Fernandez-Valverde et al., *Appl. Environ. Microbiol.* 59:1149-1154 (1993)). Information related to these proteins and genes is shown below.

| Protein | GenBank ID | GI number | Organism |
|---|---|---|---|
| AF1211 | NP_070039.1 | 11498810 | *Archaeoglobus fulgidus* DSM 4304 |
| AF1983 | NP_070807.1 | 11499565 | *Archaeoglobus fulgidus* DSM 4304 |
| SCS | YP_135572.1 | 55377722 | *Haloarcula marismortui* ATCC 43049 |
| PAE3250 | NP_560604.1 | 18313937 | *Pyrobaculum aerophilum* str. IM2 |
| sucC | NP_415256.1 | 16128703 | *Escherichia coli* |
| sueD | AAC73823.1 | 1786949 | *Escherichia coli* |
| paaF | AAC24333.2 | 22711873 | *Pseudomonas putida* |

An alternative method for adding the CoA moiety to acetate is to apply a pair of enzymes such as a phosphate-transferring acyltransferase and an acetate kinase (FIGS. 5 and 6, Step F). This activity enables the net formation of acetyl-CoA with the simultaneous consumption of ATP. In certain embodiments, phosphotransacetylase is expressed in the cytosol of a eukaryotic organism. An exemplary phosphate-transferring acyltransferase is phosphotransacetylase, encoded by pta. The pta gene from *E. coli* encodes an enzyme that can convert acetyl-CoA into acetyl-phosphate, and vice versa (Suzuki, T. *Biochim.Biophys.Acta* 191:559-569 (1969)). This enzyme can also utilize propionyl-CoA instead of acetyl-CoA forming propionate in the process (Hesslinger et al. *Mol.Microbiol* 27:477-492 (1998)). Homologs exist in several other organisms including *Salmonella enterica* and *Chlamydomonas reinhardtii*.

| Protein | GenBank ID | GI number | Organism |
|---|---|---|---|
| Pta | NP_416800.1 | 16130232 | *Escherichia coli* |
| Pta | NP_461280.1 | 16765665 | *Salmonella enterica* subsp. *enterica serovar Typhimurium* str. LT2 |
| PAT2 | XP_001694504.1 | 159472743 | *Chlamydomonas reinhardtii* |
| PAT1 | XP_001691787.1 | 159467202 | *Chlamydomonas reinhardtii* |

An exemplary acetate kinase is the *E. coli* acetate kinase, encoded by ackA (Skarstedt and Silverstein *J.Biol.Chem.* 251:6775-6783 (1976)). Homologs exist in several other organisms including *Salmonella enterica* and *Chlamydomonas reinhardtii*. Information related to these proteins and genes is shown below:

| Protein | GenBankID | GI number | Organism |
|---|---|---|---|
| AckA | NP_416799.1 | 16130231 | *Escherichia coli* |
| AckA | NP_461279.1 | 16765664 | *Salmonella enterica* subsp. *enterica serovar Typhimurium* str. LT2 |
| ACK1 | XP_001694505.1 | 159472745 | *Chlamydomonas reinhardtii* |
| ACK2 | XP_001691682.1 | 159466992 | *Chlamydomonas reinhardtii* |

In some embodiments, cytosolic oxaloacetate is transported back into a mitochondrion by an oxaloacetate transporter. Oxaloacetate transported back into a mitochondrion can then be used in the acetyl-CoA pathways described herein. Transport of oxaloacetate from the cytosol to the mitochondrion can be carried out by several transport proteins. Such proteins either import oxaloacetate directly (i.e., oxaloacetate transporter) to the mitochondrion or import oxaloacetate to the cytosol while simultaneously transporting a molecule such as citrate (i.e., citrate/oxaloacetate transporter) from the mitochondrion into the cytosol as shown in FIG. 6. Exemplary transport enzymes that carry out these transformations are provided in the table below.

| Protein | GenBankID | GI number | Organism |
|---|---|---|---|
| OAC1 | NP_012802.1 | 6322729 | *Saccharomyces cerevisiae* S288c |
| KLLA0B12826g | XP_452102.1 | 50304305 | *Kluyveromyces lactis* NRRL Y-1140 |
| YALI0E04048g | XP_503525.1 | 50552101 | *Yarrowia lipolytica* |
| CTRG_02239 | XP_002547942.1 | 255726032 | *Candida tropicalis* MYA-3404 |
| DIC1 | NP_013452.1 | 6323381 | *Saccharomyces cerevisiae* S288c |
| YALI0B03344g | XP_500457.1 | 50545838 | *Yarrowia lipolytica* |
| CTRG_02122 | XP_002547815.1 | 255725772 | *Candida tropicalis* MYA-3404 |
| PAS_chr4_0877 | XP_002494326.1 | 254574434 | *Pichia pastoris* GS115 |
| DTC | CAC84549.1 | 19913113 | *Arabidopsis thaliana* |
| DTC1 | CAC84545.1 | 19913105 | *Nicotiana tabacum* |
| DTC2 | CAC84546.1 | 19913107 | *Nicotiana tabacum* |
| DTC3 | CAC84547.1 | 19913109 | *Nicotiana tabacum* |
| DTC4 | CAC84548.1 | 19913111 | *Nicotiana tabacum* |
| DTC | AAR06239.1 | 37964368 | *Citrus junos* |

In some embodiments, cytosolic oxaloacetate is first converted to malate by a cytosolic malate dehydrogenase (FIGS. 5, step H). Cytosolic malate is transported into a mitochondrion by a malate transporter or a citrate/malate transporter (FIG. 5, step I). Mitochondrial malate is then converted to oxaloacetate by a mitochondrial malate dehydrogenase (FIG. 5, step J). Mitochondrial oxaloacetate can then be used in the acetyl-CoA pathways described herein. Exemplary examples of each of these enzymes are provided below.

Oxaloacetate is converted into malate by malate dehydrogenase (EC 1.1.1.37, FIG. 5, step H). When malate is the dicarboxylate transported from the cytosol to mitochondrion, expression of both a cytosolic and mitochondrial version of malate dehydrogenase, e.g., as shown in FIG. 4, can be used. *S. cerevisiae* possesses three copies of malate dehydrogenase, MDH1 (McAlister-Henn and Thompson, *J. Bacteriol.* 169:5157-5166 (1987), MDH2 (Minard and McAlister-Henn, *Mol. Cell. Biol.* 11:370-380 (1991); Gibson and McAlister-Henn, *J. Biol. Chem.* 278:25628-25636 (2003)), and MDH3 (Steffan and McAlister-Henn, *J. Biol. Chem.* 267:24708-24715 (1992)), which localize to the mitochondrion, cytosol, and peroxisome, respectively. Close homologs to the cytosolic malate dehydrogenase, MDH2, from *S. cerevisiae* are found in several organisms including *Kluyveromyces lacti* and *Candida tropicalis*. *E. coli* is also known to have an active malate dehydrogenase encoded by mdh. In some embodiments, the exogenous malate dehydrogenase genes are *Rhizopus delemar* malate dehydrogenase genes encoding the amino acid sequence disclosed in WO2013112939 as SEQ ID NO:167 or its variants.

| Protein | GenBank ID | GI Number | Organism |
| --- | --- | --- | --- |
| MDH1 | NP_012838 | 6322765 | *Saccharomyces cerevisiae* |
| MDH2 | NP_014515 | 116006499 | *Saccharomyces cerevisiae* |
| MDH3 | NP_010205 | 6320125 | *Saccharomyces cerevisiae* |
| Mdh | NP_417703.1 | 16131126 | *Escherichia coli* |
| KLLA0E07525p | XP_454288.1 | 50308571 | *Kluyveromyces lactis* NRRL Y-1140 |
| YALI0D16753g | XP_502909.1 | 50550873 | *Yarrowia lipolytica* |
| CTRG_01021 | XP_002546239.1 | 255722609 | *Candida tropicalis* MYA-3404 |

Transport of malate from the cytosol to the mitochondrion can be carried out by several transport proteins. Such proteins either import malate directly (i.e., malate transporter) to the mitochondrion or import malate to the cytosol while simultaneously transporting a molecule such as citrate (i.e., citrate/malate transporter) from the mitochondrion into the cytosol as shown in FIG. 5. Exemplary transport enzymes that carry out these transformations are provided in the table below.

| Protein | GenBank ID | GI number | Organism |
| --- | --- | --- | --- |
| OAC1 | NP_012802.1 | 6322729 | *Saccharomyces cerevisiae* S288c |
| KLLA0B12826g | XP_452102.1 | 50304305 | *Kluyveromyces lactis* NRRL Y-1140 |
| YALI0E04048g | XP_503525.1 | 50552101 | *Yarrowia lipolytica* |
| CTRG_02239 | XP_002547942.1 | 255726032 | *Candida tropicalis* MYA-3404 |
| DIC1 | NP_013452.1 | 6323381 | *Saccharomyces cerevisiae* S288c |
| YALI0B03344g | XP_500457.1 | 50545838 | *Yarrowia lipolytica* |
| CTRG_02122 | XP_002547815.1 | 255725772 | *Candida tropicalis* MYA-3404 |
| PAS_chr4_0877 | XP_002494326.1 | 254574434 | *Pichia pastoris* GS115 |
| DTC | CAC84549.1 | 19913113 | *Arabidopsis thaliana* |
| DTC1 | CAC84545.1 | 19913105 | *Nicotiana tabacum* |
| DTC2 | CAC84546.1 | 19913107 | *Nicotiana tabacum* |
| DTC3 | CAC84547.1 | 19913109 | *Nicotiana tabacum* |
| DTC4 | CAC84548.1 | 19913111 | *Nicotiana tabacum* |
| DTC | AAR06239.1 | 37964368 | *Citrus junos* |

Malate can be converted into oxaloacetate by malate dehydrogenase (EC 1.1.1.37, FIG. 5, step J). When malate is the dicarboxylate transported from the cytosol to mitochondrion, in certain embodiments, both a cytosolic and mitochondrial version of malate dehydrogenase is expressed, as shown in FIGS. 4 and 5. S. cerevisiae possesses three copies of malate dehydrogenase, MDH1 (McAlister-Henn and Thompson, J. Bacteriol. 169:5157-5166 (1987), MDH2 (Minard and McAlister-Henn, Mol. Cell. Biol. 11:370-380 (1991); Gibson and McAlister-Henn, J. Biol. Chem. 278: 25628-25636 (2003)), and MDH3 (Steffan and McAlister-Henn, J. Biol. Chem. 267:24708-24715 (1992)), which localize to the mitochondrion, cytosol, and peroxisome, respectively. Close homologs to the mitochondrial malate dehydrogenase, MDH1 from S. cerevisiae are found in several organisms including Kluyveromyces lactis, Yarrowia lipolytica, Candida tropicalis. E. coli is also known to have an active malate dehydrogenase encoded by mdh.

Overall, four molecules of NADH can be attained per glucose molecule metabolized. In one aspect, the fatty alcohol pathway requires three reduction steps from acetyl-CoA. Therefore, it can be possible that each of these three reduction steps will utilize NADPH or NADH as the reducing agents, in turn converting these molecules to NADP or NAD, respectively. Therefore, in some aspects, it can be desireable that all reduction steps are NADH-dependant in order to maximize the yield of fatty alcohols, fatty aldehydes or fatty acis. High yields of fatty alcohols, fatty aldehydes and fatty acids can thus be accomplished by:
   I. Identifying and implementing endogenous or exogenous fatty alcohol, fatty aldehyde or fatty acid pathway enzymes with a stronger preference for NADH than other reducing equivalents such as NADPH,
   II. Attenuating one or more endogenous fatty alcohol, fatty aldehyde or fatty acid pathway enzymes that contribute NADPH-dependant reduction activity,

| Protein | GenBank ID | GI Number | Organism |
|---|---|---|---|
| MDH1 | NP_012838 | 6322765 | Saccharomyces cerevisiae |
| MDH2 | NP_014515 | 116006499 | Saccharomyces cerevisiae |
| MDH3 | NP_010205 | 6320125 | Saccharomyces cerevisiae |
| Mdh | NP_417703.1 | 16131126 | Escherichia coli |
| KLLA0F25960g | XP_456236.1 | 50312405 | Kluyveromyces lactis NRRL Y-1140 |
| YALI0D16753g | XP_502909.1 | 50550873 | Yarrowia lipolytica |
| CTRG_00226 | XP_002545445.1 | 255721021 | Candida tropicalis MYA-3404 |

Example VIII

Utilization of Pathway Enzymes with a Preference for NADH

The production of acetyl-CoA from glucose can generate at most four reducing equivalents in the form of NADH. A straightforward and energy efficient mode of maximizing the yield of reducing equivalents is to employ the Embden-Meyerhof-Parnas glycolysis pathway (EMP pathway). In many carbohydrate utilizing organisms, one NADH molecule is generated per oxidation of each glyceraldehyde-3-phosphate molecule by means of glyceraldehyde-3-phosphate dehydrogenase. Given that two molecules of glyceraldehyde-3-phosphate are generated per molecule of glucose metabolized via the EMP pathway, two NADH molecules can be obtained from the conversion of glucose to pyruvate.

Two additional molecules of NADH can be generated from conversion of pyruvate to acetyl-CoA given that two molecules of pyruvate are generated per molecule of glucose metabolized via the EMP pathway. This could be done by employing any of the following enzymes or enzyme sets to convert pyruvate to acetyl-CoA:
   I. NAD-dependant pyruvate dehydrogenase;
   II. Pyruvate formate lyase and NAD-dependant formate dehydrogenase;
   III. Pyruvate:ferredoxin oxidoreductase and NADH:ferredoxin oxidoreductase;
   IV. Pyruvate decarboxylase and an NAD-dependant acylating acetylaldehyde dehydrogenase;
   V. Pyruvate decarboxylase, NAD-dependant acylating acetaldehyde dehydrogenase, acetate kinase, and phosphotransacetylase; and
   VI. Pyruvate decarboxylase, NAD-dependant acylating acetaldehyde dehydrogenase, and acetyl-CoA synthetase.

III. Altering the cofactor specificity of endogenous or exogenous fatty alcohol, fatty aldehyde or fatty acid pathway enzymes so that they have a stronger preference for NADH than their natural versions, or
   IV. Altering the cofactor specificity of endogenous or exogenous fatty alcohol, fatty aldehyde or fatty acid pathway enzymes so that they have a weaker preference for NADPH than their natural versions.

Exemplary NADH-dependent enzymes that participate in the elongation cycle are shown in the table below.

| Enzyme | Substrate | Gene | Organism |
|---|---|---|---|
| Multifunctional ketoacyl-CoA reductase/epimerase/dehydratase | 3-ketoacyl-CoA | fadB | Escherichia coli |
| | | Fox2 | Candida tropicalis |
| | | FOX2 | Saccharomyces cerevisiae |
| 3-Ketoacyl-CoA reductase | 3-ketoacyl-CoA | paaH1 | Ralstonia eutropha |
| | | 3HCDH | Euglena gracilis |
| Enoyl-CoA reductase | enoyl-CoA | TDE0597 | Treponema denticola |
| | | TER | Euglena gracilis |
| | | ECR1 | Euglena gracilis |
| | | ECR2 | Euglena gracilis |
| | | ECR3 | Euglena gracilis |
| | | acad1 | Ascaris suum |
| | | acad | Ascaris suum |
| | | acad | Mycobacterium smegpiatis |

The individual enzyme or protein activities from the endogenous or exogenous DNA sequences can be assayed using methods well known in the art. For example, the genes can be expressed in E. coli and the activity of their encoded proteins can be measured using cell extracts. Alternatively, the enzymes can be purified using standard procedures well known in the art and assayed for activity. Spectrophotometric based assays are particularly effective.

Several examples and methods of altering the cofactor specificity of enzymes are known in the art. For example, Khoury et al. (Protein Sci. 2009 October; 18(10): 2125-2138) created several xylose reductase enzymes with an increased affinity for NADH and decreased affinity for NADPH. Ehsani et al (Biotechnology and Bioengineering, Volume 104, Issue 2, pages 381-389, 1 Oct. 2009) drastically decreased activity of 2,3-butanediol dehydrogenase on NADH while increasing activity on NADPH. Machielsen et al (Engineering in Life Sciences, Volume 9, Issue 1, pages 38-44, February 2009) dramatically increased activity of alcohol dehydrogenase on NADH. Khoury et al (Protein Sci. 2009 October; 18(10): 2125-2138) list in Table I several previous examples of successfully changing the cofactor preference of over 25 other enzymes. Additional descriptions can be found in Lutz et al, Protein Engineering Handbook, Volume 1 and Volume 2, 2009, Wiley-VCH Verlag GmbH & Co. KGaA, in particular, Chapter 31: Altering Enzyme Substrate and Cofactor Specificity via Protein Engineering.

Example IX

Determining Cofactor Preference of Pathway Enzymes

This example describes an experimental method for determining the cofactor preference of an enzyme.

Cofactor preference of enzymes for each of the pathway steps can be determined by cloning the individual genes on a plasmid behind a constitutive or inducible promoter and transforming into a host organism such as *Escherichia coli*. For example, genes encoding enzymes that catalyze pathway steps from: 1) acetoacetyl-CoA to 3-hydroxybutyryl-CoA, 2) 3-hydroxybutyryl-CoA to 3-hydroxybutyraldehyde, 3) 3-hydroxybutyraldehyde to 1,3-butanediol (wherein $R_1$ is $C_1$; $R_3$ is OH) can be assembled onto the pZ-based expression vectors as described below.

Replacement of the Stiffer Fragment in the pZ-based Expression Vectors. Vector backbones were obtained from Dr. Rolf Lutz of Expressys (http://www.expressys.de/). The vectors and strains are based on the pZ Expression System developed by Lutz and Bujard (*Nucleic Acids Res* 25, 1203-1210 (1997)). The pZE13luc, pZA33luc, pZS*13luc and pZE22luc contain the luciferase gene as a stuffer fragment. To replace the luciferase stuffer fragment with a lacZ-alpha fragment flanked by appropriate restriction enzyme sites, the luciferase stuffer fragment is removed from each vector by digestion with EcoRI and XbaI. The lacZ-alpha fragment is PCR amplified from pUC19 with the following primers:

```
lacZalpha-RI
                                          (SEQ ID NO: 1)
5'GACGAATTCGCTAGCAAGAGGAGAAGTCGACATGTCCAATTCACTGG

CCGTCGTTTTAC3' lacZalpha 3'BB
                                          (SEQ ID NO: 2)
5'-GACCCTAGGAAGCTTTCTAGAGTCGACCTATGCGGCATCAGAGCAG

A-3'
```

This generates a fragment with a 5' end of EcoRI site, NheI site, a Ribosomal Binding Site, a SalI site and the start codon. On the 3' end of the fragment are the stop codon, XbaI, HindIII, and AvrII sites. The PCR product is digested with EcoRI and AvrII and ligated into the base vectors digested with EcoRI and XbaI (XbaI and AvrII have compatible ends and generate a non-site). Because NheI and XbaI restriction enzyme sites generate compatible ends that can be ligated together (but generate a site after ligation that is not digested by either enzyme), the genes cloned into the vectors can be "Biobricked" together (http://openwetware.org/wiki/Synthetic_Biology:BioBricks). Briefly, this method enables joining an unlimited number of genes into the vector using the same 2 restriction sites (as long as the sites do not appear internal to the genes), because the sites between the genes are destroyed after each addition. These vectors can be subsequently modified using the Phusion® Site-Directed Mutagenesis Kit (NEB, IpswichMAs., USA) to insert the spacer sequence AATTAA between the EcoRI and NheI sites. This eliminates a putative stem loop structure in the RNA that bound the RBS and start codon.

All vectors have the pZ designation followed by letters and numbers indicating the origin of replication, antibiotic resistance marker and promoter/regulatory unit. The origin of replication is the second letter and is denoted by E for ColE1, A for p15A and S for pSC101 (as well as a lower copy number version of pSC101 designated S*)-based origins. The first number represents the antibiotic resistance marker (1 for Ampicillin, 2 for Kanamycin, 3 for Chloramphenicol). The final number defines the promoter that regulated the gene of interest (1 for PLlacO-1, 2 for PLlacO-1 and 3 for PA1lacO-1). For the work discussed here we employed three base vectors, pZS*13S, pZA33S and pZE13S, modified for the biobricks insertions as discussed above.

Plasmids containing genes encoding pathway enzymes can then transformed into host strains containing lacIQ, which allow inducible expression by addition of isopropyl β-D-1-thiogalactopyranoside (IPTG). Activities of the heterologous enzymes are tested in in vitro assays, using strain *E. coli* MG1655 lacIQ as the host for the plasmid constructs containing the pathway genes. Cells can be grown aerobically in LB media (Difco) containing the appropriate antibiotics for each construct, and induced by addition of IPTG at 1 mM when the optical density (OD600) reached approximately 0.5. Cells can be harvested after 6 hours, and enzyme assays conducted as discussed below.

In Vitro Enzyme Assays. To obtain crude extracts for activity assays, cells can be harvested by centrifugation at 4,500 rpm (Beckman-Coulter, Alleges X-15R) for 10 min. The pellets are resuspended in 0.3 mL BugBuster (Novagen) reagent with benzonase and lysozyme, and lysis proceeds for about 15 minutes at room temperature with gentle shaking. Cell-free lysate is obtained by centrifugation at 14,000 rpm (Eppendorf centrifuge 5402) for 30 min at 4° C. Cell protein in the sample is determined using the method of Bradford et al., Anal. Biochem. 72:248-254 (1976), and specific enzyme assays conducted as described below. Activities are reported in Units/mg protein, where a unit of activity is defined as the amount of enzyme required to convert 1 micromol of substrate in 1 minute at room temperature.

Pathway steps can be assayed in the reductive direction using a procedure adapted from several literature sources (Durre et al., FEMS Microbiol. Rev. 17:251-262 (1995); Palosaari and Rogers, Bacteriol. 170:2971-2976 (1988) and Welch et al., Arch. Biochem. Biophys. 273:309-318 (1989). The oxidation of NADH or NADPH can be followed by reading absorbance at 340 nM every four seconds for a total of 240 seconds at room temperature. The reductive assays can be performed in 100 mM MOPS (adjusted to pH 7.5 with KOH), 0.4 mM NADH or 0.4 mM NADPH, and from 1 to 50 µmol of cell extract. For carboxylic acid reductaselike enzymes, ATP can also be added at saturating concentrations. The reaction can be started by adding the following reagents: 100 µmol of 100 mM acetoacetyl-CoA, 3-hydroxybutyryl-CoA, 3-hydroxybutyrate, or 3-hydroxybutyraldehyde. The spectrophotometer is quickly blanked and then the kinetic read is started. The resulting slope of the reduction in absorbance at 340 nM per minute, along with the molar extinction coefficient of NAD(P)H at 340 nM (6000) and the protein concentration of the extract, can be used to determine the specific activity.

Example X

Methods for Increasing NADPH Availability

In some aspects of the invention, it can be advantageous to employ pathway enzymes that have activity using NADPH as the reducing agent. For example, NADPH-dependant pathway enzymes can be highly specific for MI-FAE cycle, MD-FAE cycle and/or termination pathway intermediates or can possess favorable kinetic properties using NADPH as a substrate. If one or more pathway steps is NADPH dependant, several alternative approaches to increase NADPH availability can be employed. These include:
1) Increasing flux relative to wild-type through the oxidative branch of the pentose phosphate pathway comprising glucose-6-phosphate dehydrogenase, 6-phosphogluconolactonase, and 6-phosphogluconate dehydrogenase (decarboxylating). This will generate 2 NADPH molecules per glucose-6-phosphate metabolized. However, the decarboxylation step will reduce the maximum theoretical yield of 1,3-butanediol.
2) Increasing flux relative to wild-type through the Entner Doudoroff pathway comprising glucose-6-phosphate dehydrogenase, 6-phosphogluconolactonase, phosphogluconate dehydratase, and 2-keto-3-deoxygluconate 6-phosphate aldolase.
3) Introducing a soluble transhydrogenase to convert NADH to NADPH.
4) Introducing a membrane-bound transhydrogenase to convert NADH to NADPH.
5) Employing an NADP-dependant glyceraldehyde-3-phosphate dehydrogenase.
6) Employing any of the following enzymes or enzyme sets to convert pyruvate to acetyl-CoA
   a) NADP-dependant pyruvate dehydrogenase;
   b) Pyruvate formate lyase and NADP-dependant formate dehydrogenase;
   c) Pyruvate:ferredoxin oxidoreductase and NADPH: ferredoxin oxidoreductase.
   d) Pyruvate decarboxylase and an NADP-dependant acylating acetylaldehyde dehydrogenase;
   e) Pyruvate decarboxylase, NADP-dependant acetaldehyde dehydrogenase, acetate kinase, and phosphotransacetylase; and
   f) Pyruvate decarboxylase, NADP-dependant acetaldehyde dehydrogenase, and acetyl-CoA synthetase; and optionally attenuating NAD-dependant versions of these enzymes.
7) Altering the cofactor specificity of a native glyceraldehyde-3-phosphate dehydrogenase, pyruvate dehydrogenase, formate dehydrogenase, or acylating acetylaldehyde dehydrogenase to have a stronger preference for NADPH than their natural versions.
8) Altering the cofactor specificity of a native glyceraldehyde-3-phosphate dehydrogenase, pyruvate dehydrogenase, formate dehydrogenase, or acylating acetylaldehyde dehydrogenase to have a weaker preference for NADH than their natural versions.

The individual enzyme or protein activities from the endogenous or exogenous DNA sequences can be assayed using methods well known in the art. For example, the genes can be expressed in *E. coli* and the activity of their encoded proteins can be measured using cell extracts as described in the previous example. Alternatively, the enzymes can be purified using standard procedures well known in the art and assayed for activity. Spectrophotometric based assays are particularly effective.

Several examples and methods of altering the cofactor specificity of enzymes are known in the art. For example, Khoury et al (Protein Sci. 2009 October; 18(10): 2125-2138) created several xylose reductase enzymes with an increased affinity for NADH and decreased affinity for NADPH. Ehsani et al (Biotechnology and Bioengineering, Volume 104, Issue 2, pages 381-389, 1 Oct. 2009) drastically decreased activity of 2,3-butanediol dehydrogenase on NADH while increasing activity on NADPH. Machielsen et al (Engineering in Life Sciences, Volume 9, Issue 1, pages 38-44, February 2009) dramatically increased activity of alcohol dehydrogenase on NADH. Khoury et al (Protein Sci. 2009 October; 18(10): 2125-2138) list in Table I several previous examples of successfully changing the cofactor preference of over 25 other enzymes. Additional descriptions can be found in Lutz et al, Protein Engineering Handbook, Volume 1 and Volume 2, 2009, Wiley-VCH Verlag GmbH & Co. KGaA, in particular, Chapter 31: Altering Enzyme Substrate and Cofactor Specificity via Protein Engineering.

Enzyme candidates for these steps are provided below.
Glucose-6-Phosphate Dehydrogenase

| Protein | GenBank ID | GI Number | Organism |
|---|---|---|---|
| ZWF1 | NP_014158.1 | 6324088 | *Saccharomyces cerevisiae* S288c |
| ZWF1 | XP_504275.1 | 50553728 | *Yarrowia Upolytica* |
| Zwf | XP_002548953.1 | 255728055 | *Candida tropicalis* MYA-3404 |
| Zwf | XP_001400342.1 | 145233939 | *Aspergillus niger* CBS 513.88 |
| KLLA0D19855g | XP_453944.1 | 50307901 | *Kluyveromyces lactis* NRRL Y-1140 |

6-Phosphogluconolactonase

| Protein | GenBank ID | GI Number | Organism |
|---|---|---|---|
| SOL3 | NP_012033.2 | 82795254 | Saccharomyces cerevisiae S288c |
| SOL4 | NP_011764.1 | 6321687 | Saccharomyces cerevisiae S288c |
| YALI0E11671g | XP_503830.1 | 50552840 | Yarrowia lipolytica |
| YALI0C19085g | XP_501998.1 | 50549055 | Yarrowia lipolytica |
| ANI_1_656014 | XP_001388941.1 | 145229265 | Asperpillus niger CBS 513.88 |
| CTRG_00665 | XP_002545884.1 | 255721899 | Candida tropicalis MYA-3404 |
| CTRG_02095 | XP_002547788.1 | 255725718 | Candida tropicalis MYA-3404 |
| KLLA0A05390g | XP_451238.1 | 50302605 | Kluyveromyces lactis NRRL Y-1140 |
| KLLA0C08415g | XP_452574.1 | 50305231 | Kluyveromyces lactis NRRL Y-1140 |

6-Phosphogluconate Dehydrogenase (Decarboxylating)

| Protein | GenBank ID | GI Number | Organism |
|---|---|---|---|
| GND1 | NP_012053.1 | 6321977 | Saccharomyces cerevisiae S288c |
| GND2 | NP_011772.1 | 6321695 | Saccharomyces cerevisiae S288c |
| ANI_1_282094 | XP_001394208.2 | 317032184 | Asperyillus niger CBS 513.88 |
| ANI_1_2126094 | XP_001394596.2 | 317032939 | Aspergillus niger CBS 513.88 |
| YALI0B15598g | XP_500938.1 | 50546937 | Yarrowia lipolytica |
| CTRG_03660 | XP_002549363.1 | 255728875 | Candida tropicalis MYA-3404 |
| KLLA0A09339g | XP_451408.1 | 50302941 | Kluyveromyces lactis NRRL Y-1140 |

Phosphogluconate Sehydratase

| Protein | GenBank ID | GI Number | Organism |
|---|---|---|---|
| Edd | AAC74921.1 | 1788157 | Escherichia coli K-12MG1655 |
| Edd | AAG29866.1 | 11095426 | Zymomonas mobilis subsp. mobilis ZM4 |
| Edd | YP_350103.1 | 77460596 | Pseudomonas fluorescens Pf0-1 |
| ANI_1_2126094 | XP_001394596.2 | 317032939 | Aspergillus niger CBS 513.88 |
| YALI0B15598g | XP_500938.1 | 50546937 | Yarrowia lipolytica |
| CTRG_03660 | XP_002549363.1 | 255728875 | Candida tropicalis MYA-3404 |
| KLLA0A09339g | XP_451408.1 | 50302941 | Kluyveromyces lactis NRRL Y-1140 |

2-Keto-3-deoxygluconate 6-phosphate Aldolase

| Protein | GenBank ID | GI Number | Organism |
|---|---|---|---|
| Eda | NP_416364.1 | 16129803 | Escherichia coli K-12 MG1655 |
| Eda | Q00384.2 | 59802878 | Zymomonas mobilis subsp. mobilis ZM4 |
| Eda | ABA76098.1 | 77384585 | Pseudomonas fluorescens Pf0-1 |
| SthA | NP_418397.2 | 90111670 | Escherichia coli K-12 MG1655 |
| SthA | YP_002798658.1 | 226943585 | Azotobacter vinelandii DJ |
| SthA | O05139.3 | 11135075 | Pseudomonas fluorescens |

Soluble Transhydrogenase
Membrane-Bound Transhydrogenase

| Protein | GenBank ID | GI Number | Organism |
|---|---|---|---|
| ANI_1_29100 | XP_001400109.2 | 317027842 | Asperfillus niger CBS 513.88 |
| Pc21g18800 | XP_002568871.1 | 226943585 255956237 | Penicillium chrysogenum Wisconsin 54-1255 |
| SthA | O05139.3 | 11135075 | Pseudomonas fluorescens |
| NCU01140 | XP_961047.2 | 164426165 | Newospora crassa OR74A |

NADP-Dependant Glyceraldehyde-3-phosphate Dehydrogenase

| Protein | GenBank ID | GI Number | Organism |
|---|---|---|---|
| gapN | AAA91091.1 | 642667 | *Streptococcus mutans* |
| NP-GAPDH | AEC07555.1 | 330252461 | *Arabidopsis thaliana* |
| GAPN | AAM77679.2 | 82469904 | *Triticum aestivum* |
| gapN | CAI56300.1 | 87298962 | *Clostridium acetobutylicum* |
| NADP-GAPDH | 2D2I A | 112490271 | *Synechococcus elonpatus* PCC 7942 |
| NADP-GAPDH | CAA62619.1 | 4741714 | *Synechococcus elonpatus* PCC 7942 |
| GDP1 | XP_455496.1 | 50310947 | *Kluyveromyces lactis* NRRL Y-1140 |
| HP1346 | NP_208138.1 | 15645959 | *Helicobacter pylori* 26695 |

NAD-Dependant Glyceraldehyde-3-phosphate Dehydrogenase

| Protein | GenBank ID | GI Number | Organism |
|---|---|---|---|
| TDH1 | NP_012483.1 | 6322409 | *Saccharomyces cerevisiae* s288c |
| TDH2 | NP_012542.1 | 6322468 | *Saccharomyces cerevisiae* s288c |
| TDH3 | NP_011708.1 | 632163 | *Saccharomyces cerevisiae* s288c |
| KLLA0A11858g | XP_451516.1 | 50303157 | *Kluyveromyces lactis* NRRL Y-1140 |
| KLLA0F20988g | XP_456022.1 | 50311981 | *Kluyveromyces lactis* NRRL Y-1140 |
| ANI_1_256144 | XP_001397496.1 | 145251966 | *Aspergillus niper* CBS 513.88 |
| YALI0C06369g | XP_501515.1 | 50548091 | *Yarrowia Upolytica* |
| CTRG_05666 | XP_002551368.1 | 255732890 | *Candida tropicalis* MYA-3404 |

Mutated LpdA from *E. coli* K-12 MG1655 described in Biochemistry, 1993, 32 (11), pp 2737-2740:

(SEQ ID NO: 3)
MSTEIKTQVVVLGAGPAGYSAAFRCADLGLETVIVERYNTLGGVCLNVG
CIPSKALLHVAKVIEEAKALAEHGIVFGEPKTDIDKIRTWKEKVINQLT
GGLAGMAKGRKVKVVNGLGKFTGANTLEVEGENGKTVINFDNAIIAAGS
RPIQLPFIPHEDPRIWDSTDALELKEVPERLLVMGGGIIGLEMGTVYHA
LGSQIDVVVRKHQVIRAADKDIVKVFTKRISKKFNLMLETKVTAVEAKE
DGIYVTMEGKKAPAEPQRYDAVLVAIGRVPNGKNLDAGKAGVEVDDRGF
IRVDKQLRTNVPHIFAIGDIVGQPMLAHKGVHEGHVAAEVIAGKKHYFD
PKVIPSIAYTEPEVAWVGLTEKEAKEKGISYETATFPWAASGRAIASDC
ADGMTKLIFDKESHRVIGGAIVGTNGGELLGEIGLAIEMGCDAEDIALT
IHAHPTLHESVGLAAEVFEGSITDLPNPKAKKK

Mutated LpdA from *E. coli* K-12 MG1655 described in Biochemistry, 1993, 32 (11), pp 2737-2740:

(SEQ ID NO: 4)
MSTEIKTQVVVLGAGPAGYSAAFRCADLGLETVIVERYNTLGGVCLNVG
CIPSKALLHVAKVIEEAKALAEHGIVFGEPKTDIDKIRTWKEKVINQLT
GGLAGMAKGRKVKVVNGLGKFTGANTLEVEGENGKTVINFDNAIIAAGS
RPIQLPFIPHEDPRIWDSTDALELKEVPERLLVMGGGIIALEMATVYHA
LGSQIDVVVRKHQVIRAADKDIVKVFTKRISKKFNLMLETKVTAVEAKE
DGIYVTMEGKKAPAEPQRYDAVLVAIGRVPNGKNLDAGKAGVEVDDRGF
IRVDKQLRTNVPHIFAIGDIVGQPMLAHKGVHEGHVAAEVIAGKKHYFD
PKVIPSIAYTEPEVAWVGLTEKEAKEKGISYETATFPWAASGRAIASDC
ADGMTKLIFDKESHRVIGGAIVGTNGGELLGEIGLAIEMGCDAEDIALT
IHAHPTLHESVGLAAEVFEGSITDLPNPKAKKK

NADP-Dependant Formate Dehydrogenase

| Protein | GenBank ID | GI Number | Organism |
|---|---|---|---|
| fdh | ACF35003. | 194220249 | *Bwkholderia stabilis* |
| fdh | ABC20599.2 | 146386149 | *Moorella thermoacetica* ATCC 39073 |

Mutant *Candida bodinii* enzyme described in Journal of Molecular Catalysis B: Enzymatic, Volume 61, Issues 3-4, December 2009, Pages 157-161:

(SEQ ID NO: 5)
MKIVLVLYDAGKHAADEEKLYGCTENKLGIANWLKDQGHELITTSDKEG
ETSELDKHIPDADIIITTPFHPAYITKERLDKAKNLKLVVVAGVGSDHI
DLDYINQTGKKISVLEVTGSNVVSVAEHVVMTMLVLVRNFVPAHEQIIN
HDWEVAAIAKDAYDIEGKTIATIGAGRIGYRVLERLLPFNPKELLYYQR
QALPKEAEEKVGARRVENIEELVAQADIVTVNAPLHAGTKGLINKELLS
KFKKGAWLVNTARGAICVAEDVAAALESGQLRGYGGDVWFPQPAPKDHP
WRDMRNKYGAGNAMTPHYSGTTLDAQTRYAEGTKNILESFFTGKFDYRP
QDIILLNGEYVTKAYGKHDKK

Mutant *Candida bodinii* enzyme described in Journal of Molecular Catalysis B: Enzymatic, Volume 61, Issues 3-4, December 2009, Pages 157-161:

(SEQ ID NO: 6)
MKIVLVLYDAGKHAADEEKLYGCTENKLGIANWLKDQGHELITTSDKEG
ETSELDKHIPDADIIITTPFHPAYITKERLDKAKNLKLVVVAGVGSDHI

-continued

DLDYINQTGKKISVLEVTGSNVVSVAEHVVMTMLVLVRNFVPAHEQIIN

HDWEVAAIAKDAYDIEGKTIATIGAGRIGYRVLERLLPFNPKELLYYSP

QALPKEAEEKVGARRVENIEELVAQADIVTVNAPLHAGTKGLINKELLS

KFKKGAWLVNTARGAICVAEDVAAALESGQLRGYGGDVWFPQPAPKDHP

WRDMRNKYGAGNAMTPHYSGTTLDAQTRYAEGTKNILESFFTGKFDYRP

QDIILLNGEYVTKAYGKHDKK

Mutant *Saccharomyces cerevisiae* enzyme described in Biochem J. 2002 Nov. 1:367(Pt. 3):841-847:

(SEQ ID NO: 7)
MSKGKVLLVLYEGGKHAEEQEKLLGCIENELGIRNFIEEQGYELVTTID

KDPEPTSTVDRELKDAEIVITTPFFPAYISRNRIAEAPNLKLCVTAGVG

SDHVDLEAANERKITVTEVTGSNVVSVAEHVMATILVLIRNYNGGHQQA

INGEWDIAGVAKNEYDLEDKIISTVGAGRIGYRVLERLVAFNPKKLLYY

ARQELPAEAINRLNEASKLFNGRGDIVQRVEKLEDMVAQSDVVTINCPL

HKDSRGLFNKKLISHMKDGAYLVNTARGAICVAEDVAEAVKSGKLAGYG

GDVWDKQPAPKDHPWRTMDNKDHVGNAMTVHISGTSLDAQKRYAQGVKN

ILNSYFSKKFDYRPQDIIVQNGSYATRAYGQKK.

NADPH:Ferredoxin Oxidoreductase

| Protein | GenBank ID | GI Number | Organism |
|---|---|---|---|
| petH | YP_171276.1 | 56750575 | *Synechococcus elongatus* PCC 6301 |
| fpr | NP_457968.1 | 16762351 | *Salmonella enterica* |
| fnr1 | XP_001697352.1 | 159478523 | *Chlamydomonas reinhardtii* |
| rfnr1 | NP_567293.1 | 18412939 | *Arabidopsis thaliana* |
| aceF | NP_414657.1 | 6128108 | *Escherichia coli* K-12 MG1655 |

NADP-Dependant Acylating Acetylaldehyde Dehydrogenase

| Protein | GenBank ID | GI Number | Organism |
|---|---|---|---|
| adhB | AAB06720.1 | 1513071 | *Thermoanaerobacter pseudethanolicus* ATCC 33223 |
| TheetDRAFT_0840 | ZP_08211603. | 326390041 | *Thermoanaerobacter ethanolicus* JW 200 |
| Cbei_3832 | YP_001310903.1 | 150018649 | *Clostridium beijerinckii* NCIMB 8052 |
| Cbei_4054 | YP_001311120.1 | 150018866 | *Clostridium beijerinckii* NCIMB 8052 |
| Cbei_4045 | YP_001311111.1 | 150018857 | *Clostridium beijerinckii* NCIMB 8052 |

Exemplary genes encoding pyruvate dehydrogenase, pyruvate:ferredoxin oxidoreductase, pyruvate formate lyase, pyruvate decarboxylase, acetate kinase, phosphotransacetylase and acetyl-CoA synthetase are described above in Example V.

Example XI

Engineering *Saccharomyces cerevisiae* for Chemical Production

Eukaryotic hosts have several advantages over prokaryotic systems. They are able to support post-translational modifications and host membrane-anchored and organelle-specific enzymes. Genes in eukaryotes typically have introns, which can impact the timing of gene expression and protein structure.

An exemplary eukaryotic organism well suited for industrial chemical production is *Saccharomyces cerevisiae*. This organism is well characterized, genetically tractable and industrially robust. Genes can be readily inserted, deleted, replaced, overexpressed or underexpressed using methods known in the art. Some methods are plasmid-based whereas others modify the chromosome (Guthrie and Fink. *Guide to Yeast Genetics and Molecular and Cell Biology, Part B, Volume* 350, Academic Press (2002); Guthrie and Fink, *Guide to Yeast Genetics and Molecular and Cell Biology, Part C, Volume* 351, Academic Press (2002)).

Plasmid-mediated gene expression is enabled by yeast episomal plasmids (YEps). YEps allow for high levels of expression; however they are not very stable and they require cultivation in selective media. They also have a high maintenance cost to the host metabolism. High copy number plasmids using auxotrophic (e.g., URA3, TRP1, H1S3, LEU2) or antibiotic selectable markers (e.g., $Zeo^R$ or $Kan^R$) can be used, often with strong, constitutive promoters such as PGK1 or ACT1 and a transcription terminator-polyadenylation region such as those from CYC1 or AOX. Many examples are available for one well-versed in the art. These include pVV214 (a 2 micron plasmid with URA3 selectable marker) and pVV200 (2 micron plasmid with TRP1 selectable marker) (Van et al., *Yeast* 20:739-746 (2003)). Alternatively, low copy plasmids such as centromeric or CEN plamids can be used. Again, many examples are available for one well-versed in the art. These include pRS313 and pRS315 (Sikorski and Hieter, *Genetics* 122:19-27 (1989) both of which require that a promoter (e.g., PGK1 or ACT1) and a terminator (e.g., CYC1, AOX) are added.

For industrial applications, chromosomal overexpression of genes is preferable to plasmid-mediated overexpression. Mikkelsen and coworkers have identified 11 integration sites on highly expressed regions of the *S. cerevisiae* genome on chromosomes X, XI and XII (Mikkelsen et al, *Met Eng* 14:104-11(2012)). The sites are separated by essential genes, minimizing the possibility of recombination between sites.

Tools for inserting genes into eukaryotic organisms such as *S. cerevisiae* are known in the art. Particularly useful tools include yeast integrative plasmids (Yips), yeast artificial chromosomes (YACS) and gene targeting/homologous recombination. Note that these tools can also be used to insert, delete, replace, underexpress or otherwise alter the genome of the host.

Yeast integrative plasmids (Yips) utilize the native yeast homologous recombination system to efficiently integrate DNA into the chromosome. These plasmids do not contain an origin of replication and can therefore only be maintained after chromosomal integration. An exemplary construct includes a promoter, the gene of interest, a terminator, and a selectable marker with a promoter, flanked by FRT sites, loxP sites, or direct repeats enabling the removal and recycling of the resistance marker. The method entails the synthesis and amplification of the gene of interest with suitable primers, followed by the digestion of the gene at a unique restriction site, such as that created by the EcoRI and XhoI enzymes (Vellanki et al., *Biotechnol Lett.* 29:313-318 (2007)). The gene of interest is inserted at the EcoRI and XhoI sites into a suitable expression vector, downstream of the promoter. The gene insertion is verified by PCR and DNA sequence analysis. The recombinant plasmid is then linearized and integrated at a desired site into the chromosomal DNA of *S. cerevisiae* using an appropriate transformation method. The cells are plated on the YPD medium with an appropriate selection marker and incubated for 2-3 days. The transformants are analyzed for the requisite gene insert by colony PCR. To remove the antibiotic marker from a construct flanked by loxP sites, a plasmid containing the Cre recombinase is introduced. Cre recombinase promotes the excision of sequences flanked by loxP sites. (Gueldener et al., *Nucleic Acids Res* 30:e23 (2002)). The resulting strain is cured of the Cre plasmid by successive culturing on media without any antibiotic present. Alternately, the Cre recombinase plasmid has a URA selection marker and the plasmid is efficiently removed by growing cells on 5-FOA which acts as a counter-selection for URA. This method can also be employed for a scarless integration instead of using loxP. One skilled in the art can integrate using URA as a marker, select for integration by growing on URA-minus plates, and then select for URA mutants by growing on 5-FOA plates. 5-FOA is converted to the toxic 5-fluoruracil by the URA gene product. Alternatively, the FLP-FRT system can be used to integrate genes into the chromosome. This system involves the recombination of sequences between short Flipase Recognition Target (FRT) sites by the Flipase recombination enzyme (FLP) derived from the 2 µ plasmid of the yeast *Saccharomyces cerevisiae* (Sadowski, P. D., *Prog.Nucleic.Acid.Res.Mol.Biol.* 51:53-91 (1995); Zhu and Sadowski *J.Biol.Chem.* 270:23044-23054 (1995)). Similarly, gene deletion methodologies will be carried out as described in refs. Baudin et al. *Nucleic.Acids Res.* 21:3329-3330 (1993); Brachmann et al., *Yeast* 14:115-132 (1998); Giaever et al., *Nature* 418:387-391 (2002); Longtine et al., *Yeast* 14:953-961 (1998) Winzeler et al., *Science* 285:901-906 (1999).

Another approach for manipulating the yeast chromosome is gene targeting. This approach takes advantage of the fact that double stranded DNA breaks in yeast are repaired by homologous recombination. Linear DNA fragments flanked by targeting sequences can thus be efficiently integrated into the yeast genome using the native homologous recombination machinery In addition to the application of inserting genes, gene targeting approaches are useful for genomic DNA manipulations such as deleting genes, introducing mutations in a gene, its promoter or other regulatory elements, or adding a tag to a gene.

Yeast artificial chromosomes (YACs) are artificial chromosomes useful for pathway construction and assembly. YACs enable the expression of large sequences of DNA (100-3000 kB) containing multiple genes. The use of YACs was recently applied to engineer flavenoid biosynthesis in yeast (Naesby et al, *Microb Cell Fact* 8:49-56 (2009)). In this approach, YACs were used to rapidly test randomly assembled pathway genes to find the best combination.

The expression level of a gene can be modulated by altering the sequence of a gene and/or its regulatory regions. Such gene regulatory regions include, for example, promoters, enhancers, introns, and terminators. Functional disruption of negative regulatory elements such as repressors and/or silencers also can be employed to enhance gene expression. RNA based tools can also be employed to regulate gene expression. Such tools include RNA aptamers, riboswitches, antisense RNA, ribozymes and riboswitches.

For altering a gene's expression by its promoter, libraries of constitutive and inducible promoters of varying strengths are available. Strong constitutive promoters include pTEF1, pADH1 and promoters derived from glycolytic pathway genes. The pGAL promoters are well-studied inducible promoters activated by galactose and repressed by glucose. Another commonly used inducible promoter is the copper inducible promoter pCUP1 (Farhi et al, *Met Eng* 13:474-81 (2011)). Further variation of promoter strengths can be introduced by mutagenesis or shuffling methods. For example, error prone PCR can be applied to generate synthetic promoter libraries as shown by Alper and colleagues (Alper et al, *PNAS* 102:12678-83 (2005)). Promoter strength can be characterized by reporter proteins such as beta-galactosidase, fluorescent proteins and luciferase.

The placement of an inserted gene in the genome can alter its expression level. For example, overexpression of an integrated gene can be achieved by integrating the gene into repeating DNA elements such as ribosomal DNA or long terminal repeats.

For exogenous expression in yeast or other eukaryotic cells, genes can be expressed in the cytosol without the addition of leader sequence, or can be targeted to mitochondrion or other organelles, or targeted for secretion, by the addition of a suitable targeting sequence such as a mitochondrial targeting or secretion signal suitable for the host cells. Thus, it is understood that appropriate modifications to a nucleic acid sequence to remove or include a targeting sequence can be incorporated into an exogenous nucleic acid sequence to impart desirable properties. Genetic modifications can also be made to enhance polypeptide synthesis. For example, translation efficiency is enhanced by substituting ribosome binding sites with an optimal or consensus sequence and/or altering the sequence of a gene to add or remove secondary structures. The rate of translation can also be increased by substituting one coding sequence with another to better match the codon preference of the host.

Example XII

Termination Pathways for Making Fatty Alcohols, Aldehydes and Acids

This example describes enzymes for converting intermediates of the MI-FAE cycle or MD-FAE cycle to products of interest such as fatty alcohols, fatty aldehydes, and fatty acids. Pathways are shown in FIGS. 2 and 8. Enzymes for catalyzing steps A-G are disclosed in Example IV. This example describes enzymes suitable for catalyzing steps H—N.

Enzymes include: A. Thiolase, B. 3-Ketoacyl-CoA reductase, C. β-Hydroxyl-ACP dehydratase, D. Enoyl-CoA reductase, E. Acyl-CoA reductase (aldehyde forming), F. Alcohol dehydrogenase, G. Acyl-CoA reductase (alcohol forming), H. acyl-CoA hydrolase, transferase or synthetase, J. Acyl-ACP reductase, K. Acyl-CoA:ACP acyltransferase, L. Thioesterase, N. Aldehyde dehydrogenase (acid forming) or carboxylic acid reductase.

Pathways for converting an MI-FAE cycle intermediate to an fatty alcohol, fatty aldehyde or fatty acid product are shown in the table below. These pathways are also referred to herein as "termination pathways".

| Product | Termination pathway enzymes from FIG. 2 |
|---|---|
| Acid | H |
|  | K/L |
|  | E/N |
|  | K/J/N |
| Aldehyde | E |
|  | K/J |
|  | H/N |
|  | K/L/N |
| Alcohol | E/F |
|  | K/J/F |
|  | H/N/F |
|  | K/L/N/F |
|  | G |

Product specificity can be fine-tuned using one or more enzymes shown in FIGS. 2 and 7. Chain length is controlled by one or more enzymes of the elongation pathway in conjunction with one more enzymes of the termination pathway as described above. The structure of the product is controlled by one or more enzymes of the termination pathway. Examples of selected termination pathway enzymes reacting with various pathway intermediates are shown in the table below. Additional examples are described herein.

| Enzyme | Substrate | Example |
|---|---|---|
| Acyl-CoA reductase | Acyl-CoA | Acr1 of *A. bayliyi* (GenBank AAC45217) |
|  | 3-Hydroxyacyl-CoA | PduP of *L reuteri* (GenBank CCC03595.1) |
|  | 3-Oxoacyl-CoA | Mcr of *S. tokodaii* (GenBank NP_378167) |
| Acyl-CoA hydrolase, transferase or synthetase | Acyl-CoA | tesB of *E. coli* (GenBank NP_414986) |
|  | 3-Hydroxyacyl-CoA | hibch of *R. norvegicus* (GenBank Q5XIE6.2) |
|  | 3-Oxoacyl-CoA | MKS2 of *S. lycopersicum* (GenBank ACG69783) |
|  | Enoyl-CoA | gctAB of *Acidaminococcus fermentans* (GenBank CAA57199, CAA57200) |
| Acyl-ACP acyl-transferase | Acyl-CoA | fabH of *E. coli* (GenBank AAC74175.1) |

Step H. Acyl-CoA Hydrolase, Transferase or Synthase

Acyl-CoA hydrolase, transferase and synthase enzymes convert acyl-CoA moieties to their corresponding acids. Such an enzyme can be utilized to convert, for example, a fatty acyl-CoA to a fatty acid, a 3-hydroxyacyl-CoA to a 3-hydroxyacid, a 3-oxoacyl-CoA to a 3-oxoacid, or an enoyl-CoA to an enoic acid.

CoA hydrolase or thioesterase enzymes in the 3.1.2 family hydrolyze acyl-CoA molecules to their corresponding acids. Several CoA hydrolases with different substrate ranges are suitable for hydrolyzing acyl-CoA, 3-hydroxyacyl-CoA, 3-oxoacyl-CoA and enoyl-CoA substrates to their corresponding acids. For example, the enzyme encoded by acot12 from *Rattus norvegicus* brain (Robinson et al., Biochem.Biophys.Res.Commun. 71:959-965 (1976)) can react with butyryl-CoA, hexanoyl-CoA and malonyl-CoA. The human dicarboxylic acid thioesterase, encoded by acot8, exhibits activity on glutaryl-CoA, adipyl-CoA, suberyl-CoA, sebacyl-CoA, and dodecanedioyl-CoA (Westin et al., *J.Bi-ol.Chem.* 280:38125-38132 (2005)). The closest *E. coli* homolog to this enzyme, tesB, can also hydrolyze a range of CoA thiolesters (Naggert et al., *J Biol Chem* 266:11044-11050 (1991)). A similar enzyme has also been characterized in the rat liver (Deana R, *Biochem Int* 26:767-773 (1992)). Additional enzymes with hydrolase activity in *E. coli* include ybgC, paaI, and ybdB (Kuznetsova, et al., *FEMS Microbiol Rev,* 2005, 29(2):263-279; Song et al., *J Biol Chem,* 2006, 281(16):11028-38). Though its sequence has not been reported, the enzyme from the mitochondrion of the pea leaf has a broad substrate specificity, with demonstrated activity on acetyl-CoA, propionyl-CoA, butyryl-CoA, palmitoyl-CoA, oleoyl-CoA, succinyl-CoA, and crotonyl-CoA (Zeiher et al., *Plant.Physiol.* 94:20-27 (1990)) The acetyl-CoA hydrolase, ACH1, from *S. cerevisiae* represents another candidate hydrolase (Buu et al., *J.Biol.Chem.* 278: 17203-17209 (2003)). Additional enzymes with aryl-CoA hydrolase activity include the palmitoyl-CoA hydrolase of *Mycobacterium tuberculosis* (Wang et al., *Chem.Biol.* 14:543-551 (2007)) and the acyl-CoA hydrolase of *E. coli* encoded by entH (Guo et al., *Biochemistry* 48:1712-1722 (2009)). Additional CoA hydrolase enzymes are described above.

| Gene name | GenBank Accession # | GI# | Organism |
|---|---|---|---|
| acot12 | NP_570103.1 | 18543355 | *Rattus norvegicus* |
| tesB | NP_414986 | 16128437 | *Escherichia coli* |
| acot8 | CAA15502 | 3191970 | *Homo sapiens* |
| acot8 | NP_570112 | 51036669 | *Rattus norvegicus* |
| tesA | NP_415027 | 16128478 | *Escherichia coli* |
| ybgC | NP_415264 | 16128711 | *Escherichia coli* |
| paaI | NP_415914 | 16129357 | *Escherichia coli* |
| ybdB | NP_415129 | 16128580 | *Escherichia coli* |
| ACH1 | NP_009538 | 6319456 | *Saccharomyces cerevisiae* |
| Rv0098 | NP_214612.1 | 15607240 | *Mycobacterium tuberculosis* |
| entH | AAC73698.1 | 1786813 | *Escherichia coli* |

CoA hydrolase enzymes active on 3-hydroxyacyl-CoA, 3-oxoacyl-CoA and enoyl-CoA intermediates are also well known in the art. For example, an enzyme for converting enoyl-CoA substrates to their corresponding acids is the glutaconate CoA-transferase from *Acidaminococcus fermentans*. This enzyme was transformed by site-directed mutagenesis into an acyl-CoA hydrolase with activity on glutaryl-CoA, acetyl-CoA and 3-butenoyl-CoA (Mack et al., *FEBS.Lett.* 405:209-212 (1997)). Another suitable enzyme is the fdcM thioesterase III of *E. coli.* This enzyme is involved in oleate beta-oxidation and the preferred substrate is 3,5-tetradecadienoyl-CoA (Nie et al, *Biochem* 47:7744-51(2008)).

| Protein | GenBank ID | GI Number | Organism |
|---|---|---|---|
| gctA | CAA57199.1 | 559392 | *Acidaminococcus fermentans* |
| gctB | CAA57200.1 | 559393 | *Acidaminococcus fermentans* |
| gctA | ACJ24333.1 | 212292816 | *Clostridium symbiosum* |
| gctB | ACJ24326.1 | 212292808 | *Clostridium symbiosum* |
| gctA | NP_603109.1 | 19703547 | *Fusobacterium nucleatum* |
| gctB | NP_603110.1 | 19703548 | *Fusobacterium nucleatum* |
| fadM | NP_414977.1 | 16128428 | *Escherichia coli* |

3-Hydroxyisobutyryl-CoA hydrolase is active on 3-hydroxyacyl-CoA substrates (Shimomura et al., *J Biol Chem.* 269:14248-14253 (1994)). Genes encoding this enzyme include hibch of *Rattus norvegicus* (Shimomura et al., *Methods Enzymol.* 324:229-240 (2000)) and *Homo sapiens* (Shimomura et al., supra). Similar gene candidates can also be identified by sequence homology, including hibch of *Saccharomyces cerevisiae* and BC 2292 of *Bacillus cereus*. An exemplary 3-oxoacyl-CoA hydrolase is MKS2 of *Solanum lycopersicum* (Yu et al, *Plant Physiol* 154:67-77 (2010)). The native substrate of this enzyme is 3-oxo-myristoyl-CoA, which produces a C14 chain length product.

| Gene name | GenBank Accession # | GI# | Organism |
|---|---|---|---|
| fadM | NP_414977.1 | 16128428 | *Escherichia coli* |
| hibch | Q5XIE6.2 | 146324906 | *Rattus norvegicus* |
| hibch | Q6NVY1.2 | 146324905 | *Homo sapiens* |
| hibch | P28817.2 | 2506374 | *Saccharomyces cerevisiae* |
| BC_2292 | AP09256 | 29895975 | *Bacillus cereus* |
| MKS2 | ACG69783.1 | 196122243 | *Solanum lycopersicum* |

CoA transferases catalyze the reversible transfer of a CoA moiety from one molecule to another. Several transformations require a CoA transferase to activate carboxylic acids to their corresponding acyl-CoA derivatives. CoA transferase enzymes have been described in the open literature and represent suitable candidates for these steps. These are described below.

The gene products of cat1, cat2, and cat3 of *Clostridium kluyveri* have been shown to exhibit succinyl-CoA, 4-hydroxybutyryl-CoA, and butyryl-CoA transferase activity, respectively (Seedorf et al., *Proc.Natl.AcadSci U.S.A.* 105: 2128-2133 (2008); Sohling et al., *J Bacteriol.* 178:871-880 (1996)). Similar CoA transferase activities are also present in *Trichomonas vaginalis*, *Trypanosoma brucei*, *Clostridium aminoburicum* and *Porphyromonas gingivalis* (Riviere et al., *J.Biol.Chem.* 279:45337-45346 (2004); van Grinsven et al., *J.Biol.Chem.* 283:1411-1418 (2008)).

| Protein | GenBank ID | GI Number | Organism |
|---|---|---|---|
| cat1 | P38946.1 | 729048 | *Clostridium kluyveri* |
| cat2 | P38942.2 | 172046066 | *Clostridium kluyveri* |
| cat3 | EDK35586.1 | 146349050 | *Clostridium kluyveri* |
| TVAG_395550 | XP_001330176 | 123975034 | *Trichomonas vaginalis* G3 |
| Tb11.02.0290 | XP_828352 | 71754875 | *Trypanosoma brucei* |
| cat2 | CAB60036.1 | 6249316 | *Clostridium aminobutyricum* |
| cat2 | NP_906037.1 | 34541558 | *Porphyromonas gingivalis* W83 |

A fatty acyl-CoA transferase that utilizes acetyl-CoA as the CoA donor is acetoacetyl-CoA transferase, encoded by the *E. coli* atoA (alpha subunit) and atoD (beta subunit) genes (Korolev et al., *Acta Crystallogr.D.Biol.Crystallogr.* 58:2116-2121(2002); Vanderwinkel et al., 33:902-908 (1968)). This enzyme has a broad substrate range on substrates of chain length C3-C6 (Sramek et al., *Arch Biochem Biophys* 171:14-26 (1975)) and has been shown to transfer the CoA moiety to acetate from a variety of branched and linear 3-oxo and acyl-CoA substrates, including isobutyrate (Matthies et al., *Appl Environ.Microbiol* 58:1435-1439 (1992)), valerate (Vanderwinkel et al., *Biochem.Biophys. .Res.Commun.* 33:902-908 (1968)) and butanoate (Vanderwinkel et al., *Biochem.Biophys.Res.Commun.* 33:902-908 (1968)). This enzyme is induced at the transcriptional level by acetoacetate, so modification of regulatory control may be necessary for engineering this enzyme into a pathway (Pauli et al., *Eur.J Biochem.* 29:553-562 (1972)). Similar enzymes exist in *Corynebacterium glutamicum* ATCC 13032 (Duncan et al., 68:5186-5190 (2002)), *Clostridium acetobutylicum* (Cary et al., *Appl Environ Microbiol* 56:1576-1583 (1990); Wiesenbom et al., *Appl Environ Microbiol* 55:323-329 (1989)), and *Clostridium saccharoperbulacetonicum* (Kosaka et al., *Biosci.Biotechnol Biochem.* 71:58-68 (2007)).

| Gene | GI # | Accession No. | Organism |
|---|---|---|---|
| atoA | 2492994 | P76459.1 | *Escherichia coli* |
| atoD | 2492990 | P76458.1 | *Escherichia coli* |
| actA | 62391407 | YP_226809.1 | *Corynebacterium glutamicum* |
| cg0592 | 62389399 | YP_224801.1 | *Corynebacterium glutamicum* |
| ctfA | 15004866 | NP_149326.1 | *Clostridium acetobutylicum* |
| ctfB | 15004867 | NP_149327.1 | *Clostridium acetobutylicum* |
| ctfA | 31075384 | AAP42564.1 | *Clostridium saccharoperbutylacetonicum* |
| ctfB | 31075385 | AAP42565.1 | *Clostridium saccharoperbutylacetonicum* |

Beta-ketoadipyl-CoA transferase, also known as succinyl-CoA:3:oxoacid-CoA transferase, is active on 3-oxoacyl-CoA substrates. This enzyme is encoded by pcaI and pcaJ in *Pseudomonas putida* (Kaschabek et al., *J Bacteriol.* 184: 207-215 (2002)). Similar enzymes are found in *Acinetobacter* sp. ADP1 (Kowalchuk et al., *Gene* 146:23-30 (1994)), *Streptomyces coelicolor* and *Pseudomonas knackmussii* (formerly sp. B13) (Gobel et al., *J Bacteriol.* 184: 216-223 (2002); Kaschabek et al., *J Bacteriol.* 184:207-215 (2002)). Additional exemplary succinyl-CoA:3:oxoacid-CoA transferases have been characterized in in *Helicobacter pylori* (Corthesy-Theulaz et al., *J Biol.Chem.* 272:25659-25667 (1997)), *Bacillus subtilis* (Stols et al., *Protein Expr. .Purif.* 53:396-403 (2007)) and *Homo sapiens* (Fukao, T., et al., *Genomics* 68:144-151(2000); Tanaka, H., et al., *Mol Hum Reprod* 8:16-23 (2002)). Genbank information related to these genes is summarized below.

| Gene | GI # | Accession No. | Organism |
|---|---|---|---|
| pcaI | 24985644 | AAN69545.1 | *Pseudomonas putida* |
| pcaJ | 26990657 | NP_746082.1 | *Pseudomonas putida* |
| pcaI | 50084858 | YP_046368.1 | *Acinetobacter* sp. ADP1 |
| pcaJ | 141776 | AAC37147.1 | *Acinetobacter* sp. ADP1 |
| pcaI | 21224997 | NP_630776.1 | *Streptomyces coelicolor* |
| pcaJ | 21224996 | NP_630775.1 | *Streptomyces coelicolor* |
| catI | 75404583 | Q8VPF3 | *Pseudomonas knackmussii* |
| catJ | 75404582 | Q8VPF2 | *Pseudomonas knackmussii* |
| HPAG1_0676 | 108563101 | YP_627417 | *Helicobacter pylori* |
| HPAG1_0677 | 108563102 | YP_627418 | *Helicobacter pylori* |
| ScoA | 16080950 | NP_391778 | *Bacillus subtilis* |
| ScoB | 16080949 | NP_391777 | *Bacillus subtilis* |
| OXCT1 | NP_000427 | 4557817 | *Homo sapiens* |
| OXCT2 | NP_071403 | 11545841 | *Homo sapiens* |

The conversion of acyl-CoA substrates to their acid products can be catalyzed by a CoA acid-thiol ligase or CoA synthetase in the 6.2.1 family of enzymes. CoA synthases that convert ATP to ADP (ADP-forming) are reversible and react in the direction of acid formation, whereas AMP forming enzymes only catalyze the activation of an acid to an acyl-CoA. For fatty acid formation, deletion or attenuation of AMP forming enzymes will reduce backflux. ADP-forming acetyl-CoA synthetase (ACD, EC 6.2.1.13) is an enzyme that couples the conversion of acyl-CoA esters to their corresponding acids with the concomitant synthesis of ATP. ACD I from *Archaeoglobus fulgidus*, encoded by AF1211, was shown to operate on a variety of linear and branched-chain substrates including isobutyrate, isopentanoate, and fumarate (Musfeldt et al., *J Bacteriol.* 184:636-

644 (2002)). A second reversible ACD in *Archaeoglobus fulgidus*, encoded by AF1983, was also shown to have a broad substrate range (Musfeldt and Schonheit, *J Bacteriol.* 184:636-644 (2002)). The enzyme from *Haloarcula marismortui* (annotated as a succinyl-CoA synthetase) accepts propionate, butyrate, and branched-chain acids (isovalerate and isobutyrate) as substrates, and was shown to operate in the forward and reverse directions (Brasen et al., *Arch Microbiol* 182:277-287 (2004)). The ACD encoded by PAE3250 from hyperthermophilic crenarchaeon *Pyrobaculum aerophilum* showed the broadest substrate range of all characterized ACDs, reacting with acetyl-CoA, isobutyryl-CoA (preferred substrate) and phenylacetyl-CoA (Brasen et al, supra). Directed evolution or engineering can be used to modify this enzyme to operate at the physiological temperature of the host organism. The enzymes from *A. fulgidus, H. marismortui* and *P. aerophilum* have all been cloned, functionally expressed, and characterized in *E. coli* (Brasen and Schonheit, supra; Musfeldt and Schonheit, *J Bacteriol.* 184:636-644 (2002)). An additional candidate is succinyl-CoA synthetase, encoded by sucCD of *E. coli* and LSCJ and LSC2 genes of *Saccharomyces cerevisiae*. These enzymes catalyze the formation of succinyl-CoA from succinate with the concomitant consumption of one ATP in a reaction which is reversible in vivo (Buck et al., *Biochemistry* 24:6245-6252 (1985)). The acyl CoA ligase from *Pseudomonas putida* has been demonstrated to work on several aliphatic substrates including acetic, propionic, butyric, valeric, hexanoic, heptanoic, and octanoic acids and on aromatic compounds such as phenylacetic and phenoxyacetic acids (Femandez-Valverde et al., *Appl.Environ.Microbiol.* 59:1149-1154 (1993)). A related enzyme, malonyl CoA synthetase (6.3.4.9) from *Rhizobium leguminosarum* could convert several diacids, namely, ethyl-, propyl-, allyl-, iso-propyl-, dimethyl-, cyclopropyl-, cyclopropylmethylene-, cyclobutyl-, and benzyl-malonate into their corresponding monothioesters (Pohl et al., *J. Am. Chem. Soc.* 123:5822-5823 (2001)).

| Protein | GenBank ID | GI Number | Organism |
|---|---|---|---|
| AF1211 | NP_070039.1 | 11498810 | *Archaeoglobus fulgidus* |
| AF1983 | NP_070807.1 | 11499565 | *Archaeoglobus fulgidus* |
| scs | YP_135572.1 | 55377722 | *Haloarcula marismortui* |
| PAE3250 | NP_560604.1 | 18313937 | *Pyrobaculum aerophilum* str. IM2 |
| sucC | NP_415256.1 | 16128703 | *Escherichia coli* |
| sucD | AAC73823.1 | 1786949 | *Escherichia coli* |
| LSC1 | NP_014785 | 6324716 | *Saccharomyces cerevisiae* |
| LSC2 | NP_011760 | 6321683 | *Saccharomyces cerevisiae* |
| paaF | AAC24333.2 | 22711873 | *Pseudomonas putida* |
| matB | AAC83455.1 | 3982573 | *Rhizobium leguminosarum* |

Step J. Acyl-ACP Reductase

The reduction of an acyl-ACP to its corresponding aldehyde is catalyzed by an acyl-ACP reductase (AAR). Such a transformation is depicted in step J of FIGS. 2 and 8. Suitable enzyme candidates include the orf1594 gene product of *Synechococcus elongatus* PCC7942 and homologs thereof (Schirmer et al, *Science*, 329: 559-62 (2010)). The *S. elongates* PCC7942 acyl-ACP reductase is coexpressed with an aldehyde decarbonylase in an operon that appears to be conserved in a majority of cyanobacterial organisms. This enzyme, expressed in *E. coli* together with the aldehyde decarbonylase, conferred the ability to produce alkanes. The *P. marinus* AAR was also cloned into *E. coli* and, together with a decarbonylase, demonstrated to produce alkanes (US Application 2011/0207203).

| Protein | GenBank ID | GI Number | Organism |
|---|---|---|---|
| orf1594 | YP_400611.1 | 81300403 | *Synechococcus elongatus* PCC7942 |
| PMT9312_0533 | YP_397030.1 | 78778918 | *Prochlorococcus marinus* MIT 9312 |
| syc0051_d | YP_170761.1 | 56750060 | *Synechococcus elongatus* PCC 6301 |
| Ava_2534 | YP_323044.1 | 75908748 | *Anabaena variabilis* ATCC 29413 |
| alr5284 | NP_489324.1 | 17232776 | *Nostoc* sp. PCC 7120 |
| Aazo_3370 | YP_003722151.1 | 298491974 | *Nostoc azollae* |
| Cyan7425_0399 | YP_002481152.1 | 220905841 | *Cyanothece* sp. PCC 7425 |
| N9414_21225 | ZP_01628095.1 | 119508943 | *Nodularia spumigena* CCY9414 |
| L8106_07064 | ZP_01619574.1 | 119485189 | *Lyngbya* sp. PCC 8106 |

Step K. Acyl-CoA:ACP Acyltransferase

The transfer of an acyl-CoA to an acyl-ACP is catalyzed by acyltransferase enzymes in EC class 2.3.1. Enzymes with this activity are described above.

Step L. Thioesterase

Acyl-ACP thioesterase enzymes convert an acyl-ACP to its corresponding acid. Such a transformation is required in step L of FIG. 2. Exemplary enzymes include the FatA and FatB isoforms of *Arabidopsis thaliana* (Salas et al, Arch Biochem Biophys 403:25-34 (2002)). The activities of these two proteins vary with carbon chain length, with FatA preferring oleyl-ACP and FatB preferring palmitoyl-ACP. A number of thioesterases with different chain length specificities are listed in WO 2008/113041 and are included in the table below. For example, it has been shown previously that expression of medium chain plant thioesterases like FatB from *Umbellularia califirnica* in *E. coli* results in accumulation of high levels of medium chain fatty acids, primarily laurate (C12:0). Similarly, expression of *Cuphea palustris* FatB1 thioesterase in *E. coli* led to accumulation of C8-10:0 products (Dehesh et al, *Plant Physiol* 110:203-10 (1996)). Similarly, *Carthamus tinctorius* thioesterase expressed in *E. coli* leads to >50 fold elevation in C 18:1 chain termination and release as free fatty acid (Knutzon et al, *Plant Physiol* 100:1751-58 (1992)). Methods for altering the substrate specificity of thioesterases are also known in the art (for example, EP1605048).

| Protein | GenBank ID | GI Number | Organism |
|---|---|---|---|
| fatA | AEE76980.1 | 332643459 | *Arabidopsis thaliana* |
| fatB | AEE28300.1 | 332190179 | *Arabidopsis thaliana* |
| fatB2 | AAC49269.1 | 1292906 | *Cuphea hookeriana* |
| fatB3 | AAC72881.1 | 3859828 | *Cuphea hookeriana* |
| fatB1 | AAC49179.1 | 1215718 | *Cuphea palustris* |
| M96568.1:94..1251 | AAA33019.1 | 404026 | *Carthamus tinctorius* |
| fatB1 | Q41635.1 | 8469218 | *Umbellularia californica* |
| tesA | AAC73596.1 | 1786702 | *Escherichia coli* |

Step N. Aldehyde Dehydrogenase (Acid Forming) or Carboxylic Acid Reductase

The conversion of an aldehyde to an acid is catalyzed by an acid-forming aldehyde dehydrogenase. Several *Saccha-* romyces cerevisiae enzymes catalyze the oxidation of aldehydes to acids including ALD1 (ALD6), ALD2 and ALD3 (Navarro-Avino et al, Yeast 15:829-42 (1999); Quash et al, *Biochem Pharmacol* 64:1279-92 (2002)). The mitochondrial proteins ALD4 and ALD5 catalyze similar transformations (Wang et al, J Bacteriol 180:822-30 (1998); Boubekeur et al, Eur J Biochem 268:5057-65 (2001)). HFD1 encodes a hexadecanal dehydrogenase. Exemplary acid-forming aldehyde dehydrogenase enzymes are listed in the table below.

| Protein | GenBank ID | GI number | Organism |
|---|---|---|---|
| ALD2 | NP_013893.1 | 6323822 | *Saccharomyces cerevisiae* s288c |
| ALD3 | NP_013892.1 | 6323821 | *Saccharomyces cerevisiae* s288c |
| ALD4 | NP_015019.1 | 6324950 | *Saccharomyces cerevisiae* s288c |
| ALD5 | NP_010996.2 | 330443526 | *Saccharomyces cerevisiae* s288c |
| ALD6 | NP_015264.1 | 6325196 | *Saccharomyces cerevisiae* s288c |
| HFD1 | NP_013828.1 | 6323757 | *Saccharomyces cerevisiae* s288c |
| CaO19.8361 | XP_710976.1 | 68490403 | *Candida albicans* |
| CaO19.742 | XP_710989.1 | 68490378 | *Candida albicans* |
| YALI0C03025 | CAG81682.1 | 49647250 | *Yarrowia lipolytica* |
| ANI_1_1334164 | XP_001398871.1 | 145255133 | *Aspergillus niger* |
| ANI_1_2234074 | XP_001392964.2 | 317031176 | *Aspergillus niger* |
| ANI_1_226174 | XP_001402476.1 | 145256256 | *Aspergillus niger* |
| ALDH | P41751.1 | 1169291 | *Aspergillus niger* |
| KLLA0D09999 | CAH00602.1 | 49642640 | *Kluyveromyces lactis* |

The conversion of an acid to an aldehyde is thermodynamically unfavorable and typically requires energy-rich cofactors and multiple enzymatic steps. For example, in butanol biosynthesis conversion of butyrate to butyraldehyde is catalyzed by activation of butyrate to its corresponding acyl-CoA by a CoA transferase or ligase, followed by reduction to butyraldehyde by a CoA-dependent aldehyde dehydrogenase. Alternately, an acid can be activated to an acyl-phosphate and subsequently reduced by a phosphate reductase. Direct conversion of the acid to aldehyde by a single enzyme is catalyzed by a bifunctional carboxylic acid reductase enzyme in the 1.2.1 family. Exemplary enzymes that catalyze these transformations include carboxylic acid reductase, alpha-aminoadipate reductase and retinoic acid reductase.

Carboxylic acid reductase (CAR), found in *Nocardia iowensis*, catalyzes the magnesium, ATP and NADPH-dependent reduction of carboxylic acids to their corresponding aldehydes (Venkitasubramanian et al., *J Biol.Chem.* 282: 478-485 (2007)). The natural substrate of this enzyme is benzoic acid and the enzyme exhibits broad acceptance of aromatic and aliphatic substrates including fatty acids of length C12-C18 (Venkitasubramanian et al., *Biocatalysis in Pharmaceutical and Biotechnology Industries.* CRC press (2006); WO 2010/135624). CAR requires post-translational activation by a phosphopantetheine transferase (PPTase) that converts the inactive apo-enzyme to the active holo-enzyme (Hansen et al., *Appl.Environ.Microbiol* 75:2765-2774 (2009)). The *Nocardia* CAR enzyme was cloned and functionally expressed in *E. coli* (Venkitasubramanian et al., *J Biol.Chem.* 282:478-485 (2007)). Co-expression of the npt gene, encoding a specific PPTase, improved activity of the enzyme. A related enzyme from *Mycobacterium* sp. strain JLS catalyzes the reduction of fatty acids of length C12-C16. Variants of this enzyme with enhanced activity on fatty acids are described in WO 2010/135624. Alpha-aminoadipate reductase (AAR, EC 1.2.1.31), participates in lysine biosynthesis pathways in some fungal species. This enzyme naturally reduces alpha-aminoadipate to alpha-aminoadipate semialdehyde. The carboxyl group is first activated through the ATP-dependent formation of an adenylate that is then reduced by NAD(P)H to yield the aldehyde and AMP. Like CAR, this enzyme utilizes magnesium and requires activation by a PPTase. Enzyme candidates for AAR and its corresponding PPTase are found in *Saccharomyces cerevisiae* (Morris et al., *Gene* 98:141-145 (1991)), *Candida albicans* (Guo et al., *Mol. Genet. Genomics* 269:271-279 (2003)), and *Schizosaccharomyces pombe* (Ford et al., *Curr. Genet.* 28:131-137 (1995)). The AAR from *S. pombe* exhibited significant activity when expressed in *E. coli* (Guo et al., *Yeast* 21:1279-1288 (2004)). The AAR from *Penicillium chrysogenum* accepts S-carboxymethyl-L-cysteine as an alternate substrate, but did not react with adipate, L-glutamate or diaminopimelate (Hijarrubia et al., *J Biol.Chem.* 278:8250-8256 (2003)). The gene encoding the *P. chrysogenum* PPTase has not been identified to date and no high-confidence hits were identified by sequence comparison homology searching.

| Protein | GenBank ID | GI Number | Organism |
|---|---|---|---|
| car | AAR91681.1 | 40796035 | *Nocardia iowensis* |
| npt | ABI83656.1 | 114848891 | *Nocardia iowensis* |
| car | YP_001070587.1 | 126434896 | *Mycobacterium* sp. strain JLS |
| npt | YP_001070355.1 | 126434664 | *Mycobacterium* sp. strain JLS |
| LYS2 | AAA34747.1 | 171867 | *Saccharomyces cerevisiae* |
| LYS5 | P50113.1 | 1708896 | *Saccharomyces cerevisiae* |
| LYS2 | AAC02241.1 | 2853226 | *Candida albicans* |
| LYS5 | AAO26020.1 | 28136195 | *Candida albicans* |
| Lys1p | P40976.3 | 13124791 | *Schizosaccharomyces pombe* |
| Lys7p | Q10474.1 | 1723561 | *Schizosaccharomyces pombe* |
| Lys2 | CAA74300.1 | 3282044 | *Penicillium chrysogenum* |

Additional car and npt genes can be identified based on sequence homology.

| Gene name | GI No. | GenBank Accession No. | Organism |
|---|---|---|---|
| fadD9 | 121638475 | YP_978699.1 | *Mycobacterium bovis* BCG |
| BCG_2812c | 121638674 | YP_978898.1 | *Mycobacterium bovis* BCG |
| nfa20150 | 54023983 | YP_118225.1 | *Nocardia farcinica* IFM 10152 |
| nfa40540 | 54026024 | YP_120266.1 | *Nocardia farcinica* IFM 10152 |
| SGR_6790 | YP_001828302.1 | 182440583 | *Streptomyces griseus* subsp. *griseus* NBRC 13350 |
| SGR_665 | YP_001822177.1 | 182434458 | *Streptomyces griseus* subsp. *griseus* NBRC 13350 |
| MSMEG_2956 | YP_887275.1 | 118473501 | *Mycobacterium smegmatis* MC2 155 |
| MSMEG_5739 | YP_889972.1 | 118469671 | *Mycobacterium smegmatis* MC2 155 |
| MSMEG_2648 | YP_886985.1 | 118471293 | *Mycobacterium smegmatis* MC2 155 |
| MAP1040c | NP_959974.1 | 41407138 | *Mycobacterium avium* subsp. *paratuberculosis* K-10 |
| MAP2899c | NP_961833.1 | 41408997 | *Mycobacterium avium* subsp. *paratuberculosis* K-10 |
| MMAR_2117 | YP_001850422.1 | 183982131 | *Mycobacterium marinum* M |
| MMAR_2936 | YP_001851230.1 | 183982939 | *Mycobacterium* |

-continued

| Gene name | GI No. | GenBank Accession No. | Organism |
|---|---|---|---|
| MMAR_1916 | YP_001850220.1 | 183981929 | *Mycobacterium marinum* M |
| Tpau_1373 | YP_003646340.1 | 296139097 | *Tsukamurella paurometabola* DSM 20162 |
| Tpau_1726 | YP_003646683.1 | 296139440 | *Tsukamurella paurometabola* DSM 20162 |
| CPCC7001_1320 | ZP_05045132.1 | 254431429 | *Cyanobium* PCC7001 |
| DDBDRAFT_0187729 | XP_636931.1 | 66806417 | *Dictyostelium discoideum* AX4 |

An additional enzyme candidate found in *Streptomyces griseus* is encoded by the griC and griD genes. This enzyme is believed to convert 3-amino-4-hydroxybenzoic acid to 3-amino-4-hydroxybenzaldehyde as deletion of either griC or griD led to accumulation of extracellular 3-acetylamino-4-hydroxybenzoic acid, a shunt product of 3-amino-4-hydroxybenzoic acid metabolism (Suzuki, et al., *J. Antibiot.* 60(6):380-387 (2007)). Co-expression of gnC and griD with SGR_665, an enzyme similar in sequence to the *Nocardia iowensis* npt, can be beneficial.

| Gene name | GI No | GenBank Accession No. | Organism |
|---|---|---|---|
| griC | YP_001825755.1 | 182438036 | *Streptomyces griseus* subsp. *griseus* NBRC 13350 |
| griD | YP_001825756.1 | 182438037 | *Streptomyces griseus* subsp. *griseus* NBRC 13350 |

Example XIII

Production of 1,3-Butanediol from Glucose in *Saccharomyces cerevisiae*

This example illustrates the construction and biosynthetic production of 1,3-BDO from glucose in *Saccharomyces cerevisiae*.

The pathway for 1,3-BDO production is comprised of two MI-FAE cycle enzymes (thiolase and 3-oxoacyl-CoA reductase), in conjunction with termination pathway enzymes (acyl-CoA reductase (aldehyde forming) and alcohol dehydrogenase). The 1,3-BDO pathway engineered into *S. cerevisiae* is composed of four enzymatic steps which transform acetyl-CoA to 1,3-BDO. The first step entails the condensation of two molecules of acetyl-CoA into acetoacetyl-CoA by an acetoacetyl-CoA thiolase enzyme (THL). In the second step, acetoacetyl-CoA is reduced to 3-hydroxybutyryl-CoA by acetoacetyl-CoA reductase, also called 3-hydroxybutyryl-CoA dehydrogenase (HBD). 3-hydroxybutyryl-CoA reductase (ALD) catalyzes formation of the aldehyde from the acyl-CoA. Further reduction of 3-hydroxybutyraldehyde to 1,3-BDO is catalyzed by 1,3-BDO dehydrogenase (ADH).

To enable 13-BDO production in the cytosol, two acetyl-CoA forming pathways were engineered into *S. cerevisiae*. The first pathway entails conversion of pyruvate to acetyl-CoA by pyruvate decarboxylase (FIG. 3E), acetaldehyde dehydrogenase (FIG. 3F) and acetyl-CoA synthetase (FIG. 3B). The second pathway is pyruvate formate lyase (FIG. 3H).

For each enzymatic step of the 1,3-BDO pathway, a list of applicable genes was assembled for corroboration. The genes cloned and assessed in this study are presented below in Table 1, along with the appropriate references and URL citations to the polypeptide sequence.

TABLE 1

| Exemplary Step | ID | Gene | NCBI Accession # | GI | Source Organism |
|---|---|---|---|---|---|
| Acetoacetyl-CoA thiolase (THL) | | | | | |
| FIG. 2A | 1502 | thiI | P45359.1 | 1174677 | *Clostridium acetobutylicum* ATCC 824 |
| FIG. 2A | 1491 | atoB | NP_416728 | 16130161 | *Escherichia coli* str. K-12 substr. MG1655 |
| FIG. 2A | 560 | thiA | NP_349476.1 | 15896127 | *Clostridium acetobutylicum* ATCC 824 |
| FIG. 2A | 1512 | phbA | P07097.4 | 135759 | *Zoogloea ramigera* |
| FIG. 2A | 1501 | phbA | P14611.1 | 135754 | *Ralstonia eutropha* H16 |
| 3-Hydroxybutyryl-CoA dehydrogenase (HBD) | | | | | |
| FIG. 2B | 1495 | hbd | AAM14586.1 | 20162442 | *Clostridium beijerinckii* NCIMB 8052 |
| 3-Hydroxybutyryl-CoA reductase (ALD) | | | | | |
| FIG. 2E | 707 | Lvis_1603 | YP_795711.1 | 116334184 | *Lactobacillus brevis* ATCC 367 |
| 3-Hydroxybutyraldehyde reductase (ADH) | | | | | |
| FIG. 2F | 28 | bdh | BAF45463.1 | 124221917 | *Clostridium saccharoperbutylacetonicum* |
| Pyruvate formate lyase (PflAB) | | | | | |
| FIG. 3H | 1799 | pflA | NP_415422.1 | 16128869 | *Escherichia coli* MG1655 |
| FIG. 3H | 500 | pflB | NP_415423 | 16128870 | *Escherichia coli* MG1655 |

TABLE 1-continued

| Exemplary Step | ID | Gene | NCBI Accession # | GI | Source Organism |
|---|---|---|---|---|---|
| PDH Bypass (aldehyde dehydrogenase, acetyl-CoA synthase) | | | | | |
| FIG. 3F | 1849 | ALD6 | NP_015264.1 | 6325196 | Saccharomyces cerevisiae S288c |
| FIG. 3B | 1845 | Acs | AAL23099.1 | 16422835 | Salmonella enterica LT2 |
| FIG. 3B | 1845A | Acsm | AAL23099.1 | 16422835 | Salmonella enterica LT2 |

Genes were cloned via PCR from the genomic DNA of the native or wild-type organism. Primers used to amplify the pathway genes are (from 5' to 3'; underlined sequences are gene specific):

Thl 1502:
FP:
(SEQ ID NO: 8)
TCTAATCTAAGTTTTCTAGAACTAGTAAAGATGAGAGATGTAGTAATAG

TAAGTGCTGTA

RP:
(SEQ ID NO: 9)
GATATCGAATTCCTGCAGCCCGGGGGATCCTTAGTCTCTTTCAACTACG

AGAGCTGTT

Thl 1491:
FP:
(SEQ ID NO: 10)
TCTAATCTAAGTTTTCTAGAACTAGTAAAGATGAAAAATTGTGTCATCG

TCAGTG

RP:
(SEQ ID NO: 11)
GATATCGAATTCCTGCAGCCCGGGGGATCCTTAATTCAACCGTTCAATC

ACCATCGCAAT

Thl 560:
FP:
(SEQ ID NO: 12)
AATCTAAGTTTTCTAGAACTAGTAAAGATGAAAGAAGTTGTAATAGCTA

GTGCAGTAA

RP:
(SEQ ID NO: 13)
TATCGAATTCCTGCAGCCCGGGGGATCCTTAATGGTGATGGTGATGATG

GCACTTTTCTA

Thl 1512:
FP:
(SEQ ID NO: 14)
TCTAATCTAAGTTTTCTAGAACTAGTAAAGATGAGCACCCCGTCCATCG

TCA

PR:
(SEQ ID NO: 15)
GATATCGAATTCCTGCAGCCCGGGGGATCCCTAAAGGCTCTCGATGCAC

ATCGCC

Thl 1501:
FP:
(SEQ ID NO: 16)
TAAGCTAGCAAGAGGAGAAGTCGACATGACTGACGTTGTCATCGTATCC

GC

RP:
(SEQ ID NO: 17)
GCCTCTAGGAAGCTTTCTAGATTATTATTTGCGCTCGACTGCCAGC

Hbd 1495:
FP:
(SEQ ID NO: 18)
AAGCATACAATCAACTATCTCATATACAATGAAAAAGATTTTTGTACTT

GGAGCA

RP:
(SEQ ID NO: 19)
AAAAATCATAAATCATAAGAAATTCGCTTATTTAGAGTAATCATAGAAT

CCTTTTCCTGA

Ald 707:
FP:
(SEQ ID NO: 20)
AATCTAAGTTTTCTAGAACTAGTAAAGATGAACACAGAAAACATTGAAC

AAGCCAT

RP:
(SEQ ID NO: 21)
TATCGAATTCCTGCAGCCCGGGGGATCCCTAAGCCTCCCAAGTCCGTAA

TGAGAACCCTT

Adh 28:
FP:
(SEQ ID NO: 22)
CCAAGCATACAATCAACTATCTCATATACAATGGAGAATTTTAGATTTA

ATGCATATACA

RP:
(SEQ ID NO: 23)
AATAAAAATCATAAATCATAAGAAATTCGCTTAAAGGGACATTTCTAAA

ATTTTATATAC 1845A is a sequence variant of the wild type (1845) enzyme. The variation is a point mutation in the residue Leu-641 (L641P), described in Starai and coworkers (Starai et al, *J Biol Chem* 280: 26200-5 (2005)). The function of the mutation, e.g., is to prevent post-translational regulation by acetylation and maintain the Acs enzyme in its active state.

Shuttle plasmids shown in Table 2 were constructed for expression of heterologous genes in *S. cerevisiae*. Plasmids d9, d10, and d11 are empty plasmid controls with the selection marker of Ura, His, and Leu, respectively. Plasmids d12 or d13 contains a single ALD or ADH gene with the URA3 selection marker. Plasmids d14, d16, and d17 contains hbd and thil genes with the HIS3 selection marker.

TABLE 2

| Plasmid | Selection Marker | Gene(s) |
|---|---|---|
| pESC-L | URA3 | NA |
| pESC-H | HIS3 | NA |
| pESC-U | LEU2 | NA |
| pY3Hd1 | URA3 | 1799(pflA)-500(pflB) |

TABLE 2-continued

| Plasmid | Selection Marker | Gene(s) |
|---|---|---|
| pY3Hd2 | HIS3 | 1799(pflA)-500(pflB) |
| pY3Hd3 | LEU2 | 1799(pflA)-500(pflB) |
| pY3Hd4 | URA3 | 1849(ALD6)-1845(Acs) |
| pY3Hd5 | URA3 | 1849(ALD6)-1845A(Acsm) |
| pY3Hd6 | URA3 | 1495(Hbd) - 1491(Thl) |
| pY3Hd7 | URA3 | 1495(Hbd) - 560(Thl) |
| pY3Hd8 | LEU2 | 28(ADH)-707(ALD) |
| pY3Hd9 | URA3 | NA |
| pY3Hd10 | HIS3 | NA |
| pY3Hd11 | LEU2 | NA |
| pY3Hd12 | URA3 | 707(ALD) |
| pY3Hd13 | URA3 | 28(ADH) |
| pY3Hd14 | HIS3 | 1495(Hbd) - 1502(Thl) |
| pY3Hd15 | HIS3 | 1495(Hbd) - 1512(Thl) |
| pY3Hd16 | HIS3 | 1495(Hbd) - 1491(Thl) |
| pY3Hd17 | HIS3 | 1495(Hbd) - 560 (Thl) |

Yeast host BY4741 [MATa his3Δ0 leu2Δ0 met15Δ0 ura3Δ0] was chosen as the host strain for this work as a wild-type laboratory strain with the appropriate auxotrophic markers to host the pathway plasmids BY4741 was transformed with plasmids containing 1,3-BDO pathway genes alone or along with plasmids that contain PDH bypass genes or pflAB genes. Vector backbones used in this example include p427TEF yeast expression vectors, the pY3H bridging vectors (Sunrise Science) and pESC yeast epitope tagging vectors (Agilent Technologies). The pY3H vector containing a TEF1 promoter, CYC terminator and URA3 selection marker from *S. cerevisiae* was used to build dual-promoter plasmids with different selection markers. ADH1 promoter and terminator sequences from *S. cerevisiae* were inserted upstream of the TEF1 promoter so the two transcriptional units are in a back-to-back orientation. The SV40 nuclear localization signal sequence was removed during the cloning process. The resulting plasmid was named pY3Hd9. To construct plasmids with a different selection marker, the URA3 gene in pY3Hd9 was replaced with the HIS3 or LEU2 gene from *S. cerevisiae* to produce pY3Hd10 and pY3Hd11, respectively. Two of the four 1,3-BDO pathway genes—Hbd and Thl (see Table 103 for gene numbers)—were cloned into the dual-promoter plasmid with the HIS3 marker such that the expression of the Hbd genes is controlled by the ADH1 promoter while the expression of the Thl gene is controlled by the TEF1 promoter (pY3Hd14~17). Ald and Adh genes were cloned into the dual-promoter plasmid with the LEU2 selection marker such that the ADH1 promoter drives the adh genes and the TEF1 promoter drives the ald genes (pY3Hd8). The PflAB genes or the PDH bypass genes (ALD6 and acs) were cloned into the dual-promoter plasmid with the URA3 marker where pflA or ALD6 is controlled under the ADH1 promoter and pflB or acs is controlled under the TEF1 promoter. Yeast transformation was done using Frozen-EZ Yeast Transformation (Zymo Research).

Tables 3 and 4 show the combinations of plasmids and experimental conditions tested.

TABLE 3

| Sample | Plasmid 1 | Plasmid 2 | plasmid 3 | gene 1 | gene 2 | gene 3 | gene 4 | gene 5 | gene 6 | Aeroation | Note |
|---|---|---|---|---|---|---|---|---|---|---|---|
| 1 | pESC-L | pESC-H | | | | | | | | Anaerobic | EV2 |
| 2 | pESC-L | pESC-H | | | | | | | | 23G | EV2 |
| 3 | d8 | d16 | | 1495 | 1491 | 28 | 707 | | | Anaerobic | BDO |
| 4 | d8 | d16 | | 1495 | 1491 | | 707 | | | Anaerobic | BDO |
| 5 | d8 | d16 | | 1495 | 1491 | | 707 | | | 23G | BDO |
| 6 | d8 | d16 | | 1495 | 1491 | | 707 | | | 23G | BDO |
| 7 | d8 | d17 | | 1495 | 560 | | 707 | | | Anaerobic | BDO |
| 8 | d8 | d17 | | 1495 | 560 | | 707 | | | Anaerobic | BDO |
| 9 | d8 | d17 | | 1495 | 560 | | 707 | | | 23G | BDO |
| 10 | d8 | d17 | | 1495 | 560 | 28 | 707 | | | 23G | BDO |
| 11 | pESC-H | pESC-L | pESC-U | | | | | | | Anaerobic | EV3 |
| 12 | pESC-H | pESC-L | pESC-U | | | | | | | 23G | EV3 |
| 13 | d8 | d16 | d1 | 1495 | 1491 | 28 | 707 | pflA | pflB | Anaerobic | BDO + pflAB |
| 14 | d8 | d16 | d1 | 1495 | 1491 | 28 | 707 | pflA | pflB | Anaerobic | BDO + pflAB |
| 15 | d8 | d16 | d1 | 1495 | 1491 | 28 | 707 | pflA | pflB | 23G | BDO + pflAB |
| 16 | d8 | d16 | d1 | 1495 | 1491 | 28 | 707 | pflA | pflB | 23G | BDO + pflAB |
| 17 | d8 | d17 | d1 | 1495 | 560 | 28 | 707 | pflA | pflB | Anaerobic | BDO + pflAB |
| 18 | d8 | d17 | d1 | 1495 | 560 | 28 | 707 | pflA | pflB | Anaerobic | BDO + pflAB |
| 19 | d8 | d17 | d1 | 1495 | 560 | 28 | 707 | pflA | pflB | 23G | BDO + pflAB |
| 20 | d8 | d17 | d1 | 1495 | 560 | 28 | 707 | pflA | pflB | 23G | BDO + pflAB |
| 21 | d8 | d16 | d5 | 1495 | 1491 | 28 | 707 | ALD6 | acsm | Anaerobic | BDO + PDH |
| 22 | d8 | d16 | d5 | 1495 | 1491 | 28 | 707 | ALD6 | acsm | Anaerobic | BDO + PDH |
| 23 | d8 | d16 | d5 | 1495 | 1491 | 28 | 707 | ALD6 | acsm | 23G | BDO + PDH |
| 24 | d8 | d16 | d5 | 1495 | 1491 | 28 | 707 | ALD6 | acsm | 23G | BDO + PDH |
| 25 | d8 | d17 | d5 | 1495 | 560 | 28 | 707 | ALD6 | acsm | Anaerobic | BDO + PDH |
| 26 | d8 | d17 | d5 | 1495 | 560 | 28 | 707 | ALD6 | acsm | Anaerobic | BDO + PDH |
| 27 | d8 | d17 | d5 | 1495 | 560 | 28 | 707 | ALD6 | acsm | 23G | BDO + PDH |
| 28 | d8 | d17 | d5 | 1495 | 560 | 28 | 707 | ALD6 | acsm | 23G | BDO + PDH |

TABLE 4

| Plasmid 1 | Plasmid 2 | plasmid 3 | gene 1 | gene 2 | gene 3 | gene 4 | gene 5 | gene 6 | Aeroation | Note |
|---|---|---|---|---|---|---|---|---|---|---|
| d9 | d11 | | | | | | | | aerobic | EVC |
| d8 | d17 | | 1495 | 560 | 28 | 707 | | | aerobic | BDO |
| d8 | d17 | d5 | 1495 | 560 | 28 | 707 | 1849 | 1845A | aerobic | BDO + PDH |
| d8 | d14 | | 1495 | 1502 | 28 | 707 | | | aerobic | BDO |
| d8 | d14 | d5 | 1495 | 1502 | 28 | 707 | 1849 | 1845A | aerobic | BDO + PDH |

In Table 3, colonies were inoculated in 5 ml of 2% glucose medium with corresponding amino acid dropouts and cultured at 30 degree for approximately 48 hrs. Cells were briefly spun down and re-suspended in 2 ml fresh 2% glucose medium with tween-80 and ergosterol added. Resuspended cultures were added to 10 ml fresh glucose medium in 20 ml bottles to obtain a starting OD of 0.2. For anaerobic cultures, the bottles containing cultures were vacuumed and filled with nitrogen. For micro-aerobic growth, a 23G needle was inserted. All the cultures were incubated at 30 degree with shaking for 24 hours. In Table 4, the experiment was carried out in a 96-well plate and cells grown aerobically in 1.2 ml of medium with varying glucose and acetate concentrations (5% glucose, 10% glucose, 5% glucose+50 mM acetate, and 10% glucose+50 mM acetate).

Concentrations of glucose, 1,3-BDO, alcohols, and other organic acid byproducts in the culture supernatant were determined by HPLC using an HPX-87H column (BioRad).

Figure 9:
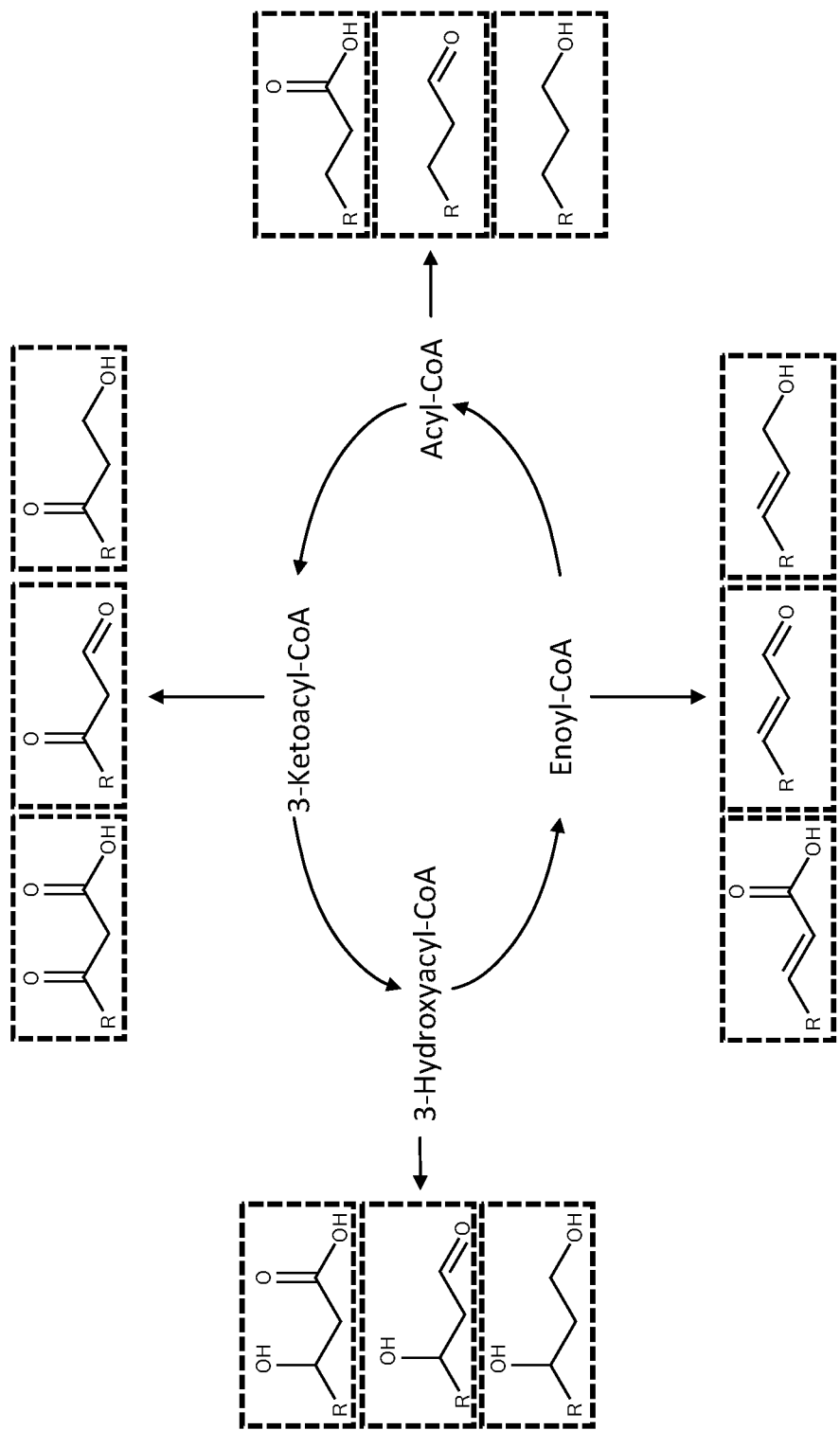
FIG. 9 shows exemplary compounds that can be produced from the four MI-FAE or MD-FAE cycle intermediates using the cycles depicted in FIG. 6 and the termination pathways depicted in FIG. 7. R is $C_{1-24}$ linear alkyl.

MI-FAE cycle and termination pathway genes were tested with or without pflAB or PDH bypass. As shown in FIGS. 9-11, these constructs produced 0.3-3.35 mM 1,3-BDO in yeast S. cerevisiae BY4741, and ethanol was produced in the tested samples tested. The PDH bypass (here, overexpression of ALD6 and acs or acsm genes) improved production of 1,3-BDO.

Example XIV

Enzymatic Activity of 1,3-Butanediol Pathway Enzymes

This example describes the detection of 1,3-BDO pathway enzyme activity using in vitro assays.

Activity of the heterologous enzymes was tested in in vitro assays, using an internal yeast strain as the host for the plasmid constructs containing the pathway genes. Cells were grown aerobically in yeast media containing the appropriate amino acid for each construct. To obtain crude extracts for activity assays, cells were harvested by centrifugation. The pellets were resuspended in 0.1 mL 100 mM Tris pH 7.0 buffer containing protease inhibitor cocktail. Lysates were prepared using the method of bead beating for 3 min. Following bead beating, the solution was centrifuged at 14,000 rpm (Eppendorf centrifuge 5402) for 15 min at 4° C. Cell protein in the sample was determined using the method of Bradford et al., Anal. Biochem. 72:248-254 (1976), and specific enzyme assays conducted as described below.

Thiolase

Figure 13A:
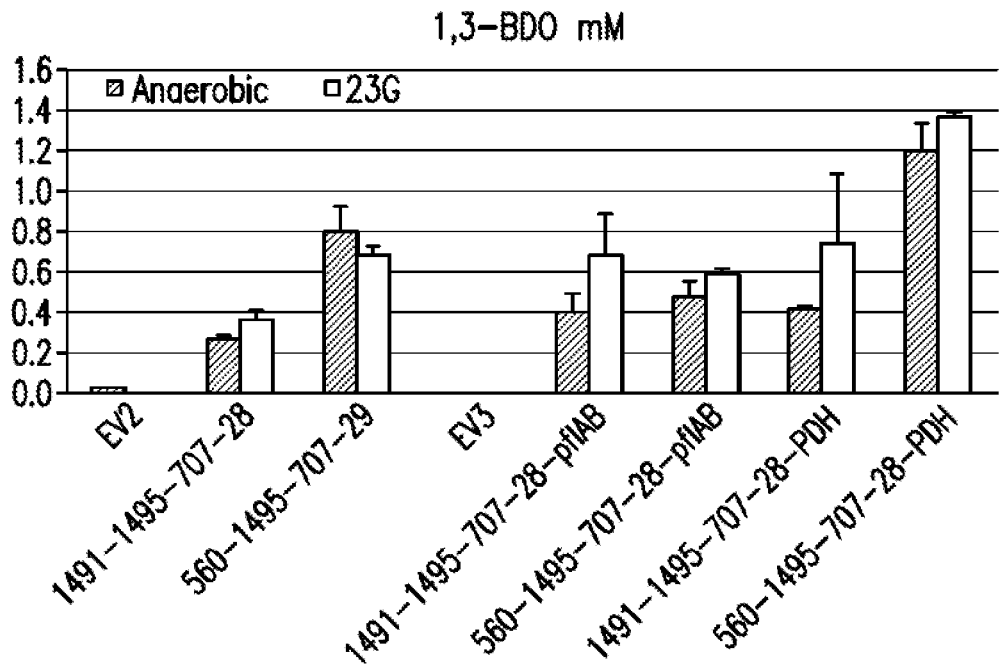
FIGS. 13A and 13B depict the production of 1,3-butanediol (FIG. 13A) or ethanol (FIG. 13B) in S. cerevisiae transformed with plasmids comprising genes encoding various MI-FAE cycle and termination pathway enzymes, either with or without pflAV or PDH bypass, as provided in Example XIII.
Figure 13B:
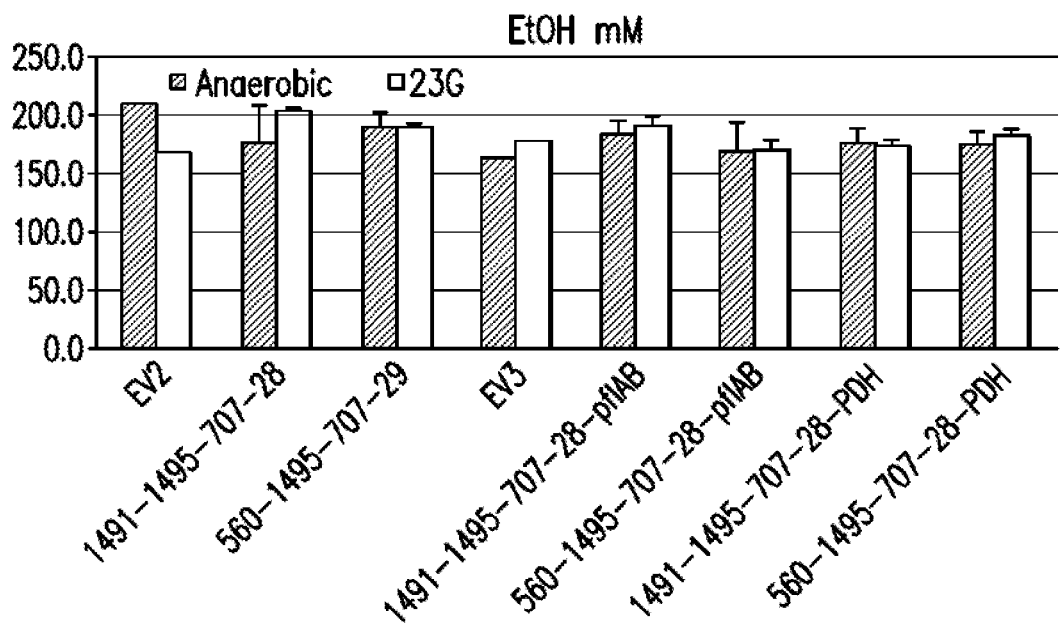

Thiolase enzymes catalyze the condensation of two acetyl-CoA to form acetoacetyl-CoA. In the reaction, coenzyme A (CoA) is released and the free CoA can be detected using 5,5'-dithiobis-2-nitrobenzoic acid (DTNB) which absorbs at 410 nm upon reaction with CoA. Five thiolases were tested (see Example XIII, Table 1). Estimated specific activity in E. coli crude lysates is shown in FIGS. 13A and 13B.

Among the Thl that showed expressed protein, 1512 and 1502 demonstrated the highest specific activity for acetyl-CoA condensation activity n E. coli crude lysates.

Both 1491 and 560 were cloned in dual promoter yeast vectors with 1495, which is the 3-hydroxybutyryl-CoA dehydrogenase (see FIGS. 14A-14D). These thiolases were evaluated for acetyl-CoA condensation activity, and the data is shown in FIGS. 14A-14D. The results indicate that both 560 and 1491 demonstrate an initial burst of activity that is too fast to measure. However, after the initial enzyme rate, the condensation rate of 560 is greater than 1491. Thus, there is protein expression and active enzyme with the yeast dual promoter vectors as indicated by active thiolase activity observed in crude lysates.

3-Hydroxybutyryl-CoA Dehydrogenase (Hbd)

Figure 15:
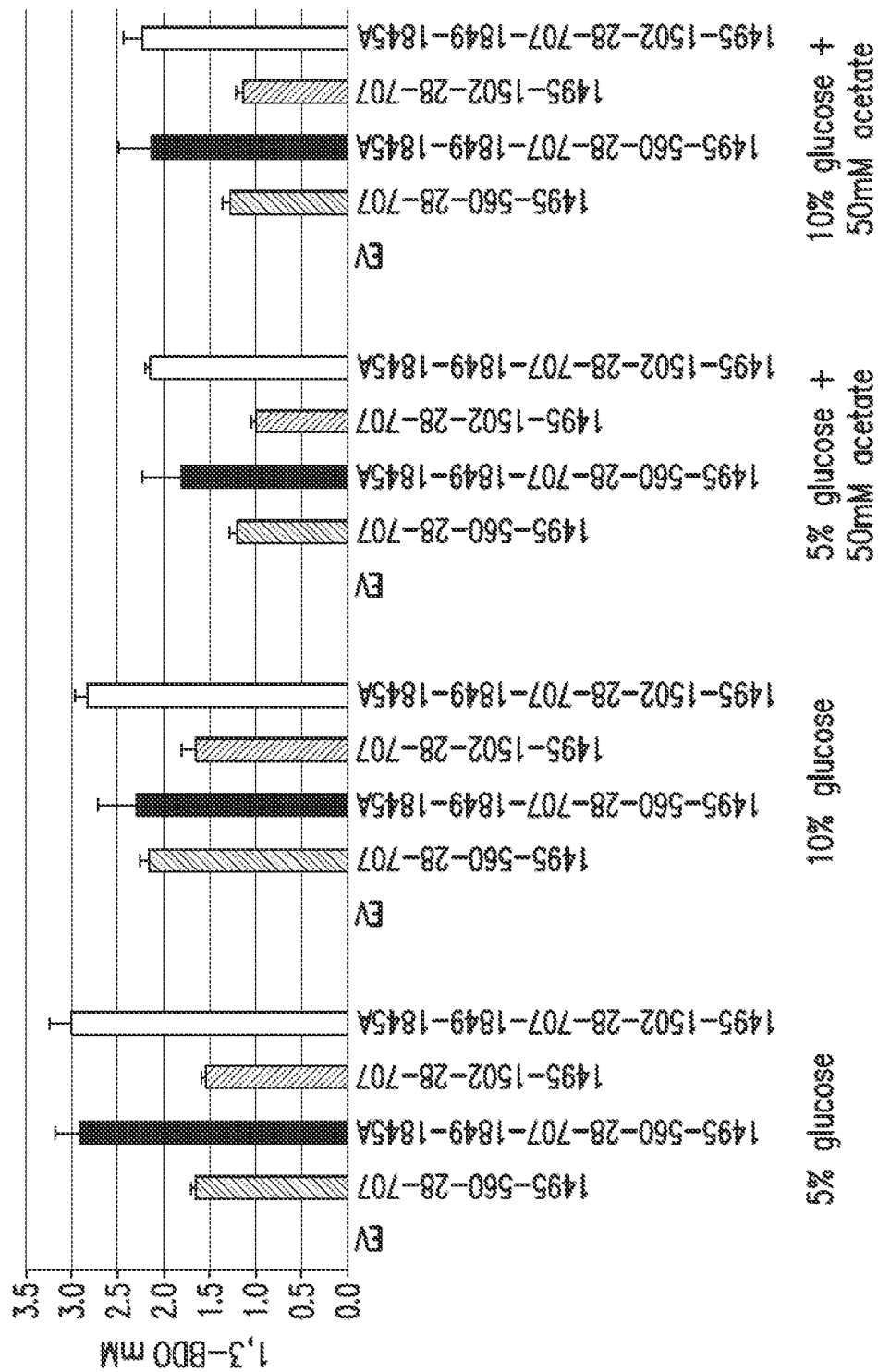
FIG. 15 depicts the production of 1,3-butanediol in *S. cerevisiae* transformed with plasmids comprising genes encoding various MI-FAE cycle and termination pathway enzymes, either with or without pflAV or PDH bypass, as provided in Example XIII.

Acetoacetyl-CoA is metabolized to 3-hydroxybutyryl-CoA by 3-hydroxybutyryl-CoA dehydrogenase. The reaction requires oxidation of NADH, which can be monitored by fluorescence at an excitation wavelength at 340 nm and an emission at 460 nm. The oxidized form, NAD+, does not fluoresce. This detection strategy was used for all of the dehydrogenase steps. 1495, the Hbd from Clostridium beijerinckii, was assayed in the dual promoter yeast vectors that contained either 1491 (vector id=pY3Hd17) or 560 (vector id=pY3Hd16). See Table 1 for GenBank identifiers of each enzyme. The time course data is shown in FIG. 15.

Figure 16:
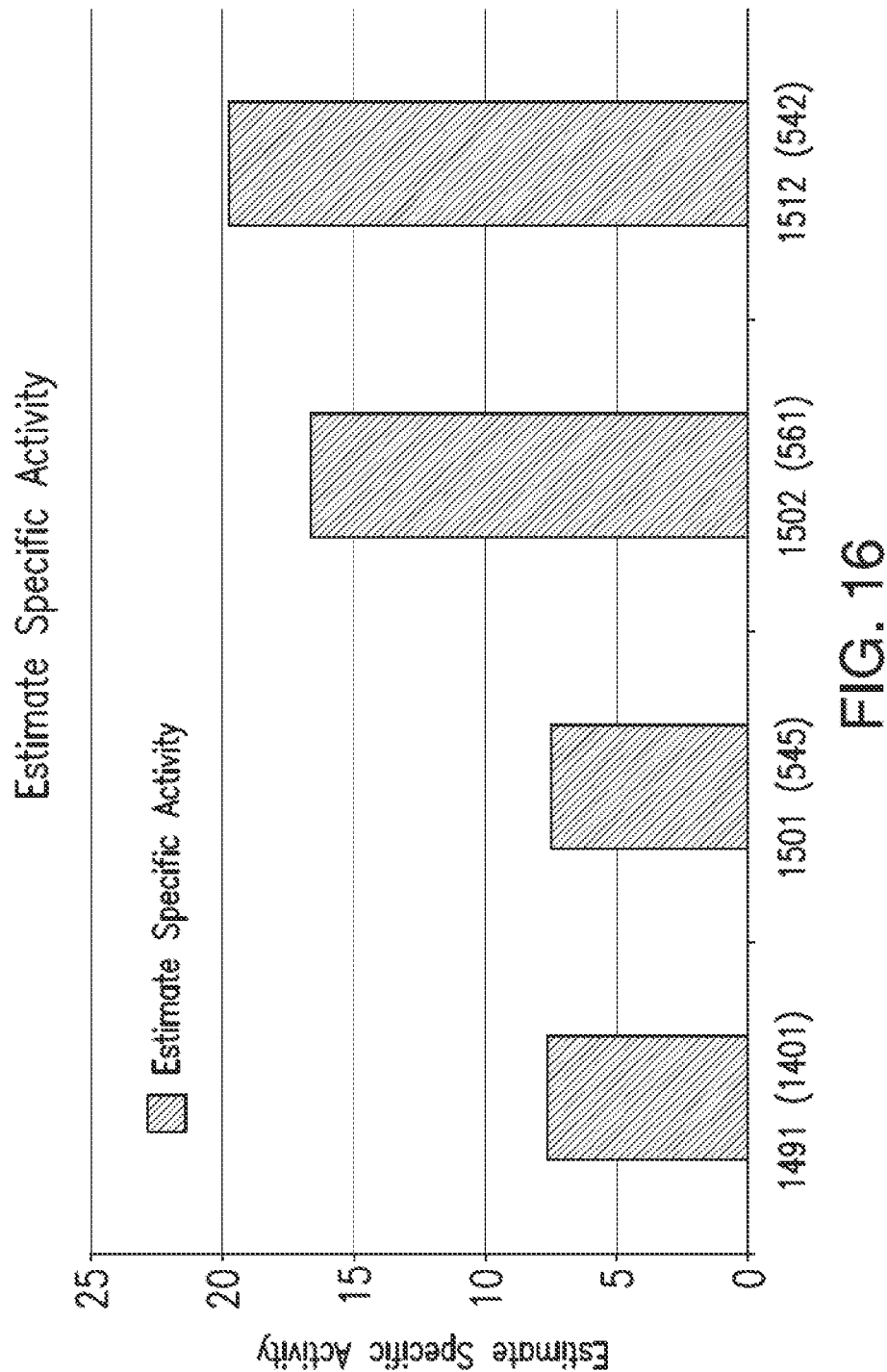
FIG. 16 depicts the estimated specific activity of five thiolases for acetyl-CoA condensation activity in *E. coli* as provided in Example XIV.

The Hbd rate of 1495 containing 560 was much faster than 1491. The results provided in FIG. 16 show that the Hbd prefers NADH over NADPH. The Hbd enzyme appears to display the fastest catalytic activity among the four pathway enzymes in crude lysates. The Hbd enzyme, i.e. a 3-ketoacyl-CoA reductase, is an example of a MI-FAE cycle or MD-FAE cycle enzyme that preferentially reacts with an NADH cofactor.

Aldehyde Deyhdrogenase (Ald)

An aldehyde reductase converts 3-hydroxybutyryl-CoA to 3-hydroxybutyraldehyde. This reaction requires NAD(P)H oxidation, which can be used to monitor enzyme activity. The Ald from Lactobacillus brevis (Gene ID 707) was cloned in a dual vector that contained the alcohol dehydrogenase from Clostridium saccharoperbutylacetonicum (Gene ID 28). These two enzymes were cloned in another dual promoter yeast vector containing a Leu marker.

Figures 17A, 17B:
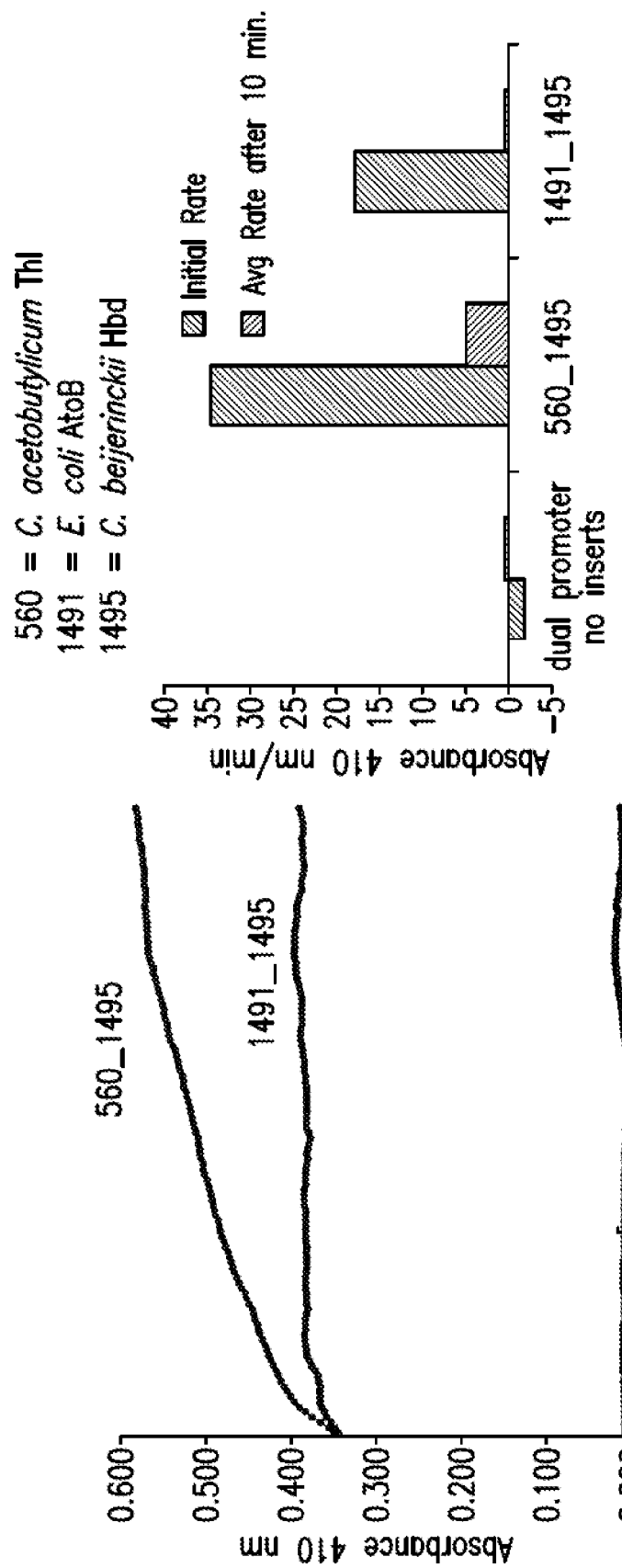
FIGS. 17A and 17B depict the estimated specific activity of two thiolases (1491 and 560) cloned in dual promoter yeast vectors with 1495 (a 3-hydroxybutyryl-CoA dehydrogenase) for acetyl-CoA condensation activity in *E. coli* as provided in Example XIV.

The Ald activity data for crude lysates is shown in FIGS. 17A and 17B with a 707 lysate from E. coli used as a standard. The results indicate the 707 showed enzyme activity in yeast lysates that is comparable to the lysate from bacteria. In addition, the 707 gene product prefers NADH to NADPH as the cofactor. The 707 gene product, i.e. an acy-CoA reductase (aldehyde forming), is an example of a termination pathway enzyme that preferentially reacts with an NADH cofactor.

Alcohol Dehydrogenase (Adh)

1,3-BDO is formed by an alcohol dehydrogenase (Adh), which reduces 3-hydroxybutyraldehyde in the presence of NAD(P)H. The oxidation of NAD(P)H can be used to monitor the reaction as described above.

Figure 18:
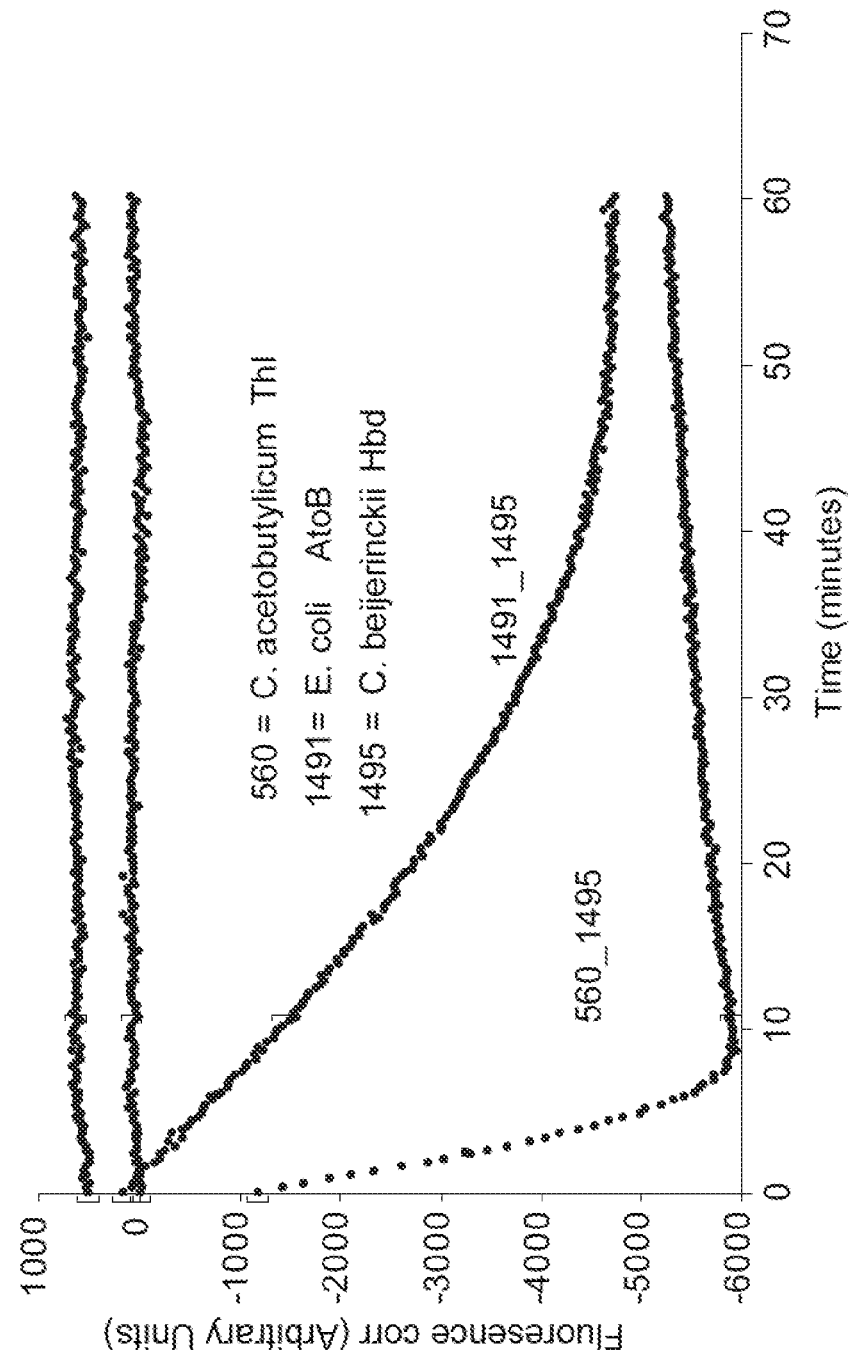
FIG. 18 depicts the time course of fluorescence detection of oxidation of NADH, which is used to measure the metabolism of acetoacetyl-CoA to 3-hydroxybutyryl-CoA by 3-hydroxybutyryl-CoA dehydrogenase, as provided in Example XIV. Acetoacetyl-CoA is metabolized to 3-hydroxybutyryl-CoA by 3-hydroxybutyryl-CoA dehydrogenase. The reaction requires oxidation of NADH, which can be monitored by fluorescence at an excitation wavelength at 340 nm and an emission at 460 nm. The oxidized form, NAD+, does not fluoresce. 1495, the Hbd from *Clostridium beijerinckii*, was assayed in the dual promoter yeast vectors that contained either 1491 (vector id=pY3Hd17) or 560 (vector id=pY3Hd16).
Figure 19:
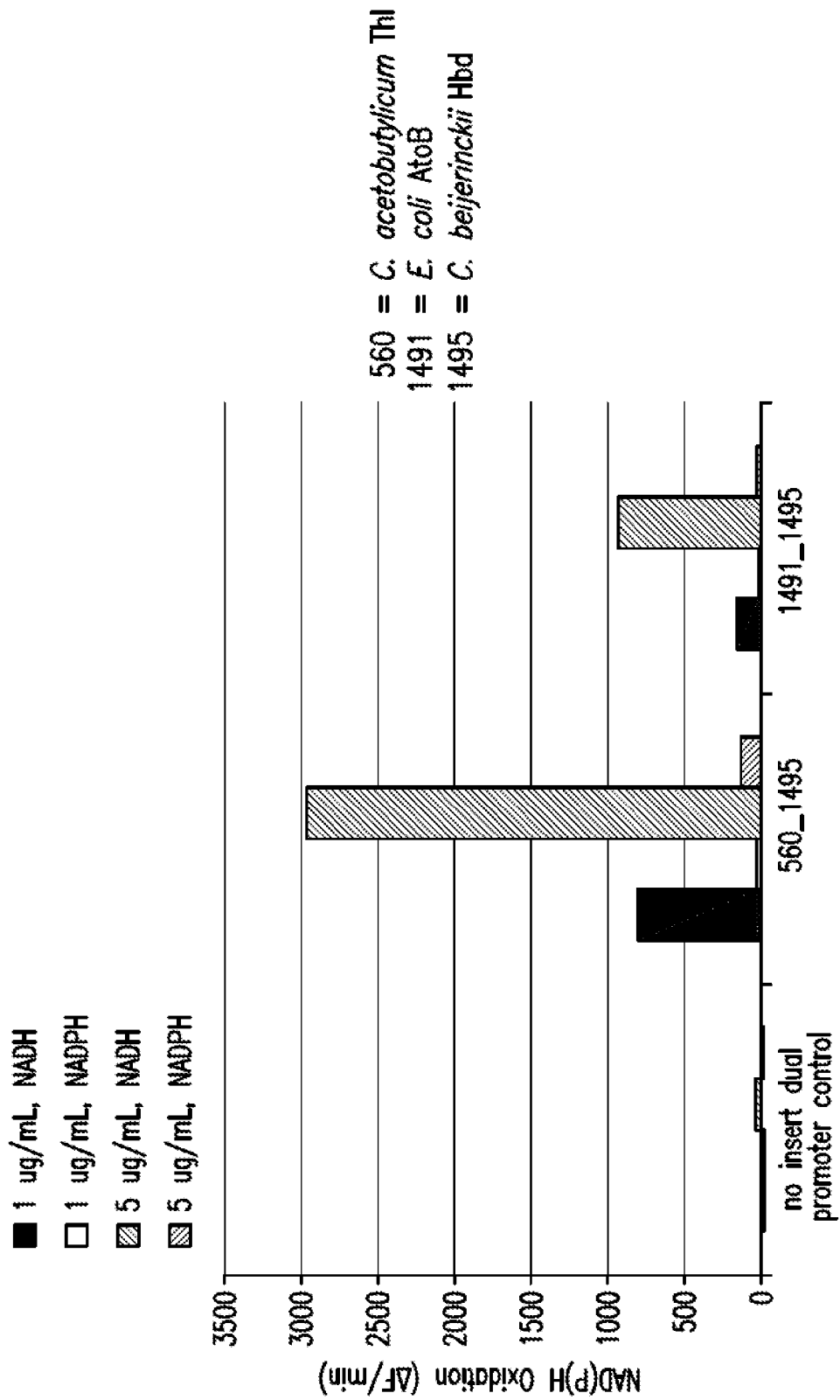
FIG. 19 depicts levels of NAD(P)H oxidation in the presence of 1 or 5 ug/ml NADH or 1 or 5 ug/ml NADPH, and shows that the Hbd prefers NADH over NADPH, as provided in Example XIV.
Figure 20:
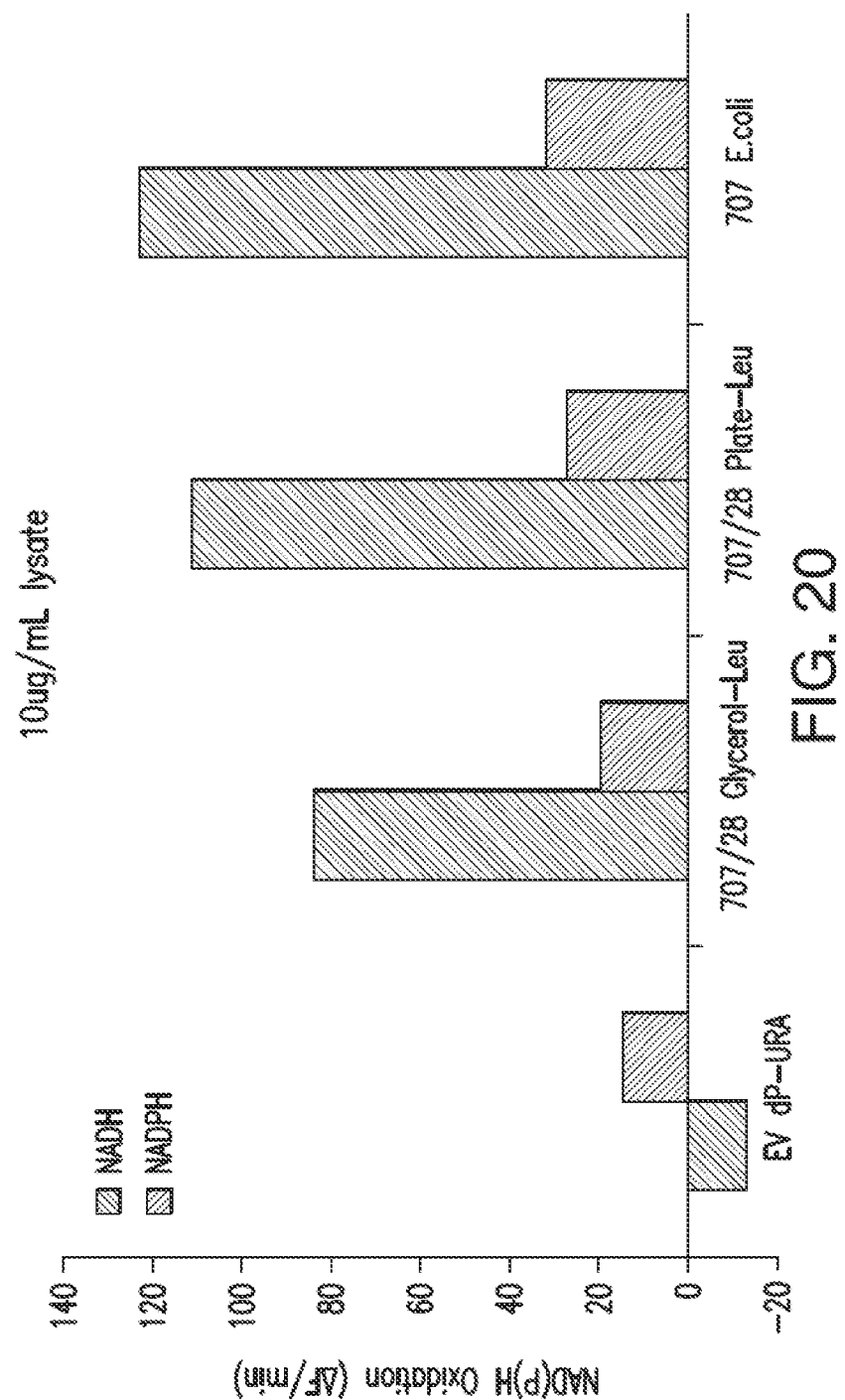
FIG. 20 depicts the activity data for crude lysates of an aldehyde reductase that converts 3-hydroxybutyryl-CoA to 3-hydroxybutyraldehyde and requires NAD(P)H oxidation, which can be used to monitor enzyme activity, as provided in Example XIV. The Ald from *Lactobacillus brevis* (Gene ID 707) was cloned in a dual vector that contained the alcohol dehydrogenase from *Clostridium saccharoperbulacetonicum* (Gene ID 28). These two enzymes were cloned in another dual promoter yeast vector containing a Leu marker. A 707 lysate from *E. coli* was used as a standard.
Figure 21:
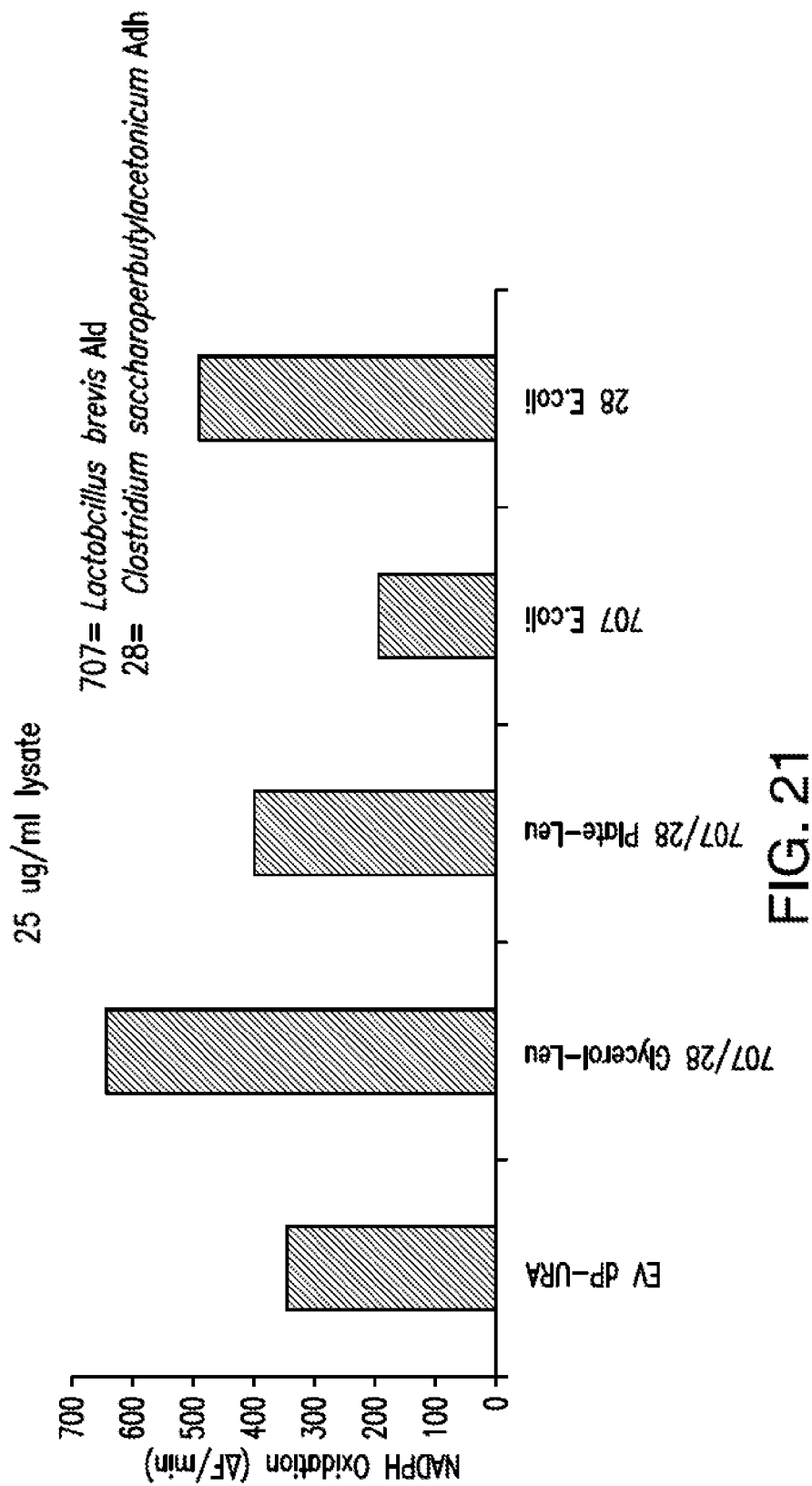
FIG. 21 depicts the evaluation of ADH (Gene 28) in the dual promoter vector with ALD (Gene 707) with butyraldehyde, a surrogate substrate for 3-hydroxybutymldehyde. 1,3-BDO is formed by an alcohol dehydrogenase (Adh), which reduces 3-hydroxybutyraldehyde in the presence of NAD(P)H, and the oxidation of NAD(P)H is used to monitor the reaction.

The evaluation of ADH (Gene 28) in the dual promoter vector with ALD (Gene 707) is shown in FIG. 18 with butyraldehyde, a surrogate substrate for 3-hydroxybutyraldehyde. The data indicate that Gene 28 have Adh activity similar to the no insert control (EV) with butyraldehyde and NADPH. This is likely caused by endogenous ADH enzymes present in yeast that may function in the same capability as 28.

In summary, candidates for the Thl, Hbd, Ald, and Adh to produce 1,3-BDO showed enzyme activity in yeast crude lysates for the dual promoter vectors constructed.

Example XV

Isopropanol Synthesis Pathway

This example describes enzymes for converting acetyl-CoA to isopropanol. Pathways are shown in FIG. 11. Enzymes for catalyzing steps T-Y are disclosed herein.

Isopropanol production was achieved in recombinant E. coli following expression of two heterologous genes from C. acetobutylicum (thl and adc encoding acetoacetyl-CoA thiolase and acetoacetate decarboxylase, respectively) and one from C. beijerinckii (adh encoding a secondary alcohol dehydrogenase), along with the increased expression of the native atoA and atoD genes which encode acetoacetyl-CoA:

acetate:CoA transferase activity (Hanai et al., *Appl. Environ. Microbiol.* 73:7814-7818 (2007)). The acetoacetyl-CoA thiolase (AtoB) enzymes are described herein.

Acetyl-CoA:acetyl-CoA Acyltransferase (Acetoacetyl-CoA thiolase)—Step V, FIG. 11

Acetoacetyl-CoA thiolase (also known as acetyl-CoA acetyltransferase) converts two molecules of acetyl-CoA into one molecule each of acetoacetyl-CoA and CoA. Exemplary acetoacetyl-CoA thiolase enzymes include the gene products of atoB from *E. coli* (Martin et al., *Nat.Biotechnol* 21:796-802 (2003)), th1A and th1B from *C. acetobutylicum* (Hanai et al., *Appl Environ Microbiol* 73:7814-7818 (2007); Winzer et al., *J.Mol.Microbiol Biotechnol* 2:531-541(2000), and ERG10 from *S. cerevisiae* Hiser et al., *J.Biol.Chem.* 269:31383-31389 (1994)). These genes/proteins are identified in the Table below.

| Gene | GenBank ID | GI Number | Organism |
|---|---|---|---|
| AtoB | NP_416728 | 16130161 | *Escherichia coli* |
| ThlA | NP_349476.1 | 15896127 | *Clostridium acetobutylicum* |
| ThlB | NP_149242.1 | 15004782 | *Clostridium acetobutylicum* |
| ERG10 | NP_015297 | 6325229 | *Saccharomyces cerevisiae* |

Acetyl-CoA carboxylase (6.4.1.2)—Step T, FIG. 11

The conversion of acetyl-CoA to malonyl-CoA can be carried out by acetyl-CoA carboxylase. The *E. coli* enzyme complex is composed of two catalytic units and one carrier protein, encoded by four different genes. The catalytic units are biotin carboxylase (6.3.4.14), a homodimer encoded by the accC gene, and acetyl-CoA carboxylase (ACCT), an $\alpha_2\beta_2$ tetramer, encoded by the accA and accD genes. The carrier protein is the biotin carboxyl carrier protein, a homodimer encoded by accB. Several such candidates can be found in US20120142979.

| Gene | Accession number | GI Number | Organism |
|---|---|---|---|
| accA | AAC73296.1 | 1786382 | *Escherichia coli* K-12 |
| accB | AAC76287.1 | 1789653 | *Escherichia coli* K-12 |
| accC | AAC76288.1 | 1789654 | *Escherichia coli* K-12 |
| accD | AAC75376.1 | 1788655 | *Escherichia coli* K-12 |
| accA | CAD08690.1 | 16501513 | *Salmonella enterica* |
| accB | CAD07894.1 | 16504441 | *Salmonella enterica* |
| accC | CAD07895.1 | 16504442 | *Salmonella enterica* |
| accD | CAD07598.1 | 16503590 | *Salmonella enterica* |
| YMR207C | NP_013934.1 | 6323863 | *Saccharomyces cerevisiae* |
| YNR016C | NP_014413.1 | 6324343 | *Saccharomyces cerevisiae* |
| YGR037C | NP_011551.1 | 6321474 | *Saccharomyces cerevisiae* |
| YKL182W | NP_012739.1 | 6322666 | *Saccharomyces cerevisiae* |
| YPL231W | NP_015093.1 | 6325025 | *Saccharomyces cerevisiae* |
| accA | ZP_00618306.1 | 69288468 | *Kineococcus radiotolerans* |
| accB | ZP_00618387.1 | 69288621 | *Kineococcus radiotolerans* |
| accC | ZP_00618040.1/ ZP_00618387.1 | 69287824/69288621 | *Kineococcus radiotolerans* |
| accD | ZP_00618306.1 | 69288468 | *Kineococcus radiotolerans* |

Acetoacetyl-CoA synthase (EC 2.3.1.194)—Step U, FIG. 11

Acetoacetyl-CoA can also be synthesized from acetyl-CoA and malonyl-CoA by acetoacetyl-CoA synthase (EC 2.3.1.194). This enzyme (FhsA) has been characterized in the soil bacterium *Streptomyces* sp. CL190 where it participates in mevalonate biosynthesis (Okamura et al, *PNAS USA* 107:11265-70 (2010)). As this enzyme catalyzes an essentially irreversible reaction, it is particularly useful for metabolic engineering applications for overproducing metabolites, fuels or chemicals derived from acetoacetyl-CoA such as long chain alcohols. Other acetoacetyl-CoA synthase genes can be identified by sequence homology to fhsA. Acyl-CoA synthase enzymes such as fhsA and homologs can be engineered or evolved to accept longer acyl-CoA substrates by methods known in the art.

| Protein | GenBank ID | GI Number | Organism |
|---|---|---|---|
| fhsA | BAJ83474.1 | 325302227 | *Streptomyces* sp CL190 |
| AB183750.1:11991 ... 12971 | BAD86806.1 | 57753876 | *Streptomyces* sp. KO-3988 |
| epzT | ADQ43379.1 | 312190954 | *Streptomyces cinnamonensis* |
| ppzT | CAX48662.1 | 238623523 | *Streptomyces anulatus* |
| O3I_22085 | ZP_09840373.1 | 378817444 | *Nocardia brasiliensis* |

Acetoacetyl-CoA Transferase—Step W, FIG. 11

The conversion of acetoacetyl-CoA to acetoacetate can be carried out by an acetoacetyl-CoA transferase. These enzymes conserve the energy stored in the CoA-ester bonds of acetoacetyl-CoA. Many transferases have broad specificity and thus may utilize CoA acceptors as diverse as acetate, succinate, propionate, butyrate, 2-methylacetoacetate, 3-ketohexanoate, 3-ketopentanoate, valerate, crotonate, 3-mercaptopropionate, propionate, vinylacetate, butyrate, among others. Acetoacetyl-CoA transferase catalyzes the conversion of acetoacetyl-CoA to acetoacetate while transferring the CoA moiety to a CoA acceptor molecule. Several exemplary transferase enzymes capable of catalyzing this transformation are provided below. These enzymes either naturally exhibit the desired acetoacetyl-CoA transferase activity or they can be engineered via directed evolution to accept acetoacetyl-CoA as a substrate with increased efficiency.

In one embodiment an exemplary acetoacetyl-CoA transferase is acetoacetyl-CoA:acetate-CoA transferase. This enzyme naturally converts acetate to acetyl-CoA while converting acetoacetyl-CoA to acetoacetate. In another embodiment, a succinyl-CoA:3-ketoacid CoA transferase (SCOT)

catalyzes the conversion of the 3-ketoacyl-CoA, acetoacetyl-CoA, to the 3-ketoacid, acetoacetate.

Acetoacetyl-CoA:acetyl-CoA transferase naturally converts acetoacetyl-CoA and acetate to acetoacetate and acetyl-CoA. This enzyme can also accept 3-hydroxybutyryl-CoA as a substrate or could be engineered to do so. Exemplary enzymes include the gene products of atoAD from *E. coli* (Hanai et al., *Appl Environ Microbiol* 73:7814-7818 (2007)), cffAB from *C. acetobutylicum* (Jojima et al., *Appl Microbiol Biotechnol* 77:1219-1224 (2008)), and cffAB from *Clostridium saccharoperbutylacetonicum* (Kosaka et al., *Biosci.Biotechnol Biochem.* 71:58-68 (2007)). Information related to these proteins and genes is shown below:

| Protein | GENBANK ID | GI NUMBER | ORGANISM |
|---|---|---|---|
| AtoA | P76459.1 | 2492994 | *Escherichia coli* |
| AtoD | P76458.1 | 2492990 | *Escherichia coli* |
| CtfA | NP_149326.1 | 15004866 | *Clostridium acetobutylicum* |
| CtfB | NP_149327.1 | 15004867 | *Clostridium acetobutylicum* |
| CtfA | AAP42564.1 | 31075384 | *Clostridium saccharoperbutylacetonicum* |
| CtfB | AAP42565.1 | 31075385 | *Clostridium saccharoperbutylacetonicum* |

Succinyl-CoA:3-ketoacid-CoA transferase naturally converts succinate to succinyl-CoA while converting a 3-ketoacyl-CoA to a 3-ketoacid. Exemplary succinyl-CoA:3-ketoacid-CoA transferases are present in *Helicobacter pylori* (Corthesy-Theulaz et al., *J.Biol.Chem.* 272:25659-25667 (1997)), *Bacillus subtilis* (Stols et al., *Protein.Expr.Purif.* 53:396-403 (2007)), and *Homo sapiens* (Fukao et al., *Genomics* 68:144-151(2000); Tanaka et al., *Mol.Hum.Reprod* 8:16-23 (2002)). Information related to these proteins and genes is shown below:

| Protein | GENBANK ID | GI NUMBER | ORGANISM |
|---|---|---|---|
| HPAG1_0676 | YP_627417 | 108563101 | *Helicobacter pylori* |
| HPAG1_0677 | YP_627418 | 108563102 | *Helicobacter pylori* |
| ScoA | NP_391778 | 16080950 | *Bacillus subtilis* |
| ScoB | NP_391777 | 16080949 | *Bacillus subtilis* |
| OXCT1 | NP_000427 | 4557817 | *Homo sapiens* |
| OXCT2 | NP_071403 | 11545841 | *Homo sapiens* | transferase activities are also present in *Trichomonas vaginalis* (van Grinsven et al., *J. Biol. Chem.* 283:1411-1418 (2008)) and *Trypanosoma brucei* (Riviere et al., *J. Biol. Chem.* 279:45337-45346 (2004)). Yet another transferase capable of the desired conversions is butyryl-CoA:acetoacetate CoA-transferase. Exemplary enzymes can be found in *Fusobacterium nucleatum* (Barker et al., *J. Bacteriol.* 152 (1):201-7 (1982)), *Clostridium* SB4 (Barker et al. *J. Biol. Chem.* 253(4):1219-25 (1978)), and *Clostridium acetobutylicum* (Wiesenbom et al., *Appl. Environ. Microbiol.* 55(2):323-9 (1989)). Although specific gene sequences were not provided for butyryl-CoA:acetoacetate CoA-transferase in these references, the genes FN0272 and FN0273 have been annotated as a butyrate-acetoacetate CoA-transferase (Kapatral et al., *J. Bact.* 184(7) 2005-2018 (2002)). Homologs in *Fusobacterium nucleatum* such as FN1857 and FN1856 also likely have the desired acetoacetyl-CoA transferase activity. FN1857 and FN1856 are located adjacent to many other genes involved in lysine fermentation and are thus very likely to encode an acetoacetate:butyrate CoA transferase (Kreimeyer, et al., *J Biol. Chem.* 282 (10) 7191-7197 (2007)). Additional candidates from *Porphyrmonas gingivalis* and *Thermoanaerobacter tengcongensis* can be identified in a similar fashion (Kreimeyer, et al., *J. Biol. Chem.* 282 (10) 7191-7197 (2007)). Information related to these proteins and genes is shown below:

| Protein | GENBANK ID | GI NUMBER | ORGANISM |
|---|---|---|---|
| Cat1 | P38946.1 | 729048 | *Clostridium kluyveri* |
| Cat2 | P38942.2 | 1705614 | *Clostridium kluyveri* |
| Cat3 | EDK35586.1 | 146349050 | *Clostridium kluyveri* |
| TVAG_395550 | XP_001330176 | 123975034 | *Trichomonas vaginalis* G3 |
| Tb11.02.0290 | XP_828352 | 71754875 | *Trypanosoma brucei* |
| FN0272 | NP_603179.1 | 19703617 | *Fusobacterium nucleatum* |
| FN0273 | NP_603180.1 | 19703618 | *Fusobacterium nucleatum* |
| FN1857 | NP_602657.1 | 19705162 | *Fusobacterium nucleatum* |
| FN1856 | NP_602656.1 | 19705161 | *Fusobacterium nucleatum* |
| PG1066 | NP_905281.1 | 34540802 | *Porphyromonas gingivalis* W83 |
| PG1075 | NP_905290.1 | 34540811 | *Porphyromonas gingivalis* W83 |
| TTE0720 | NP_622378.1 | 20807207 | *Thermoanaerobacter tengcongensis* MB4 |
| TTE0721 | NP_622379.1 | 20807208 | *Thermoanaerobacter tengcongensis* MB4 |

Additional suitable acetoacetyl-CoA transferases are encoded by the gene products of cat1, cat2, and cat3 of *Clostridium kluyveri*. These enzymes have been shown to exhibit succinyl-CoA, 4-hydroxybutyryl-CoA, and butyryl-CoA transferase activity, respectively (Seedorf et al., *Proc. Natl. Acad. Sci. USA* 105:2128-2133 (2008); Sohling and Gottschalk, *J Bacteriol* 178:871-880 (1996)). Similar CoA Acetoacetyl-CoA can be hydrolyzed to acetoacetate by acetoacetyl-CoA hydrolase. Many CoA hydrolases (EC 3.1.2.1) have broad substrate specificity and are suitable enzymes for these transformations either naturally or following enzyme engineering. Though the sequences were not reported, several acetoacetyl-CoA hydrolases were identified in the cytosol and mitochondrion of the rat liver (Aragon and Lowenstein, *J. Biol. Chem.* 258(8):4725-4733 (1983)). Additionally, an enzyme from *Rattus norvegicus* brain (Robinson et al., *Biochem. Biophys. Res. Commun.* 71:959-965 (1976)) can react with butyryl-CoA, hexanoyl-CoA and malonyl-CoA. The acot12 enzyme from the rat liver was shown to hydrolyze C2 to C6 acyl-CoA molecules (Suematsu et al., *Eur. J. Biochem.* 268:2700-2709 (2001)). Though its sequence has not been reported, the enzyme from the mitochondrion of the pea leaf showed activity on acetyl-CoA, propionyl-CoA, butyryl-CoA, palmitoyl-CoA, oleoyl-CoA, succinyl-CoA, and crotonyl-CoA (Zeiher and Randall, *Plant.Physiol.* 94:20-27 (1990)). Additionally, a glutaconate CoA-transferase from *Acidaminococcus fermentans* was transformed by site-directed mutagenesis into an acyl-CoA hydrolase with activity on glutaryl-CoA, acetyl-CoA and 3-butenoyl-CoA (Mack and Buckel, *FEBS Lett.* 405:209-212 (1997)). This indicates that the enzymes encoding acetoacetyl-CoA transferases can also be used as hydrolases with certain mutations to change their function. The acetyl-CoA hydrolase, ACH1, from *S. cerevisiae* represents another candidate hydrolase (Buu et al., *J.Biol.Chem.* 278:17203-17209 (2003)). Information related to these proteins and genes is shown below:

| Protein | GENBANK ID | GI NUMBER | ORGANISM |
|---|---|---|---|
| Acot12 | NP_570103.1 | 18543355 | *Rattus norvegicus* |
| GctA | CAA57199 | 559392 | *Acidaminococcus fermentans* |
| GctB | CAA57200 | 559393 | *Acidaminococcus fermentans* |
| ACH1 | NP_009538 | 6319456 | *Saccharomyces cerevisiae* |

Another candidate hydrolase is the human dicarboxylic acid thioesterase, acot8, which exhibits activity on glutaryl-CoA, adipyl-CoA, suberyl-CoA, sebacyl-CoA, and dodecanedioyl-CoA (Westin et al., *J. Biol. Chem.* 280:38125-38132 (2005)) and the closest *E. coli* homolog, tesB, which can also hydrolyze a broad range of CoA thioesters (Naggert et al., *J. Biol. Chem.* 266:11044-11050 (1991)) including 3-hydroxybutyryl-CoA (Tseng et al., *Appl. Environ. Microbiol.* 75(10):3137-3145 (2009)). A similar enzyme has also been characterized in the rat liver (Deana, *Biochem. Int* 26:767-773 (1992)). Other potential *E. coli* thioester hydrolases include the gene products of tesA (Bonner and Bloch, *J. Biol. Chem.* 247:3123-3133 (1972)), ybgC (Kuznetsova et al., *FEMS Microbiol. Rev.* 29:263-279 (2005); Zhuang et al., *FEBS Lett.* 516:161-163 (2002)), pad (Song et al., *J. Biol. Chem.* 281:11028-11038 (2006)), and ybdB (Leduc et al., *J. Bacteriol.* 189:7112-7126 (2007)). Information related to these proteins and genes is shown below:

| Protein | GENBANK ID | GI NUMBER | ORGANISM |
|---|---|---|---|
| Acot8 | CAA15502 | 3191970 | *Homo sapiens* |
| TesB | NP_414986 | 16128437 | *Escherichia coli* |
| Acot8 | NP_570112 | 51036669 | *Rattus norvegicus* |
| TesA | NP_415027 | 16128478 | *Escherichia coli* |
| YbgC | NP_415264 | 16128711 | *Escherichia coli* |
| PaaI | NP_415914 | 16129357 | *Escherichia coli* |
| YbdB | NP_415129 | 16128580 | *Escherichia coli* |

Additional hydrolase enzymes include 3-hydroxyisobutyryl-CoA hydrolase which has been described to efficiently catalyze the conversion of 3-hydroxyisobutyryl-CoA to 3-hydroxyisobutyrate during valine degradation (Shimomura et al., *J. Biol. Chem.* 269:14248-14253 (1994)). Genes encoding this enzyme include hibch of *Rattus norvegicus* (Shimomura et al., supra (1994); Shimomura et al., *Methods Enzymol.* 324:229-240 (2000)) and *Homo sapiens* (Shimomura et al., supra (1994)). Candidate genes by sequence homology include hibch of *Saccharomyces cerevisiae* and BC 2292 of *Bacillus cereus*. BC_2292 was shown to demonstrate 3-hydroxybutyryl-CoA hydrolase activity and function as part of a pathway for 3-hydroxybutyrate synthesis when engineered into *Escherichia coli* (Lee et al., *Appl. Microbiol. Biotechnol.* 79:633-641 (2008)). Information related to these proteins and genes is shown below:

| Protein | GENBANK ID | GI NUMBER | ORGANISM |
|---|---|---|---|
| Hibch | Q5XIE6.2 | 146324906 | *Rattus norvegicus* |
| Hibch | Q6NVY1.2 | 146324905 | *Homo sapiens* |
| Hibch | P28817.2 | 2506374 | *Saccharomyces cerevisiae* |
| BC_2292 | AP09256 | 29895975 | *Bacillus cereus* ATCC 14579 |

The hydrolysis of acetoacetyl-CoA can alternatively be carried out by a single enzyme or enzyme complex that exhibits acetoacetyl-CoA hydrolase activity. This activity enables the net hydrolysis of the CoA-ester of either molecule, and in some cases, results in the simultaneous generation of ATP. For example, the product of the LSC1 and LSC2 genes of *S. cerevisiae* and the sucC and sucD genes of *E. coli* naturally form a succinyl-CoA synthetase complex that catalyzes the formation of succinyl-CoA from succinate with the concomitant consumption of one ATP, a reaction which is reversible in vivo (Grays et al., U.S. Pat. No. 5,958,745, filed Sep. 28, 1999). Information related to these proteins and genes is shown below:

| Protein | GENBANK ID | GI NUMBER | ORGANISM |
|---|---|---|---|
| SucC | NP_415256.1 | 16128703 | *Escherichia coli* |
| SucD | AAC73823.1 | 1786949 | *Escherichia coli* |
| LSC1 | NP_014785 | 6324716 | *Saccharomyces cerevisiae* |
| LSC2 | NP_011760 | 6321683 | *Saccharomyces cerevisiae* |

Additional exemplary CoA-ligases include the rat dicarboxylate-CoA ligase for which the sequence is yet uncharacterized (Vamecq et al., Biochemical J. 230:683-693 (1985)), either of the two characterized phenylacetate-CoA ligases from *P. chrysogenum* (Lamas-Maceiras et al., Biochem. J. 395:147-155 (2005); Wang et al., Biochem Biophy Res Commun 360(2):453-458 (2007)), the phenylacetate-CoA ligase from Pseudomonas putida (Martinez-Blanco et al., J. Biol. Chem. 265:7084-7090 (1990)), and the 6-carboxyhexanoate-CoA ligase from *Bacilis subtilis* (Bower et al., J. Bacteriol. 178(14):4122-4130 (1996)). Additional candidate enzymes are acetoacetyl-CoA synthetases from Mus musculus (Hasegawa et al., Biochim. Biophys. Acta 1779:414-419 (2008)) and *Homo sapiens* (Ohgami et al., Biochem. Pharmacol. 65:989-994 (2003)), which naturally catalyze the ATP-dependant conversion of acetoacetate into acetoacetyl-CoA. 4-Hydroxybutyryl-CoA synthetase activity has been demonstrated in *Metallosphaera sedula* (Berg et al., Science 318:1782-1786 (2007)). This function has been tentatively assigned to the Msed_1422 gene. Information related to these proteins and genes is shown below:

| Protein | GENBANK ID | GI NUMBER | ORGANISM |
|---|---|---|---|
| Phl | CAJ15517.1 | 77019264 | *Penicillium chrysogenum* |
| PhlB | ABS19624.1 | 152002983 | *Penicillium chrysogenum* |
| PaaF | AAC24333.2 | 22711873 | *Pseudomonas putida* |
| BioW | NP_390902.2 | 50812281 | *Bacillus subtilis* |
| AACS | NP_084486.1 | 21313520 | *Mus musculus* |
| AACS | NP_076417.2 | 31982927 | *Homo sapiens* |
| Msed_1422 | YP_001191504 | 146304188 | *Metallosphaera sedula* |

ADP-forming acetyl-CoA synthetase (ACD, EC 6.2.1.13) is another candidate enzyme that couples the conversion of acyl-CoA esters to their corresponding acids with the concurrent synthesis of ATP. Several enzymes with broad substrate specificities have been described in the literature. ACDI from *Archaeoglobus fulgidus*, encoded by AF1211, was shown to operate on a variety of linear and branched-chain substrates including acetyl-CoA, propionyl-CoA, butyryl-CoA, acetate, propionate, butyrate, isobutyrate, isovalerate, succinate, fumarate, phenylacetate, indoleacetate (Musfeldt et al., *J. Bacteriol.* 184:636-644 (2002)). The enzyme from *Haloarcula marismortui* (annotated as a succinyl-CoA synthetase) accepts propionate, butyrate, and branched-chain acids (isovalerate and isobutyrate) as substrates, and was shown to operate in the forward and reverse directions (Brasen et al., *Arch. Microbiol.* 182:277-287 (2004)). The ACD encoded by PAE3250 from hyperthermophilic crenarchaeon *Pyrobaculum aerophilum* showed the broadest substrate range of all characterized ACDs, reacting with acetyl-CoA, isobutyryl-CoA (preferred substrate) and phenylacetyl-CoA (Brasen et al., supra (2004)). The enzymes from *A. filgidus, H. marismortui* and *P. aerophilum* have all been cloned, functionally expressed, and characterized in *E. coli* (Musfeldt et al., supra; Brasen et al., supra (2004)). Information related to these proteins and genes is shown below:

| Protein | GENBANK ID | GI NUMBER | ORGANISM |
|---|---|---|---|
| AF1211 | NP_070039.1 | 11498810 | *Archaeoglobus fulgidus* DSM 4304 |
| Scs | YP_135572.1 | 55377722 | *Haloarcula marismortui* ATCC 43049 |
| PAE3250 | NP_560604.1 | 18313937 | *Pyrobaculum aerophilum* str. IM2 |

An alternative method for removing the CoA moiety from acetoacetyl-CoA is to apply a pair of enzymes such as a phosphate-transferring acyltransferase and a kinase to impart acetoacetyl-CoA synthetase activity. Exemplary names for these enzymes include phosphotransacetoacetylase/acetoacetate kinase which can remove the CoA moiety from acetoacetyl-CoA. This general activity enables the net hydrolysis of the CoA-ester of either molecule with the simultaneous generation of ATP. For example, the butyrate kinase (buk)/phosphotransbutyrylase (ptb) system from *Clostridium acetobutylicum* has been successfully applied to remove the CoA group from 3-hydroxybutyryl-CoA when functioning as part of a pathway for 3-hydroxybutyrate synthesis (Tseng et al., *Appl. Environ. Microbiol.* 75(10): 3137-3145 (2009)). Specifically, the ptb gene from *C. acetobutylicum* encodes an enzyme that can convert an acyl-CoA into an acyl-phosphate (Walter et al. *Gene* 134(1): p. 107-11(1993)); Huang et al. *J Mol Microbiol Biotechnol* 2(1): p. 33-38 (2000). Additional ptb genes can be found in butyrate-producing bacterium L2-50 (Louis et al. *J.Bacteriol.* 186: 2099-2106 (2004)) and *Bacillus megaterium* (Vazquez et al. *Curr.Microbiol* 42:345-349 (2001)). Additional exemplary phosphate-transferring acyltransferases include phosphotransacetylase, encoded by pta. The pta gene from *E. coli* encodes an enzyme that can convert acetyl-CoA into acetyl-phosphate, and vice versa (Suzuki, T. *Biochim.Biophys.Acta* 191:559-569 (1969)). This enzyme can also utilize propionyl-CoA instead of acetyl-CoA forming propionate in the process (Hesslinger et al. *Mol.Microbiol* 27:477-492 (1998)). Information related to these proteins and genes is shown below:

| Protein | GENBANK ID | GI NUMBER | ORGANISM |
|---|---|---|---|
| Pta | NP_416800.1 | 16130232 | *Escherichia coli* |
| Ptb | NP_349676 | 15896327 | *Clostridium acetobutylicum* |
| Ptb | AAR19757.1 | 38425288 | butyrate-producing bacterium L2-50 |
| Ptb | CAC07932.1 | 10046659 | *Bacillus megaterium* |

Exemplary kinases include the *E. coli* acetate kinase, encoded by ackA (Skarstedt and Silverstein *J.Bid Chem.* 251:6775-6783 (1976)), the *C. acetobutylicum* butyrate kinases, encoded by buk1 and buk2 ((Walter et al. *Gene* 134(1):107-111(1993); Huang et al. *J Mol Microbiol Biotechnol* 2(1):33-38 (2000)), and the *E. coli* gamma-glutamyl kinase, encoded by proB (Smith et al. *J.Bacteriol.* 157:545-551 (1984)). These enzymes phosphorylate acetate, butyrate, and glutamate, respectively. The ackA gene product from *E. coli* also phosphorylates propionate (Hesslinger et al. *Mol.Microbiol* 27:477-492 (1998)). Information related to these proteins and genes is shown below:

| Protein | GENBANK ID | GI NUMBER | ORGANISM |
|---|---|---|---|
| AckA | NP_416799.1 | 16130231 | *Escherichia coli* |
| Buk1 | NP_349675 | 15896326 | *Clostridium acetobutylicum* |
| Buk2 | Q97II1 | 20137415 | *Clostridium acetobutylicum* |
| ProB | NP_414777.1 | 16128228 | *Escherichia coli* |

Acetoacetate Decarboxylase—Step X, FIG. 11

Acetoacetate decarboxylase converts acetoacetate into carbon dioxide and acetone. Exemplary acetoacetate decarboxylase enzymes are encoded by the gene products of adc from *C. acetobutylicum* (Petersen and Bennett, *Appl. Environ. Microbiol.* 56:3491-3498 (1990) and adc from *Clostridium saccharoperbulylacetonicum* (Kosaka et al., *Biosci. Biotechnol. Biochem.* 71:58-68 (2007)). The enzyme from *C. beijerinkii* can be inferred from sequence similarity.

| Protein | GenBank ID | GI Number | Organism |
|---|---|---|---|
| Adc | NP_149328.1 | 15004868 | Clostridium acetobutylicum |
| Adc | AAP42566.1 | 31075386 | Clostridium saccharoperbutylacetonicum |
| Adc | YP_001310906.1 | 150018652 | Clostridium beijerinckii |

Acetone Reductase or Isopropanol Dehydrogenase—Step Y, FIG. 11

The final step in the isopropanol synthesis pathway involves the reduction of acetone to isopropanol. Exemplary alcohol dehydrogenase enzymes capable of this transformation include adh from *C. beijerinckii* (Jojima et al., *Appl. Microbiol. Biotechnol.* 77:1219-1224 (2008); Hanai et al., *Appl. Environ. Microbiol.* 73:7814-7818 (2007) and adh from *Thermoanaerobacter brockii* (Hanai et al., supra; Peretz et al., *Anaerobe* 3:259-270 (1997)). Additional characterized enzymes include alcohol dehydrogenases from *Ralstonia eutropha* (formerly *Alcaligenes eutrophus*) (Steinbuchel and Schlegel, *Eur. J. Biochem.* 141:555-564 (1984) and *Phytomonas* species (Uttaro and Opperdoes, *Mol. Biochen. Parasitol.* 85: 213-219 (1997)).

| Protein | GenBank ID | GI Number | Organism |
|---|---|---|---|
| Adh | P14941.1 | 113443 | Thermoanaerobobacter brockii |
| Adh | AAA23199.2 | 60592974 | Clostridium beijerinckii |
| Adh | YP_299391.1 | 73539024 | Ralstonia eutropha |
| iPDH | AAP39869.1 | 31322946 | Phtomonas sp. |

Example XVI

Production of Fatty Alcohols, Fatty Aldehydes, and Fatty Acids via the Fatty Acyl-ACP Elongation (FAACPE) Cycle and Termination Pathways This example describes enzymes for converting acetyl-CoA to products of interest such as fatty alcohols, fatty aldehydes, and fatty acids through the FAACPE cycle and termination pathways. Pathways are shown in FIG. 12. Enzymes for catalyzing steps A-O are disclosed herein.

Fatty acid biosynthesis requires several steps. The initiation of fatty acid biosynthesis requires the conversion of acetyl-CoA to malonyl CoA by an enzyme called acetyl CoA carboxylase (Step A, FIG. 12). Malonyl-CoA is then converted into malonyl-ACP by a CoA-ACP transacylase (Step B, FIG. 12). This is the substrate for the first step of the elongation cycle, namely the condensation step (Steps C and H, FIG. 12). This reaction is called β-keto acyl ACP synthase. The keto group is then reduced to a hydroxyl group by a β-keto acyl ACP reductase (Step E, FIG. 12). The next step is a dehydration step that involves conversion of the hydroxyl group into an enoyl moiety (Step F, FIG. 12). This is catalyzed by a β-hydoxy acyl ACP dehydratase. The enoyl group is finally reduced to form an acyl-ACP by enoyl-ACP reductase (Step G, FIG. 12). At this point, the acyl-ACP can either be further elongated by the condensation reaction carried out by the β-keto acyl ACP synthase or can be converted into a fatty acid by a thioesterase (Step I, FIG. 12). The acid can be further activated to acyl-CoA by an acyl-CoA synthetase or ligase (Step K, FIG. 12) or can be directly reduced to an acid by a carboxylic acid reductase (CAR) (Step O, FIG. 12). The acyl-CoA can have multiple fates too and can either be converted into an aldehyde by acyl-CoA reductase (Step L, FIG. 12) or can be converted into a fatty alcohol by a fatty alcohol forming acyl-CoA reductase (FAR) (Step N, FIG. 12). The fatty aldehyde can also be converted into a fatty alcohol by a fatty aldehyde reductase (Step M, FIG. 12).

There are two basic types of fatty acid (FAS) biosynthesis mechanisms. The type I system is found in mammals and lower eukaryotes. The mammalian system consists of a single gene product that contains all of the reaction centers required to produce a fatty acid, e.g., the fatty acid synthase from *Homo sapiens*. In lower eukaryotes such as yeast, fatty acid synthase function is catalyzed by two genes (FAS I and FAS II), whose polypeptides form a eukaryotic complex.

Type II systems are found in bacteria and plants (White et al. (2005), *The structural biology of type II fatty acid biosynthesis*, Annu Rev Biochem, 74 (791-831)) among other organisms. The reactions in these systems are catalyzed by a series of individual soluble proteins that are each encoded by a discrete gene, and the pathway intermediates are transferred between the enzymes as thioesters of a holo acyl carrier protein (ACP).

Acetyl-CoA Carboxylase (6.4.1.2)—Step A, FIG. 12

The conversion of acetyl-CoA to malonyl-CoA can be carried out by acetyl-CoA carboxylase. The *E. coli* enzyme complex is composed of two catalytic units and one carrier protein, encoded by four different genes. The catalytic units are biotin carboxylase (6.3.4.14), a homodimer encoded by the accC gene, and acetyl-CoA carboxylase (ACCT), an $\alpha_2\beta_2$ tetramer, encoded by the accA and accD genes. The carrier protein is the biotin carboxyl carrier protein, a homodimer encoded by accB. Several such candidates can be found in US20120142979.

| Gene | Accession number | GI Number | Organism |
|---|---|---|---|
| accA | AAC73296.1 | 1786382 | Escherichia coli K-12 |
| accB | AAC76287.1 | 1789653 | Escherichia coli K-12 |
| accC | AAC76288.1 | 1789654 | Escherichia coli K-12 |
| accD | AAC75376.1 | 1788655 | Escherichia coli K-12 |
| accA | CAD08690.1 | 16501513 | Salmonella enterica |
| accB | CAD07894.1 | 16504441 | Salmonella enterica |
| accC | CAD07895.1 | 16504442 | Salmonella enterica |
| accD | CAD07598.1 | 16503590 | Salmonella enterica |
| YMR207C | NP_013934.1 | 6323863 | Saccharomyces cerevisiae |
| YNR016C | NP_014413.1 | 6324343 | Saccharomyces cerevisiae |
| YGR037C | NP_011551.1 | 6321474 | Saccharomyces cerevisiae |
| YKL182W | NP_012739.1 | 6322666 | Saccharomyces cerevisiae |

-continued

| Gene | Accession number | GI Number | Organism |
| --- | --- | --- | --- |
| YPL231W | NP_015093.1 | 6325025 | *Saccharomyces cerevisiae* |
| accA | ZP_00618306.1 | 69288468 | *Kineococcus radiotolerans* |
| accB | ZP_00618387.1 | 69288621 | *Kineococcus radiotolerans* |
| accC | ZP_00618040.1/ ZP_00618387.1 | 69287824/69288621 | *Kineococcus radiotolerans* |
| accD | ZP_00618306.1 | 69288468 | *Kineococcus radiotolerans* |

CoA-ACP Acyltransferase (2.3.1.f)—Step B, FIG. 12

The exchange of an ACP moiety for a CoA is catalyzed by enzymes in EC class 2.3.1. Activation of acetyl-CoA to acetyl-ACP and malonyl-CoA to malonyl-ACP are also catalyzed by a CoA:ACP acyltransferase. Enzymes with CoA-ACP acyltransferase activity include acetyl-CoA:ACP transacylase (EC 2.3.1.38) and malonyl-CoA:ACP transacylase (EC 2.3.1.39).

The FabH (KASIII) enzyme of *E. coli* functions as an acyl-CoA:ACP transacylase, in addition to its primary activity of forming acetoacetyl-ACP. Butyryl-ACP is accepted as an alternate substrate of FabH (Prescott et al, Adv. Enzymol. Relat. Areas Mol, 36:269-311(1972)). Acetyl-CoA:ACP transacylase enzymes from *Plasmodium falciparum* and *Streptomyces avermitillis* have been heterologously expressed in *E. coli* (Lobo et al, Biochem 40:11955-64 (2001)). A synthetic KASIII (FabH) from *P. falciparum* expressed in a fabH-deficient *Lactococcus lactis* host was able to complement the native fadcs activity (Du et al, AEM 76:3959-66 (2010)). The acetyl-CoA:ACP transacylase enzyme from *Spinacia oleracea* accepts other acyl-ACP molecules as substrates, including butyryl-ACP (Shimakata et al, Methods Enzym 122:53-9 (1986)). The sequence of this enzyme has not been determined to date. Malonyl-CoA:ACP transacylase enzymes include FabD of *E. coli* and *Brassica napsus* (Verwoert et al, J Bacteriol, 174:2851-7 (1992); Simon et al, FEBS Lett 435:204-6 (1998)). FabD of *B. napsus* was able to complement fabD-deficient *E. coli*. The multifunctional eukaryotic fatty acid synthase enzyme complexes (described in EC 2.3.1.) also catalyze this activity. More exemplary gene candidates can be found in WO2007136762A2.

| Gene | GenBank ID | GI Number | Organism |
| --- | --- | --- | --- |
| fabH | AAC74175.1 | 1787333 | *Escherichia coli* |
| fabH | ZP_00618003.1 | 69287672 | *Kineococcus radiotolerans* |
| fabH | YP_388920.1 | 7835747 | *Desulfovibrio alaskensis* |
| fabH | YP_425507.1 | 83591755 | *Rhodospirillum rubrum* |

Alternately, acetyl-CoA can first be activated to acetyl-ACP and subsequently condensed to acetoacetyl-ACP by two enzymes, acetyl-CoA:ACP transacylase (EC 2.3.1.38) and acetoacetyl-ACP synthase (EC 2.3.1.41). Acetyl-CoA:ACP transacylase converts acetyl-CoA and an acyl carrier protein to acetyl-ACP, releasing CoA. Enzyme candidates for acetyl-CoA:ACP transacylase are described in section EC 2.3.1.f above. Acetoacetyl-ACP synthase enzymes catalyze the condensation of acetyl-ACP and malonyl-ACP. This activity is catalyzed by FabF and FabB of *E. coli*, as well as the multifunctional eukaryotic fatty acid synthase enzyme complexes described in EC 2.3.1.g. FabB and FabF catalyze the condensation of malonyl-ACP with acyl-ACP substrates (β-ketoacyl-ACP synthase activity) and function primarily in fatty acid elongation. Specifically, a β-ketoacyl-ACP synthase catalyzes the conversion of a saturated fatty acyl ACP and malonyl-ACP into 3-oxoacyl-ACP that is 2 carbons longer that the substrate fatty acyl ACP. When it reacts with acetyl-ACP, it participates in fatty acid initiation. The *Bacillus subtilis* KAS enzymes are similar to FabH but are less selective, accepting branched acyl-CoA substrates (Choi et al, J Bacteriol 182:365-70 (2000)).

| Gene | GenBank ID | GI Number | Organism |
| --- | --- | --- | --- |
| fabH | AAC74175.1 | 1787333 | *Escherichia coli* |
| fadA | NP_824032.1 | 29829398 | *Streptomyces avermitillis* |
| fabH | AAC63960.1 | 3746429 | *Plasmodium falciparum* |
| Synthetic construct | ACX34097.1 | 260178848 | *Plasmodium falciparum* |
| fabH | CAL98359.1 | 124493385 | *Lactococcus lactis* |
| fabD | AAC74176.1 | 1787334 | *Escherichia coli* |
| fabD | CAB45522.1 | 5139348 | *Brassica napsus* |
| fabD | ZP_00617602.1 | 69286751 | *Kineococcus radiotolerans* |
| fabD | YP_388786.1 | 78357337 | *Desulfovibrio alaskensis* |
| fabD | YP_425507 | 83591755 | *Rhodospirillum rubrum* |

Acyl-ACP C-acyltransferase (Decarboxylating) or β-ketoacyl-ACP Synthase (2.3.1.e)—Steps C, D and H, FIG. 12

Acetoacetyl-ACP is formed from malonyl-ACP and either acetyl-CoA or acetyl-ACP. *E. coli* has three ketoacyl-ACP synthases (KAS enzymes), KAS I, KAS II and KAS III, encoded by fabB, fabF and fabH respectively. FabH (KAS III), the key enzyme of initiation of fatty acid biosynthesis in *E coli*, is selective for the formation of acetoacetyl-ACP from acetyl-CoA and malonyl-ACP. Some gene candidates for this step are shown below.

| Gene | GenBank ID | GI Number | Organism |
| --- | --- | --- | --- |
| fabB | AAC75383.1 | 1788663 | *Escherichia coli* |
| fabF | AAC74179.1 | 1787337 | *Escherichia coli* |
| FabHA | NP_389015.1 | 16078198 | *Bacillus subtilis* |
| FabHB | NP_388898.1 | 16078081 | *Bacillus subtilis* |

More exemplary gene candidates for acyl-ACP C-acyl transferase can be found in WO2007136762A2 (Production of fatty acids and derivatives thereof). Some of the enzymes listed below are from US20110250663 (Methods and compositions related to fatty alcohol biosynthetic enzymes). Several more keto-acyl synthases have been identified in these applications. Exempalry aeto Acyl-ACP synthases from E. coli are described below.

| Gene | GenBank ID | GI number | Organism |
|---|---|---|---|
| fabB | ACY27486.1 | 262176863 | Escherichia coli LW1655F+ |
| fabF | ACY27487 | 262176865 | Escherichia coli LW1655F+ |
| fadJ | ACX38989.1 | 260448567 | Escherichia coli DH1 |
| xerC | ACX41768.1 | 260451346 | Escherichia coli DH1 |
| vqeF | ACX38529.1 | 260448107 | Escherichia coli DH1 |
| murQ | ACX38907.1 | 260448485 | Escherichia coli DH1 |

Oxidoreductase (Oxo to Alcohol) (1.1.1.a)—Step E, FIG. 12

The reduction of 3-oxoacyl-ACP to 3-hydroxyacetyl-ACP is catalyzed by 3-oxoacyl-ACP reductase (EC 1.1.1.100). The E. coli 3-oxoacyl-ACP reductase is encoded by fabG. Key residues responsible for binding the acyl-ACP substrate to the enzyme have been elucidated (Zhang et al, J Biol Chem 278:52935-43 (2003)). Additional enzymes with this activity have been characterized in Bacillus anthracis (Zaccai et al, Prot Struct Funct Gen 70:562-7 (2008)) and Mycobacterium tuberculosis (Gurvitz, Mol Genet Genomics 282:407-16 (2009)). The beta-ketoacyl reductase (KR) domain of eukaryotic fatty acid synthase also catalyzes this activity (Smith, FASEB J, 8:1248-59 (1994)). While many FabG enzymes preferentially utilize NADH, NADH-dependent FabG enzymes also known in the art and are shown in the table below (Javidpour et al, AEM 80: 597-505 (2014)).

| Gene | GenBank ID | GI Number | Organism |
|---|---|---|---|
| fabG | P0AEK2.1 | 84028081 | Escherichia coli |
| fabG | AAP27717.1 | 30258498 | Bacillus anthracis |
| FabG1 | NP_215999.1 | 15608621 | Mycobacterium tuberculosis |
| FabG4 | YP_003030167.1 | 253797166 | Mycobacterium tuberculosis |
| FabG | EDM75366.1 | 149815845 | Plesiocystis Pacifica |
| FabG | WP_018008474.1 | 516633699 | Cupriavidus Taiwanensis |
| FabG | WP_012242413.1 | 501199395 | Acholeplasma Laidlawii |
| FabG | EDL65432.1 | 148851283 | Bacillus sp SG-1 |

Hydro-lyase (4.2.1.a)—Step F, FIG. 12

3-Hydroxyacyl-ACP dehydratase enzymes catalyze the conversion of 3-hydroacyl-ACP to trans-2-enoyl-ACP. Enzymes with this activity include FabA and FabZ of E. coli, which possess overlapping broad substrate specificities (Heath, J Biol Chem 271:1833-6 (1996)). Fatty acid synthase complexes, described above, also catalyze this reaction. The FabZ protein from Plasmodium falciparum has been crystallized (Kostrew et al, Protein Sci 14:1570-80 (2005)). Additional candidates are the mitochondria β-hydroxyacyl-ACP dehydratase encoded by Htd2p in yeast and TbHTD2 in Homo sapiens and Trypanosoma brucei (Kastanoitis et al, Mol Micro 53:1407-21 (2004); Kaija et al, FEBS Lett 582:729-33 (2008)).

| Gene | GenBank ID | GI Number | Organism |
|---|---|---|---|
| fabA | AAC74040.1 | 1787187 | Escherichia coli |
| fabZ | AAC73291.1 | 1786377 | Escherichia coli |
| PfFabZ | AAK83685.1 | 15080870 | Plasmodium falciparum |
| Htd2p | NP_011934.1 | 6321858 | Saccharomyces cerevisiae |
| HTD2 | P86397.1 | 281312149 | Homo sapiens |

Enoyl ACP Reductase (13.1.a)—Step G, FIG. 12

Enoyl-ACP reductase catalyzes the formation of a saturated acyl-ACP by an NAD(P)H-dependent reduction of the enoyl-ACP double bond. The FabI protein of E. coli is a well-characterized enoyl-ACP reductase that catalyzes the reduction of enoyl substrates of length 4 to 16 carbons (Raft et al, JBC 281:39285-93 (2006)). FabI utilizes both NADH and NADPH as a cofactor (Bergler et al, Eur J Biochem 242:689-94 (1996)) and is inhibited by acyl-ACP via product inhibition (Heath, J Biol Chem 271:1833-6 (1996)). Bacillus subtilis contains two enoyl-ACP reductase isozymes, FabI and FabL (Heath et al, J Biol Chem 275: 40128-33 (2000)). The Streptococcus pneumoniae FabK protein is a triclosan-resistant flavoprotein catalyzing the same activity (Heath and Rock, Nature 406:145-6 (2000)). An additional candidate is the Pseudomonas aeruginosa FabI protein, which was recently crystallized (Lee et al, Acta Cryst Sect F 67:214-216 (2011)).

| Gene | GenBank ID | GI Number | Organism |
|---|---|---|---|
| fabI | P0AEK4.2 | 84028072 | Escherichia coli |
| fabI | P54616.2 | 7531269 | Bacillus subtilis |
| fabL | P71079.1 | 81817482 | Bacillus subtilis |
| fabK | AAF98273.1 | 9789231 | Streptococcus pneumoniae |
| fabI | Q9ZFE4.1 | 7531118 | Pseudomonas aeruginosa |

Fatty Acid Synthase (23.1.2), FIG. 12

Fatty acid synthase or fatty-acyl-CoA synthase are multifunctional enzyme complexes composed of multiple copies of one or more subunits and can together catalyze all the reactions required for fatty acid synthesis: activation, priming, elongation and termination (Lomakin et al, Cell 129: 319-32 (2007)). The fatty acid synthase of Saccharomyces cerevisiae is a dodecamer composed of two multifunctional subunits FAS1 and FAS2. This enzyme complex catalyzes the formation of long chain fatty acids from acetyl-CoA and malonyl-CoA. The favored product of eukaryotic FAS systems is palmitic acid (C16). Similar fatty acid synthase complexes are found in Candida parapsilosis and Thermomyces lanuginosus (Nguyen et al, PLoS One 22:e8421 (2009); Jenni et al, Science 316:254-61 (2007)). The multifunctional Fas enzymes of Mycobacterium tuberculosis and mammals such as Homo sapiens are also suitable candidates (Fernandes and Kolattukudy, Gene 170:95-99 (1996) and Smith et al, Prog Lipid Res 42:289-317 (2003)).

| Gene | GenBank ID | GI Number | Organism |
|---|---|---|---|
| FAS1 | CAA82025.1 | 486321 | Saccharomyces cerevisiae |
| FAS2 | CAA97948.1 | 1370478 | Saccharomyces cerevisiae |
| Fas1 | ABO37973.1 | 133751597 | Thermomyces lanuginosus |

-continued

| Gene | GenBank ID | GI Number | Organism |
|---|---|---|---|
| Fas2 | ABO37974.1 | 133751599 | *Thermomyces lanuginosus* |
| Fas | AAB03809.1 | 1036835 | *Mycobacterium tuberculosis* |
| Fas | NP_004095.4 | 41872631 | *Homo sapiens* |

Multiple genes are involved in fatty acid synthesis in bacteria and plants, including: 1. Acetyl-CoA: ACP transcylase (2.3.1.38)—for converting acetyl-CoA to acetyl-ACP, 2. malonyl-CoA:ACP transacylase that converts malonyl-CoA into malonyl-ACP (2.3.1.39), 3. acetyl[acp]:malonyl-[acp] C-acyl transferase (2.3.1.41) and others in fatty acid elongation. Some exemplary gene candidates for the steps are shown below.

| Gene | GenBank ID | GI number | Organism |
|---|---|---|---|
| fabH | AP_001717.1 | 89107937 | *Escherichia coli* K12 |
| fabB | NP_416826.1 | 16130258 | *Escherichia coli* K12 |
| fabF | NP_415613.1 | 16129058 | *Escherichia coli* K12 |
| fabD | NP_415610.1 | 16129055 | *Escherichia coli* K12 |
| fabI | NP_415804.1 | 16129249 | *Escherichia coli* K12 |
| fabA | NP_415474.1 | 16128921 | *Escherichia coli* K12 |
| fabZ | NP_414722.1 | 16128173 | *Escherichia coli* K12 |
| fabG | NP_415611.1 | 16129056 | *Escherichia coli* K12 |
| FasII (fatty acid synthase, alpha subunit) | AAA34601.1 | 171502 | *Saccahromyces cerevisiae* |
| FasI (fatty acid synthase, beta subunit) | AAA34602.1 | 171506 | *Saccahromyces cerevisiae* |
| fas | NP_217040.1 | 15609661 | *Mycobacterium tuberculosis* H37Rv |
| fas | AAN25329.1 | 23326820 | *Bifidobacterium longum* NCC2705 |
| fas | YP_003971698.1 | 311064972 | *Bifidobacterium bifidum* |
| fas | AEG82252.1 | 334697455 | *Corynebacterium ulcerans* |

Acyl acp Thioesterase (3.1.2.a)—Step F, FIG. 12

Acyl-ACP thioesterase releases free fatty acids from Acyl-ACPs, thus terminating fatty acid biosynthesis. There are two isoforms of acyl-ACP thioesterase, FatA and FatB. Substrate specificity of these isoforms determines the chain length and level of saturated fatty acids in plants. The highest activity of FatA is with C18:1-ACP. FatA has very low activities towards other acyl-ACPs when compared with C18:1-ACP. FatB has highest activity with C16:0-ACP. It also has significant high activity with C18:1-ACP, followed by C18:0-ACP and C16:1-ACP. Kinetics studies of FatA and FatB indicate that their substrate specificities with different acyl-ACPs came from the Kcat values, rattler than from Km. Km values of the two isoforms with different substrates are similar, in the micromolar order.

Exemplary enzymes include the FatA and FatB isoforms of *Arabidopsis thaliana* (Salas et al, Arch Biochem Biophys 403:25-34 (2002)). A number of thioesterases with different chain length specificities are listed in WO 2008/113041 and are included in the table below [seep 126 Table 2A of patent]. For example, it has been shown previously that expression of medium chain plant thioesterases like FatB from *Umbellularia califirnica* in *E. coli* results in accumulation of high levels of medium chain fatty acids, primarily laurate (C12:0). Similarly, expression of *Cuphea palustris* FatB1 thioesterase in *E. coli* led to accumulation of C8-10:0 acyl-ACPs (Dehesh et al, *Plant Physiol* 110:203-10 (1996)). Similarly, *Carthamus tinctorius* thioesterase, when expressed in *E. coli* leads to >50 fold elevation in C 18:1 chain termination and release as free fatty acid (Knutzon et al, *Plant Physiol* 100:1751-58 (1992)). Methods for altering the substrate specificity of acyl-ACP thioesterases are also known in the art (for example, EP1605048).

| Gene | GenBank ID | GI number | Organism |
|---|---|---|---|
| fatA | AEE76980.1 | 332643459 | *Arabidopsis thaliana* |
| fatA | ACC41415 | 183176305 | *Mycobacterium marinum* M |
| fatA | AAX54527 | 61741120 | *Helianthus annuus* |
| fatA | CAC14164 | 10944734 | *Brassica juncea* |
| fatA | ZP_04749108 | 240170449 | *Mycobacterium kansasii* ATCC 12478 |
| fatA | ZP_04384386.1 | 229490548 | *Rhodococcus erythropolis* SK121 |
| fatA | YP_885312.1 | 118472377 | *Mycobacterium smegmatis* str. MC2 155 |
| fatB | AAQ08202.1 | 33325193 | *Helianthus annuus* |
| fatB | AEE28300.1 | 332190179 | *Arabidopsis thaliana* |
| fatB | ABI18986.1 | 112455672 | *Brassica juncea* |
| tesA | NP_415027.1 | 16128478 | *Escherichia coli* K12 |
| fatB2 | AAC49269.1 | 1292906 | *Cuphea hookeriana* |
| fatB1 | AAC49179.1 | 1215718 | *Cuphea palustris* |
| M96568.1:94 . . . 1251 | AAA33019.1 | 404026 | *Carthamus tinctorius* |
| fatB | Q41635.1 | 8469218 | *Umbellularia californica* |
| tesA | AAC73596.1 | 1786702 | *Escherichia coli* |

Several more of these candidates can be found in WO2007136762A2 (Production of fatty acids and derivatives thereof) and are described below.

| Gene | GenBank ID | GI number | Source Organism |
|---|---|---|---|
| fatB1 | AAA34215.1 | 170556 | *Umbellularia California* |
| fatB1 | Q39513 | 8469217 | *Cuphea hookeriana* |
| fatB | Q39473 | 8469216 | *Cinnamonum camphorum* |
| fatB[M141T} | CAA85388 | 804948 | *Arabidopsis thaliana* |
| fatA | NP 189147, NP 193041 | 15230256; 15235555 | *Arabidopsis thaliana* |
| fatA | CAC39106 | 14148965 | *Brassica juncea* |
| fatA | AAC72883 | 3859832 | *Cuphea hookeriana* |

Acyl CoA Synthetase and Acyl CoA Ligase (6.2.13)—Step K, FIG. 12

Fatty acids are often found in the cell in the activated form of an acyl-coA. The activation requires energy in the form of ATP. Acyl-CoAs are used in the biosynthesis of many cellular products and components, including membrane lipids. Acyl CoA cannot move across membranes. Therefore, fatty acids are transported in their free form and converted to acyl-CoAs while crossing the membrane by the enzymes acyl-CoA synthetases (ACS). These enzymes catalyze the esterification of fatty acids into the CoA thioesters concomitant with transport.

| Gene | GenBank ID | GI number | Organism |
|---|---|---|---|
| scs | YP_135572.1 | 55377722 | *Haloarcula marismortui* |
| sucC | NP_415256.1 | 16128703 | *Escherichia coli* |
| sucD | AAC73823.1 | 1786949 | *Escherichia coli* |
| LSC1 | NP_014785 | 6324716 | *Saccharomyces cerevisiae* |
| LSC2 | NP_011760 | 6321683 | *Saccharomyces cerevisiae* |
| paaF | AAC24333.2 | 22711873 | *Pseudomonas putida* |
| matB | AAC83455.1 | 3982573 | *Rhizobium leguminosarum* |
| bioW | NP_390902.2 | 50812281 | *Bacillus subtilis* |
| bioW | CAA10043.1 | 3850837 | *Pseudomonas mendocina* |
| bioW | P22822.1 | 115012 | *Bacillus sphaericus* |
| phlI | CAJ15517.1 | 77019264 | *Penicillium chrysogenum* |
| phlB | ABS19624.1 | 152002983 | *Penicillium chrysogenum* |
| paaF | AAC24333.2 | 22711873 | *Pseudomonas putida* |
| bioW | NP_390902.2 | 50812281 | *Bacillus subtilis* |
| AACS | NP_084486.1 | 21313520 | *Mus musculus* |
| AACS | NP_076417.2 | 31982927 | *Homo sapiens* |
| acs | AAC77039.1 | 1790505 | *Escherichia coli* |
| acoE | AAA21945.1 | 141890 | *Ralstonia eutropha* |
| acs1 | ABC87079.1 | 86169671 | *Methanothermobacter thermautotrophicus* |
| acs1 | AAL23099.1 | 16422835 | *Salmonella enterica* |
| ACS1 | Q01574.2 | 257050994 | *Saccharomyces cerevisiae* |
| AF1211 | NP_070039.1 | 11498810 | *Archaeoglobus fulgidus* |
| AF1983 | NP_070807.1 | 11499565 | *Archaeoglobus fulgidus* |

Oxidoreductase (acyl-ACP to Aldehyde) 1.2.11—Step J, FIG. 12

The reduction of an acyl-ACP to its corresponding aldehyde is catalyzed by an acyl-ACP reductase (AAR). Such a transformation is depicted in Step J of FIG. 12. Suitable enzyme candidates include the orf1594 gene product of *Synechococcus elongatus* PCC7942 and homologs thereof (Schirmer et al, Science, 329: 559-62 (2010)). The *S. elongates* PCC7942 acyl-ACP reductase is coexpressed with an aldehyde decarbonylase in an operon that appears to be conserved in a majority of cyanobacterial organisms. This enzyme, expressed in *E. coli* together with the aldehyde decarbonylase, conferred the ability to produce alkanes. The *P. marinus* AAR was also cloned into *E. coli* and, together with a decarbonylase, demonstrated to produce alkanes (US Application 2011/0207203).

| Gene | GenBank ID | GI Number | Organism |
|---|---|---|---|
| orf1594 | YP_400611.1 | 81300403 | *Synechococcus elongatus* PCC7942 |
| PMT9312_0533 | YP_397030.1 | 78778918 | *Prochlorococcus marinus* MIT 9312 |
| syc0051_d | YP_170761.1 | 56750060 | *Synechococcus elongatus* PCC 6301 |
| Ava_2534 | YP_323044.1 | 75908748 | *Anabaena variabilis* ATCC 29413 |
| alr5284 | NP_489324.1 | 17232776 | *Nostoc* sp. PCC 7120 |
| Aazo_3370 | YP_003722151.1 | 298491974 | *Nostoc azollae* |
| Cyan7425_0399 | YP_002481152.1 | 220905841 | *Cyanothece* sp. PCC 7425 |
| N9414_21225 | ZP_01628095.1 | 119508943 | *Nodularia spumigena* CCY9414 |
| L8106_07064 | ZP_01619574.1 | 119485189 | *Lyngbya* sp. PCC 8106 |

The gene candidates for Acyl-CoA reductase (Step L), CAR (Step O), FAR (Step N) and fatty aldehyde reductase (Step M) are described elsewhere in this application.

Oxidoreductase (acyl-ACP to Alcohol) Step O, FIG. 2 and Step P, FIG. 12

The reduction of an acyl-ACP to its corresponding alcohol is catalyzed by an acyl-ACP reductase (alcohol forming). Such a transformation is depicted in step P of FIG. 12. Fatty acyl reductase enzymes that use acyl-ACP substrates to produce alcohols are known in the art. Alcohol forming acyl-ACP reductases include Maqu_2220 of *Marinobacter aquaeolei* VT8 and Hch_05075 of *Hahella chejuensis* KCTC2396 (see WO2013/048557). These enzymes convert both acyl-ACP substrates and acyl-CoA substrates to their corresponding alcohols. The *M. aquaeolei* AAR was previously characterized as an aldehyde reductase (Wahlen et al, AEM 75:2758-2764 (2009)) and US 2010/0203614). Alcohol forming acyl-ACP reductase enzymes are shown in the table below.

| Protein | GenBank ID | GI Number | Organism |
|---|---|---|---|
| Maqu_2220 | ABM19299 | 120324984 | *Marinobacter aquaeolei* |
| Hch_05075 | YP_436183 | 83647748 | *Hahella chejuensis* |
| MDG893_11561 | ZP_01892457.1 | 149374683 | *Marinobacter algicola* DG893 |
| HP15_810 | ADP96574.1 | 311693701 | *Marinobacter adhaerens* HP15 |
| RED65_09894 | ZP_01305629.1 | 94499091 | *Oceanobacter* sp. RED65 |

Odd Chain Length Fatty acid Biosynthesis

Fatty acids with odd numbers of carbon can be formed by a similar mechanism as shown in FIG. 12. The starting metabolite in this case is propionyl-CoA instead of acetyl-CoA. The product of malonyl-ACP and propionyl-CoA is 3-oxovaleryl-ACP. This reaction is catalyzed by a β-ketoacyl-ACP synthase (EC 2.3.1.180) as shown in FIG. 12. The subsequent steps of fatty acid biosynthesis for an odd-chain fatty acid are the same as shown in FIG. 12. Several exemplary gene candidates for this step have been listed in US20120070868 (Odd chain fatty acid derivatives) and are shown below.

| Gene symbol | GenBank ID | GI number | Organism |
| --- | --- | --- | --- |
| fabH | AAC74175 | 1787333 | E. coli |
| fabH1 | NP_389015 | 16078198 | B. subtilis 168 |
| fabH2 | NP_388898 | 16078081 | B. subtilis 168 |
| fabH | CAB99151 | 9368919 | Streptomyces coelicolor |
| fabH | AAA99447 | 870807 | Streptomyces glaucescens |
| fabH3 | NP_823466 | 29828832 | Streptomyces avermitilis MA-4680 |
| fabH | YP_002349314 | 217963636 | Listeria monocytogenes |
| fabH | NP_645682 | 21282594 | Staphylococcus aureus MW2 |
| fabH | AAK74580 | 14971886 | Streptococcus pneumoniae |
| fabH | NP_722071 | 24380116 | Streptococcus mutans UA159 |
| fabH | NP_266927 | 15672753 | Lactococcus lactis subsp. lactis |
| fabH | YP_003687907 | 297626144 | Propionibacterium freundenreichii subsp. Shermanii |

Example XVII

Production of Propionyl-CoA

This example describes enzymes for production of Propionyl-CoA. Exemplary pathways are described FIG. 22. The pathways for production of propionyl-CoA can proceed via oxaloacetate, which includes conversion of PEP into oxaloacetate either via PEP carboxykinase or PEP carboxylase. Alternatively, PEP is converted first to pyruvate by pyruvate kinase and then to oxaloacetate by methylmalonyl-CoA carboxytransferase or pyruvate carboxylase. Oxaloacetate is converted to propionyl-CoA by means of the reductive TCA cycle, a methylmutase, a decarboxylase, an epimerase and a decarboxylase.

PEP Carboxykinase

Although the net conversion of phosphoenolpyruvate to oxaloacetate is redox-neutral, the mechanism of this conversion is important to the overall energetics of the co-production pathway. The most desirable enzyme for the conversion of PEP to oxaloacetate is PEP carboxykinase which simultaneously forms an ATP while carboxylating PEP. In most organisms, however, PEP carboxykinase serves a gluconeogenic function and converts oxaloacetate to PEP at the expense of one ATP. S. cerevisiae is one such organism whose native PEP carboxykinase, PCK1, serves a gluconeogenic role (Valdes-Hevia, FEBS. Lett. 258:313-316 (1989)). E. coli is another such organism, as the role of PEP carboxykinase in producing oxaloacetate is believed to be minor when compared to PEP carboxylase, which does not form ATP, possibly due to the higher $K_m$ for bicarbonate of PEP carboxykinase (Kim, Appl Environ Microbiol 70:1238-1241 (2004)). Nevertheless, activity of the native E. coli PEP carboxykinase from PEP towards oxaloacetate has been recently demonstrated inppc mutants of E. coli K-12 (Kwon, Journal of Microbiology and Biotechnology 16:1448-1452 (2006)). These strains exhibited no growth defects and had increased succinate production at high $NaHCO_3$ concentrations. In some organisms, particularly rumen bacteria, PEP carboxykinase is quite efficient in producing oxaloacetate from PEP and generating ATP. Examples of PEP carboxykinase genes that have been cloned into E. coli include those from Mannheimia succiniciproducens (Lee, Biotechnol. Bioprocess Eng. 7:95-99 (2002)), Anaerobiospirillum succiniciproducens (Laivenieks, Appl Environ Microbial 63:2273-2280 (1997)), and Actinobacillus succinogenes (Kim, Appl Environ Microbial 70:1238-1241 (2004)). Internal experiments have also found that the PEP carboxykinase enzyme encoded by Haemophilus influenza is highly efficient at forming oxaloacetate from PEP. These proteins are identified below.

| Protein | GenBank ID | GI Number | Organism |
| --- | --- | --- | --- |
| PCK1 | NP_013023 | 6322950 | Saccharomyces cerevisiae |
| pck | NP_417862.1 | 16131280 | Escherichia coli |
| pckA | YP_089485.1 | 52426348 | Mannheimia succiniciproducens |
| pckA | O09460.1 | 3122621 | Anaerobiospirillum succiniciproducens |
| pckA | Q6W6X5 | 75440571 | Actinobacillus succinogenes |
| pckA | P43923.1 | 1172573 | Haemophilus influenza |

These sequences and sequences for subsequent enzymes listed in this report can be used to identify homologue proteins in GenBank or other databases through sequence similarity searches (e.g. BLASTp). The resulting homologue proteins and their corresponding gene sequences provide additional DNA sequences for transformation into the host organism of choice.

PEP Carboxylase

PEP carboxylase represents an alternative enzyme for the formation of oxaloacetate from PEP. Since the enzyme does not generate ATP upon decarboxylating oxaloacetate, its utilization decreases the maximum ATP yield of the production pathway and represents a less favorable alternative for converting oxaloacetate to PEP. Nevertheless, the maximum theoretical C3 alcohols yield of 1.33 mol/mol will remain unchanged if PEP carboxylase is utilized to convert PEP to oxaloacetate. S. cerevisiae does not naturally encode a PEP carboxylase, but exemplary organisms that possess genes that encode PEP carboxylase include E. coli (Kai, Arch. Biochem. Biophys. 414:170-179 (2003)), Methylobacterium extorquens AM1 (Arps, J. Bacteriol. 175:3776-3783 (1993)), and Corynebacterium glutamicum (Eikmanns, Mol. Gen. Genet. 218:330-339 (1989)). These proteins are identified below.

| Protein | GenBank ID | GI Number | Organism |
| --- | --- | --- | --- |
| ppc | NP_418391 | 16131794 | Escherichia coli |
| ppcA | AAB58883 | 28572162 | Methylobacterium extorquens |
| ppc | ABB53270 | 80973080 | Corynebacterium glutamicum |

Pyruvate Kinase and Methylmalonyl-CoA Carboxyltransferase

An additional energetically efficient route to oxaloacetate from PEP requires two enzymatic activities: pyruvate kinase and methylmalonyl-CoA carboxytransferase. Pyruvate kinase catalyzes the ATP-generating conversion of PEP to pyruvate and is encoded by the PYK1 (Burke, *J. Biol. Chem.* 258:2193-2201 (1983)) and PYK2 (Boles et al., *J. Bacteriol.* 179:2987-2993 (1997)) genes in *S. cerevisiae*. In *E. coli*, this activity is catalyzed by the gene product of pykF and pykA. Methylmalonyl-CoA carboxytransferase catalyzes the conversion of pyruvate to oxaloacetate. Importantly, this reaction also simultaneously catalyzes the conversion of (S)-methylmalonyl-CoA to propionyl-CoA (see FIG. 22). An exemplary methylmalonyl-CoA carboxytransferase which is comprised of 1.3S, 5S, and 12S subunits can be found in *Propionibacterium freudenreichii* (Thornton et al., *J. Bacteriol* 175:5301-5308 (1993)). These proteins are identified below.

| Protein | GenBank ID | GI Number | Organism |
|---|---|---|---|
| PYK1 | NP_009362 | 6319279 | Saccharomyces cerevisiae |
| PYK2 | NP_014992 | 6324923 | Saccharomyces cerevisiae |
| pykF | NP_416191.1 | 16129632 | Escherichia coli |
| pykA | NP_416368.1 | 16129807 | Escherichia coli |
| 1.3S subunit | P02904 | 114847 | Propionibacterium freudenreichii |
| 5S subunit | Q70AC7 | 62901478 | Propionibacterium freudenreichii |
| 12S subunit | Q8GBW6 | 62901481 | Propionibacterium freudenreichii |

Pyruvate Kinase and Pyruvate Carboxylase

A combination of enzymes can convert PEP to oxaloacetate with a stoichiometry identical to that of PEP carboxylase. These enzymes are encoded by pyruvate kinase, PYK1 (Burke, *J. Biol. Chem.* 258:2193-2201 (1983)) or PYK2 (Boles et al., *J. Bacteriol*, 179:2987-2993 (1997)) and pyruvate carboxylase, PYC1 (Walker, *Biochem. Biophys. Res. Commun.* 176:1210-1217 (1991)) or PYC2 (Walker, *Biochem. Biophys. Res. Commun.* 176:1210-1217 (1991)). The latter proteins are identified below.

| Protein | GenBank ID | GI Number | Organism |
|---|---|---|---|
| PYC1 | NP_011453 | 6321376 | Saccharomyces cerevisiae |
| PYC2 | NP_009777 | 6319695 | Saccharomyces cerevisiae |
| Pyc | YP_890857.1 | 118470447 | Mycobacterium smegmatis |

Malate Dehydrogenase, Fumarase, Fumarate Reductase

Oxaloacetate can be converted to succinate by malate dehydrogenase, fumarase and fumarate reductase when the TCA cycle is operating in the reductive cycle. *S. cerevisiae* possesses three copies of malate dehydrogenase, MDH1 (McAlister-Henn, *J. Bacteriol* 169:5157-5166 (1987)) MDH2 (Minard, *Mol. Cell. Biol.* 11:370-380 (1991); and Gibson, *J. Biol. Chem.* 278:25628-25636 (2003)), and MDH3 (Steffan, *J. Biol. Chem.* 267:24708-24715 (1992)), which localize to the mitochondrion, cytosol, and peroxisome, respectively. *S. cerevisiae* contains one copy of a fumarase-encoding gene, FUM1, whose product localizes to both the cytosol and mitochondrion (Sass, *J. Biol. Chem.* 278:4510945116 (2003)). Fumarate reductase is encoded by two soluble enzymes, FRDS1 (Enomoto, *DNA. Res.* 3:263-267 (1996)) and FRDS2 (Muratsubaki, *Arch. Biochem. Biophys.* 352:175-181 (1998)), which localize to the cytosol and promitochondria, respectively, and are required for anaerobic growth on glucose (Arikawa, *Microbiol Lett.* 165:111-116 (1998)). *E. coli* is known to have an active malate dehydrogenase. It has three fumarases encoded byfumA, B and C, each one of which is active under different conditions of oxygen availability. The fumarate reductase in *E. coli* is composed of four subunits. These proteins are identified below.

| Protein | GenBank ID | GI Number | Organism |
|---|---|---|---|
| MDH1 | NP_012838 | 6322765 | Saccharomyces cerevisiae |
| MDH2 | NP_014515 | 116006499 | Saccharomyces cerevisiae |
| MDH3 | NP_010205 | 6320125 | Saccharomyces cerevisiae |
| FUM1 | NP_015061 | 6324993 | Saccharomyces cerevisiae |
| FRDS1 | P32614 | 418423 | Saccharomyces cerevisiae |
| FRDS2 | NP_012585 | 6322511 | Saccharomyces cerevisiae |
| frdA | NP_418578.1 | 16131979 | Escherichia coli |
| frdB | NP_418577.1 | 16131978 | Escherichia coli |
| frdC | NP_418576.1 | 16131977 | Escherichia coli |
| frdD | NP_418475.1 | 16131877 | Escherichia coli |

| Protein | GenBank ID | GI Number | Organism |
|---|---|---|---|
| Mdh | NP_417703.1 | 16131126 | Escherichia coli |
| FumA | NP_416129.1 | 16129570 | Escherichia coli |
| FumB | NP_418546.1 | 16131948 | Escherichia coli |
| FumC | NP_416128.1 | 16129569 | Escherichia coli |

Further exemplary enzymes are found in several organisms including *E. coli*, *Bacillus subtilis*, and *Rhizopus oryzae*.

| Protein | GenBank ID | GI number | Organism |
|---|---|---|---|
| mdh | AAC76268.1 | 1789632 | Escherichia coli |
| mdh | NP_390790.1 | 16079964 | Bacillus subtilis |
| MDH | ADG65261.1 | 296011196 | Rhizopus oryzae |

Succinyl-CoA:3-Ketoacid-CoA Transferase

The conversion of succinate to succinyl-CoA is ideally carried by a transferase which does not require the direct consumption of an ATP or GTP. This type of reaction is common in a number of organisms. Perhaps the top candidate enzyme for this reaction step is succinyl-CoA:3-ketoacid-CoA transferase. This enzyme converts succinate to succinyl-CoA while converting a 3-ketoacyl-CoA to a 3-ketoacid. Exemplary succinyl-CoA:3:ketoacid-CoA transferases are present in *Helicobacter pylori* (Corthesy-Theulaz et al., *J. Biol. Chem.* 272:25659-25667 (1997)), *Bacillus subtilis* (Stols et al., *Protein. Expr. Purif.* 53:396-403 (2007)), and *Homo sapiens* (Fukao et al., *Genomics*, 68:144-151 (2000); and Tanaka, *Mol. Hum. Reprod.* 8:16-23 (2002)). These proteins are identified below.

| Protein | GenBank ID | GI Number | Organism |
|---|---|---|---|
| HPAG1_0676 | YP_627417 | 108563101 | *Helicobacter pylori* |
| HPAG1_0677 | YP_627418 | 108563102 | *Helicobacter pylori* |
| ScoA | NP_391778 | 16080950 | *Bacillus subtilis* |
| ScoB | NP_391777 | 16080949 | *Bacillus subtilis* |
| OXCT1 | NP_000427 | 4557817 | *Homo sapiens* |
| OXCT2 | NP_071403 | 11545841 | *Homo sapiens* |

Succinyl-CoA: Acetyl-CoA Transferase

The conversion of succinate to succinyl-CoA can also be catalyzed by succinyl-CoA: Acetyl-CoA transferase. The gene product of cat1 of *Clostridium kluyveri* has been shown to exhibit succinyl-CoA: acetyl-CoA transferase activity (Sohling, *J Bacteriol.* 178:871-880 (1996)). In addition, the activity is present in *Trichomonas vaginalis* (van Grinsven et al., *J. Biol. Chem.* 283:1411-1418 (2008)) and *Trypanosoma brucei* (Riviere et al., *J. Biol. Chem.* 279:45337-45346 (2004)). These proteins are identified below.

| Protein | GenBank ID | GI Number | Organism |
|---|---|---|---|
| cat1 | P38946.1 | 729048 | *Clostridium kluyveri* |
| TVAG_395550 | XP_001330176 | 123975034 | *Trichomonas vaginalis* G3 |
| Tb11.02.0290 | XP_828352 | 71754875 | *Trypanosoma brucei* |

Succinyl-CoA Synthetase

The product of the LSC1 and LSC2 genes of *S. cerevisiae* and the sucC and sucD genes of *E. coli* naturally form a succinyl-CoA synthetase complex that catalyzes the formation of succinyl-CoA from succinate with the concomitant consumption of one ATP, a reaction which is reversible in vivo (Przybyla-Zawilask et al., *Eur. J. Biochem.* 258(2):736-743 (1998) and Buck et al., *J. Gen. Microbiol.* 132(6):1753-1762 (1986)). These proteins are identified below.

| Protein | GenBank ID | GI Number | Organism |
|---|---|---|---|
| LSC1 | NP_014785 | 6324716 | *Saccharomyces cerevisiae* |
| LSC2 | NP_011760 | 6321683 | *Saccharomyces cerevisiae* |
| SucC | NP_415256.1 | 16128703 | *Escherichia coli* |
| SucD | AAC73823.1 | 1786949 | *Escherichia coli* |

Methylmalonyl-CoA Mutase

Succinyl-CoA can be converted into (R)-methylmalonyl-CoA by methylmalonyl-CoA mutase (MCM). In *E. coli*, the reversible adenosylcobalamin-dependant mutase participates in a three-step pathway leading to the conversion of succinate to propionate (Haller, *Biochemistry* 39:4622-9 (2000)). MCM is encoded by genes scpA in *Escherichia coli* (Haller, *Biochemistry* 39: 4622-4629 (2000); and Bobik, *Anal. Bioanal. Chem.* 375:344-349 (2003)) and mutA in *Homo sapiens* (Padovani, *Biochemistry* 45:9300-9306 (2006)). In several other organisms MCM contains alpha and beta subunits and is encoded by two genes. Exemplary gene candidates encoding the two-subunit protein are *Propionibacterium fredenreichii* sp. *shermani* mutA and mutB (Korotkova, *J Biol Chem.* 279:13652-13658 (2004)) and *Methylobacterium extorquens* mcmA and mcmB (Korotkova, *J Biol Chem.* 279:13652-13658 (2004)). These proteins are identified below.

| Protein | GenBank ID | GI Number | Organism |
|---|---|---|---|
| ScpA | NP_417392.1 | 16130818 | *Escherichia coli* K12 |
| MutA | P22033.3 | 67469281 | *Homo sapiens* |
| MutA | P11652.3 | 127549 | *Propionibacterium fredenreichii* sp. *shermanii* |
| MutB | P11653.3 | 127550 | *Propionibacterium fredenreichii* sp. *shermanii* |
| mcmA | Q84FZ1 | 75486201 | *Methylobacterium extorquens* |
| McmB | Q6TMA2 | 75493131 | *Methylobacterium extorquens* |

Additional enzyme candidates identified based on high homology to the *E. coli* spcA gene product are identified below.

| Protein | GenBank ID | GI Number | Organism |
|---|---|---|---|
| Sbm | NP_838397.1 | 30064226 | Shigella flexneri |
| SARI_04585 | ABX24358.1 | 160867735 | Salmonella enterica |
| YfreA_01000861 | ZP_00830776.1 | 77975240 | Yersinia frederiksenii |

There further exists evidence that genes adjacent to the methylmalonyl-CoA mutase catalytic genes are also required for maximum activity. For example, it has been demonstrated that the meaB gene from *M. extorquens* forms a complex with methylmalonyl-CoA mutase, stimulates in vitro mutase activity, and possibly protects it from irreversible inactivation (Korotkova, *J Biol Chem.* 279:13652-13658 (2004)). The *M extorquens* meaB gene product is highly similar to the product of the *E. coli* argK gene (BLASTp: 45% identity, e-value: 4e-67) which is adjacent to scpA on the chromosome. No sequence for a meaB homolog in *P. freudenreichii* is catalogued in GenBank. However, the *Propionibacterium acnes* KPA171202 gene product, YP_055310.1, is 51% identical to the *M. extorquens* meaB protein and its gene is also adjacent to the methylmalonyl-CoA mutase gene on the chromosome. These proteins are identified below.

nyl-CoA to propionyl-CoA in *E. coli* (Benning, *Biochemistry.* 39:4630-4639 (2000); and Haller, *Biochemistry.* 39:4622-4629 (2000)). The stereo specificity of the *E. coli* enzyme was not reported, but the enzyme in *Propionigenium modestum* (Bott et al., *Eur. J. Biochem.* 250:590-599 (1997)) and *Veillonella parvula* (Huder, *J. Biol. Chem.* 268:24564-24571 (1993)) catalyzes the decarboxylation of the (S)-stereoisomer of methylmalonyl-CoA (Hoffmann, *FEBS. Lett.* 220:121-125 (1987). The enzymes from *P. modestum* and *V. parvula* are comprised of multiple subunits that not only decarboxylate (S)-methylmalonyl-CoA, but also create a pump that transports sodium ions across the cell membrane as a means to generate energy. These proteins are identified below.

| Protein | GenBank ID | GI Number | Organism |
|---|---|---|---|
| ArgK | AAC75955.1 | 1789285 | Escherichia coli K12 |
| KPA171202 | YP_055310.1 | 50842083 | Propionibacterium acnes |
| MeaB | 2QM8_B | 158430328 | Methylobacterium extorquens |

Methylmalonyl-CoA Epimerase

Methylmalonyl-CoA epimemse (MMCE) is the enzyme that interconverts (R)-methylmalonyl-CoA and (S)-methylmalonyl-CoA. MMCE is an essential enzyme in the breakdown of odd-numbered fatty acids and of the amino acids valine, isoleucine, and methionine. Methylmalonyl-CoA epimemse is present in organisms such as *Bacillus subtilis* (YqjC) (Haller, *Biochemistry.* 39:4622-4629 (2000)), *Homo sapiens* (YqjC) (Fuller, *Biochem. J* 213:643-650 (1983)), *Rattus norvegicus* (Mcee) (Bobik, *J Biol Chem.* 276:37194-37198 (2001)), *Propionibacterium shermanii* (AF454511) (Haller, *Biochemistry* 39:4622-9 (2000); McCarthy, *Structure* 9:637-46 (2001) and (Fuller, *Biochem. J* 213:643-650 (1983)) and *Caenorhabditis elegans* (mmce) (Kuhnl et al., *FEBS J* 272:1465-1477 (2005)). The additional gene candidate, AE016877 in *Bacillus cereus*, has high sequence homology to the other characterized enzymes. MMCE activity is required if the employed methylmalonyl-CoA decarboxylase or methylmalonyl-CoA carboxytransferase requires the (S) stereoisomer of methylmalonyl-CoA. These proteins are identified below.

| Protein | GenBank ID | GI Number | Organism |
|---|---|---|---|
| YgfG | NP_417394 | 90111512 | Escherichia coli |
| mmdA | CAA05137 | 2706398 | Propionigenium modestum |
| mmdD | CAA05138 | 2706399 | Propionigenium modestum |
| mmdC | CAA05139 | 2706400 | Propionigenium modestum |
| mmdB | CAA05140 | 2706401 | Propionigenium modestum |
| mmdA | CAA80872 | 415915 | Veillonella parvula |
| mmdC | CAA80873 | 415916 | Veillonella parvula |
| mmdE | CAA80874 | 415917 | Veillonella parvula |
| mmdD | CAA80875 | 415918 | Veillonella parvula |
| mmdB | CAA80876 | 415919 | Veillonella parvula |

Example XVIII

In Vivo Labeling Assay for Conversion of Methanol to $CO_2$

This example describes a functional methanol pathway in a microbial organism.

| Protein | GenBank ID | GI Number | Organism |
|---|---|---|---|
| YqjC | NP_390273 | 255767522 | Bacillus subtilis |
| MCEE | Q96PE7.1 | 50401130 | Homo sapiens |
| Mcee_predicted | NP_001099811.1 | 157821869 | Rattus norvegicus |
| AF454511 | AAL57846.1 | 18042135 | Propionibacterium fredenreichii sp. shermanii |
| Mmce | AAT92095.1 | 51011368 | Caenorhabditis elegans |
| AE016877 | AAP08811.1 | 29895524 | Bacillus cereus ATCC 14579 |

Methylmalonyl-CoA Decarboxylase

Methylmalonyl-CoA decarboxylase, is a biotin-independent enzyme that catalyzes the conversion of methylmalo- Strains with functional reductive TCA branch and pyruvate formate lyase deletion were grown aerobically in LB medium overnight, followed by inoculation of M9 high-seed media containing IPTG and aerobic growth for 4 hrs. These strains had methanol dehydrogenase/ACT pairs in the presence and absence of formaldehyde dehydrogenase or formate dehydrogenase. ACT is an activator protein (a Nudix hydrolase). At this time, strains were pelleted, resuspended in fresh M9 medium high-seed media containing 2% $^{13}CH_3OH$, and sealed in anaerobic vials. Head space was replaced with nitrogen and strains grown for 40 hours at 37° C. Following growth, headspace was analyzed for $^{13}CO_2$. Media was examined for residual methanol as well as BDO and byproducts. All constructs expressing methanol dehydrogenase (MeDH) mutants and MeDH/ACT pairs grew to slightly lower ODs than strains containing empty vector controls. This is likely due to the high expression of these constructs (Data not shown). One construct (2315/2317) displayed significant accumulation of labeled $CO_2$ relative to controls in the presence of FaIDH, FDH or no coexpressed protein. This shows a functional MeOH pathway in E. coli and that the endogenous glutathione-dependent formaldehyde detoxification genes (frmAB) are sufficient to carry flux generated by the current MeDH/ACT constructs.

2315 is internal laboratory designation for the MeDH from Bacillus methanolicus MGA3 (GenBank Accession number: EIJ77596.1; GI number: 387585261), and 2317 is internal laboratory designation for the activator protein from the same organism (locus tag: MGA3_09170; GenBank Accession number:EIJ83380; GI number: 387591061).

Sequence analysis of the NADH-dependent MeDH from Bacillus methanolicus places the enzyme in the alcohol dehydrogenase family III. It does not contain any tryptophan residues, resulting in a low extinction coefficient (18,500 $M^{-1}$, $cm^{-1}$) and should be detected on SDS gels by Coomassie staining.

The enzyme has been characterized as a multisubunit complex built from 43 kDa subunits containing one Zn and 1-2 Mg atoms per subunit. Electron microscopy and sedimentation studies determined it to be a decamer, in which two rings with five-fold symmetry are stacked on top of each other (Vonck et al., J. Biol. Chem. 266:3949-3954, 1991). It is described to contain a tightly but not covalently bound cofactor and requires exogenous $NAD^+$ as $e^-$-acceptor to measure activity in vitro. A strong increase (10-40-fold) of in vitro activity was observed in the presence of an activator protein (ACT), which is a homodimer (21 kDa subunits) and contains one Zn and one Mg atom per subunit.

The mechanism of the activation was investigated by Kloosterman et al., J. Biol. Chem. 277:34785-34792, 2002, showing that ACT is a Nudix hydrolase and Hektor et al., J. Biol. Chem. 277:46966-46973, 2002, demonstrating that mutation of residue S97 to G or Tin MeDH changes activation characteristics along with the affinity for the cofactor. While mutation of residues G15 and D88 had no significant impact, a role of residue G13 for stability as well as of residues G95, D100, and K103 for the activity is suggested. Both papers together propose a hypothesis in which ACT cleaves MeDH-bound $NAD^+$. MeDH retains AMP bound and enters an activated cycle with increased turnover.

The stoichiometric ratio between ACT and MeDH is not well defined in the literature. Kloosterman et al., supra determine the ratio of dimeric Act to decameric MeDH for full in vitro activation to be 10:1. In contrast, Arfman et al. J. Biol. Chem. 266:3955-3960, 1991 determined a ratio of 3:1 in vitro for maximum and a 1:6 ratio for significant activation, but observe a high sensitivity to dilution. Based on expression of both proteins in Bacillus, the authors estimate the ratio in vivo to be around 1:17.5.

However, our in vitro experiments with purified activator protein (2317A) and methanol dehydrogenase (2315A) showed the ratio of ACT to MeDH to be 10:1. This in vitro test was done with 5 M methanol, 2 mM NAD and 10 μM methanol dehydrogenase 2315A at pH 7.4.

Example XIX

Improving Product Yields on Methanol Using Phosphoketolase-dependent cetyl-CoA Synthesis Acetyl-CoA is the immediate precursor for the synthesis of isopropanol, fatty acyl-CoA molecules, and fatty acyl-ACP molecules as shown in FIGS. 2, 11, and 12. Phosphoketolase pathways make possible synthesis of acetyl-CoA without requiring decarboxylation of pyruvate (Bogorad et al, Nature, 2013, published online 29 Sep. 2013; United States Publication 2006-0040365), which thereby provides higher yields of fatty alcohols, fatty acids, fatty aldehydes, and isopropanol from carbohydrates and methanol than the yields attainable without phosphoketolase enzymes.

For example, synthesis of an exemplary fatty alcohol, dodecanol, from methanol using methanol dehydrogenase (step A of FIG. 1), a formaldehyde assimilation pathway (steps B, C, D of FIG. 1), the pentose phosphate pathway, and glycolysis can provide a maximum theoretical yield of 0.0556 mole dodecanol/mole methanol.

$18CH_4O+9O_2 \rightarrow C_{12}H_{26}O+23H_2O+6CO_2$

However, if these pathways are combined with a phosphoketolase pathway (steps T, U, V, W, X of FIG. 1), a maximum theoretical yield of 0.0833 mole dodecanol/mole methanol can be obtained if we assume that the pathway is not required to provide net generation of ATP for cell growth and maintenance requirements.

$12CH_4O \rightarrow C_{12}H_{26}O+11H_2O$

ATP for energetic requirements can be synthesized, at the expense of lowering the maximum theoretical product yield, by oxidizing methanol to $CO_2$ using several combinations of enzymes depicted in FIG. 10, glycolysis, the TCA cycle, the pentose phosphate pathway, and oxidative phosphorylation.

Similarly, synthesis of isopropanol from methanol using methanol dehydrogenase (step A of FIG. 1), a formaldehyde assimilation pathway (steps B, C, D of FIG. 1), the pentose phosphate pathway and glycolysis can provide a maximum theoretical yield of 0.1667 mole isopropanol/mole methanol.

$6CH_4O+4.5O_2 \rightarrow C_3H_8O+8H_2O+3CO_2$

However, if these pathways are applied in combination with a phosphoketolase pathway (steps T, U, V, W, X of FIG. 1), a maximum theoretical yield of 0.250 mole isopropanol/mole methanol can be obtained.

$4CH_4O+1.5O_2 \rightarrow C_3H_8O+4H_2O+CO_2$

The overall pathway is ATP and redox positive enabling synthesis of both ATP and NAD(P)H from conversion of MeOH to isopropanol. Additional ATP can be synthesized, at the expense of lowering the maximum theoretical product yield, by oxidizing methanol to $CO_2$ using several combinations of enzymes depicted in FIG. 10, glycolysis, the TCA cycle, the pentose phosphate pathway, and oxidative phosphorylation.

Example XX

Improving Product Yeilds on Carbohydrates using Phosphoketolase-Dependent Acetyl-CoA Synthesis and Exogenous Reducing Equivalents The theoretical yield of fatty acyl-CoA molecules, fatty acyl-ACP molecules, and isopropanol from carbohydrates including but not limited to glucose, glycerol, sucrose, fructose, xylose, arabinose, and galactose, can also be enhanced by phosphoketolase enzymes, particularly when reducing equivalents are provided by an exogenous source such as hydrogen or methanol. This is because phosphoketolase enzymes provide acetyl-CoA synthesis with 100% carbon conversion efficiency (e.g., 3 acetyl-CoA's per glucose, 2.5 acetyl-CoA's per xylose, 1.5 acetyl-CoA's per glycerol).

For example, synthesis of an exemplary fatty alcohol, dodecanol, from glucose in the absence of phosphoketolase enzymes can reach a maximum theoretical dodecanol yield of 0.3333 mole dodecanol/mole glucose.

$$3C_6H_{12}O_6 \rightarrow C_{12}H_{26}O + 5H_2O + 6CO_2$$

However, if enzyme steps T, U, V, W, X of FIG. 1 are applied in combination with glycolysis, the pentose phosphate pathway, and an external redox source (e.g., methanol, hydrogen) using the pathways shown in FIG. 10, the maximum theoretical yield can be increased to 0.5000 mole dodecanol/mole glucose.

$$2C_{61}H_{12}O_6 + 4CH_4O \rightarrow C_{12}H_{26}O + 7H_2O + 4CO_2$$

This assumes that the pathway is not required to provide net generation of ATP for cell growth and maintenance requirements. ATP for energetic requirements can be synthesized by oxidizing additional methanol to $CO_2$ using several combinations of enzymes depicted in FIG. 10.

Similarly, synthesis of isopropanol from glucose in the absence of phosphoketolase enzymes can achieve a maximum theoretical isopropanol yield of 1.000 mole isopropanol/mole glucose.

$$C_6H_{12}O_6 + 1.5O_2 \rightarrow C_3H_8O + 2H_2O + 3CO_2$$

However, if enzyme steps T, U, V, W, X of FIG. 1 are applied in combination with glycolysis and the pentose phosphate pathway, the maximum theoretical yield can be increased to 1.333 mole isopropanol/mole glucose.

$$C_6H_{12}O_6 \rightarrow 1.333C_3H_8O + 0.667H_2O + 2CO_2$$

If enzyme steps T, U, V, W, X of FIG. 1 are applied in combination with glycolysis, the pentose phosphate pathway, and external redox source (e.g., methanol, hydrogen) using the pathways shown in FIG. 10, the maximum theoretical yield can be increased to 1.500 mole isopropanol/mole glucose.

$$C_6H_{12}O_6 + 0.5CH_4O \rightarrow 1.5C_3H_8O + H_2O + 2CO_2$$

Example XXI

Phosphoketolase-Dependent Acetyl-CoA Synthesis Enzymes

This Example provides genes that can be used for enhancing carbon flux through acetyl-CoA using phosphoketolase enzymes.

FIG. 1, Step T—Fructose-6-Phosphate Phosphoketolase

Conversion of fructose-6-phosphate and phosphate to acetyl-phosphate and erythrose-5-phosphate can be carried out by fructose-6-phosphate phosphoketolase (EC 4.1.2.22). Conversion of fructose-6-phosphate and phosphate to acetyl-phosphate and erythrose-5-phosphate is one of the key reactions in the *Bifidobacterium* shunt. There is evidence for the existence of two distinct phosphoketolase enzymes in *bifidobacteria* (Sgorbati et al, 1976, Antonie Van Leeuwenhoek, 42(1-2) 49-57; Grill et al, 1995, Curr Microbiol, 31(1); 49-54). The enzyme from *Bifidobacterium dentium* appeared to be specific solely for fructose-6-phosphate (EC: 4.1.2.22) while the enzyme from *Bifidobacterium pseudolongum* subsp. *globosum* is able to utilize both fructose-6-phosphate and D-xylulose 5-phosphate (EC: 4.1.2.9) (Sgorbati et al, 1976, Antonie Van Leeuwenhoek, 42(1-2) 49-57). The enzyme encoded by the xfp gene, originally discovered in *Bifidobacterium animalis lactis*, is the dual-specificity enzyme (Meik et al., 2001, J Bacteriol, 183, 2929-2936; Yin et al, 2005, FEMS Microbiol Lett, 246(2); 251-257). Additional phosphoketolase enzymes can be found in *Leuconostoc* mesenteroides (Lee et al, Biotechnol Lett. 2005 June; 27(12):853-8), *Clostridium acetobutylicum* ATCC 824 (Servinsky et al, Journal of Industrial Microbiology & Biotechnology, 2012, 39, 1859-1867), *Aspergillus nidulans* (Kocharin et al, 2013, Biotechnol Bioeng, 110(8), 2216-2224; Papini, 2012, Appl Microbiol Biotechnol, 95 (4), 1001-1010), *Bifidobacterium breve* (Suzuki et al, 2010, Acta Crystallogr Sect F Struct Biol Cryst Commun., 66(Pt 8):941-3), *Lactobacillus paraplantarum* (Jeong et al, 2007, J Microbiol Biotechnol, 17(5), 822-9).

| Protein | GENBANK ID | GI NO. | ORGANISM |
| --- | --- | --- | --- |
| xfp | YP_006280131.1 | 386867137 | *Bifidobacterium animalis lactis* |
| xfp | AAV66077.1 | 55818565 | *Leuconostoc mesenteroides* |
| CAC1343 | NP_347971.1 | 15894622 | *Clostridium acetobutylicum* ATCC 824 |
| xpkA | CBF76492.1 | 259482219 | *Aspergillus nidulans* |
| xfp | WP_003840380.1 | 489937073 | *Bifidobacterium dentium* ATCC 27678 |
| xfp | AAR98788.1 | 41056827 | *Bifidobacterium pseudolongum* subsp. *globosum* |
| xfp | WP_022857642.1 | 551237197 | *Bifidobacterium pseudolongum* subsp. *globosum* |
| xfp | ADF97524.1 | 295314695 | *Bifidobacterium breve* |
| xfp | AAQ64626.1 | 34333987 | *Lactobacillus paraplantarum* |

FIG. 1, Step U—Xylulose-5-Phosphate Phosphoketolase

Conversion of xylulose-5-phosphate and phosphate to acetyl-phosphate and glyceraldehyde-3-phosphate can be carried out by xylulose-5-phosphate phosphoketolase (EC 4.1.2.9). There is evidence for the existence of two distinct phosphoketolase enzymes in *bifidobacteria* (Sgorbati et al, 1976, Antonie Van Leeuwenhoek, 42(1-2) 49-57; Grill et al, 1995, Curr Microbiol, 31(1); 49-54). The enzyme from *Bifidobacterium dentium* appeared to be specific solely for fructose-6-phosphate (EC: 4.1.2.22) while the enzyme from *Bifidobacterium pseudolongum* subsp. *globosum* is able to utilize both fructose-6-phosphate and D-xylulose 5-phosphate (EC: 4.1.2.9) (Sgorbati et al, 1976, Antonie Van Leeuwenhoek, 42(1-2) 49-57). Many characterized enzymes have dual-specificity for xylulose-5-phosphate and fructose-6-phosphate. The enzyme encoded by the xfp gene, originally discovered in *Bifidobacterium animalis lactis*, is the dual-specificity enzyme (Meik et al., 2001, J Bacteriol, 183, 2929-2936; Yin et al, 2005, FEMS Microbiol Lett, 246(2); 251-257). Additional phosphoketolase enzymes can be found in *Leuconostoc mesenteroides* (Lee et al, Biotechnol Lett. 2005 June; 27(12):853-8), *Clostridium acetobutylicum* ATCC 824 (Servinsky et al, Journal of Industrial Microbiology & Biotechnology, 2012, 39, 1859-1867), *Aspergillus nidulans* (Kocharin et al, 2013, Biotechnol Bioeng, 110(8), 2216-2224; Papini, 2012, Appl Microbiol Biotechnol, 95 (4), 1001-1010), *Bifidobacterium breve* (Suziki et al, 2010, Acta Crystallogr Sect F Struct Biol Cryst Commun., 66(Pt 8):941-3), and *Lactobacillus paraplantarum* (Jeong et al, 2007, J Microbiol Biotechnol, 17(5), 822-9).

product of *E. coli* purT (Marolewski et al., Biochemistry 33:2531-2537 (1994). Some butyrate kinase enzymes (EC 2.7.2.7), for example buk1 and buk2 from *Clostridium acetobutylicum*, also accept acetate as a substrate (Hartmanis, M. G., J. Biol. Chem. 262:617-621 (1987)). Homologs exist in several other organisms including *Salmonella enterica* and *Chlamydomonas reinhardtii*.

| Protein | GENBANK ID | GI NO. | ORGANISM |
|---|---|---|---|
| xfp | YP_006280131.1 | 386867137 | *Bifidobacterium animalis lactis* |
| xfp | AAV66077.1 | 55818565 | *Leuconostoc mesenteroides* |
| CAC1343 | NP_347971.1 | 15894622 | *Clostridium acetobutylicum* ATCC 824 |
| xpkA | CBF76492.1 | 259482219 | *Aspergillus nidulans* |
| xfp | AAR98788.1 | 41056827 | *Bifidobacterium pseudolongum* subsp. *globosum* |
| xfp | WP_022857642.1 | 551237197 | *Bifidobacterium pseudolongum* subsp. *globosum* |
| xfp | ADF97524.1 | 295314695 | *Bifidobacterium breve* |
| xfp | AAQ64626.1 | 34333987 | *Lactobacillus paraplantarum* |

FIG. 1, Step V—Phosphotransacetylase

The formation of acetyl-CoA from acetyl-phosphate can be catalyzed by phosphotransacetylase (EC 2.3.1.8). The pta gene from *E. coli* encodes an enzyme that reversibly converts acetyl-CoA into acetyl-phosphate (Suzuki, T., Biochim. Biophys. Acta 191:559-569 (969)). Additional acetyltransferase enzymes have been characterized in *Bacillus subtilis* (Rado and Hoch, Biochim. Biophys. Acta 321:114-125 (1973), *Clostridium kluyveri* (Stadtman, E., Methods Enzymol. 1:5896-599 (1955), and *Thermotoga maritima* (Bock et al., J. Bacteriol. 181:1861-1867 (1999)). This reaction can also be catalyzed by some phosphotranbutyrylase enzymes (EC 2.3.1.19), including the ptb gene products from *Clostridium acetobutylicum* (Wiesenbom et al., App. Environ. Microbiol. 55:317-322 (1989); Walter et al., Gene 134:107-111(1993)). Additional ptb genes are found in butyrate-producing bacterium L2-50 (Louis et al., J. Bacteriol. 186:2099-2106 (2004) and *Bacillus megaterium* (Vazquez et al., Curr. Microbiol. 42:345-349 (2001). Homologs to the *E. coli* pta gene exist in several other organisms including *Salmonella enterica* and *Chlamydomonas reinhardtii*.

| Protein | GenBank ID | GI Number | Organism |
|---|---|---|---|
| ackA | NP_416799.1 | 16130231 | *Escherichia coli* |
| Ack | AAB18301.1 | 1491790 | *Clostridium acetobutylicum* |
| Ack | AAA72042.1 | 349834 | *Methanosarcina thermophila* |
| purT | AAC74919.1 | 1788155 | *Escherichia coli* |
| buk1 | NP_349675 | 15896326 | *Clostridium acetobutylicum* |
| buk2 | Q97II1 | 20137415 | *Clostridium acetobutylicum* |
| ackA | NP_461279.1 | 16765664 | *Salmonella typhimurium* |
| ACK1 | XP_001694505.1 | 159472745 | *Chlamydomonas reinhardtii* |
| ACK2 | XP_001691682.1 | 159466992 | *Chlamydomonas reinhardtii* |

FIG. 1, Step X—Acetyl-CoA Transferase, Synthetase, or Ligase

The acylation of acetate to acetyl-CoA can be catalyzed by enzymes with acetyl-CoA synthetase, ligase or transferase activity. Two enzymes that can catalyze this reaction are AMP-forming acetyl-CoA synthetase or ligase (EC 6.2.1.1) and ADP-forming acetyl-CoA synthetase (EC 6.2.1.13). AMP-forming acetyl-CoA synthetase (ACS) is the predominant enzyme for activation of acetate to acetyl-CoA. Exemplary ACS enzymes are found in *E. coli* (Brown et al., J. Gen. Microbiol. 102:327-336 (1977)), *Ralstonia eutropha*

| Protein | GenBank ID | GI Number | Organism |
|---|---|---|---|
| Pta | NP_416800.1 | 71152910 | *Escherichia coli* |
| Pta | P39646 | 730415 | *Bacillus subtilis* |
| Pta | A5N801 | 146346896 | *Clostridium kluyveri* |
| Pta | Q9X0L4 | 6685776 | *Thermotoga maritime* |
| Ptb | NP_349676 | 34540484 | *Clostridium acetobutylicum* |
| Ptb | AAR19757.1 | 38425288 | butyrate-producing bacterium L2-50 |
| Ptb | CAC07932.1 | 10046659 | *Bacillus megaterium* |
| Pta | NP_461280.1 | 16765665 | *Salmonella enterica* subsp. *enterica* serovar Typhimurium str. LT2 |
| PAT2 | XP_001694504.1 | 159472743 | *Chlamydomonas reinhardtii* |
| PAT1 | XP_001691787.1 | 159467202 | *Chlamydomonas reinhardtii* |

FIG. 1, Step W—Acetate Kinase

Acetate kinase (EC 2.7.2.1) can catalyze the reversible ATP-dependent phosphorylation of acetate to acetylphosphate. Exemplary acetate kinase enzymes have been characterized in many organisms including *E. coli*, *Clostridium acetobutylicum* and *Methanosarcina thermophila* (Ingram-Smith et al., J. Bacteriol. 187:2386-2394 (2005); Fox and Roseman, J. Biol. Chem. 261:13487-13497 (1986); Winzer et al., Microbioloy 143 (Pt 10):3279-3286 (1997)). Acetate kinase activity has also been demonstrated in the gene product of *E. coli* purT (Marolewski et al., Biochemistry 33:2531-2537 (1994). Some butyrate kinase enzymes (EC 2.7.2.7), for example buk1 and buk2 from *Clostridium acetobutylicum*, also accept acetate as a substrate (Hartmanis, M. G., J. Biol. Chem. 262:617-621 (1987)). (Priefert and Steinbuchel, J. Bacteriol. 174:6590-6599 (1992)), *Methanothermobacter thermautotrophicus* (Ingram-Smith and Smith, Archaea 2:95-107 (2007)), *Salmonella enterica* (Gulick et al., Biochemistry 42:2866-2873 (2003)) and *Saccharomyces cerevisiae* (Jogl and Tong, Biochemistry 43:1425-1431(2004)). ADP-forming acetyl-CoA synthetases are reversible enzymes with a generally broad substrate range (Musfeldt and Schonheit, J. Bacteriol. 184: 636-644 (2002)). Two isozymes of ADP-forming acetyl-CoA synthetases are encoded in the *Archaeoglobus fulgidus* genome by are encoded by AF1211 and AF1983 (Musfeldt and Schonheit, supra (2002)). The enzyme from *Haloarcula marismortui* (annotated as a succinyl-CoA synthetase) also accepts acetate as a substrate and reversibility of the enzyme was demonstrated (Brasen and Schonheit, *Arch. Microbiol.* 182:277-287 (2004)). The ACD encoded by PAE3250 from hyperthermophilic crenarchaeon *Pyrobaculum aerophilum* showed the broadest substrate range of all characterized ACDs, reacting with acetate, isobutyryl-CoA (preferred substrate) and phenylacetyl-CoA (Brasen and Schonheit, supra (2004)). Directed evolution or engineering can be used to modify this enzyme to operate at the physiological temperature of the host organism. The enzymes from *A. fulgidus, H. marismortui* and *P. aerophilum* have all been cloned, functionally expressed, and characterized in *E. coli* (Brasen and Schonheit, supra (2004); Musfeldt and Schonheit, supra (2002)). Additional candidates include the succinyl-CoA synthetase encoded by sucCD in *E. coli* (Buck et al., *Biochemistry* 24:6245-6252 (1985)) and the acyl-CoA ligase from *Pseudomonas putida* (Fernandez-Valverde et al., *Appl. Environ. Microbiol.* 59:1149-1154 (1993)). The aforementioned proteins are shown below.

| Protein | GenBank ID | GI Number | Organism |
|---|---|---|---|
| Acs | AAC77039.1 | 1790505 | *Escherichia coli* |
| acoE | AAA21945.1 | 141890 | *Ralstonia eutropha* |
| acs1 | ABC87079.1 | 86169671 | *Methanothermobacter thermautotrophicus* |
| acs1 | AAL23099.1 | 16422835 | *Salmonella enterica* |
| ACS1 | Q01574.2 | 257050994 | *Saccharomyces cerevisiae* |
| AF1211 | NP_070039.1 | 11498810 | *Archaeoglobus fulgidus* |
| AF1983 | NP_070807.1 | 11499565 | *Archaeoglobus fulgidus* |
| Scs | YP_135572.1 | 55377722 | *Haloarcula marismortui* |
| PAE3250 | NP_560604.1 | 18313937 | *Pyrobaculum aerophilum* str. IM2 |
| sucC | NP_415256.1 | 16128703 | *Escherichia coli* |
| sucD | AAC73823.1 | 1786949 | *Escherichia coli* |
| paaF | AAC24333.2 | 22711873 | *Pseudomonas putida* |

An acetyl-CoA transferase that can utilize acetate as the CoA acceptor is acetoacetyl-CoA transferase, encoded by the *E. coli* atoA (alpha subunit) and atoD (beta subunit) genes (Vanderwinkel et al., *Biochem.Biophys.Res Commun.* 33:902-908 (1968); Korolev et al., *Acta Crystallogr.D Biol Crystallogr.* 58:2116-2121(2002)). This enzyme has also been shown to transfer the CoA moiety to acetate from a variety of branched and linear acyl-CoA substrates, including isobutyrate (Matthies et al., *Appl Environ Microbiol* 58:1435-1439 (1992)), valerate (Vanderwinkel et al., supra) and butanoate (Vanderwinkel et al., supra). Similar enzymes exist in *Corynebacterium glutamicum* ATCC 13032 (Duncan et al., *Appl Environ Microbiol* 68:5186-5190 (2002)), *Clostridium acetobutylicum* (Cary et al., *Appl Environ Microbiol* 56:1576-1583 (1990)), and *Clostridium saccharoperbuylacetonicum* (Kosaka et al., *Biosci.Biotechnol Biochem.* 71:58-68 (2007)). These proteins are identified below.

| Protein | GenBank ID | GI Number | Organism |
|---|---|---|---|
| atoA | P76459.1 | 2492994 | *Escherichia coli* K12 |
| atoD | P76458.1 | 2492990 | *Escherichia coli* K12 |
| actA | YP_226809.1 | 62391407 | *Corynebacterium glutamicum* ATCC 13032 |
| cg0592 | YP_224801.1 | 62389399 | *Corynebacterium glutamicum* ATCC 13032 |
| ctfA | NP_149326.1 | 15004866 | *Clostridium acetobutylicum* |
| ctfB | NP_149327.1 | 15004867 | *Clostridium acetobutylicum* |
| ctfA | AAP42564.1 | 31075384 | *Clostridium saccharoperbutylacetonicum* |
| ctfB | AAP42565.1 | 31075385 | *Clostridium saccharoperbutylacetonicum* |

Additional exemplary acetyl-CoA transferase candidates are catalyzed by the gene products of cat1, cat2, and cat3 of *Clostridium kluyveri* which have been shown to exhibit succinyl-CoA, 4-hydroxybutyryl-CoA, and butyryl-CoA transferase activity, respectively (Seedorf et al., supra; Sohling et al., *Eur.J Biochem.* 212:121-127 (1993); Sohling et al., *J Bacteriol.* 178:871-880 (1996)). Similar CoA transferase activities are also present in *Trichomonas vaginalis* (van Grinsven et al., *J.Biol.Chem.* 283:1411-1418 (2008)) and *Trypanosoma brucei* (Riviere et al., *J.Biol.Chem.* 279: 45337-45346 (2004)). These proteins are identified below.

| Protein | GenBank ID | GI Number | Organism |
| --- | --- | --- | --- |
| cat1 | P38946.1 | 729048 | Clostridium kluyveri |
| cat2 | P38942.2 | 172046066 | Clostridium kluyveri |
| cat3 | EDK35586.1 | 146349050 | Clostridium kluyveri |
| TVAG_395550 | XP_001330176 | 123975034 | Trichomonas vaginalis G3 |
| Tb11.02.0290 | XP_828352 | 71754875 | Trypanosoma brucei |

Example XXII

Attenuation or Disruption of Endogenous Enzymes

This example provides endogenous enzyme targets for attenuation or disruption that can be used for enhancing carbon flux through methanol dehydrogenase and formaldehyde assimilation pathways.

DHA Kinase

Methylotrophic yeasts typically utilize a cytosolic DHA kinase to catalyze the ATP-dependent activation of DHA to DHAP. DHAP together with G3P is combined to form fructose-1,6-bisphosphate (FBP) by FBP aldolase. FBP is then hydrolyzed to F6P by fructose bisphosphatase. The net conversion of DHA and G3P to F6P by this route is energetically costly (1 ATP) in comparison to the F6P aldolase route, described above and shown in FIG. 1. DHA kinase also competes with F6P aldolase for the DHA substrate. Attenuation of endogenous DHA kinase activity will thus improve the energetics of formaldehyde assimilation pathways, and also increase the intracellular availability of DHA for DHA synthase. DHA kinases of *Saccharomyces cerevisiae*, encoded by DAK1 and DAK2, enable the organism to maintain low intracellular levels of DHA (Molin et al, *J Biol Chem* 278:1415-23 (2003)). In methylotrophic yeasts DHA kinase is essential for growth on methanol (Luers et al, *Yeast* 14:759-71(1998)). The DHA kinase enzymes of *Hansenula polymorpha* and *Pichia pastoris* are encoded by DAK (van der Klei et al, Curr Genet 34:1-11(1998); Luers et al, supra). DAK enzymes in other organisms can be identified by sequence similarity to known enzymes.

| Protein | GenBank ID | GI Number | Organism |
| --- | --- | --- | --- |
| DAK1 | NP_013641.1 | 6323570 | Saccharomyces cerevisiae |
| DAK2 | NP_116602.1 | 14318466 | Saccharomyces cerevisiae |
| DAK | AAC27705.1 | 3171001 | Hansenula polymorpha |
| DAK | AAC39490.1 | 3287486 | Pichia pastoris |
| DAK2 | XP_505199.1 | 50555582 | Yarrowia lipolytica |

Methanol Oxidase

Attenuation of redox-inefficient endogenous methanol oxidizing enzymes, combined with increased expression of a cytosolic NADH-dependent methanol dehydrogenase, will enable redox-efficient oxidation of methanol to formaldehyde in the cytosol. Methanol oxidase, also called alcohol oxidase (EC 1.1.3.13), catalyzes the oxygen-dependent oxidation of methanol to formaldehyde and hydrogen peroxide. In eukaryotic organisms, alcohol oxidase is localized in the peroxisome. Exemplary methanol oxidase enzymes are encoded by AOD of *Candida boidinii* (Sakai and Tani, *Gene* 114:67-73 (1992)); and AOX of *H. polymorpha, P. methanolica* and *P. pastoris* (Ledeboer et al, Nucl Ac Res 13:3063-82 (1985); Koutz et al, Yeast 5:167-77 (1989); Nakagawa et al, Yeast 15:1223-1230 (1999)).

| Protein | GenBank ID | GI Number | Organism |
| --- | --- | --- | --- |
| AOX2 | AAF02495.1 | 6049184 | Pichia methanolica |
| AOX1 | AAF02494.1 | 6049182 | Pichia methanolica |
| AOX1 | AAB57849.1 | 2104961 | Pichia pastoris |
| AOX2 | AAB57850.1 | 2104963 | Pichia pastoris |
| AOX | P04841.1 | 113652 | Hansenula polymorpha |
| AOD1 | Q00922.1 | 231528 | Candida boidinii |
| AOX1 | AAQ99151.1 | 37694459 | Ogataea pini |

PQQ-Dependent Methanol Dehydrogenase

PQQ-dependent methanol dehydrogenase from *M. extorquens* (mxaIF) uses cytochrome as an electron carrier (Nunn et al, Nucl Acid Res 16:7722 (1988)). Methanol dehydrogenase enzymes of methanotrophs such as *Methylococcus capsulatis* function in a complex with methane monooxygenase (MMO) (Myronova et al, Biochem 45:11905-14 (2006)). Note that of accessory proteins, cytochrome CL and PQQ biosynthesis enzymes are needed for active methanol dehydrogenase. Attenuation of one or more of these required accessory proteins, or retargeting the enzyme to a different cellular compartment, would also have the effect of attenuating PQQ-dependent methanol dehydrogenase activity.

| Protein | GenBank ID | GI Number | Organism |
| --- | --- | --- | --- |
| MCA0299 | YP_112833.1 | 53802410 | Methylococcus capsulatis |
| MCA0782 | YP_113284.1 | 53804880 | Methylococcus capsulatis |
| mxaI | YP_002965443.1 | 240140963 | Methylobacterium extorquens |
| mxaF | YP_002965446.1 | 240140966 | Methylobacterium extorquens |

DHA Synthase and Other Competing Formaldehyde Assimilation and Dissimilation Pathways Carbon-efficient formaldehyde assimilation can be improved by attenuation of competing formaldehyde assimilation and dissimilation pathways. Exemplary competing assimilation pathways in eukaryotic organisms include the peroxisomal dissimilation of formaldehyde by DHA synthase, and the DHA kinase pathway for converting DHA to F6P, both described herein. Exemplary competing endogenous dissimilation pathways include one or more of the enzymes shown in FIG. 1.

Methylotrophic yeasts normally target selected methanol assimilation and dissimilation enzymes to peroxisomes during growth on methanol, including methanol oxidase, DHA synthase and S-(hydroxymethyl)-glutathione synthase (see review by Yurimoto et al, supra). The peroxisomal targeting mechanism comprises an interaction between the peroxisomal targeting sequence and its corresponding peroxisomal receptor (Lametschwandtner et al, J Biol Chem 273:33635-43 (1998)). Peroxisomal methanol pathway enzymes in methylotrophic organisms contain a PTS1 targeting sequence which binds to a peroxisomal receptor, such as Pex5p in Candida boidinii (Horiguchi et al, J Bacteriol 183:6372-83 (2001)). Disruption of the PTS1 targeting sequence, the Pex5p receptor and/or genes involved in peroxisomal biogenesis would enable cytosolic expression of DHA synthase, S-(hydroxymethyl)-glutathione synthase or other methanol-inducible peroxisomal enzymes. PTS1 targeting sequences of methylotrophic yeast are known in the art (Horiguchi et al, supra) Identification of peroxisomal targeting sequences of unknown enzymes can be predicted using bioinformatic methods (eg. Neuberger et al, *J Mol Biol* 328:581-92 (2003))).

Example XXIII

Methanol Assimilation via Methanol Dehydrogenase and the Ribulose Monophosphate Pathway This example shows that co-expression of an active methanol dehydrogenase (MeDH) and the enzymes of the Ribulose Monophosphate (RuMP) pathway can effectively assimilate methanol derived carbon.

An experimental system was designed to test the ability of a MeDH in conjunction with the enzymes H6P synthase (HPS) and 6-phospho-3-hexuloisomerase (PHI) of the RuMP pathway to assimilate methanol carbon into the glycolytic pathway and the TCA cycle. *Escherichia coli* strain ECh-7150 (ΔlacIA, ΔpflB, ΔptsI, ΔPpckA(pckA), ΔPglk(glk), glk::glfB, ΔhycE, ΔfrmR, ΔfrmA, ΔfrmB) was constructed to remove the glutathione-dependent formaldehyde detoxification capability encoded by the FrmA and FrmB enzyme. This strain was then transformed with plasmid pZA23S variants that either contained or lacked gene 2616A encoding a fusion of the HPS and PHI enzymes. These two transformed strains were then each transformed with pZS*13S variants that contained gene 2315L (encoding an active MeDH), or gene 2315 RIP2 (encoding a catalytically inactive MeDH), or no gene insertion. Genes 2315 and 2616 are internal nomenclatures for NAD-dependent methanol dehydrogenase from *Bacillus methanolicus* MGA3 and 2616 is a fused phs-hpi constructs as described in Orita et al. (2007) *Appl Microbiol Biotechnol* 76:439-45.

The six resulting strains were aerobically cultured in quadruplicate, in 5 ml minimal medium containing 1% arabinose and 0.6 M 13C-methanol as well as 100 ug/ml carbenicillin and 25 µg/ml kanamycin to maintain selection of the plasmids, and 1 mM IPTG to induce expression of the methanol dehydrogenase and HPS—PHI fusion enzymes. After 18 hours incubation at 37° C., the cell density was measured spectrophotometrically at 600 nM wavelength and a clarified sample of each culture medium was submitted for analysis to detect evidence of incorporation of the labeled methanol carbon into TCA-cycle derived metabolites. The label can be further enriched by deleting the gene araD that competes with ribulose-5-phosphate.

$^{13}$C carbon derived from labeled methanol provided in the experiment was found to be significantly enriched in the metabolites pyruvate, lactate, succinate, fumarate, malate, glutamate and citrate, but only in the strain expressing both catalytically active MeDH 2315L and the HPS—PHI fusion 2616A together (data not shown). Moreover, this strain grew significantly better than the strain expressing catalytically active MeDH but lacking expression of the HPS—PHI fusion (data not shown), suggesting that the HPS—PHI enzyme is capable of reducing growth inhibitory levels of formaldehyde that cannot be detoxified by other means in this strain background. These results show that co-expression of an active MeDH and the enzymes of the RuMP pathway can effectively assimilate methanol derived carbon and channel it into TCA-cycle derived products.

Throughout this application various publications have been referenced. The disclosures of these publications in their entireties, including GenBank and GI number publications, are hereby incorporated by reference in this application in order to more fully describe the state of the art to which this invention pertains. Although the invention has been described with reference to the examples provided above, it should be understood that various modifications can be made without departing from the spirit of the invention.

What is claimed is:

1. A non-naturally occurring microbial organism having:
   (i) a formaldehyde fixation pathway; and
   (ii) a methanol metabolic pathway, and
   a fatty acyl-ACP elongation (FAACPE) cycle in combination with a termination pathway,
   wherein said formaldehyde fixation pathway comprises a 3-hexulose-6-phosphate synthase and a 6-phospho-3-hexuloisomerase
   wherein said methanol metabolic pathway comprises a methanol dehydrogenase,
   wherein said FAACPE cycle comprises one or more β-ketoacyl-ACP synthase, one or more β-ketoacyl-ACP reductase, one or more β-hydroxyacyl-ACP reductase, and one or more enoyl ACP-reductase,
   wherein said termination pathway comprises a thioesterase
   wherein an enzyme of the formaldehyde fixation pathway, the methanol metabolic pathway, the FAACPE cycle or the termination pathway is encoded by at least one exogenous nucleic acid and is expressed in a sufficient amount to produce a compound of Formula (I):

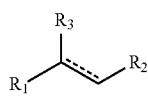
(I)

wherein $R_1$ is $C_{1-24}$ linear alkyl; $R_2$ is H; and ═══ represents a single, wherein the substrate of each of said enzymes of the FAACPE cycle and the termination pathway are independently selected from a compound of Formula (II) or malonyl-ACP:

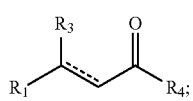
(II)

wherein R₁ is C₁₋₂₄ linear alkyl; R₃ is H, OH, or oxo (=O)); R₄ is S-CoA, ACP, OH or H; and ═══ represents a single bond with the proviso that the valency of the carbon atom to which R₃ is attached is four, wherein said one or more enzymes of the FAACPE cycle are each selective for a compound of Formula (II) having a number of carbon atoms at R₁ that is no greater than the number of carbon atoms at R₁ of said compound of Formula (I), and wherein said one or more enzymes of the termination pathway are each selective for a compound of Formula (II) having a number of carbon atoms at R₁ that is no less than the number of carbon atoms at R₁ of said compound of Formula (I).

2. The non-naturally occurring microbial organism of claim 1, wherein said microbial organism further comprises a formate assimilation pathway.

3. The non-naturally occurring microbial organism of claim 1, wherein the microbial organism further comprises an acetoacetyl-ACP pathway of:
(1) 12A, 12B, and 12C; or (2) 12A, 12B, and 12D, wherein 12A is an acetyl-CoA carboxylase, wherein 12B is malonyl-CoA ACP transacylase, wherein 12C is an acetoacetyl-ACP synthase, and wherein 12D is a β-ketoacyl-ACP synthase, or
wherein the microbial organism further comprises a 3-oxovalery-ACP pathway comprising an acetyl-CoA carboxylase, a malonyl-CoA ACP transacylase, and a β-ketoacyl-ACP synthase.

4. The non-naturally occurring microbial organism of 3, wherein an enzyme of the acetoacetyl-ACP pathway is encoded by at least one exogenous nucleic acid and is expressed in a sufficient amount to produce acetoacetyl-ACP, wherein an enzyme of the 3-oxovalery-ACP pathway is encoded by at least one exogenous nucleic acid and is expressed in a sufficient amount to produce 3-oxovalery-ACP, and wherein the acetoacetyl-ACP or the 3-oxovalery-ACP is a β-ketoacyl-ACP of the FAACPE cycle.

5. The non-naturally occurring microbial organism of claim 1, wherein R₁ is C₉ linear alkyl, C₁₀ linear alkyl, Cn, linear alkyl, C₁₂ linear alkyl or Cis linear alkyl.

6. The non-naturally occurring microbial organism of claim 1, wherein said microbial organism comprises two, three, or four exogenous nucleic acids each encoding an enzyme of said FAACPE cycle or said termination pathway.

7. The non-naturally occurring microbial organism of claim 1, wherein said microbial organism comprises one, two, or three exogenous nucleic acids each encoding a formaldehyde fixation pathway enzyme, or a methanol metabolic pathway enzyme.

8. The non-naturally occurring microbial organism of claim 1, wherein said microbial organism comprises exogenous nucleic acids encoding each of the enzymes 3-hexulose-6-phosphate synthase, 6-phospho-3-hexuloisomerase, and methanol dehydrogenase.

9. The non-naturally occurring microbial organism of claim 1, wherein said organism comprises at least one exogenous nucleic acid encoding the methanol dehydrogenase.

10. The non-naturally occurring microbial organism of claim 1, wherein said microbial organism further comprises 3H or 3P, wherein 3H is a hydrogenase, wherein 3P a carbon monoxide dehydrogenase.

11. The non-naturally occurring microbial organism of claim 1, wherein said at least one exogenous nucleic acid encoding said formaldehyde fixation pathway enzyme, said methanol metabolic pathway enzyme, said FAACPE cycle enzyme, or said termination pathway enzyme is a heterologous nucleic acid.

12. The non naturally occurring microbial organism of claim 1, wherein said enzyme of the formaldehyde fixation pathway, methanol metabolic pathway, FAACPE cycle or termination pathway is expressed in a sufficient amount to produce a compound of Formula (XIV):

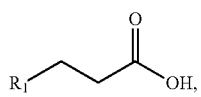

(XIV)

wherein
R₁ is C₉ linear alkyl, C₁₀ linear alkyl, C₁₁, linear alkyl, C₁₂ linear alkyl or Cis linear alkyl.

13. The non-naturally occurring microbial organism of claim 1, wherein said microbial organism further comprises an acetyl-CoA pathway and at least one exogenous nucleic acid encoding an acetyl-CoA pathway enzyme expressed in a sufficient amount to produce or enhance carbon flux through acetyl-CoA, wherein said acetyl-CoA pathway comprises a pathway selected from:
(1) 3A and 3B; (2) 3A, 3C, and 3D; (3) 3H; (4) 3G and 3D; (5) 3E, 3F and 3B; (6) 3E and 31; (7) 3J, 3F and 3B; (8) 3J and 31; (9) 4A, 4B, and 4C; (10) 4A, 4B, 4J, 4K, and 4D; (11) 4A, 4B, 4G, and 4D; (12) 4A, 4F, and 4D; (13) 4N, 4H, 4B and 4C; (14) 4N, 4H, 4B, 4J, 4K, and 4D; (15) 4N, 4H, 4B, 4G, and 4D; (16) 4N, 4H, 4F, and 4D; (17) 4L, 4M, 4B and 4C; (18) 4L, 4M, 4B, 4J, 4K, and 4D; (19) 4L, 4M, 4B, 4G, and 4D; (20) 4L, 4M, 4F, and 4D; (21) 5A, 5B, 5D, 5H, 5I, and 5J; (22) 5A, 5B, 5E, 5F, 5H, 5I, and 5J; (23) 5A, 5B, 5E, 5K, 5L, 5H, 5I, and 5J; (24) 5A, 5C, 5D, 5H, and 5J; (25) 5A, 5C, 5E, 5F, 5H, and 5J; (26) 5A, 5C, 5E, 5K, 5L, 5H, and 5J; (27) 6A, 6B, 6D, and 6G; (28) 6A, 6B, 6E, 6F, and 6G; (29) 6A, 6B, 6E, 6K, 6L, and 6G; (30) 6A, 6C, and 6D; (31) 6A, 6C, 6E, and 6F; (32) 6A, 6C, 6E, 6K, and 6L; (33) 1T and 1V; (34) 1T, 1W, and 1X; (35) 1U and 1V; and (36) 1U, 1W, and 1X,
wherein 3A is a pyruvate oxidase (acetate-forming), wherein 3B is an acetyl-CoA synthetase, an acetyl-CoA ligase or an acetyl-CoA transferase, wherein 3C is an acetate kinase, wherein 3D is a phosphotransacetylase, wherein 3E is a pyruvate decarboxylase, wherein 3F is an acetaldehyde dehydrogenase, wherein 3G is a pyruvate oxidase (acetyl-phosphate forming), wherein 3H is a pyruvate dehydrogenase, a pyruvate: ferredoxin oxidoreductase, a pyruvate: NAD(P)H oxidoreductase or a pyruvate formate lyase, wherein 31 is an acetaldehyde dehydrogenase (acylating), wherein 3J is a threonine aldolase, wherein 4A is a phosphoenolpyruvate (PEP) carboxylase or a PEP carboxykinase, wherein 4B is an oxaloacetate decarboxylase, wherein 4C is a malonate semialdehyde dehydrogenase (acetylating), wherein 4D is an acetyl-CoA carboxylase or a malonyl-CoA decarboxylase, wherein 4F is an oxaloacetate dehydrogenase or an oxaloacetate oxidoreductase, wherein 4G is a malonate semialdehyde dehydrogenase (acylating), wherein 4H is a pyruvate carboxylase, wherein 4J is a malonate semialdehyde dehydrogenase, wherein 4K is a malonyl-CoA synthetase or a malonyl-CoA transferase, wherein 4L is a malic enzyme, wherein 4M is a malate dehydrogenase or a malate oxidoreductase, wherein 4N is a pyruvate kinase or a PEP phosphatase, wherein 5A is a citrate synthase, wherein 5B is a citrate transporter, wherein 5C is a citrate/malate transporter, wherein 5D is an ATP citrate lyase, wherein 5E is a citrate lyase, wherein 5F is an acetyl-CoA synthetase or an acetyl-CoA transferase, wherein 5H is a cytosolic malate dehydrogenase, wherein 5I is a malate transporter, wherein 5J is a mitochondrial malate dehydrogenase, wherein 5K is an acetate kinase, wherein 5L is a phosphotransacetylase, wherein 6A is a citrate synthase, wherein 6B is a citrate transporter, wherein 6C is a citrate/oxaloacetate transporter, wherein 6D is an ATP citrate lyase, wherein 6E is a citrate lyase, wherein 6F is an acetyl-CoA synthetase or an acetyl-CoA transferase, wherein 6G is an oxaloacetate transporter, wherein 6K is an acetate kinase, and wherein 6L is a phosphotransacetylase, wherein 1T is a fructose-6-phosphate phosphoketolase, wherein 1U is a xylulose-5-phosphate phosphoketolase, wherein 1V is a phosphotransacetylase, wherein 1W is an acetate kinase, wherein 1X is an acetyl-CoA transferase, an acetyl-CoA synthetase, or an acetyl-CoA ligase.

14. The non-naturally occurring microbial organism of claim 13, wherein said microbial organism comprises two, three, four, five, six, seven or eight exogenous nucleic acids each encoding an acetyl-CoA pathway enzyme.

15. The non-naturally occurring microbial organism of claim 13, wherein said microbial organism comprises exogenous nucleic acids encoding each of the acetyl-CoA pathway enzymes of at least one of the pathways selected from (1)-(36).

16. The non-naturally occurring microbial organism of claim 1, further comprising one or more gene disruptions, said one or more gene disruptions occurring in endogenous genes encoding proteins or enzymes involved in: native production of ethanol, glycerol, acetate, formate, lactate, CO2, fatty acids, or malonyl-CoA by said microbial organism; transfer of pathway intermediates to cellular compartments other than the cytosol; or native degradation of a FAACPE cycle intermediate or a termination pathway intermediate by said microbial organism, wherein said one or more gene disruptions confer increased production of the compound of Formula (I) in said microbial organism.

17. The non-naturally occurring microbial organism of claim 1, wherein one or more enzymes of the FAACPE cycle or the termination pathway preferentially react with an NADH cofactor or have reduced preference for reacting with an NAD(P)H cofactor, wherein said one or more enzymes of the FAACPE cycle are a 3-ketoacyl-ACP reductase or an enoyl-ACP reductase, and wherein said one or more enzymes of the termination pathway are selected from an acyl-CoA reductase (aldehyde forming), an alcohol dehydrogenase, an acyl-CoA reductase (alcohol forming), a fatty acyl-ACP reductase, and a carboxylic acid reductase.

18. The non-naturally occurring microbial organism of claim 1, further comprising one or more gene disruptions, said one or more gene disruptions occurring in genes encoding proteins or enzymes that result in an increased ratio of NAD(P)H to NAD(P) present in the cytosol of said microbial organism following said disruptions.

19. The non-naturally occurring microbial organism of claim 1, wherein said microbial organism is Crabtree positive and is in culture medium comprising excess glucose, thereby increasing the ratio of NAD(P)H to NAD(P) present in the cytosol of said microbial organism.

20. The non-naturally occurring microbial organism of claim 1, further comprising at least one exogenous nucleic acid encoding an extracellular transporter or an extracellular transport system for the compound of Formula (1).

21. The non-naturally occurring microbial organism of claim 1, wherein one or more endogenous enzymes involved in: native production of ethanol, glycerol, acetate, formate, lactate, CO2, fatty acids, or malonyl-CoA by said microbial organism; transfer of pathway intermediates to cellular compartments other than the cytosol; or native degradation of a FAACPE cycle intermediate or a termination pathway intermediate by said microbial organism, has attenuated enzyme activity or expression levels.

22. The non-naturally occurring microbial organism of claim 1, wherein one or more endogenous enzymes involved in the oxidation of NAD(P)H or NADH, has attenuated enzyme activity or expression levels.

23. A method for producing a compound of Formula (I):

wherein $R_1$ is $C_{1-24}$ linear alkyl; $R_2$ is; and ====== represents a single bond, comprising culturing the non-naturally occurring microbial organism of claim 1 under conditions for a sufficient period of time to produce said compound of Formula (I).

24. The method of claim 23, wherein said method further comprises separating the compound of Formula (I) from other components in the culture.

25. The method of claim 24, wherein the separating comprises extraction, continuous liquid-liquid extraction, pervaporation, membrane filtration, membrane separation, reverse osmosis, electrodialysis, distillation, crystallization, centrifugation, extractive filtration, ion exchange chromatography, absorption chromatography, or ultrafiltration.

26. The non-naturally occurring microbial organism of claim 2, wherein said formate assimilation pathway comprises a pathway selected from:
(1) 1E; (2) 1F, and 1G; (3) 1H, 1I, 1J, and 1K; (4) 1H, 1I, 1J, 1L, 1M, and 1N; 5) 1E, 1H, 1I, 1J, 1L, 1M, and 1N; (6) 1F, 1G, 1H, 1I, 1J, 1L, 1M, and 1N; (7) 1K, 1H, 1I, 1J, 1L, 1M, and 1N; and (8) 1H, 1I, 1J, 1O, and 1P,
    wherein 1E is a formate reductase, 1F is a formate ligase, a formate transferase, or a formate synthetase, wherein 1G is a formyl-CoA reductase, wherein 1H is a formyltetrahydrofolate synthetase, wherein 1I is a methenyltetrahydrofolate cyclohydrolase, wherein 1J is a methylenetetrahydrofolate dehydrogenase, wherein 1K is a formaldehyde-forming enzyme or spontaneous, wherein 1L is a glycine cleavage system, wherein 1M is a serine hydroxymethyltransferase, wherein 1N is a serine deaminase, wherein 1O is a methylenetetrahydrofolate reductase, and wherein 1P is an acetyl-CoA synthase.

27. The non-naturally occurring microbial organism of claim 1, wherein said termination pathway further comprises an acyl-CoA synthase and an acyl-CoA reductase for production of a fatty aldehyde.

28. The non-naturally occurring microbial organism of claim 27, wherein said termination pathway further comprises a fatty aldehyde reductase for production of a fatty alcohol.

* * * * *

SEQUENCE LISTING

```
<160> NUMBER OF SEQ ID NOS: 24

<210> SEQ ID NO 1
<211> LENGTH: 59
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
gacgaattcg ctagcaagag gagaagtcga catgtccaat tcactggccg tcgttttac          59

<210> SEQ ID NO 2
<211> LENGTH: 47
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 2
gaccctagga agctttctag agtcgaccta tgcggcatca gagcaga                    47

<210> SEQ ID NO 3
<211> LENGTH: 474
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3
```

| | | | | | | | | | | | | | | |
|---|---|---|---|---|---|---|---|---|---|---|---|---|---|---|
| Met | Ser | Thr | Glu | Ile | Lys | Thr | Gln | Val | Val | Leu | Gly | Ala | Gly | Pro |
| 1 | | | | 5 | | | | | 10 | | | | | 15 |

| | | | | | | | | | | | | | | |
|---|---|---|---|---|---|---|---|---|---|---|---|---|---|---|
| Ala | Gly | Tyr | Ser | Ala | Ala | Phe | Arg | Cys | Ala | Asp | Leu | Gly | Leu | Glu | Thr |
| | | | 20 | | | | | 25 | | | | | 30 | |

Val Ile Val Glu Arg Tyr Asn Thr Leu Gly Gly Val Cys Leu Asn Val
            35                  40                  45

Gly Cys Ile Pro Ser Lys Ala Leu Leu His Val Ala Lys Val Ile Glu
50                  55                  60

Glu Ala Lys Ala Leu Ala Glu His Gly Ile Val Phe Gly Glu Pro Lys
65                  70                  75                  80

Thr Asp Ile Asp Lys Ile Arg Thr Trp Lys Glu Lys Val Ile Asn Gln
                85                  90                  95

Leu Thr Gly Gly Leu Ala Gly Met Ala Lys Gly Arg Lys Val Lys Val
            100                 105                 110

Val Asn Gly Leu Gly Lys Phe Thr Gly Ala Asn Thr Leu Glu Val Glu
            115                 120                 125

Gly Glu Asn Gly Lys Thr Val Ile Asn Phe Asp Asn Ala Ile Ile Ala
        130                 135                 140

Ala Gly Ser Arg Pro Ile Gln Leu Pro Phe Ile Pro His Glu Asp Pro
145                 150                 155                 160

Arg Ile Trp Asp Ser Thr Asp Ala Leu Glu Leu Lys Glu Val Pro Glu
                165                 170                 175

Arg Leu Leu Val Met Gly Gly Gly Ile Ile Gly Leu Glu Met Gly Thr
            180                 185                 190

Val Tyr His Ala Leu Gly Ser Gln Ile Asp Val Val Arg Lys His
            195                 200                 205

Gln Val Ile Arg Ala Ala Asp Lys Asp Ile Val Lys Val Phe Thr Lys
        210                 215                 220

Arg Ile Ser Lys Lys Phe Asn Leu Met Leu Glu Thr Lys Val Thr Ala
225                 230                 235                 240

Val Glu Ala Lys Glu Asp Gly Ile Tyr Val Thr Met Glu Gly Lys Lys
                245                 250                 255

Ala Pro Ala Glu Pro Gln Arg Tyr Asp Ala Val Leu Val Ala Ile Gly
            260                 265                 270

Arg Val Pro Asn Gly Lys Asn Leu Asp Ala Gly Lys Ala Gly Val Glu
            275                 280                 285

Val Asp Asp Arg Gly Phe Ile Arg Val Asp Lys Gln Leu Arg Thr Asn
        290                 295                 300

Val Pro His Ile Phe Ala Ile Gly Asp Ile Val Gly Gln Pro Met Leu
305                 310                 315                 320

```
Ala His Lys Gly Val His Glu Gly His Val Ala Ala Glu Val Ile Ala
                325                 330                 335

Gly Lys Lys His Tyr Phe Asp Pro Lys Val Ile Pro Ser Ile Ala Tyr
            340                 345                 350

Thr Glu Pro Glu Val Ala Trp Val Gly Leu Thr Glu Lys Glu Ala Lys
            355                 360                 365

Glu Lys Gly Ile Ser Tyr Glu Thr Ala Thr Phe Pro Trp Ala Ala Ser
        370                 375                 380

Gly Arg Ala Ile Ala Ser Asp Cys Ala Asp Gly Met Thr Lys Leu Ile
385                 390                 395                 400

Phe Asp Lys Glu Ser His Arg Val Ile Gly Ala Ile Val Gly Thr
                405                 410                 415

Asn Gly Gly Glu Leu Leu Gly Glu Ile Gly Leu Ala Ile Glu Met Gly
                420                 425                 430

Cys Asp Ala Glu Asp Ile Ala Leu Thr Ile His Ala His Pro Thr Leu
                435                 440                 445

His Glu Ser Val Gly Leu Ala Ala Glu Val Phe Glu Gly Ser Ile Thr
            450                 455                 460

Asp Leu Pro Asn Pro Lys Ala Lys Lys Lys
465                 470

<210> SEQ ID NO 4
<211> LENGTH: 474
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Met Ser Thr Glu Ile Lys Thr Gln Val Val Leu Gly Ala Gly Pro
1               5                   10                  15

Ala Gly Tyr Ser Ala Ala Phe Arg Cys Ala Asp Leu Gly Leu Glu Thr
            20                  25                  30

Val Ile Val Glu Arg Tyr Asn Thr Leu Gly Gly Val Cys Leu Asn Val
        35                  40                  45

Gly Cys Ile Pro Ser Lys Ala Leu Leu His Val Ala Lys Val Ile Glu
    50                  55                  60

Glu Ala Lys Ala Leu Ala Glu His Gly Ile Val Phe Gly Glu Pro Lys
65                  70                  75                  80

Thr Asp Ile Asp Lys Ile Arg Thr Trp Lys Glu Lys Val Ile Asn Gln
                85                  90                  95

Leu Thr Gly Gly Leu Ala Gly Met Ala Lys Gly Arg Lys Val Lys Val
            100                 105                 110

Val Asn Gly Leu Gly Lys Phe Thr Gly Ala Asn Thr Leu Glu Val Glu
        115                 120                 125

Gly Glu Asn Gly Lys Thr Val Ile Asn Phe Asp Asn Ala Ile Ile Ala
    130                 135                 140

Ala Gly Ser Arg Pro Ile Gln Leu Pro Phe Ile Pro His Glu Asp Pro
145                 150                 155                 160

Arg Ile Trp Asp Ser Thr Asp Ala Leu Glu Leu Lys Glu Val Pro Glu
                165                 170                 175

Arg Leu Leu Val Met Gly Gly Gly Ile Ile Ala Leu Glu Met Ala Thr
            180                 185                 190

Val Tyr His Ala Leu Gly Ser Gln Ile Asp Val Val Val Arg Lys His
```

195                 200                 205
Gln Val Ile Arg Ala Ala Asp Lys Asp Ile Val Lys Val Phe Thr Lys
    210                 215                 220

Arg Ile Ser Lys Lys Phe Asn Leu Met Leu Glu Thr Lys Val Thr Ala
225                 230                 235                 240

Val Glu Ala Lys Glu Asp Gly Ile Tyr Val Thr Met Glu Gly Lys Lys
                245                 250                 255

Ala Pro Ala Glu Pro Gln Arg Tyr Asp Ala Val Leu Val Ala Ile Gly
            260                 265                 270

Arg Val Pro Asn Gly Lys Asn Leu Asp Ala Gly Lys Ala Gly Val Glu
        275                 280                 285

Val Asp Asp Arg Gly Phe Ile Arg Val Asp Lys Gln Leu Arg Thr Asn
    290                 295                 300

Val Pro His Ile Phe Ala Ile Gly Asp Ile Val Gly Gln Pro Met Leu
305                 310                 315                 320

Ala His Lys Gly Val His Glu Gly His Val Ala Ala Glu Val Ile Ala
                325                 330                 335

Gly Lys Lys His Tyr Phe Asp Pro Lys Val Ile Pro Ser Ile Ala Tyr
            340                 345                 350

Thr Glu Pro Glu Val Ala Trp Val Gly Leu Thr Glu Lys Glu Ala Lys
        355                 360                 365

Glu Lys Gly Ile Ser Tyr Glu Thr Ala Thr Phe Pro Trp Ala Ala Ser
    370                 375                 380

Gly Arg Ala Ile Ala Ser Asp Cys Ala Asp Gly Met Thr Lys Leu Ile
385                 390                 395                 400

Phe Asp Lys Glu Ser His Arg Val Ile Gly Gly Ala Ile Val Gly Thr
                405                 410                 415

Asn Gly Gly Glu Leu Leu Gly Glu Ile Gly Leu Ala Ile Glu Met Gly
            420                 425                 430

Cys Asp Ala Glu Asp Ile Ala Leu Thr Ile His Ala His Pro Thr Leu
        435                 440                 445

His Glu Ser Val Gly Leu Ala Ala Glu Val Phe Glu Gly Ser Ile Thr
    450                 455                 460

Asp Leu Pro Asn Pro Lys Ala Lys Lys Lys
465                 470

<210> SEQ ID NO 5
<211> LENGTH: 364
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Met Lys Ile Val Leu Val Leu Tyr Asp Ala Gly Lys His Ala Ala Asp
1               5                   10                  15

Glu Glu Lys Leu Tyr Gly Cys Thr Glu Asn Lys Leu Gly Ile Ala Asn
                20                  25                  30

Trp Leu Lys Asp Gln Gly His Glu Leu Ile Thr Thr Ser Asp Lys Glu
            35                  40                  45

Gly Glu Thr Ser Glu Leu Asp Lys His Ile Pro Asp Ala Asp Ile Ile
        50                  55                  60

Ile Thr Thr Pro Phe His Pro Ala Tyr Ile Thr Lys Glu Arg Leu Asp
65                  70                  75                  80

```
Lys Ala Lys Asn Leu Lys Leu Val Val Ala Gly Val Gly Ser Asp
                85                  90                  95

His Ile Asp Leu Asp Tyr Ile Asn Gln Thr Gly Lys Lys Ile Ser Val
            100                 105                 110

Leu Glu Val Thr Gly Ser Asn Val Val Ser Val Ala Glu His Val Val
            115                 120                 125

Met Thr Met Leu Val Leu Val Arg Asn Phe Val Pro Ala His Glu Gln
    130                 135                 140

Ile Ile Asn His Asp Trp Glu Val Ala Ala Ile Ala Lys Asp Ala Tyr
145                 150                 155                 160

Asp Ile Glu Gly Lys Thr Ile Ala Thr Ile Gly Ala Gly Arg Ile Gly
                165                 170                 175

Tyr Arg Val Leu Glu Arg Leu Leu Pro Phe Asn Pro Lys Glu Leu Leu
            180                 185                 190

Tyr Tyr Gln Arg Gln Ala Leu Pro Lys Glu Ala Glu Lys Val Gly
            195                 200                 205

Ala Arg Arg Val Glu Asn Ile Glu Glu Leu Val Ala Gln Ala Asp Ile
        210                 215                 220

Val Thr Val Asn Ala Pro Leu His Ala Gly Thr Lys Gly Leu Ile Asn
225                 230                 235                 240

Lys Glu Leu Leu Ser Lys Phe Lys Lys Gly Ala Trp Leu Val Asn Thr
                245                 250                 255

Ala Arg Gly Ala Ile Cys Val Ala Glu Asp Val Ala Ala Ala Leu Glu
            260                 265                 270

Ser Gly Gln Leu Arg Gly Tyr Gly Gly Asp Val Trp Phe Pro Gln Pro
        275                 280                 285

Ala Pro Lys Asp His Pro Trp Arg Asp Met Arg Asn Lys Tyr Gly Ala
        290                 295                 300

Gly Asn Ala Met Thr Pro His Tyr Ser Gly Thr Thr Leu Asp Ala Gln
305                 310                 315                 320

Thr Arg Tyr Ala Glu Gly Thr Lys Asn Ile Leu Glu Ser Phe Phe Thr
                325                 330                 335

Gly Lys Phe Asp Tyr Arg Pro Gln Asp Ile Ile Leu Leu Asn Gly Glu
            340                 345                 350

Tyr Val Thr Lys Ala Tyr Gly Lys His Asp Lys Lys
            355                 360

<210> SEQ ID NO 6
<211> LENGTH: 364
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Met Lys Ile Val Leu Val Leu Tyr Asp Ala Gly Lys His Ala Ala Asp
1               5                   10                  15

Glu Glu Lys Leu Tyr Gly Cys Thr Glu Asn Lys Leu Gly Ile Ala Asn
            20                  25                  30

Trp Leu Lys Asp Gln Gly His Glu Leu Ile Thr Thr Ser Asp Lys Glu
        35                  40                  45

Gly Glu Thr Ser Glu Leu Asp Lys His Ile Pro Asp Ala Asp Ile Ile
    50                  55                  60

Ile Thr Thr Pro Phe His Pro Ala Tyr Ile Thr Lys Glu Arg Leu Asp
65                  70                  75                  80
```

Lys Ala Lys Asn Leu Lys Leu Val Val Ala Gly Val Gly Ser Asp
                85                  90                  95

His Ile Asp Leu Asp Tyr Ile Asn Gln Thr Gly Lys Lys Ile Ser Val
                100                 105                 110

Leu Glu Val Thr Gly Ser Asn Val Val Ser Val Ala Glu His Val Val
                115                 120                 125

Met Thr Met Leu Val Leu Val Arg Asn Phe Val Pro Ala His Glu Gln
    130                 135                 140

Ile Ile Asn His Asp Trp Glu Val Ala Ala Ile Ala Lys Asp Ala Tyr
145                 150                 155                 160

Asp Ile Glu Gly Lys Thr Ile Ala Thr Ile Gly Ala Gly Arg Ile Gly
                165                 170                 175

Tyr Arg Val Leu Glu Arg Leu Leu Pro Phe Asn Pro Lys Glu Leu Leu
                180                 185                 190

Tyr Tyr Ser Pro Gln Ala Leu Pro Lys Glu Ala Glu Lys Val Gly
                195                 200                 205

Ala Arg Arg Val Glu Asn Ile Glu Glu Leu Val Ala Gln Ala Asp Ile
                210                 215                 220

Val Thr Val Asn Ala Pro Leu His Ala Gly Thr Lys Gly Leu Ile Asn
225                 230                 235                 240

Lys Glu Leu Leu Ser Lys Phe Lys Lys Gly Ala Trp Leu Val Asn Thr
                245                 250                 255

Ala Arg Gly Ala Ile Cys Val Ala Glu Asp Val Ala Ala Ala Leu Glu
                260                 265                 270

Ser Gly Gln Leu Arg Gly Tyr Gly Gly Asp Val Trp Phe Pro Gln Pro
                275                 280                 285

Ala Pro Lys Asp His Pro Trp Arg Asp Met Arg Asn Lys Tyr Gly Ala
                290                 295                 300

Gly Asn Ala Met Thr Pro His Tyr Ser Gly Thr Thr Leu Asp Ala Gln
305                 310                 315                 320

Thr Arg Tyr Ala Glu Gly Thr Lys Asn Ile Leu Glu Ser Phe Phe Thr
                325                 330                 335

Gly Lys Phe Asp Tyr Arg Pro Gln Asp Ile Ile Leu Leu Asn Gly Glu
                340                 345                 350

Tyr Val Thr Lys Ala Tyr Gly Lys His Asp Lys Lys
                355                 360

<210> SEQ ID NO 7
<211> LENGTH: 376
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Met Ser Lys Gly Lys Val Leu Leu Val Leu Tyr Glu Gly Gly Lys His
1               5                   10                  15

Ala Glu Glu Gln Glu Lys Leu Leu Gly Cys Ile Glu Asn Glu Leu Gly
                20                  25                  30

Ile Arg Asn Phe Ile Glu Glu Gln Gly Tyr Glu Leu Val Thr Thr Ile
                35                  40                  45

Asp Lys Asp Pro Glu Pro Thr Ser Thr Val Asp Arg Glu Leu Lys Asp
                50                  55                  60

Ala Glu Ile Val Ile Thr Thr Pro Phe Phe Pro Ala Tyr Ile Ser Arg

```
                65                  70                  75                  80
        Asn Arg Ile Ala Glu Ala Pro Asn Leu Lys Leu Cys Val Thr Ala Gly
                            85                  90                  95

Val Gly Ser Asp His Val Asp Leu Glu Ala Ala Asn Glu Arg Lys Ile
                    100                 105                 110

Thr Val Thr Glu Val Thr Gly Ser Asn Val Val Ser Val Ala Glu His
                    115                 120                 125

Val Met Ala Thr Ile Leu Val Leu Ile Arg Asn Tyr Asn Gly Gly His
                130                 135                 140

Gln Gln Ala Ile Asn Gly Glu Trp Asp Ile Ala Gly Val Ala Lys Asn
        145                 150                 155                 160

Glu Tyr Asp Leu Glu Asp Lys Ile Ile Ser Thr Val Gly Ala Gly Arg
                        165                 170                 175

Ile Gly Tyr Arg Val Leu Glu Arg Leu Val Ala Phe Asn Pro Lys Lys
                    180                 185                 190

Leu Leu Tyr Tyr Ala Arg Gln Glu Leu Pro Ala Glu Ala Ile Asn Arg
                    195                 200                 205

Leu Asn Glu Ala Ser Lys Leu Phe Asn Gly Arg Gly Asp Ile Val Gln
                210                 215                 220

Arg Val Glu Lys Leu Glu Asp Met Val Ala Gln Ser Asp Val Val Thr
        225                 230                 235                 240

Ile Asn Cys Pro Leu His Lys Asp Ser Arg Gly Leu Phe Asn Lys Lys
                        245                 250                 255

Leu Ile Ser His Met Lys Asp Gly Ala Tyr Leu Val Asn Thr Ala Arg
                    260                 265                 270

Gly Ala Ile Cys Val Ala Glu Asp Val Ala Glu Ala Val Lys Ser Gly
                    275                 280                 285

Lys Leu Ala Gly Tyr Gly Gly Asp Val Trp Asp Lys Gln Pro Ala Pro
                290                 295                 300

Lys Asp His Pro Trp Arg Thr Met Asp Asn Lys Asp His Val Gly Asn
        305                 310                 315                 320

Ala Met Thr Val His Ile Ser Gly Thr Ser Leu Asp Ala Gln Lys Arg
                        325                 330                 335

Tyr Ala Gln Gly Val Lys Asn Ile Leu Asn Ser Tyr Phe Ser Lys Lys
                    340                 345                 350

Phe Asp Tyr Arg Pro Gln Asp Ile Ile Val Gln Asn Gly Ser Tyr Ala
                    355                 360                 365

Thr Arg Ala Tyr Gly Gln Lys Lys
                370                 375

<210> SEQ ID NO 8
<211> LENGTH: 60
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
tctaatctaa gttttctaga actagtaaag atgagagatg tagtaatagt aagtgctgta        60

<210> SEQ ID NO 9
<211> LENGTH: 58
<212> TYPE: DNA
<213> ORGANISM: Artificial Sequence
<220> FEATURE:
<223> OTHER INFORMATION: Description of Artificial Sequence: Synthetic
```

-continued primer

<400> SEQUENCE: 9
gatatcgaat tcctgcagcc cgggggatcc ttagtctctt tcaactacga gagctgtt        58

<210> SEQ ID NO 10
<211> LENGTH: 55
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
tctaatctaa gttttctaga actagtaaag atgaaaaatt gtgtcatcgt cagtg        55

<210> SEQ ID NO 11
<211> LENGTH: 60
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
gatatcgaat tcctgcagcc cgggggatcc ttaattcaac cgttcaatca ccatcgcaat        60

<210> SEQ ID NO 12
<211> LENGTH: 58
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
aatctaagtt ttctagaact agtaaagatg aaagaagttg taatagctag tgcagtaa        58

<210> SEQ ID NO 13
<211> LENGTH: 60
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
tatcgaattc ctgcagcccg ggggatcctt aatggtgatg gtgatgatgg cactttcta        60

<210> SEQ ID NO 14
<211> LENGTH: 52
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
tctaatctaa gttttctaga actagtaaag atgagcaccc cgtccatcgt ca        52

<210> SEQ ID NO 15
<211> LENGTH: 55
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
gatatcgaat tcctgcagcc cgggggatcc ctaaaggctc tcgatgcaca tcgcc    55

<210> SEQ ID NO 16
<211> LENGTH: 51
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
taagctagca agaggagaag tcgacatgac tgacgttgtc atcgtatccg c    51

<210> SEQ ID NO 17
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
gcctctagga agctttctag attattattt gcgctcgact gccagc    46

<210> SEQ ID NO 18
<211> LENGTH: 55
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
aagcatacaa tcaactatct catatacaat gaaaaagatt tttgtacttg gagca    55

<210> SEQ ID NO 19
<211> LENGTH: 60
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
aaaaatcata atcataaga aattcgctta tttagagtaa tcatagaatc cttttcctga    60

<210> SEQ ID NO 20
<211> LENGTH: 56
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
aatctaagtt ttctagaact agtaaagatg aacacagaaa acattgaaca agccat    56

-continued

```
<210> SEQ ID NO 21
<211> LENGTH: 60
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
tatcgaattc ctgcagcccg ggggatccct aagcctccca agtccgtaat gagaaccctt    60

<210> SEQ ID NO 22
<211> LENGTH: 60
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
ccaagcatac aatcaactat ctcatataca atggagaatt ttagatttaa tgcatataca    60

<210> SEQ ID NO 23
<211> LENGTH: 60
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
aataaaaatc ataatcata agaaattcgc ttaaagggac atttctaaaa ttttatatac    60

<210> SEQ ID NO 24
<211> LENGTH: 20
<212> TYPE: PRT
<213> ORGANISM: Euglena gracilis

<400> SEQUENCE: 24

Met Thr Tyr Lys Ala Pro Val Lys Asp Val Lys Phe Leu Leu Asp Lys
1               5                   10                  15

Val Phe Lys Val
            20
```